(12) United States Patent
Shimizu et al.

(10) Patent No.: US 11,439,802 B2
(45) Date of Patent: Sep. 13, 2022

(54) INGESTIBLE DEVICE FOR DELIVERY OF THERAPEUTIC AGENT TO THE GASTROINTESTINAL TRACT

(71) Applicant: Biora Therapeutics, Inc., San Diego, CA (US)

(72) Inventors: Jeffrey A. Shimizu, Poway, CA (US); Mitchell Lawrence Jones, La Jolla, CA (US); Mark Sasha Drlik, Victoria (CA); Iman Niknia, Victoria (CA); Nathan John Muller, Victoria (CA); Tuyen Nguyen, Victoria (CA); Christopher Loren Wahl, San Diego, CA (US); Edward Mudge, Cambridgeshire (GB); Nicholas Mark Salt, Cambridgeshire (GB); Nia Eleri Stevens, Cambridgeshire (GB); Stuart Robert Abercrombie, Cambridgeshire (GB); Christopher Ian Bunce, Cambridgeshire (GB); Nelson Quintana, Temecula, CA (US)

(73) Assignee: Biora Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/319,800

(22) Filed: May 13, 2021

(65) Prior Publication Data
US 2021/0283385 A1 Sep. 16, 2021

Related U.S. Application Data

(63) Continuation of application No. 17/024,176, filed on Sep. 17, 2020, now Pat. No. 11,007,356, which is a
(Continued)

(51) Int. Cl.
*A61M 31/00* (2006.01)

(52) U.S. Cl.
CPC ..... *A61M 31/002* (2013.01); *A61M 2210/106* (2013.01); *A61M 2210/1042* (2013.01); *A61M 2210/1064* (2013.01)

(58) Field of Classification Search
CPC ............... A61M 31/00; A61M 31/003; A61M 2210/1042; A61M 2210/106;
(Continued)

(56) References Cited

U.S. PATENT DOCUMENTS

| 3,057,344 A | 10/1962 | Alberto et al. |
| 3,118,439 A | 1/1964 | Perrenoud |

(Continued)

FOREIGN PATENT DOCUMENTS

| CA | 2139822 | 7/1995 |
| CA | 2347274 | 4/2000 |

(Continued)

OTHER PUBLICATIONS

Wang, Xing-Chun. "Effects of Glucagon-like Peptide-1 Receptor Agonists on Non-Alcoholic Fatty Liver Disease and Inflammation." World Journal of Gastroenterology, vol. 20, No. 40, Oct. 28, 2014, p. 14821., doi:10.3748/wjg.v20.i40.14821. (Year: 2014).*

(Continued)

*Primary Examiner* — James D Ponton
(74) *Attorney, Agent, or Firm* — Perkins Coie LLP

(57) ABSTRACT

A method of treating a disease or condition in a subject in need thereof is disclosed. The method comprising: transepithelially administering a dispensable substance to the gastrointestinal (GI) tract of the subject by orally administering an ingestible device comprising the dispensable substance to the subject. The ingestible device is configured for trans-epithelial delivery of the dispensable substance to the GI tract of the subject and the dispensable substance comprises a pharmaceutical formulation comprising a therapeu-
(Continued)

tically effective amount of a glucagon receptor agonist or a glucagon-like peptide-1 (GLP-1) receptor agonist. The ingestible device releases the dispensable substance as at least one jet to a desired location of the GI tract of the subject.

24 Claims, 73 Drawing Sheets

Specification includes a Sequence Listing.

Related U.S. Application Data continuation of application No. PCT/US2019/062193, filed on Nov. 19, 2019.

(60) Provisional application No. 62/932,459, filed on Nov. 7, 2019, provisional application No. 62/819,513, filed on Mar. 15, 2019, provisional application No. 62/818,731, filed on Mar. 14, 2019, provisional application No. 62/769,496, filed on Nov. 19, 2018.

(58) Field of Classification Search
CPC ........ A61M 2210/1064; A61M 31/002; A61B 5/073; A61B 2010/0061
See application file for complete search history.

(56) References Cited

U.S. PATENT DOCUMENTS

| | | | |
|---|---|---|---|
| 3,315,660 A | 4/1967 | Abella | |
| 3,485,235 A | 12/1969 | Felson | |
| 4,036,214 A | 7/1977 | Bucalo | |
| 4,172,446 A | 10/1979 | Bucalo | |
| 4,223,680 A | 9/1980 | Jobsis | |
| 4,239,040 A | 12/1980 | Hosoya et al. | |
| 4,292,961 A | 10/1981 | Kawashima | |
| 4,425,117 A | 1/1984 | Hugeman | |
| 4,481,952 A | 11/1984 | Pawelec | |
| 4,507,115 A | 3/1985 | Kambara | |
| 4,522,625 A | 6/1985 | Edgren | |
| 4,573,447 A | 3/1986 | Thrash et al. | |
| 4,844,076 A | 7/1989 | Lesho | |
| 5,167,626 A | 12/1992 | Casper et al. | |
| 5,170,801 A | 12/1992 | Casper et al. | |
| 5,279,607 A | 1/1994 | Schentag | |
| 5,316,015 A | 5/1994 | Sinaiko | |
| 5,318,557 A | 6/1994 | Gross | |
| 5,395,366 A | 3/1995 | Andrea | |
| 5,604,531 A | 2/1997 | Iddan et al. | |
| 5,738,110 A | 4/1998 | Beal et al. | |
| 5,858,001 A | 1/1999 | Tsais et al. | |
| 5,951,538 A | 9/1999 | Joshi | |
| 5,971,942 A | 10/1999 | Gu et al. | |
| 6,344,027 B1 | 2/2002 | Goll | |
| 6,344,028 B1 | 2/2002 | Barty | |
| 6,369,039 B1 | 4/2002 | Palasis et al. | |
| 6,576,429 B1 | 6/2003 | Hallgren | |
| 6,632,216 B2 | 10/2003 | Houzego | |
| 6,836,377 B1 | 12/2004 | Kislev et al. | |
| 6,934,093 B2 | 8/2005 | Kislev et al. | |
| 7,056,673 B2 | 6/2006 | Kamme et al. | |
| 7,144,366 B2 | 12/2006 | Takizawa et al. | |
| 7,160,258 B2 | 1/2007 | Imran et al. | |
| 7,347,817 B2 | 3/2008 | Glukhovsky et al. | |
| 7,433,133 B2 | 10/2008 | Kislev et al. | |
| 7,460,896 B2 | 12/2008 | Iddan | |
| 7,553,276 B2 | 6/2009 | Iddan | |
| 7,611,480 B2 | 11/2009 | Levy | |
| 7,643,865 B2 | 1/2010 | Iddan et al. | |
| 7,647,090 B1 | 1/2010 | Frisch et al. | |
| 7,662,093 B2 | 2/2010 | Gilad et al. | |
| 7,662,094 B2 | 2/2010 | Iddan | |
| 7,684,840 B2 | 3/2010 | Palti | |
| 7,763,014 B2 | 7/2010 | Houzeao et al. | |
| 7,796,043 B2 | 9/2010 | Euliano et al. | |
| 7,797,033 B2 | 9/2010 | D'Andrea et al. | |
| 7,801,584 B2 | 9/2010 | Iddan et al. | |
| 7,813,789 B2 | 10/2010 | Glukhovsky | |
| 7,821,564 B2 | 10/2010 | Avron et al. | |
| 7,824,347 B2 | 11/2010 | Imran et al. | |
| 7,857,767 B2 | 12/2010 | Ferren et al. | |
| 7,938,775 B2 | 5/2011 | Rabinovitz et al. | |
| 7,946,979 B2 | 5/2011 | Gilad et al. | |
| 7,998,065 B2 | 8/2011 | Avni | |
| 8,000,784 B2 | 8/2011 | Ferren et al. | |
| 8,005,536 B2 | 8/2011 | Imran | |
| 8,185,185 B2 | 5/2012 | Gilreath | |
| 8,206,285 B2 | 6/2012 | Blijevsky | |
| 8,216,130 B2 | 6/2012 | Glukhovsky et al. | |
| 8,213,698 B2 | 7/2012 | Wang | |
| 8,262,566 B2 | 9/2012 | Gilad et al. | |
| 8,360,976 B2 | 1/2013 | Imran | |
| 8,394,034 B2 | 3/2013 | Iddan | |
| 8,491,495 B1 | 7/2013 | Shuck | |
| 8,500,630 B2 | 8/2013 | Gilad et al. | |
| 8,512,219 B2 | 8/2013 | Ferren et al. | |
| 8,540,623 B2 | 9/2013 | Blijevsky | |
| 8,626,268 B2 | 1/2014 | Adler | |
| 8,659,696 B2 | 2/2014 | Avron et al. | |
| 8,660,642 B2 | 2/2014 | Ferren et al. | |
| 8,696,602 B2 | 4/2014 | Semler et al. | |
| 8,809,271 B2 | 8/2014 | Imran | |
| 8,911,368 B2 | 12/2014 | Rabinovitz et al. | |
| 8,915,863 B2 | 12/2014 | Shuck | |
| 8,926,526 B2 | 1/2015 | Shuck | |
| 8,956,281 B2 | 2/2015 | Wilson | |
| 9,026,192 B2 | 5/2015 | Blit et al. | |
| 9,131,842 B2 | 9/2015 | Old | |
| 9,324,145 B1 | 4/2016 | Cherevatsky | |
| 9,511,121 B2 | 12/2016 | Imran | |
| 10,172,598 B2 | 1/2019 | Amoako-Tuffour et al. | |
| 10,588,608 B2 | 3/2020 | Jones et al. | |
| 11,007,356 B2 | 5/2021 | Shimizu et al. | |
| 2002/0099310 A1* | 7/2002 | Kimchy | A61B 6/425 600/587 |
| 2003/0139661 A1 | 7/2003 | Kimchy | |
| 2003/0191430 A1 | 10/2003 | Andrea et al. | |
| 2004/0162469 A1 | 8/2004 | Imran | |
| 2004/0199054 A1 | 10/2004 | Wakefield et al. | |
| 2004/0253304 A1 | 12/2004 | Gross et al. | |
| 2004/0254455 A1 | 12/2004 | Iddan | |
| 2005/0010168 A1 | 1/2005 | Kendal | |
| 2005/0049462 A1 | 3/2005 | Kanazawa | |
| 2005/0065441 A1 | 3/2005 | Glukhovsky | |
| 2005/0154277 A1 | 7/2005 | Tang et al. | |
| 2005/0158246 A1 | 7/2005 | Takizawa et al. | |
| 2005/0266074 A1 | 12/2005 | Zilberstein et al. | |
| 2006/0069317 A1 | 3/2006 | Horn et al. | |
| 2006/0178557 A1 | 8/2006 | Mintchev | |
| 2007/0027362 A1 | 2/2007 | Handa | |
| 2007/0043320 A1 | 2/2007 | Kenany | |
| 2007/0092401 A1 | 4/2007 | Liao et al. | |
| 2007/0122488 A1 | 5/2007 | Windhab | |
| 2007/0161928 A1 | 7/2007 | Sprenkels | |
| 2007/0173738 A1 | 7/2007 | Stoltz | |
| 2007/0293736 A1 | 12/2007 | Casset | |
| 2008/0027329 A1 | 1/2008 | Glukhovsky | |
| 2008/0033569 A1 | 2/2008 | Ferren et al. | |
| 2008/0051633 A1 | 2/2008 | Blijevsky | |
| 2008/0114224 A1 | 5/2008 | Bandy | |
| 2008/0146896 A1 | 6/2008 | Rabinowitz et al. | |
| 2008/0194912 A1 | 8/2008 | Trovato | |
| 2008/0208077 A1 | 8/2008 | Iddan et al. | |
| 2008/0234548 A1 | 9/2008 | Amit | |
| 2008/0294023 A1 | 11/2008 | Rabinovitz et al. | |
| 2009/0124872 A1 | 5/2009 | Uchiyama et al. | |
| 2009/0131784 A1 | 5/2009 | Betesh | |
| 2009/0275923 A1 | 11/2009 | Shimizu et al. | |
| 2010/0045786 A1 | 2/2010 | Kitamura | |
| 2010/0049012 A1 | 2/2010 | Dijksman | |
| 2010/0063486 A1 | 3/2010 | Dijksman et al. | |
| 2010/0111763 A1 | 5/2010 | Kahn et al. | |

(56) References Cited

U.S. PATENT DOCUMENTS

| | | |
|---|---|---|
| 2010/0285475 A1 | 11/2010 | Palanisamy et al. |
| 2010/0303200 A1 | 12/2010 | Kimchy et al. |
| 2010/0324381 A1 | 12/2010 | Glukhovsky et al. |
| 2011/0046458 A1 | 2/2011 | Pinedo |
| 2011/0092959 A1 | 4/2011 | Zou et al. |
| 2011/0106063 A1 | 5/2011 | Dijksman et al. |
| 2011/0125007 A1 | 5/2011 | Steinberg |
| 2011/0125031 A1 | 5/2011 | Blit et al. |
| 2011/0156799 A1 | 6/2011 | Zanardi |
| 2011/0275880 A1 | 11/2011 | Ferren et al. |
| 2011/0306055 A1 | 12/2011 | Haince |
| 2011/0313348 A1 | 12/2011 | Potter et al. |
| 2012/0136209 A1 | 5/2012 | Kostenich et al. |
| 2012/0208755 A1* | 8/2012 | Leung ............... C07K 14/605 |
| | | 514/11.7 |
| 2012/0258473 A1 | 10/2012 | Moriya et al. |
| 2013/0013031 A1 | 1/2013 | Ben-Yehuda et al. |
| 2013/0018279 A1 | 1/2013 | Plante et al. |
| 2013/0022983 A1 | 1/2013 | Grifantini |
| 2013/0085414 A1 | 4/2013 | Yamatani |
| 2013/0158344 A1 | 6/2013 | Taniguchi |
| 2014/0113313 A1 | 4/2014 | Moreau |
| 2014/0128833 A1 | 5/2014 | Vogt |
| 2014/0206956 A1 | 7/2014 | Rabinovitz et al. |
| 2014/0296666 A1 | 10/2014 | Rabinovitz et al. |
| 2014/0343451 A1 | 11/2014 | Pannell |
| 2015/0011874 A1 | 1/2015 | Amoako-Tuffour et al. |
| 2015/0057548 A1 | 2/2015 | Kaufman |
| 2016/0033373 A1 | 2/2016 | Hill et al. |
| 2016/0038086 A1 | 2/2016 | Wrigglesworth |
| 2016/0066855 A1 | 3/2016 | Hyde |
| 2016/0114142 A1 | 4/2016 | Ziaie |
| 2016/0213234 A1 | 7/2016 | Poon |
| 2016/0249793 A1 | 9/2016 | Wang |
| 2017/0006202 A1 | 1/2017 | Otani |
| 2017/0106099 A1 | 4/2017 | Bellinger |
| 2017/0246438 A1* | 8/2017 | Aran ............... A61K 39/0005 |
| 2017/0258583 A1 | 9/2017 | McCawley |
| 2017/0296092 A1 | 10/2017 | Jones et al. |
| 2018/0049725 A1 | 2/2018 | Jones et al. |
| 2018/0052084 A1 | 2/2018 | Jones et al. |
| 2018/0070857 A1 | 3/2018 | Jones et al. |
| 2018/0160950 A1 | 6/2018 | Rabinovitz et al. |
| 2018/0279908 A1 | 10/2018 | Jones et al. |
| 2019/0083073 A1 | 3/2019 | Amoako-Tuffour et al. |
| 2019/0388502 A1* | 12/2019 | Corvari ............... A61K 38/16 |
| 2020/0245897 A1 | 8/2020 | Jones et al. |
| 2020/0308268 A1 | 10/2020 | Imran |
| 2021/0038872 A1 | 2/2021 | Shimizu et al. |

FOREIGN PATENT DOCUMENTS

| | | |
|---|---|---|
| CA | 2390153 | 6/2001 |
| CA | 2451807 | 1/2003 |
| CA | 2616010 | 2/2007 |
| CN | 103209632 | 7/2013 |
| DE | 19801573 | 7/1999 |
| EP | 108607 | 2/1983 |
| EP | 0662304 | 1/1996 |
| EP | 1243524 | 9/2002 |
| EP | 1530950 | 5/2005 |
| EP | 1861007 | 7/2006 |
| EP | 1954197 | 5/2007 |
| EP | 1868487 | 12/2007 |
| EP | 1932462 | 6/2008 |
| EP | 2057934 | 5/2009 |
| EP | 2117104 | 11/2009 |
| EP | 3108810 | 12/2016 |
| EP | 2515992 | 10/2018 |
| GB | 993734 | 6/1965 |
| JP | 53049880 | 5/1978 |
| JP | 2005073888 | 3/2005 |
| JP | 2013500815 | 1/2013 |
| JP | 2015509744 | 4/2015 |
| KR | 100931946 | 12/2009 |
| SE | 101738 | 6/1941 |
| WO | WO 1979/00811 | 10/1979 |
| WO | WO 1999/044066 | 9/1999 |
| WO | WO 2001/045552 | 6/2001 |
| WO | WO 2001/45789 | 6/2001 |
| WO | WO 2002/102243 | 12/2002 |
| WO | WO 2004/14227 | 2/2004 |
| WO | WO 2004/59568 | 7/2004 |
| WO | WO 2004/64636 | 8/2004 |
| WO | WO 2004/066903 | 8/2004 |
| WO | WO 2005/46485 | 5/2005 |
| WO | WO 2006/077530 | 7/2006 |
| WO | WO 2006/103684 | 10/2006 |
| WO | WO 2007/013952 | 2/2007 |
| WO | WO 2007/045859 | 4/2007 |
| WO | WO 2007/061305 | 5/2007 |
| WO | WO 2008/053396 | 5/2008 |
| WO | 2009104110 A1 | 8/2009 |
| WO | WO 2009/154707 | 12/2009 |
| WO | WO 2010/091926 | 8/2010 |
| WO | WO 2010/146588 | 12/2010 |
| WO | WO 2011/016002 | 2/2011 |
| WO | WO 2013/003 824 | 1/2013 |
| WO | WO 2013/088444 | 6/2013 |
| WO | WO 2013/120184 | 8/2013 |
| WO | WO 2015/059569 | 4/2015 |
| WO | WO 2015/099749 | 7/2015 |
| WO | WO 2015/147305 | 10/2015 |
| WO | WO 2016/054015 | 4/2016 |
| WO | WO 2017/004000 | 1/2017 |
| WO | WO 2016/049602 | 3/2018 |
| WO | WO 2018/050647 | 3/2018 |
| WO | WO 2018/183934 | 10/2018 |
| WO | 2018213588 A1 | 11/2018 |
| WO | 2020041774 A1 | 2/2020 |
| WO | 2020157324 A1 | 8/2020 |
| WO | 2020160399 A1 | 8/2020 |

OTHER PUBLICATIONS

Marso, Steven P et al. "Semaglutide and Cardiovascular Outcomes in Patients with Type 2 Diabetes." The New England Journal of Medicine, Nov. 10, 2016. (Year: 2016).*
Ambery P, Parker et al. "MEDI0382, a GLP-1 and glucagon receptor dual agonist, in obese or overweight patients with type 2 diabetes: a randomised, controlled, double-blind, ascending dose and phase 2a study". Lancet. Jun. 30, 2018 (Year: 2018).*
Trietley et al.—"Albiglutide (Tanzeum) for Diabetes Mellitus", STEPS, New Drug Reviews, Apr. 15, 2017 (Year: 2017).*
[No Author Listed], " 11 RU 86FG 3MR1—Enteric Film Coating for Bile Intake Capsules Technology Collaboration Request," Enterprise Europe Network in Yorkshire, Apr. 10, 2011, 1 page.
[No Author Listed], "MotiliGI Software Product Overview," The SmartPill Corporation, 2010, 1 page.
[No Author Listed], "pH.p Capsule Operational Specifications," The SmartPill Corporation, 2003, 1 page.
[No Author Listed], "Redefining Capsule Endoscopy," Brochure, Olympus, Created Oct. 25, 2007, 4 pages.
[No Author Listed], "SmartPill: The data you need to evaluate motility disorders," The SmartPill Corporation, 2009, 6 pages.
Anselmo et al., "Non-invasive delivery strategies for biologies," Nat Rev Drug Discov, 2019, 18(1): 19-40.
Aran et al., "An oral microjet vaccination system elicits antibody production in rabbits," Sci. Transl. Med., 2017, 9(380):eaaf6413, 10 pages.
Bao et al., "Motion estimation of the endoscopy capsule using region-based kernel SVM classifier," IEEE International. Conf. Electro-Information Technol., EIT, 2013, 5 pages.
Barolet et al., "Current trends in needle-free jet injection: an update," Clinical Cosmetic and Investigational Dermatology, 2018, 11:231-238.
Battula et al., "A Miniature Shock Wave Driven Micro-Jet Injector for Needle-Free Vaccine/Drug Delivery," Biotechnology and Bioengineering, 2016, 113(11):2507-2512.

(56) References Cited

OTHER PUBLICATIONS

Boquete et al., "Dynamically Programmable Electronic Pill Dispenser System," J. Med. Sys., 2010, 34:357-366.
Charbonneau, "Ingestible Medical Devices," NRG CNRC, Feb. 9, 2009, 6 pages.
Chen et al., "Developing assessment system for wireless capsule endoscopy videos based on event detection," Proceedings of SPIE, 2009, 7260:72601G-1, 22 pages.
Dingle et al., "Stable and Noncompetitive RNA Internal Control for Routine Clinical Diagnostic Reverse Transcription-PCR," Journal of Clinical Microbiology, Mar. 2004, 42(3): 1003-1011.
Hunter et al., "Aerosol delivery of Virus-like Particles to the genital tract induces local and systemic antibody responses," Vaccine, 2011, 29(28):4584-4592.
Iverson et al., "An innate antiviral pathway acting before interferons at epithelial surfaces," Nature Immunology, 2016, 17(2): 150-158.
Jacques, "Optical properties of biological tissues: a review," Phys. Med. Biol,, 2013, 58(11):R37-61.
Kale et al., "Needle free injection technology—An overview," Innovations in Pharmacy, 2014, 5(1):148, 9 pages.
Kane et al., "Fecal Lactoferrin Is a Sensitive and Specific Marker in Identifying Intestinal Inflammation," The American Journal of Gastroenterology, 2003, 98(6): 1309-1314.
Kostic et al., "The Gut Microbiome and Disease," Gastroenterology, 2014, 146(6):1489-1499.
Lambert et al., "Autonomous telemetric capsule to explore the small bowel," Med Biol Eng Comput, 1991, 29(2):191-196.
Lee et al., "Automatic Classification of Digestive Organs in Wireless Capsule Endoscopy Videos," Proceedings of the 2007 ACM Symposium on Applied Computing, 2007, pp. 1041-1045.
Lehmann et al., "The role and utility of faecal markers in inflammatory bowel disease," Therapeutic Advances in Gastroenterology, 2015, 8(1):23-36.
Li et al., "Outlier detection and removal improves accuracy of machine learning approach to multispectral burn diagnostic imaging," J. Biomed. Opt., 2015, 20(12): 121305-1-121305-9.
Lo et al., "The use of carbon dioxide in gastrointestinal endoscopy," Gastrointestinal Endoscopy, 2016, 83(5):857-865.
PCT International Search Report and Written Opinion in International Application No. PCT/US2017/050642, dated Jan. 29, 2018, 24 pages.
PCT International Search Report and Written Opinion in International Appln. No. PCT/US2019/062193, dated Apr. 30, 2020, 21 pages.
PCT International Search Report and Written Opinion in International Appln. No. PCT/US2019/062261, dated Mar. 31, 2020, 16 pages.
PCT International Search Report and Written Opinion in International Appln. No. PCT/US2019/062266, dated Mar. 31, 2020, 16 pages.
PCT International Search Report and Written Opinion in International Appln. No. PCT/US2019/062270, dated Mar. 31, 2020, 16 pages.
PCT International Search Report in International Appln. No. PCT/CA2013/000133, dated Jun. 12, 2013, 5 pages.
PCT Invitation to Pay Additional Fees in International Appln. No. PCT/US2019/062193, dated Apr. 21, 2020, 15 pages.
PCT Invitation to Pay Additional Fees in International Appln. No. PCT/US2019/062261, dated Feb. 28, 2020, 11 pages.
PCT Invitation to Pay Additional Fees in International Appln. No. PCT/US2019/062266, dated Feb. 28, 2020, 11 pages.
PCT Invitation to Pay Additional Fees in International Appln. No. PCT/US2019/062270, dated Feb. 28, 2020, 11 pages.
Quirini et al., "Design of a Pill-Sized 12-legged Endoscopic Capsule Robot," 2007 IEEE International Conference on Robotics and Automation, Roma, Italy, Apr. 10-14, 2007, pp. 1856-1862.
Sanschagrin et al., "Next-generation Sequencing of 16S Ribosomal RNA Gene Amplicons," Journal of Visualized Experiments, Aug. 2014, 90:51709, 6 pages.
Sartor et al., "Intestinal Microbes in Inflammatory Bowel Diseases," The American Journal of Gastroenterology Supplements, 2012, 1(1): 12-21.
Susilo et al., "A Miniaturized Wireless Control Platform for Robotic Capsular Endoscopy Using Advanced Pseudokemel Approach," Sensors and Actuators A: Physical, 2009, 156(1):49-58.
Tan et al., "Design of Accelerometer-Based Inertial Navigation Systems," IEEE Transactions on Instrumentation and Measurement, Dec. 2005, 54(6):2520-2530.
Toennies et al., "Swallowable medical devices for diagnosis and surgery: the state of the art," Proceedings of the Institution of Mechanical Engineers, Part C: Journal of Mechanical Engineering Science, 2009, 224(7): 1397-1414.
Tortora et al., "Propeller-based wireless device for active capsular endoscopy in the gastric district," Minimally Invasive Therapy & Allied Technologies, 2009, 18:280-290.
Valdastri et al., "Transmission Power Requirements for Novel ZigBee Implants in the Gastrointestinal Tract," IEEE Transactions on Biomedical Engineering, Jun. 2008, 55(6): 1705-1710.
Wright et al., "Recent Advances in Characterizing the Gastrointestinal Microbiome in Crohn's Disease: A Systematic Review," Inflammatory Bowel Disease Journal, 2015, 21(6): 1219-1228.
Aran et al., "An oral microjet vaccination system elicits antibody production in rabbits", Science Translation Medicine, Mar. 8, 2017, pp. 1-9.
Moroz, Elena, Simon Matoori, and Jean-Christophe Leroux. "Oral delivery of macromolecular drugs: Where we are after almost 100 years of attempts." Advanced drug delivery reviews 101 (2016): 108-121.
Caffarel-Salvador, Ester, et al. "Oral delivery of biologies using drug-device combinations." Current opinion in pharmacology 36 (2017): 8-13.

\* cited by examiner

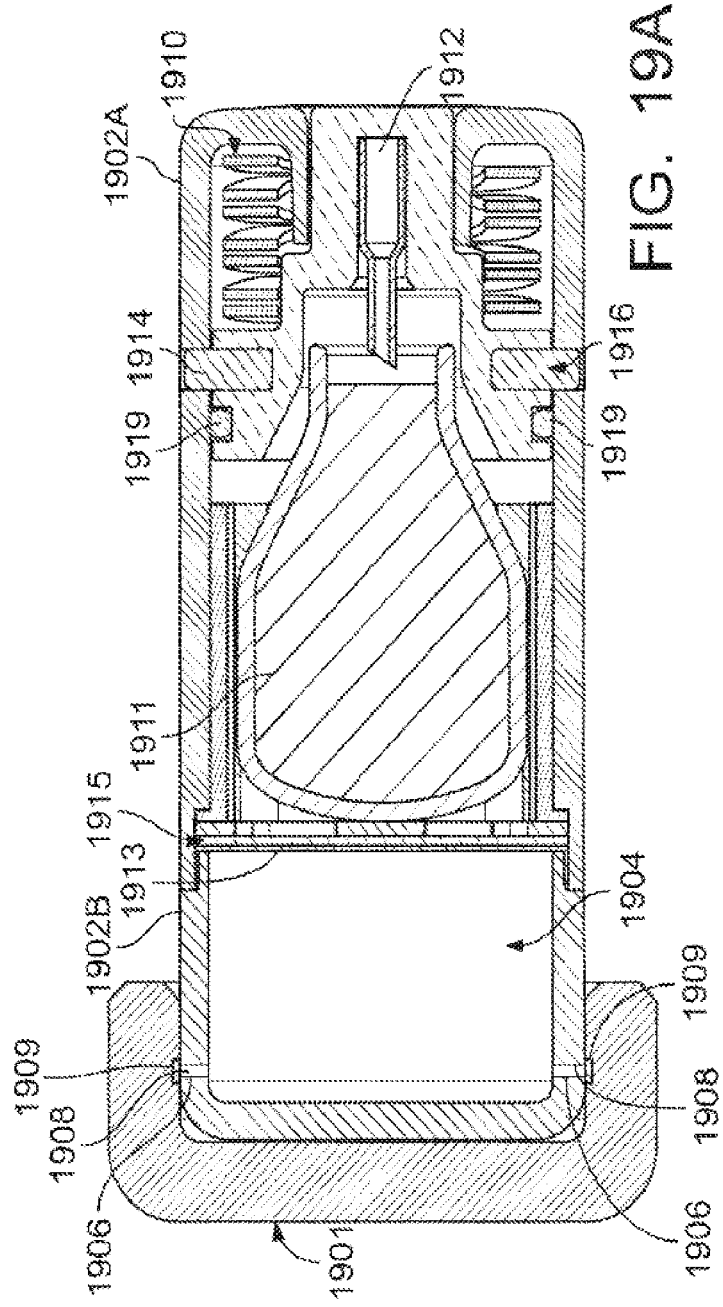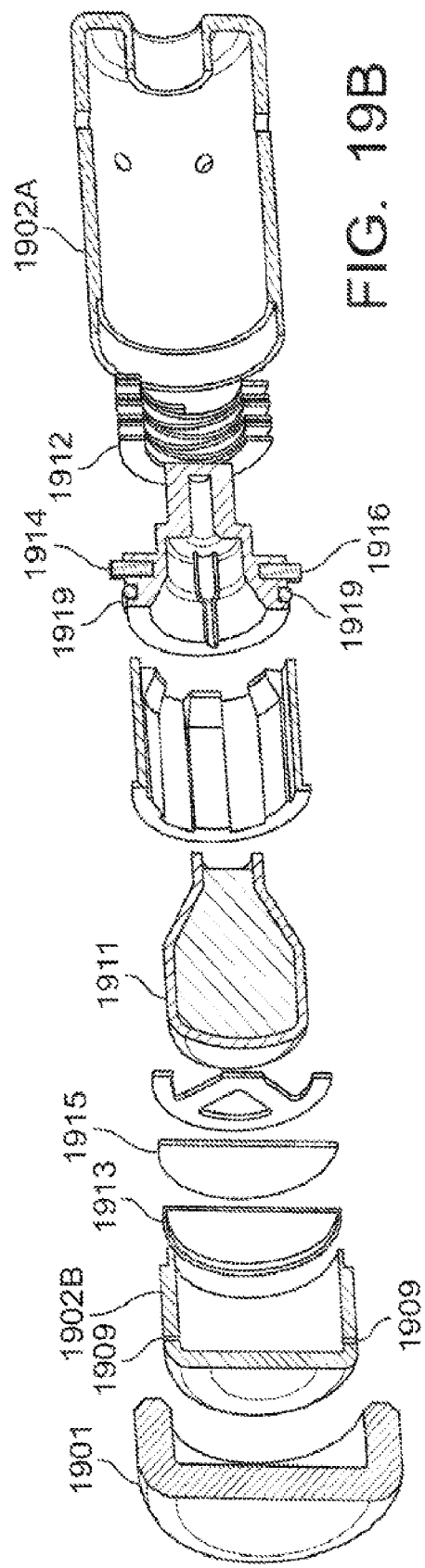
FIG. 19A
FIG. 19B

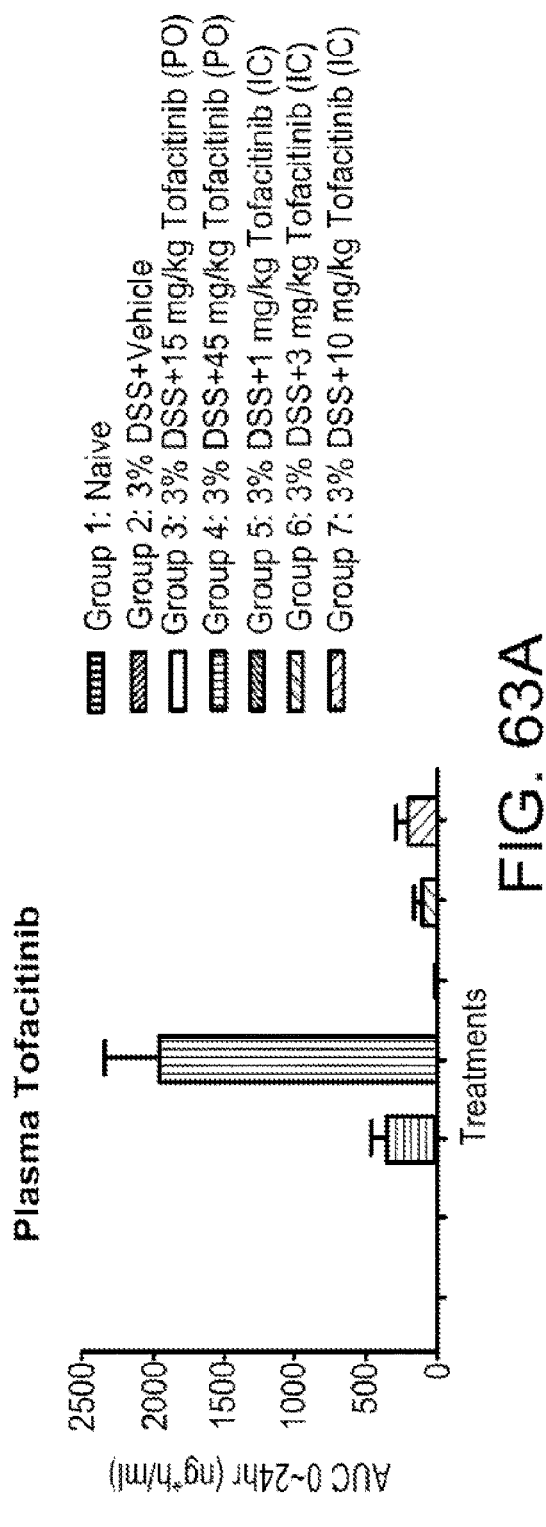
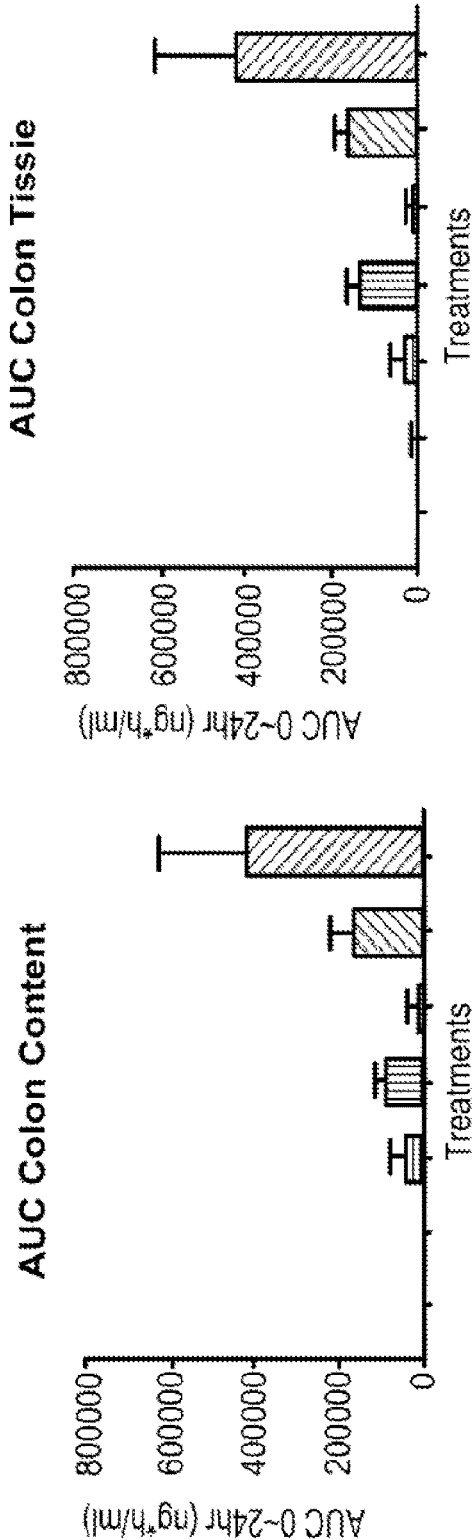
FIG. 63A
FIG. 63B
FIG. 63C

Anti-TNFαIC
(IHC: CD4+)

Anti-TNFαIP
(IHC: CD4+)

INGESTIBLE DEVICE FOR DELIVERY OF THERAPEUTIC AGENT TO THE GASTROINTESTINAL TRACT

RELATED APPLICATIONS

This application claims the benefit of the following patent applications:

U.S. Ser. No. 17/024,176, filed Sep. 17, 2020, and entitled "Ingestible Device for Delivery of Therapeutic Agent to the Gastrointestinal Tract";

PCT/US2019/062193, filed Nov. 19, 2019, and entitled "Ingestible Device for Delivery of Therapeutic Agent to the Gastrointestinal Tract";

U.S. Ser. No. 62/769,496, filed Nov. 19, 2018, and entitled "Ingestible Device With High Pressure Substance Delivery to the Gastrointestinal Tract";

U.S. Ser. No. 62/818,731, filed Mar. 14, 2019, and entitled "Ingestible Device With High Pressure Substance Delivery to the Gastrointestinal Tract";

U.S. Ser. No. 62/819,513, filed Mar. 15, 2019, and entitled "Ingestible Device With High Pressure Substance Delivery to the Gastrointestinal Tract"; and U.S. Ser. No. 62/932,459, filed Nov. 7, 2019, and entitled "Ingestible Device and Method of Use to Deliver Therapeutic Agent to the Gastrointestinal Tract."

The entire disclosure of each of these applications is incorporated by reference in its entirety.

INCORPORATION BY REFERENCE OF SEQUENCE LISTING FILED ELECTRONICALLY

An electronic version of the Sequence Listing is filed herewith, the contents of which are incorporated by reference in their entirety. The electronic file was created on May 12, 2021 and is 967 bytes and is titled 44090-0107002_SEQ.txt.

FIELD

The disclosure generally relates to ingestible devices capable of delivering a dispensable substance, such as a therapeutic agent, as well as related components, systems and methods.

BACKGROUND

The gastrointestinal (GI) tract generally provides a therapeutic medium for an individual's body. At times, it is desirable to dispense therapeutic agents to the GI tract to treat a medical condition.

SUMMARY

The disclosure provides ingestible devices that can directly deliver therapeutic agents to desired tissue(s) of the GI tract of a subject, such as the submucosa, the mucosa, and/or the mucus layer of the GI tract, and methods of using the same. The ingestible devices can deliver therapeutic agents in a safe, effective, and reliable manner. The disclosure also provides pharmaceutical compositions for use in methods of treating a disease or condition in a subject in need thereof.

Ingestible devices of the present disclosure are configured to provide at least three different modes of direct delivery of therapeutic agents to the GI tract of a subject, referred to herein as trans-epithelial, epithelial, and topical delivery. Direct delivery, as used herein, refers to a force-driven delivery mechanism.

Thus, in one aspect, this disclosure relates to trans-epithelial delivery of a therapeutic agent to the GI tract of a subject. Accordingly, the disclosure provides an ingestible device that can directly deliver a therapeutic agent past the epithelial cell layer of the mucosa of the GI tract of a subject to yield systemic exposure of the therapeutic agent to the subject. In such embodiments, the ingestible device is configured to directly deliver the therapeutic agent past the epithelial cell layer of the mucosa and into the submucosa and/or into a region of the mucosa beneath the epithelial layer (e.g., into the lamina propria) of the GI tract, where it is available for systemic uptake. This can be particularly relevant when the oral bioavailability of the therapeutic agent is otherwise low. In some embodiments, systemic exposure of the therapeutic agent is achieved by trans-epithelial delivery of the therapeutic agent into the submucosa and/or into a region of the mucosa beneath the epithelial layer (e.g., into the lamina propria) of the small intestine, for example, in the duodenum, the jejunum, and/or the ileum. In further embodiments, the trans-epithelial delivery directly delivers the therapeutic agent into the submucosa and/or into a region of the mucosa beneath the epithelial layer (e.g., into the lamina propria) of the GI tract such that the percent systemic uptake of the trans-epithelial delivery relative to intravenous or subcutaneous administration is at least about 10% (e.g., at least about 15%, at least about 20%, at least about 25% or more).

Without wishing to be bound by theory, it is believed that trans-epithelial delivery to the submucosa and/or into a region of the mucosa beneath the epithelial layer (e.g., into the lamina propria) of the GI tract is achieved by using an appropriate value for one or more performance parameters associated with the ingestible device configured for such use. Such performance parameters include, for example, internal pressure of the ingestible device, peak fluid pressure of the ingestible device, nozzle pressure of the ingestible device, peak jet power of the dispensable substance (e.g., a pharmaceutical formulation containing the therapeutic agent) delivered from the ingestible device, peak jet velocity of the dispensable substance (e.g., a pharmaceutical formulation containing the therapeutic agent) delivered from the ingestible device, peak jet pressure of the dispensable substance (e.g., a pharmaceutical formulation containing the therapeutic agent) delivered from the ingestible device, peak jet force of the dispensable substance (e.g., a pharmaceutical formulation containing the therapeutic agent) delivered from the ingestible device, peak jet stable length of the dispensable substance (e.g., a pharmaceutical formulation containing the therapeutic agent) delivered from the ingestible device, nozzle shape, nozzle length and nozzle diameter.

As an example, in some embodiments, the ingestible device is configured for trans-epithelial delivery and may provide/exhibit one or more of the following properties. The ingestible device is configured to deliver the dispensable substance to tissue of the GI tract of a subject at a peak jet power of from about one Watt to about three Watts. The ingestible device has a drive force generator that provides an internal pressure of from about 225 psig to about 400 psig. The ingestible device contains the dispensable substance at a peak fluid pressure of from about 200 psig to about 375 psig. The ingestible device is configured to deliver the dispensable substance at a peak jet velocity of from about 25 meters per second to about 45 meters per second. The ingestible device is configured to deliver the dispensable substance as a jet having jet stable length of at least about one millimeter. The ingestible device is configured to deliver the dispensable substance to tissue of the GI tract of a subject at a peak jet pressure of from about 100 psig to about 250 psig. The ingestible device is configured to deliver the dispensable substance to tissue of the GI tract of a subject at a peak jet force of from about 0.09 N to about 0.15 N. The ingestible device has one or more nozzles, each having a diameter of from about 0.1 millimeter to about two millimeters and/or a length of from about one millimeter to about five millimeters.

In another aspect, this disclosure relates to epithelial delivery of a therapeutic agent to the GI tract of a subject. Accordingly, the disclosure provides an ingestible device configured to directly deliver the therapeutic agent into the mucus and/or onto the epithelial layer, but not past the epithelial layer of the mucosa, of the small or large intestine, from which it can act locally, and in some cases away from the site of direct delivery. In some embodiments, the device is configured so that the therapeutic agent is delivered from the device with sufficient force to provide the epithelial delivery, the force being lower than that required for trans-epithelial delivery.

In yet another aspect, this disclosure relates to topical delivery of a therapeutic agent to the GI tract of a subject. Accordingly, the disclosure provides an ingestible device configured to deliver the therapeutic agent into the lumen and/or onto the mucus or other surface of the GI tract facing the lumen of the small or large intestine, from which it can act locally, and in some cases away from the site of delivery. In some embodiments, the device is configured so that the therapeutic agent is delivered from the device with sufficient force so that the therapeutic agent is delivered topically, the force being lower than that required for the epithelial or the trans-epithelial delivery.

The ingestible device, whether configured for trans-epithelial, epithelial or topical delivery, can have a streamlined and/or relatively simple mechanical design, be relatively small, and/or be inexpensive to manufacture. In general, the device protects a dispensable substance (e.g., a therapeutic agent, or a pharmaceutical formulation comprising the therapeutic agent) until the device reaches a desired location of the subject. As an example, the device can be designed to deliver dispensable substance to a desired location in the GI tract of a subject, and the device can be designed so that the dispensable substance is not subject to constituents of the GI tract (e.g., acids, enzymes) prior to reaching the desired location in the GI tract. As another example, the device can be designed to deliver dispensable substance such that the therapeutic properties of the dispensable substance are not altered during delivery (e.g., the dispensable substance is a therapeutic agent that binds its therapeutic target after delivery).

The present disclosure provides ingestible devices that can directly deliver therapeutic agents to desired tissue(s) of the GI tract of a subject (such as the submucosa, the mucosa, and/or the mucus layer of the GI tract), e.g., to treat a particular class of disease, or a specific disease. Relatedly, methods of using the device to deliver the therapeutic agents to desired tissue(s) of the GI tract, e.g., to treat a particular class of disease, or a specific disease, are disclosed. These disclosures also inherently provide disclosures of corresponding medical uses—that is, disclosures of the recited therapeutic agents for use in a method of treating the recited class of disease, or specific disease, by using the device to deliver the recited agents to desired tissue(s) of the GI tract of a subject.

First Group of Aspects of the Disclosure

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to directly deliver the dispensable substance to the GI tract of a subject via trans-epithelial delivery. The ingestible device may be configured to directly deliver the dispensable substance into the lamina propria of the GI tract of the subject, and/or the ingestible device may be to directly deliver the dispensable substance into the submucosa of the GI tract of the subject.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance to tissue of the GI tract of a subject as a jet with a peak jet power of from about one Watt to about three Watts. The peak jet power may be from about 1.3 Watts to about 2.8 Watts, from about 1.5 Watts to about 2.5 Watts, or about 2.3 Watts.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to provide an internal pressure of from about 225 psig to about 425 psig. The internal pressure may be from about 250 psig to about 400 psig, or from about 300 psig to about 375 psig.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to contain the dispensable substance at a peak fluid pressure of from about 200 psig to about 400 psig.

The ingestible device may be configured to deliver the dispensable substance at a mean jet velocity of from about 25 m/s to about 35 m/s.

The ingestible device may be configured to contain the dispensable substance at a peak fluid pressure of: from about 200 psig to about 375 psig; at least about 220 psig; from about 220 psig to about 375 psig; from about 220 psig to about 350 psig; at least about 225 psig; from about 225 psig to about 375 psig; from about 225 psig to about 350 psig; from about 225 psig to about 325 psig; at least about 250 psig; from about 250 psig to about 375 psig; from about 250 psig to about 350 psig; from about 250 psig to about 325 psig; at least about 275 psig; from about 275 psig to about 375 psig; from about 275 psig to about 350 psig; from about 275 psig to about 325 psig; from about 280 psig to about 320 psig; at least about 300 psig; from about 300 psig to about 375 psig; from about 300 psig to about 350 psig; from about 300 psig to about 325 psig; about 200 psig; about 210 psig; about 220 psig; about 230 psig; about 240 psig; about 250 psig; about 260 psig; about 270 psig; about 280 psig; about 290 psig; about 300 psig; about 310 psig; or about 320 psig.

The ingestible device may be configured to deliver the dispensable substance at a mean jet velocity of from about 20 m/s to about 30 m/s, from about 25 m/s to about 30 m/s, or from about 27 m/s to about 30 m/s or from about 28 m/s to about 30 m/s.

The opening in the ingestible device may comprise a nozzle opening having a diameter of from about 0.1 mm to about 2 mm, from about 0.1 mm to about 1 mm, from about 0.2 mm to about 0.8 mm, from about 0.3 mm to about 0.5 mm, from about 0.3 mm to about 0.4 mm, or about 0.35 mm.

The ingestible device may be 1 to 5 nozzles, 2 to 4 nozzles or 2 nozzles.

The ingestible device may be configured to release a dispensable substance volume ranging from about 50 microliters to about 500 microliters, from about 100 microliters to about 450 microliters, from about 200 microliters to about 400 microliters, from 250 microliters to about 400 microliters, or from about 300 microliters to about 400 microliters.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to contain the dispensable substance at a peak fluid pressure of from about 150 psig to about 350 psig. The ingestible device may be configured to deliver the dispensable substance at a mean jet velocity of from about 20 m/s to about 30 m/s, about 20 m/s, 21 m/s, 22 m/s 23 m/s, 24 m/s, 25 m/s, 26 m/s, 27 m/s, 28 m/s, 29 m/s or 30 m/s.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance at a peak jet velocity of from about 25 meters per second to about 45 meters per second. The peak jet velocity may be from about 30 meters per second to about 42 meters per second, or from about 34 meters per second to about 39 meters per second.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance as a jet having jet stable length of at least about 0.5 millimeter. The jet stable length may be from 0.5 millimeter to 20 millimeters, from about 2 millimeters to 20 millimeters, or from about 5 millimeters to 20 millimeters.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance to tissue of the GI tract of a subject at a peak jet pressure of from about 100 psig to about 250 psig. The peak jet pressure may be from about 140 psig to about 225 psig, or from about 180 psig to about 205 psig.

In a general aspect, the disclosure provides an ingestible device, comprising: a housing configured to contain a dispensable substance comprising a therapeutic agent; and an opening in the housing configured to fluidly connect the dispensable substance to an environment outside the housing via the opening, wherein the ingestible device is configured to deliver the dispensable substance to tissue of the GI tract of a subject at a peak jet force of from about 0.09 N to about 0.15 N. The ingestible device may be configured to deliver the dispensable substance to tissue of the GI tract of a subject at a peak jet force of from about 0.1 N to about 0.14 N, or from about 0.11 N to about 0.14 N.

The ingestible device may comprises a nozzle, and the opening may comprise a nozzle opening. The nozzle may have a nozzle diameter of from about 0.1 millimeter to about two millimeters, and/or a nozzle length of from about one millimeter to about five millimeters.

The ingestible device may comprise a plurality of nozzles. The nozzles may be directed perpendicular to a longitudinal axis of the ingestible device. The nozzles may be uniformly distributed relative to a circumference of the ingestible device. The plurality of nozzles may comprise an even number of nozzles or an odd number of nozzles. The plurality of nozzles comprises two nozzles.

The ingestible device may be configured to deliver from about 20 microliters to about 800 microliters of the dispensable substance through each nozzle.

The ingestible device may further include the dispensable substance, wherein the dispensable substance comprises a fluid. The ingestible device may further include the dispensable substance, wherein the dispensable substance comprises a fluid. The dispensable substance may comprise a therapeutic agent. The dispensable substance may comprise a solution. The dispensable substance may comprise a suspension. The dispensable substance may have a viscosity of less than or equal to 10 cP. The dispensable substance may have a viscosity of at least about 0.8 cP. The dispensable substance may a viscosity of at most about 8 cP or at most about 9 cP.

The jet may have an average jet diameter of from about 0.1 millimeter to about two millimeters.

The jet may have a jet stable length of at least about 0.5 millimeter.

The ingestible device may contain from about 50 microliters to about 800 microliters of the dispensable substance.

The ingestible device may be configured to deliver from about 50 microliters to about 800 microliters of the dispensable substance.

The ingestible device may further comprise a drive force generator configured to apply a force to the dispensable substance to force the dispensable substance out of the ingestible device via the opening. The drive force generator may comprise a member selected from the group consisting of a spring, a gas cell, a compressed gas, and a liquid-gas mixture. The ingestible device may comprise chemicals configured to react to provide a gas as the drive force generator. The drive force generator may be configured to provide an internal pressure of from about 225 psig to about 400 psig.

The ingestible device may further comprise a drive coupling configured to transfer force from the drive force generator to the dispensable substance. The drive coupling may comprise a member selected from the group consisting of a piston and a membrane.

The ingestible device may further comprise a restraining mechanism having a first state and a second state, wherein, when the restraining mechanism is in its first state, the restraining mechanism prevents the dispensable substance from being delivered out of the ingestible device. In some embodiments, when the restraining mechanism is in its second state, the restraining mechanism does not prevent the dispensable substance from being delivered out of the ingestible device. The ingestible device may be configured so that, when the restraining mechanism is in its first state, the drive force generator does not apply an internal pressure to the dispensable substance. The ingestible device may be configured so that, when the restraining mechanism is in its first state, the drive force generator applies an internal pressure to the dispensable substance. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a dowel, a clasp, a clamp, a flange, and a rivet. The restraining mechanism may comprise a cap. The cap may be located at a distal end of the ingestible device.

The ingestible device may be configured to directly deliver the dispensable substance to the GI tract of a subject via trans-epithelial delivery.

The ingestible device may be configured to deliver the dispensable substance to tissue of the GI tract of a subject as a jet with a peak jet power of from about one Watt to about three Watts.

The ingestible device may be configured to provide an internal pressure of from about 225 psig to about 425 psig.

The ingestible device may be configured to contain the dispensable substance at a peak fluid pressure of from about 200 psig to about 375 psig.

The ingestible device may be configured to contain the dispensable substance at a peak fluid pressure of from about 150 psig to about 350 psig.

The ingestible device may be configured to deliver the dispensable substance at a peak jet velocity of from about 25 meters per second to about 45 meters per second.

The ingestible device may be configured to deliver the dispensable substance as a jet having jet stable length of at least about 0.5 millimeter.

The ingestible device may be configured to deliver the dispensable substance at a peak jet pressure of from about 100 psig to about 250 psig.

The ingestible device may be configured to deliver the dispensable substance to tissue of the GI tract of a subject at a peak jet force of from about 0.09 N to about 0.15.

The housing has a length of from about 20 mm to about 28 mm.

The housing may have a diameter of from about 7 mm to about 12 mm.

The housing may comprise a wall having a wall thickness of from about 0.5 mm to about 1 mm.

A ratio of the length of the housing to the width of the housing may be selected from the group consisting of: from about 0.75 to about 4; from about 1 to about 3; and from about 1 to about 2.

In some embodiments, at least one of the following holds: the housing comprises end regions that are spline-shaped; the housing comprises end regions that are spherical; the housing comprises an end round of from about 1 mm to about 2 mm; the housing comprises an end round of from about 4 mm to about 4.5 mm; the housing comprises an end round that is from about 4.9 to about 5 mm; and the housing comprises an end round of from about 5.4 mm to about 5.6 mm.

The housing may have an internal volume of from about 700 μL to about 1700 μL.

The housing may have a fluid volume from about 50 μL to about 800 μL.

In a general aspect, the disclosure provides an ingestible device, comprising: a housing; an opening in the housing configured to fluidly connect the dispensable substance to an environment outside the housing via the opening; a drive force generator configured to provide a force to the dispensable substance to deliver the dispensable substance through the opening; a drive force coupling configured to transfer the force from the drive force generator to the dispensable substance; and a restraining mechanism having a first state in which the restraining mechanism prevents the dispensable substance from being delivered out of the ingestible device.

The drive force generator may comprise a member selected from the group consisting of a spring, a gas cell, a compressed gas, and a liquid-gas mixture. The ingestible device may comprise chemicals configured to react to provide a gas as the drive force generator. The drive force generator may be configured to provide an internal pressure of from about 225 psig to about 400 psig.

The drive coupling may comprise a member selected from the group consisting of a piston and a membrane.

In some embodiments, when the restraining mechanism is in its first state, the drive force generator does not apply an internal pressure to the dispensable substance. In certain embodiments, when the restraining mechanism is in its first state, the drive force generator applies an internal pressure to the dispensable substance. The restraining mechanism may have second state different from its first state, and, when the restraining mechanism is in its second state, the restraining mechanism does not prevent the dispensable substance from being delivered out of the ingestible device. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a band, a dowel, a clasp, a clamp, a flange, and a rivet. The restraining mechanism may comprise a cap. The cap may be located at a distal end of the ingestible device.

The housing may have a length of from about 20 mm to about 28 mm, from about 21 mm to about 27 mm, about 26 mm, or about 23.3 mm.

The housing may have a diameter of from about 7 mm to about 12 mm, from about 8 mm to about 11 mm, about 11 mm, about 9.9 mm, or about 8.5 mm.

A ratio of the length of the housing to the width of the housing may be from about 0.75 to about 4, from about 1 to about 3, or from about 1 to about 2.

The housing may comprise a wall having a wall thickness of from about 0.5 mm to about 1 mm, from about 0.6 mm to about 0.9 mm, about 0.8 mm, or about 0.7 m.

The housing may have end regions that are spline-shaped or that are spherical.

The housing may comprise an end round of from about 1 mm to about 2 mm, about 1.5 mm, from about 4 mm to about 4.5 mm, about 4.25 mm, from about 4.9 to about 5 mm, about 4.95 mm, from about 5.4 mm to about 5.6 mm, or about 5.5 mm.

The housing may comprise an internal volume of from about 700 μL to about 1700 μL, from about 750 μL to about 1650 μL, from about 800 μL to about 1600 μL, or from about 850 μL to about 1550 μL.

The housing may comprise a fluid volume of from about 50 μL to about 800 μL, from about 100 μL to about 600 μL, or from about 200 μL to about 400 μL.

The ingestible device may comprise a plurality of openings in the housing configured to fluidly connect the dispensable substance to an environment outside the housing via the opening. The plurality of openings may comprise an even number of openings or an odd number of openings. The plurality of openings may comprise a member selected from group consisting of 2 openings, 3 openings, 4 openings, 5 openings, 6 openings, 7 openings and 8 openings. Each opening may comprise a nozzle opening.

The opening may comprise a nozzle opening having a diameter from about 0.1 mm to about 2 mm, from about 0.1 mm to about 1 mm, from about 0.2 mm to about 0.8 mm, or from about 0.3 mm to about 0.4 mm.

The ingestible device may comprise a nozzle having a length of from about 1 mm to about 5 mm, from about 2 mm to about 5 mm, or from about 3 mm to about 5 mm.

The ingestible device may comprise a plurality of openings in the housing configured to fluidly connect the dispensable substance to an environment outside the housing via the opening, and the ingestible device is configured to provide a delivered fluid volume per opening for delivery of dispensable substance of from about 25 µL to about 400 µL.

The ingestible device may comprise a plurality of openings in the housing configured to fluidly connect the dispensable substance to an environment outside the housing via the opening, and the ingestible device is configured to provide a delivered fluid volume per opening for delivery of dispensable substance of from about 25 µL to about 300 µL.

The ingestible device may comprise a plurality of openings in the housing configured to fluidly connect the dispensable substance to an environment outside the housing via the opening, and the ingestible device may be configured to provide a delivered fluid volume per opening for delivery of dispensable substance of from about 100 µL to about 300 µL.

The ingestible device may further comprise the dispensable substance. The dispensable substance may comprise a fluid. The dispensable substance may comprise a liquid. The dispensable substance may comprise a therapeutic agent. The dispensable substance may comprise a solution. The dispensable substance may comprise a suspension.

The ingestible device may be configured to directly deliver the dispensable substance to the GI tract of a subject via trans-epithelial delivery.

The ingestible device may be configured to deliver the dispensable substance to tissue of the GI tract of a subject as a jet with a peak jet power of from about one Watt to about three Watts.

The ingestible device may be configured to ingestible device is configured to provide an internal pressure of from about 225 psig to about 425 psig.

The ingestible device may be configured to contain the dispensable substance at a peak fluid pressure of from about 200 psig to about 375 psig.

The ingestible device may be configured to deliver the dispensable substance at a peak jet velocity of from about 25 meters per second to about 45 meters per second.

The ingestible device may be configured to deliver the dispensable substance as a jet having jet stable length of at least about 0.5 millimeter.

The ingestible device may be configured to deliver the dispensable substance at a peak jet pressure of from about 100 psig to about 250 psig.

The ingestible device may be configured to deliver the dispensable substance to tissue of the GI tract of a subject at a peak jet force of from about 0.09 N to about 0.15.

In a general aspect, the disclosure provides an ingestible device, comprising: a housing configured to contain a dispensable substance comprising a therapeutic agent, wherein the dispensable substance is a fluid; and an opening in the housing configured to fluidly connect the dispensable substance to an environment outside the housing via the opening, wherein the ingestible device is configured for trans-epithelial delivery of the dispensable subject to the GI tract of a subject as a jet.

The ingestible device may be configured to provide an internal pressure of from about 220 psig to about 420 psig. The ingestible device may be configured to contain the dispensable substance at a peak fluid pressure of from about 200 psig to about 400 psig.

The ingestible device may be configured to provide an internal pressure of from about 220 psig to about 395 psig. The ingestible device may be configured to contain the dispensable substance at a peak fluid pressure of from about 200 psig to about 375 psig.

The ingestible device may be configured to provide an internal pressure of from about 220 psig to about 350 psig. The ingestible device may be configured to contain the dispensable substance at a peak fluid pressure of from about 200 psig to about 330 psig.

The ingestible device may be configured to provide an internal pressure of from about 225 psig to about 400 psig. The ingestible device may be configured to contain the dispensable substance at a peak fluid pressure of from about 205 psig to about 380 psig.

The ingestible device may be configured to provide an internal pressure of from about 230 psig to about 370 psig. The ingestible device may be configured to contain the dispensable substance at a peak fluid pressure of from about 210 psig to about 350 psig.

The ingestible device may be configured to provide an internal pressure of from about 240 psig to about 370 psig. The ingestible device may be configured to contain the dispensable substance at a peak fluid pressure of from about 220 psig to about 350 psig.

The ingestible device may be configured to provide an internal pressure of from about 250 psig to about 375 psig. The ingestible device may be configured to contain the dispensable substance at a peak fluid pressure of from about 230 psig to about 355 psig.

The ingestible device may be configured to provide an internal pressure of from about 250 psig to about 350 psig. The ingestible device may be configured to contain the dispensable substance at a peak fluid pressure of from about 230 psig to about 330 psig.

The ingestible device may be configured to provide an internal pressure of from about 270 psig to about 370 psig. The ingestible device may be configured to contain the dispensable substance at a peak fluid pressure of from about 250 psig to about 350 psig.

The ingestible device may be configured to provide an internal pressure of from about 270 psig to about 350 psig. The ingestible device may be configured to contain the dispensable substance at a peak fluid pressure of from about 250 psig to about 330 psig.

The ingestible device may be configured to provide an internal pressure of from about 300 psig to about 340 psig. The ingestible device may be configured to contain the dispensable substance at a peak fluid pressure of from about 280 psig to about 320 psig.

The ingestible device may be configured to provide an internal pressure of from about 310 psig to about 340 psig. The ingestible device may be configured to contain the dispensable substance at a peak fluid pressure of from about 290 psig to about 320 psig.

The ingestible device may be configured to provide an internal pressure of from about 320 psig to about 340 psig.

The ingestible device may be configured to contain the dispensable substance at a peak fluid pressure of from about 300 psig to about 320 psig.

The ingestible device may be configured to provide an internal pressure of about 220 psig, about 230 psig, about 240 psig, about 250 psig, about 260 psig, about 270 psig, about 280 psig, about 290 psig, about 300 psig, about 310 psig, about 320 psig, about 330 psig, about 340 psig or about 350 psig. The ingestible device may be configured to contain the dispensable substance at a peak fluid pressure of about 200 psig, about 210 psig, about 220 psig, about 230 psig, about 240 psig, about 250 psig, about 260 psig, about 270 psig, about 280 psig, about 290 psig, about 300 psig, about 310 psig, about 320 psig or about 330 psig.

The ingestible device may be configured to deliver the dispensable substance as the jet with a peak jet velocity of from about 25 m/s to about 45 m/s, from about 25 m/s to about 40 m/s, from about 30 m/s to about 40 m/s, from about 32 m/s to about 40 m/s, or from about 35 m/s to about 40 m/s.

The ingestible device may be configured to deliver the dispensable substance to the GI tract of the subject as the jet with a peak jet power of from about 1 Watt to about 3 Watts. The ingestible device may be configured to contain the dispensable substance as the jet with a peak fluid pressure of from about 200 psig to about 375 psig. The ingestible device may be configured to deliver the dispensable substance to the GI tract of the subject as the jet with a peak jet pressure of from about 100 psig to about 250 psig, or with a peak jet force of from about 0.09 N to about 0.15 N.

The ingestible device of claim 191 or claim 194, wherein the ingestible device is configured may be configured to deliver the dispensable substance to the GI tract of the subject as the jet with a peak jet power of from about 1.3 Watts to about 2.8 Watts. The ingestible device may be configured to contain the dispensable substance as the jet with a peak fluid pressure of from about 220 psig to about 350 psig. The ingestible device may be configured to deliver the dispensable substance to the GI tract of the subject as the jet with a peak jet pressure of from about 140 psig to about 225 psig, or with a peak jet force of from about 0.1 N to about 0.14 N.

The ingestible device o may be configured to deliver the dispensable substance to the GI tract of the subject as the jet with a peak jet power of from about 1.5 Watts to about 2.5 Watts. The ingestible device may be configured to contain the dispensable substance as the jet with a peak fluid pressure of from about 280 psig to about 320 psig. The ingestible device may be configured to deliver the dispensable substance to the GI tract of the subject as the jet with a peak jet pressure of from about 180 psig to about 205 psig, or with a peak jet force of from about 0.11 N to about 0.14 N.

In some embodiments, the ingestible device may be configured to deliver the dispensable substance as the jet with a mean jet velocity of from about 18 m/s to about 30 m/s, from about 19 m/s to about 30 m/s, from about 20 m/s to about 30 m/s, from about 21 m/s to about 30 m/s, from about 22 m/s to about 30 m/s, from about 23 m/s to about 30 m/s, from about 24 m/s to about 30 m/s, from about 25 m/s to about 30 m/s, from about 25 m/s to about 28 m/s, about 20 m/s, 21 m/s, 22 m/s 23 m/s, 24 m/s, 25 m/s, 26 m/s, 27 m/s, 28 m/s, 29 m/s or 30 m/s.

In certain embodiments, the ingestible device may be configured to deliver the dispensable substance as the jet with a mean jet velocity of from about 25 m/s to about 35 m/s.

In some embodiments: the opening in the housing is a plurality of openings, each opening comprising a nozzle, or the opening in the housing comprises a plurality of nozzles; and each nozzle has an orifice to fluidly connect the dispensable substance to the environment outside the housing and to release the dispensable substance from the ingestible device as a jet. Each nozzle orifice may be directed perpendicular to a longitudinal axis of the ingestible device. Each nozzle orifice may have a diameter of from about 0.1 mm to about 2 mm, each jet when dispensed from each nozzle orifice has a diameter of from about 0.1 mm to about 2 mm, or both. Each nozzle orifice may have a diameter of from about 0.1 mm to about 1 mm, each jet when dispensed from each nozzle orifice has a diameter of from about 0.1 mm to about 1 mm, or both. Each nozzle orifice may have a diameter of from about 0.2 mm to about 0.8 mm, each jet when dispensed from each nozzle has a diameter of from about 0.2 mm to about 0.8 mm, or both. Each nozzle orifice may have a diameter of from about 0.3 mm to about 0.5 mm, each jet when dispensed from each nozzle may have a diameter of from about 0.3 mm to about 0.5 mm, or both. Each nozzle orifice may have a diameter of from about 0.3 mm to about 0.4 mm, each jet when dispensed from each nozzle may have a diameter of from about 0.3 mm to about 0.4 mm, or both. Each nozzle orifice may have a diameter of about 0.35 mm, each jet when dispensed from each nozzle may have a diameter of about 0.35 mm, or both.

The ingestible device may be configured to deliver the dispensable substance as the jet with a jet stable length of at least about 0.5 mm.

The ingestible device may be configured to deliver the dispensable substance as the jet with a jet stable length of from about 0.5 mm to about 20 mm.

The ingestible device may be configured to deliver the dispensable substance as the jet with a jet stable length of from about 2 mm to about 20 mm.

The ingestible device may be configured to deliver the dispensable substance as the jet with a jet stable length of from about 5 mm to about 20 mm.

The ingestible device may comprise at least two nozzles, and the at least two nozzles may be uniformly distributed relative to a circumference of the ingestible device.

The ingestible device may comprise an even number of nozzles or an odd number of nozzles.

The ingestible device may comprise 2 nozzles, 3 nozzles, 4 nozzles, 5 nozzles, 6 nozzles, 7 nozzles or 8 nozzles.

Each nozzle may have a length of from about 0.5 mm to about 5 mm, about 1 mm to about 5 mm, about 2 mm to about 5 mm, or about 3 mm to about 5 mm. Each nozzle may have a length of from about 1 mm to about 4 mm.

Each nozzle may have a length of from about 1 mm to about 3 mm.

The ingestible device may be configured to release a dispensable substance volume ranging from about 50 microliters to about 800 microliters, about 50 microliters to about 500 microliters, from about 100 microliters to about 450 microliters, from about 200 microliters to about 400 microliters, from 250 microliters to about 400 microliters, or from about 300 microliters to about 400 microliters.

The ingestible device may be configured to release a dispensable substance volume ranging from about 200 microliters to about 400 microliters.

The ingestible device may comprise: a drive force generator configured to provide a force to the dispensable substance to deliver the dispensable substance through the opening or nozzle orifice; a drive force coupling configured to transfer the force from the drive force generator to the dispensable substance; and a restraining mechanism having a first state in which the restraining mechanism prevents the dispensable substance from being delivered out of the ingestible device; and a second state in which the restraining mechanism does not prevent the dispensable substance from being delivered out of the ingestible device.

In some embodiments, when the restraining mechanism is in its first state, the drive force generator does not apply an internal pressure to the dispensable substance.

In certain embodiments, when the restraining mechanism is in its first state, the drive force generator applies an internal pressure to the dispensable substance.

The drive force generator may comprise a member selected from the group consisting of a spring, a gas cell, a compressed gas, and a liquid-gas mixture.

The ingestible device may comprise chemicals configured to react to provide a gas as the drive force generator.

The drive force generator may be configured to provide the internal pressure.

The drive coupling may comprise a member selected from the group consisting of a piston and a membrane.

The restraining mechanism may have second state different from its first state, and, when the restraining mechanism is in its second state, the restraining mechanism does not prevent the dispensable substance from being delivered out of the ingestible device. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a band, a dowel, a clasp, a clamp, a flange, and a rivet. The restraining mechanism may comprise a cap. The cap may be located at a distal end of the ingestible device.

The housing may have a length of from about 20 mm to about 28 mm, from about 21 mm to about 27 mm, about 26 mm, or about 23.3 mm.

The housing may have a diameter of from about 7 mm to about 12 mm, from about 8 mm to about 11 mm, about 11 mm, about 9.9 mm, or about 8.5 mm.

The housing may comprise a wall having a wall thickness of from about 0.5 mm to about 1 mm, from about 0.6 mm to about 0.9 mm, about 0.8 mm, or about 0.7 mm.

The housing may have end regions that are spline-shaped or that are spherical.

The housing may have an end round of from about 1 mm to about 2 mm, about 1.5 mm, from about 4 mm to about 4.5 mm, about 4.25 mm, from about 4.9 to about 5 mm, about 4.95 mm, from about 5.4 mm to about 5.6 mm, or about 5.5 mm.

In some embodiments, at least one of the following holds: the housing has end regions that are spline-shaped; the housing has end regions that are spherical; the housing has an end round of from about 1 mm to about 2 mm; the housing has an end round of from about 4 mm to about 4.5 mm; the housing has an end round that is from about 4.9 to about 5 mm; and the housing has an end round of from about 5.4 mm to about 5.6 mm. The housing may have an internal volume of from about 700 microliters to about 1700 microliters, from about 750 microliters to about 1650 microliters, from about 800 microliters to about 1600 microliters, or from about 850 microliters to about 1550 microliters.

The ingestible device may have a fluid volume from about 50 microliters to about 800 microliters, from about 100 microliters to about 600 microliters, or from about 200 microliters to about 400 microliters.

The ingestible device may be configured to deliver from about 20 microliters to about 800 microliters of the dispensable substance through each opening or nozzle orifice, from about 25 microliters to about 400 microliters of the dispensable substance through each opening or nozzle orifice, from about 25 microliters to about 300 microliters of the dispensable substance through each opening or nozzle orifice, or from about 100 microliters to about 300 microliters of the dispensable substance through each nozzle.

A ratio of the length of the housing to the width of the housing may be from about 0.75 to about 4, from about 1 to about 3, or from about 1 to about 2.

The ingestible device may be configured as a 00 capsule.

The ingestible device may be configured as a 000 capsule.

In a general aspect, the disclosure provides a method, comprising: using an ingestible device to deliver a dispensable substance to the GI tract of the subject.

In a general aspect, the disclosure provides a method, comprising: using an ingestible device to directly deliver a dispensable substance to the GI tract of a subject via trans-epithelial delivery. The method may comprise using the ingestible device to directly deliver the dispensable substance into the lamina propria of the GI tract of the subject, and/or using the ingestible device to directly deliver the dispensable substance into the submucosa of the GI tract of the subject.

In a general aspect, the disclosure provides a method, comprising: using an ingestible device to directly deliver a dispensable substance to tissue of the GI tract of a subject as a jet with a peak jet power of from about one Watt to about three Watts. The peak jet power may be from about 1.3 Watts to about 2.8 Watts, from about 1.5 Watts to about 2.5 Watts, or about 2.3 Watts.

In a general aspect, the disclosure provides a method, comprising: using an ingestible device to deliver a dispensable substance to the GI tract of a subject as a jet having a peak jet velocity of from about 25 meters per second to about 45 meters per second. The peak jet velocity may of the jet be from about 30 meters per second to about 42 meters per second, or from about 34 meters per second to about 39 meters per second.

In a general aspect, the disclosure provides a method, comprising: using an ingestible device to deliver a dispensable substance to the GI tract of a subject as a jet having a jet stable length of at least about 0.5 millimeter. The jet may have jet stable length of from 0.5 millimeter to 20 millimeters, from about 2 millimeters to 20 millimeters, or from about 5 millimeters to 20 millimeters.

In a general aspect, the disclosure provides a method, comprising: using an ingestible device to deliver a dispensable substance to the GI tract of a subject as a jet having a peak jet pressure of from about 100 psig to about 250 psig. The peak jet pressure may be from about 140 psig to about 225 psig, or from about 180 psig to about 205 psig.

In a general aspect, the disclosure provides a method, comprising: using an ingestible device to deliver a dispensable substance to the GI tract of a subject as a jet having a peak jet force of from about 0.09 N to about 0.15 N. The peak jet force may be from about 0.1 N to about 0.14 N, or from about 0.11 N to about 0.14 N. In such methods, the dispensable substance may have a viscosity of less than or equal to 10 cP, at least about 0.8 cP, at most about 8 cP, and/or or at most about 9 cP. In such methods, the device may be configured as a 00 capsule, or the device may be configured as a 000 capsule.

Second Group of General Aspects of the Disclosure

In a general aspect, the disclosure provides an ingestible device, comprising: a housing; an opening in the housing configured to fluidly connect the dispensable substance to an environment outside the housing via the opening; a drive force generator configured to provide a force to the dispensable substance to deliver the dispensable substance through the opening; a drive force coupling configured to transfer the force from the drive force generator to the dispensable substance; and a restraining mechanism having a first state in which the restraining mechanism prevents the dispensable substance from being delivered out of the ingestible device, wherein at least one of the following holds: the drive force generator is configured to provide an internal pressure of from about 3.62 psig to about 21.76 psig; and the housing comprises at least 25 openings configured to fluidly connect the dispensable substance to an environment outside the housing via the opening.

The drive force generator may comprise a member selected from the group consisting of a spring, a gas cell, a compressed gas, and a liquid-gas mixture. The ingestible device may comprise chemicals configured to react to provide a gas as the drive force generator. The drive force generator may be to provide an internal pressure of from about 3.62 psig to about 21.76 psig.

The drive coupling may comprise a member selected from the group consisting of a piston and a membrane.

In some embodiments, when the restraining mechanism is in its first state, the drive force generator does not apply an internal pressure to the dispensable substance. In certain embodiments, when the restraining mechanism is in its first state, the drive force generator applies an internal pressure to the dispensable substance. The restraining mechanism may have a second state different from its first state, and, when the restraining mechanism is in its second state, the restraining mechanism does not prevent the dispensable substance from being delivered out of the ingestible device. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a band, a dowel, a clasp, a clamp, a flange, and a rivet. The restraining mechanism may comprise a cap. The cap may be located at a distal end of the ingestible device.

The housing may have a length of from about 20 mm to about 28 mm. from about 21 mm to about 27 mm, about 26 mm or about 23.3 mm.

The housing may have a diameter of from about 7 mm to about 12 mm, from about 8 mm to about 11 mm, about 11 mm, about 9.9 mm, or about 8.5 mm.

A ratio of the length of the housing to the width of the housing may be from about 0.75 to about 4, from about 1 to about 3, or from about 1 to about 2.

The housing may comprise a wall having a wall thickness of from about 0.5 mm to about 1 mm, from about 0.6 mm to about 0.9 mm, about 0.8 mm, or about 0.7 mm.

The housing may comprise end regions that are spline-shaped or end regions that are spherical.

The housing may comprise an end round of from about 1 mm to about 2 mm, about 1.5 mm, from about 4 mm to about 4.5 mm, about 4.25 mm, from about 4.9 to about 5 mm, about 4.95 mm, from about 5.4 mm to about 5.6 mm, or about 5.5 mm.

The housing may comprise an internal volume of from about 700 µL to about 1700 L, from about 750 µL to about 1650 µL, from about 800 µL to about 1600 µL, or from about 850 µL to about 1550 µL.

The housing may comprise a fluid volume from about 50 µL to about 800 µL, from about 100 µL to about 600 µL, or from about 200 µL to about 400 µL.

The ingestible may comprise a plurality of openings in the housing configured to fluidly connect the dispensable substance to an environment outside the housing via the opening. The plurality of openings may comprise an even number of openings or an odd number of openings. The plurality of openings may at least 25 openings, and/or the plurality of openings may comprise at most 50 openings. Each opening may comprise a nozzle opening.

The opening may comprise a nozzle opening having a diameter from about 1 mm to about 3 mm, at least about 1.5 mm, at least about 2 mm, and/or at most about 2.5 mm.

The ingestible device may comprise a nozzle having a length of from about 1 mm to about 5 mm, from about 2 mm to about 5 mm, or from about 3 mm to about 5 mm.

The ingestible may comprise a plurality of openings in the housing configured to fluidly connect the dispensable substance to an environment outside the housing via the opening, and the ingestible device is configured to provide a delivered fluid volume per opening for delivery of dispensable substance of from about 25 µL to about 400 µL.

The ingestible device may comprise a plurality of openings in the housing configured to fluidly connect the dispensable substance to an environment outside the housing via the opening, and the ingestible device is configured to provide a delivered fluid volume per opening for delivery of dispensable substance of from about 25 µL to about 300 µL.

The may comprise a plurality of openings in the housing configured to fluidly connect the dispensable substance to an environment outside the housing via the opening, and the ingestible device is configured to provide a delivered fluid volume per opening for delivery of dispensable substance of from about 100 µL to about 300 µL.

The ingestible may further comprise the dispensable substance. The dispensable substance may comprise a fluid. The dispensable substance may comprise a liquid. The dispensable substance may comprise a therapeutic agent. The dispensable substance may comprise a solution. The dispensable substance may comprise a suspension. The dispensable substance may have a viscosity of less than or equal to 10 cP, of at least about 0.8 cP, of at most about 8 cP, and/or at most about 9 cP.

The ingestible may be configured to directly deliver the dispensable substance to the GI tract of a subject via epithelial delivery.

The ingestible device may be configured to deliver the dispensable substance to tissue of the GI tract of a subject as a jet with a peak jet power of from about 1 mW to about 4 mW.

The ingestible d may be configured to contain the dispensable substance at a peak fluid pressure of from about 3.62 psig to about 21.76 psig.

The ingestible device may be configured to deliver the dispensable substance as a jet having a peak jet velocity of from about 2 meters per second to about 20 meters per second.

The ingestible device may be configured to deliver the dispensable substance as a jet having a peak jet pressure of from about 2 psig to about 10 psig.

The ingestible device o may be configured to deliver the dispensable substance to tissue of the GI tract of a subject as a jet having a peak jet force of from about 0.05 mN to about 2 mN.

The ingestible device configured as a 00 capsule.

The ingestible device may be configured as a 000 capsule.

In a general aspect, the disclosure provides a method, comprising: using an ingestible device to directly deliver a dispensable substance to the GI tract of a subject via epithelial delivery.

In a general aspect, the disclosure provides a method, comprising: using an ingestible device to directly deliver a dispensable substance to tissue of the GI tract of a subject as a jet with a peak jet power of from about 1 mW to about 4 mW.

In a general aspect, the disclosure provides a method, comprising: using an ingestible device to deliver a dispensable substance to the GI tract of a subject as a jet having a peak jet velocity of from about 2 meters per second to about 20 meters per second.

In a general aspect, the disclosure provides a method, comprising: using an ingestible device to deliver a dispensable substance to the GI tract of a subject as a jet having a peak jet force of from about 0.05 mN to about 2 mN.

In a general aspect, the disclosure provides a method, comprising: using an ingestible device to directly deliver a dispensable substance to the GI tract of a subject via epithelial delivery, wherein the ingestible device comprises: a housing; an opening in the housing configured to fluidly connect the dispensable substance to an environment outside the housing via the opening; a drive force generator configured to provide a force to the dispensable substance to deliver the dispensable substance through the opening; a drive force coupling configured to transfer the force from the drive force generator to the dispensable substance; and a restraining mechanism having a first state in which the restraining mechanism prevents the dispensable substance from being delivered out of the ingestible device.

The drive force generator may comprise a member selected from the group consisting of a spring, a gas cell, a compressed gas, and a liquid-gas mixture. The ingestible device may comprise chemicals configured to react to provide a gas as the drive force generator.

The drive coupling may comprise a member selected from the group consisting of a piston and a membrane.

In some embodiments, when the restraining mechanism is in its first state, the drive force generator does not apply an internal pressure to the dispensable substance. In certain embodiments, when the restraining mechanism is in its first state, the drive force generator applies an internal pressure to the dispensable substance. The restraining mechanism may have second state different from its first state, and, when the restraining mechanism is in its second state, the restraining mechanism does not prevent the dispensable substance from being delivered out of the ingestible device. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a band, a dowel, a clasp, a clamp, a flange, and a rivet. The restraining mechanism may comprise a cap. The cap may be located at a distal end of the ingestible device.

The housing may have a length of from about 20 mm to about 28 mm, from about 21 mm to about 27 mm, about 26 mm, or about 23.3 mm.

The housing may have a diameter of from about 7 mm to about 12 mm, from about 8 mm to about 11 mm, about 11 mm, about 9.9 mm, or about 8.5 mm.

The housing may comprise a wall having a wall thickness of from about 0.5 mm to about 1 mm, from about 0.6 mm to about 0.9 mm, about 0.8 mm, about 0.7 mm.

The housing may comprise end regions that are spline-shaped or that are spherical.

The housing may comprise an end round of from about 1 mm to about 2 mm, about 1.5 mm, from about 4 mm to about 4.5 mm, about 4.25 mm, from about 4.9 to about 5 mm, about 4.95 mm, from about 5.4 mm to about 5.6 mm, or about 5.5 mm.

The housing may comprise an internal volume of from about 700 μL to about 1700 L, from about 750 μL to about 1650 μL, from about 800 μL to about 1600 μL, or from about 850 μL to about 1550 μL.

The housing may comprise a fluid volume from about 50 μL to about 800 μL, from about 100 μL to about 600 μL, or from about 200 μL to about 400 μL.

The ingestible device may comprise a plurality of openings in the housing configured to fluidly connect the dispensable substance to an environment outside the housing via the opening. The plurality of openings may comprise an even number of openings or an odd number of openings. The plurality of openings may comprise at least 25 openings, and/or at most 50 openings. Each opening may comprise a nozzle opening.

The opening may comprise a nozzle opening having a diameter from about 1 mm to about 3 mm, at least about 1.5 mm, at least about 2 mm, and/or at most about 2.5 mm.

The ingestible device may comprise a nozzle having a length of from about 1 mm to about 5 mm, from about 2 mm to about 5 mm, or from about 3 mm to about 5 mm.

The dispensable substance may comprise a fluid. The dispensable substance may comprise a liquid. The dispensable substance may comprise a therapeutic agent. The dispensable substance may comprise a solution. The dispensable substance may comprise a suspension. The dispensable substance may have a viscosity of less than or equal to 10 cP, at least about 0.8 cP, at most about 8 cP, and/or or at most about 9 cP.

The ingestible device may be configured as a 00 capsule.

The ingestible device may be configured as a 000 capsule.

Third Group of General Aspects of the Disclosure

In a general aspect, the disclosure provides an ingestible device, comprising: a housing comprising first and second housing parts; and a restraining mechanism comprising a material having at least one property selected from the group consisting of selected being degradable, being erodible and being dissolvable, wherein the ingestible device is configured so that: when the restraining mechanism is in a first state, the restraining mechanism has sufficient strength so that the first and second housing parts are connected such that a dispensable substance is storable in the housing at a fluid pressure that is greater than 0 psig; and when the restraining mechanism is in a second state in which the material is at least partially degraded, eroded and/or dissolved, the restraining mechanism has reduced strength such that the first and second housing parts are sufficiently disconnected so that at least a portion of the dispensable substance leaves the ingestible device.

The fluid pressure may be greater than 5 psig. The fluid pressure may be at most about 50 psig. The fluid pressure may be from about 5 psig to about 50 psig, from about 5 psig to about 30 psig, from about 5 psig to about 20 psig, from about 8 psig to about 20 psig, or from about 10 psig to about 15 psig.

The second material may change from its first state to its second state in response to at least one condition selected from the group consisting of temperature, pH, presence of one or more enzymes, and time.

The restraining mechanism may comprise an enteric material. The restraining mechanism may comprise at least one member selected from the group consisting of a seal, a pin, a band, a dowel, a clasp, a clamp, a flange, and a rivet.

The ingestible device may further comprise a drive force generator configured to provide an internal pressure. The drive force generator may comprise a gas. The gas may comprise a member selected from the group consisting of air, nitrogen, oxygen, carbon dioxide and a noble gas. The drive force generator may comprise a spring.

The ingestible device may further comprise a drive coupling configured to transfer the internal pressure to the dispensable fluid. The drive coupling may comprise a member selected from the group consisting of a piston and a membrane.

The internal pressure may be greater than 5 psig. The internal pressure may be at most about 50 psig. The internal pressure may be from about 5 psig to about 50 psig, from about 5 psig to about 30 psig, from about 5 psig to about 20 psig, from about 8 psig to about 20 psig, or from about 10 psig to about 15 psig.

The housing may have a length of from about 20 mm to about 28 mm, from about 21 mm to about 27 mm, about 26 mm, or about 23.3 mm.

The housing may have a diameter of from about 7 mm to about 12 mm, from about 8 mm to about 11 mm, about 11 mm, about 9.9 mm, or about 8.5 mm.

A ratio of the length of the housing to the width of the housing may be from about 0.75 to about 4, from about 1 to about 3, or from about 1 to about 2.

The ingestible device may be configured as a 00 capsule.

The ingestible device may be configured as a 000 capsule.

The housing may comprise a wall having a wall thickness of from about 0.5 mm to about 1 mm, from about 0.6 mm to about 0.9 mm, about 0.8 mm, or about 0.7 mm.

The housing may comprise end regions that are spline-shaped or that are spherical.

The housing may comprise an end round of from about 1 mm to about 2 mm, about 1.5 mm, from about 4 mm to about 4.5 mm, about 4.25 mm, from about 4.9 to about 5 mm, about 4.95 mm, from about 5.4 mm to about 5.6 mm, or about 5.5 mm.

The ingestible device may be configured to deliver at least 50% of the dispensable substance into the lumen of the GI tract of a subject.

The ingestible device may further comprise the dispensable substance. The dispensable substance may comprise a fluid. The dispensable substance may comprise a liquid. The dispensable substance may comprise a therapeutic agent. The dispensable substance may comprise a solution. The dispensable substance may comprise a suspension. The dispensable substance may have a viscosity of less than or equal to 10 cP, at least about 0.8 cP, at most about 8 cP, or/or at most about 9 cP.

The ingestible device may be configured to deliver the dispensable substance to the lumen of the GI tract of a subject via topical delivery.

In a general aspect, the disclosure provides a method, comprising: using an ingestible to deliver a dispensable substance to the GI tract of the subject.

In a general aspect, the disclosure provides a method, comprising: using an ingestible device to deliver a dispensable substance to the lumen of the GI tract of a subject via topical delivery, wherein the ingestible device comprises: a housing; an opening in the housing configured to fluidly connect the dispensable substance to an environment outside the housing via the opening; a drive force generator configured to provide a force to the dispensable substance to deliver the dispensable substance through the opening; a drive force coupling configured to transfer the force from the drive force generator to the dispensable substance; and a restraining mechanism having a first state in which the restraining mechanism prevents the dispensable substance from being delivered out of the ingestible device.

The drive force generator may comprise a member selected from the group consisting of a spring, a gas cell, a compressed gas, and a liquid-gas mixture. The ingestible device may comprise chemicals configured to react to provide a gas as the drive force generator.

The drive coupling may comprise a member selected from the group consisting of a piston and a membrane.

In some embodiments, when the restraining mechanism is in its first state, the drive force generator does not apply an internal pressure to the dispensable substance. In certain embodiments, when the restraining mechanism is in its first state, the drive force generator applies an internal pressure to the dispensable substance. The restraining mechanism may have second state different from its first state, and, when the restraining mechanism is in its second state, the restraining mechanism does not prevent the dispensable substance from being delivered out of the ingestible device. The restraining mechanism may comprise a material selected from the group consisting of a degradable material, an erodible material and a dissolvable material. The restraining mechanism may comprise an enteric material. The restraining mechanism may comprise at least one member selected from the group consisting of a seal, a pin, a band, a dowel, a clasp, a clamp, a flange, and a rivet. The restraining mechanism may comprise a cap. The cap may be located at a distal end of the ingestible device.

The housing may have a length of from about 20 mm to about 28 mm, from about 21 mm to about 27 mm, about 26 mm, or about 23.3 mm.

The housing may have a diameter of from about 7 mm to about 12 mm, from about 8 mm to about 11 mm, about 11 mm, about 9.9 mm, or of about 8.5 mm.

A ratio of the length of the housing to the width of the housing may be from about 0.75 to about 4, from about 1 to about 3, or from about 1 to about 2.

The ingestible device may be configured as a 00 capsule.

The ingestible device may be configured as a 000 capsule.

The housing may comprise a wall having a wall thickness of from about 0.5 mm to about 1 mm, from about 0.6 mm to about 0.9 mm, about 0.8 mm, or about 0.7 mm.

The housing may comprise end regions that are spline-shaped or that are spherical.

The housing may comprise an end round of from about 1 mm to about 2 mm, about 1.5 mm, from about 4 mm to about 4.5 mm, about 4.25 mm, from about 4.9 to about 5 mm, about 4.95 mm, from about 5.4 mm to about 5.6 mm, or about 5.5 mm.

The housing may have an internal volume of from about 700 µL to about 1700 µL, from about 750 µL to about 1650 µL, from about 800 µL to about 1600 µL, or from about 850 µL to about 1550 µL.

The housing may have a fluid volume from about 50 μL to about 800 μL, from about 100 μL to about 600 μL, or from about 200 μL to about 400 μL.

The ingestible device may comprise a plurality of openings in the housing configured to fluidly connect the dispensable substance to an environment outside the housing via the opening. The plurality of openings may comprise an even number of openings or an odd number of openings. The plurality of openings may comprise at least 25 openings and/or at most 50 openings. Each opening may comprise a nozzle opening.

The opening may comprise a nozzle opening having a diameter from about 1 mm to about 3 mm, at least about 1.5 mm, at least about 2 mm, and/or at most about 2.5 mm.

The ingestible device may comprise a nozzle having a length of from about 1 mm to about 5 mm, from about 2 mm to about 5 mm, or from about 3 mm to about 5 mm.

The dispensable substance may comprise a fluid. The dispensable substance may comprise a liquid. The dispensable substance may comprise a therapeutic agent. The dispensable substance may comprise a solution. The dispensable substance may comprise a suspension. The dispensable substance may have a viscosity of less than or equal to 10 cP, at least about 0.8 cP, at most about 8 cP, and/or at most about 9 cP.

The details of one or more embodiments of the device and methods are set forth in the accompanying drawings and the description below. Other features and advantages will be apparent from the description and drawings, and from the claims.

BRIEF DESCRIPTION OF THE DRAWINGS

FIG. 19A shows an ingestible device.

FIG. 19B shows an exploded view of the ingestible device of FIG. 19A.

FIG. 55A represents animals treated with adalimumab after ID administration via the endoscopically placed ingestible device having 4 nozzles and an internal pressure of 320 psig. FIG. 55B represents animals treated with adalimumab after ID administration via the endoscopically placed ingestible device having 4 nozzles and an internal pressure of 350 psig.

FIG. 57A shows binding of anti-TNFα to the TNFα receptor without drug, where uninhibited binding brings the Donor and Acceptor beads into close proximity for singlet oxygen transfer detection. FIG. 57B shows binding of anti-TNFα to TNFα that is inhibited by drug binding to TNFα, thus preventing binding to anti-TNFα antibodies and proximity oxygen singlet transfer detection.

FIG. 58A shows the dose response curve after 10,000 pg/mL of adalimumab was dispensed into collection tubes under various conditions as described in Example 8. FIG. 58B is an enlarged view of a section of the graph shown in FIG. 58A.

FIGS. 63A-63C show plasma (FIG. 63A), colon content (FIG. 63B) and colon tissue (FIG. 63C) tofacitinib exposure ($AUC_{0-24h}$) after treatment with vehicle or tofacitinib citrate via per oral (PO) or intracecal (IC) administration in a DSS-induced colitis mouse model.

FIG. 64A shows IL-6 concentrations in colon tissue at various timepoints on Study Day 12. FIG. 64B shows the relationship between tofacitinib concentration in colon tissue (open shapes and dotted lines; right y-axis) and % IL-6 in colon tissue after treatment with tofacitinib citrate, normalized to DSS vehicle control (Group 2) (solid shapes and solid lines; left y-axis).

FIG. 69A shows the influence of anti-TNF-alpha; FIG. 69B shows the influence of anti-IL 12p40. The AUC was calculated using the trapezoidal rule and is shown in the figure inset. Differences in body weight loss were calculated as AUC for individual mouse from Days 0 to 42. Two-tailed Mann-Whitney U-Test; $p<0.05$*; $p<0.01$; $p<0.005$*, n=5-9.

Figure 71A:
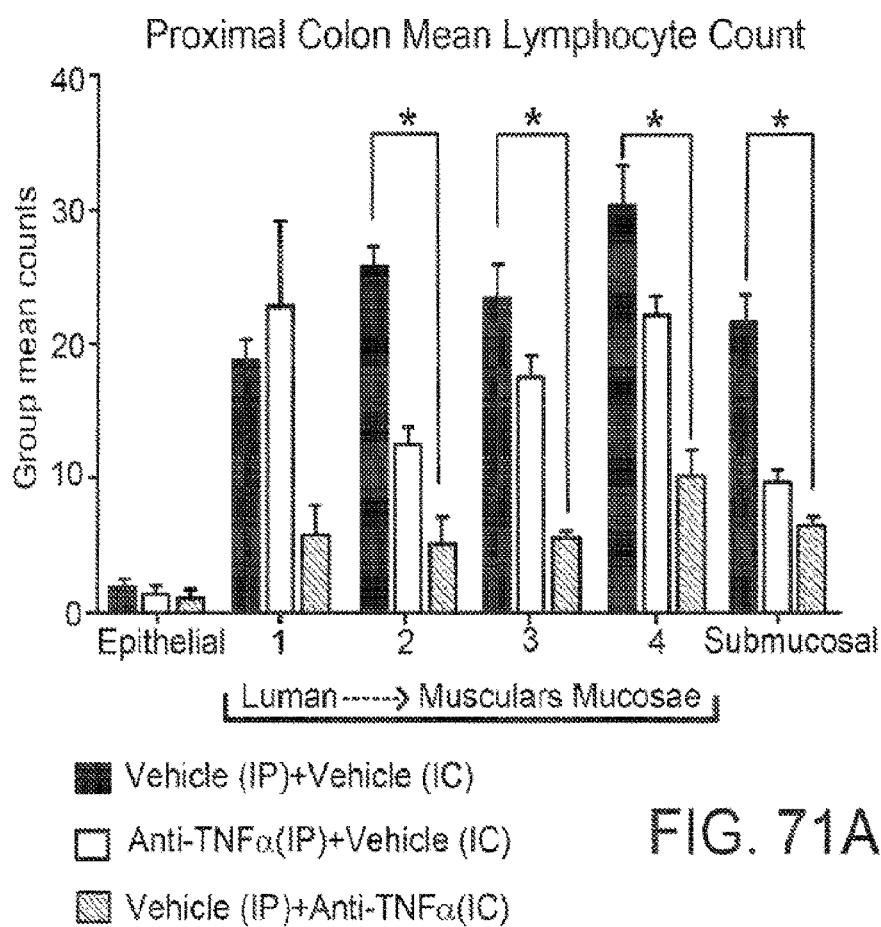
FIGS. 71A-71D show mean lymphocyte counts from luminal to external submucosa of proximal colon and represented images of H&E stains and IHC stains of the proximal colon.
Figure 71B:
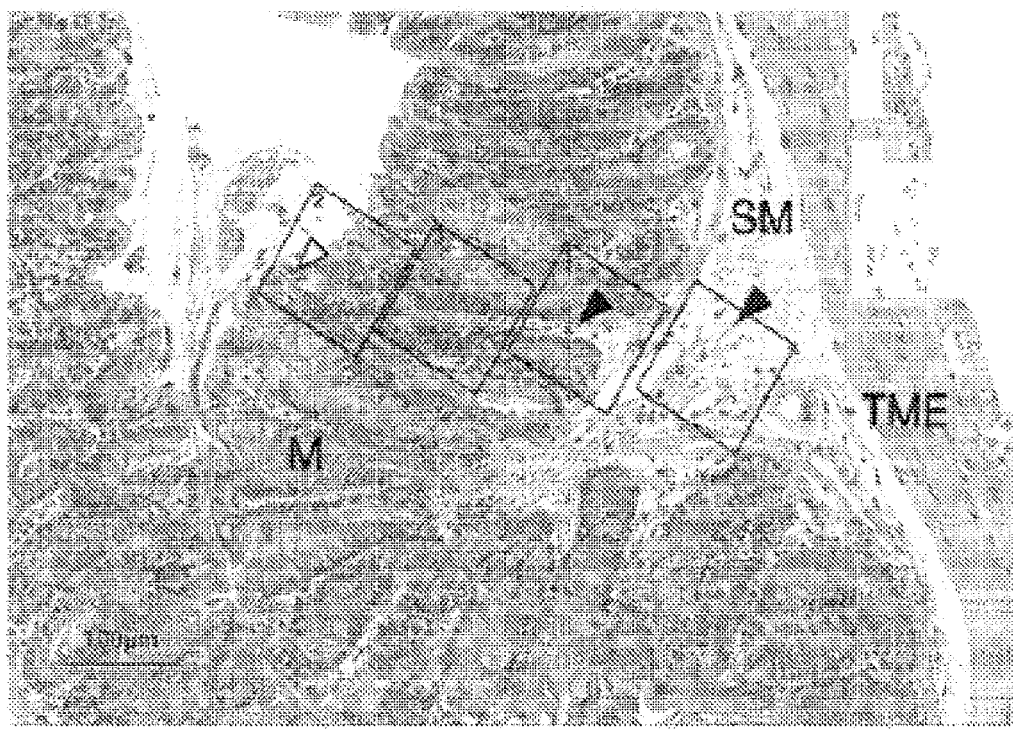
Figure 71C:
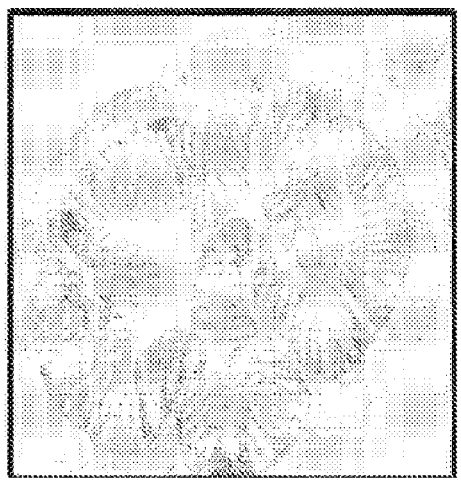
Figure 71D:
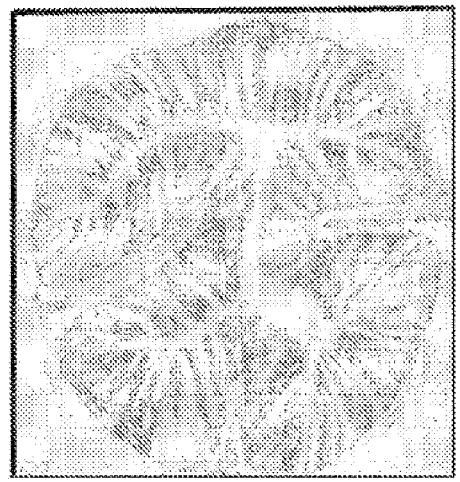

FIG. 71A shows the mean lymphocyte count from most inner lumen to submucosal of the proximal colon in groups treated with Vehicle controls, anti-TNFα (IP) and anti-TNFα (IC), Group mean+/−SEM. Kruskal-Wallis Test with Dunn's multiple comparison for treatment effects; $p<0.05$*. FIG. 71B is a representative image of H&E stain of proximal colon in proximal colon of anti-TNFα (IC) group. An intraepithelial lymphocyte (white arrowhead), example lamina proprial lymphocytes (black arrowheads), and the tunica muscularis externa (TME) are indicate. FIGS. 71C and 71D are representative images of IHC stain of CD4 marker for lymphocytes in proximal colon of anti-TNFα (IC) (FIG. 71C) or anti-TNFα (IP) (FIG. 71D) group.

Figure 72A:
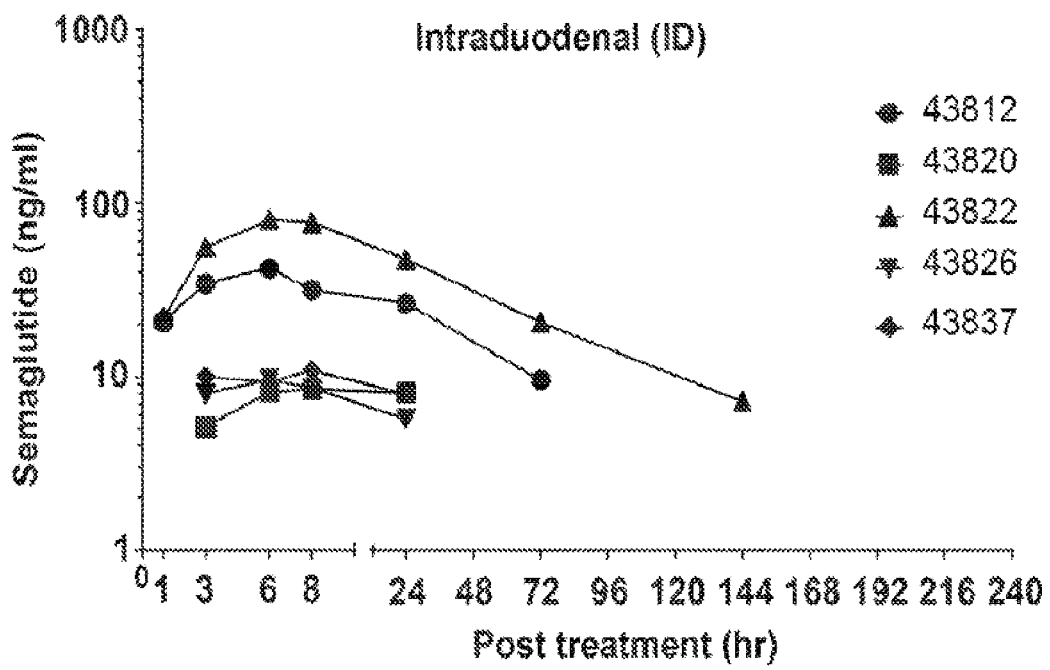
Figure 72B:
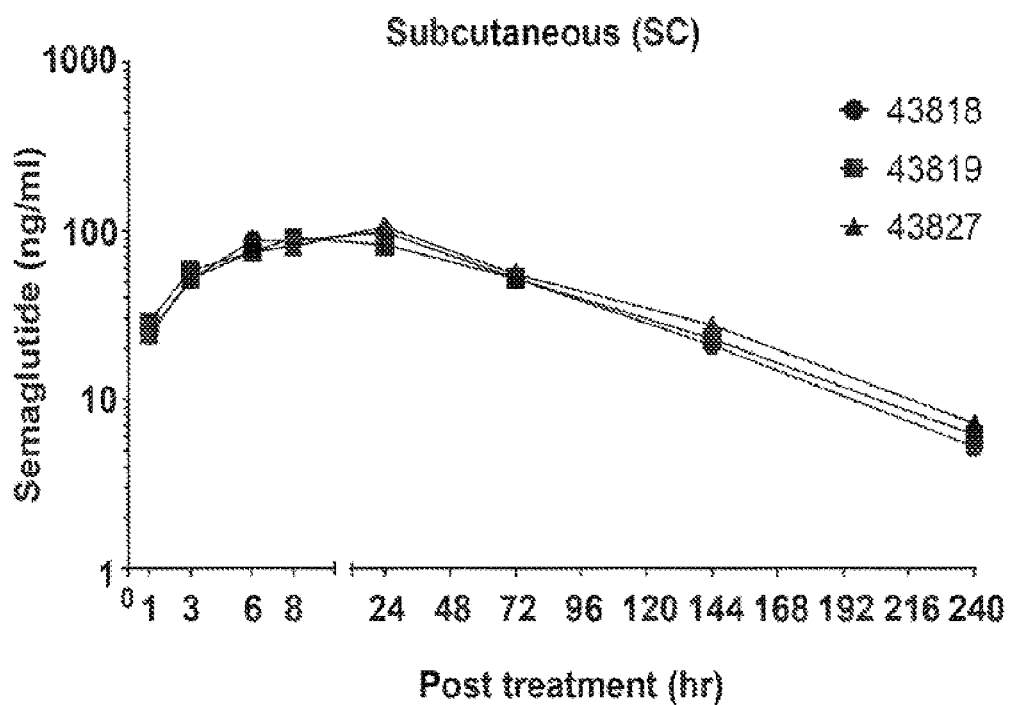
Figure 72C:
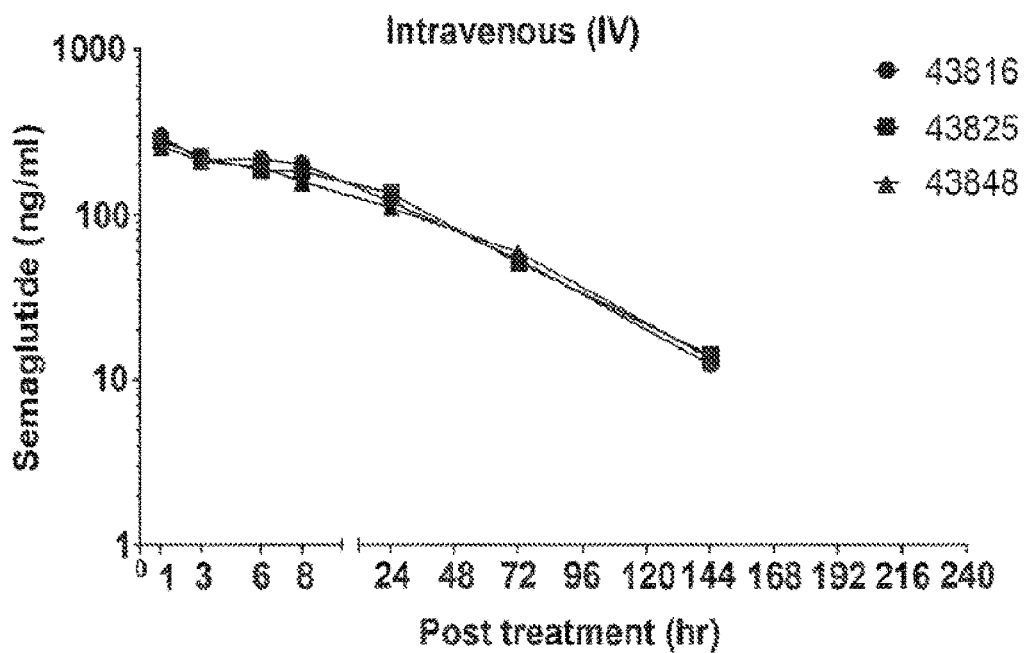

FIGS. 72A-72C show semaglutide concentration in blood over time after: ID administration via the endoscopically placed ingestible jet delivery device (FIG. 72A); SC administration (FIG. 72B); and IV administration (FIG. 72C).

Figure 73:
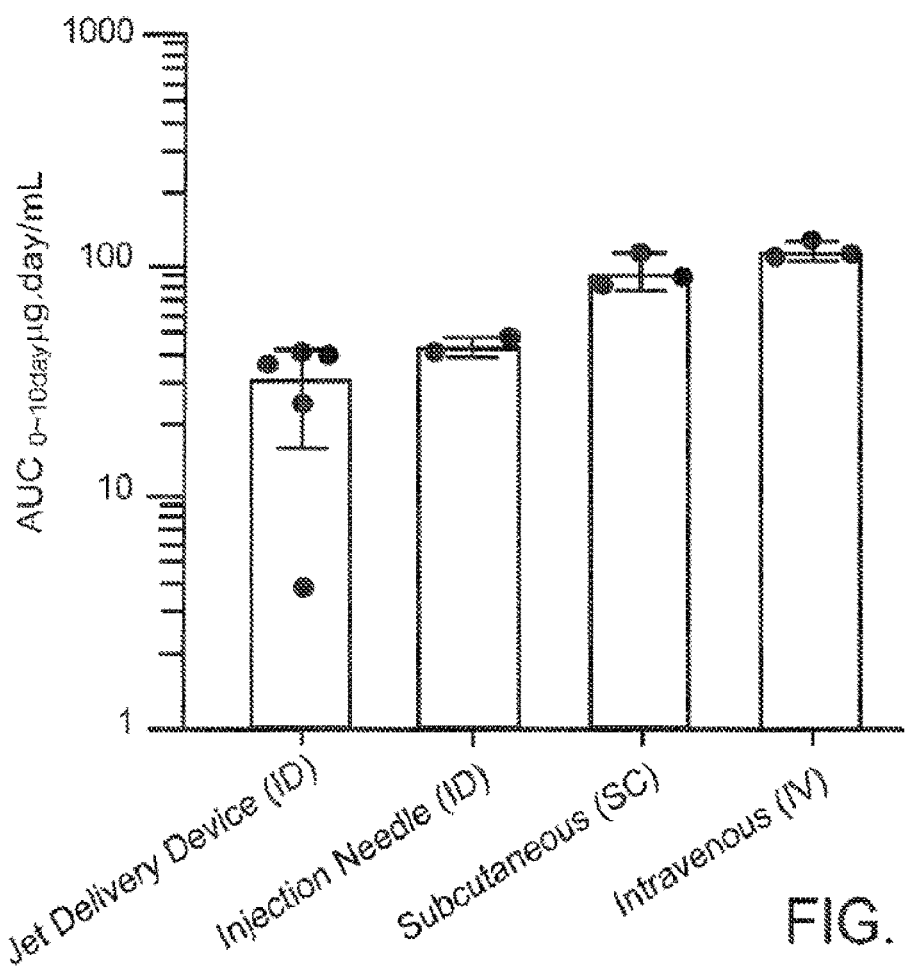

FIG. 73 shows the $(AUC)_{T0-T10d}$ observed after administration of adalimumab intraduodenally (ID) via an ingestible jet delivery device having an internal pressure of 320 psig (Example 5, Group 3), ID via an endoscopic injection needle (Example 12), subcutaneously (Example 5, Group 4) and intravenously (Example 5, Group 5).

DETAILED DESCRIPTION

Definitions

"Ingestible," as used herein in reference to the device, means that the device can be swallowed whole.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. The terms "antibody" and "immunoglobulin" are used interchangeably in the broadest sense. As used herein, the terms encompass monoclonal antibodies (for example, full length or intact monoclonal antibodies), polyclonal antibodies (for example, full length or intact polyclonal antibodies), and fragments thereof (such as Fab, Fab', F(ab')2, Fv, single chain (ScFv) and domain antibodies), fusion proteins including an antibody portion, multivalent antibodies, multispecific antibodies (e.g., bispecific, trispecific, etc. antibodies so long as they exhibit the desired biological activity), and any other modified configuration of the immunoglobulin molecule that includes an antigen recognition site. An antibody can be human, humanized and/or affinity matured.

The term antibody includes antibody fragments (e.g., antigen-binding fragments) such as an Fv fragment, a Fab fragment, a F(ab')2 fragment, and a Fab' fragment. "Antibody fragments" comprise only a portion of an intact antibody, where in certain embodiments, the portion retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment. Additional examples of antigen-binding fragments include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen or antigenic site. Furthermore, in contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, Proc. Natl. Acad. Sci. USA 81:6851-6855 (1984)).

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, (5th ed., 1991, National Institutes of Health, Bethesda Md.)); and (2) an approach based on crystallographic studies of antigen-antibody complexes (Al-Lazikani et al., 1997, J. Molec. Biol. 273:927-948). As used herein, a CDR may refer to CDRs defined by either approach or by a combination of both approaches.

As known in the art, a "constant region" of an antibody refers to the constant region of the antibody light chain or the constant region of the antibody heavy chain, either alone or in combination.

"Bioavailability," as used herein, may be reported based on the ratio of the area under a curve (AUC) of the therapeutic agent concentration in systemic circulation versus time that is achieved when the drug is administered by another form of administration (e.g., trans-epithelial administration [hereinafter, $AUC_{TE}$] or topical administration [hereinafter, $AUC_{TOP}$], respectively) versus the AUC of the therapeutic agent concentration in systemic circulation versus time that is achieved when the same amount of the drug is administered intravenously [hereinafter, $(AUC)_{IV}$], or subcutaneously [hereinafter, $(AUC)_{SC}$], expressed as a percentage. In some aspects, especially when the pharmacokinetic data are derived from more than one subject, the AUC is a mean AUC. In some embodiments, the mean is a geometric mean. In other aspects, as used herein, drug exposure may be reported based on a different pharmacokinetic parameter. For example, drug exposure may be reported as a ratio of maximum therapeutic agent concentration ($C_{max}$) in systemic circulation that is achieved when the drug is administered by another form of administration (e.g., trans-epithelial administration [hereinafter, $(C_{max})_{TE}$] or topical administration [hereinafter, $(C_{max})_{TOP}$]), versus the $C_{max}$ of the therapeutic agent concentration in systemic circulation that is achieved when the same amount of the drug is administered intravenously [hereinafter, $(C_{max})_{IV}$], or subcutaneously [hereinafter, $(C_{max})_{SC}$], expressed as a percentage.

As used herein, "non-oral," when used in reference to a therapeutic suitable for use with the devices and methods of the present disclosure, refers to a therapeutic or active agent that has poor bioavailability and/or is not administered by an oral route of administration.

The term "chemokine/chemokine receptor inhibitors" refers to an agent which decreases the ability of a chemokine to bind to its receptor, where the chemokine is one of CXCL10 (IL-10), CCL11, or an ELR chemokine, or the chemokine receptor is CCR2 or CCR9.

"Effective amount" as used herein refers to an amount of therapeutic agent that offers beneficial response to a patient receiving the treatment. For example, an effective amount may be a Human Equivalent Dose (HED). The phrase "therapeutically effective amount," as used herein, refers to the amount of the therapeutic agent that is effective for producing a desired therapeutic effect. In some embodiments, a therapeutically effective amount treats or prevents a disease or condition disclosed herein.

"Mucosa-associated lymphoid tissue" or "MALT" used herein refers to a diffuse system of small concentrations of lymphoid tissue found in various submucosal membrane sites of the body, such as the gastrointestinal tract, oral passage, nasopharyngeal tract, thyroid, breast, lung, salivary glands, eye, and skin.

"Gut-associated lymphoid tissue" or "GALT" as used herein refers to a part of the broader MALT and includes, e.g., Peyer's patches, mesenertic lymph nodes, and isolated lymphoid follicles/intestinal lymphoid aggregates.

"Peyer's patches" as used herein refers to aggregated lymphoid modules organized into follicles and are important part of GALT. Peyer's patches are mainly present in the distal jejunum and the ileum.

"Mesenteric lymph nodes" as used herein refers to part of the paraaortic lymph node system that is a group of lymph nodes that lie between the layers of the mesentery and drain the gut tissues and deliver lymph to the thoracic duct. Mesenteric lymph nodes include the "superior mesenteric lymph nodes" which receive afferents from the jejunum, ileum, cecum, and the ascending and parts of the transverse colon. Mesenteric lymph nodes also include "inferior mesenteric lymph nodes" which are lymph nodes present throughout the hindgut. The hindgut, e.g., includes the distal third of the transverse colon and the splenic flexure, the descending colon, sigmoid colon, and the rectum. The lymph nodes drain into the superior mesenteric lymph nodes and ultimately to the preaortic lymph nodes.

"Paraaortic lymph nodes" as used herein refers to a group of mesenteric lymph nodes that lie in front of the lumbar vertebrae near the aorta. The paraaortic lymph nodes receive drainage from the gastrointestinal tract and the abdominal organs. Paraaortic lymph nodes include, e.g., retroaortic lymph nodes, lateral aortic lymph nodes, preaortic lymph nodes (e.g., Celiac, gastric, hepatic, and splenic lymph nodes), superior mesenteric lymph nodes (e.g., mesenteric, ileocolic, and mesocolic lymph nodes), and inferior mesenteric lymph nodes (e.g., pararectal lymph nodes).

A drug's international nonproprietary name (INN), as used herein, is to be interpreted as including generic, bioequivalent and biosimilar versions of that drug, including but not limited to any drug that has received abbreviated regulatory approval by reference to an earlier regulatory approval of that drug. Additionally, all drugs disclosed herein optionally include the pharmaceutically acceptable salts and solvates of the drugs thereof, and the biosimilars thereof, and/or glycosylation variants thereof, in the case of biologics such as antibodies, unless expressly indicated otherwise.

As used herein, each listed small molecule, peptide or nucleic acid agent optionally includes a pharmaceutically acceptable salt thereof, whether or not such a form is expressly indicated. Each listed antibody agent optionally includes a biosimilar thereof, or a glycosylation variant thereof, whether or not such a biosimilar or glycosylation variant is expressly indicated.

"Dispensable" as used herein with reference to any substance, refers to any substance that may be released from an ingestible device as disclosed herein, or from a component of the device such as a reservoir. For example, a dispensable substance may be a therapeutic agent as disclosed herein, and/or a formulation that includes a therapeutic agent as disclosed herein. A dispensable substance may be a fluid, such as a liquid, a suspension or a semi-solid. For example, a dispensable substance can be a liquid in the form of a solution, such as an aqueous solution. In some embodiments, when disposed in an ingestible device, a substance is a non-fluid, such as a solid. In such embodiments, the substance may be converted to a fluid prior to being delivered from the ingestible device. In some embodiments, the therapeutic agent is a small molecule. In other embodiments, the therapeutic agent is a large molecule, such as a biologic drug. Nonlimiting examples of biologic drugs include antibodies (including monoclonal antibodies), proteins (including fusion proteins), peptides (including cyclic peptides), cells (including stem cells), and nucleic acids (including inhibitory nucleic acids, antisense nucleic acids, siRNA, ribozymes). In some embodiments, the dispensable substance is a pharmaceutical formulation comprising a therapeutic agent and a liquid carrier. In some embodiments, the pharmaceutical formulation comprising the therapeutic agent and the liquid carrier is a solution formulation. In other embodiments, the pharmaceutical formulation comprising the therapeutic agent and the liquid carrier is a suspension formulation, or an emulsion formulation. In some embodiments, a dispensable substance delivered as described herein is particularly well-suited for treatment of diseases and conditions of the endoderm, for example, it may be more efficacious in gut-associated lymphoid tissue (GALT) or the hepatic system as compared to subcutaneous or intravenous administration. In general, the viscosity of a dispensable substance can be selected as appropriate. In some embodiments, the dispensable substance has a viscosity of at least about 0.5 centiPoise (cP) (e.g., at least about 0.8 cP, at least about 1 cP, at least about 2 cP, at least about 3 cP, at least about 4 cP, at least about 5 cP) and/or at most about 10 cP (e.g., at most about 9 cP, at most about 8 cP, at most about 7 cP). In certain embodiments the dispensable substance has a viscosity of from about 0.5 cP to about 10 cP (e.g., from about 0.8 cP to about 9 cP, from about 0.8 cP to about 8 cP).

As used herein, the term "enteric" refers to a material that permits transition to a desired location in the GI tract (e.g., through the stomach to the intestine) before being dissolved/degraded/eroded due to exposure of certain conditions (e.g., pH, temperature, enzymes) of the GI tract. An enteric material may prevent a drug from degradation by gastric fluid and enzymes. In some embodiments, an enteric composition (e.g., when formed as a coating on the housing of an ingestible device) is selected from mixtures of fats and fatty acids; shellac and shellac derivatives; and cellulose acetate phthalates. An enteric material can be an enteric polymer. In some embodiments, an enteric polymer can remain insoluble in the stomach, but dissolve at the higher pH of the intestine (e.g., small intestine or large intestine), and are used to deliver drugs to the intestine. Examples include Colorcon's Opadry Enteric 91 series Polyvinyl Acetate Phthalate, Opadry Enteric 94 series Methacrylic Acid, Opadry Enteric 95 series Methacrylic Acid, Sureteric PVAP (Polyvinyl Acetate Phthalate), Nutrateric Ethylcellulose Evonik Acryl-EZE (Colorcon & Evonik collaboration—Eudragit L 100-55 Mixture Methacrylic copolymers); Evonik's Eudragit L 100-55 Methacrylic copolymers, Eudragit L 30 D-55 Methacrylic copolymers (30%), Eudragit L 100 Methacrylic copolymers, Eudragit L 12.5 Methacrylic copolymers (12.5%), Eudragit S 100 Methacrylic copolymers, Eudragit S 12.5 Methacrylic copolymers (12.5%), Eudragit FS 30 D Methacrylic copolymers (30%); Kerry's SheffCoat ENT Cellulose Acetate Phthalate, Acrylate copolymer, HPMC-P; Eastman's C-A-P NF Cellulose Acetate Phthalate; Sensient's PROTECT™ ENTERIC Shellac & Sodium Alginate. In certain embodiments, an enteric material dissolves in the small intestine and is suitable for small intestine release. Examples of such enteric materials include, but are not limited to, cellulose derivatives, e.g., cellulose acetate phthalate, hydroxypropylmethylcellulose phthalate (HPMCP), hydroxypropylmethylcellulose acetate succinate (HPMCAS) and RL100 (e.g., HP-55), malic acid-propane 1,2-diol, polyvinyl acetate phthalate, anionic polymers of methacrylic acid and methyl methacrylate, hydroxypropylcellulose acetate phthalate, polyvinyl acetate phthalate, methacrylate-methacrylic acid copolymers, styrol, maleic acid copolymers, shellac, and others. Another suitable enteric material is a water emulsion of ethylacrylate methylacrylic acid copolymer, or hydroxypropyl methyl cellulose acetate succinate (HPMAS). (See, e.g., U.S. Pat. No. 5,591,433). In some embodiments, an enteric material dissolves in the large intestine and is suitable for colonic release. Enteric materials suitable for large intestine (e.g., colonic) release are known to one of skill in the art. In some embodiments, degradation of the coating is microbially triggered, e.g., the bacteria in the colon enzymatically trigger degradation of the coating (see, e.g., Archana et al., Int. J. Pharm. Sci. Res. (2016) 1(5):40-47; and Sethi et al., Int. J. Pharm. Sci. Res. (2012) 3(9):2989-3000). In some embodiments, the coating is a pH-dependent polymer that is insoluble at low pH but becomes increasingly soluble as pH increases. In some embodiments, the coating is a polymethacrylates with a pH-dependent dissolution threshold of about pH 6.0 to about 7.0. Examples of suitable enteric materials include, but are not limited to, chitosan, alginates (e.g., as calcium salts), Eudragit® L (e.g., Eudragit® 100), Eudragit® S (e.g., Eudragit® S 100), Eudragit® L (e.g., Eudragit® L-30D), Eudragit® FS (e.g., Eudragit® FS 30D), hydroxypropylmethylcellulose phthalate 50, hydroxypropylmethylcellulose phthalate 55, and cellulose acetate trimellate. In some embodiments, an enteric material is a material described in U.S. Pat. No. 10,226,430; Sethi et al., Int. J. Pharm. Sci. Res. (2012) 3(9):2989-3000; or Archana et al., Int. J. Pharm. Sci. Res. (2016) 1(5):40-47, each of which are herein incorporated by reference in their entireties. In some embodiments, the colon-specific degradation of an enteric material can be based on the presence of microorganisms that reside only in the colon, more particularly, biodegradable enzymes produced by these microorganisms. In general, such microorganisms are anaerobic bacteria, e.g., Bacteroides, Bifidobacteria, Enterobacteria, Eubacteria, Clostridia, Enterococci, and Ruminococcus, etc. These micro floras fulfill their energy needs by fermenting various types of substrates that have been left undigested in the small intestine, e.g., polysaccharides, di- and tri-saccharides, etc. These polymers are stable in the environments of the stomach and small intestine. On reaching the colon, the polymers undergo degradation by the enzyme or break down of the polymer backbone leads to a subsequent reduction in their molecular weight and thereby loss of the mechanical strength. The term "jet," as used herein, refers to a collimated stream of fluid, e.g., liquid or suspension, that is stable without breaking up into a spray. A jet may be formed by forcing the fluid, e.g., liquid or suspension, through an opening in an ingestible device. Generally, a jet maintains a stable form and is capable of achieving its intended purpose by maintaining appropriate properties (e.g., to penetrate a surface), such as its diameter and/or velocity.

As used herein, "jet diameter" is the cross-sectional diameter of a jet at a given location.

As used herein, "average jet diameter" refers to the average cross-sectional diameter of a jet between the location where the jet is formed (e.g., a nozzle opening through which the dispensable substance is delivered from the ingestible device) and the location where the jet impacts the GI tissue of the subject.

"Jet stable length," as used herein, refers to the distance from an opening (e.g., nozzle opening) of an ingestible device that a dispensable substance delivered through the opening remains in the form of a jet.

"Jet velocity," as used herein is the average fluid velocity across the cross-section of a jet at a given point in time.

As used herein, "peak jet velocity," refers to the maximum jet velocity of a jet at the interface of the lumen and the surface of the GI tract facing the lumen. In general, the peak jet velocity is achieved at the time of initial delivery of the dispensable substance from the ingestible device.

As used herein, "minimum jet velocity," refers to the minimum velocity of a jet at the interface of the lumen and the surface of the GI tract facing the lumen. In general, the minimum jet velocity is achieved at the end of delivery of the dispensable substance from the ingestible device.

"Mean jet velocity" and "average jet velocity," as used herein, refer to the average velocity of a jet at the interface of the lumen and the surface of the GI tract facing the lumen as determined over the time that the ingestible device delivers the dispensable substance.

As used herein, "peak jet power" refers to the maximum power of a jet at the interface of the lumen and the surface of the GI tract facing the lumen. In general, the peak jet power is achieved at the time of initial delivery of the dispensable substance from the ingestible device.

As used herein, "minimum jet power," refers to the minimum power of a jet at the interface of the lumen and the surface of the GI tract facing the lumen. In general, the minimum jet power is achieved at the end of delivery of the dispensable substance from the ingestible device.

"Mean jet power" and "average jet power," as used herein, refer to the average power of a jet at the interface of the lumen and the surface of the GI tract facing the lumen as determined over the time that the ingestible device delivers the dispensable substance.

"Jet power during delivery," as used herein, refers to the power of a jet at the interface of the lumen and the mucosa of the GI tract of a subject.

"Jet pressure," as used herein, refers to the pressure of a jet at the interface of the lumen and the surface of the GI tract facing the lumen. As an example, the jet pressure can be the pressure by the jet measured at the intestinal wall. In some embodiments, jet pressure is referred to herein as "impact pressure."

"Peak jet pressure," as used herein, refers to the maximum pressure of a jet at the interface of the lumen and the surface of the GI tract facing the lumen. In general, the peak jet pressure is achieved at the time of initial delivery of the dispensable substance from the ingestible device.

As used herein, "minimum jet pressure," refers to the minimum pressure of a jet at the interface of the lumen and the surface of the GI tract facing the lumen. In general, the minimum jet pressure is achieved at the end of delivery of the dispensable substance from the ingestible device.

"Mean jet pressure" and "average jet pressure," as used herein, refer to the average pressure of a jet at the interface of the lumen and the surface of the GI tract facing the lumen as determined over the time that the ingestible device delivers the dispensable substance.

"Jet force," as used herein, refers to the force of a jet at the interface of the lumen and the surface of the GI tract facing the lumen. In some embodiments, jet force is referred to herein as "impact force."

"Peak jet force," as used herein, refers to the maximum force of a jet at the interface of the lumen and the surface of the GI tract facing the lumen. In general, the peak jet force is achieved at the time of initial delivery of the dispensable substance from the ingestible device. In some embodiments, peak jet force is referred to herein as "impact force."

As used herein, "minimum jet force," refers to the minimum force of a jet at the interface of the lumen and the mucosa of the GI tract of a subject. In general, the minimum jet force is achieved at the end of delivery of the dispensable substance from the ingestible device.

"Mean jet force" and "average jet force," as used herein, refer to the average pressure of a jet at the interface of the lumen and the surface of the GI tract facing the lumen as determined over the time that the ingestible device delivers the dispensable substance.

As used herein, "fluid volume" refers to the volume of the dispensable substance contained in the ingestible device.

"Initial fluid volume," as used herein, refers to the volume of the dispensable substance contained in the ingestible device just prior to delivery of the dispensable substance from the ingestible device.

"Final fluid volume," as used herein, refers to the volume of the dispensable substance contained in the ingestible device just after delivery of the dispensable substance from the ingestible device has ended.

As herein, "delivered fluid volume" refers to the volume of dispensable substance delivered from the ingestible device. In some embodiments, the delivered fluid volume is less than the fluid volume.

"End round" as used herein is the radius on the curve at the end of the housing of the ingestible device.

"Fluid pressure" as used herein refers to the pressure in the fluid volume.

As used herein, "peak fluid pressure" refers to maximum pressure generated in the fluid volume. Generally, the peak fluid pressure is achieved at initial delivery of the dispensable substance from the ingestible device. In some embodiments, peak fluid pressure is referred to herein as "internal pressure on the pharmaceutical formulation in the device, prior to release from the device."

As used herein, "minimum fluid pressure" refers to minimum pressure generated in the fluid volume. Generally, the minimum fluid pressure is achieved at the end of delivery of the dispensable substance from the ingestible device.

"Fluid pressure during delivery," as used herein, refers to the pressure in the fluid volume as it decreases during the delivery process.

As used herein, "nozzle" refers to a channel between a fluid reservoir space and an external environment. Generally, in embodiments in which a nozzle is used, pressure in the fluid volume generates a high speed flow of fluid through the nozzle to produce a fluid jet at the opening of the nozzle through which the dispensable substance leaves the ingestible device and enters an environment exterior to the ingestible device.

"Nozzle diameter," as used herein, refers to the diameter of the opening of the nozzle at the opening of the nozzle through which the dispensable substance leaves the ingestible device and enters an environment exterior to the ingestible device.

As used herein, "nozzle length" refers to the length of the opening of the nozzle.

"Nozzle stand-off distance," as used herein, refers to the distance between: 1) the opening of the nozzle through which the dispensable substance leaves the ingestible device and enters an environment exterior to the ingestible device; and 2) the interface of the lumen and the surface of the GI tract facing the lumen.

As used herein, the "internal pressure" of an ingestible device refers to the pressure applied to a dispensable substance, such as a therapeutic agent, or a formulation containing a therapeutic agent, contained in the ingestible device prior to delivery of the dispensable substance from the ingestible device. In some embodiments, the internal pressure is provided by the drive force generator of the ingestible device. In certain embodiments, the internal pressure is greater than the fluid pressure. This may be due, for example, to friction, such as O-ring friction, acting on the drive coupling of the ingestible device. This friction is referred to herein as the "piston friction."

"Nozzle pressure" as used herein refers to the pressure of a dispensable substance at a nozzle opening as measured at the surface facing the interior of the nozzle as the dispensable substance is delivered from the ingestible device. In general, for a given ingestible device at a given point in time, the nozzle pressure is approximately the same as the fluid pressure.

"Topical delivery" or "topical administration," as used herein, refers to a route of administration of a dispensable substance (for example, a therapeutic agent or a pharmaceutical formulation containing a therapeutic agent) where the dispensable substance is delivered to a localized area of the body or to the surface of a body part, regardless of the location of the effect; more particularly, the topical administration of the dispensable substance comprises releasing the dispensable substance to the lumen of the GI tract, a surface of the GI tract facing the lumen, a mucous membrane and/or a lining of the gastrointestinal tract of a subject, including, but not limited to, a surface, mucous membrane or lining containing one or more disease sites, such as gastrointestinal mucosal lesions. The effect of the topical delivery or topical administration of the dispensable substance may be local to, or away from (e.g., distal to), the site of the topical administration.

"Epithelial delivery" or "epithelial administration," as used herein, refers to a route of administration of a dispensable substance (for example, a therapeutic agent or a pharmaceutical formulation containing a therapeutic agent) where the dispensable substance is directly delivered into the mucus or onto the epithelium, but not past the epithelial layer, of the GI tract of a subject, such as the small or large intestine, from which the dispensable substance can act locally or peripherally. In some embodiments of epithelial delivery or epithelial administration, the therapeutic agent can move deeper into the GI tissue (i.e., past the epithelial layer) away from the site of direct delivery, such as, for example, via diffusion or active transport.

"Trans-epithelial delivery" or "trans-epithelial administration," as used herein, refers to a route of administration of a dispensable substance (for example, a therapeutic agent or a pharmaceutical formulation containing a therapeutic agent) where the dispensable substance is directly delivered through the epithelial layer of the mucosa of the GI tract to the submucosa of the GI tract of a subject; optionally, at least a portion of the dispensable substance is directly delivered past the epithelial layer to a region of the mucosa beneath the epithelial layer. In embodiments of trans-epithelial delivery in which a portion of the dispensable substance is directly delivered to a region of the mucosa beneath the epithelial layer, at least some (e.g., all) of the portion of the dispensable substance is directly delivered to the lamina propria. Once the therapeutic agent or a pharmaceutical formulation containing a therapeutic agent is directly delivered past the epithelial layer of the GI tract, it is available for systemic exposure of the therapeutic agent to the subject.

The term "response" refers to a measurable response, including complete response (CR) and partial response (PR).

"Complete response" or "CR" as used herein refers to the disappearance of all signs of disease or remission in response to treatment. This does not necessarily mean the disease has been cured.

"Partial response" or "PR" as used herein refers to a decrease of at least 50% in the severity of disease in response to treatment.

"Beneficial response" of a patient to treatment with a therapeutic agent, as used herein, and similar wording, refers to the clinical or therapeutic benefit imparted to a patient at risk for or suffering from a disease or condition. Such benefit includes cellular or biological responses, a complete response, a partial response, a stable disease (without progression or relapse), or a response with a later relapse of the patient from or as a result of the treatment with the agent.

A patient's response can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

General Introduction

Figure 1A:
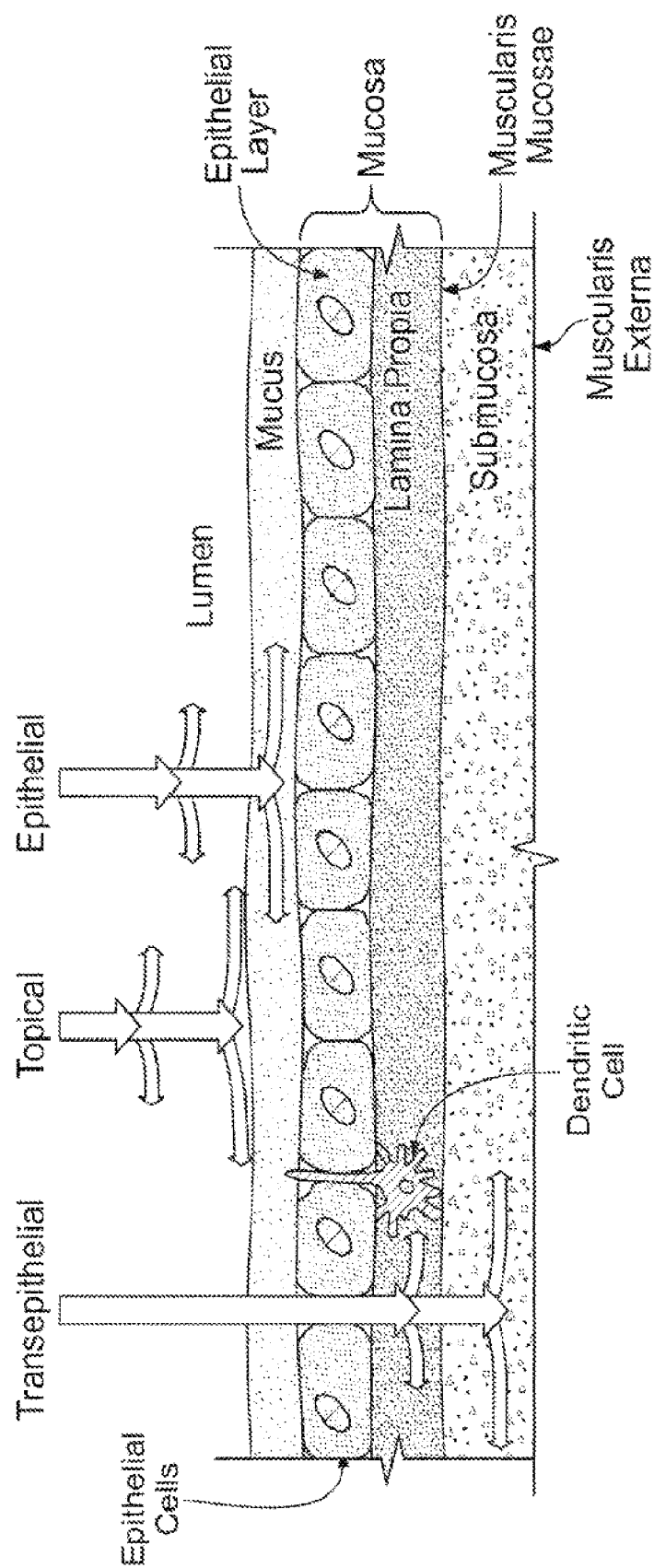
FIG. 1A is a schematic cross section of the different regions of healthy intestinal tissue.
Figure 1B:
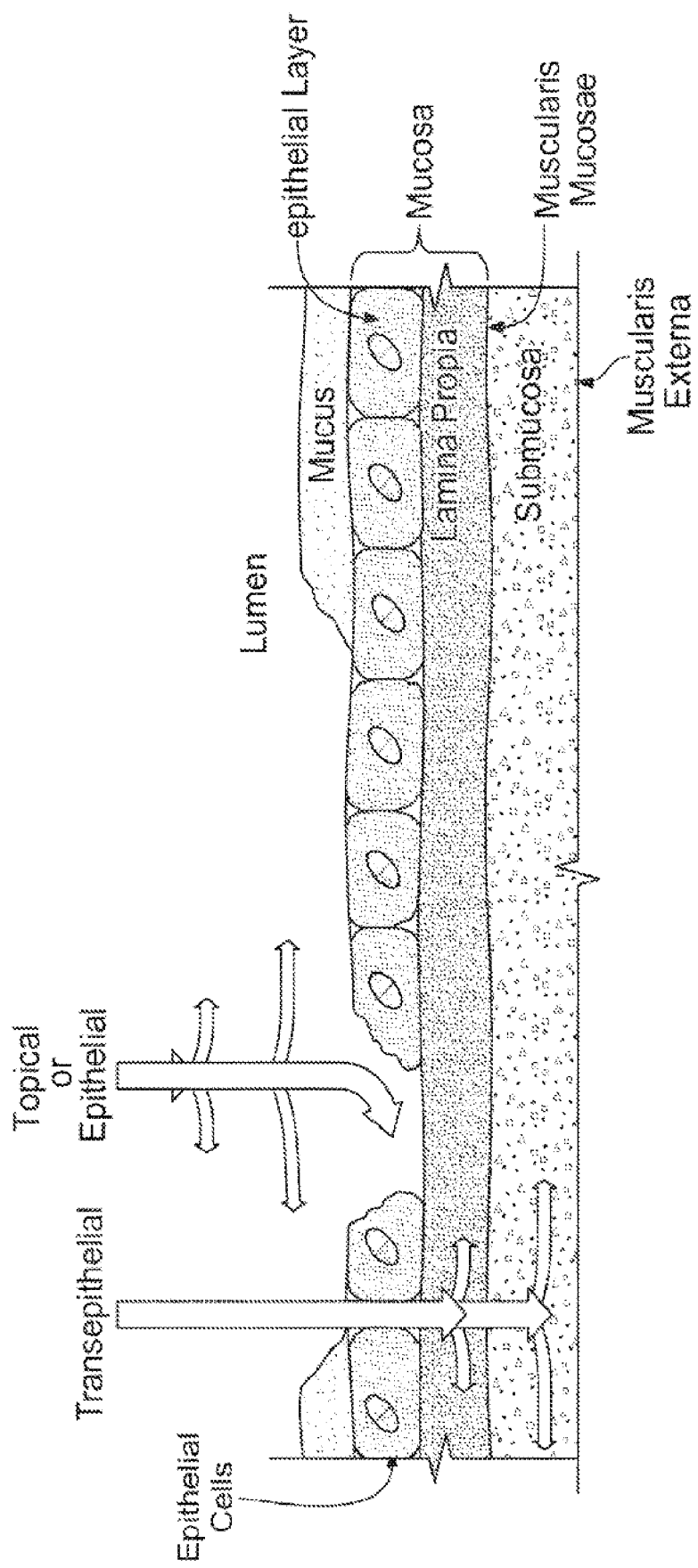
FIG. 1B is a schematic cross section corresponding to FIG. 1A but for diseased intestinal tissue.

FIG. 1A schematically describes the different regions of healthy intestinal tissue, presented in a cross section. The regions include the lumen of the GI tract, the mucus of the GI tissue, the mucosa of the GI tissue and the submucosa of the GI tissue. The mucosa of the GI tissue includes the epithelial layer and the lamina propria. The muscularis mucosae separates the mucosa from the submucosa. The muscularis extrema is below the submucosa. FIG. 1B schematically describes corresponding regions of diseased intestinal tissue, presented in a cross section.

An ingestible device described herein can deliver a therapeutic agent via topical delivery (without being directly delivered to the mucus, mucosa or submucosa), epithelial delivery (directly delivered to the mucus or epithelium without being directly delivered past the epithelial layer to the mucosa or submucosa) or trans-epithelial delivery (directly delivered to the submucosa and/or into a region of the mucosa beneath the epithelial layer, such as the lamina propria.

In general, the form of delivery may depend on the design of the ingestible device and parameters used with the device (e.g., internal pressure, fluid pressure, number of nozzles, design of nozzles). Holding other parameters constant, at relatively low fluid pressures and/or internal pressures, the therapeutic agent may be topically delivered, while higher fluid pressures and/or internal pressures may result in epithelial delivery, and still higher fluid pressures and/or internal pressure may result in trans-epithelial delivery. During trans-epithelial delivery, a bolus of the therapeutic agent initially contained in the dispensable substance may form within the submucosa and/or into a region of the mucosa beneath the epithelial layer, such as the lamina propria.

In some embodiments, the following holds. The ingestible device is designed to deliver a dispensable substance, for example, a therapeutic agent or a pharmaceutical formulation containing a therapeutic agent through the epithelial layer of the mucosa of the GI tract. In some embodiments, the dispensable substance is a solution formulation; optionally, a suspension. In some embodiments, the dispensable substance enters the submucosa and/or into a region of the mucosa beneath the epithelial layer, such as the lamina propria, of the small intestine, where it can be absorbed systemically. After the patient swallows the device, it passes through the GI tract and eventually reaches the small intestine. The device includes a restraining mechanism, an optionally a triggering mechanism (e.g., a degradable and/or erodible coating, such as an enteric coating, that partially or completely degrades and/or erodes when the device reaches the desired location in the GI tract). The desired location can be the small intestine or the large intestine. When the device is configured for trans-epithelial GI tract delivery to the submucosa and/or into a region of the mucosa beneath the epithelial layer, such as the lamina propria, the preferred location can be the small intestine. With the restraining element is removed, relative movement between certain components (e.g., sliding of a component) occurs such that one or more openings in the ingestible device (e.g., in a compartment containing the dispensable substance, such as a reservoir, sometimes referred to herein as the "drug reservoir," "storage reservoir" or "substance reservoir") become aligned with one or more additional openings (e.g., one or more nozzles) in the ingestible device (e.g., in the housing). With the ingestible device now in this open position, a force (e.g., generated by a force generator and/or transferred by a drive coupling, such as a membrane or a piston) forces the dispensable substance from the drug reservoir out of the device via the one or more openings (e.g., the one or more nozzles). The dispensable substance is delivered as a jet of fluid (e.g., liquid) through the epithelial layer of the mucosa and directly into the submucosa and/or into a region of the mucosa beneath the epithelial layer, such as the lamina propria, of the GI tract in the form of single or multiple boluses. After swallowing the device, the device travels through the GI tract (mouth, esophagus, stomach, duodenum, jejunum, ileum, cecum and colon), ultimately exiting the GI tract via the anus.

Thus, in general, the ingestible devices disclosed herein provide delivery of therapeutic agent to the GI tract of a subject. In one aspect, the disclosure relates to trans-epithelial delivery of a dispensable substance (e.g., a therapeutic agent or a formulation comprising a therapeutic agent) to the GI tract of a subject. Accordingly, the disclosure provides an ingestible device that can directly deliver a dispensable substance (e.g., a therapeutic agent or a formulation comprising a therapeutic agent) to the submucosa and/or into a region of the mucosa beneath the epithelial layer, such as the lamina propria, of the GI tract of a subject, which may result in systemic exposure of the therapeutic agent to the subject. In such embodiments, the ingestible device is configured to directly deliver the dispensable substance past the epithelial cell layer of the mucosa and into the submucosa and/or into a region of the mucosa beneath the epithelial layer, such as the lamina propria, of the GI tract, where the therapeutic agent so delivered is available for systemic uptake. In some embodiments, systemic exposure of the therapeutic agent is achieved by trans-epithelial delivery of the dispensable substance into the submucosa and/or into a region of the mucosa beneath the epithelial layer, such as the lamina propria, of the small intestine, for example, in the duodenum, the jejunum, and/or the ileum. In some further embodiments, the trans-epithelial delivery directly delivers the dispensable substance into the submucosa and/or into a region of the mucosa beneath the epithelial layer, such as the lamina propria, of the GI tract such that the percent systemic uptake of the therapeutic agent via the trans-epithelial delivery relative to intravenous or subcutaneous administration is at least about 10% (e.g., at least about 15%, at least about 20%, at least about 25% or more).

In some embodiments, the direct delivery of the therapeutic agent to the submucosa and/or into a region of the mucosa beneath the epithelial layer, such as the lamina propria, via trans-epithelial delivery may also or alternatively provide therapeutic effects locally and/or away from (e.g., distal to) the site of the direct delivery.

In some embodiments, the trans-epithelial delivery may directly deliver a first portion of the dispensable substance to the submucosa of the GI tract, and a second portion of the dispensable substance to the mucosa, all or a further portion of which may be directly delivered to the lamina propria. In some embodiments, the second portion of the dispensable substance delivered to the mucosa, such as the lamina propria, of the GI tract via the trans-epithelial delivery may provide therapeutic effects locally and/or away from (e.g., distal to) the site of the direct delivery.

In another aspect, the disclosure relates to epithelial delivery of a dispensable substance (e.g., a therapeutic agent or a formulation comprising a therapeutic agent) to the GI tract of a subject. Accordingly, the disclosure provides an ingestible device configured to directly deliver a dispensable substance (e.g., a therapeutic agent or a formulation comprising a therapeutic agent) into the mucus, but not past the epithelial layer of the mucosa, of the small or large intestine, from which it may provide therapeutic effects locally and/or away from (e.g., distal to) the site of the direct delivery. In some further embodiments, the ingestible device directly delivers the dispensable substance such that it contacts the surface of the epithelial cell layer of the mucosa facing the lumen, but as previously noted, the epithelial delivery does not directly delivery the dispensable substance past the epithelial layer of the mucosa. In some embodiments, the device is configured so that the dispensable substance is delivered from the device with sufficient force to provide the epithelial delivery, the force being lower than that required for trans-epithelial delivery to the GI tract. In some further embodiments, the epithelial delivery directly delivers the dispensable substance into the mucus of the GI tract such that the percent systemic uptake of the therapeutic agent via the epithelial delivery relative to intravenous or subcutaneous administration is greater than that for topical delivery, but less than for trans-epithelial delivery. In other embodiments, the epithelial delivery directly delivers the dispensable substance into the mucus of the GI tract such that the percent systemic uptake of the therapeutic agent via the epithelial delivery relative to intravenous or subcutaneous administration is about 0.5% to about 10% or more (e.g., about 0.5%, about 2%, about 3%, about 4%, about 5%, about 6%, about 7%, about 8%, about 9%, about 10%, or more).

In some embodiments of epithelial delivery, the therapeutic agent directly delivered into the mucus of the GI tract via the epithelial delivery may undergo active or passive transport or diffusion past the epithelial layer. Once past the epithelial layer, the therapeutic agent may provide therapeutic effects locally and/or away from (e.g., distal to) the site of the direct delivery. In some embodiments, the therapeutic agent binds to a therapeutic target present in the GI epithelial layer or elicits other pharmacodynamic effects locally or away from the site of delivery via immune cells or tissue in the GI tract (e.g., dendritic cells, lymphocytes, mucosa-associated lymphoid tissue).

In yet another aspect, this disclosure relates to topical delivery of a dispensable substance (e.g., a therapeutic agent or a formulation comprising a therapeutic agent) to the GI tract of a subject. Accordingly, the disclosure provides an ingestible device configured to deliver the dispensable substance (e.g., a therapeutic agent or a formulation comprising a therapeutic agent) into the lumen and/or onto the mucus or other surface (e.g., a diseased surface) of the GI tract facing the lumen of the small or large intestine, from which it may provide therapeutic effects locally and/or away from (e.g., distal to) the site of delivery. In some embodiments, the device is configured so that the dispensable substance is delivered from the device with sufficient force so that the dispensable substance is delivered topically, the force being lower than that required for the epithelial or the trans-epithelial delivery to the GI tract. In some embodiments, the topical delivery to the GI tract results in reduced systemic uptake of the therapeutic agent compared to trans-epithelial delivery to the GI tract, intravenous or subcutaneous delivery.

In some further embodiments, topical delivery delivers the dispensable substance into the lumen and/or onto the mucus or the other surface facing the lumen of the GI tract such that the percent systemic uptake of the therapeutic agent via the topical delivery relative to intravenous or subcutaneous administration is less than about 20%, less than about 10%, less than about 5%, less than about 4%, less than about 3%, less than about 2% or less than about 1%. In some embodiments, the topical delivery to the GI tract results in negligible or no systemic uptake of the therapeutic agent compared to trans-epithelial delivery to the GI tract, intravenous or subcutaneous delivery.

In some embodiments, the topically delivered dispensable substance may spread over the mucus or other surface facing the lumen of the GI tract, thereby coating the surface of the GI tract at or away from (e.g., distal to) the site of delivery. In some embodiments, upon or after the dispensable substance has been topically delivered, the therapeutic agent may undergo transport (e.g., diffusion) from the surface of the mucus into the mucus, and optionally, active or passive transport or diffusion past the epithelial layer of the mucosa. In some embodiments, the mucus and/or epithelial layer of the mucosa may be disrupted or even absent, such as in a patient having a disease or condition of the GI tract.

In such embodiments, the topical delivery of the dispensable substance to the GI tract of the patient may provide direct delivery of the dispensable substance to the surface of the GI tract facing the lumen, such as mucosal tissue exposed by said disruption and/or absence (e.g., both the mucus layer and/or epithelial layer are completely or partially absent or compromised in portions of the GI tract due to a disease or condition). For example, in some embodiments, the topical delivery of the dispensable substance to the GI tract of the patient may provide topical delivery to one or more lesions of the GI tract. In some embodiments, the disease or condition is an inflammatory bowel disease. In some further embodiments, the inflammatory bowel disease is ulcerative colitis. In some other embodiments, the inflammatory bowel disease is Crohn's disease.

Accordingly, provided herein are new systemic delivery devices and methods that deliver therapeutic agents into the small intestinal mucosa and/or submucosa by jet injection. Current methods of administration for most large molecule therapeutic agents are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

Also, by providing a higher concentration of therapeutic in GI tissue, the devices and methods described herein are particularly well-suited for treatment of diseases and conditions of the endoderm, including the liver.

In some embodiments of any of the devices or methods described herein, the pharmaceutical composition is an ingestible device, that includes: a housing; a drug reservoir located within the housing and containing the therapeutic; a pre-pressurized air reservoir; a sliding mechanism; and an exit nozzle configured to allow the therapeutic agent to be released out of the housing from the reservoir and into the submucosa and/or the mucosa (e.g., into the lamina propria) of the gastrointestinal tract.

In some embodiments of the devices or methods described herein, the therapeutic is released at a location in the large intestine of the subject. In some embodiments of any of the devices or methods described herein, the location is in the proximal portion of the large intestine. In some embodiments of any of the devices or methods described herein, the location is in the distal portion of the large intestine.

In some embodiments of any of the devices or methods described herein, the therapeutic is released at a location in the ascending colon of the subject. In some embodiments of any of the devices or methods described herein, the location is in the proximal portion of the ascending colon. In some embodiments of any of the devices or methods described herein, the location is in the distal portion of the ascending colon.

In some embodiments of any of the devices or methods described herein, the therapeutic is released at a location in the cecum of the subject. In some embodiments of any of the devices or methods described herein, the location is in the proximal portion of the cecum. In some embodiments of any of the devices or methods described herein, the location is in the distal portion of the cecum.

In some embodiments of any of the devices or methods described herein, the therapeutic is released at a location in the sigmoid colon of the subject. In some embodiments of any of the devices or methods described herein, the location is in the proximal portion of the sigmoid colon. In some embodiments of any of the devices or methods described herein, the location is in the distal portion of the sigmoid colon.

In some embodiments of any of the devices or methods described herein, the therapeutic is released at a location in the transverse colon of the subject. In some embodiments of any of the devices or methods described herein, the location is in the proximal portion of the transverse colon. In some embodiments of any of the devices or methods described herein, the location is in the distal portion of the transverse colon.

In some embodiments of any of the devices or methods described herein, the therapeutic is released at a location in the descending colon of the subject. In some embodiments of any of the devices or methods described herein, the location is in the proximal portion of the descending colon. In some embodiments of any of the devices or methods described herein, the location is in the distal portion of the descending colon.

In some embodiments of any of the devices or methods described herein, the therapeutic is released at a location in the small intestine of the subject. In some embodiments of any of the devices or methods described herein, the location is in the proximal portion of the small intestine. In some embodiments of any of the devices or methods described herein, the location is in the distal portion of the small intestine.

In some embodiments of any of the devices or methods described herein, the therapeutic is released at a location in the duodenum of the subject. In some embodiments of any of the devices or methods described herein, the location is in the proximal portion of the duodenum. In some embodiments of any of the devices or methods described herein, the location is in the distal portion of the duodenum.

In some embodiments of any of the devices or methods described herein, the therapeutic is released at a location in the jejunum of the subject. In some embodiments of any of the devices or methods described herein, the location is in the proximal portion of the jejunum. In some embodiments of any of the devices or methods described herein, the location is in the distal portion of the jejunum.

In some embodiments of any of the devices or methods described herein, the therapeutic is released at a location in the ileum of the subject. In some embodiments of any of the devices or methods described herein, the location is in the proximal portion of the ileum. In some embodiments of any of the devices or methods described herein, the location is in the distal portion of the ileum.

Device Description

General

In general, the ingestible device is suitable for swallowing by a patient and for safely and effectively passing through the GI tract of the patient. Generally, the device can be in the shape of a capsule, a pill or any other swallowable form that may be orally consumed by the subject. In some embodiments, the ingestible device can be swallowed voluntarily under medical supervision or in a home use environment with instruction provided ahead of subsequent ingestion. Generally, ingestible devices are intended for single subject, single use. The ingestible device can have a density high enough to cause the ingestible device to sink within human stomach fluid, e.g., the unfilled ingestible device can have a density of greater than 1.01 g/cm$^3$. The ingestible device can have maximum dimensions that allow the ingestible device to pass through an average human GI tract. In some embodiments, the ingestible device is configured to prevent tumbling in the small intestine of a human. For example, the ingestible device is of sufficient length whereby it will not tumble in the small intestine of a human before, during, or after the dispensable substance is released. Generally, the ingestible device is configured to deliver a sufficient amount of therapeutic agent contained in the dispensable substance to be effective for its intended purpose. In general, the ingestible device's patient-contacting portions (e.g., exterior surface) and dispensable substance-contacting portions are biocompatible. Preferably, the device can withstand an indirect bite force without damaging the housing damage or resulting in leakage. As an example, when containing the dispensable substance, the ingestible device can withstand a bite force of at least about 60 Newtons (N). Generally, unless otherwise intended (see discussion below) components of the ingestible device can withstand exposure to a pH range expected in the human GI tract without substantial loss of functionality, substantial structural damage, or substantial leakage. As an example, in some embodiments, the ingestible device can withstand submersion in a pH 1.5±0.5 fluid environment for at least about 24 hours without substantial loss of functionality, substantial structural damage, or substantial leakage. In general, the ingestible device can maintain an external fluid barrier between the inside of the ingestible device and the GI tract of the subject during transit therethrough. Generally, the ingestible device can withstand external fluid pressures to which it is exposed during use without substantial loss of functionality, substantial structural damage, or substantial leakage. As an example, in some embodiments, the ingestible device undergoes no substantial loss of functionality, substantial structural damage, or substantial leakage when exposed to a sustained pressure of at least about 2 psig for at least about 24 hours and/or when exposed to a momentary pressure of at least about 5 psig momentary pressure for at least about 1 minute.

In general, an ingestible device disclosed herein includes the following features.

Housing

In some embodiments, the ingestible device comprises a housing configured to maintain its mechanical integrity during use of the ingestible device. In some embodiments, the housing has a first portion and a second portion. In some further embodiments, the housing has a first actuation component on the housing, and a second actuation component within the housing. In some embodiments, a storage reservoir is located within the housing, wherein the storage reservoir is configured to store a dispensable substance. In some embodiments, the housing has an opening in fluid communication with the storage reservoir. In some embodiments, the ingestible device employs an electrolytic mechanism for creating one or more openings in the ingestible device, wherein a substance can be dispensed through said opening as described in PCT Application Number PCT/US2019/021814, which published as WO2019178071, and which is incorporated by reference herein. For example, the housing may comprise an external electrolytic circuit (electrolytically erodible surface being on the exterior of the device), whereby the surrounding gastric fluids are the electrolyte that completes an electrolytic circuit between anode and cathode. With sufficient bias voltage (e.g., 1.5-15 volts, such as 3-5 volts), the anode will dissolve or erode electrolytically and thus create an opening in the housing within a desired time interval. In some embodiments, the one or more openings created by an electrolytic mechanism are coupled to one or more nozzles, thereby allowing for trans-epithelial, epithelial, or topical delivery as described herein. In some embodiments an ingestible device includes an enteric coating on the housing. In certain embodiments, the enteric coating covers only certain regions of the housing. The housing may be designed to withstand the chemical and mechanical environment of the GI tract (e.g., effects of muscle contractile forces and concentrated hydrochloric acid in the stomach). A broad range of materials that may be used for the housing. Examples of these materials include, but are not limited to, thermoplastics, fluoropolymers, elastomers, stainless steel, and glass complying with ISO 10993 and USP Class VI specifications for biocompatibility; and any other suitable materials and combinations thereof. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Use of different materials for different components may enable functionalization of certain surfaces for interaction with proteins, antibodies, and other biomarkers. For example, Teflon® may be used as a material in the ingestible device for movable components in order to reduce friction between these components. Other example materials may include other materials commonly used in micro-fabrication, such as polydimethylsiloxane (PDMS), borosilicate glass, and/or silicon. Although specific materials may be referred to herein as being used to construct the device for illustrative purposes, the materials recited are not intended to be limiting, and one skilled in the art may easily adapt the device to use any number of different materials without affecting the overall operation or functionality of the device. In some embodiments, the housing of the ingestible device may be manufactured from a type of plastic, such as a photosensitive acrylic polymer material or an inert polycarbonate material. The housing may also be formed using material that can be sterilized by chemicals. In some embodiments, the wall of the housing may have a thickness of, for example, from about 0.5 millimeter to about 1 millimeter. In some embodiments, in addition to being biocompatible, the material from which the housing is made is non-ferric and non-magnetic. Such materials include various plastics (e.g., PVC, or polycarbonate). Optionally, the housing can include a metal-based material, such as an alloy, stainless steel or a substantially pure metal. Such materials can be sterilized without affecting the mechanical workings of the ingestible device or the exterior surface of the ingestible device. In some embodiments, the metal-based material is compatible with the dispensable substance over long duration of storage. A wide variety of stainless steel alloys satisfy these criteria, including SAE grades 303, 304, 304L, 316, 316L, 440. In consideration of nickel content, purity, and/or traceability, in some embodiments, the stainless steel grade is approved for use as a surgical implant material, such as ASTM grades F138, F1314, F1586, F2229, or F2581. The walls of the housing of the ingestible device generally are sufficiently thick to withstand internal and external pressures to which they are exposed without substantial loss of functionality, substantial structural damage, or substantial leakage. In general, the walls of the housing are desirably as thin as possible to enhance the volume available for containing dispensable substance. As an example, in some embodiments, the walls are from about 0.05 mm to about 0.5 mm thick (e.g., if made of metal-based material, such as stainless steel) or from about 0.1 to about 1 mm thick (e.g., if made of plastic, such as polycarbonate). In general, the housing is made of material with a thermal expansion coefficient low enough that the device does not substantially deform at temperatures encountered during shipping and storage, or within the GI tract. In some embodiments, the walls of the housing are made of an electrolytically erodible surface as described in PCT/US2019/021814, which published as WO2019178071. For example, in some embodiments, the housing includes an electrolytically erodible valve coupled to a nozzle for exposing the liquid volume to its surrounding environment. The exposed metal anode material acting as valve can include a metal alloy or substantially pure metal that is acceptable for human ingestion from consideration of its biocompatibility in the amounts electrolyzed during opening of the valve. It can be desirable to have the thickness of metal in the valve area be small (e.g., to reduce the time and amount of current used to open the valve). For example, the metal portion of the drug container can be 0.025 mm thick across a diameter that matches or slightly exceeds the diameter of the coupled nozzle (e.g., 0.60 mm). In general, the thickness of the metal in the valve area can be in the range 0.002 mm to 0.200 mm.

In some embodiments, the housing of an ingestible device is assembled from multiple modules. For example, in some embodiments, the housing is assembled from two modules. In such embodiments, one of the modules can contain the dispensable substance ("drug module"), and the other module can contain the drive force generator and the drive coupling ("drive module"). Typically, the drug module includes a housing part of appropriate size, shape and material(s) as discussed herein. Usually, the housing part is sterilized, and dispensable substance is subsequently disposed within the housing under aseptic conditions. Optionally a sterile seal (e.g., a sterile foil seal) is incorporated into the drug module. The components of the drug module (e.g., a housing part, a drive force generator, a drive coupling) are assembled in a clean environment. The drug module and the drive module are subsequently combined to form the ingestible device. Representative examples of modules, their separate assembly, and their combination to form an ingestible device, are provide elsewhere herein.

Generally, an ingestible device is sized and shaped for relatively safe and effective movement and intended use within the GI tract of the subject. In certain embodiments, an ingestible device is a capsule having an industry standard size. For example, in some embodiments, an ingestible device is configured as a 00 capsule or a 000 capsule. In certain embodiments, the housing of an ingestible device has a length of at least about 20 mm (e.g., at least about 21 mm, at least about 22 mm, at least about 23 mm) and/or at most about 28 mm (e.g., at most about 27 mm, at most about 26 mm).

In some embodiments, the housing of an ingestible device has a diameter of at least about 7 mm (e.g., at least about 7.5 mm, at least about 8 mm, at least about 8.5 mm, at least about 9 mm, at least about 9.5 mm) and/or at most about 12 mm (e.g., at most about 11.5 mm, at most about 11 mm, at most about 10.5 mm, at most about 10 mm, at most about 9.5 mm, at most about 9 mm).

In certain embodiments, the housing of an ingestible device has an aspect ratio (ratio of length to width) of at least about 0.75 (e.g. at least about 1) and/or at most about 4 (e.g., at most about 3, at most about 2). In some embodiments, the housing of an ingestible device has an aspect ratio of from about 0.75 to 4 (e.g., from about 1 to about 3, from about 1 to about 2). For example, in some embodiments, the housing aspect ratio is about 1.5:1 (length:diameter). In some other embodiments, the housing aspect ratio is about 2:1 (length:diameter).

In certain embodiments, the housing of an ingestible device has a wall thickness of at least about 0.05 mm (e.g., at least about 0.5 mm, at least about 0.6 mm, at least about 0.7 mm) and/or at most about 1 mm (e.g., at most about 0.9 mm, at most about 0.8 mm). In certain embodiments, an ingestible device has a wall thickness of from about 0.05 mm to about 0.5 mm. In some embodiments, an ingestible device has a wall thickness of from about 0.1 mm to about 1 mm. In certain embodiments, one region of the housing of an ingestible device may have a wall thickness that is different from that of a different region of the housing of the ingestible device.

In some embodiments, the housing of an ingestible device has an end round that is spline-shaped or that is spherical. In certain embodiments, an ingestible device has an end round that is from about 1 mm to about 2 mm (e.g., about 1.5 mm). In some embodiments, an ingestible device has an end round that is from about 4 mm to about 4.5 mm (e.g., about 4.25 mm). In certain embodiments, an ingestible device has an end round that is from about 4.9 to about 5 mm (e.g., about 4.95 mm). In some embodiments, an ingestible device has an end round that is from about 5.4 mm to about 5.6 mm (e.g., about 5.5 mm).

In certain embodiments, the housing of an ingestible device has an internal volume of at least about 700 µL (e.g., at least about 750 µL, at least about 800 µL, at least about 850 µL) and/or most about 1700 µL (e.g., at most about 1650 µL, at most about 1600 µL, at most about 1500 µL, at most about 1400 µL, at most about 1300 µL, at most about 1200 L).

In an exemplary embodiment, the housing of an ingestible device has a diameter of about 11 mm, a length of about 26 mm, a wall thickness of about 0.8 mm, an end round of about 1.5 mm, and an internal volume of about 1685 µL.

In another exemplary embodiment, the housing of an ingestible device has a diameter of about 11 mm, a length of about 26 mm, a wall thickness of about 0.8 mm, an end round of about 5.5 mm (spherical), and an internal volume of about 1475 µL.

In a further exemplary embodiment, the housing of an ingestible device has a diameter of about 9.9 mm, a length of about 26 mm, a wall thickness of about 0.8 mm, an end round of about 1.5 mm, and an internal volume of about 1315 µL.

In yet another exemplary embodiment, the housing of an ingestible device has a diameter of about 9.9 mm, a length of about 26 mm, a wall thickness of about 0.8 mm, an end round of about 4.95 mm (spherical), and an internal volume of about 1177 µL.

In a further exemplary embodiment, the housing of an ingestible device has a diameter of about 8.5 mm, a length of about 23.3 mm, a wall thickness of about 0.7 mm, an end round of about 1.5 mm, and an internal volume of about 861 µL.

In still a further exemplary embodiment, the housing of an ingestible device has a diameter of about 8.5 mm, a length of about 23.3 mm, a wall thickness of about 0.7 mm, an end round of about 4.25 mm (spherical), and an internal volume of about 773 µL.

In yet a further exemplary embodiment, the housing of an ingestible device has a diameter of about 8.5 mm, a length of about 23.3 mm, a wall thickness of about 0.7 mm, an end round that is spline-shaped, and an internal volume of about 820 µL.

Fluid Volume

The ingestible device includes a fluid volume to contain a dispensable substance (e.g., a liquid, a suspension). In some embodiments, the fluid volume is completely disposed within the housing. Optionally, the fluid volume can be defined by a storage reservoir. Such a storage reservoir can be a component that can be prepared separately from the housing. In such a storage reservoir, the dispensable substance can be disposed in the storage reservoir before the storage reservoir is associated with the ingestible device.

Dispensable Substance

The device may include one or more dispensable substances, with each dispensable substance including one or more therapeutic agents and/or one or more pharmaceutical formulations including one or more therapeutic agents.

Nozzles

In some embodiments, an ingestible device includes one or more nozzles in fluid communication with the one or more openings in the ingestible device. The nozzle(s) is(are) configured so that the dispensable substance through the nozzle(s) when the dispensable substance is delivered from the ingestible device. In general, a nozzle can have any desired size and shape appropriate for the desired type of delivery of a dispensable substance from the ingestible device. In certain embodiments, a nozzle has a shape and/or size appropriate for trans-epithelial delivery, epithelial delivery or topical delivery. In some embodiments, an ingestible device includes more than one nozzle. For example, an ingestible device can include, for example, up to 50 nozzles (e.g., up to 40 nozzles, up to 35 nozzles, up to 30 nozzles, up to 25 nozzles, up to 20 nozzles, up to 15 nozzles, 10 nozzles). In some embodiments, an ingestible device includes from 2 nozzles to 50 nozzles. In certain embodiments, an ingestible device includes 2 nozzles, three nozzles, four nozzles, five nozzles, six nozzles, seven nozzles, eight nozzles, 10 nozzles, 20 nozzles, 30 nozzles, 36 nozzles, 40 nozzles, 50 nozzles). In some embodiments, the nozzles are arranged at even intervals (optionally pairwise if an even number of nozzles are used) around the circumference of the device.

Restraining Mechanism

In some embodiments, the ingestible device comprises a restraining mechanism. Generally, a restraining mechanism has a first state in which it is configured to prevent the dispensable substance from exiting the ingestible device via the opening(s), and a second state in which it is configured so that it does not prevent the dispensable substance from exiting the ingestible device via the opening(s). The restraining mechanism can be configured to transition from its first state to its second state when it is exposed to a triggering condition. The restraining mechanism may be provided by one or more restraining elements. The restraining elements can have a first state in which they are configured to prevent the dispensable substance from exiting the ingestible device via the openings, and a second state in which they are configured to allow the dispensable substance to exit the ingestible device via the openings. The restraining elements can be configured to transition from the first state to the second state when the restraining elements are exposed to a triggering condition. In some embodiments, the restraining elements comprise a first type of restraining element and a second type of restraining element different from the first type of restraining element. The first type of restraining element can be configured to transition to its second state before the second type of restraining element transitions to its second state. In some embodiments, a restraining elements comprises a lid, a pin, a band, a plug, a dowel, a clasp, a clamp, a flange, a rivet, or any combination thereof. In some embodiments, the restraining elements comprise a plasticizer such as triethyl citrate (TEC). In some embodiments, the restraining elements comprise a degradable and/or erodible material, such as, for example, an enteric material. The enteric material may be degradable and/or erodible in the small intestine of the GI tract, or may be degradable and/or erodible in the large intestine of the GI tract, for example, the colon. In some embodiments, a restraining mechanism can be a mechanism that prevents the dispensable substance from being delivered from the ingestible device even when the drive force generator (or optionally the drive coupling) applies an internal force. For example, such a restraining can be an element (e.g., a pin, a band, a plug) in the opening (e.g., nozzle opening) through which the dispensable substance can be delivered from the ingestible device. Such a restraining element can be formed, for example, of a material that degrades and/or erodes as discussed above.

Triggering Mechanism

In some embodiments, the ingestible device comprises a triggering mechanism. In some embodiments, a triggering mechanism is configured to cause the dispensable substance within the fluid volume to be released under one or more triggering conditions. In some embodiments, a triggering mechanism initiates a drive force generator. In some embodiments, a triggering mechanism incorporates a mechanical feature like a restraining mechanism. As an example, one or more restraining elements degrade and/or erode in the presence of certain GI tract conditions (e.g., pH greater than 5), thereby triggering a drive force generator, such as a compressed spring. As another example, a spring may have a piercing element that pierces a cylinder with compressed gas, whereby the released gas acts as a force applied to a dispensable substance. In certain embodiments, a triggering mechanism incorporates an electrical feature. For example, an enteric coating degrades and/or erodes in the presence of certain GI tract conditions (e.g., pH greater than 5), thereby exposing conductors to intestinal fluid, which acts as a liquid conductor to triggering the drive force generator. In some embodiments, a triggering condition relates to a condition of the GI tract. In some embodiments, the condition of the GI tract comprises at least one condition selected from the group consisting of temperature, pH, presence of one or more enzymes, and time. In some more particular embodiments, the condition of the GI tract is a pH of greater than 5. In certain embodiments, the triggering mechanism is configured so that the release mechanism is autonomously triggered (e.g., due to degradation, dissolution and/or erosion of the restraining mechanism due to conditions in the GI tract).

In some embodiments of any of the devices or methods described herein, the releasing of the therapeutic is triggered by one or more of: a pH in the jejunum of about 6.1 to about 7.2, a pH in the mid small bowel of about 7.0 to about 7.8, a pH in the ileum of about 7.0 to about 8.0, a pH in the right colon of about 5.7 to about 7.0, a pH in the mid colon of about 5.7 to about 7.4, or a pH in the left colon of about 6.3 to about 7.7, such as about 7.0.

Drive Force Generator

The drive force generator is configured to provide the requisite force to the dispensable substance such that, when the restraining mechanism is removed, the dispensable substance is delivered from the ingestible device as desired. The drive force generator can apply force using different mechanisms, including, for example, a compressed gas, a gas generated by chemical reaction, a spring, a liquid-gas mixture, an impact ram, a sudden expansion caused by a controlled exothermic reaction, or the like. When the drive force generator is a spring, the spring can have one or more of the following properties: the outer diameter of the spring is smaller than the inner diameter of the ingestible device; the compressed length of the spring is minimized to leave more space for dispensable substance; the spring is of a conical shape, potentially with a reduction in the solid length of the spring; the free length of the spring is maximized and larger than the free length of the inner cavity of the ingestible device to ensure an acceptable driving pressure is provided throughout the entire time step of delivery; and the spring rate is large enough to provide acceptable pressure from the beginning until the end of delivery of the dispensable substance. Examples of springs include parallel springs, wave springs and conical springs. Examples of chemical reactants include an airbag inflator, a hydrogen cell (e.g., a Varta hydrogen cell), sodium bicarbonate and acid (e.g., alka seltzer and water on board the ingestible device, alka seltzer and GI tract fluid). Examples of compressed gas include a gas charged within the ingestible device, and a container (e.g., cylinder) of compressed gas. In some embodiments, the compressed gas is a gas cylinder from Picocyl. Exemplary gas cylinders are disclosed, for example, in US 2017-0258583, which is incorporated by reference herein. An example of a liquid-gas mixture is liquid nitrogen/HFA (hexafluoroacetone)/propane. An example of an impact ram is a two-phase spring/ram. Other examples of drive force generators include a wax actuator, heat generated by electric power (Peltier effect-based mechanism), and a mechanical puncture of tissue followed by delivery.

Drive Coupling

In general, the drive force coupling transfers a force from the drive force generator to the dispensable substance. Examples of a drive coupling include a piston and a membrane. Examples of membranes include balloons and elastomeric materials. An example of a piston is an O-ring sealed piston. In some embodiments, a piston is provided by a gas cylinder, e.g., with added O-rings or a custom housing. In some embodiments, a drive coupling is a vein, such as a rotating vein. In certain embodiments, a drive coupling is a double piston configured to counteract cap impact. In certain embodiments, a drive coupling is a collapsing bag, such as a collapsing foil bag. In some embodiments, a drive coupling is a collapsing bellows.

Storage Reservoir

In some embodiments, an ingestible device includes a storage reservoir configured to store a dispensable substance. In some embodiments, the storage reservoir stores the dispensible substance. In some embodiments, the storage reservoir is completely disposed within the housing.

Figure 2:
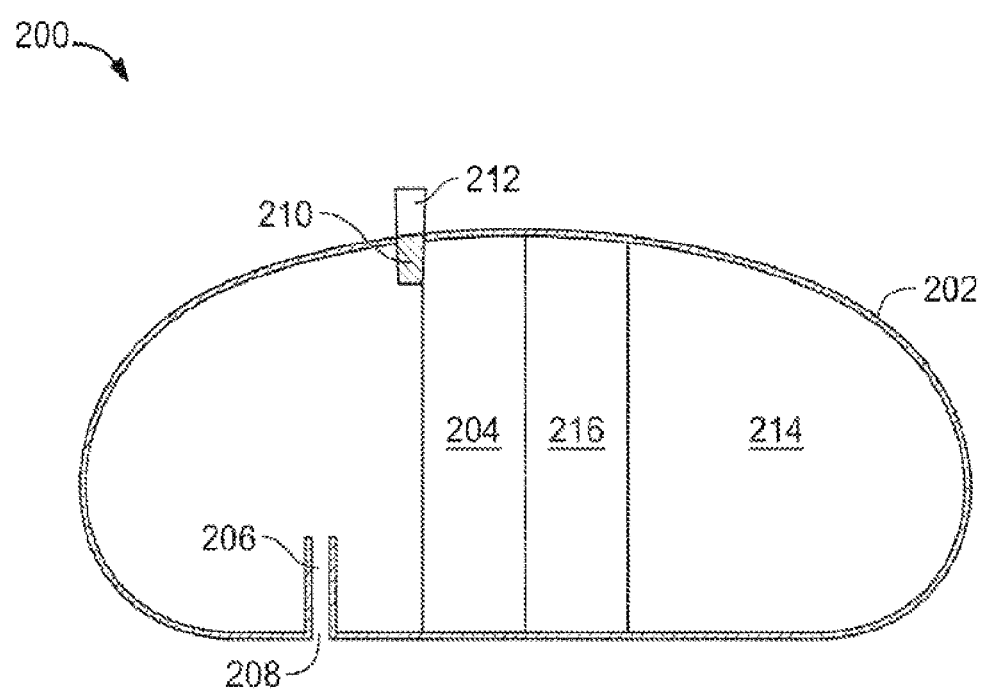
FIG. 2 is a cross section of an ingestible device.

FIG. 2 is a schematic representation of an ingestible device 200 which includes a housing 202, a fluid volume 204 containing a dispensable substance, a nozzle 206 with a nozzle opening 208, a restraining mechanism 210, a triggering mechanism 212, a drive force generator 214 and drive coupling 216. During use, ingestible device 200 is swallowed by a subject and traverses the GI tract. At an appropriate location, the triggering mechanism 212 is triggered, allowing the drive force generator to apply pressure to the drive coupling 216, which then applies pressure to the fluid volume such that at least some of the dispensable substance is delivered out of fluid volume 204, through the nozzle 206, and out of the device 200 via the nozzle opening 208. In some embodiments, the internal pressure is applied, even before the triggering mechanism 212 is triggered. As an example, at an appropriate location, the triggering mechanism 212 is triggered, allowing the drive coupling 216 to apply pressure to the fluid volume 204. In certain embodiments, the internal pressure is not applied until the triggering mechanism 212 is triggered.

Device for Trans-Epithelial Delivery

Generally, trans-epithelial delivery can be achieved at any desired location within the GI tract of a subject. In some embodiments, trans-epithelial delivery is achieved in the small intestine of the subject, such as, for example, in the duodenum, the jejunum and/or the ileum. In certain embodiments, trans-epithelial delivery is achieved in the large intestine of the subject, such as, for example, the cecum or the colon.

In general, an ingestible device for trans-epithelial delivery is configured to deliver a jet of the dispensable substance having a peak jet power of from at least about 1 Watt (e.g., at least about 1.1 Watts, at least about 1.2 Watts, at least about 1.3 Watts, at least about 1.4 Watts, at least about 1.5 Watts, at least about 1.6 Watts, at least about 1.7 Watts, at least about 1.8 Watts) and/or at most about 3 Watts (e.g., at most about 2.9 Watts, at most about 2.8 Watts, at most about 2.7 Watts, at most about 2.6 Watts, at most about 2.5 Watts, at most about 2.4 Watts, at most about 2.3 Watts, at most about 2.2 Watts, at most about 2.1 Watts). In some embodiments, an ingestible device for trans-epithelial delivery is configured to deliver a jet of the dispensable substance having a peak jet power of from about 1 Watt to about 3 Watts (e.g., of from about 1.3 Watts to about 2.8 Watts, of from about 1.5 Watts to about 2.5 Watts).

In general, an ingestible device for trans-epithelial delivery is configured to deliver a jet of the dispensable substance having a minimum jet power of at least about 0.1 W (e.g., at least about 0.2 W, at least about 0.3 W) and/or at most about 0.6 W (e.g., at most about 0.5 W, at most about 0.4 W). In some embodiments, a device for trans-epithelial delivery is configured to deliver a jet of the dispensable substance having a minimum jet power of from about 0.1 W to about 0.6 W (e.g., from about 0.2 W to about 0.5 W, from about 0.3 W to about 0.4 W).

In general, an ingestible device for trans-epithelial delivery is configured to deliver a jet of the dispensable substance having an average jet power of at least about 0.5 W (e.g., about 0.8 W, about 1 W) and/or at most about 2 W (e.g., at most about 1.7 W, at most about 1.5 W). In some embodiments, a device for trans-epithelial delivery is configured to deliver a jet of the dispensable substance having an average jet power of from about 0.5 W to about 2 W (e.g., from about 0.8 W to about 1.7 W, from about 1 W to about 1.5 W).

Generally, an ingestible device for trans-epithelial delivery is configured to deliver a jet of the dispensable substance having a peak jet pressure of at least about 100 psig (e.g., at least about 110 psig, at least about 120 psig, at least about 130 psig, at least about 140 psig, at least about 150 psig, at least about 160 psig, at least about 170 psig, at least about 180 psig, at least about 190 psig) and/or at most about 250 psig (e.g., at most about 240 psig, at most about 230 psig, at most about 220 psig, at most about 210 psig). In certain embodiments, an ingestible device for trans-epithelial delivery is configured to deliver a jet of the dispensable substance having a peak jet pressure of from about 100 psig to about 250 psig (e.g., from about 140 psig to about 225 psig, from about 180 psig to about 205 psig).

In general, an ingestible device for trans-epithelial delivery is configured to deliver a jet of the dispensable substance having a minimum jet pressure of at least about 30 psig (e.g., at least about 40 psig, at least about 50 psig) and/or at most about 80 psig (e.g., at most about 70 psig, at most about 60 psig. In some embodiments, an ingestible device for trans-epithelial delivery is configured to deliver a jet of the dispensable substance having a minimum jet pressure of from about 30 psig to about 80 psig (e.g., from about 40 psig to about 70 psig, from about 50 psig to about 60 psig).

In general, an ingestible device for trans-epithelial delivery is configured to deliver a jet of the dispensable substance having an average jet pressure of 60 psig (e.g., at least about 80 psig, at least about 100 psig) and/or at most about 160 psig (e.g., at most about 140 psig, at most about 120 psig). In some embodiments, an ingestible device for trans-epithelial delivery is configured to deliver a jet of the dispensable substance having an average jet pressure of from about 60 psig to about 160 psig (e.g., from about 80 psig to about 140 psig, from about 100 psig to about 120 psig).

In general, an ingestible device for trans-epithelial delivery is configured to deliver a jet of the dispensable substance having a peak jet force of at least about 0.09 Newton (N) (e.g., at least about 0.1 N, at least about 0.11 N, at least about 0.12 N, at least about 0.13N) and/or at most about 0.15 N (e.g., at most about 0.14 N). In some embodiments, an ingestible device for trans-epithelial delivery is configured to deliver a jet of the dispensable substance having a peak jet force of from about 0.09 N to about 0.15 N (e.g., from about 0.1 N to about 0.14 N, from about 0.11 N to about 0.14 N). In general, an ingestible device for trans-epithelial delivery is configured to deliver a jet of the dispensable substance having a minimum jet force of at least about 0.01 N (e.g., at least about 0.02 N, at least about 0.03 N) and/or at most about 0.06 N (e.g., at most about 0.05 N at most about 0.04 N). In some embodiments, an ingestible device for trans-epithelial delivery is configured to deliver a jet of the dispensable substance having a minimum jet force of from about 0.01 N to about 0.06 N (e.g., from about 0.02 N to about 0.05 N, from about 0.03 N to about 0.04 N).

In general, an ingestible device for trans-epithelial delivery is configured to deliver a jet of the dispensable substance having an average jet force of at least about 0.05 N (e.g., at least about 0.06 N, at least about 0.07 N) and/or at most about 0.1 N (e.g., at most about 0.09 N, at most about 0.08 N). In some embodiments, an ingestible device for trans-epithelial delivery is configured to deliver a jet of the dispensable substance having an average jet force of from about 0.05 N to about 0.1 N (e.g., from about 0.06 N to about 0.09 N, from about 0.07 N to about 0.08 N).

Generally, an ingestible device for trans-epithelial delivery is configured to deliver a jet of the dispensable substance having a peak jet velocity of at least about 25 meters per second (m/s) (e.g., at least about 26 m/s, at least about 27 m/s, at least about 28 m/s, at least about 29 m/s, at least about 30 m/s, at least about 31 m/s, at least about 32 m/s, at least about 34 m/s, at least about 35 m/s, at least about 36 m/s) and/or at most about 45 m/s (e.g., at most about 44 m/s, at most about 43 m/s, at most about 42 m/s, at most about 41 m/s, at most about 40 m/s, at most about 39 m/s, at most about 38 m/s, at most about 37 m/s). In some embodiments, an ingestible device for trans-epithelial delivery is configured to deliver a jet of the dispensable substance having a peak jet velocity of from about 25 m/s to about 45 m/s (e.g., from about 30 m/s to about 42 m/s, from about 34 m/s to about 39 m/s, about 36.5 m/s).

In general, an ingestible device for trans-epithelial delivery is configured to deliver a jet of the dispensable substance having a minimum jet velocity of at least about 15 m/s (e.g., at least about 16 m/s, at least about 17 m/s) and/or at most about 22 m/s (e.g., at most about 21 m/s, at most about 20 m/s). In some embodiments, an ingestible device for trans-epithelial delivery is configured to deliver a jet of the dispensable substance having a minimum jet velocity of from about 15 m/s to about 22 m/s (e.g., from about 16 m/s to about 21 m/s, from about 17 m/s to about 20 m/s).

In general, an ingestible device for trans-epithelial delivery is configured to deliver a jet of the dispensable substance having an average jet velocity of at least about 20 m/s (e.g., at least about 25 m/s) and/or at most about 35 m/s (e.g., at most about 30 m/s). In some embodiments, an ingestible device for trans-epithelial delivery is configured to deliver a jet of dispensable substance having an average jet velocity of from about 20 m/s to about 30 m/s (e.g., about 20 m/s, about 21 m/s, about 22 m/s, about 23 m/s, about 24 m/s, about 25 m/s, about 26 m/s, about 27 m/s, about 28 m/s about 29 m/s, about 30 m/s). In certain embodiments, an ingestible device for trans-epithelial delivery is configured to deliver a jet of dispensable substance having an average jet velocity of from about 25 m/s to about 35 m/s (e.g., about 25 m/s, about 26 m/s, about 27 m/s, about 28 m/s, about 29 m/s, about 30 m/s, about 31 m/s, about 32 m/s, about 33 m/s about 34 m/s, about 35 m/s).

In general, an ingestible device for trans-epithelial delivery is configured to deliver a jet of a dispensable substance having a jet stable length of at least about 0.5 millimeter (mm) (e.g., at least about 1 mm, at least about 1.5 mm, at least about 2 mm, at least about 2.5 mm, at least about 3 mm, at least about 3.5 mm, at least about 4 mm, at least about 4.5 mm, at least about 5 mm) and/or at most about 20 mm (e.g., at most about 15 mm, at most about 10 mm). In certain embodiments, an ingestible device for trans-epithelial delivery is configured to deliver a jet of a dispensable substance having a jet stable length of from about 0.5 mm to about 20 mm (e.g., from about 2 mm to about 20 mm, from about 5 mm to about 20 mm).

In some embodiments, an ingestible device for trans-epithelial delivery is configured to deliver a jet of a dispensable substance having a jet diameter of at least about 0.1 mm (e.g., at least about 0.2 mm, at least about 0.3 mm, at least about 0.4 mm) and/or at most about 2 mm (e.g., at most about 1.5 mm, at most about 1 mm, at most about 0.9 mm, at most about 0.8 mm, at most 0.7 mm, at most about 0.6 mm, at most about 0.5 mm). For example, such an ingestible device for trans-epithelial delivery is configured to deliver a jet of a dispensable substance having a jet diameter of from about 0.1 mm to about 2 mm (e.g., from about 0.2 mm to about 0.5 mm, from about 0.3 mm to about 0.4 mm, from about 0.3 mm to about 0.5 mm, about 0.35 mm).

In general, an ingestible device for trans-epithelial delivery is configured to provide an internal pressure of at least about 225 psig (e.g., at least about 235 psig, at least about 245 psig, at least about 255 psig, at least about 265 psig, at least about 275 psig, at least about 285 psig, at least about 295 psig, at least about 305 psig, at least about 315 psig) and/or at most about 425 psig (e.g., at most about 400 psig, at most about 390 psig, at most about 380 psig, at most about 375 psig, at most about 370 psig, at most about 360 psig, at most about 350 psig, at most about 340 psig, at most about 330 psig). In certain embodiments, an ingestible device for trans-epithelial delivery is configured to provide an internal pressure of from about 225 psig to about 400 psig (e.g., from about 250 psig to about 375 psig, from about 300 psig to about 340 psig).

In general, an ingestible device for trans-epithelial delivery is configured to have a nozzle pressure at least about 150 psig (e.g., at least about 175 psig, at least about 200 psig, at least about 210 psig, at least about 220 psig, at least about 225 psig, at least about 230 psig, at least about 240 psig, at least about 250 psig, at least about 260 psig, at least about 270 psig, at least about 275 psig, at least about 280 psig, at least about 290 psig, at least about 300 psig, at least about 325 psig) and/or at most about 400 psig (e.g., at most about 375 psig, at most about 365 psig, at most about 355 psig, at most about 350 psig, at most about 345 psig, at most about 335 psig, at most about 325 psig, at most about 315 psig, at most about 305 psig). In certain embodiments, an ingestible device for trans-epithelial delivery is configured to have a nozzle pressure of from about 150 psig to about 400 psig (e.g., from about 150 psig to about 300 psig, from about 180 psig to about 400 psig, from about 190 psig to about 400 psig, from about 200 psig to about 400 psig, from about 200 psig to about 375 psig, from about 210 psig to about 400 psig, from about 220 psig to about 400 psig, from about 220 psig to about 375 psig, from about 220 psig to about 350 psig, from about 225 psig to about 400 psig, from about 225 psig to about 375 psig, from about 225 psig to about 350 psig, from about 225 psig to about 325 psig, from about 230 psig to about 400 psig, from about 235 psig to about 250 psig, from about 240 psig to about 400 psig, from about 245 psig to about 400 psig, from about 250 psig to about 400 psig, from about 250 psig to about 375 psig, from about 250 psig to about 350 psig, from about 250 psig to about 325 psig, from about 255 psig to about 400 psig, from about 260 psig to about 400 psig, from about 265 psig to about 400 psig, from about 270 psig to about 400 psig, from about 275 psig to about 400 psig, from about 275 psig to about 375 psig, from about 275 psig to about 350 psig, from about 275 psig to about 325 psig, from about 280 psig to about 400 psig, from about 280 psig to about 320 psig, from about 300 psig to about 375 psig, from about 285 psig to about 400 psig, from about 290 psig to about 400 psig, from about 300 psig to about 400 psig, from about 300 psig to about 375 psig, from about 300 psig to about 350 psig, from about 300 psig to about 325 psig, from about 305 psig to about 400 psig, from about 310 psig to about 400 psig, from about 315 psig to about 400 psig, from about 320 psig to about 400 psig, from about 320 psig to about 375 psig, from about 330 psig to about 400 psig, from about 335 psig to about 400 psig, from about 340 psig to about 400 psig, from about 345 psig to about 400 psig, from about 350 psig to about 400 psig). In some embodiments, an ingestible device for trans-epithelial delivery is configured to have a nozzle pressure of between about 220-350 psig (e.g., about 225-350 psig, about 230-350 psig, about 235-350 psig, about 240-350 psig, about 245-350 psig, about 250-350 psig, about 255-350 psig, about 260-350 psig, about 265-350 psig, about 270-350 psig, about 275-350 psig, about 280-350 psig, about 285-350 psig, about 290-350 psig, about 300-350 psig, about 220-325 psig, about 225-325 psig, about 230-325 psig, about 235-325 psig, about 240-325 psig, about 245-325 psig, about 250-325 psig, about 255-325 psig, about 260-325 psig, about 265-325 psig, about 270-325 psig, about 275-325 psig, about 280-325 psig, about 285-325 psig, about 290-325 psig, about 300-300 psig, about 220-300 psig, about 225-300 psig, about 230-300 psig, about 235-300 psig, about 240-300 psig, about 245-300 psig, about 250-300 psig, about 255-300 psig, about 260-300 psig, about 265-300 psig, about 270-300 psig, about 275-300 psig, about 280-300 psig, about 285-300 psig, about 290-300 psig, about 220-290 psig, about 225-290 psig, about 230-290 psig, about 235-290 psig, about 240-290 psig, about 245-290 psig, about 250-290 psig, about 255-290 psig, about 260-290 psig, about 265-290 psig, about 270-290 psig, about 275-290 psig, about 280-290 psig, about 285-290 psig, about 220-280 psig, about 225-280 psig, about 230-280 psig, about 235-280 psig, about 240-280 psig, about 245-280 psig, about 250-280 psig, about 255-280 psig, about 260-280 psig, about 265-280 psig, about 270-280 psig, about 275-280 psig, about 220-270 psig, about 225-270 psig, about 230-270 psig, about 235-270 psig, about 240-270 psig, about 245-270 psig, about 250-270 psig, about 255-270 psig, about 260-270 psig, about 265-270 psig, about 220-260 psig, about 225-260 psig, about 230-260 psig, about 235-260 psig, about 240-260 psig, about 245-260 psig, about 250-260 psig, about 255-260 psig, about 220-225 psig, about 225-235 psig, about 230-240 psig, about 235-245 psig, about 240-250 psig, about 245-260 psig, about 250-265 psig, about 255-270 psig, about 260-275 psig, about 265-285 psig, about 270-290 psig, about 275-295 psig, about 280-300 psig, about 285-305 psig, about 290-310 psig, about 300-315 psig, about 310-320 psig, about 220-230 psig, about 220-235 psig, about 220-240 psig, about 220-245 psig, about 220-250 psig, about 220-260 psig, about 220-265 psig, about 220-270 psig, about 220-275 psig, about 220-285 psig, about 220-290 psig, about 220-295 psig, about 220-300 psig, about 220-305 psig, about 220-310 psig, about 220-315 psig, about 220-320 psig, about 230-235 psig, about 230-240 psig, about 230-245 psig, about 230-250 psig, about 230-260 psig, about 230-265 psig, about 230-270 psig, about 230-275 psig, about 230-285 psig, about 230-290 psig, about 230-295 psig, about 230-300 psig, about 230-305 psig, about 230-310 psig, about 230-315 psig, about 230-320 psig, about 240-245 psig, about 240-250 psig, about 240-260 psig, about 240-265 psig, about 240-270 psig, about 240-275 psig, about 240-285 psig, about 240-290 psig, about 240-295 psig, about 240-300 psig, about 240-305 psig, about 240-310 psig, about 240-315 psig, about 240-320 psig, about 250-260 psig, about 250-265 psig, about 250-270 psig, about 250-275 psig, about 250-285 psig, about 250-290 psig, about 250-295 psig, about 250-300 psig, about 250-305 psig, about 250-310 psig, about 250-315 psig, about 250-320 psig, about 260-265 psig, about 260-270 psig, about 260-275 psig, about 260-285 psig, about 260-290 psig, about 260-295 psig, about 260-300 psig, about 260-305 psig, about 260-310 psig, about 260-315 psig, about 260-320 psig, about 270-275 psig, about 270-285 psig, about 270-290 psig, about 270-295 psig, about 270-300 psig, about 270-305 psig, about 270-310 psig, about 270-315 psig, about 270-320 psig, about 280-285 psig, about 280-290 psig, about 280-295 psig, about 280-300 psig, about 280-305 psig, about 280-310 psig, about 280-315 psig, about 280-320 psig, about 290-295 psig, about 290-300 psig, about 290-305 psig, about 290-310 psig, about 290-315 psig, about 290-320 psig, about 150 psig, about 300 psig, or about 320 psig). In certain embodiments, an ingestible device for trans-epithelial delivery has a nozzle pressure of about 200 psig, about 210 psig, about 220 psig, about 230 psig, about 240 psig, about 250 psig, about 260 psig, about 270 psig, about 280 psig, about 290 psig, about 300 psig, about 310 psig or about 320 psig.

Generally, an ingestible device for trans-epithelial delivery is configured to contain a dispensable substance at a peak fluid pressure of at least about 150 psig (e.g., at least about 175 psig, at least about 200 psig, at least about 210 psig, at least about 220 psig, at least about 225 psig, at least about 230 psig, at least about 240 psig, at least about 250 psig, at least about 260 psig, at least about 270 psig, at least about 275 psig, at least about 280 psig, at least about 290 psig, at least about 300 psig, at least about 325 psig) and/or at most about 400 psig (e.g., at most about 375 psig, at most about 365 psig, at most about 355 psig, at most about 350 psig, at most about 345 psig, at most about 335 psig, at most about 325 psig, at most about 315 psig, at most about 305 psig). In certain embodiments, an ingestible device for trans-epithelial delivery is configured to contain a dispensable substance at a peak fluid pressure of from about 150 psig to about 400 psig (e.g., from about 150 psig to about 300 psig, from about 180 psig to about 400 psig, from about 190 psig to about 400 psig, from about 200 psig to about 400 psig, from about 200 psig to about 375 psig, from about 210 psig to about 400 psig, from about 220 psig to about 400 psig, from about 220 psig to about 375 psig, from about 220 psig to about 350 psig, from about 225 psig to about 400 psig, from about 225 psig to about 375 psig, from about 225 psig to about 350 psig, from about 225 psig to about 325 psig, from about 230 psig to about 400 psig, from about 235 psig to about 250 psig, from about 240 psig to about 400 psig, from about 245 psig to about 400 psig, from about 250 psig to about 400 psig, from about 250 psig to about 375 psig, from about 250 psig to about 350 psig, from about 250 psig to about 325 psig, from about 255 psig to about 400 psig, from about 260 psig to about 400 psig, from about 265 psig to about 400 psig, from about 270 psig to about 400 psig, from about 275 psig to about 400 psig, from about 275 psig to about 375 psig, from about 275 psig to about 350 psig, from about 275 psig to about 325 psig, from about 280 psig to about 400 psig, from about 280 psig to about 320 psig, from about 300 psig to about 375 psig, from about 285 psig to about 400 psig, from about 290 psig to about 400 psig, from about 300 psig to about 400 psig, from about 300 psig to about 375 psig, from about 300 psig to about 350 psig, from about 300 psig to about 325 psig, from about 305 psig to about 400 psig, from about 310 psig to about 400 psig, from about 315 psig to about 400 psig, from about 320 psig to about 400 psig, from about 320 psig to about 375 psig, from about 330 psig to about 400 psig, from about 335 psig to about 400 psig, from about 340 psig to about 400 psig, from about 345 psig to about 400 psig, from about 350 psig to about 400 psig). In some embodiments, an ingestible device for trans-epithelial delivery is configured to contain a dispensable substance at a peak fluid pressure of between about 220-350 psig (e.g., about 225-350 psig, about 230-350 psig, about 235-350 psig, about 240-350 psig, about 245-350 psig, about 250-350 psig, about 255-350 psig, about 260-350 psig, about 265-350 psig, about 270-350 psig, about 275-350 psig, about 280-350 psig, about 285-350 psig, about 290-350 psig, about 300-350 psig, about 220-325 psig, about 225-325 psig, about 230-325 psig, about 235-325 psig, about 240-325 psig, about 245-325 psig, about 250-325 psig, about 255-325 psig, about 260-325 psig, about 265-325 psig, about 270-325 psig, about 275-325 psig, about 280-325 psig, about 285-325 psig, about 290-325 psig, about 300-300 psig, about 220-300 psig, about 225-300 psig, about 230-300 psig, about 235-300 psig, about 240-300 psig, about 245-300 psig, about 250-300 psig, about 255-300 psig, about 260-300 psig, about 265-300 psig, about 270-300 psig, about 275-300 psig, about 280-300 psig, about 285-300 psig, about 290-300 psig, about 220-290 psig, about 225-290 psig, about 230-290 psig, about 235-290 psig, about 240-290 psig, about 245-290 psig, about 250-290 psig, about 255-290 psig, about 260-290 psig, about 265-290 psig, about 270-290 psig, about 275-290 psig, about 280-290 psig, about 285-290 psig, about 220-280 psig, about 225-280 psig, about 230-280 psig, about 235-280 psig, about 240-280 psig, about 245-280 psig, about 250-280 psig, about 255-280 psig, about 260-280 psig, about 265-280 psig, about 270-280 psig, about 275-280 psig, about 220-270 psig, about 225-270 psig, about 230-270 psig, about 235-270 psig, about 240-270 psig, about 245-270 psig, about 250-270 psig, about 255-270 psig, about 260-270 psig, about 265-270 psig, about 220-260 psig, about 225-260 psig, about 230-260 psig, about 235-260 psig, about 240-260 psig, about 245-260 psig, about 250-260 psig, about 255-260 psig, about 220-225 psig, about 225-235 psig, about 230-240 psig, about 235-245 psig, about 240-250 psig, about 245-260 psig, about 250-265 psig, about 255-270 psig, about 260-275 psig, about 265-285 psig, about 270-290 psig, about 275-295 psig, about 280-300 psig, about 285-305 psig, about 290-310 psig, about 300-315 psig, about 310-320 psig, about 220-230 psig, about 220-235 psig, about 220-240 psig, about 220-245 psig, about 220-250 psig, about 220-260 psig, about 220-265 psig, about 220-270 psig, about 220-275 psig, about 220-285 psig, about 220-290 psig, about 220-295 psig, about 220-300 psig, about 220-305 psig, about 220-310 psig, about 220-315 psig, about 220-320 psig, about 230-235 psig, about 230-240 psig, about 230-245 psig, about 230-250 psig, about 230-260 psig, about 230-265 psig, about 230-270 psig, about 230-275 psig, about 230-285 psig, about 230-290 psig, about 230-295 psig, about 230-300 psig, about 230-305 psig, about 230-310 psig, about 230-315 psig, about 230-320 psig, about 240-245 psig, about 240-250 psig, about 240-260 psig, about 240-265 psig, about 240-270 psig, about 240-275 psig, about 240-285 psig, about 240-290 psig, about 240-295 psig, about 240-300 psig, about 240-305 psig, about 240-310 psig, about 240-315 psig, about 240-320 psig, about 250-260 psig, about 250-265 psig, about 250-270 psig, about 250-275 psig, about 250-285 psig, about 250-290 psig, about 250-295 psig, about 250-300 psig, about 250-305 psig, about 250-310 psig, about 250-315 psig, about 250-320 psig, about 260-265 psig, about 260-270 psig, about 260-275 psig, about 260-285 psig, about 260-290 psig, about 260-295 psig, about 260-300 psig, about 260-305 psig, about 260-310 psig, about 260-315 psig, about 260-320 psig, about 270-275 psig, about 270-285 psig, about 270-290 psig, about 270-295 psig, about 270-300 psig, about 270-305 psig, about 270-310 psig, about 270-315 psig, about 270-320 psig, about 280-285 psig, about 280-290 psig, about 280-295 psig, about 280-300 psig, about 280-305 psig, about 280-310 psig, about 280-315 psig, about 280-320 psig, about 290-295 psig, about 290-300 psig, about 290-305 psig, about 290-310 psig, about 290-315 psig, about 290-320 psig, about 150 psig, about 300 psig, or about 320 psig). In certain embodiments, an ingestible device for trans-epithelial delivery is configured to contain a dispensable substance at a peak fluid pressure of about 200 psig, about 210 psig, about 220 psig, about 230 psig, about 240 psig, about 250 psig, about 260 psig, about 270 psig, about 280 psig, about 290 psig, about 300 psig, about 310 psig or about 320 psig.

Generally, an ingestible device for trans-epithelial delivery is configured to contain a dispensable substance at a minimum fluid pressure of at least about 50 psig (e.g., at least about 60 psig, at least about 70 psig) and/or at most about 100 psig (e.g., at most about 90 psig, at most about 80 psig). In some embodiments, an ingestible device for trans-epithelial delivery is configured to contain a dispensable substance at a minimum fluid pressure from about 50 psig to about 100 psig (e.g., from about 60 psig to about 90 psig, from about 70 psig to about 80 psig).

In general, an ingestible device for trans-epithelial delivery is configured to have a piston friction of at least about 1 N (e.g., at least about 2 N, at least about 3 N) and/or at most about 20 N (e.g., at most about 15 N, at most about 12 N). In certain embodiments, an ingestible device for trans-epithelial delivery is configured to have a piston friction of from 1 N to 20 N (e.g., from 2 N to 15 N, from about 3N to about 12N). In general, an ingestible device for trans-epithelial delivery contains the dispensable substance at an initial fluid volume of at least about 50 microliters (µL) (e.g., at least about 100 µL, at least about 150 µL, at least about 200 µL, at least about 250 µL) and/or at most about 800 µL (e.g., at most about 700 µL, at most about 600 µL, at most about 500 µL, at most about 400 µL). In some embodiments, an ingestible device for trans-epithelial delivery contains the dispensable substance at an initial fluid volume of from about 50 µL to about 800 µL (e.g., from about 100 µL to about 600 µL, from about 200 µL to about 400 µL).

Generally, an ingestible device for trans-epithelial delivery is configured to provide a delivered fluid volume of dispensable substance of at least about 50 microliters (µL) (e.g., at least about 100 µL, at least about 150 µL, at least about 200 µL, at least about 250 µL) and/or at most about 800 µL (e.g., at most about 700 µL, at most about 600 µL, at most about 500 µL, at most about 400 µL). In some embodiments, an ingestible device for trans-epithelial delivery has a fluid volume of dispensable substance of from about 50 µL to about 800 µL (e.g., from about 50 µL to about 500 µL, from about 100 µL to about 450 µL, from about 100 µL to about 600 µL, from about 200 µL to about 400 µL, from about 250 µL to about 400 µL, from about 300 µL to about 400 µL).

In general, an ingestible device for trans-epithelial delivery contains the dispensable substance at a final fluid volume of at most about 100 microliters (µL) (e.g., at least about 90 µL, at least about 80 µL, at least about 70 µL, at least about 60 µL) and/or at most least 5 µL (e.g., at most about 10 µL, at most about 20 µL, at most about 30 µL, at most about 40 µL). In some embodiments, an ingestible device for trans-epithelial delivery contains the dispensable substance at a fluid volume of from about 30 µL to about 70 µL (e.g., from about 40 µL to about 60 µL, from about 45 µL to about 55 µL). In general, an ingestible device for trans-epithelial delivery is configured to directly deliver at least about 50% (e.g., at least about 60%, at least about 70%, at least about 80%, at least about 90%, at least about 95%, at least about 97%) of the dispensable substance from the ingestible device to the submucosa and/or the mucosa (e.g., into the lamina propria).

In general, an ingestible device for trans-epithelial delivery has at least 1 opening for delivery of dispensable substance (e.g. at least 2 openings for delivery of dispensable substance, at least 3 openings for delivery of dispensable substance, at least 4 openings for delivery of dispensable substance) and/or most about 8 openings for delivery of dispensable substance (e.g., at most 7 openings for delivery of dispensable substance, at most 6 openings for delivery of dispensable substance, at most 5 openings for delivery of dispensable substance, at most 4 openings for delivery of dispensable substance). In certain embodiments, an ingestible device for trans-epithelial delivery has from 1 to 8 openings for delivery of dispensable substance (e.g., from 2 to 4 openings for delivery of dispensable substance, 2 opening for delivery of dispensable substance). In some embodiments, an ingestible device for trans-epithelial delivery has one or more nozzles, with each nozzle having a nozzle opening for delivering dispensable substance. In such embodiments, the ingestible device can have at least 1 nozzle (e.g., at least 2 nozzles, at least 3 nozzles, at least 4 nozzles) and/or at most 8 nozzles (e.g., at most 7 nozzles, at most 6 nozzles, at most 5 nozzles, at most 4 nozzles). For example, the ingestible device can have from 1 to 8 nozzles (e.g., from 1 to 5 nozzles, from 2 to 4 nozzles, 2 nozzles). In embodiments in which an ingestible device for trans-epithelial delivery includes one or more nozzles, each nozzle can have a nozzle length of at least about 1 mm (e.g., at least about 2 mm, at least about 3 mm) and/or at most about 5 mm (e.g., at most about 4 mm). In some embodiments, each nozzle can have a nozzle length of from about 1 mm to about 5 mm. In embodiments in which an ingestible device for trans-epithelial delivery includes one or more nozzles, each nozzle can have a nozzle diameter of at least about 0.1 mm (e.g., at least about 0.2 mm, at least about 0.3 mm) and/or at most about 2 mm (e.g., at most about 1 mm, at most about 0.8 mm, at most bout 0.5 mm, at most about 0.4 mm). In some embodiments, each nozzle can have a nozzle diameter of from about 0.1 mm to about 2 mm (e.g., from about 0.1 mm to about 1 mm, from about 0.15 mm to about 0.5 mm, from about 0.2 mm to about 0.8 mm, from about 0.25 mm to about 0.45 mm, from about 0.3 mm to about 0.4 mm, from about 0.3 mm to about 0.5 mm, from about 0.34 mm to about 0.36 mm, about 0.35 mm). In certain embodiments, each nozzle can have a nozzle diameter independently selected from the group consisting of about 0.15 mm, about 0.16 mm, about 0.17 mm, about 0.18 mm, about 0.19 mm, about 0.20 mm, about 0.21 mm, about 0.22 mm, about 0.23 mm, about 0.24 mm, about 0.25 mm, about 0.26 mm, about 0.27 mm, about 0.28 mm, about 0.29 mm, about 0.30 mm, about 0.31 mm, about 0.32 mm, about 0.33 mm, about 0.34 mm, about 0.35 mm, about 0.36 mm, about 0.37 mm, about 0.38 mm, about 0.39 mm, about 0.40 mm, about 0.41 mm, about 0.42 mm, about 0.43 mm, about 0.44 mm, about 0.45 mm, about 0.46 mm, about 0.47 mm, about 0.48 mm, about 0.49 mm, and about 0.50 mm; or more particularly, about 0.30 mm, about 0.31 mm, about 0.32 mm, about 0.33 mm, about 0.34 mm, about 0.35 mm, about 0.36 mm, about 0.37 mm, about 0.38 mm, about 0.39 mm and about 0.40 mm.

In general, an ingestible device for trans-epithelial delivery is configured to provide a delivered fluid volume per opening for delivery of dispensable substance (e.g., per nozzle) of at least about 20 microliters (µL) (e.g., at least about 25 µL, at least about L, at least about 50 µL, at least about 75 µL, at least about 100 µL) and/or at most about 800 µL (e.g., at most about 700 µL, at most about 600 µL, at most about 500 µL, at most about 400 µL, at most about 300 µL). In some embodiments, an ingestible device for trans-epithelial delivery is configured to provide a delivered fluid volume per opening for delivery of dispensable substance (e.g., per nozzle) of from about 25 µL to about 400 µL (e.g., from about 25 µL to about 300 µL, from about 100 µL to about 300 µL).

In one example, an ingestible device with a nozzle having a nozzle diameter of 0.35 mm diameter and containing a dispensable substance at a peak fluid pressure of 150 psig can deliver a jet of the dispensable substance at an average jet velocity of about 20 m/s and at an average jet impact pressure of about 29 psig.

In another example, an ingestible device having a nozzle pressure of 300 psig can deliver a dispensable substance at an average jet velocity of about 27 m/s and an average jet impact pressure of about 58 psig. In some embodiments, such an arrangement results in piercing of the intestinal wall.

In another example, an ingestible device having a nozzle with a nozzle diameter of 0.35 mm diameter and containing a dispensable substance at a peak fluid pressure of 320 psig can deliver a jet of the dispensable substance having an average jet velocity of about 28 m/s and an average jet impact pressure of about 62.4 psig.

Figure 3:
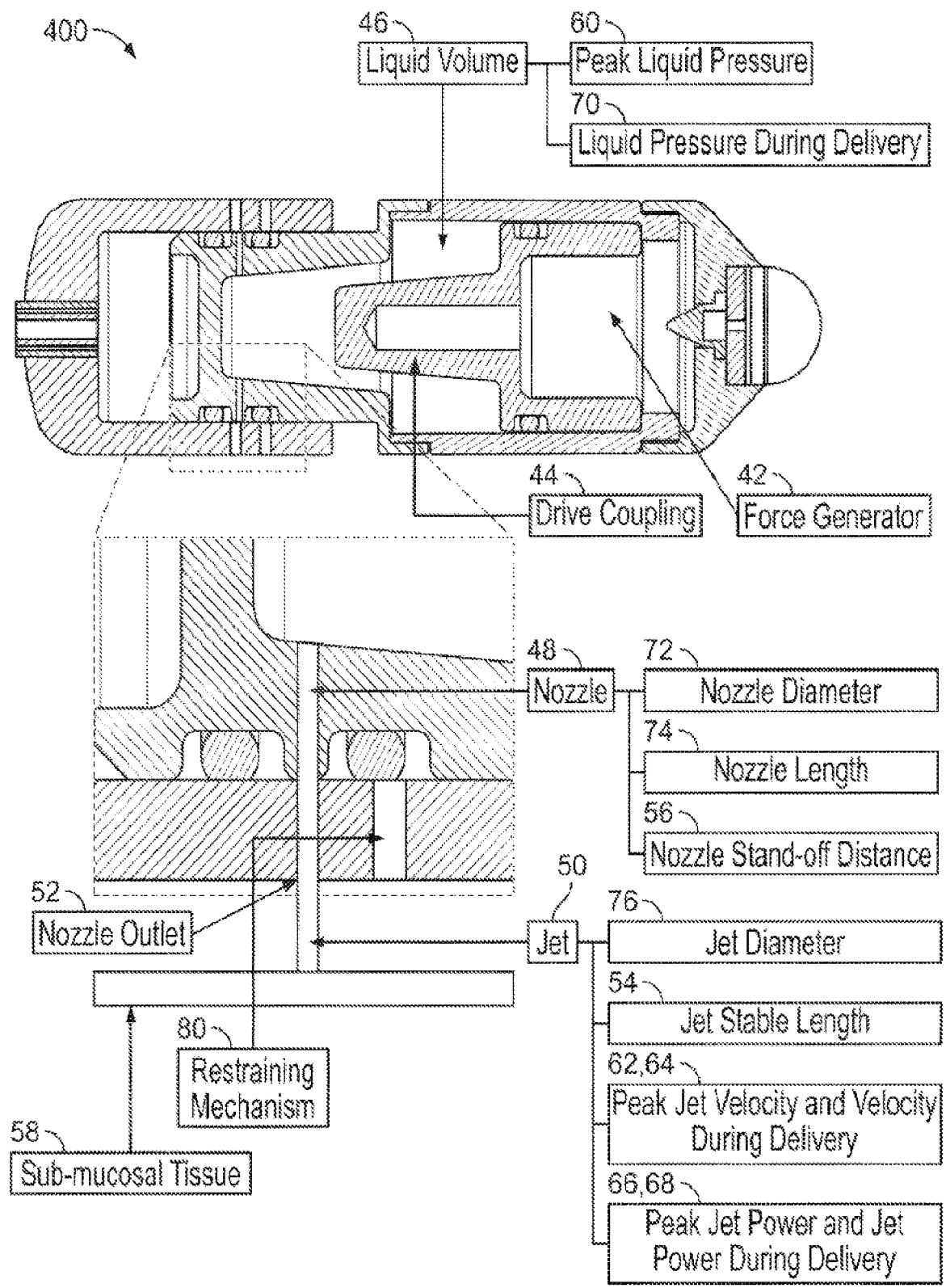
FIG. 3 is a cross section of an ingestible device.

FIG. 3 shows cross sectional views of a representative ingestible device 400 for trans-epithelial delivery, schematically illustrating certain parameters and components of action for the device 400. These include a drive force generator 42 which applies a force (resulting in an internal pressure) to a drive coupling 44. The drive coupling 44 transfers force from the force generator 42 to a fluid volume 46 containing a dispensable substance (e.g., a liquid, a suspension). The force applied to the fluid volume 46 by the drive coupling 44 generates pressure in the fluid volume 46 (fluid pressure). The pressure in the fluid volume 46 generates high-speed flow through an open nozzle 48 to produce a jet 50 of fluid at the nozzle outlet 52 that has a nozzle diameter 72 and the nozzle has a nozzle length 74.

During trans-epithelial delivery, the fluid jet 50 has a jet stable length 54 that is sufficient for the fluid jet 50 to travel across a nozzle stand-off distance 56 to reach the interface of the lumen of the GI tract and the surface of the GI tract facing the lumen. Ultimately, the fluid (e.g., liquid, suspension) impacts the mucosal layer of the GI tract (e.g., the epithelial layer and any mucus that may be present on the epithelial layer) as a stable stream of fluid with little breakup into a spray and is deposited in the submucosal and/or the mucosal tissue 58. That is, between the nozzle outlet 52 and the site of impact at the mucosa, the jet 50 has a jet diameter 76 that can vary in the manner discussed above with respect to the average jet diameter.

The fluid volume 46 experiences a peak fluid pressure 60 that generates the fluid jet 50 that exits the device 40 with a peak jet velocity, and impacts the interface of the lumen of the GI tract and the surface of the GI tract facing the lumen with a peak jet power, peak jet pressure and peak jet force. One of ordinary skill in the art recognizes that these three parameters are interconnected.

The pressure in the fluid volume 46 decreases during delivery so that the fluid pressure during delivery 70 varies, as does the jet power, jet force, and jet pressure. The fluid pressure during delivery 70 maintains the fluid jet 50 at sufficient jet impact force during delivery to continue fluid (dispensable substance including one or more therapeutic agents) delivery from the fluid volume 46 into the submucosal and/or mucosal tissue 58. The surrounding tissue can then absorb the delivered therapeutic agents for systemic delivery of the therapeutic agent.

Even prior to when the subject swallows the ingestible device, the drive coupling 44 transmits force from the force generator 42 to the fluid volume 46. The drive coupling 44 is prevented from moving by a restraining mechanism 80 (e.g., a pin or plug that selectively degrades and/or selectively erodes) until movement of the drive coupling is triggered by a triggering mechanism, and/or an opening becomes open.

FIGS. 4A-5B show cross sections of an example ingestible device 100.

Figure 4A:
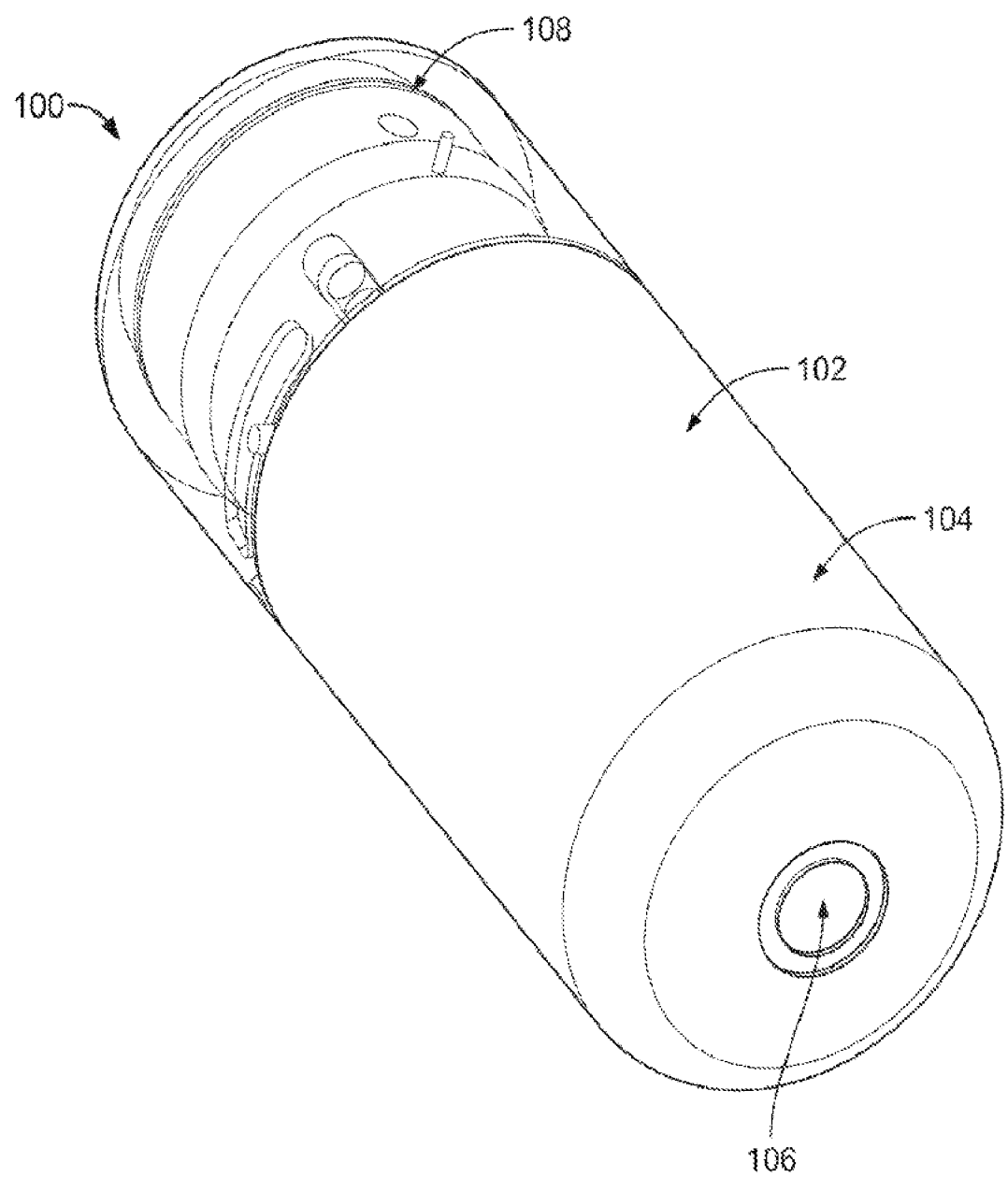
FIG. 4A shows the exterior surface of an ingestible device.

FIG. 4A shows an exterior view of the ingestible device 100. The device 100 is generally cylindrical with a longitudinal axis and a generally smooth exterior surface 102. The exterior surface 102 includes a bottom housing 104 with an inlet 106 at one end, and a slider 108 (shown transparent) at the opposite end from the inlet 106 (e.g., a pressurization inlet port). The device 100 is a purely mechanical device for the delivery of a therapeutic agent to the GI tract, and does not contain any electronics.

Figure 4B:
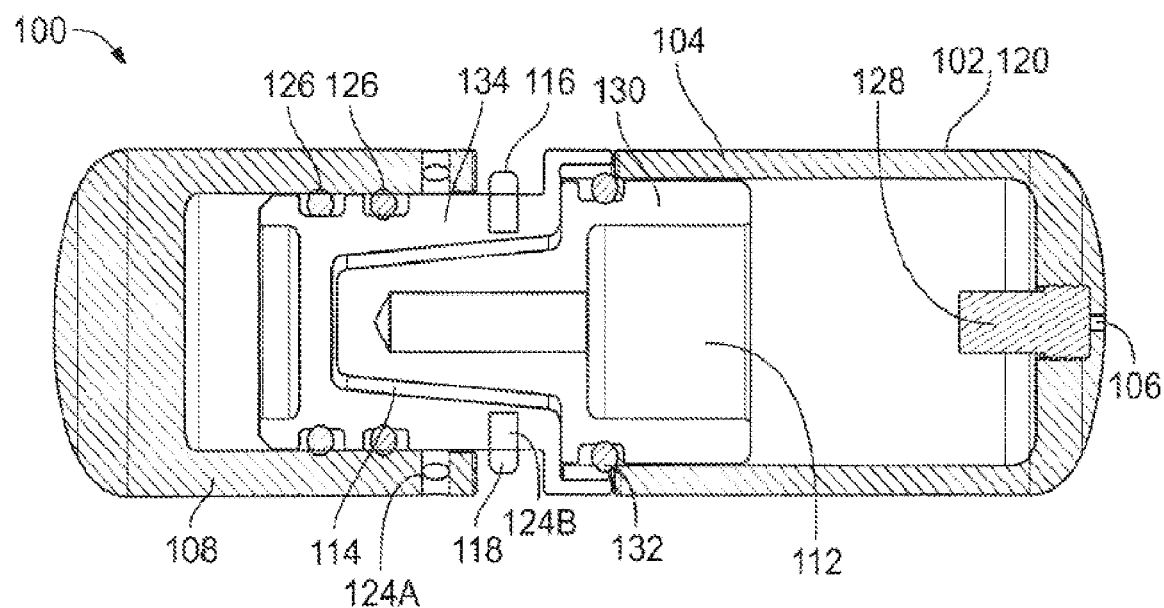
FIG. 4B is a top view cross section of the ingestible device in an open position.

FIG. 4B shows an embodiment of the device 100. The device 100 includes a gas reservoir 112, a dispensable substance reservoir 114 that contains the substance to be dispensed (e.g., a pharmaceutical formulation), a slider 108, degradable and/or erodible elements 116 (e.g., shear pins), and structural elements 118 (e.g., structural shear pins). In general, the degradable and/or erodible elements 116 are configured to degrade and/or erode under certain conditions, while the structural elements 118 are configured to provide additional mechanical strength beyond that provided by the degradable and/or erodible elements 116. Together, the degradable and/or erodible elements 116 and structural elements 118 are able to hold back the force of the force generator (e.g., a pressurized gas within the gas reservoir 112). However, when the degradable and/or erodible elements 116 begin to or completely degrade and/or erode in the presence of GI fluid, the structural elements 118 cannot alone hold back the force of the force generator (e.g., the pressurized gas), and the slider 108 moves to the open position. In some embodiments, the degradable and/or erodible elements 116 and structural elements 118 are placed in pairs with like elements on opposite sides of the device. In some embodiments, the degradable and/or erodible elements 116 are made of an enteric material. For example, the enteric material may be degradable and/or erodible in the small intestine of the GI tract, or the enteric material may be degradable and/or erodible in the large intestine of the GI tract, such as the colon. Although shown in FIGS. 2A-4B as including both the degradable and/or erodible elements 116 and the structural elements 118, in some embodiments, the device 100 includes the degradable and/or erodible elements 116 but does not include the structural elements 118.

FIGS. 4A-5B show cross sections of an embodiment of the device 100, which includes gas reservoir 112, a dispensable substance reservoir 114 that contains the substance to be dispensed (e.g., a pharmaceutical formulation), a slider 108, degradable and/or erodible elements 116 (e.g., shear pins), and structural elements 118 (e.g., structural shear pins). In general, the degradable and/or erodible elements 116 are configured to degrade and/or erode under certain conditions, while the structural elements 118 are configured to provide additional mechanical strength beyond that provided by the degradable and/or erodible elements 116. Together, the degradable and/or erodible elements 116 and structural elements 118 are able to hold back the force of the force generator (e.g., a pressurized gas within the gas reservoir 112). However, when the degradable and/or erodible elements 116 begin to or completely degrade and/or erode in the presence of GI fluid, the structural elements 118 cannot alone hold back the force of the force generator (e.g., the pressurized gas), and the slider 108 moves to the open position. In some embodiments, the degradable and/or erodible elements 116 and structural elements 118 are placed in pairs with like elements on opposite sides of the device. In some embodiments, the degradable and/or erodible elements 116 are made of an enteric material. For example, the enteric material may be degradable and/or erodible in the small intestine of the GI tract, or the enteric material may be degradable and/or erodible in the large intestine of the GI tract, such as the colon. Although shown in FIGS. 2A-4B as including both the degradable and/or erodible elements 116 and the structural elements 118, in some embodiments, the device 100 includes the degradable and/or erodible elements 116 but does not include the structural elements 118.

As shown in FIGS. 4A-5B, the ingestible device 100 is encased by a coating 120, such as a degradable and/or erodible coating, for example, an enteric coating, that covers the exterior surface 102. Optionally, the ingestible device 120 does not include the coating 120. Further, in certain embodiments, only certain portions of the ingestible device 100 include the coating 120. As an example, in some embodiments, only the pockets 124 (described below) are coated, e.g., coated with a degradable and/or erodible material, for example, an enteric material.

Figure 4C:
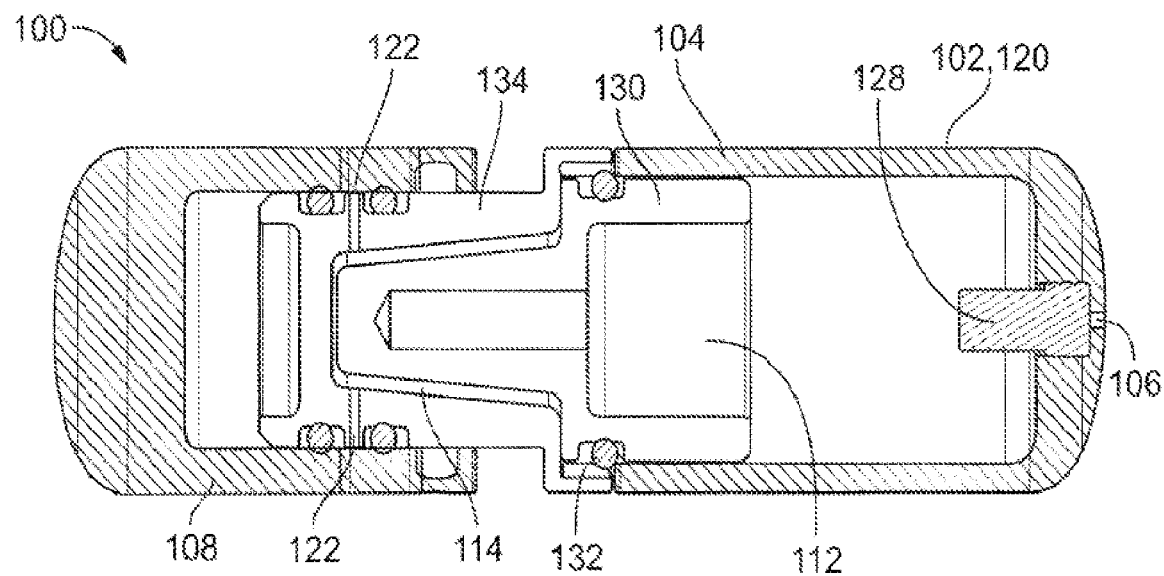
FIG. 4C is a front view cross section of the ingestible device in the open position.

FIGS. 4B and 4C show the device 100 in its open position, where the substance reservoir 114 is fluidly connected to the outside of the device via the nozzles 122 (visible in FIG. 3C). To prepare the device for use, the dispensable substance (e.g., a therapeutic agent or a pharmaceutical formulation containing a therapeutic agent) is loaded into the substance reservoir 114 via the nozzles 122 with the device in this open position. Once the dispensable substance is loaded into the substance reservoir 114, the slider 108 is shut by sliding it axially, disconnecting the nozzles 122 from the exterior of the device so that the device 100 is in its closed position. Note that the location of the structural elements 118 and elements 116 are depicted in FIGS. 4B and 4C as these elements are not yet on the device 100 while it is in the open position depicted. The device 100 may also include a guide pin that provides alignment of nozzles 122 to the hole provided by the slider 108, and may also prevent the slider from continuing to translate axially.

Figure 5A:
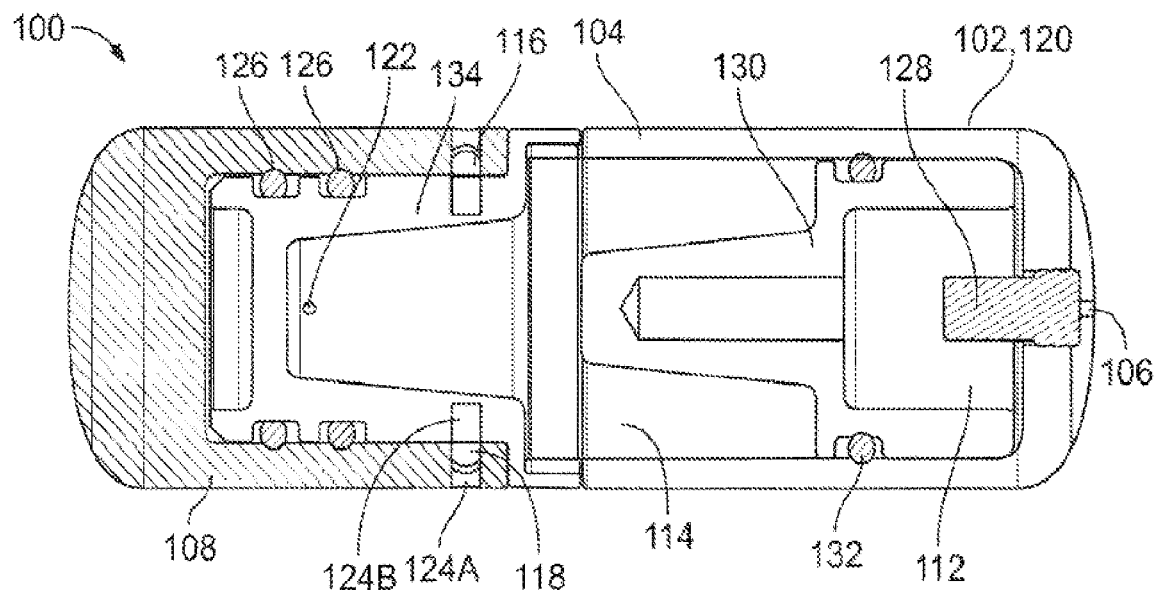
FIG. 5A is a top view cross section of the ingestible device in the closed position.
Figure 5B:
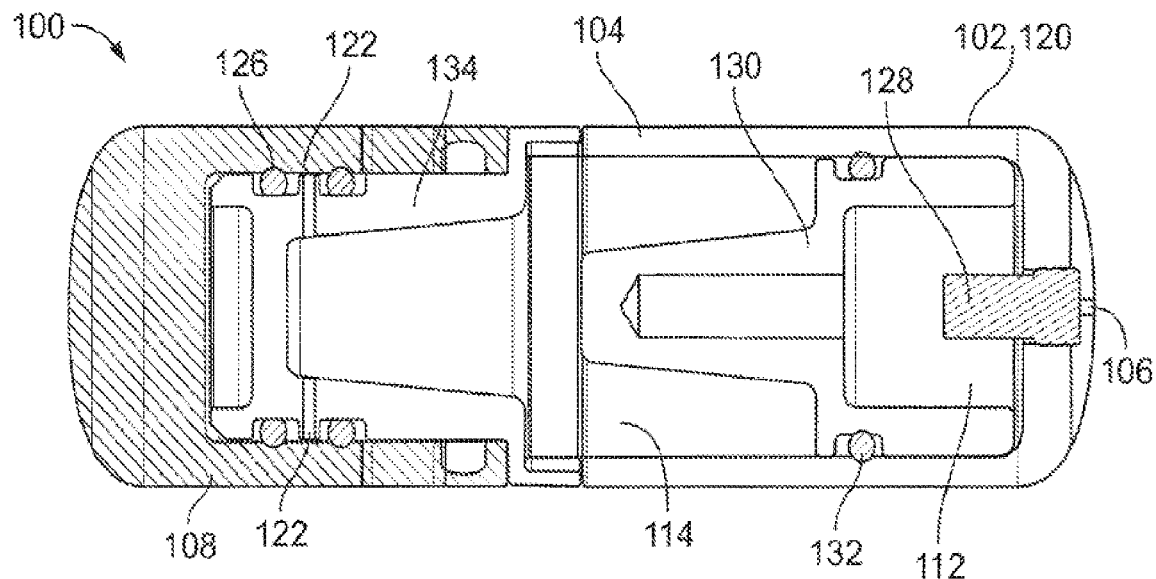
FIG. 5B is a front view cross section of the ingestible device of in the closed position.
Figure 6I:
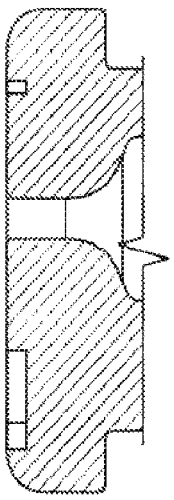
FIGS. 6A-6L shows exemplary nozzle cross sections for the ingestible device.
Figure 6J:
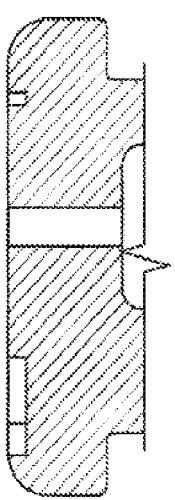
Figure 6K:
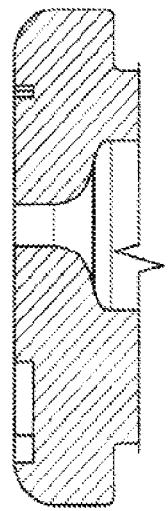
Figure 6L:
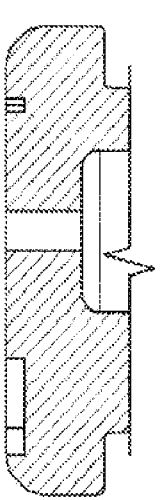
Figure 6E:
Figure 6F:
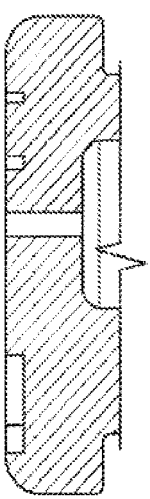
Figure 6G:
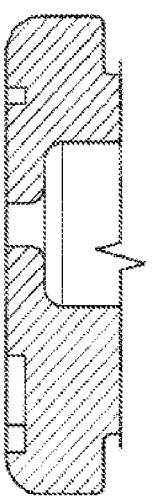
Figure 6H:
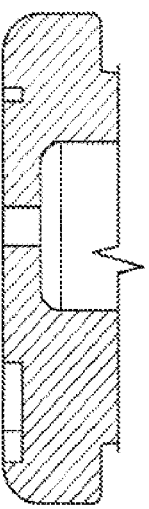
Figure 6A:
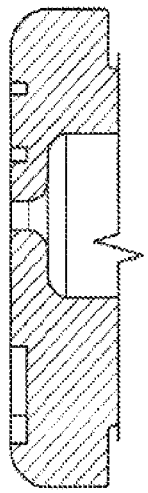
Figure 6B:
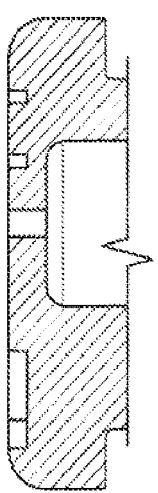
Figure 6C:
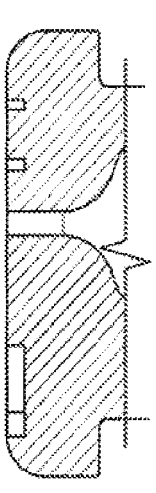
Figure 6D:
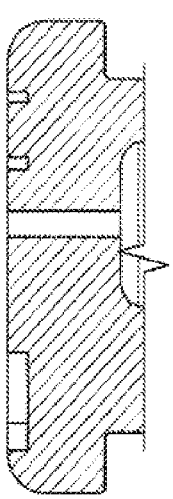

FIGS. 5A and 5B show the device in its closed position in which the slider 108 is held in place by a number of elements 116 and 118 that mate with pockets (e.g., pin pockets) 124. The location of elements 116 extend through the housing at the positions indicated while the device 100 is in the closed position. A single nozzle 122 is shown in the view of FIG. 5A and two nozzles are shown in the view of FIG. 5B. One or more top housing seals (e.g., sealing O-rings) 126 assist in containing the dispensable substance behind the slider 108 so that the dispensable substance does not leak to the environment external to the device 100. A piston (e.g., substance/gas piston) 130 and a seal (e.g., sealing O-ring) 132 assist in separating the gas in the gas reservoir 112 from the dispensable substance in the substance reservoir 114. The piston 130 surrounds the gas reservoir 112 and is configured to slide axially within the bottom housing 104. In some embodiments, the slider 108 is not an external sliding mechanism as shown, but is an internal slider.

With the dispensable substance loaded within the substance reservoir 114, the slider 108 is held in place with respect to the top housing 134 with the elements 116 and structural elements 118 within the pockets 124. The pockets 124 each have a through-portion 124A piercing the slider 108, and a blind hole portion 124B within the top housing 134. In the closed position (FIGS. 5A and 5B), the through-portion 124A and the blind hole portion 124B of each of the pockets 124 align, allowing the elements 116 and/or 118 to be inserted through the slider 108 and fasten it to the top housing 134. Once in this fixed position, the gas reservoir 112 is charged with pressurized gas up to a predetermined pressure (e.g., about 300 psig) via the inlet 106. The inlet 106 includes a valve 128 that allows gas to flow into the gas reservoir 112, but prevents the pressurized gas from travelling back out through the inlet 106. In general, any appropriate valve may be used. Examples of valves include check valves, ball check valves, umbrella valves, duckbill valves, or the like. In some embodiments, the valve 128 is replaced by a static plug (e.g., an adhesive applied to the inlet 106) that can withstand the pressure of the pressurized gas reservoir 112.

The elements 116 and 118 are generally made of materials and are sized and shaped such that they, in combination, provide enough rigidity to hold the slider 108 in the closed position under the internal pressure of the pressurized air in the gas reservoir 112, e.g., in the range of about 150-400 psig. Upon dissolution, degradation and or erosion of the elements 116, the maximum pressure that the remaining structural elements 118 can withstand without breaking drops below the internal pressure within the gas reservoir 112. In some embodiments, the structural elements 118 are made from a relatively brittle material, and thereby fail and release the slider 108 and allow the dispensable substance to forcefully leave the device via the nozzles 122. Although FIGS. 4A-5B show a single element 116 and a single element 118, the disclosure is not limited in this sense. For example, the device 100 can include more than one (e.g., two, three, four, etc.) elements 116, and/or more than one (e.g., two, three, four, etc.) elements 118. In some embodiments, there is an even number of elements 116 and of structural elements 118, and the elements 116 and 118 are arranged in an alternating configuration around the longitudinal axis of the device 100. In other embodiments, there is an even number of elements 116 and of structural elements 118, and the elements 116 and 118 are arranged such that elements 116 are opposite other elements 116 and structural elements 118 are opposite other structural elements 118 around the longitudinal axis of the device 100. In certain embodiments, elements 116 and 118 are co-located within the same pocket 124 and may comprise a matrix of materials such as 118 consisting of fibers, or consisting of a coaxial pin 118 surrounded by an annulus of element 116. In some embodiments, the coating 120 may be placed only in the region of the elements 116 and/or 118, e.g., in an annulus. Alternatively, enteric material may be in the pocket portions 124A and/or 124B as a plug separating the elements 116 and/or 118 from the exterior environment.

The properties of the elements 116 can be varied to select the desired performance. For example, their effective force-restraining area can be increased by increasing the diameter and thus the cross section of each element 116, and/or by increasing the number of the elements 116. Increasing the area allows for a safety factor to permit longer periods of storage and shipping, variation in dissolvability, degradability and or erodability between batches of elements 116 and/or 118, and variations in the pressure within the gas reservoir 112, or the like. In some embodiments, elements 116 and 118 are pins having a diameter of about 0.9 mm, but can be thinner (e.g., about 0.8 mm) or wider.

In some embodiments, the elements 116 and/or the structural elements 118 have configurations other than straight pins. For example, one or more elements 116 can be an annular member that fits within a grooved pocket (rather than the discrete pockets 124 shown) that encircles the circumference of the slider 108. The element(s) can be cotters, shear pins, linchpins, split pins, straight pins, dowels, biscuits, clasps, clamps, flanges, rivets, or the like. In some embodiments one or more of the elements 116 is a restraining device other than a pin, such as a clamp, a spacer, or the like.

The gas reservoir 112 contains pressurized gas. In some embodiments, the gas is air, however gases other than air are possible. Nonlimiting examples of compressed gases include, nitrogen ($N_2$), oxygen ($O_2$), argon (Ar), krypton (Kr), helium (He) or other inert or noble gases that do not interact or are compatible with the GI tract, with preference to higher molecular weight gasses that would decrease any permeation of the drive gas out of the device and therefore increase shelf life. In some embodiments, the gas is carbon dioxide ($CO_2$).

The device 100 maintains a gas/fluid barrier internally, and the gas reservoir 112 can keep pressurized gas from interacting with a fluid dispensable substance (e.g., dispensable substance in the substance reservoir 114). The substance reservoir 114 may have a residual volume of <0.050 mL after the dispensing period is complete, and does not induce agglomeration that would prevent therapeutic agent delivery.

The device 100 also can have several characteristics that make it safe to be stored and transported before being swallowed by a patient. The device 100 can maintain an internal pressure of about 350 psig over the shelf life of the device, e.g., hold a pressure of about 350 psig for about 6 months. The dispensable substance-contacting substance reservoir 114 does not have an effect on the therapeutic agent contained within, and the device and the therapeutic agent are not affected (in efficacy, safety, consistency, or bioavailability) by each other during device storage, transit, and dispensing (e.g., with a storage time up to about six months, or up to about 12 months). The substance reservoir 114 can resist contamination from outside sources prior to dispensing.

In some embodiments, as shown in FIG. 6, the diameter of a nozzle as measured at the point of interface with the dispensable substance reservoir can be the same as, smaller than, or larger than the diameter as measured at the nozzle opening (location of delivery of the dispensable substance from the ingestible device). Table 1 provides nozzle diameter (in millimeters) and nozzle length (in millimeters) for the nozzle designs shown in FIG. 6.

TABLE 1

| FIG. 6 | Nozzle diameter | Nozzle length |
|---|---|---|
| A | 0.35 | 0.5 |
| B | 0.35 | 0.5 |
| C | 0.35 | 1.5 |
| D | 0.35 | 1.5 |
| E | 0.35 | 1 |
| F | 0.35 | 1 |
| G | 0.5 | 0.5 |
| H | 0.5 | 0.5 |
| I | 0.5 | 1.5 |
| J | 0.5 | 1.5 |
| K | 0.5 | 1 |

In some embodiments, a tapered nozzle may exhibit enhanced jetting properties. In certain embodiments, a non-tapered nozzle relatively may be relatively inexpensive and simple to manufacture. In some embodiments, a small reducing in certain jet properties with a relatively simplified (e.g., non-tapered) nozzle can be compensated with variation of more easily controlled parameters such as the internal pressure and/or fluid pressure. In some embodiments where the jet exhibits turbulent flow, considering the variations in the flow profile which is inherent to the turbulent nature of the flow, and small impacts of nozzle length variations on the jet velocity, the length of the nozzle may be selected based on mechanical design constraints and required thickness of the ingestible devices.

In some embodiments, a smaller nozzle diameter (e.g., about 0.35 millimeter) is can result in longer dispensing time (~120 milliseconds), which can better align with achievable opening times of ~10 milliseconds and higher velocity for a given peak internal pressure. In some embodiments, a smaller nozzle diameter can also provide actual dispensing times and jet velocities that are closer to the predicted values.

FIG. 6 shows exemplary cross sections of the nozzles 122 within the slider 108 (although nozzles depicted in FIG. 6 may be used in one or more of other embodiments of ingestible devices disclosed herein). In some embodiments, the nozzles are about 0.15-0.5 mm in diameter and about 0.3-1.5 mm in length. The throat (e.g., the narrowing portion) of the nozzle can be rounded (as in the top right) or sharp (as in the bottom left) and the neck can have varying lengths. Each of these parameters have an effect on the jet(s) generated by the nozzle, modulating, for example, average jet diameter, jet velocity, peak jet power, peak jet pressure, peak jet force, and average dispensing time. These characteristics can affect the efficacy of delivery and/or subject uptake of the therapeutic agent.

Figure 7:
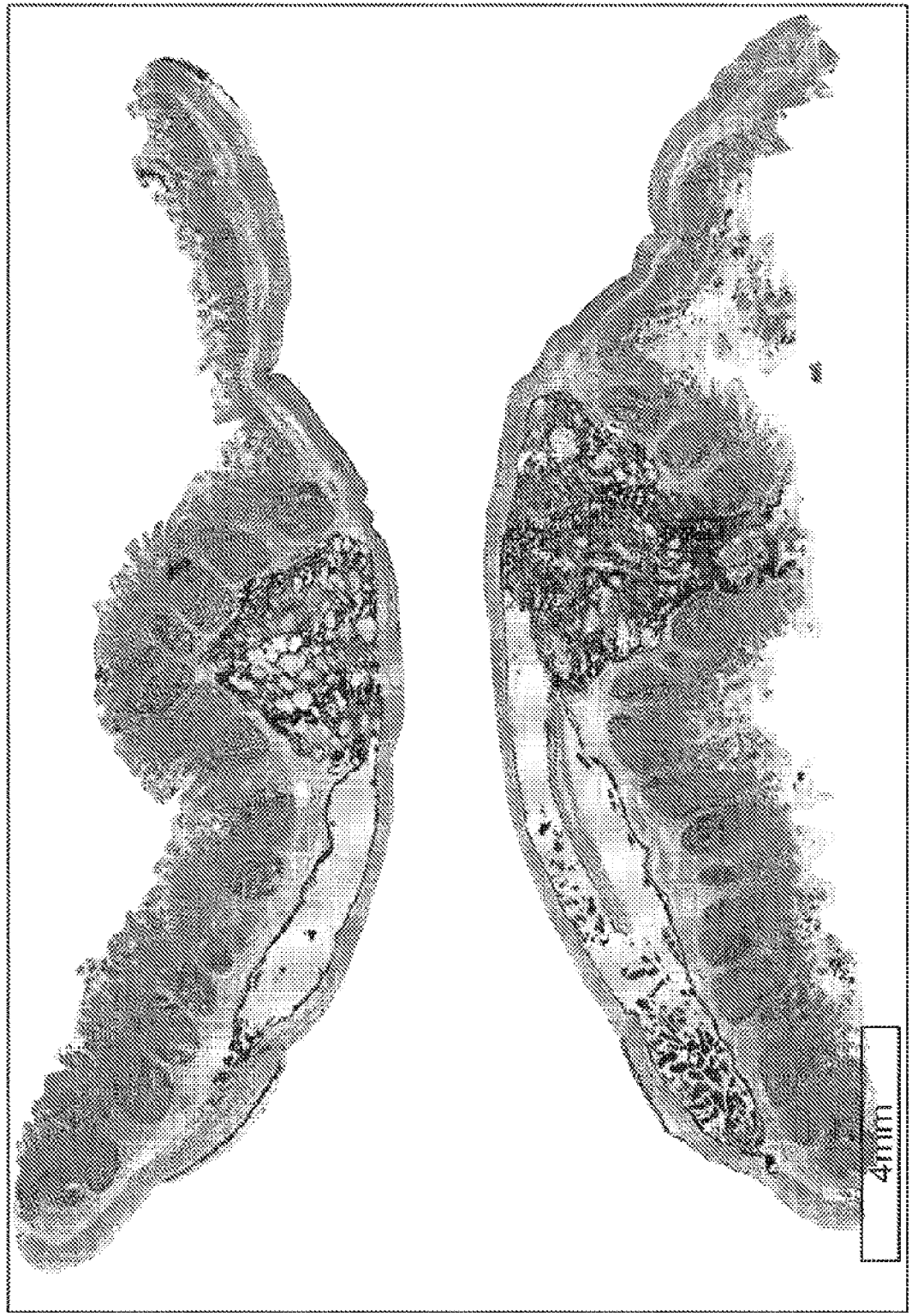
FIG. 7 shows an exemplary histology slide resulting from a bolus of therapeutic agent in situ.

FIG. 7 shows a histologic example of a jetted fluid in situ. This result was achieved with a 0.35 mm nozzle and jetting pressure of 250 psig, and an estimated 181 µL bolus volume. The fluid passed through the mucosa and is within the submucosal region. In this example, the complete bolus was not delivered, possibly due to the physical volume constraints of the region. This indicates that multiple nozzles each delivering a smaller bolus of therapeutic agent may be preferred to maximize the bioavailability of the therapeutic agent.

Referring back to FIGS. 4A-5B, the ingestible device 100 has a triggering mechanism that causes the device 100 to release the dispensable substance within the substance reservoir 114 when the ingestible device reaches the desired location within the GI tract. The trigger that initiates dispensable substance release can have two parts: the enteric coating 120 enrobing the exterior surface 102 of the device 100, and the elements 116. The elements 116 are either covered with an enteric coating or are themselves are made of an enteric material. The enteric material may be degradable and/or erodible in the small intestine of the GI tract, or may be degradable and/or erodible in the large intestine of the GI tract, for example, the colon. Such a two-stage release mechanism allows the device 100 to transit through the GI tract to the desired location intact before releasing the therapeutic agent.

In the first stage, the enteric coating 120 dissolves, degrades and/or erodes while the device 100 is within a desired portion of the GI tract, e.g., the small intestine or the large intestine. The enteric coating 120 is chosen such that it is stable in the acidic environment of the stomach and dissolves, degrades and/or erods only when exposed to the more neutral environment of the small intestines (e.g., pH>5) or the slightly acidic to neutral environment of the large intestine (e.g., pH 5.5-7). The thickness of the coating 120 is chosen such that it dissolves, degrades and/or erodes (either entirely, or enough to expose the elements 116) when the swallowed device 100 is predicted to have transited through the stomach and be within the small intestine or large intestine.

Once the enteric coating 120 has dissolved, degraded and/or eroded from the exterior surface 102 of the device 100, the elements 116 of the device 100 are exposed to the GI tract. The elements 116 are configured to dissolve, degrade and/or erod upon exposure to the environment of the small intestine (e.g., a water soluble material). Generally, the elements 116 dissolve, degrade and/or erode more rapidly than does the enteric coating 120. The elements 116 can dissolve, for example, within about 1 minute of the enteric coating 120 dissolving, degrading and/or eroding and exposing the elements 116 to the small intestine environment, compared to, for example, about 30 minutes for the enteric coating 120 to degrade. It is not necessary that the enteric coating 120 dissolves, degrades and/or erodes in its entirety. As the enteric coating 120 starts to degrade water or other luminal contents may pass through it and cause the elements 116 to dissolve and thereby lose their mechanical holding strength.

Materials for the elements 116 can be isomalt, sugars like maltose or sucrose, or degrading materials of different sorts.

The elements 116 and the structural elements 118 can be made of materials and are sized and shaped such that they, in combination, provide enough rigidity to hold the slider 108 in the closed position under the pressure of the pressurized gas in the gas reservoir 112, which can be in the range of 150-400 psig. For example, if the gas reservoir 112 is to be pressurized to 260 psig, the elements 116 and the structural elements 118 can be designed to hold back 300 psig of pressure. In one arrangement, the retaining strength of the elements 116 is 80 psig, and the retaining strength of the structural elements 118 is 220 psig. Upon dissolution, degradation and/or erosion of the elements 116, the structural elements 118 are exposed to the pressure of 260 psig within the gas reservoir 112. As the 260 psig within the gas reservoir 112 exceeds the reduced restraining strength of 220 psig, the remaining structural elements 118 break. The combination of the dissolution, degradation and/or erosion of the elements 116 followed by the breaking of the structural elements 118 releases the slider 108.

In some embodiments, the elements 116 and the structural elements 118 are made of the same material. The elements 116 have a smaller cross sectional area than the structural elements 118 and thus fail more quickly than the structural elements 118. In other embodiments, the elements 116 and the structural elements 118 are made of different materials, where the structural elements 118 are stronger but more brittle than the elements 116.

In some embodiments, only elements 116 are present, without structural elements 118. In such instances, the elements 116 are configured to break and release the piston 130 and slider 108 in a single step (following dissolving, degrading and/or eroding of the enteric coating 120).

To dispense the therapeutic agent, the device 100 moves from the closed position in FIGS. 5A and 5B back to the open position of FIGS. 3B and 3C where the substance reservoir 114 is fluidly connected to the outside of the device (in this instance, with the GI tract). Once the shear pins dissolve/degrade/erode and/or are sheared, the piston 130 is released to slide axially within the bottom housing 104, and the slider 108 slides relative to the top housing 134. The motion of the slider 108 positions the nozzles 122 such that the portion of the nozzles 122 within the top housing 134 aligns with the fluid outlet portion of the nozzles 122 within the slider 108. The movement of the piston 130, driven by the now-unrestrained pressure within the air reservoir 122, forces the therapeutic within the substance reservoir 114 out through the nozzles 122. The elements 116 and 118 may remain only in the blind hole portion 124B of the pockets 124. In some embodiments, the dispensing time is approximately 120 ms. In some embodiments, the time for the slider 108 to move from the closed to the open position is approximately 10 ms.

Figure 8:
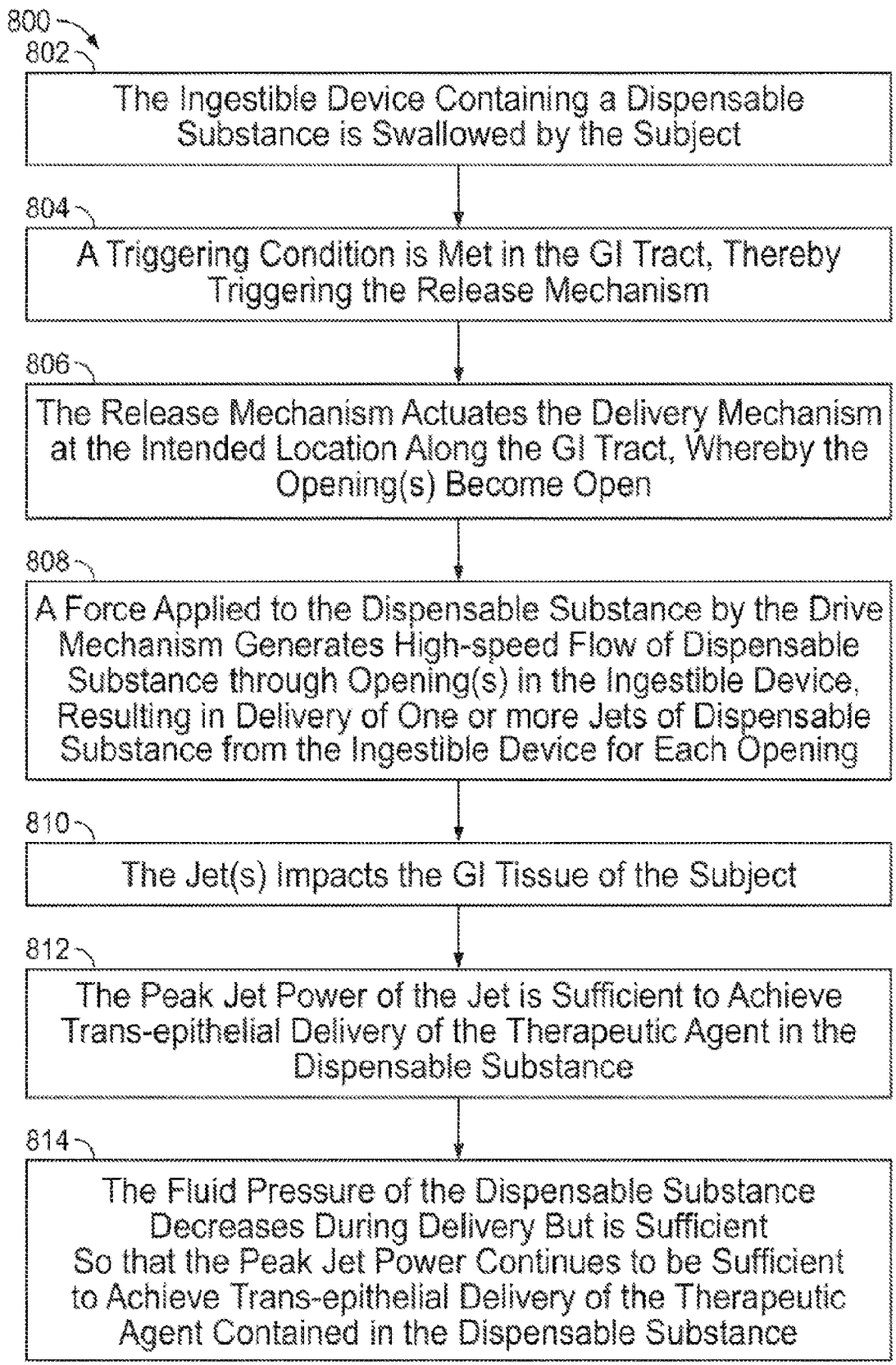
FIG. 8 shows an exemplary process flow chart for use of an ingestible device in which pressure is applied to the dispensable substance before the subject swallows the ingestible device.

FIG. 8 shows an exemplary process flow chart 800 for use of an ingestible device in which pressure is applied to the dispensable substance before the subject swallows the ingestible device. The process begins at step 802, when the patient swallows the ingestible device. In step 804, a triggering condition (e.g., pH, change in pH, presence of certain enzyme, concentration of certain enzyme) is met in the GI tract, thereby triggering the release mechanism. In step 806, the release mechanism actuates the delivery mechanism at the intended location of the GI tract, whereby the opening(s) of the ingestible device become open. In step 808, force applied to the dispensable substance by the drive mechanism generates high-speed flow of the dispensable substance through the opening(s) in the ingestible device, resulting in delivery of a jet of the dispensable substance from the ingestible device for each opening. In step 810, the jet has a sufficient jet stable length for the jet to impact the GI tissue of the subject. In step 812, the peak jet power of the jet is sufficient to achieve trans-epithelial delivery of the therapeutic agent contained in the dispensable substance. In step 814, the fluid pressure of the dispensable substance decreases during delivery but is sufficiently so that the peak jet power continues to be sufficient to achieve trans-epithelial delivery of the therapeutic agent contained in the dispensable substance.

Figure 9A:
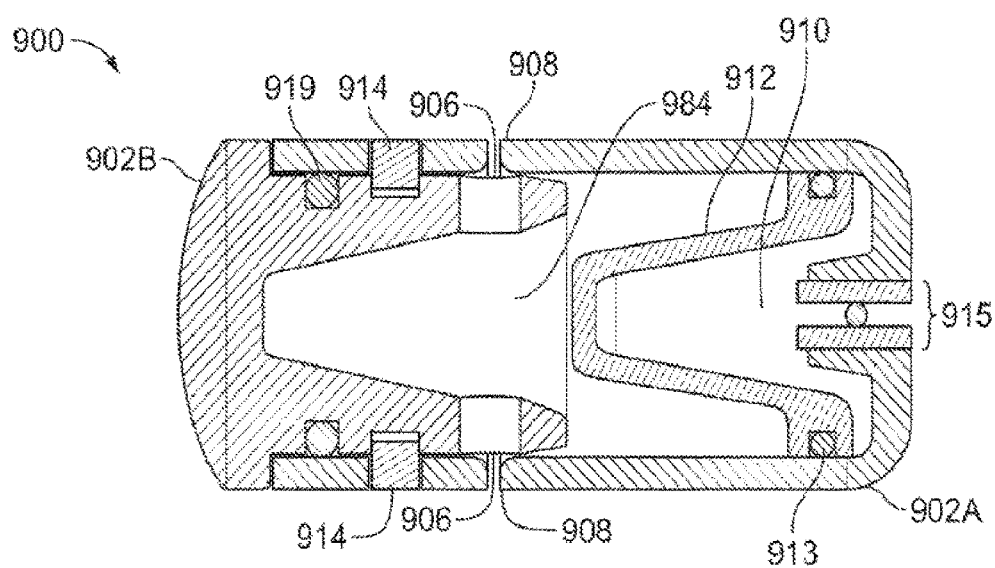
FIG. 9A shows an ingestible device.
Figure 9B:
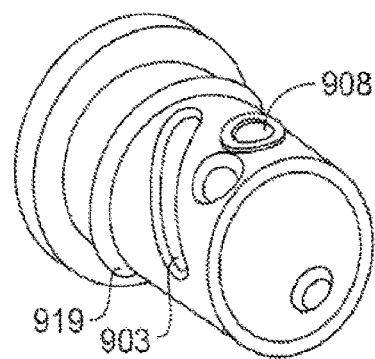
FIG. 9B shows certain elements of the ingestible device of FIG. 9A.

FIG. 9A shows an embodiment of an ingestible device 900 for trans-epithelial delivery. The device 900 includes housing parts 902A and 902B, a fluid volume 904 containing a dispensable substance, nozzles 906 with nozzle openings 908, pressurized gas as a drive force generator 910, a drive coupling 912 with an O-ring 913 seal, a ring 914 and a valve 915 (inlet for compressed gas). Similar to the device shown in FIGS. 4A-5B, when the device 900 is swallowed by the subject, the dispensable substance in the device is already pressurized. However, the ring 914 prevents the pressure of the drive force generator 910 and the drive coupling 912 from forcing the dispensable substance in the fluid volume 904 through the nozzle openings 908. When the device 900 reaches the appropriate location in the GI tract, the ring 914 erodes, degrades and/or dissolves. Thus, the pressure of the drive force generator 910 and the drive coupling 912 is applied to the dispensable substance 904, forcing the cap to move to expose openings 908. As shown in FIG. 9B, the housing part 902B has a slot 903 into which a portion of housing part 902A fits such that the motion of the housing part 902A is both axial and rotational (e.g., a track and cam arrangement). This arrangement can result in relatively reduced axial movement of the housing part 902B during delivery of the dispensable substance, which can result in maintenance of a relatively high internal pressure during delivery of the dispensable substance.

Figure 10A:
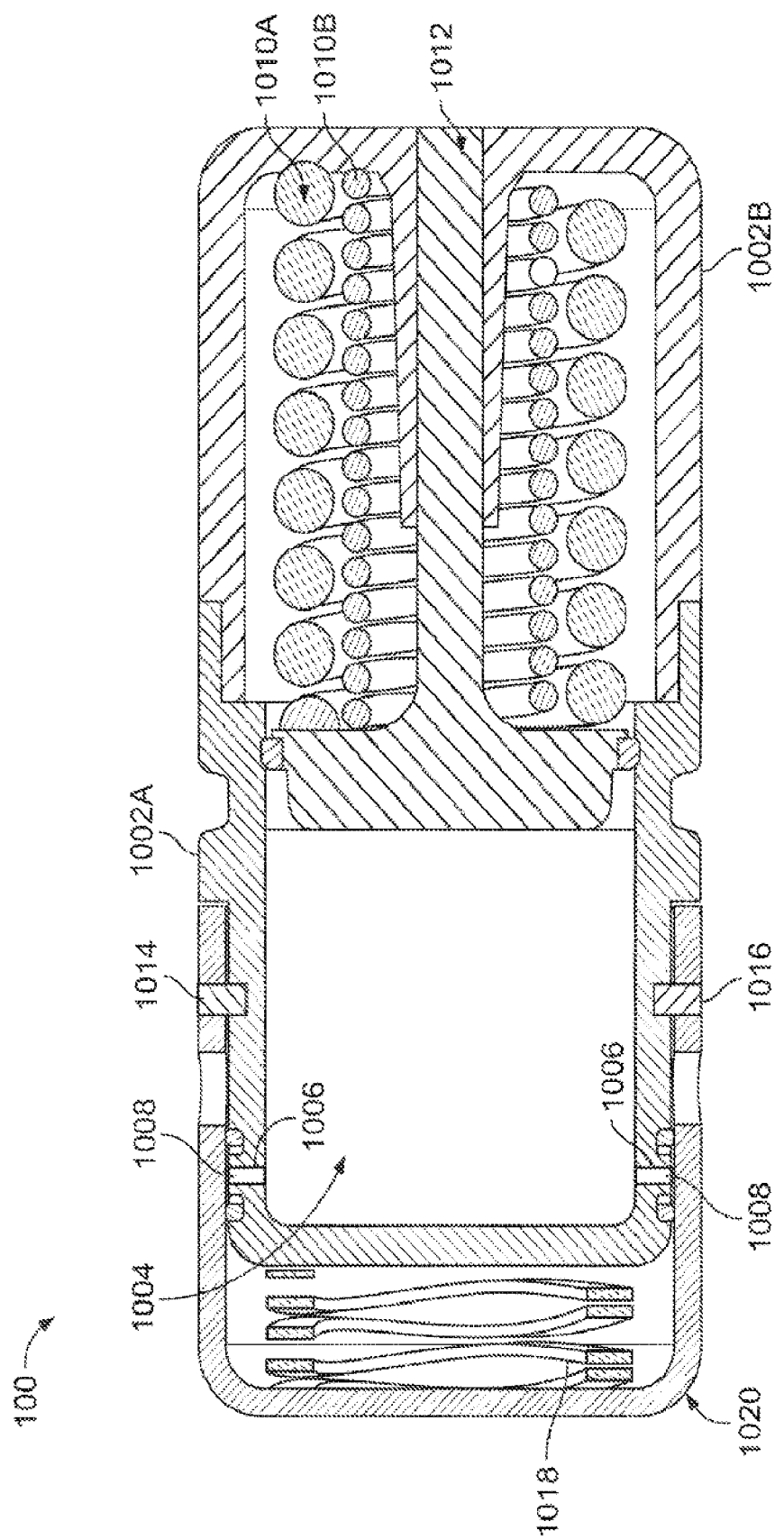
FIG. 10A shows an ingestible device.
Figure 10B:
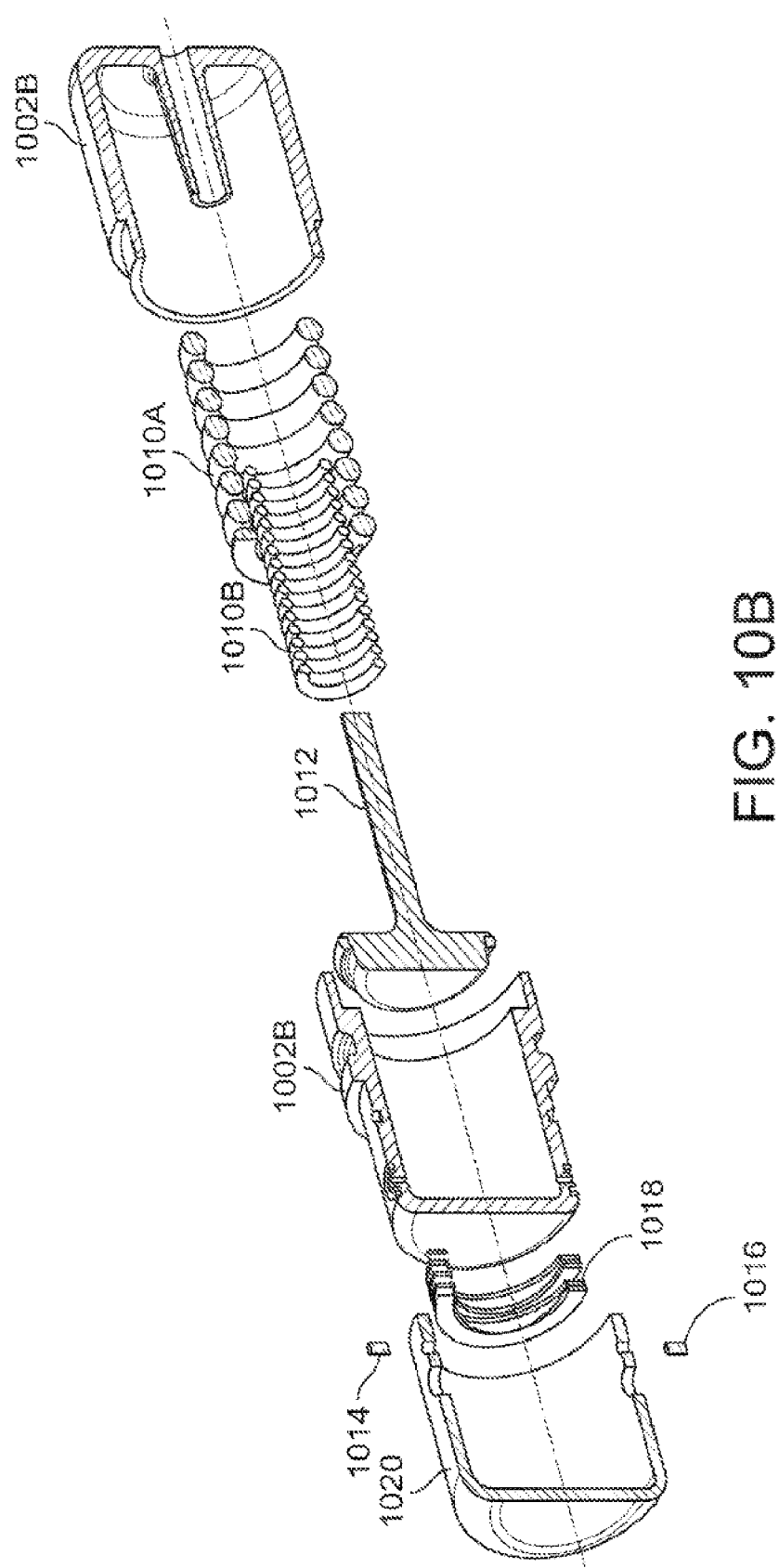
FIG. 10B shows an exploded view of the ingestible device of FIG. 10A.

FIG. 10A shows an embodiment of an ingestible device 1000 for trans-epithelial delivery. FIG. 10B is an exploded view of the ingestible device 1000. The ingestible device 1000 has housing parts 1002A and 1002B, a fluid volume 1004 containing a dispensable substance, nozzles 1006, nozzle openings 1008, parallel springs 1010A and 1010B, a piston 1012, a pin 1014, a pin 1016, a spring 1018 and a cap 1020. Similar to the device shown in FIGS. 4A-5B, when the device 1000 is swallowed by the subject, the dispensable substance in the device is already pressurized. However, the pins 1014 and 1016 prevent the pressure of the springs 1010A and 1010B and the piston 1012 from forcing the dispensable substance in the fluid volume 1004 through the nozzle openings 1008. When the device 1000 reaches the appropriate location in the GI tract, the pin 1014 erodes, degrades and/or dissolves, and the pin 1016 is not sufficient to hold back the pressure from the springs 1010A and 1010B and the piston 1012. Thus, the pressure of the springs 1010A an 1010B and the piston 1012 is applied to the dispensable substance, forcing the spring 1020 to quickly move the cap 1018 forward. This rapidly exposes the nozzle openings 1008 to the environment exterior to the device 1000 so that the dispensable substance is delivered out of the openings 1008 in the form of a jet. This results in in trans-epithelial delivery of the therapeutic agent contained in the dispensable substance. In some embodiments, the housing of the ingestible device 1000 has a diameter of about 11 mm, a length of about 26 mm, a wall thickness of about 0.8 mm, an end round of about 1.5 mm and an internal volume of about 1685 µL. In such embodiments, the fluid volume 1004 can be about 325 L.

Figure 10C:
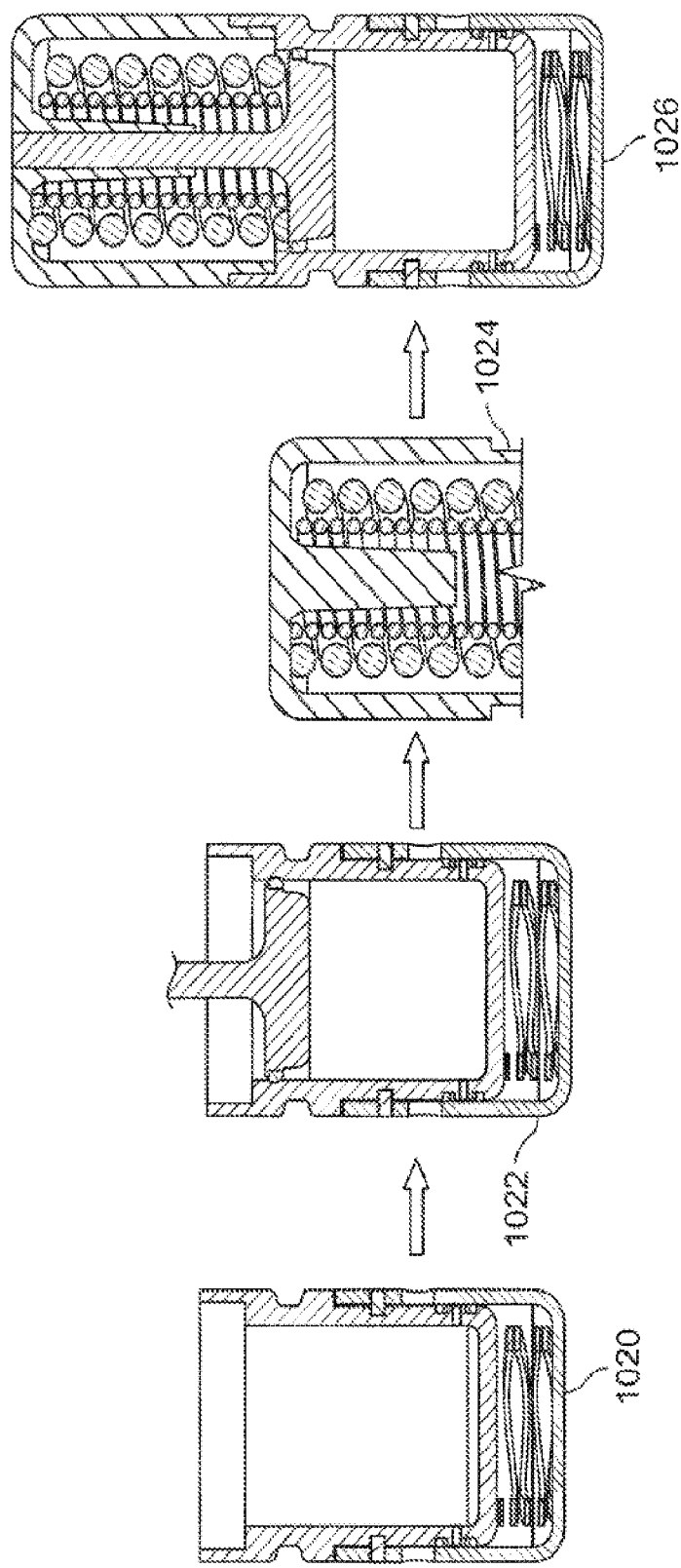
FIG. 10C shows aspects of steps in assembling the ingestible device of FIG. 10A.

FIG. 10C shows aspects of steps in assembling the ingestible device 1000. In step 1020, the cap 1020 and spring 1018 are combined with the housing part 1002B and pins 1014 and 1016, and this module is sterilized. In step 1022, the dispensable substance 1004 is disposed in the housing part 1002B in an aseptic environment and then sealed within the housing part 1002B via the piston 1012. In step 1024, the housing part 1002A and its components are assembled in a clean environment. In step 1026, the resulting modules are joined together in a clean environment to compress the springs 1010A and 1010B to provide the ingestible device 1000. As shown in step 1026, the assembly process can include using a jig to hold the housing part 1002A to prevent over-loading of the cap 1020/spring 1018/pin 1014/pin 1016 combination.

Figure 10D:
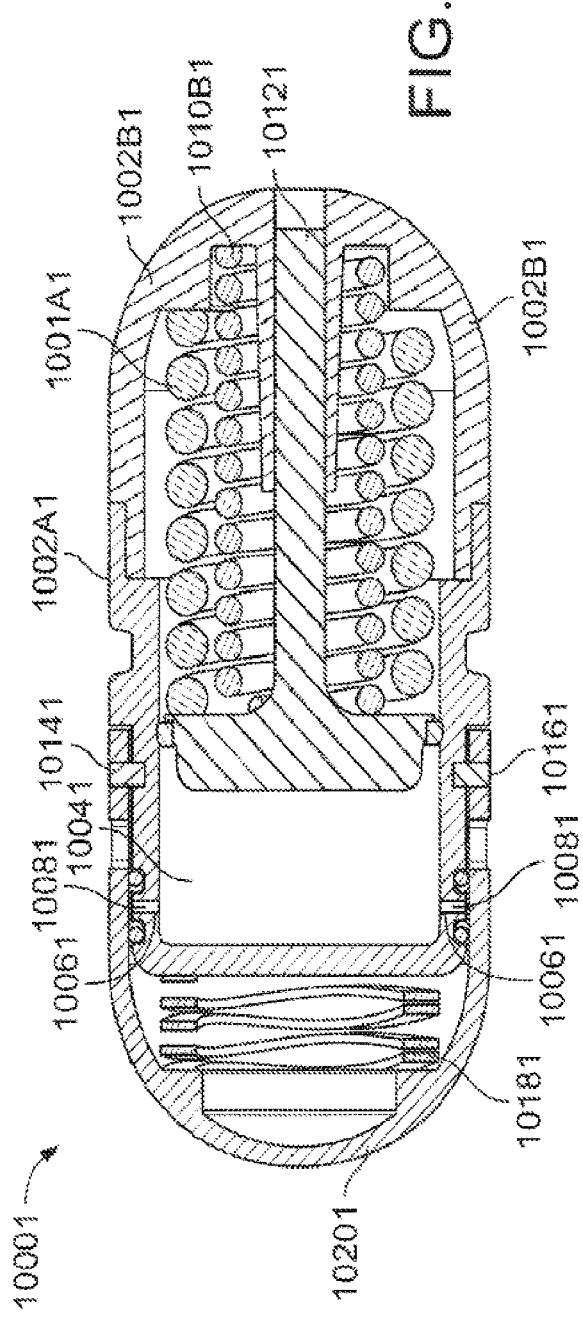
FIG. 10D shows an ingestible device with aspects similar to those shown in FIG. 10A.

FIG. 10D shows an embodiment of an ingestible device 10001 for trans-epithelial delivery. The ingestible device 10001 has housing parts 1002A1 and 1002B1, a fluid volume 10041 containing a dispensable substance, nozzles 10061, nozzle openings 10081, parallel springs 1010A1 and 1010B1, a piston 10121, a pin 10141, a pin 10161, a spring 10181 and a cap 10201. Similar to the device shown in FIGS. 4A-5B, when the device 10001 is swallowed by the subject, the dispensable substance in the device is already pressurized. However, the pins 10141 and 10161 prevent the pressure of the springs 1010A1 and 1010B1 and the piston 10121 from forcing the dispensable substance in the fluid volume 10041 through the nozzle openings 10081. When the device 10001 reaches the appropriate location in the GI tract, the pin 10141 erodes, degrades and/or dissolves, and the pin 10161 is not sufficient to hold back the pressure from the springs 1010A1 and 1010B1 and the piston 10121. Thus, the pressure of the springs 1010A1 an 1010B1 and the piston 10121 is applied to the dispensable substance, forcing the spring 10201 to quickly remove move the cap 10181 forward. This rapidly exposes the nozzle openings 10081 to the environment exterior to the device 10001 so that the dispensable substance is delivered out of the openings 10081 in the form of a jet. This results in in trans-epithelial delivery of the therapeutic agent contained in the dispensable substance. In some embodiments, the spring force of the spring 10181 has a force of about 30 Newtons, the parallel springs 1010A1 and 1010B1 have a force of 110 Newtons to provide an internal pressure of about 320 psig with about 50 Newtons of force at the end of the stroke, and the fluid volume 10041 is about 225 µL. In some embodiments, the housing of the ingestible device 10001 has a diameter of about 11 mm, a length of about 26 mm, a wall thickness of about 0.8 mm, an end round of about 5.5 mm (spherical) and an internal volume of about 1475 µL. In such embodiments, the fluid volume 10041 can be about 225 µL.

Figure 10E:
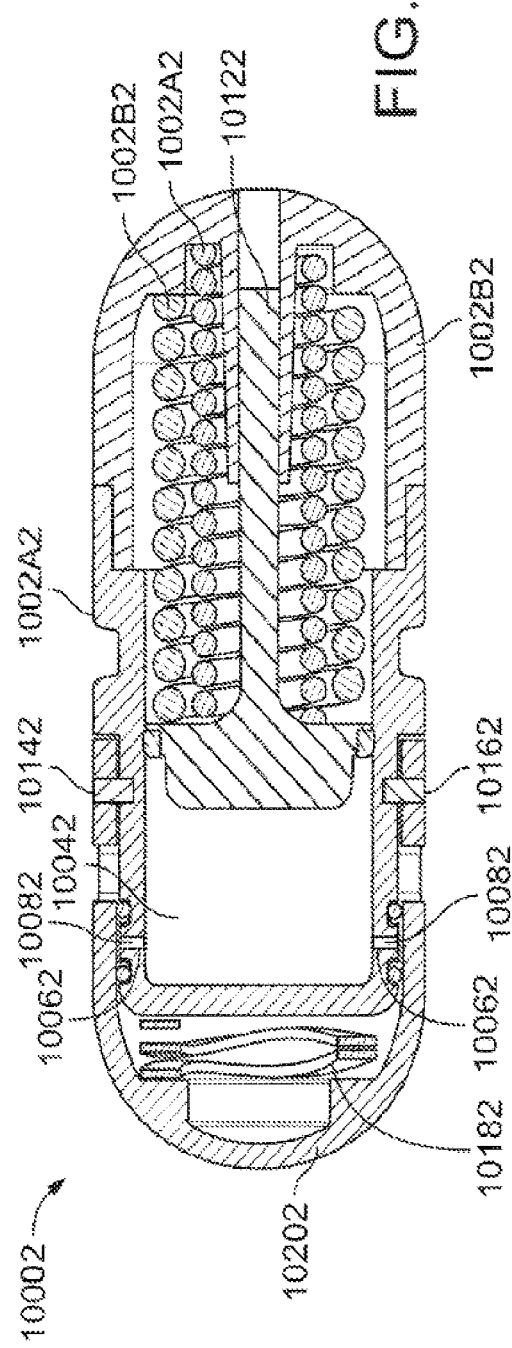
FIG. 10E shows an ingestible device with aspects similar to those shown in FIG. 10A.

FIG. 10E shows an embodiment of an ingestible device 10002 for trans-epithelial delivery. The ingestible device 10002 has housing parts 1002A2 and 1002B2, a fluid volume 10042 containing a dispensable substance, nozzles 10062, nozzle openings 10082, parallel springs 1010A2 and 1010B2, a piston 10122, a pin 10142, a pin 10162, a spring 10182 and a cap 10202. Similar to the device shown in FIGS. 4A-5B, when the device 10002 is swallowed by the subject, the dispensable substance in the device is already pressurized. However, the pins 10142 and 10162 prevent the pressure of the springs 1010A2 and 1010B2 and the piston 10122 from forcing the dispensable substance in the fluid volume 10042 through the nozzle openings 10082. When the device 10002 reaches the appropriate location in the GI tract, the pin 10142 erodes, degrades and/or dissolves, and the pin 10162 is not sufficient to hold back the pressure from the springs 1010A2 and 1010B2 and the piston 10122. Thus, the pressure of the springs 1010A2 an 1010B2 and the piston 10122 is applied to the dispensable substance, forcing the spring 10202 to quickly remove move the cap 10182 forward. This rapidly exposes the nozzle openings 10082 to the environment exterior to the device 10002 so that the dispensable substance is delivered out of the openings 10082 in the form of a jet. This results in in trans-epithelial delivery of the therapeutic agent contained in the dispensable substance. In some embodiments, the spring force of the spring 10182 has a force of about 12 Newtons, the parallel springs 1010A2 and 1010B2 have a force of 58 Newtons to provide an internal pressure of about 320 psig with about 25 Newtons of force at the end of the stroke, and the fluid volume 10042 is about 120 µL. In some embodiments, the housing of the ingestible device 10002 has a diameter of about 8.5 mm, a length of about 23.3 mm, a wall thickness of about 0.75 mm, an end round of about 4.25 mm (spherical) and an internal volume of about 775 µL. In such embodiments, the fluid volume 10042 can be about 120 µL.

Figure 11:
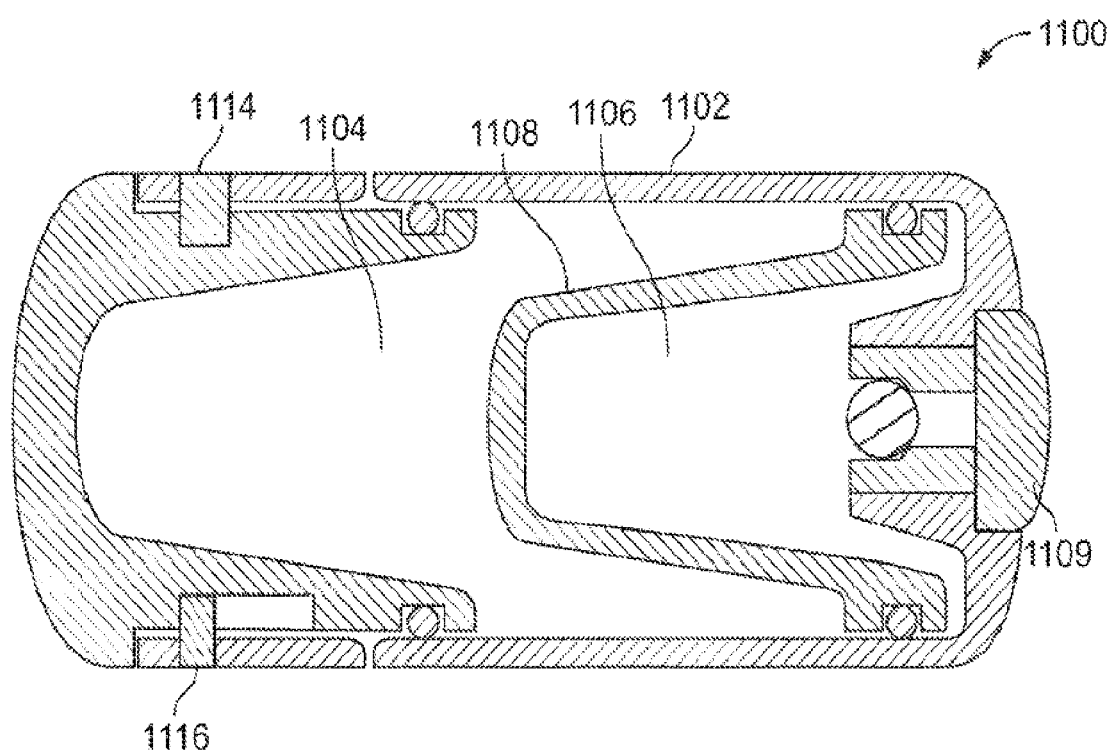
FIG. 11 shows an ingestible device.

FIG. 11 shows an ingestible device 1100 which includes a housing 1102, a fluid volume 1104, a liquid-gas reservoir (drive force generator) 1106, a drive coupling 1108, a seal 1109, a pin 1114 and a pin 1116. The ingestible device 1100 is configured so that, before the subject swallows the device, the dispensable substance in fluid volume 1104 is under pressure from the liquid-gas reservoir 1106 via the drive coupling 1108, but the pins 1114 and 1116 prevent the dispensable substance in fluid volume 1004 from being delivered from the device 1100 via nozzle(s) with nozzle opening(s) (not shown). When the device 1100 reaches the appropriate location in the GI tract, the pin 1114 erodes, degrades and/or dissolves (e.g., due to pH, change in pH, presence of certain enzyme, and/or concentration of certain enzyme), and the pin 1116 is no longer sufficient to hold back the pressure from the liquid-gas reservoir 1106 and the drive coupling 1108. Thus, this pressure is applied to the dispensable substance in the fluid volume 1104, forcing the dispensable substance out of the nozzle openings (not shown) in the form of a jet. This results in in trans-epithelial delivery of the therapeutic agent contained in the dispensable substance.

Figure 12:
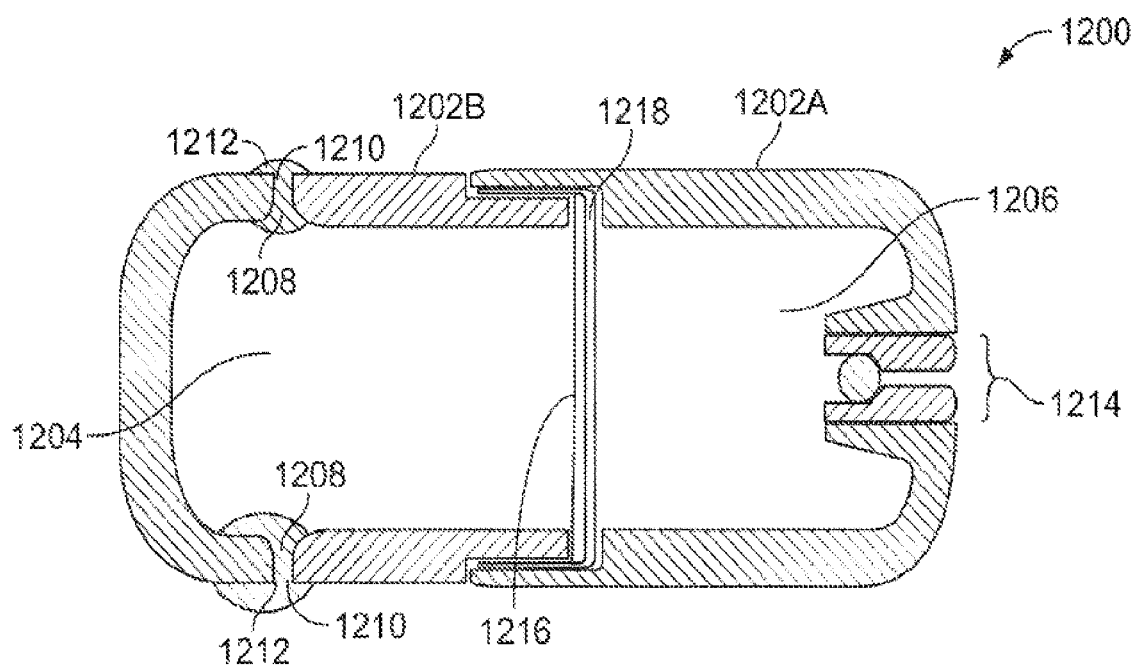
FIG. 12 shows an ingestible device.

FIG. 12 shows an ingestible device 1200 which includes a first housing part 1202A, a second housing part 1202B, a fluid volume 1204, a drive force generator 1206, nozzles 1208 with nozzle openings 1210, plugs 1212, a seal 1214, a seal 1216 and a membrane 1218. The ingestible device 1200 is configured so that, before the subject swallows the device, the dispensable substance in fluid volume 1204 is under pressure from the drive force generator 1206, but the plugs 1212 prevent the dispensable substance in fluid volume 1204 from being delivered from the device 1200 via nozzle openings 1210. When the device 1200 reaches the appropriate location in the GI tract, the plugs 1212 erode, degrade and/or dissolve (e.g., due to pH, change in pH, presence of certain enzyme, and/or concentration of certain enzyme), so that the pressure from the drive force generator 1206 breaks the seal 1216 (made of a relatively low mechanical strength material, such as a seal), which causes the membrane 1218 to expand into the fluid volume 1204, forcing the dispensable substance out of the nozzle openings 1210 in the form of a jet. This results in in trans-epithelial delivery of the therapeutic agent contained in the dispensable substance.

The housing parts 1202A and (including the membrane 1218) are initially separate from each other. The plugs are disposed in the nozzles 1210, the dispensable substance is disposed in the fluid volume 1204, and the seal 1216 is added. The dispensable substance (including the therapeutic agent) is first sterilized, and then disposed in the fluid volume 1204 under aseptic conditions. The drive force generator 1206 is manufactured in a clean environment and then incorporated with the housing part 1202B, after which the membrane 1218 is added. Subsequently, the housing parts 1202A and 1202B are joined in a clean environment to produce the ingestible device 1200.

Figure 13:
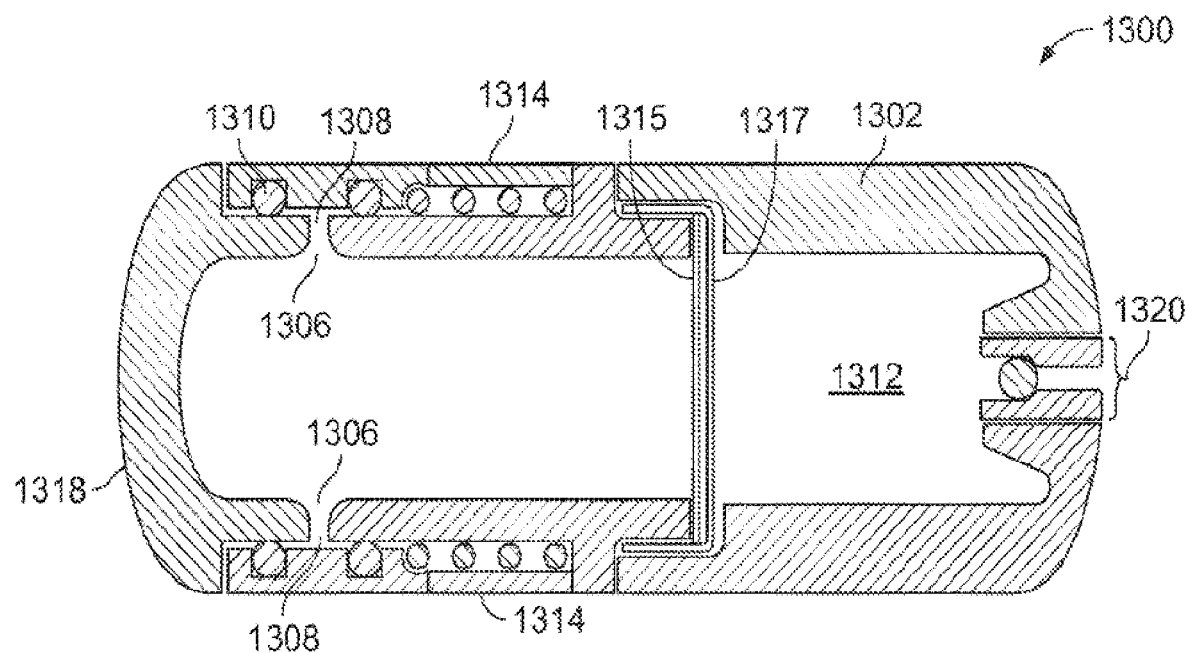
FIG. 13 shows an ingestible device.

FIG. 13 shows an embodiment of an ingestible device 1300 for trans-epithelial delivery. The device 1300 has a housing 1302 with a fluid volume 1304 containing a dispensable substance, nozzles 1306, nozzle openings 1308, a tensioned spring 1310, a drive force generator 1312, a band 1314 around the device, a seal 1315, a cap 1318, a membrane 1317 and a seal 1320. When the device 1300 is swallowed by the subject, the dispensable substance in the device is already pressurized. However, the band 1314 prevents the pressure of the drive force generator 1312 from relieving the tension in the spring 1310 so that the dispensable substance in the fluid volume 1304 is prevented from going through the nozzle openings 1308. When the device 1300 reaches the appropriate location in the GI tract, the band 1314 erodes, degrades and/or dissolves. Thus, the tension in the spring 1310 is relieved, and the spring moves to where the band 1314 was located, thereby rapidly exposing the nozzle openings 1308 to the environment exterior to the device 1300 so that the dispensable substance is delivered out of the openings 1308 in the form of a jet. This results in in trans-epithelial delivery of the therapeutic agent contained in the dispensable substance.

Figure 14:
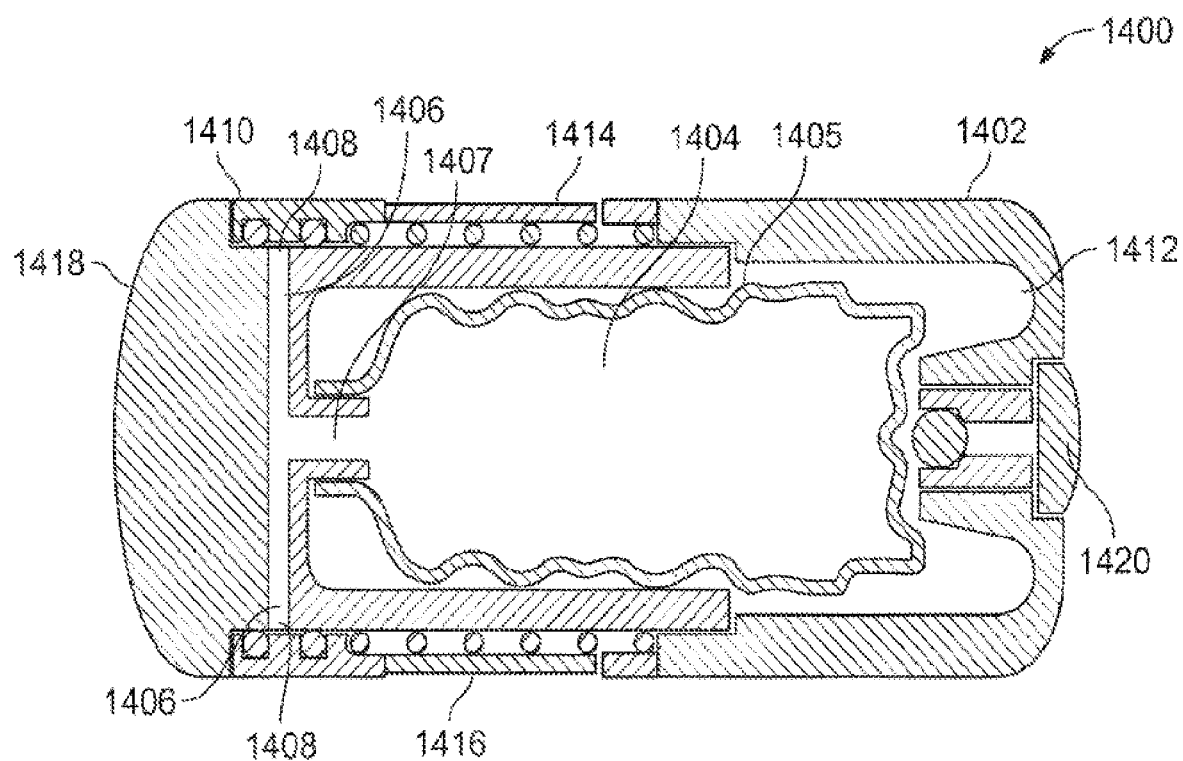
FIG. 14 shows an ingestible device.

FIG. 14 shows an embodiment of an ingestible device 1400 for trans-epithelial delivery. The device 1400 has a housing 1402 with a fluid volume 1404 containing a dispensable substance, a membrane 1405 defining the fluid volume 1404, an opening 1407 leading to nozzles 1406, nozzle openings 1408, a tensioned spring 1410, a pressurized gas (drive force generator) 1412, a band 1414, a cap 1418 and a seal 1420. When the device 1400 is swallowed by the subject, the dispensable substance in the device is already pressurized. However, the band 1414 keeps the spring 1410 tensioned so that the dispensable substance in the fluid volume 1404 is prevented from going through the nozzle openings 1408. When the device 1400 reaches the appropriate location in the GI tract, the band 1414 erodes, degrades and/or dissolves, relieving the tension in the spring 1410, which moves to where the band 1414 had been located, thereby rapidly exposing the nozzle openings 1408 to the environment exterior to the device 1400 so that the dispensable substance is delivered out of the openings 1408 in the form of a jet. This results in in trans-epithelial delivery of the therapeutic agent contained in the dispensable substance.

In some embodiments, the dispensable substance is not under pressure when the subject swallows the ingestible device. The following are illustrative examples of such ingestible devices.

Figure 15A:
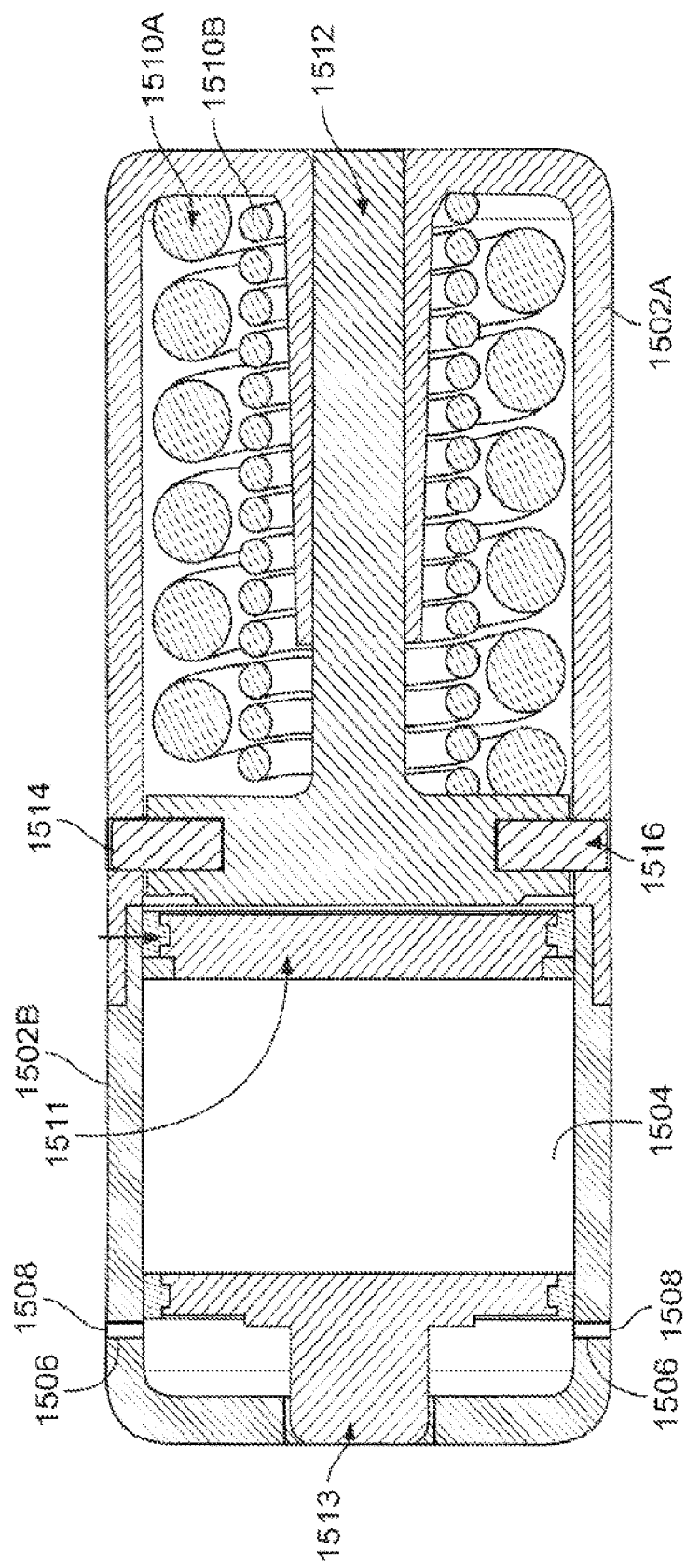
FIG. 15A shows an ingestible device.
Figure 15B:
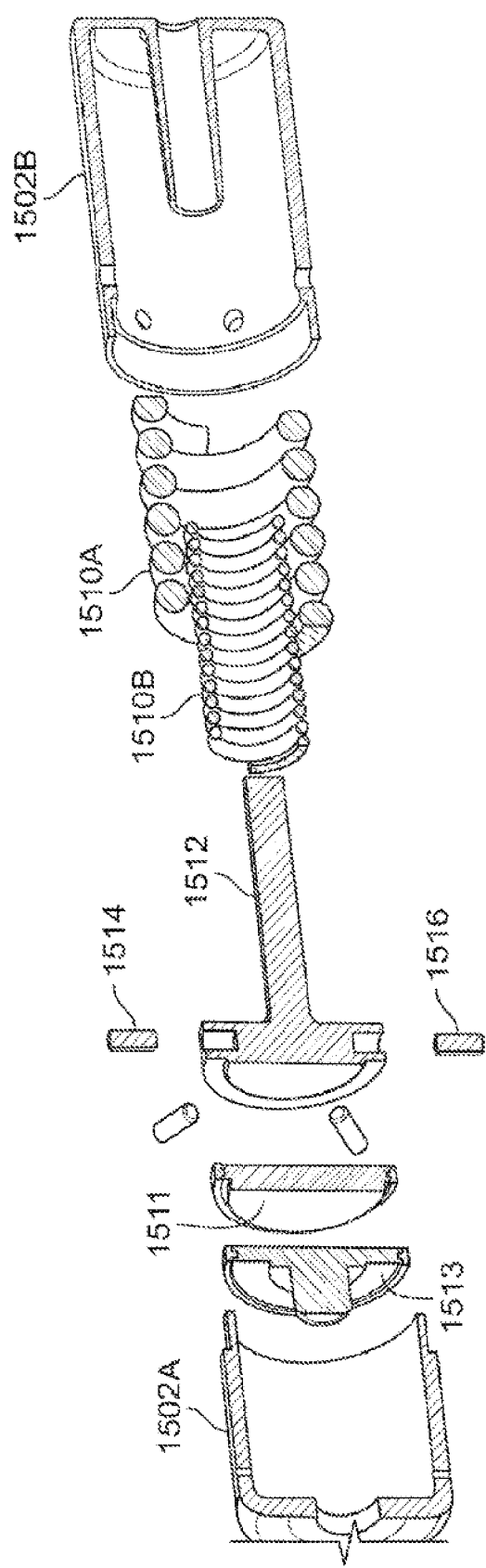
FIG. 15B shows an exploded view of the ingestible device of FIG. 15A.

As an example, FIG. 15A shows an embodiment of an ingestible device 1500 for trans-epithelial delivery. FIG. 15B shows an exploded view of the ingestible device 1500. The ingestible device 1500 has housing parts 1502A and 1502B, a fluid volume 1504 containing a dispensable substance, nozzles 1506, nozzle openings 1508, parallel springs 1510A and 1510B, a plunger 1511, a piston 1512, a piston 1513, a pin 1514 and a pin 1516. When the device 1500 is swallowed by the subject, the pins 1514 and 1516 prevent the dispensable substance in fluid volume 1504 from being under pressure from the springs 1510A and 1510B, the plunger 1511 and the piston 1512. Thus, the pins 1514 and 1516 prevent the pressure of the springs 1510A and 1510B, the plunger 1511 and the piston 1512 from forcing the dispensable substance in the fluid volume 1504 through the openings 1508. When the device 1500 reaches the appropriate location in the GI tract, the pin 1514 erodes, degrades and/or dissolves (e.g., due to pH, change in pH, presence of certain enzyme, and/or concentration of certain enzyme), and the pin 1516 is no longer sufficient to hold back the pressure from the springs 1510A and 1510B, the plunger 1511 and the piston 1512. Thus, the pressure of the springs 1510A and 1510B, the plunger 1511 and the piston 1512 is applied to the dispensable substance in the fluid volume 1504, forcing the dispensable substance out of the nozzle openings 1508 in the form of a jet. This results in in trans-epithelial delivery of the therapeutic agent contained in the dispensable substance.

Figure 15C:
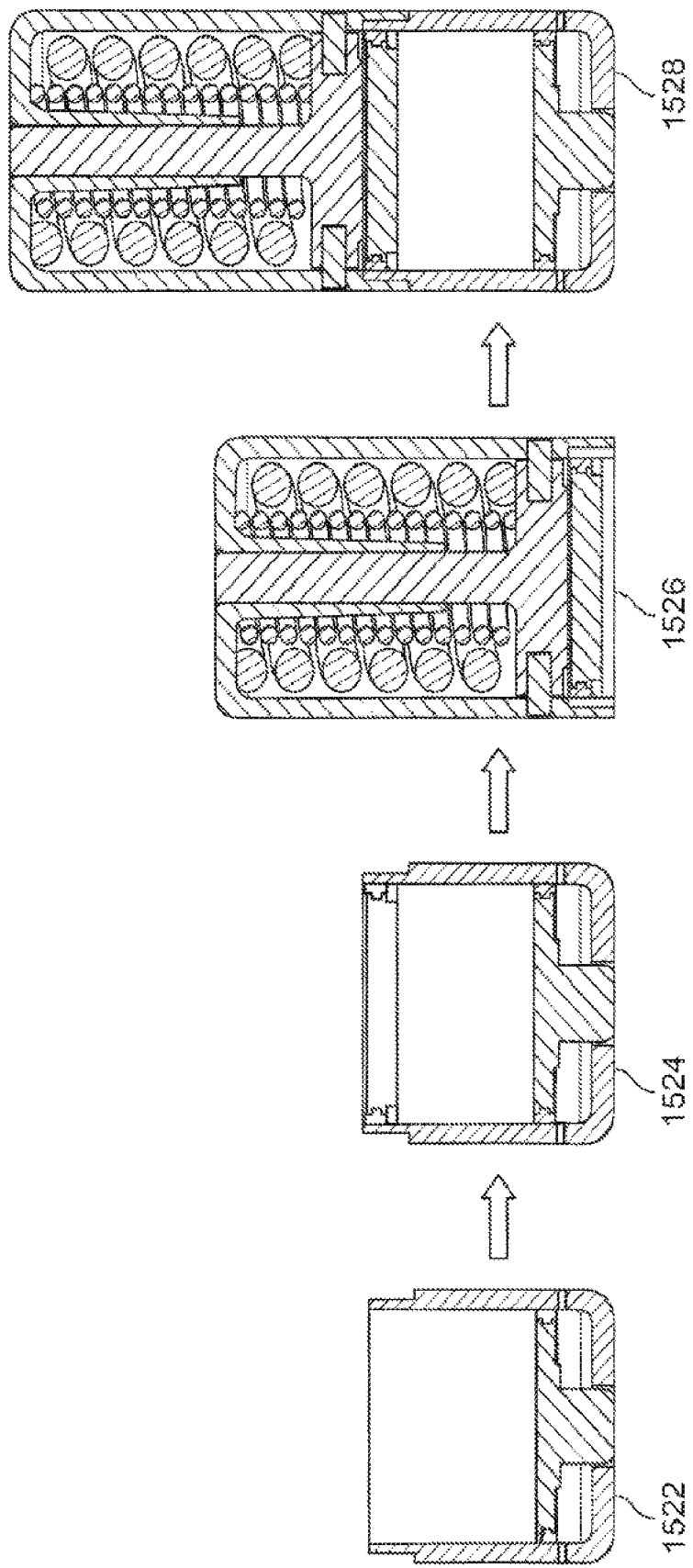
FIG. 15C shows aspects of steps in assembling the ingestible device of FIG. 15A.

FIG. 15C shows aspects of a process of assembling the ingestible device of 1500. In steps 1520 and 1522, the housing part 1502B and piston 1513 are combined and sterilized, the dispensable substance 1504 is added to the housing part 1502B in an aseptic environment, and drive piston 1511 is added to the housing part 1502B to seal the dispensable substance 1504 in the housing part 1502B. In step 1524, the housing part 1502A and its components are assembled in a clean environment. The drive plunger 1512 is used to compress the springs 1510A and 1510B, and the drive plunger 1512 is held in place via the pins 1514 and 1516. In step 1526, the resulting modules are assembled in a clean environment to produce the ingestible device 1500.

Figure 16:
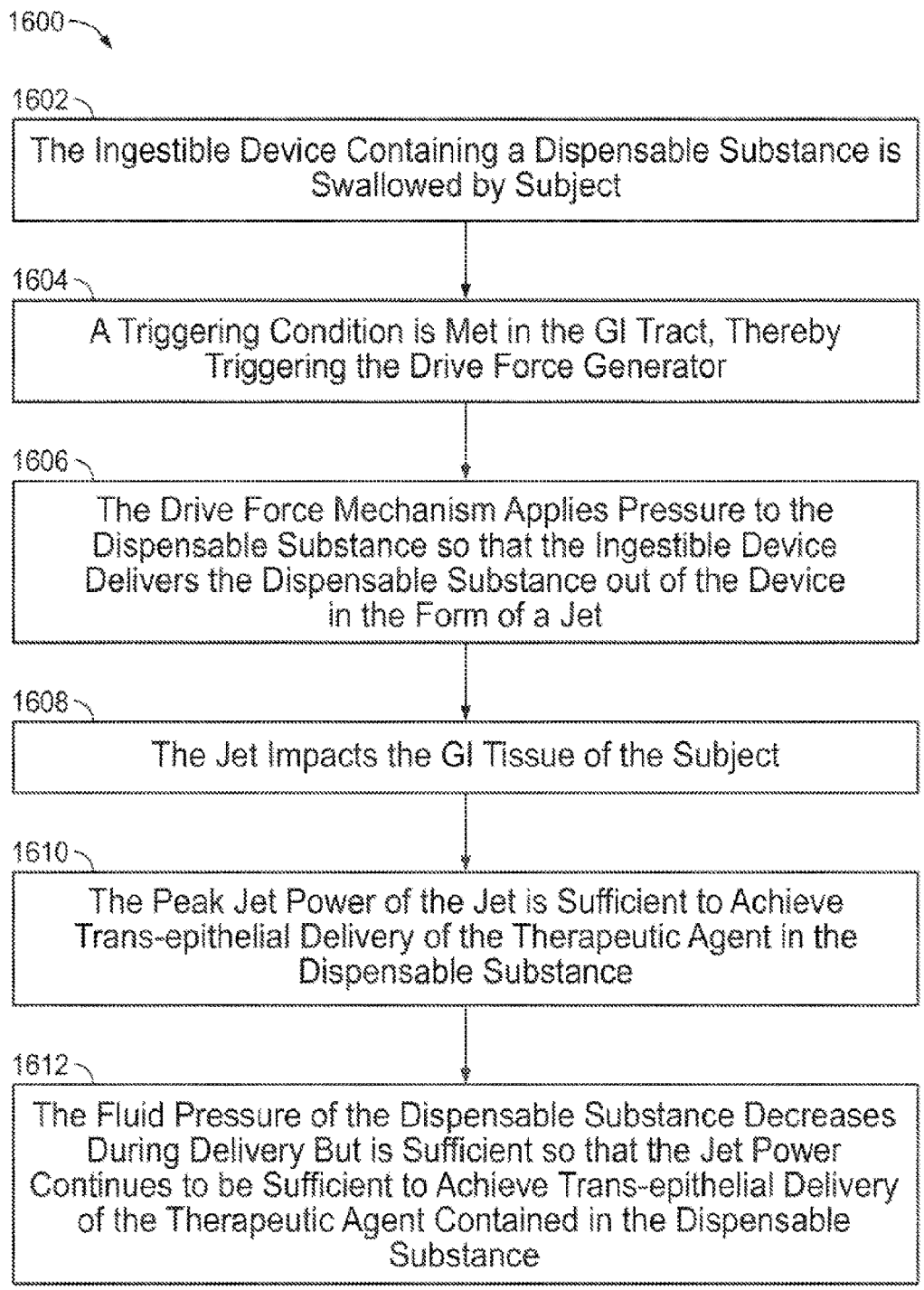
FIG. 16 shows an exemplary process flow chart for use of an ingestible device in which pressure is not applied to the dispensable substance before the subject swallows the ingestible device.

FIG. 16 shows an exemplary process flow chart 1600 for use of an ingestible device in which pressure is not applied to the dispensable substance before the subject swallows the ingestible device. The process beings at step 1602, when the patient swallows the ingestible device. In step 1604, a triggering condition (e.g., pH, change in pH, presence of certain enzyme, concentration of certain enzyme) is met in the GI tract, thereby triggering the drive force generator. In step 1606, the drive force mechanism applies pressure to the dispensable substance, resulting delivery of a jet of each dispensable substance from the ingestible device for each opening. In step 1608, the jet has a sufficient jet stable length for the jet to impact the GI tissue of the subject. In step 1610, the peak jet power of the jet is sufficient to achieve trans-epithelial delivery of the therapeutic agent contained in the dispensable substance. In step 1612, the fluid pressure of the dispensable substance decreases during delivery but is sufficiently so that the peak jet power continues to be sufficient to achieve trans-epithelial delivery of the therapeutic agent contained in the dispensable substance.

Figure 17:
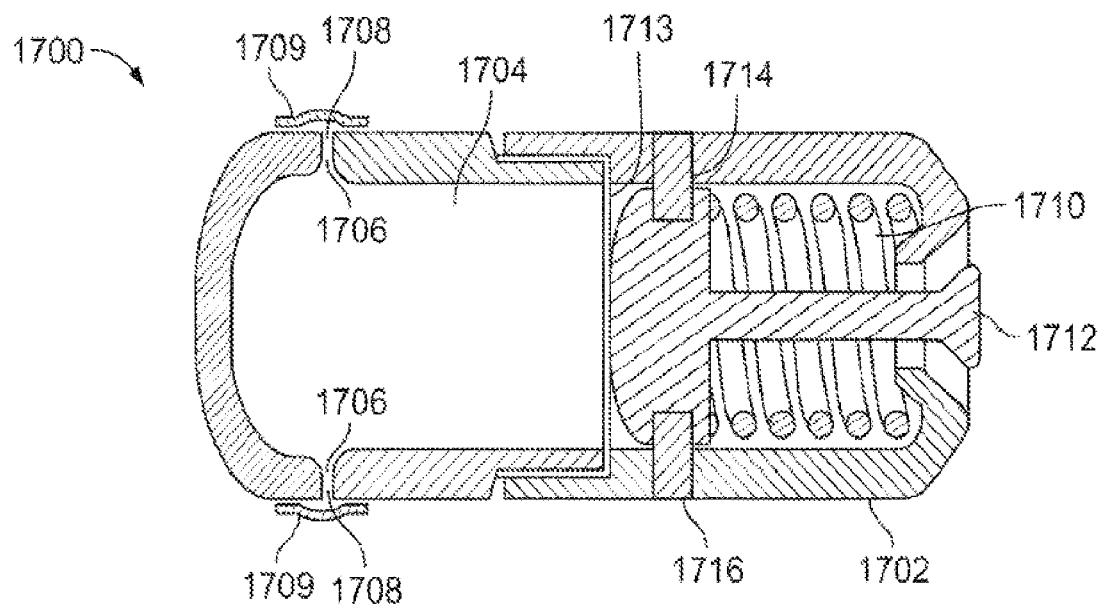
FIG. 17 shows an ingestible device.

FIG. 17 shows an embodiment of an ingestible device 1700 for trans-epithelial delivery, which contains a dispensable substance that is not under pressure when the subject swallows the ingestible device. The device 1700 has a housing 1702 with a fluid volume 1704 containing a dispensable substance, nozzles 1706, nozzle openings 1708, coverings 1709 over openings 1708, a spring 1710, a piston 1712, a fluid barrier 1713 (to prevent the dispensable substance from contacting the piston 1712 or the spring 1710), a pin 1714 and a pin 1716. When the device 1700 is swallowed by the subject, the pins 1714 and 1716 prevent the dispensable substance in fluid volume 1704 from being under pressure from the spring 1710 and the piston 1712, and the coverings 1709 prevent the dispensable substance from exiting the device via openings 1708. When the device 1700 reaches the appropriate location in the GI tract, the pin 1714 erodes, degrades and/or dissolves (e.g., due to pH, change in pH, presence of certain enzyme, and/or concentration of certain enzyme), and the pin 1716 is no longer sufficient to hold back the pressure from the spring 1710 and the piston 1712. Thus, the pressure of the spring 1710 and the piston 1712 is applied to the dispensable substance in the fluid volume 1704, forcing the seals 1709, which are made of a relatively low mechanical strength material (e.g., a foil or a film) to break so that the dispensable substance is delivered out of the nozzle openings 1708 in the form of a jet. This results in in trans-epithelial delivery of the therapeutic agent contained in the dispensable substance.

Figure 18:
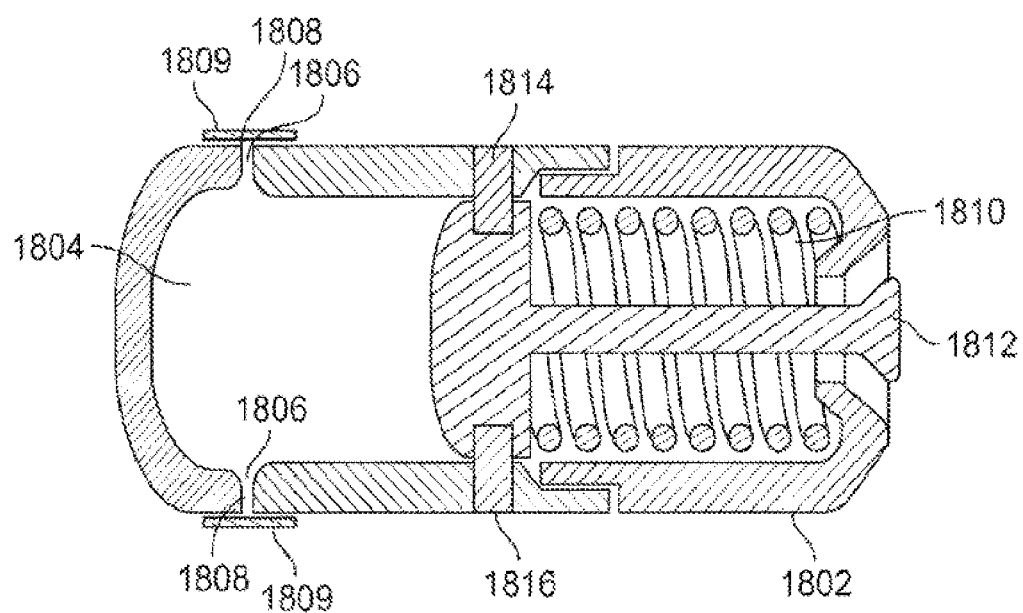
FIG. 18 shows an ingestible device.

FIG. 18 shows an embodiment of an ingestible device 1800 for trans-epithelial delivery, which contains a dispensable substance that is not under pressure when the subject swallows the ingestible device. The device 1800 has a housing 1802 with a fluid volume 1804 containing a dispensable substance, nozzles 1806, nozzle openings 1808, coverings 1809 over openings 1808, a spring 1810, a piston 1812, a pin 1814 and a pin 1816. When the device 1800 is swallowed by the subject, the pins 1814 and 1816 prevent the dispensable substance in fluid volume 1804 from being under pressure from the spring 1810 and the piston 1812, and the coverings 1809 prevent the dispensable substance from exiting the device via openings 1808. When the device 1800 reaches the appropriate location in the GI tract, the pin 1814 erodes, degrades and/or dissolves (e.g., due to pH, change in pH, presence of certain enzyme, and/or concentration of certain enzyme), and the pin 1816 is no longer sufficient to hold back the pressure from the spring 1810 and the piston 1812. Thus, the pressure of the spring 1810 and the piston 1812 is applied to the dispensable substance in the fluid volume 1804, forcing the seals 1809, which are made of a relatively low mechanical strength material (e.g., a foil or a film) to break so that the dispensable substance is delivered out of the nozzle openings 1808 in the form of a jet. This results in in trans-epithelial delivery of the therapeutic agent contained in the dispensable substance.

FIG. 19A shows an embodiment of an ingestible device 1900 for trans-epithelial delivery, which contains a dispensable substance that is not under pressure when the subject swallows the ingestible device. FIG. 19B is an exploded view of the ingestible device 1900. The ingestible device 1900 has a cap 1901, housing parts 1902A and 1902B with a fluid volume 1904 containing a dispensable substance, nozzles 1906, nozzle openings 1908, coverings 1909 over openings 1908, a seal 1913, a spring 1910, a gas cylinder 1911, a membrane 1915 surrounding the gas cylinder 1911, a piercer 1912, a pin 1914, a pin 1916, and an O-ring 1919. The cap 1901 is removed before the subject swallows the ingestible device 1900. When the device 1900 is swallowed by the subject, the pins 1914 and 1916 prevent the dispensable substance in fluid volume 1904 from being under pressure by holding the spring 1910 and the piercer 1912 in place. When the device 1900 reaches the appropriate location in the GI tract, the pin 1914 erodes, degrades and/or dissolves (e.g., due to pH, change in pH, presence of certain enzyme, and/or concentration of certain enzyme), and the pin 1916 is no longer sufficient to hold back the pressure from the spring 1910. The spring forces the piercer 1912 into the gas cylinder 1911, puncturing the gas cylinder 1911 and causing gas at elevated pressure to leave the cylinder 1911. This causes the cylinder to press against the membrane 1915, which expands against the seal 1913. The seal 1913 is made of a relatively low mechanical strength material (e.g., a foil or a film), which breaks when pressed against by the expanding membrane 1915. This causes the expanding membrane 1915 to apply pressure against the dispensable substance in the fluid volume 1904. This causes the coverings 1909, which are made of a relatively low mechanical strength material (e.g., a foil or a film), to break so that the dispensable substance is delivered out of the nozzle openings 1908 in the form of a jet. This results in in trans-epithelial delivery of the therapeutic agent contained in the dispensable substance. In some embodiments, the housing of the ingestible device 1900 is about 26 millimeters long, has a diameter of about 11 mm, a wall thickness of about 0.8 mm Newtons, an end round of about 1.5 mm, an internal volume of about 1685 µL. In such embodiments, the fluid volume 1904 can be about 425 µL. In some embodiments, the ingestible device 1900 does not include coverings 1909.

Figure 19C:
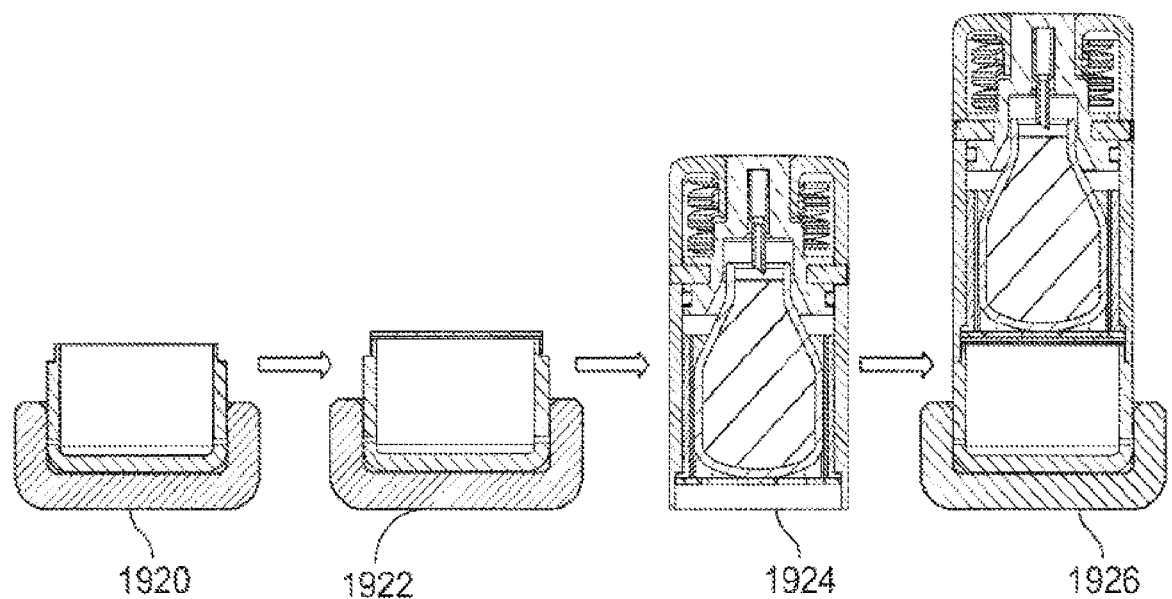
FIG. 19C shows aspects of steps in assembling the ingestible device of FIG. 19A.

FIG. 19C schematically shows certain aspects of a process for the assembly of the ingestible device 1900. In step 1920, the housing part 1902 is combined with the cap 1901 and coverings 1909. In step 1922, the dispensable substance 1904 is added to the housing part 1902B in an aseptic environment, and the seal 1913 is added. In step 1924, the housing part 1902A and its components are assembled in a clean environment. The piercer 1912 is held in place by pins 1914 and 1916, and the gas cylinder 1911 is held in place by components of this assembly. In step 1926, the resulting modules are combined to provide the ingestible device 1900.

Figure 19D:
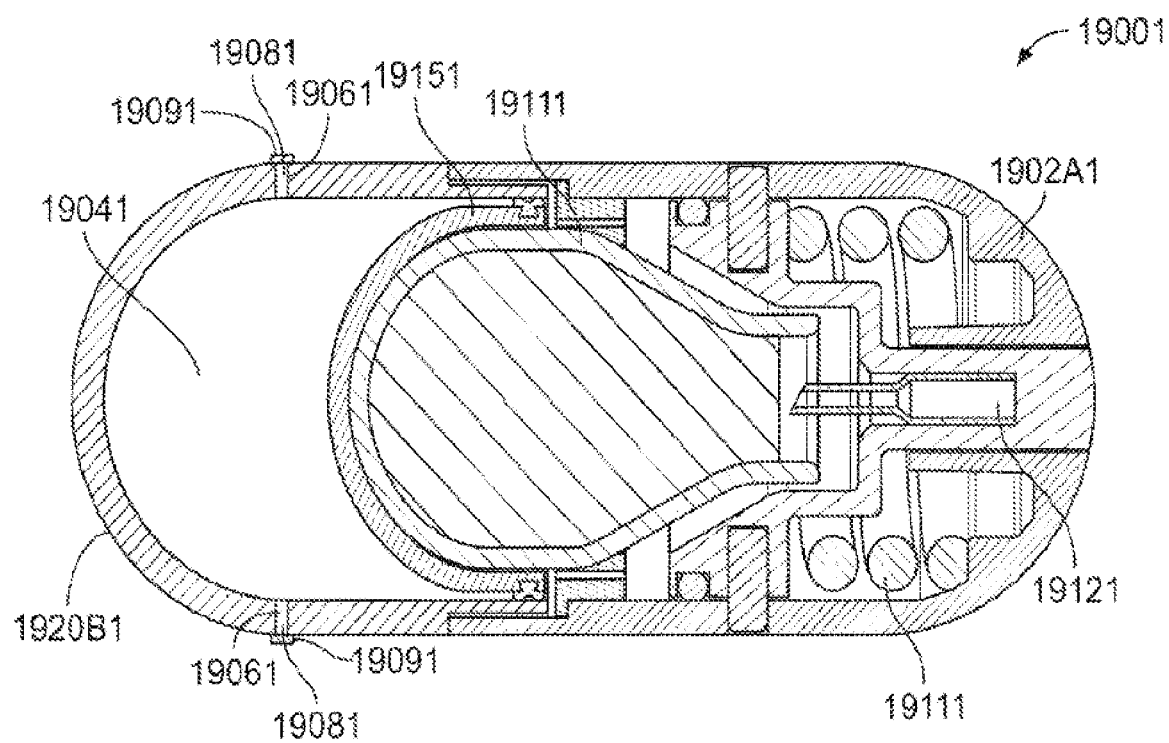
FIG. 19D shows an ingestible device with aspects similar to those shown in FIG. 19A.

FIG. 19D shows an ingestible device 19001 for trans-epithelial delivery, which contains a dispensable substance that is not under pressure when the subject swallows the ingestible device. The ingestible device 19001 has housing parts 1902A1 and 1902B1 with a fluid volume 19041 containing a dispensable substance, nozzles 19061, nozzle openings 19081, coverings 19091 over openings 19081, a spring 19101, a gas cylinder 19111, a piston 19151, a piercer 19121, and an O-ring 19191. The pins used as the triggering mechanism are not shown in FIG. 19D but are similarly configured as pins 1914 and 1916 in FIG. 19A. When the device 19001 is swallowed by the subject, the pins prevent the dispensable substance in fluid volume 19041 from being under pressure by holding the spring 19101 and the piercer 19121 in place. When the device 19001 reaches the appropriate location in the GI tract, one of the pins erodes, degrades and/or dissolves (e.g., due to pH, change in pH, presence of certain enzyme, and/or concentration of certain enzyme), and the other pin is no longer sufficient to hold back the pressure from the spring 19101. The spring forces the piercer 19121 into the gas cylinder 19111, puncturing the gas cylinder 19111 and causing gas at elevated pressure to leave the cylinder 19111. This causes the gas cylinder 19111 to press against the piston 19151 and apply pressure to the fluid volume 19041. This causes the coverings 19091, which are made of a relatively low mechanical strength material (e.g., a foil or a film), to break so that the dispensable substance is delivered out of the nozzle openings 19081 in the form of a jet. This results in in trans-epithelial delivery of the therapeutic agent contained in the dispensable substance. In some embodiments, the housing of the ingestible device 19001 has a diameter of about 11 mm, a length of about 26 mm, a wall thickness of about 0.8 mm, an end round of about 5.5 mm (spherical), and an internal volume of about 1475 µL. In such embodiments, a fluid volume 19041 can be about 400 µL, and a gas volume in the gas cylinder 19111 can be about 255 µL.

Figure 19E:
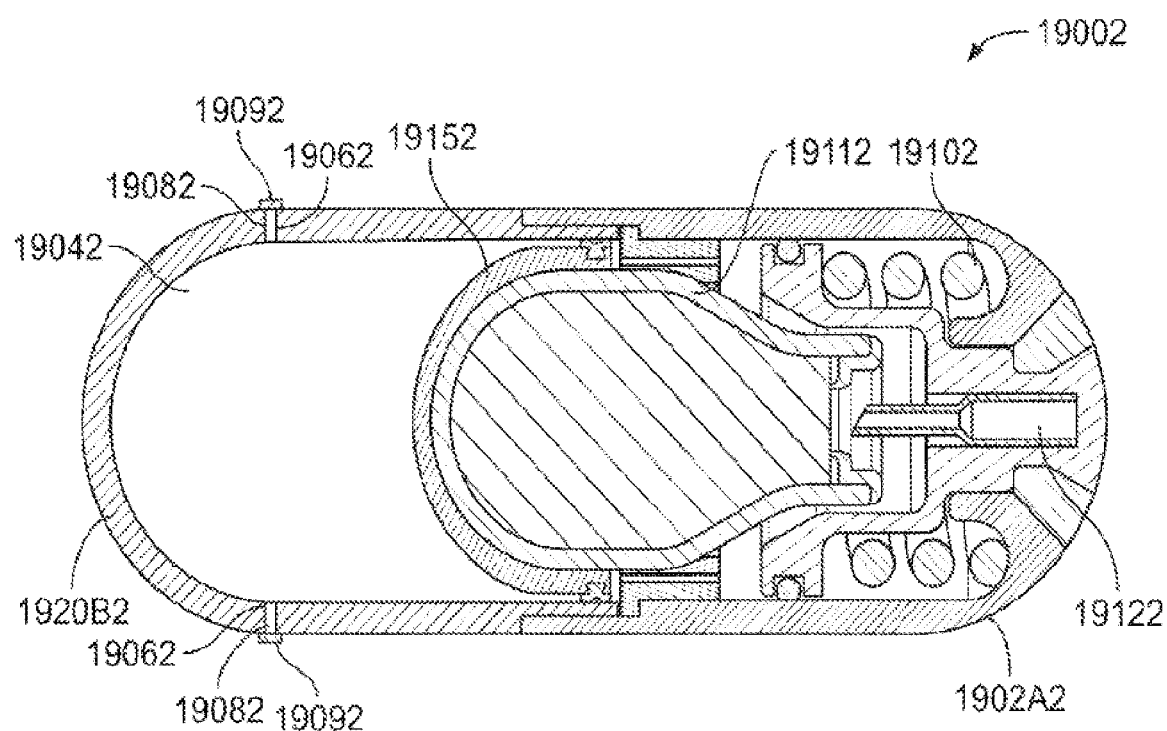
FIG. 19E shows an ingestible device with aspects similar to those shown in FIG. 19A.

FIG. 19E shows an ingestible device 19002 for trans-epithelial delivery, which contains a dispensable substance that is not under pressure when the subject swallows the ingestible device. The ingestible device 19002 has housing parts 1902A2 and 1902B2 with a fluid volume 19042 containing a dispensable substance, nozzles 19062, nozzle openings 19082, coverings 19092 over openings 19082, a spring 19102, a gas cylinder 19112, a piston 19152, a piercer 19122, and an O-ring 19192. The pins used as the triggering mechanism are not shown in FIG. 19E but are similarly configured as pins 1914 and 1916 in FIG. 19A. When the device 19002 is swallowed by the subject, the pins prevent the dispensable substance in fluid volume 19042 from being under pressure by holding the spring 19102 and the piercer 19122 in place. When the device 19002 reaches the appropriate location in the GI tract, one of the pins erodes, degrades and/or dissolves (e.g., due to pH, change in pH, presence of certain enzyme, and/or concentration of certain enzyme), and the other pin is no longer sufficient to hold back the pressure from the spring 19102. The spring forces the piercer 19122 into the gas cylinder 19112, puncturing the gas cylinder 19112 and causing gas at elevated pressure to leave the cylinder 19112. This causes the gas cylinder 19112 to press against the piston 19152 and apply pressure to the fluid volume 19042. This causes the coverings 19092, which are made of a relatively low mechanical strength material (e.g., a foil or a film), to break so that the dispensable substance is delivered out of the nozzle openings 19082 in the form of a jet. This results in in trans-epithelial delivery of the therapeutic agent contained in the dispensable substance. In some embodiments, the housing of the ingestible device 19002 has a diameter of about 9.9 mm, a length of about 26.1 mm, a wall thickness of about 0.7 mm, a fluid volume 19042 of about 445 µL, a gas volume in the gas cylinder 19112 of about 193 µL.

Figure 19F:
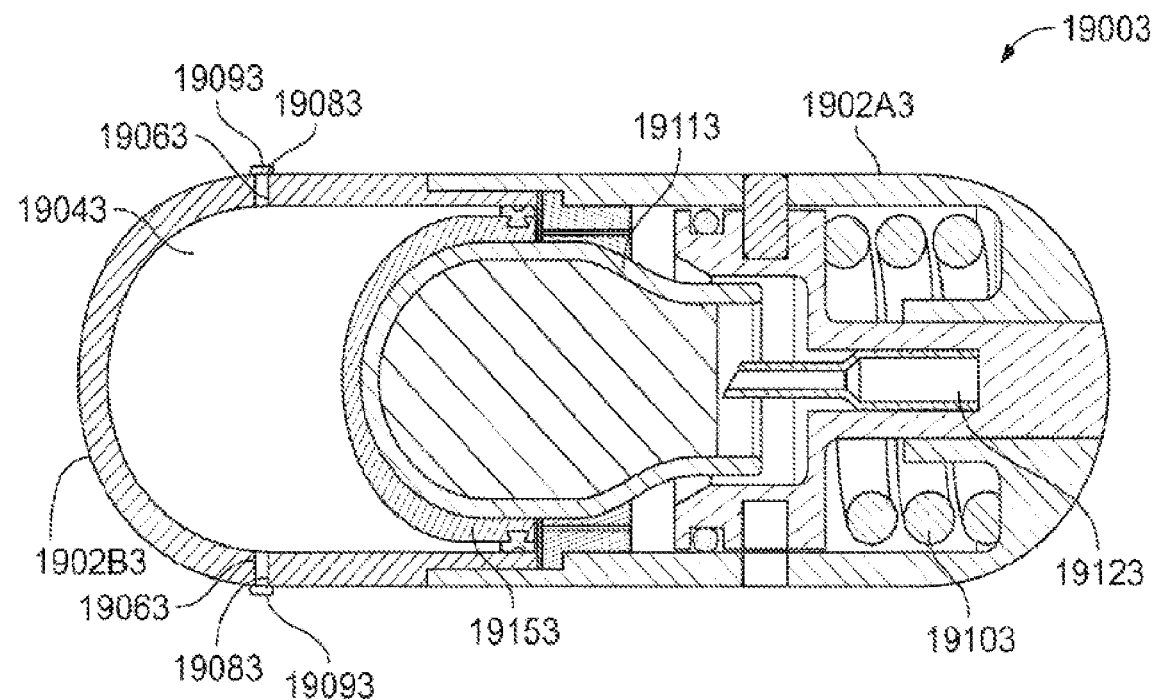
FIG. 19F shows an ingestible device with aspects similar to those shown in FIG. 19A.

FIG. 19F shows an ingestible device 19003 for trans-epithelial delivery, which contains a dispensable substance that is not under pressure when the subject swallows the ingestible device. The ingestible device 19003 has housing parts 1902A3 and 1902B3 with a fluid volume 19043 containing a dispensable substance, nozzles 19063, nozzle openings 19083, coverings 19093 over openings 19083, a spring 19103, a gas cylinder 19113, a pin 19143, a pin 19163, a piston 19153, a piercer 19123, and an O-ring 19193. When the device 19003 is swallowed by the subject, the pins 19143 and 19163 prevent the dispensable substance in fluid volume 19043 from being under pressure by holding the spring 191033 and the piercer 19123 in place. When the device 19003 reaches the appropriate location in the GI tract, the pin 19143 erodes, degrades and/or dissolves (e.g., due to pH, change in pH, presence of certain enzyme, and/or concentration of certain enzyme), and the pin 19163 is no longer sufficient to hold back the pressure from the spring 19103. The spring forces the piercer 19123 into the gas cylinder 19113, puncturing the gas cylinder 19113 and causing gas at elevated pressure to leave the cylinder 19113. This causes the gas cylinder 19113 to press against the piston 19153 and apply pressure to the fluid volume 19043. This causes the coverings 19093, which are made of a relatively low mechanical strength material (e.g., a foil or a film), to break so that the dispensable substance is delivered out of the nozzle openings 19083 in the form of a jet. This results in in trans-epithelial delivery of the therapeutic agent contained in the dispensable substance. In some embodiments, the housing of the ingestible device 19003 has a diameter of about 8.5 mm, a length of about 23.3 mm, a wall thickness of about 0.7 mm, an end round of about 4.25 mm (spherical), and an internal volume of about 775 µL. In such embodiments, the fluid volume 19043 can be about 205 µL, and a gas volume in the gas cylinder 19113 can be about 160 µL.

Figure 19G:
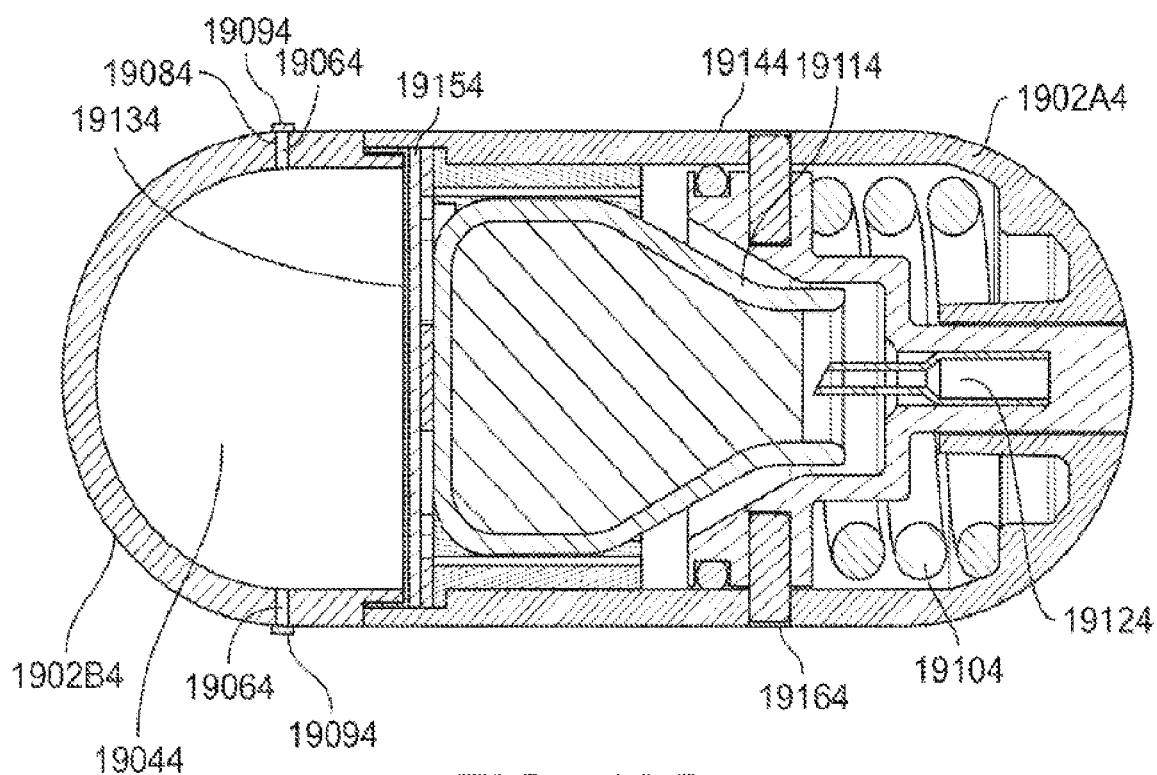
FIG. 19G shows an ingestible device with aspects similar to those shown in FIG. 19A.

FIG. 19G shows an ingestible device 19004 for trans-epithelial delivery, which contains a dispensable substance that is not under pressure when the subject swallows the ingestible device. The ingestible device 19004 has housing parts 1902A4 and 1902B4 with a fluid volume 19044 containing a dispensable substance, nozzles 19064, nozzle openings 19084, coverings 19094 over openings 19084, a spring 19104, a gas cylinder 19114, a pin 19144, a pin 19164, a gas cylinder 19114, a seal 19134, a membrane 19154, a piercer 19124, a pin 19144, and a pin 19164, and an O-ring 19194. When the device 19004 is swallowed by the subject, the pins 19144 and 19164 prevent the dispensable substance in fluid volume 19044 from being under pressure by holding the spring 19104 and the piercer 19124 in place. When the device 19004 reaches the appropriate location in the GI tract, the pin 19144 erodes, degrades and/or dissolves (e.g., due to pH, change in pH, presence of certain enzyme, and/or concentration of certain enzyme), and the pin 19164 is no longer sufficient to hold back the pressure from the spring 19104. The spring forces the piercer 19124 into the gas cylinder 19114, puncturing the gas cylinder 19114 and causing gas at elevated pressure to leave the cylinder 19114. This causes the cylinder to press against the membrane 19154, which expands against the seal 19134. The seal 19134 is made of a relatively low mechanical strength material (e.g., a foil or a film), which breaks when pressed against by the expanding membrane 19154. This causes the expanding membrane 19154 to apply pressure against the dispensable substance in the fluid volume 19044. This causes the coverings 19094, which are made of a relatively low mechanical strength material (e.g., a foil or a film), to break so that the dispensable substance is delivered out of the nozzle openings 19084 in the form of a jet. This results in in trans-epithelial delivery of the therapeutic agent contained in the dispensable substance. In some embodiments, the housing of the ingestible device 19004 is about 26 millimeters long, has a diameter of about 11 mm, and a wall thickness of about 0.8 mm Newtons. In such embodiments, the fluid volume 19044 can be about 410 µL. In such embodiments, the gas volume of the gas cylinder 19114 can be about 216 µL, and the spring 19104 can provide a force of about 80 Newtons.

Figure 19H:
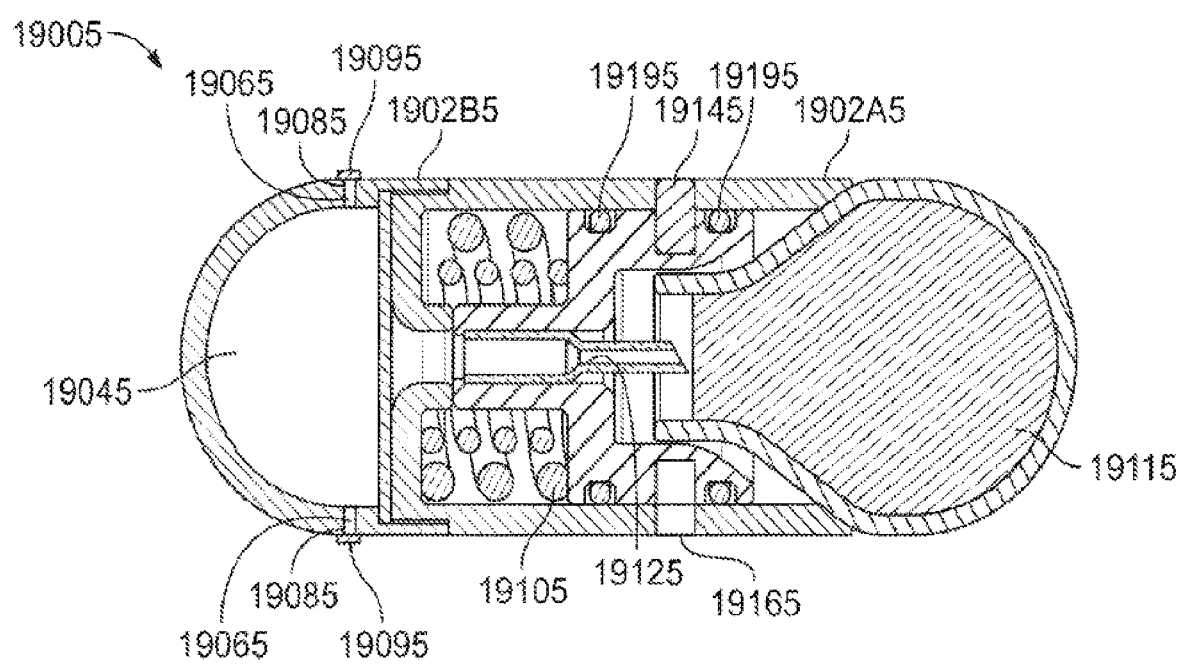
FIG. 19H shows an ingestible device with aspects similar to those shown in FIG. 19A.

FIG. 19H shows an ingestible device 19005 for trans-epithelial delivery, which contains a dispensable substance that is not under pressure when the subject swallows the ingestible device. The ingestible device 19005 has housing parts 1902A5 and 1902B5 with a fluid volume 19045 containing a dispensable substance, nozzles 19065, nozzle openings 19085, coverings 19095 over openings 19085, a spring 19105, a gas cylinder 19115, a pin 19145, a pin 19165, a gas cylinder 19115, a membrane 19155, a piercer 19125, a pin 19145, and a pin 19165, and O-rings 19195. When the device 19005 is swallowed by the subject, the pins 19145 and 19165 prevent the dispensable substance in fluid volume 19045 from being under pressure by holding the spring 19105 and the piercer 19125 in place. When the device 19005 reaches the appropriate location in the GI tract, the pin 19145 erodes, degrades and/or dissolves (e.g., due to pH, change in pH, presence of certain enzyme, and/or concentration of certain enzyme), and the pin 19165 is no longer sufficient to hold back the pressure from the spring 19105. The spring forces the piercer 19125 into the gas cylinder 19115, puncturing the gas cylinder 19115 and causing gas at elevated pressure to leave the cylinder 19115. This causes the cylinder to press against the membrane 19155, which causes the expanding membrane 19155 to apply pressure against the dispensable substance in the fluid volume 19045. This causes the coverings 19095, which are made of a relatively low mechanical strength material (e.g., a foil or a film), to break so that the dispensable substance is delivered out of the nozzle openings 19085 in the form of a jet. This results in in trans-epithelial delivery of the therapeutic agent contained in the dispensable substance. In some embodiments, the housing of the ingestible device 19005 is about 23.3 millimeters long, has a diameter of about 8.5 mm, and a wall thickness of about 0.7 mm. In such embodiments, the fluid volume 19045 can be about 300 µL. In such embodiments, the gas volume of the gas cylinder 19115 can be about 247 µL.

Figure 19I:
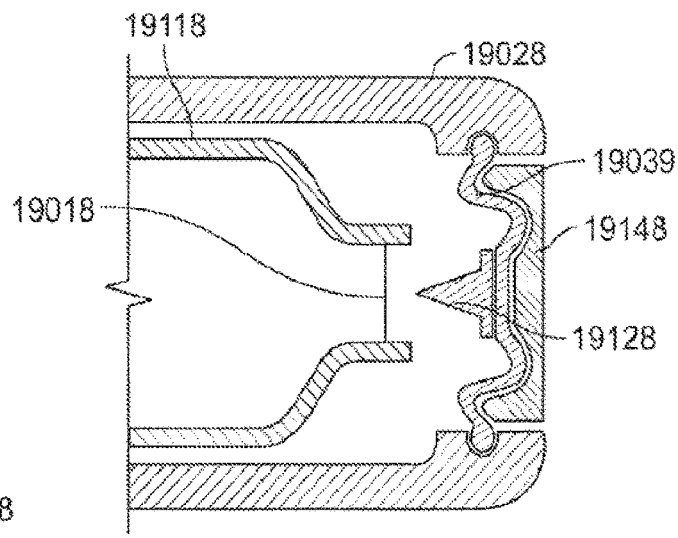
FIGS. 19I and 19J show aspects of states of an ingestible device.
Figure 19J:
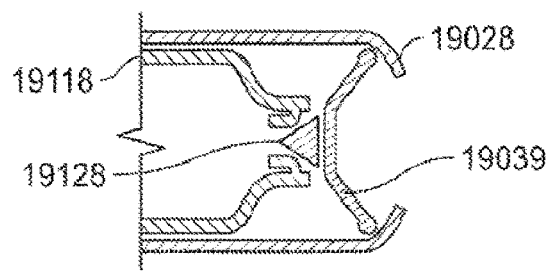

FIG. 19I shows a portion of an ingestible device including a housing part 19028, a gas cylinder 19118 with a membrane 19018, a piercer 19128 that is held in place via an enteric material 19148, and a biased diaphragm 19039. FIG. 19J shows corresponding portions of the ingestible device after the enteric material 19148 degrades/dissolves/erodes. The diaphragm 19038 has moved so that the piercer 19126 has pierced the membrane 19016, causing the gas in the gas cylinder 19116 to escape. Although not shown, the gas pressure causes another housing part (e.g., the housing part of the drug module) to move, to expose nozzle openings so that the dispensable substance leaves the ingestible device in the form jets for trans-epithelial delivery.

Figure 19K:
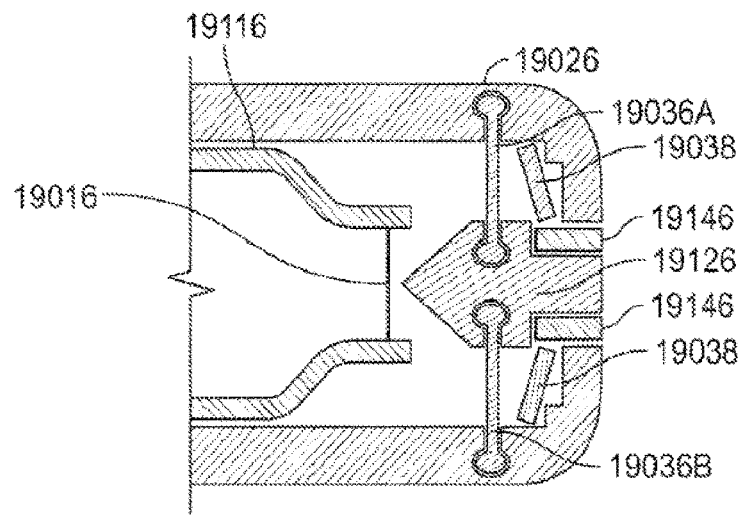
FIGS. 19K and 19L show aspects of states of an ingestible device.
Figure 19L:
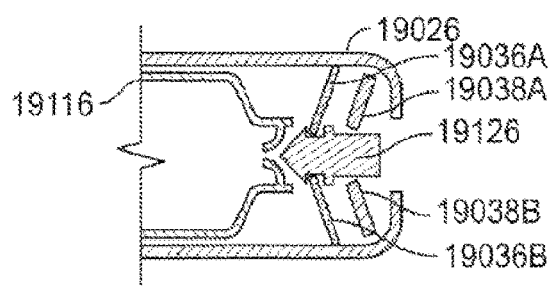

FIG. 19K shows a portion of an ingestible device including a housing part 19026, a gas cylinder 19116 with a membrane 19016, a piercer 19126 that is held in place via an enteric material 19146, stabilizing elements 19036A and 19036B, and a biasing element 19038 (e.g., a disc spring). FIG. 19K shows corresponding portions of the ingestible device after the enteric material 19146 degrades/dissolves/erodes. The spring biasing element 19038 has moved so that the piercer 19126 has pierced the membrane 19016, causing the gas in the gas cylinder 19116 to escape. Although not shown, the gas pressure causes another housing part (e.g., the housing part of the drug module) to move, to expose nozzle openings so that the dispensable substance leaves the ingestible device in the form jets for trans-epithelial delivery.

Figure 20A:
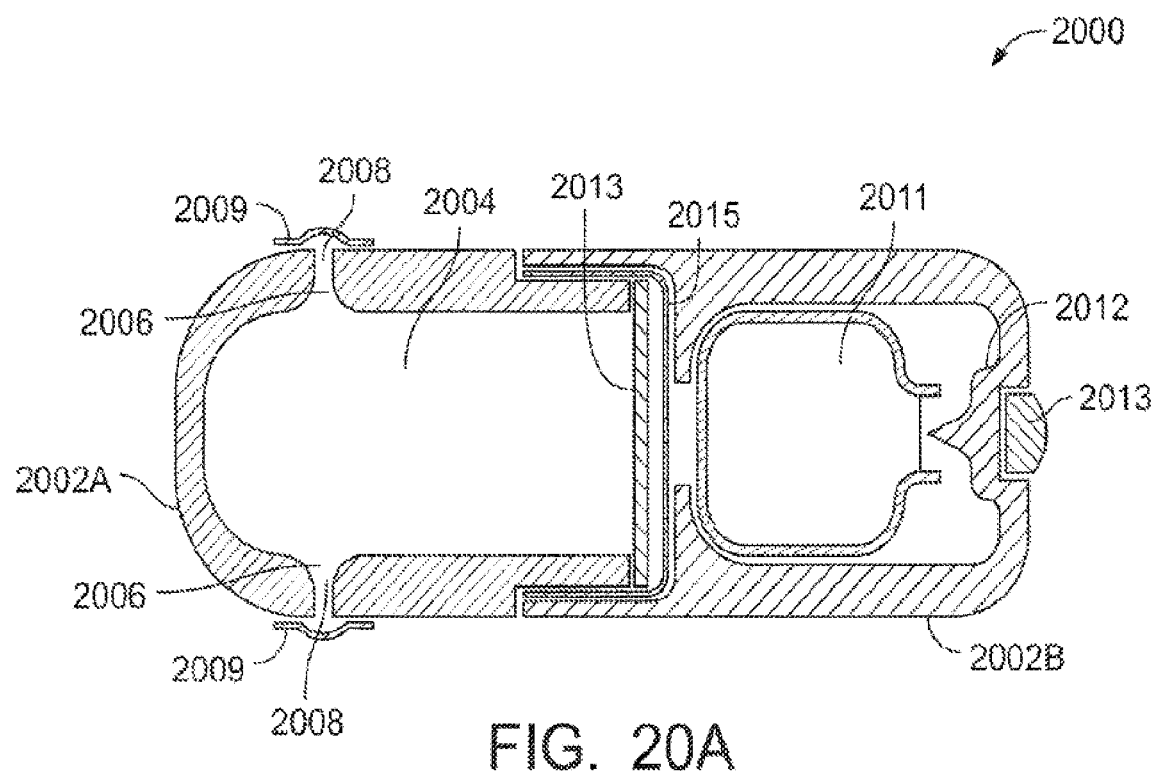
FIGS. 20A and 20B show an ingestible device.

FIG. 20A shows an embodiment of an ingestible device 2000 for trans-epithelial delivery, containing a dispensable substance that is not under pressure when the subject swallows the ingestible device. The device 2000 has housing parts 2002A and 2002B with a fluid volume 2004 containing a dispensable substance, nozzles 2006, nozzle openings 2008, seals 2009 over openings 2008, a seal 2013, a gas cylinder 2011, a membrane 2015 between the seal 2013 and the gas cylinder 2011, a biased piercer 2012, and a plug 2013. When the device 2000 is swallowed by the subject, the plug 2013 keeps the piercer in its biased position as shown in FIG. 20A. When the device 2000 reaches the appropriate location in the GI tract, the plug 2013 erodes, degrades and/or dissolves (e.g., due to pH, change in pH, presence of certain enzyme, and/or concentration of certain enzyme), and the piercer 2012 moves axially to pierce the gas cylinder 2011 and cause gas at elevated pressure to leave the cylinder 2011. This causes the cylinder to press against the membrane 2015, which breaks the seal 2013 so that the pressure is applied against the dispensable substance in the fluid volume 2004. This causes the coverings 2009, which are made of a relatively low mechanical strength material (e.g., a foil or a film), to break so that the dispensable substance is delivered out of the nozzle openings 2008 in the form of a jet. This results in trans-epithelial delivery of the therapeutic agent contained in the dispensable substance.

Figure 20B:
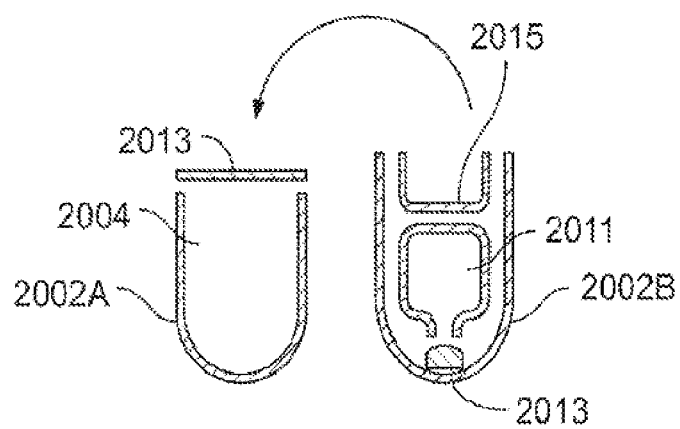

FIG. 20B schematically shows certain aspects of the assembly of the ingestible device 2000. The housing parts 2002A (including the seal 2013) and 2002B (including the membrane 2015, the gas cylinder 2011 and the piercer 2012) are initially separate from each other. The dispensable substance (including the therapeutic agent) is first sterilized, and then disposed in the fluid volume 2004 under aseptic conditions. The components in housing part 2002B are assembled in a clean environment. Subsequently, the housing parts 2002A and 2002B are joined in a clean environment to produce the ingestible device 2000.

Figure 21A:
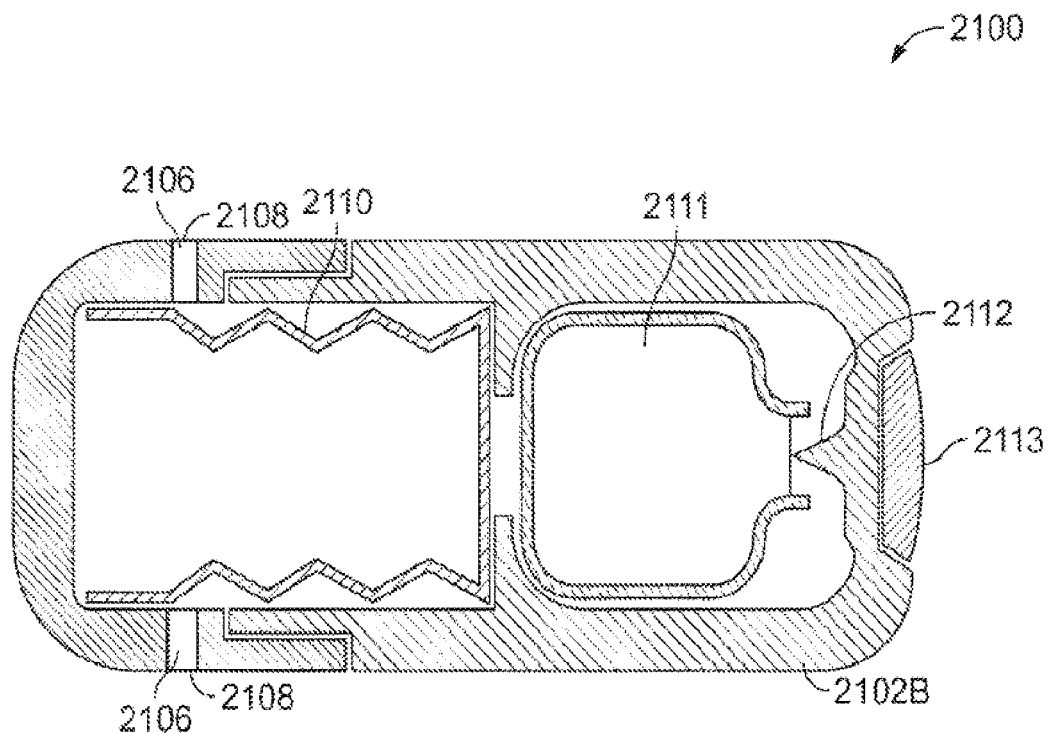
FIGS. 21A and 21B show an ingestible device.

FIG. 21A shows an embodiment of an ingestible device 2100 for trans-epithelial delivery, containing a dispensable substance that is not under pressure when the subject swallows the ingestible device. The device 2100 has housing parts 2102A and 2102B with a fluid volume 2104 containing a dispensable substance, nozzles 2106, nozzle openings 2108, a bellows 2110, a gas cylinder 2111, a biased piercer 2112, and a plug 2113. When the device 2100 is swallowed by the subject, the plug 2113 keeps the piercer in its biased position as shown in FIG. 20A. When the device 2100 reaches the appropriate location in the GI tract, the plug 2113 erodes, degrades and/or dissolves (e.g., due to pH, change in pH, presence of certain enzyme, and/or concentration of certain enzyme), and the piercer 2112 moves axially to pierce the gas cylinder 2111 and cause gas at elevated pressure to leave the cylinder 2111. This gas pressure is applied against press against the bellows 2110, causing the bellows 2110 such that holes in the bellows 21120 (not shown) align with the nozzles 2106 so that the dispensable substance is delivered out of the nozzle openings 2008 in the form of a jet. This results in trans-epithelial delivery of the therapeutic agent contained in the dispensable substance.

Figure 21B:
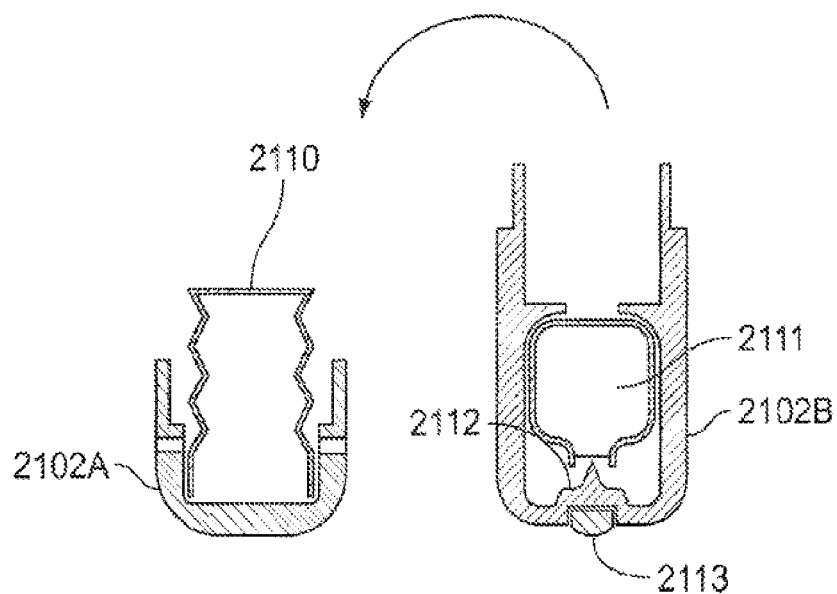
Figure 22:
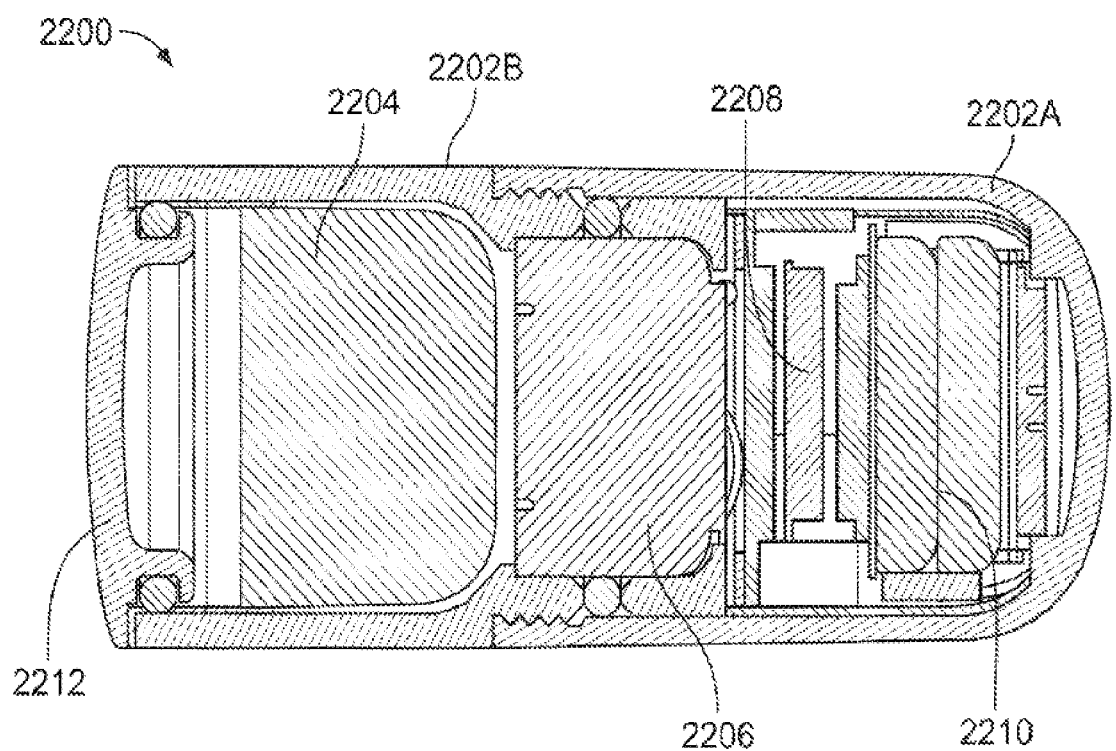
FIG. 22 shows an ingestible device.

FIG. 21B schematically shows certain aspects of the assembly of the ingestible device 2100. The housing parts 2102A (including the bellows 2110) and 2102B (including the gas cylinder 2111 and the piercer 2112) are initially separate from each other. The dispensable substance (including the therapeutic agent) is first sterilized, and then disposed in the fluid volume 2104 under aseptic conditions. The components in housing part 2102B are assembled in a clean environment. Subsequently, the housing parts 2102A and 2102B are joined in a clean environment to produce the ingestible device 2100.

Device for Epithelial Delivery

Generally, epithelial delivery can be achieved at any desired location within the GI tract of a subject. In some embodiments, epithelial delivery is achieved in the small intestine of the subject, such as, for example, in the duodenum, the jejunum and/or the ileum. In certain embodiments, epithelial delivery is achieved in the large intestine of the subject, such as, for example, the cecum or the colon.

In some embodiments, epithelial delivery can be achieved using any one of the ingestible devices described above with respect to epithelial delivery. In such embodiments, the relevant parameters are usually modified accordingly. Typically, this modification involves modifying the values for the relevant parameters. Examples are provided in the following paragraphs.

In general, an ingestible device for epithelial delivery is configured to deliver a jet of the dispensable substance having a peak jet power of at least about 1 mW (e.g., at least about 1.5 mW, at least about 2 mW, at least about 2.5 mW) and/or at most about 4 mW (e.g., at most about 3.5 mW, at most about 3 mW). In some embodiments, an ingestible device for epithelial delivery is configured to deliver a jet of the dispensable substance having a peak jet power of from about 1 mW to about 4 mW (e.g., from about 1 mW to about 3.5 mW, from about 2 mW to about 3 mW).

Generally, an ingestible device for epithelial delivery is configured to deliver a jet of the dispensable substance having a peak jet pressure of about 2 psig (e.g., about 2.5 psig, about 3 psig, about 3.5 psig, about 4 psig) and/or at most about 10 psig (e.g., at most about 8 psig, at most about 6 psig, at most about 5 psig). In some embodiments, an ingestible device for epithelial delivery is configured to deliver a jet of the dispensable substance having a peak jet pressure of from about 2 psig to about 10 psig (e.g., from about 2.5 psig to about 8 psig, from about 3 psig to about 6 psig, from about 3.5 psig to about 5 psig, from about 4 psig to about 5 psig).

In general, an ingestible device for epithelial delivery is configured to deliver a jet of the dispensable substance having a peak jet force of at least about 0.5 mN (e.g., at least about 0.6 mN, at least about 0.7 mN, at least about 0.8 mN, at least about 0.9 mN) and/or at most about 2 mN (e.g., at most about 1.8 mN, at most about 1.6 mN, at most about 1.4 mN, at most about 1.2 mN). In some embodiments, an ingestible device for epithelial delivery is configured to deliver a jet of the dispensable substance having a peak jet force of from about 0.5 mN to about 2 mN (e.g., from about 0.6 mN to about 1.8 mN, from about 0.7 mN to about 1.6 mN, from about 0.8 mN to about 1.4 mN, from about 0.9 mN to about 1.2 mN).

In general, an ingestible device for epithelial delivery is configured to deliver a jet of the dispensable substance having a minimum jet velocity of from at least about 2 m/s (e.g., at least about 3 m/s, at least about 4 m/s, at least about 5 m/s) and/or at most about 20 m/s (e.g., at most about 15 m/s, at most about 10 m/s, at most about 8 m/s). In some embodiments, an ingestible device for epithelial delivery is configured to deliver a jet of the dispensable substance having a peak jet velocity of from about 2 m/s to about 20 m/s (e.g., from about 3 m/s to about 15 m/s, from about 4 m/s to about 10 m/s, from about 5 m/s to about 8 m/s).

In general, an ingestible device for epithelial delivery is configured to provide an internal pressure of from about 3.62 psig to about 21.76 psig (e.g., from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, about 4.35 psig).

In general, an ingestible device for epithelial delivery is configured to provide a nozzle pressure of from about 3.62 psig to about 21.76 psig (e.g., from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, about 4.35 psig).

Generally, an ingestible device for epithelial delivery is configured to contain a dispensable substance at a peak fluid pressure from 3.62 psig to about 21.76 psig (e.g., from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, about 4.35 psig).

In general, an ingestible device for epithelial delivery contains the dispensable substance at an initial fluid volume of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for epithelial delivery contains the dispensable substance at an initial fluid volume of from about 50 μL to about 800 μL (e.g., from about 100 μL to about 600 μL, from about 200 μL to about 400 μL).

Generally, an ingestible device for epithelial delivery is configured to provide a delivered fluid volume of dispensable substance of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for epithelial delivery has a fluid volume of dispensable substance of from about 50 μL to about 800 μL (e.g., from about 100 μL to about 600 μL, from about 200 μL to about 400 L).

In general, an ingestible device for epithelial delivery contains the dispensable substance at a final fluid volume of at most about 100 microliters (μL) (e.g., at least about 90 μL, at least about 80 μL, at least about 70 μL, at least about 60 μL) and/or at most least L (e.g., at most about 10 μL, at most about 20 μL, at most about 30 μL, at most about L). In some embodiments, an ingestible device for epithelial delivery contains the dispensable substance at a fluid volume of from about 30 μL to about 70 μL (e.g., from about 40 μL to about 60 μL, from about 45 μL to about 55 μL).

In general, an ingestible device for epithelial delivery is configured to directly deliver at least about 50% (e.g., at least about 60%, at least about 70%, at least about 80%, at least about 90%, at least about 95%, at least about 97%) of the dispensable substance from the ingestible device to the mucus.

In general, an ingestible device for epithelial delivery is configured to provide a delivered fluid volume per opening for delivery of dispensable substance (e.g., per nozzle) of at least about 20 microliters (μL) (e.g., at least about 25 μL, at least about μL, at least about 50 μL, at least about 75 μL, at least about 100 μL) and/or at most about 800 μL (e.g., at most about 700 μL, at most about 600 μL, at most about 500 μL, at most about 400 μL, at most about 300 μL). In some embodiments, an ingestible device for epithelial delivery is configured to provide a delivered fluid volume per opening for delivery of dispensable substance (e.g., per nozzle) of from about 25 μL to about 400 μL (e.g., from about 25 μL to about 300 μL, from about 100 μL to about 300 μL).

In certain embodiments, an ingestible device for epithelial delivery is configured as disclosed in the above-discussion regarding trans-epithelial delivery, but with a relatively large number of nozzles and a relatively large nozzle diameter such that performance properties for epithelial delivery (discussed above) can be achieved. As an example, in some embodiments, an ingestible device for epithelial delivery has at least 25 nozzles (e.g., at least 30 nozzles, at least 40 nozzles, 50 nozzles). In some embodiments, such an ingestible device for epithelial delivery has 30 nozzles, 31 nozzles, 32 nozzles, 33 nozzles, 34 nozzles, 35 nozzles, 36 nozzles, 37 nozzles, 38 nozzles or 40 nozzles. Each nozzle can have a diameter, for example, of at least about 1 mm (e.g., at least about 1.5 mm, at least about 2 mm) and/or at most about 3 mm (e.g., at most about 2.5 mm). For example, in such an ingestible device, each nozzle can have a diameter of from about 1 mm to about 3 mm (e.g., from about 1 mm to about 2.5 mm, from about 2 to 2.5 mm).

Device for Topical Delivery

Generally, topical delivery can be achieved at any desired location within the GI tract of a subject. In some embodiments, topical delivery is achieved in the small intestine of the subject, such as, for example, in the duodenum, the jejunum and/or the ileum. In certain embodiments, topical delivery is achieved in the large intestine of the subject, such as, for example, the cecum or the colon.

In general, an ingestible device for topical delivery is configured to provide an internal pressure of at least about 5 psig (e.g., at least about 8 psig, at least about 10 psig) and/or at most about 50 psig (e.g., at most about 40 psig, at most about 30 psig, at most about 20 psig, at most about 15 psig). In certain embodiments, an ingestible device for topical delivery is configured to provide an internal pressure of from about 5 psig to about 50 psig (e.g., from about 5 psig to about 30 psig, from about 5 psig to about 20 psig, from about 8 psig to about 20 psig, from about 10 psig to about 15 psig).

Generally, an ingestible device for topical delivery is configured to contain a dispensable substance at a peak fluid pressure of at least about 5 psig (e.g., at least about 8 psig, at least about 10 psig) and/or at most about 50 psig (e.g., at most about 40 psig, at most about 30 psig, at most about 20 psig, at most about 15 psig). In certain embodiments, an ingestible device for topical delivery is configured to deliver a jet of the dispensable substance having a peak fluid pressure of from about 5 psig to about 50 psig (e.g., from about 5 psig to about 30 psig, from about 5 psig to about 20 psig, from about 8 psig to about 20 psig, from about 10 psig to about 15 psig).

In general, an ingestible device for topical delivery is configured to deliver at least about 50% (e.g., at least about 60%, at least about 70%, at least about 80%, at least about 90%, at least about 95%, at least about 97%) of the dispensable substance from the ingestible device into the lumen of the GI tract.

In general, an ingestible device for topical delivery contains the dispensable substance at an initial fluid volume of at least about 50 microliters (μL) (e.g., at least about 100 μL, at least about 150 μL, at least about 200 μL, at least about 250 μL) and/or at most about 800 μL (e.g., at most about 700 μL, at most about 600 μL, at most about 500 μL, at most about 400 μL). In some embodiments, an ingestible device for topical delivery contains the dispensable substance at an initial fluid volume of from about 50 μL to about 800 μL (e.g., from about 100 μL to about 600 μL, from about 200 μL to about 400 μL).

In general, an ingestible device for topical delivery contains the dispensable substance at a final fluid volume of at most about 100 microliters (μL) (e.g., at least about 90 μL, at least about 80 μL, at least about 70 μL, at least about 60 μL) and/or at most least L (e.g., at most about 10 μL, at most about 20 μL, at most about 30 μL, at most about L). In some embodiments, an ingestible device for topical delivery contains the dispensable substance at a fluid volume of from about 30 μL to about 70 μL (e.g., from about 40 μL to about 60 μL, from about 45 μL to about 55 μL).

Figure 23A:
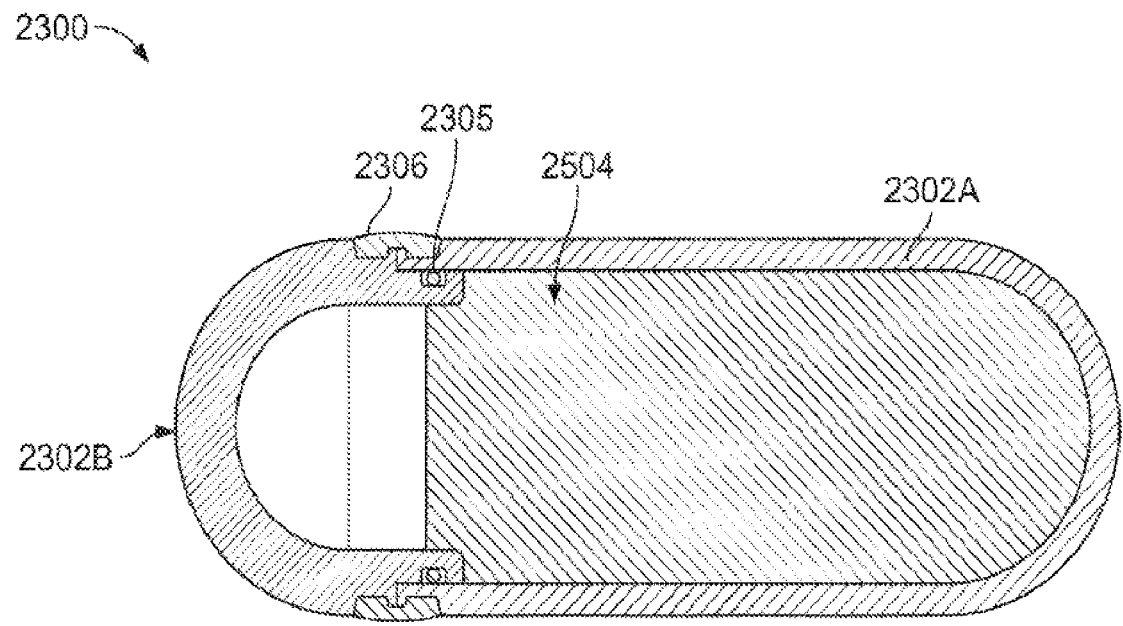
FIG. 23A shows an ingestible device.
Figure 23B:
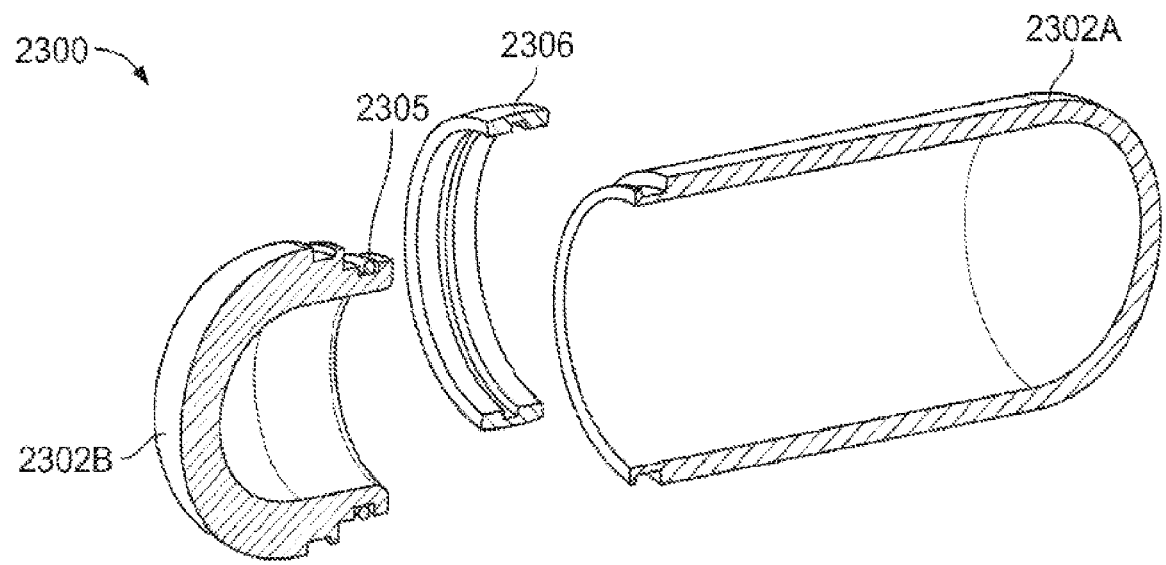
FIG. 23B shows an exploded view of the device of FIG. 23A.

FIG. 23A shows an embodiment of an ingestible device 2300 for topical delivery. FIG. 23B is an exploded view of the ingestible device 2300. The ingestible device 2300 has housing parts 2302A and 2302B, a fluid volume 2304 containing a dispensable substance, an O-ring 2305, and a band 2306. The device 2300 has a head space pressure in the housing part 2302B, but the band 2306 holds the components of device 2300 in place when the device 2300 is swallowed by the subject. When the device 2300 reaches the appropriate location in the GI tract, the band 2306 erodes, degrades and/or dissolves, and the head space pressure causes the housing part 2302B to leave device 2300, resulting in the therapeutic agent in the dispensable substance being topically delivered to the GI tract of the subject. In embodiments having a design substantially similar to the ingestible device 2300, the head space pressure is provided by a gas, such as, for example, air nitrogen ($N_2$), oxygen ($O_2$), an inert gas (e.g., argon (Ar), krypton (Kr), helium (He)), and/or carbon dioxide ($CO_2$). In embodiments having a design substantially similar to the ingestible device 2300, the head space pressure can correspond to the internal pressure of the ingestible device. In embodiments having a design substantially similar to the ingestible device 2300, the head space pressure can correspond to the fluid pressure of the ingestible device.

Figure 24:
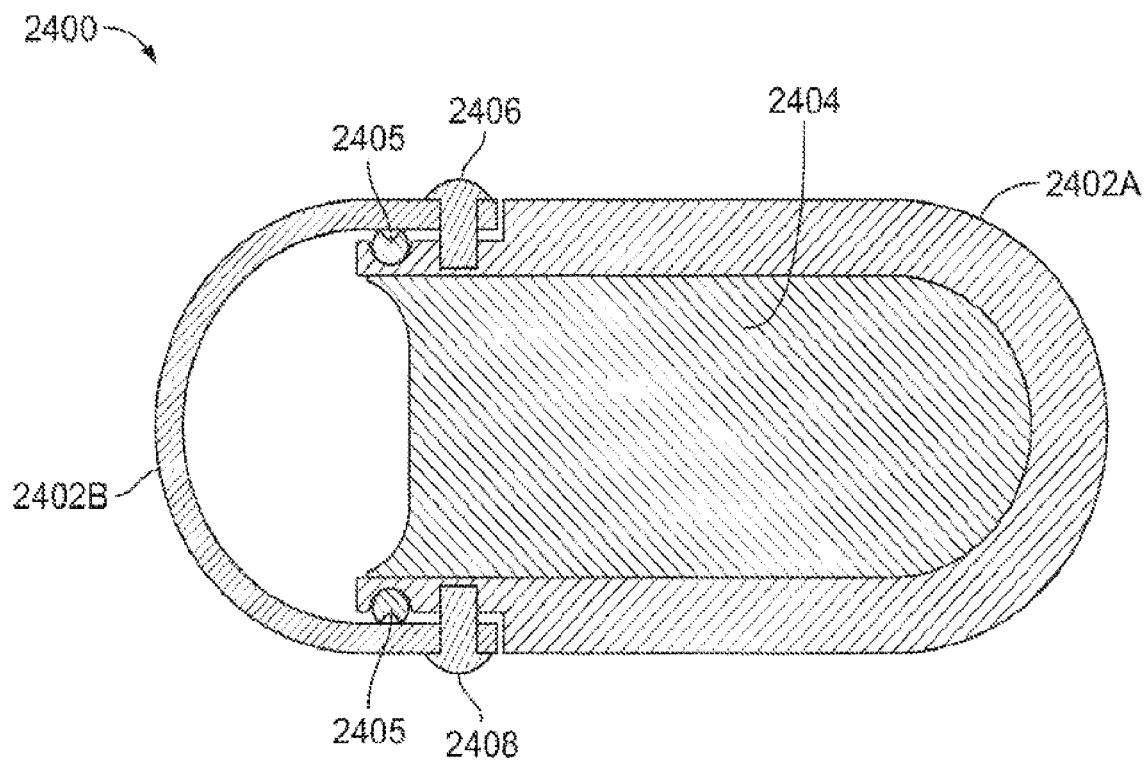
FIG. 24 shows an ingestible device.

FIG. 24 shows an embodiment of an ingestible device 2400 for topical delivery. The ingestible device 2400 has housing parts 2402A and 2402B, a fluid volume 2404 containing a dispensable substance, an O-ring 2405, and pins 2406 and 2408. The device 2400 has a head space pressure in the housing part 2402B, but the pins 2406 and 2408 hold the components of device 2400 in place when the device 2400 is swallowed by the subject. When the device 2400 reaches the appropriate location in the GI tract, the pins 2406 and 2408 erode, degrade and/or dissolve, and the head space pressure causes the housing part 2402B to leave device 2400, resulting in the therapeutic agent in the dispensable substance being topically delivered to the GI tract of the subject. In embodiments having a design substantially similar to the ingestible device 2400, the head space pressure is provided by a gas, such as, for example, air nitrogen ($N_2$), oxygen ($O_2$), an inert gas (e.g., argon (Ar), krypton (Kr), helium (He)), and/or carbon dioxide ($CO_2$). In embodiments having a design substantially similar to the ingestible device 2400, the head space pressure can correspond to the internal pressure of the ingestible device. In embodiments having a design substantially similar to the ingestible device 2400, the head space pressure can correspond to the fluid pressure of the ingestible device.

Figure 25:
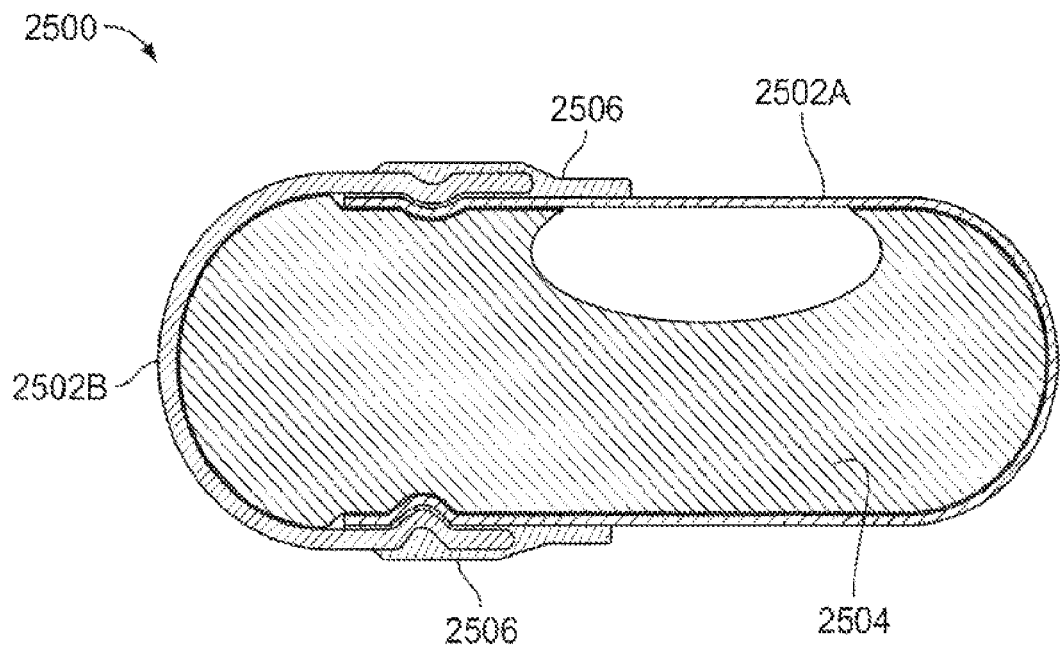
FIG. 25 shows an ingestible device.

FIG. 25 shows an embodiment of an ingestible device 2500 for topical delivery. The ingestible device 2500 has housing parts 2502A and 2502B, a fluid volume 2504 containing a dispensable substance, and a partial coating 2506. The device 2500 has a head space pressure within the housing part 2502A, but the partial coating 2506 holds the components of device 2500 in place when the device 2500 is swallowed by the subject. When the device 2500 reaches the appropriate location in the GI tract, the partial coating 2506 erodes, degrades and/or dissolves, and the head space pressure causes the housing parts 2502A and 2502B to separate from each other, resulting in the therapeutic agent in the dispensable substance being topically delivered to the GI tract of the subject. In embodiments having a design substantially similar to the ingestible device 2500, the head space pressure is provided by a gas, such as, for example, air nitrogen ($N_2$), oxygen ($O_2$), an inert gas (e.g., argon (Ar), krypton (Kr), helium (He)), and/or carbon dioxide ($CO_2$). In embodiments having a design substantially similar to the ingestible device 2500, the head space pressure can correspond to the internal pressure of the ingestible device. In embodiments having a design substantially similar to the ingestible device 2500, the head space pressure can correspond to the fluid pressure of the ingestible device.

Figure 26A:
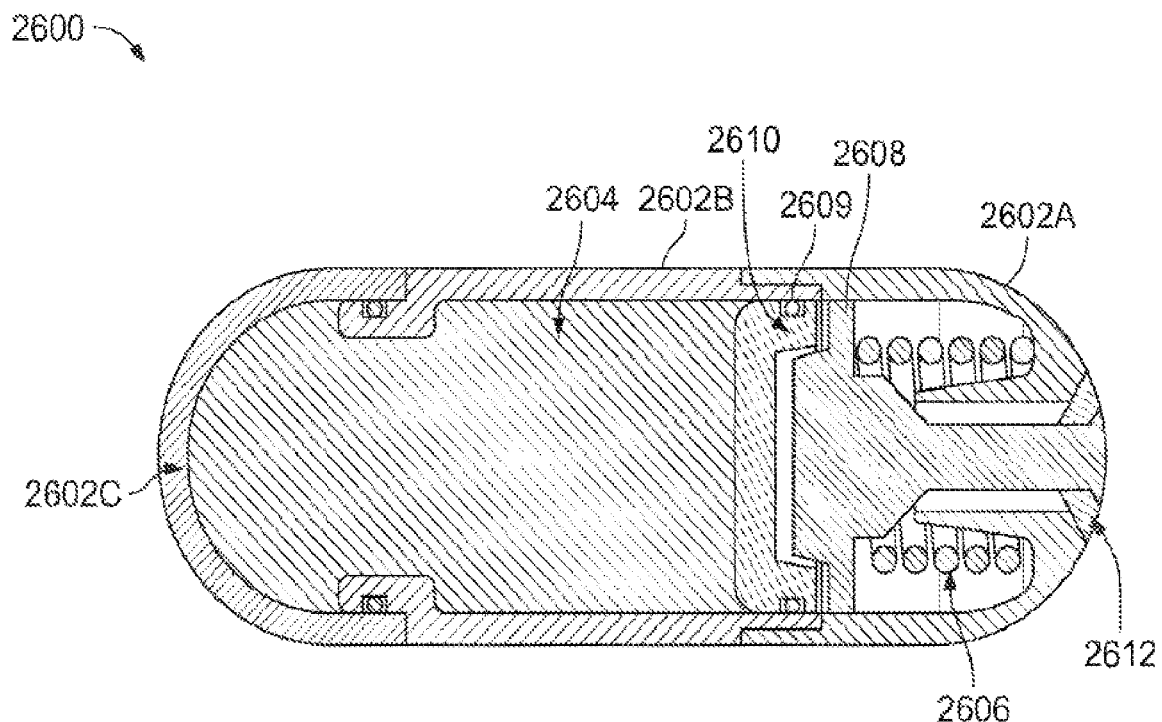
FIG. 26A shows an ingestible device.
Figure 26B:
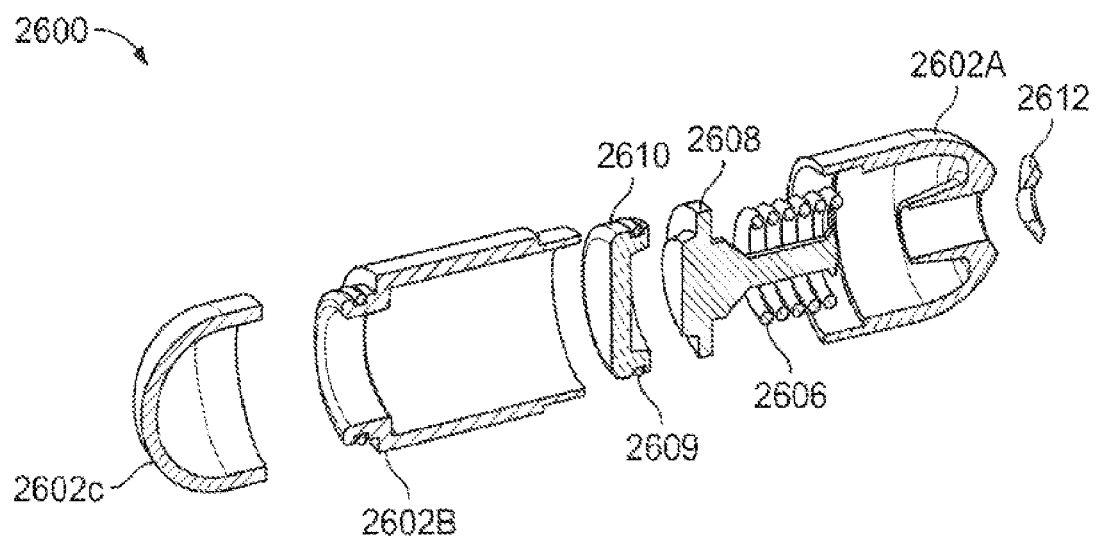
FIG. 26B shows an exploded view of the device of FIG. 26A.

FIG. 26A shows an ingestible device 2600 that can be used for topical delivery. FIG. 26B is an exploded view of the device 2600. The device 2600 includes a first housing part 2602A, a second housing part 2602B and a third housing part 2602C. The device 2600 further includes a fluid volume 2604 containing a dispensable substance, a spring 2606, a plunger 2608, a piston 2610, an O-ring 2609, and a stopper pin 2612 which holds the components of the device 2600 when the subject swallows the device 2600. When the device 2600 reaches the appropriate location in the GI tract, the pin 2612 erodes, degrades and/or dissolves. Thus, the pressure of the spring 2606 is applied to the plunger 2608, which moves the piston 2610 axially. This pressure is transferred to the dispensable substance in the fluid volume 2604, which forces the housing part 2602C to be removed from the device 2600, and the therapeutic agent in the dispensable substance is topically delivered.

Figure 26C:
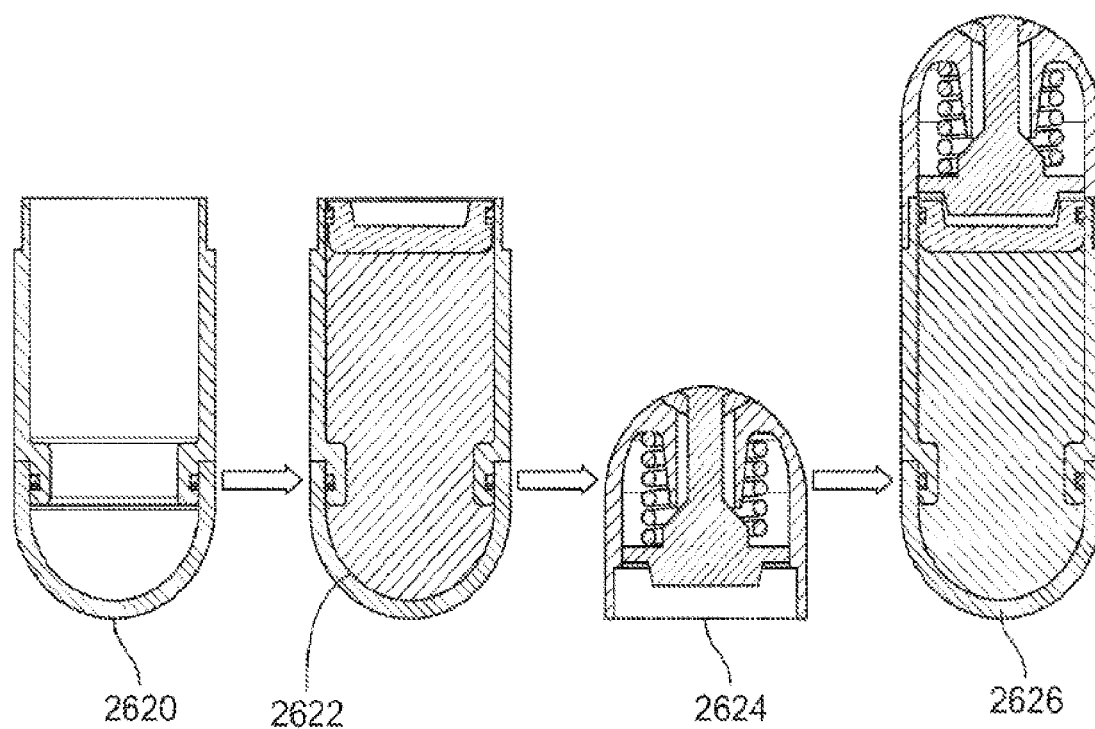
FIG. 26C shows aspects of states of the ingestible device of FIG. 26A.

FIG. 26C shows aspects of steps in assembling the ingestible device 2600. In step 2620, the housing parts 2602B and 2602C are combined and then sterilized. In step 2622, the dispensable substance 2604 is disposed in the housing parts 2602B and 2602C in an aseptic environment and then sealed within the piston 2610. In step 2624, the housing part 2602A and its components are assembled in a clean environment. In step 2626, the resulting modules are joined together in a clean environment to provide the ingestible device 2600.

Figure 27:
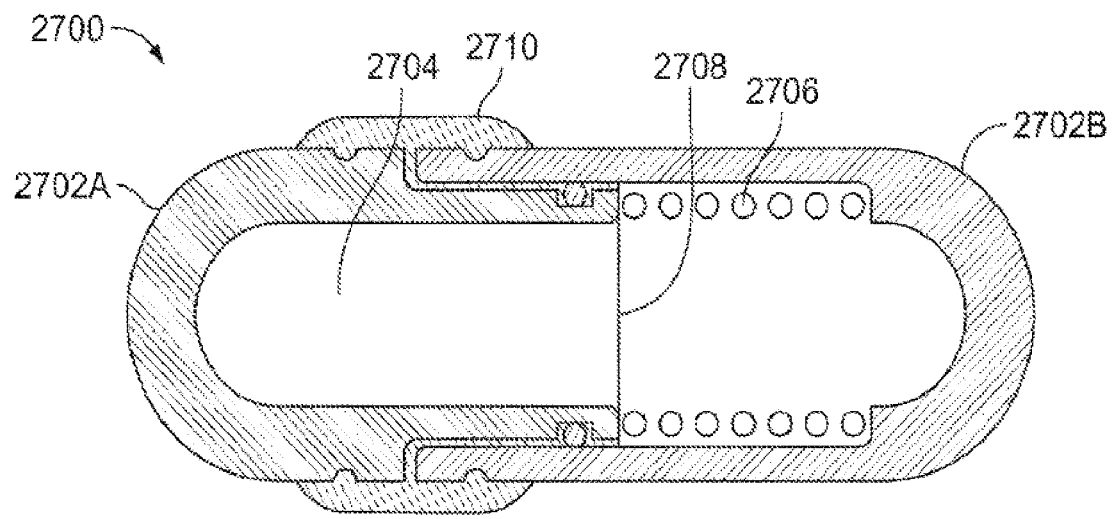
FIG. 27 shows an ingestible device.

FIG. 27 shows an ingestible device 2700 that can be used for topical delivery. The device 2700 includes a first housing part 2702A and a second housing part 2702B. The device 2700 further includes a fluid volume 2704 containing a dispensable substance, a spring 2706, a seal 2708 (e.g., a foil or a film) and a partial coating 2710 which holds the components of the device 2700 when the subject swallows the device 2700. When the device 2700 reaches the appropriate location in the GI tract, the partial coating 2710 erodes, degrades and/or dissolves. The spring 2706 then exerts a pressure axially against the dispensable substance 2704, breaking the seal 2708 and also causing the housing parts 2702A and 2702B to separate, which results in topical delivery of the therapeutic agent in the dispensable substance.

Figure 28A:
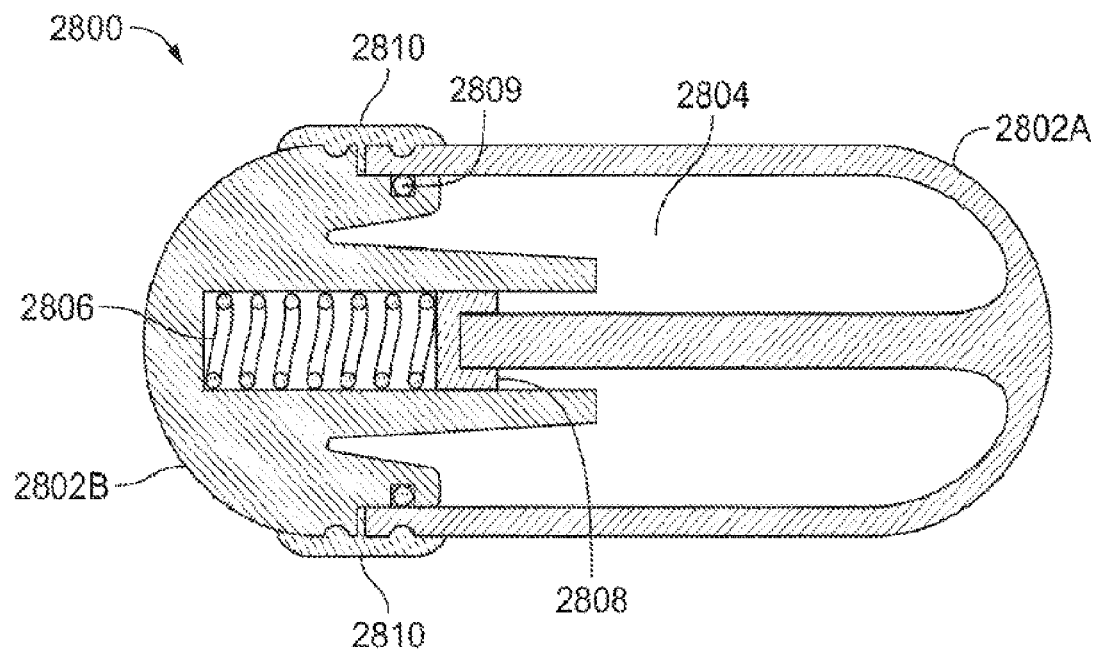
FIG. 28A shows an ingestible device.
Figure 28B:
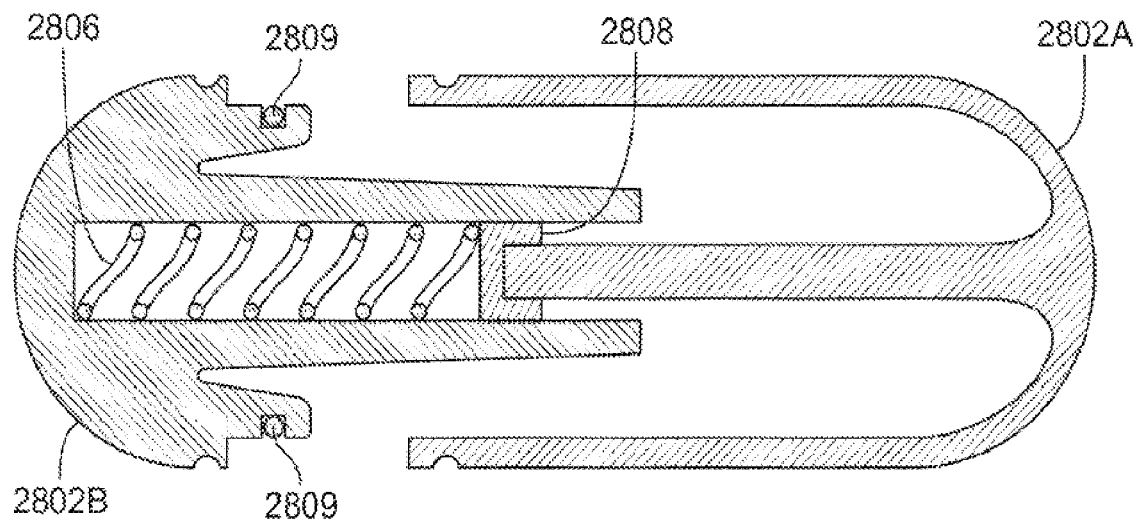
FIG. 28B shows an exploded view of the device of FIG. 28A.

FIG. 28A shows an ingestible device 2800 that can be used for topical delivery. The device 2800 includes a first housing part 2802A and a second housing part 2802B. The device 2800 further includes a fluid volume 2804 containing a dispensable substance, a spring 2806, a seal 2808, an O-ring 2809, and a partial coating 2810 which holds the components of the device 2800 when the subject swallows the device 2800. When the device 2800 reaches the appropriate location in the GI tract, the partial coating 2810 erodes, degrades and/or dissolves. As shown in FIG. 28B, this causes the spring 2806 to expand so that housing parts 2802A and 2802B separate, resulting in topical delivery of the therapeutic agent in the dispensable substance.

Figure 29A:
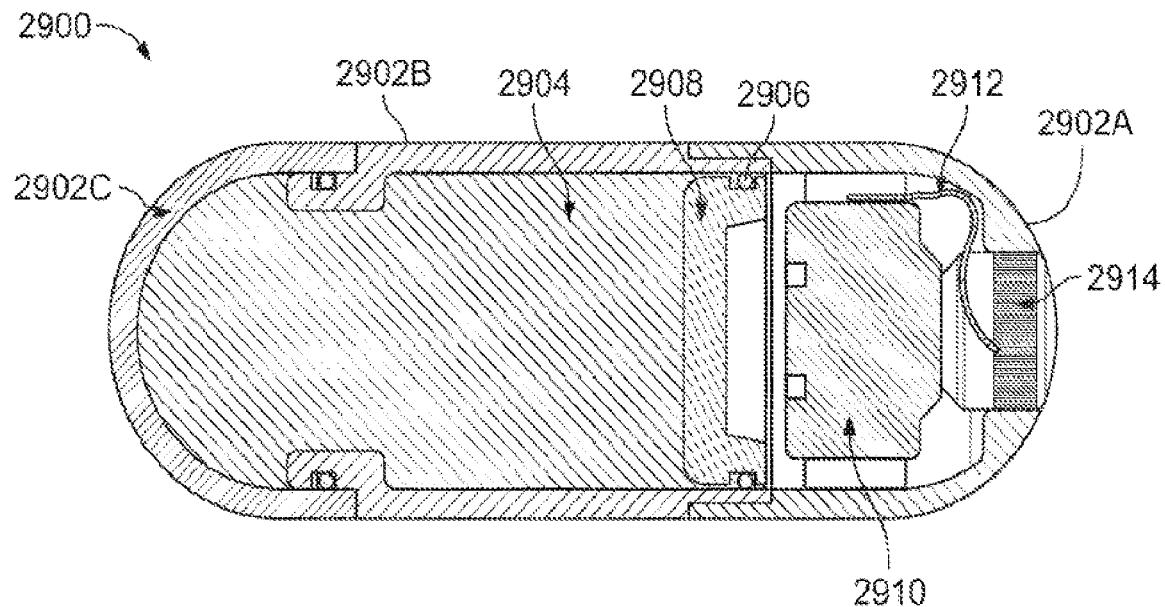
FIG. 29A shows an ingestible device.
Figure 29B:
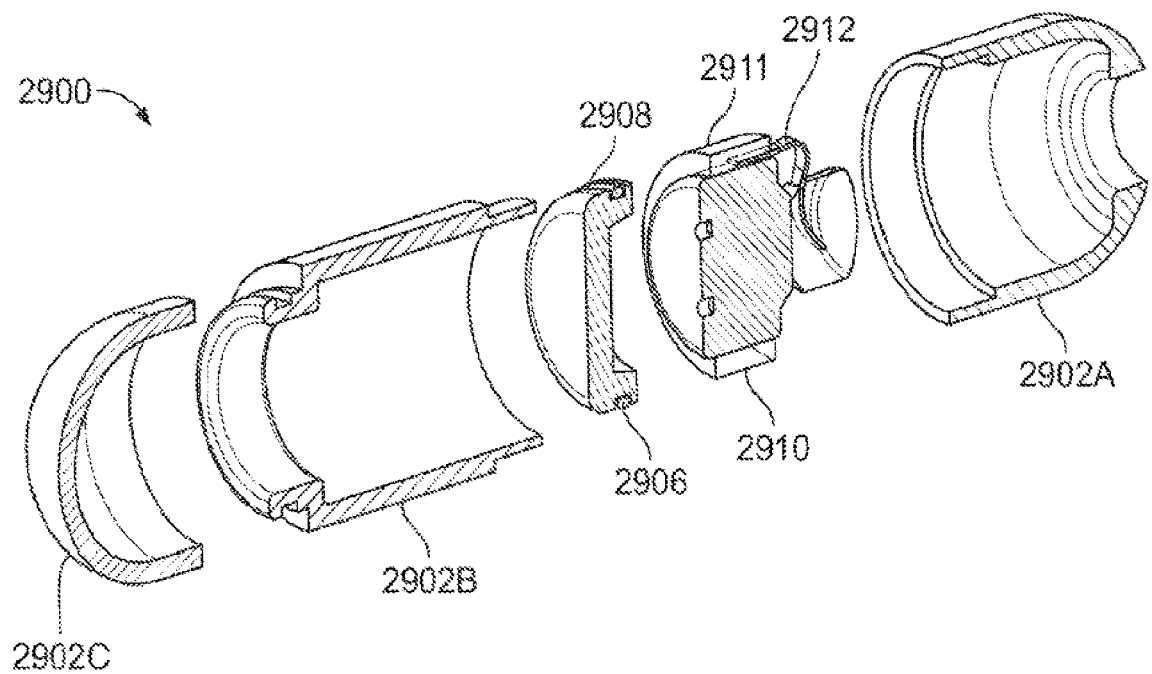
FIG. 29B shows an exploded view of the device of FIG. 29A.

FIG. 29A shows an ingestible device 2900 for topical delivery. FIG. 29B is an exploded view of the device 2900. The device 2900 includes housing parts 2902A, 2902B and 2902C. The device also includes a fluid volume 2904 containing a dispensable substance, an O-ring 2906, a piston 2908 a gas cell 2910 (e.g., a hydrogen cell), a potting material 2911, an electrical contact 2912, and a plug 2914. The subject swallows the device 2900, and, when the device 2900 reaches an appropriate location in the GI tract of the subject, the plug 2914 erodes, degrades and/or dissolves. This causes the electrical contact 2912 to energize the gas cell 2910, which produces a pressurized gas (e.g., pressurized hydrogen) that pushes the piston 2908 axially. This movement applies a pressure to the fluid volume 2904, which transfers the pressure to the housing part 2902C. This causes the housing part 2902C to separate from the device 2900 so that the therapeutic agent in the dispensable substance is topically delivered.

Figure 29C:
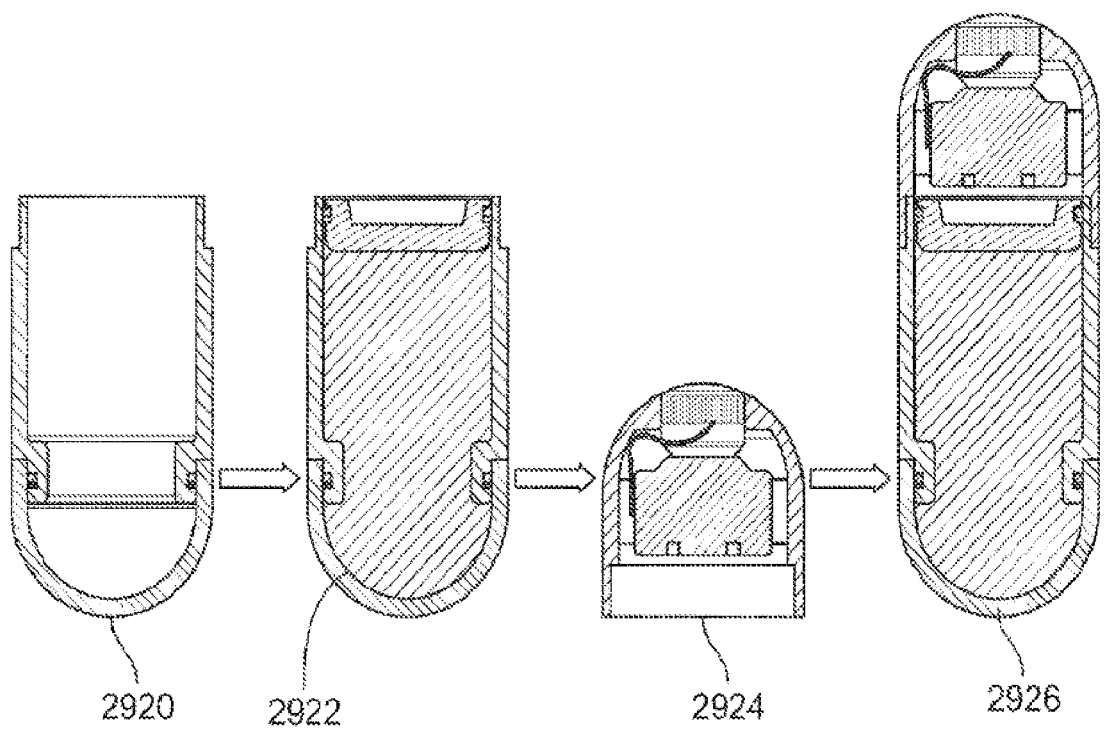
FIG. 29C shows aspects of states of the ingestible device of FIG. 29A.

FIG. 29C shows aspects of steps in assembling the ingestible device 2900. In step 2920, the housing parts 2902B and 2902C are combined and then sterilized. In step 2922, the dispensable substance 2904 is disposed in the housing parts 2902B and 2902C in an aseptic environment and then sealed within the piston 2908. In step 2924, the housing part 2902A and its components are assembled in a clean environment. In step 2926, the resulting modules are joined together in a clean environment to provide the ingestible device 2900.

Figure 30:
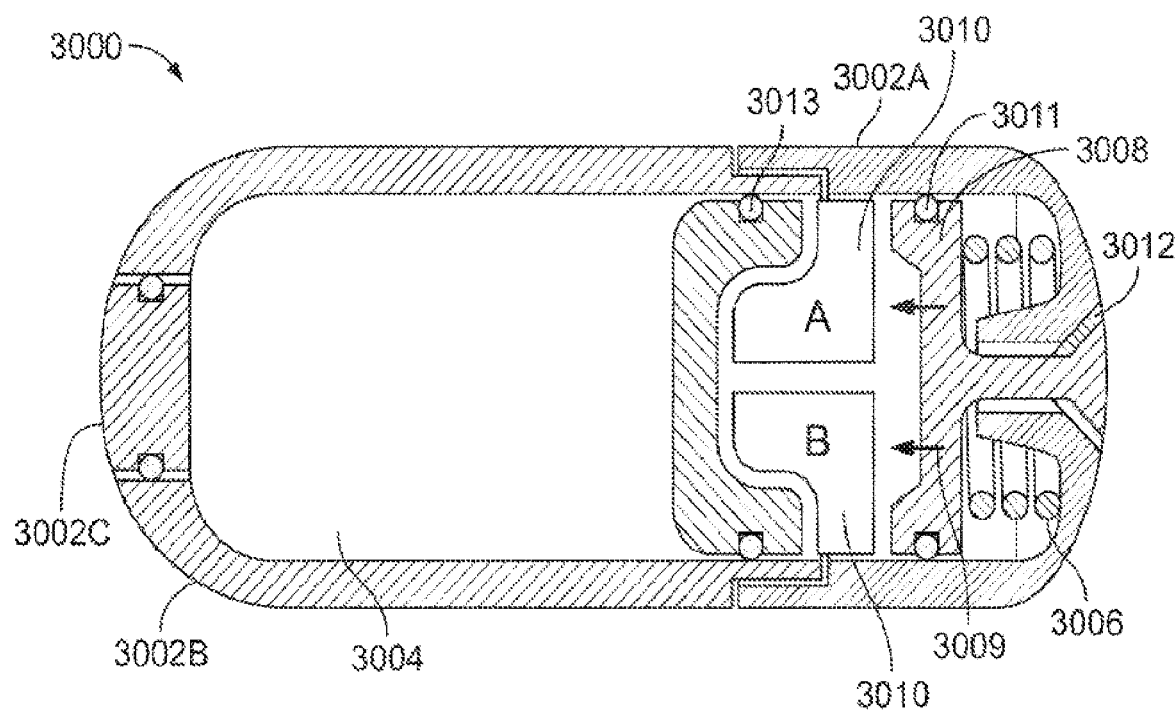
FIG. 30 shows an ingestible device.

FIG. 30 shows an ingestible device 3000 that can be used for topical delivery. The device 3000 includes housing parts 3002A, 3002B and 3002C. The device 2800 further includes a fluid volume 3004 containing a dispensable substance, a spring 3006, a plunger 3008 with piercing elements 3009, an O-Ring 3011, a sealed compartment 3010 containing separated reactants A and B, a piston 3010, and O-ring 3013, and a stopper pin 3012 which holds the components of the device 3000 when the subject swallows the device 3000. When the device 3000 reaches the appropriate location in the GI tract, the pin 3012 erodes, degrades and/or dissolves. This causes the spring 3006 to expand axially, moving the plunger 3008 axially so that the piercing elements 3009 puncture the sealed compartment 3010. This causes the reactants A and B to chemically react and form a pressurized gas which moves the piston axially, thereby applying a pressure against the fluid volume 3004. This pressure is transferred to the housing part 3002C, which forces the housing part 3002C to be removed from the device 3000, and the therapeutic agent in the dispensable substance is topically delivered.

Figure 31A:
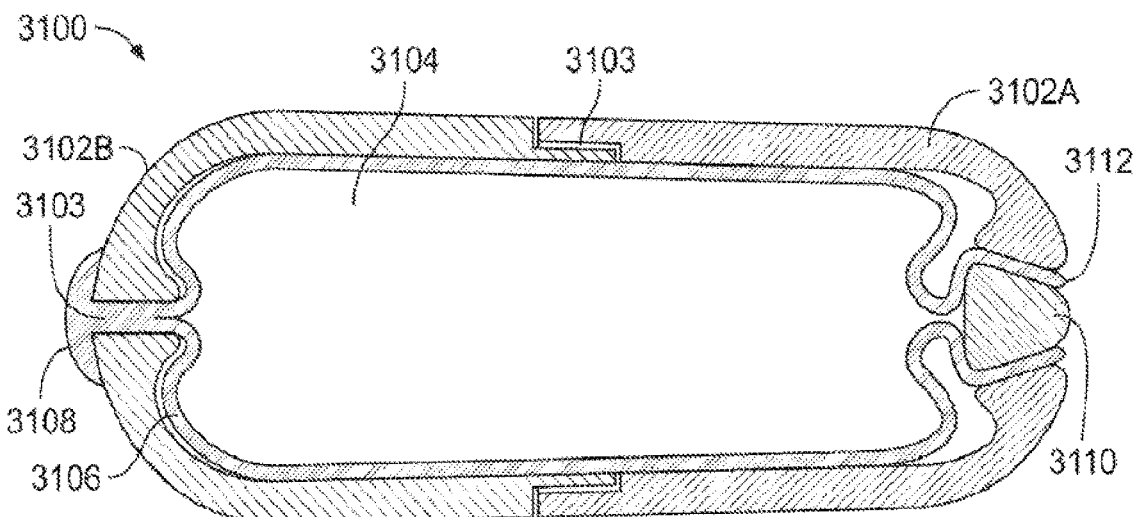
FIG. 31A shows an ingestible device.

FIG. 31A shows an ingestible device 3100 for topical delivery. The device 3100 includes housing parts 3102A and 3102B, a joint 3103, a pressurized fluid volume 3104 containing a dispensable substance, a membrane 3106 (e.g., balloon) containing the dispensable substance, a seal 3108 located in an opening 3103 of the housing part 3102B, and a plug 3110 in an opening 3112 of the housing part 3102A. The subject swallows the ingestible device 3100. When the device 3100 reaches the appropriate location in the GI tract, the plug 3110 erodes, degrades and/or dissolves. This causes the pressurized fluid 3104 in the membrane 3104 to leave the device 3100 via the opening 3112 so that the therapeutic agent in the dispensable substance is topically delivered.

Figure 31B:
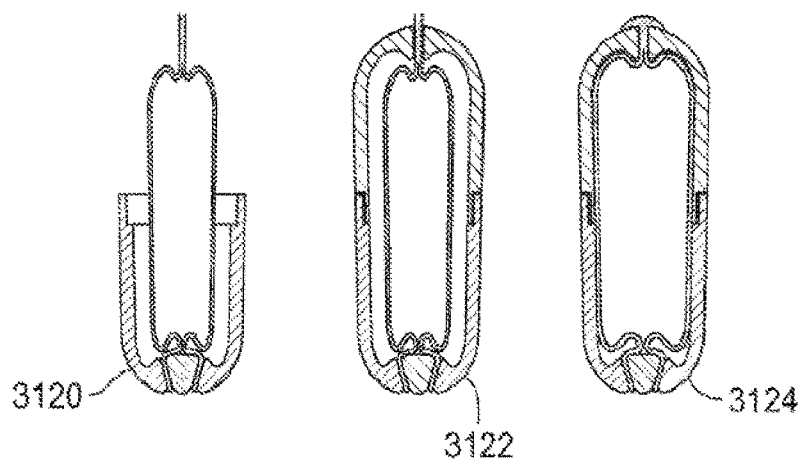
FIG. 31B shows aspects of states of the ingestible device of FIG. 31A.

FIG. 31B shows aspects of steps in assembling the ingestible device 3100. In step 3120, the plug 3112 is formed in the opening 3112 of the housing part 3102A, the membrane 3104 is put inside the housing part 3102A, and the dispensable substance is disposed in the membrane 3104 under aseptic conditions. In step 3122, the housing part 3102B is combined with the housing part 3102A, and the open portion of the membrane 3104 is sealed (e.g., hot sealed) within the opening 3103, thereby forming the ingestible device 3100.

Figure 32:
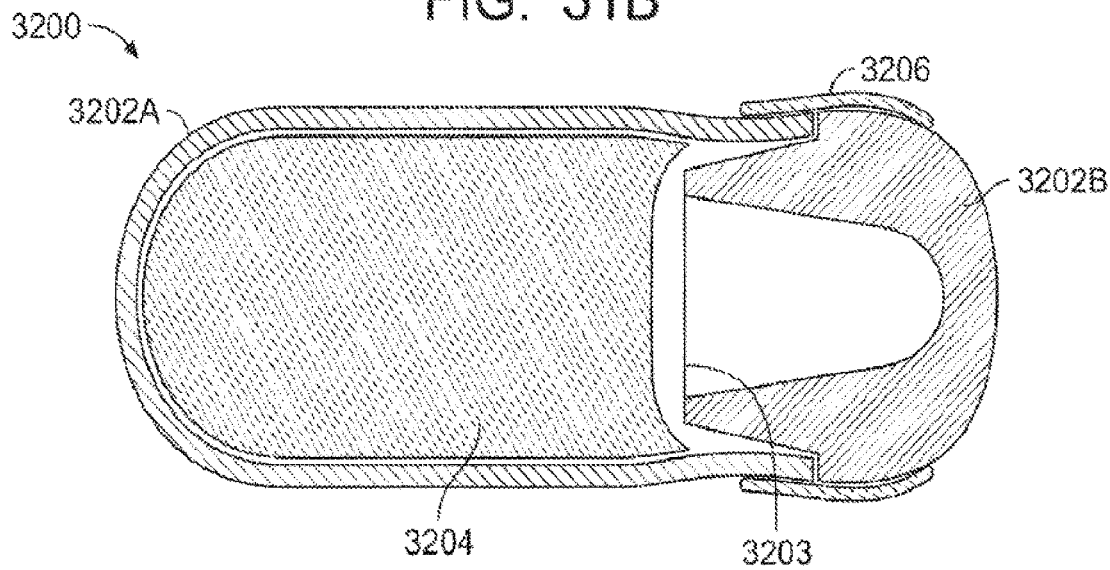
FIG. 32 shows an ingestible device.
Figure 33:
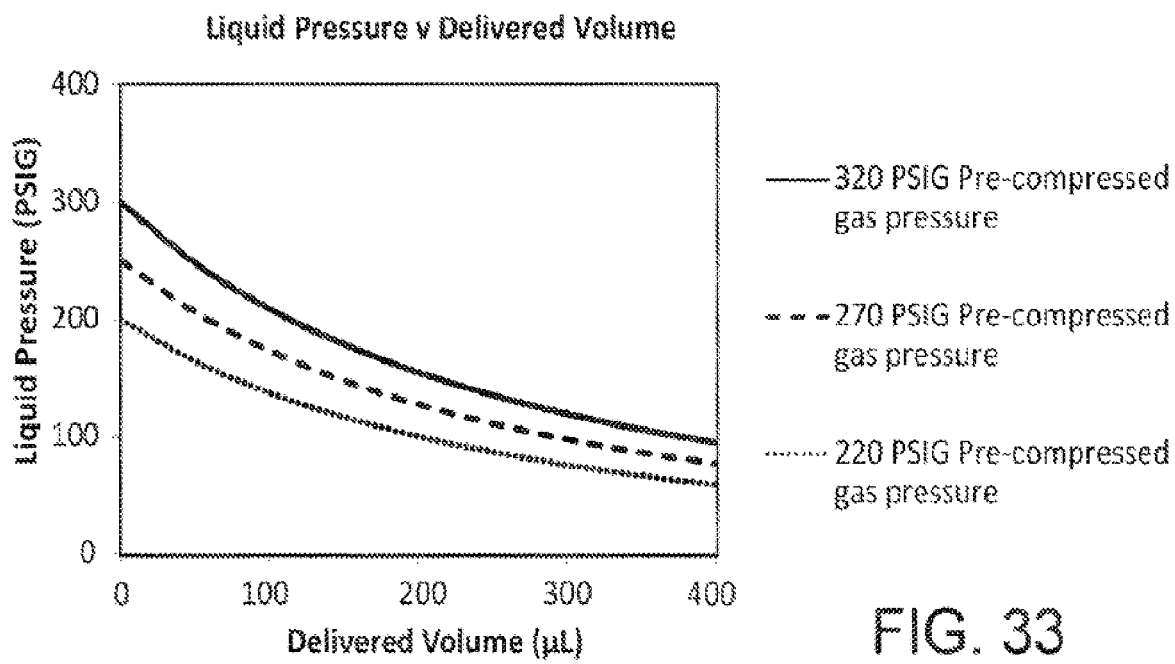
FIGS. 33-37 are graphs showing modelling results for ingestible devices having two nozzles.
Figure 34:
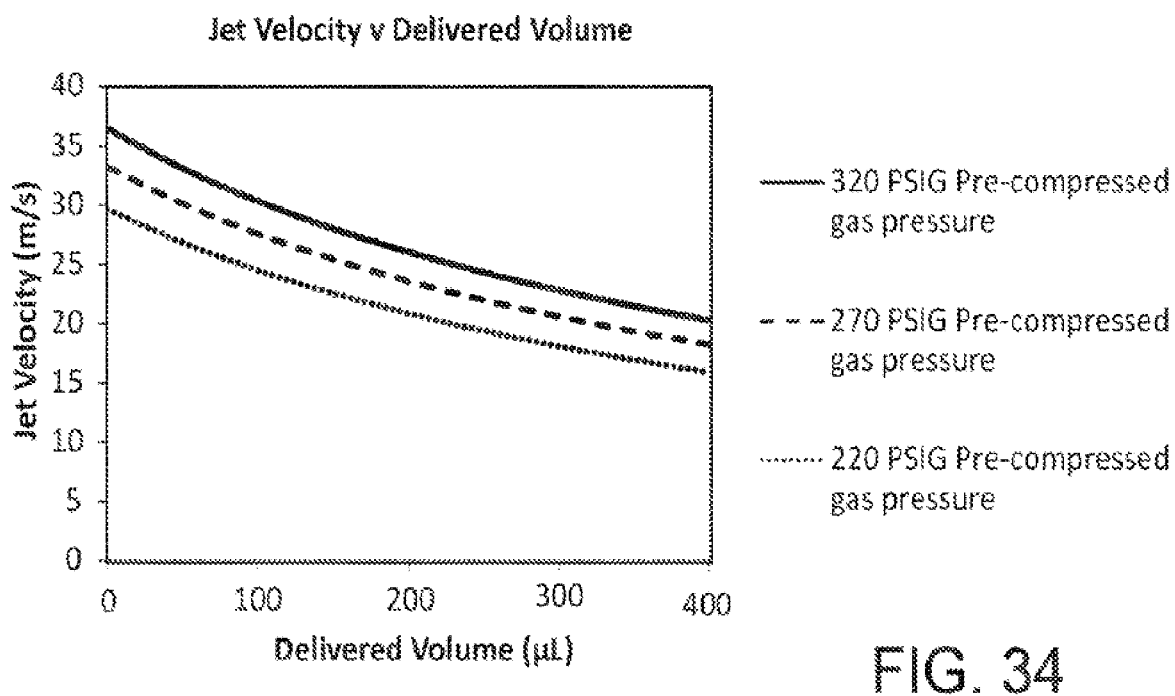
Figure 35:
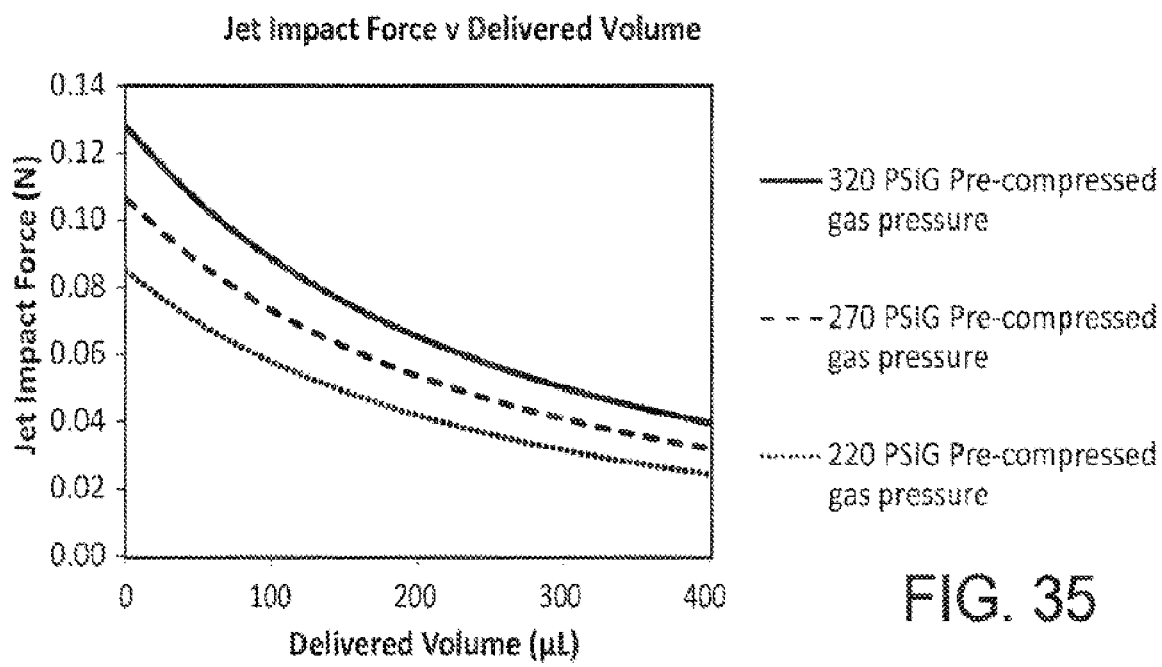
Figure 36:
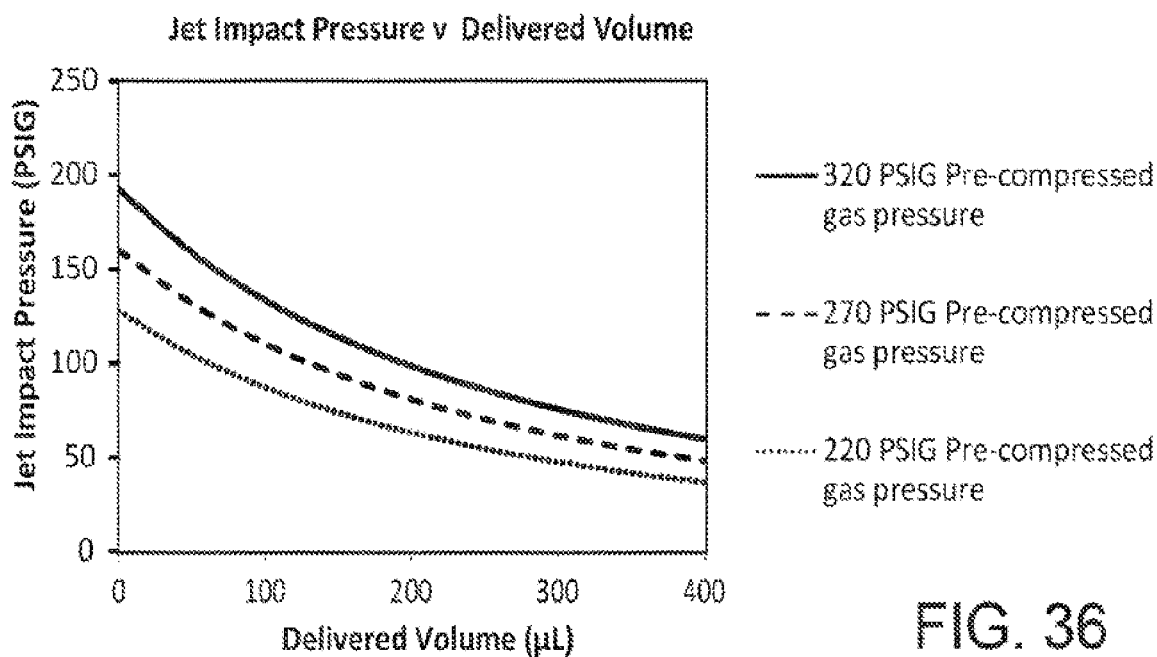
Figure 37:
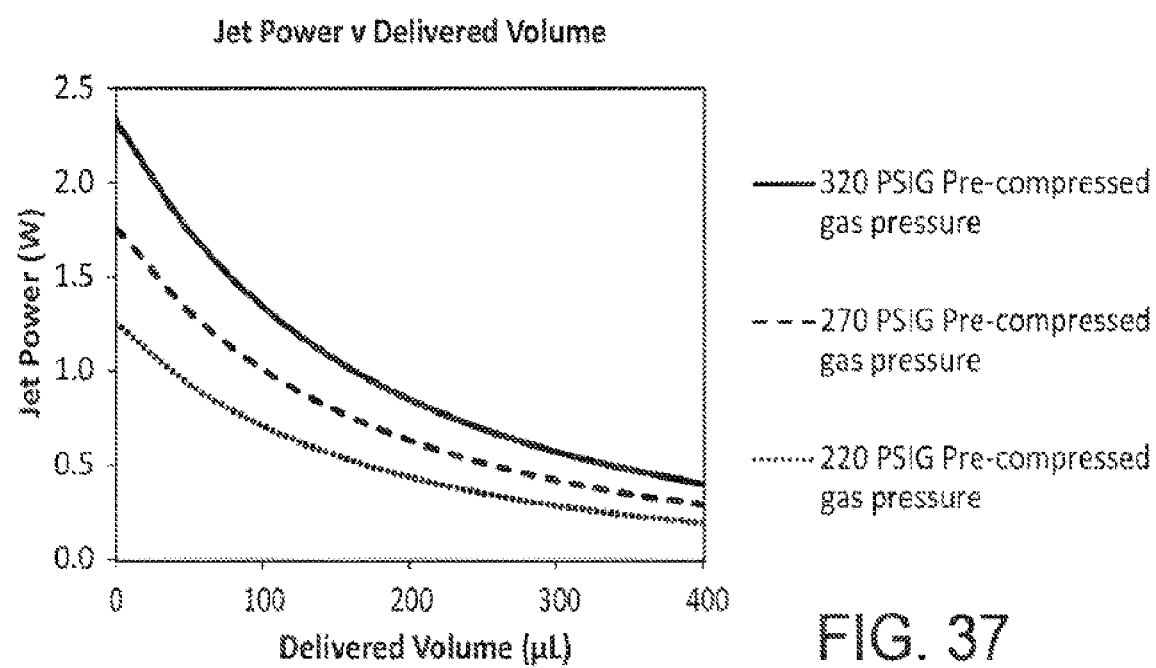
Figure 38:
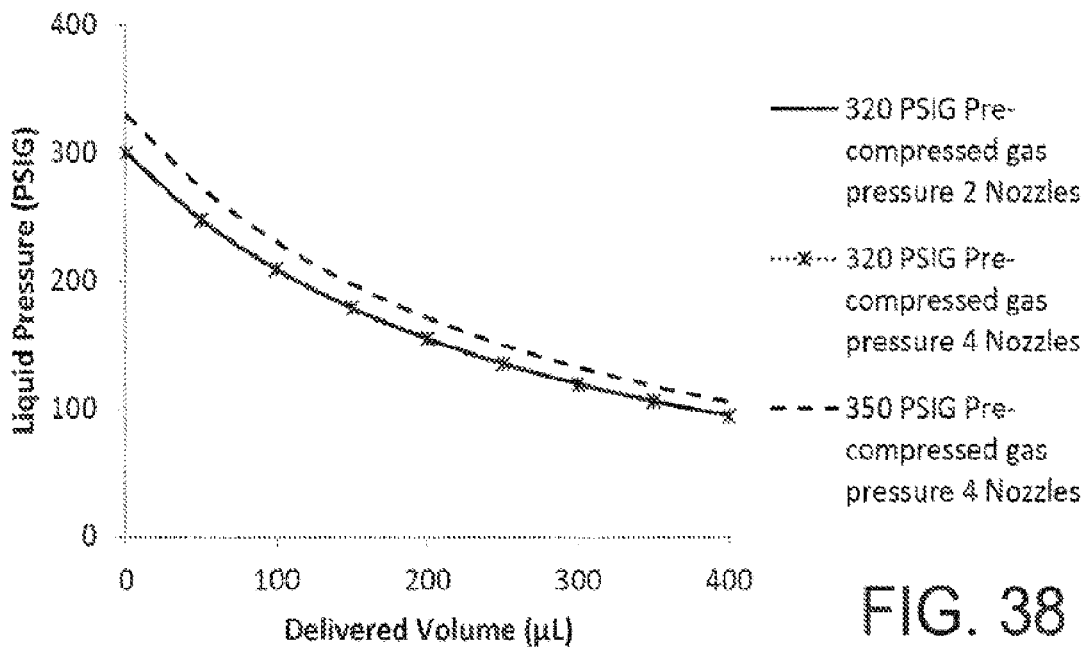
FIGS. 38-47 are graphs showing modelling results for ingestible devices having two or four nozzles.
Figure 39:
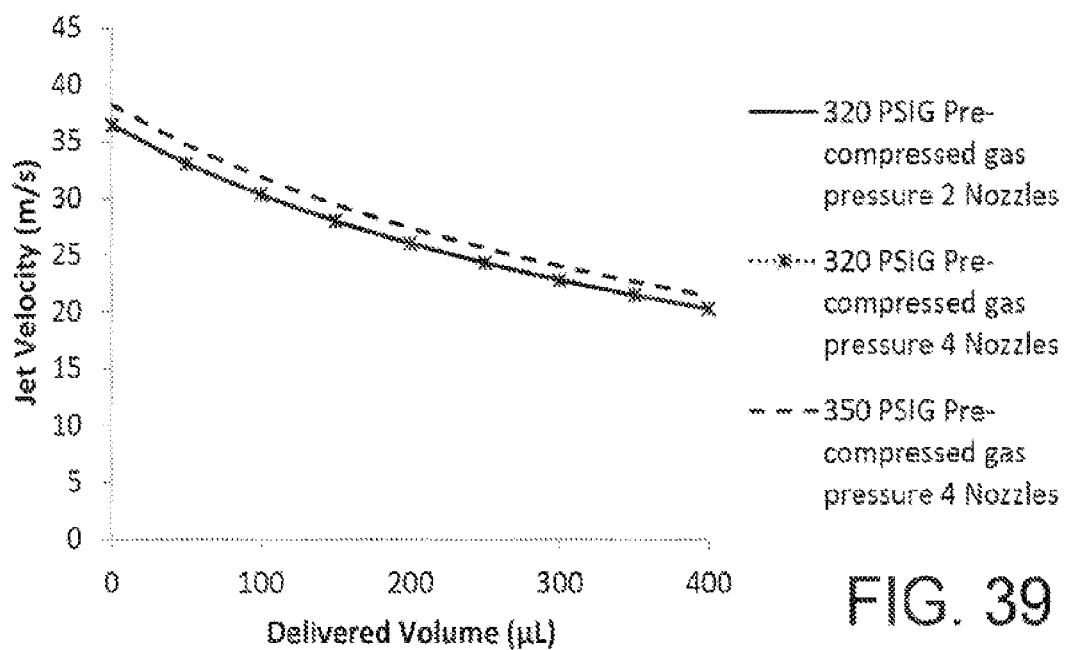
Figure 40:
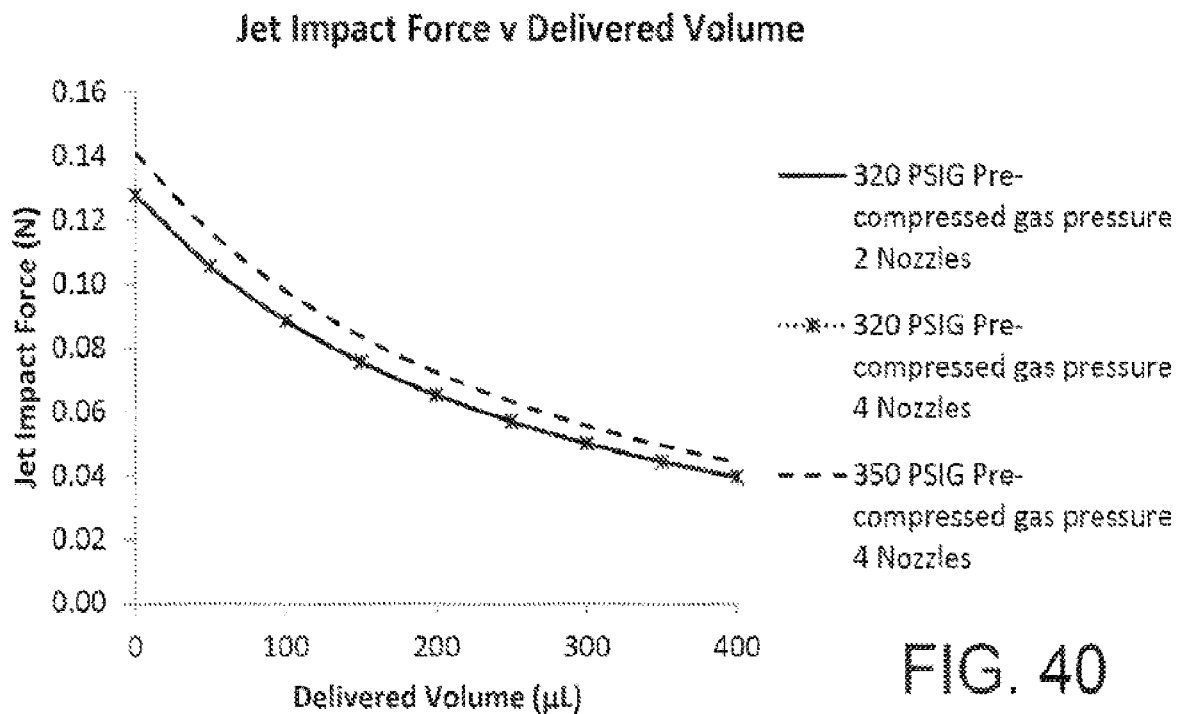
Figure 41:
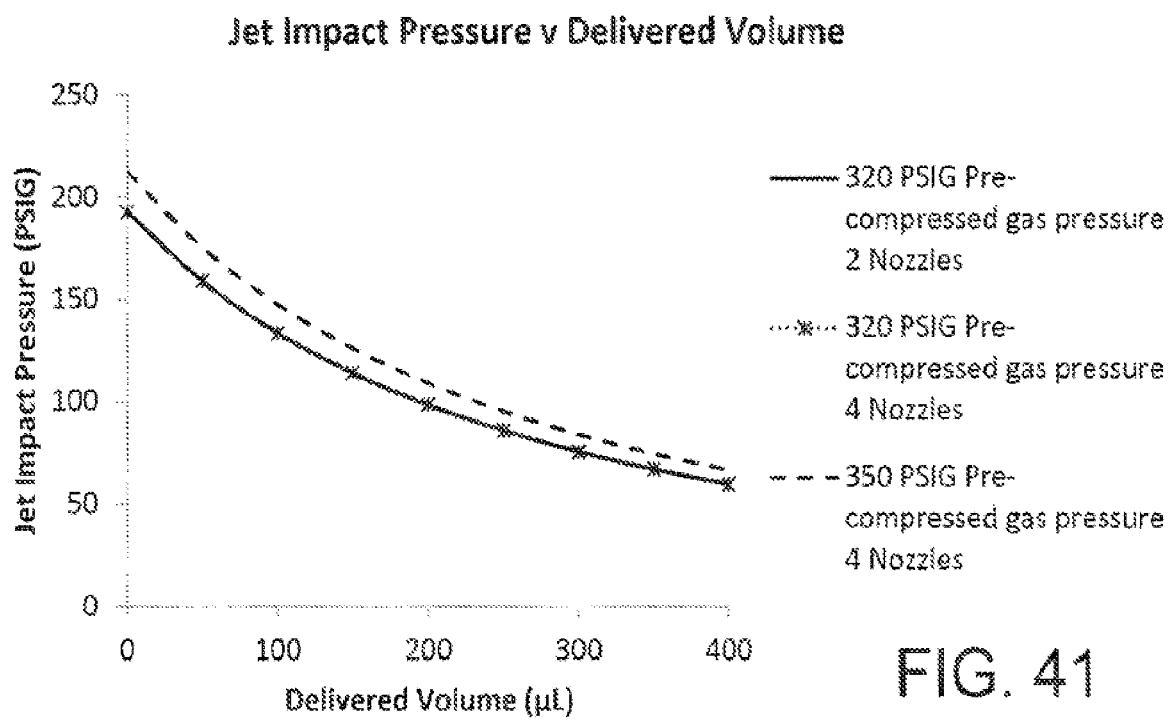
Figure 42:
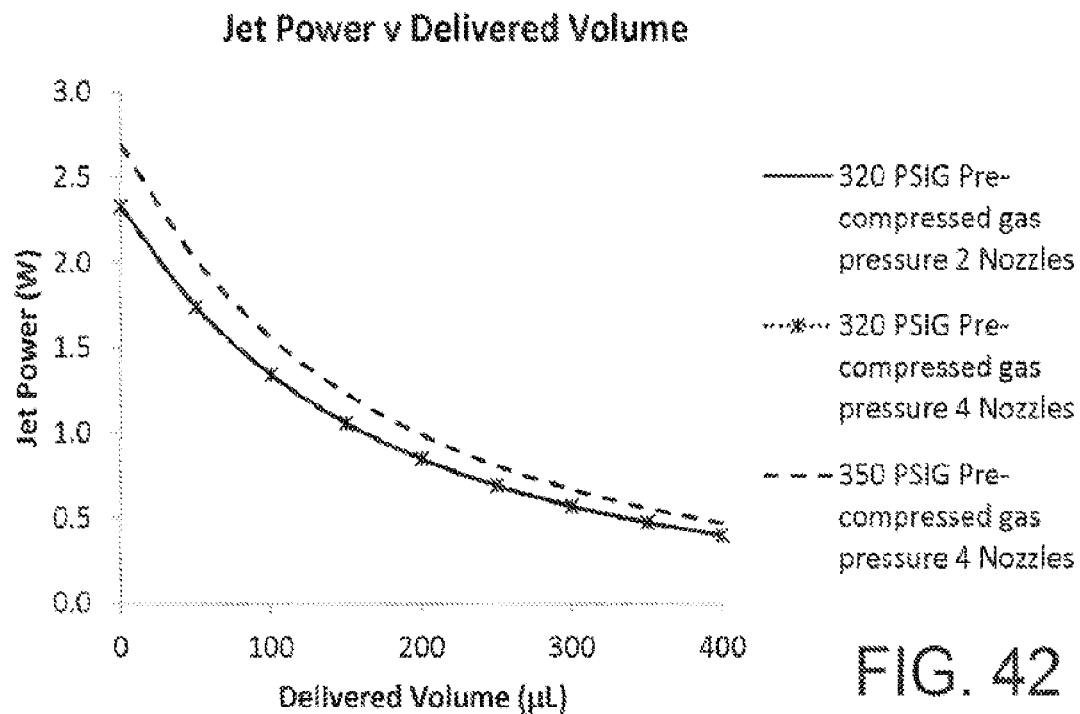
Figure 43:
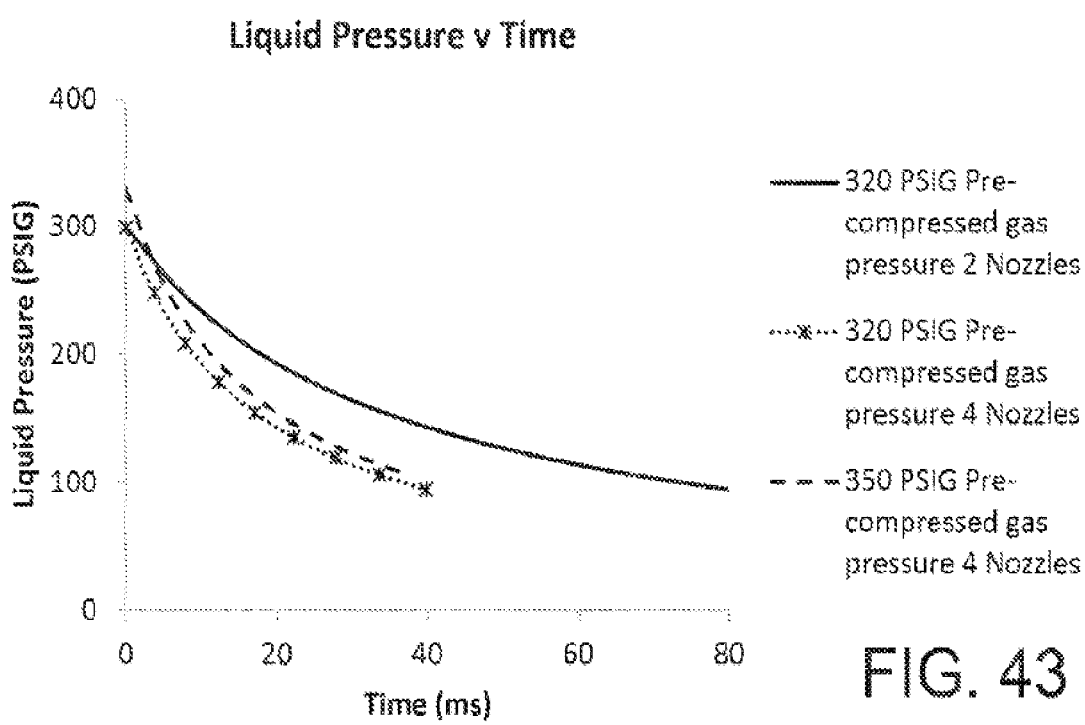
Figure 44:
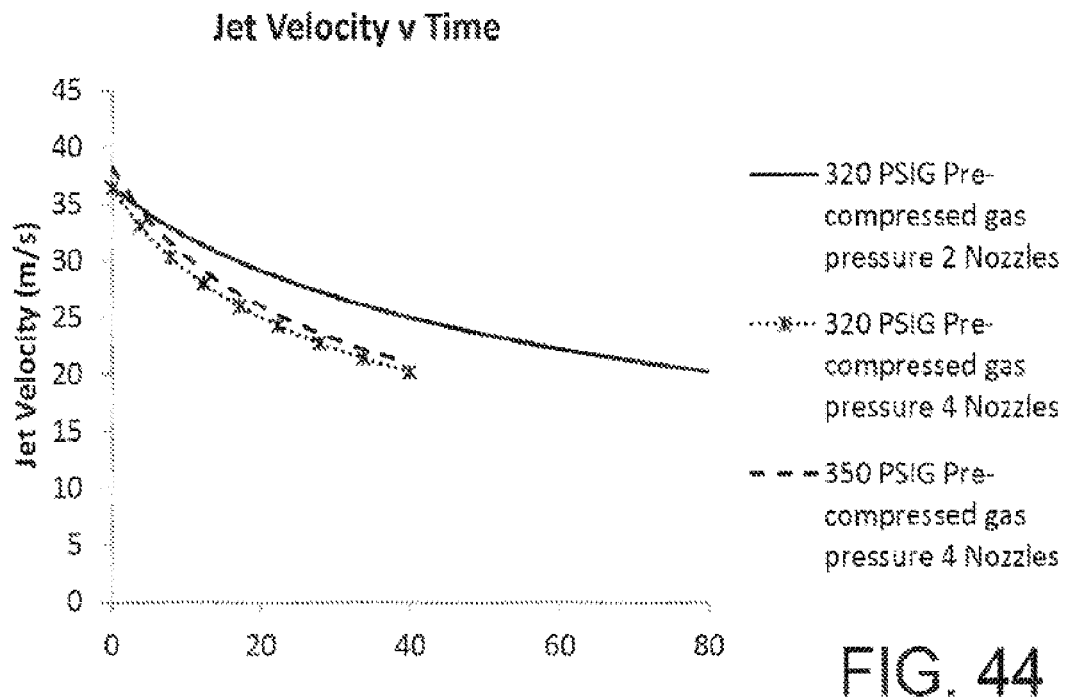
Figure 45:
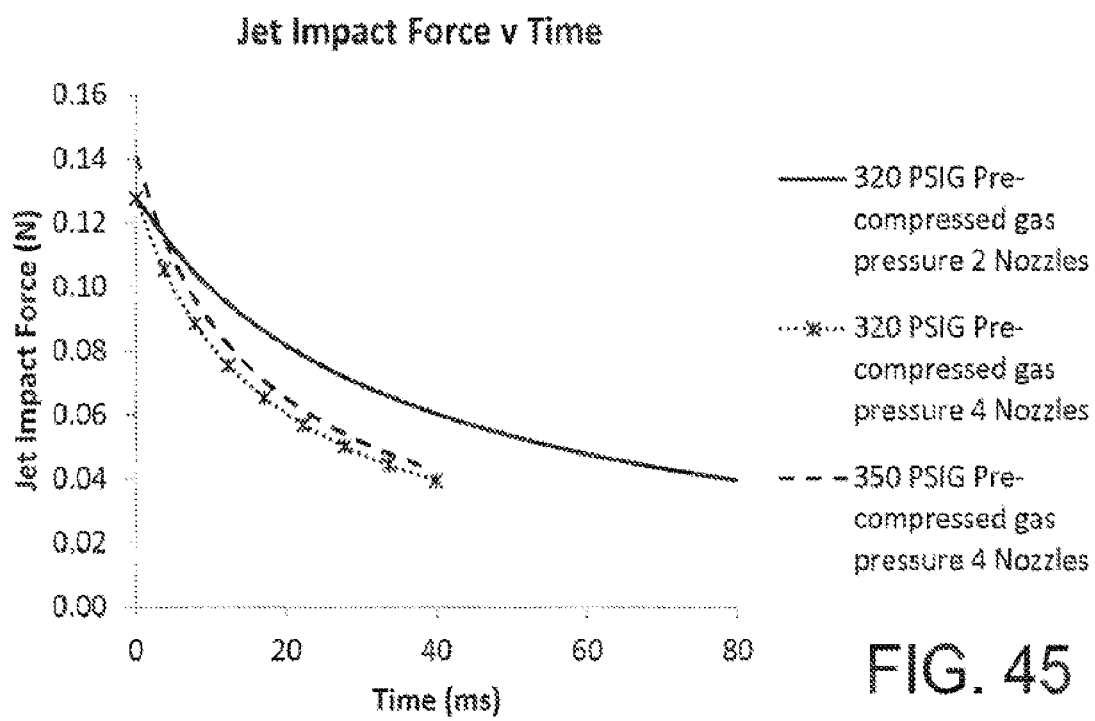
Figure 46:
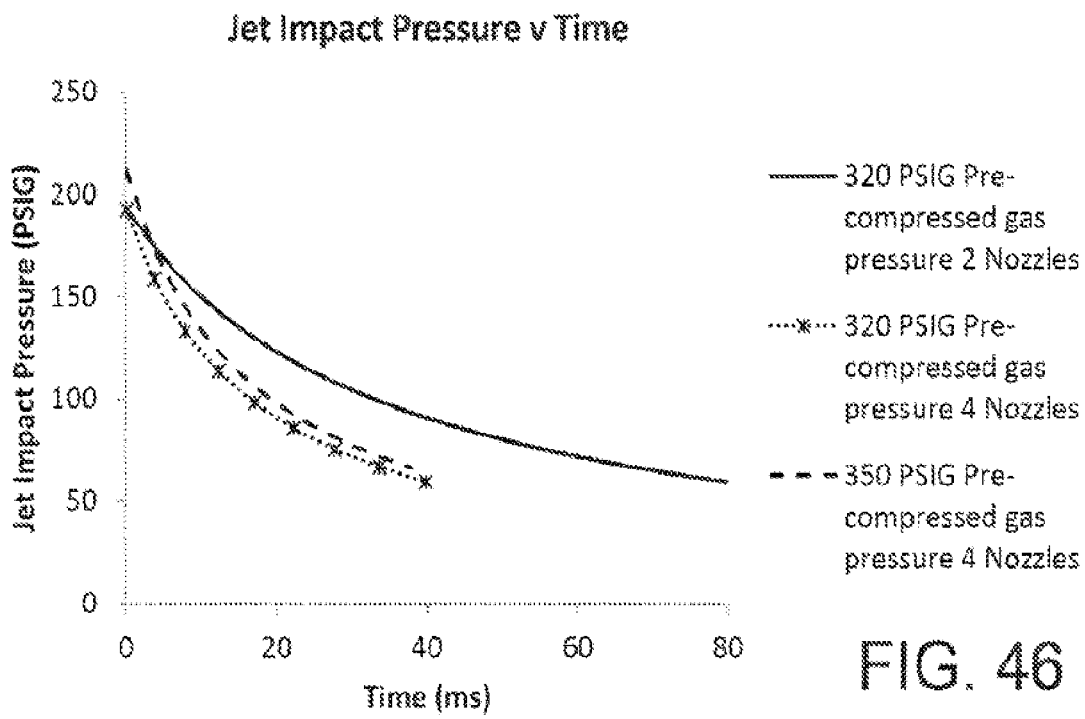
Figure 47:
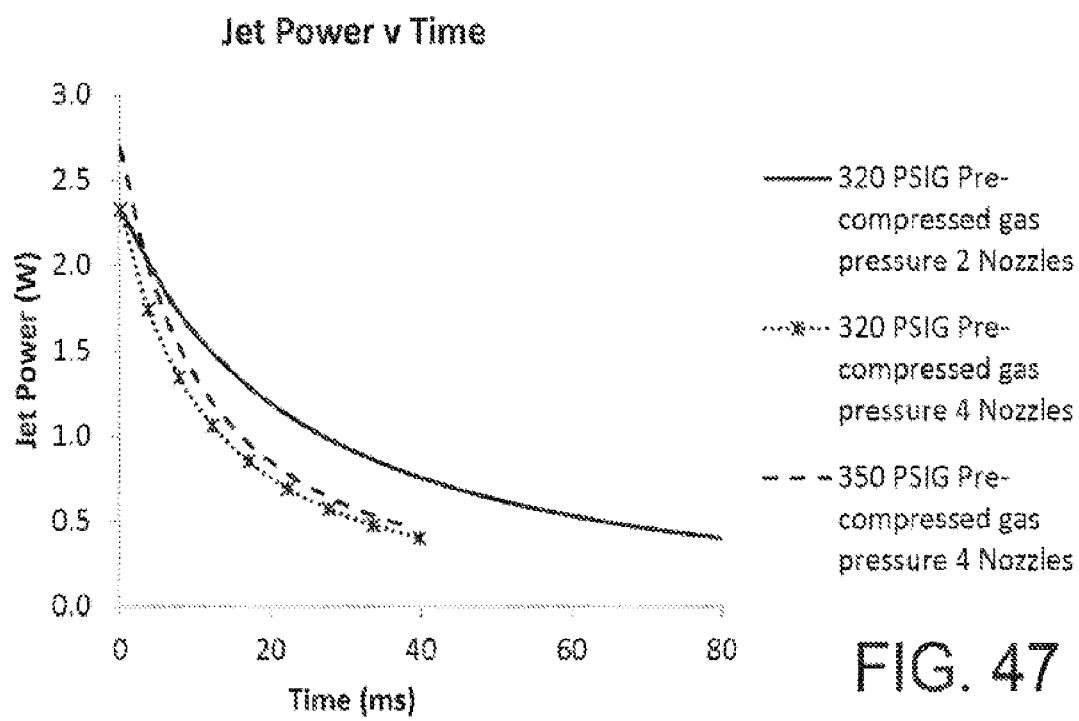

FIG. 32 shows an ingestible device 3200 for topical delivery. The device 3200 includes housing parts 3202A and 3202B. The housing part 3202B includes a seal 3203. The housing part 3202A is made from a flexible material that is biased against the housing part 3202B and joined to the housing part 3202B by a partial coating 3206 such that housing. The device 3200 also includes a fluid volume 3204 containing a dispensable substance. The subject swallows the ingestible device 3200. When the device 3200 reaches the appropriate location in the GI tract, the partial coating 3206 erodes, degrades and/or dissolves. This causes the flexible housing part 3202A to expand radially so that the housing parts 3202A and 3202B are separated, resulting in topical delivery of the therapeutic agent in the dispensable substance.

FIG. 32B shows aspects of steps in assembling the ingestible device 3200. In step 3220, the housing plug 3212 is formed in the opening 3212 of the housing part 3202A, the membrane 3204 is put inside the housing part 3202A, and the dispensable substance is disposed in the membrane 3204 under aseptic conditions. In step 3222, the housing part 3202B is combined with the housing part 3202A, and the open portion of the membrane 3204 is sealed (e.g., hot sealed) within an opening 3203 in the housing part 3202B, thereby forming the ingestible device 3200.

In certain embodiments, an ingestible device for topical delivery is configured as disclosed in the above-discussion regarding trans-epithelial delivery, but with a relatively large number of nozzles and a relatively large nozzle diameter such that performance properties for topical delivery (discussed above) can be achieved. As an example, in some embodiments, an ingestible device for topical delivery has at least 25 nozzles (e.g., at least 30 nozzles, at least 40 nozzles, 50 nozzles). In some embodiments, such an ingestible device for topical delivery has 30 nozzles, 31 nozzles, 32 nozzles, 33 nozzles, 34 nozzles, 35 nozzles, 36 nozzles, 37 nozzles, 38 nozzles or 40 nozzles. Each nozzle can have a diameter, for example, of at least about 1 mm (e.g., at least about 1.5 mm, at least about 2 mm) and/or at most about 3 mm (e.g., at most about 2.5 mm). For example, in such an ingestible device, each nozzle can have a diameter of from about 1 mm to about 3 mm (e.g., from about 1 mm to about 2.5 mm, from about 2 to 2.5 mm).

Delivery of Therapeutics

Provided herein are ingestible devices and methods that deliver therapeutic agents into the intestinal lumen, mucus, mucosa and/or submucosa by topical, epithelial or trans-epithelial administration to the GI tract of a subject. Current methods of administration for most large molecule therapeutic agents or small molecule therapeutic agents with poor oral bioavailability are subcutaneous (SC), intramuscular (IM), or bolus intravenous (IV) injection targeting the systemic circulation. The devices and methods described herein provide an alternative route of administration to current injectable medications, which can lead to greater convenience and compliance since they minimize or avoid the logistical challenges, patient compliance and adherence challenges, pain, and discomfort associated with traditional routes of administration.

In some embodiments of the devices or methods described herein, the therapeutic is released at a location in the small intestine of the subject. In some embodiments of any of the devices or methods described herein, the location is in the proximal portion of the small intestine (e.g., duodenum or jejunum). In some embodiments of any of the devices or methods described herein, the location is in the distal portion of the small intestine (e.g., jejunum or ileum). In some embodiments of the devices or methods described herein, the therapeutic is released at a location in the large intestine of the subject. In some embodiments of any of the devices or methods described herein, the location is in the proximal portion of the large intestine (e.g., cecum, ascending colon, or transverse colon). In some embodiments of any of the devices or methods described herein, the location is in the distal portion of the large intestine (e.g., transverse colon or descending colon).

Also, by providing a higher concentration of therapeutic in GI tissue, the devices and methods described herein are particularly well-suited for treatment of diseases and conditions of the endoderm, including the liver.

In some embodiments of any of the devices or methods described herein, the releasing of the therapeutic is triggered by one or more of: a pH in the jejunum of about 6.1 to about 7.2, a pH in the mid small bowel of about 7.0 to about 7.8, a pH in the ileum of about 7.0 to about 8.0, a pH in the right colon of about 5.7 to about 7.0, a pH in the mid colon of about 5.7 to about 7.4, or a pH in the left colon of about 6.3 to about 7.7, such as about 7.0.

In some embodiments of any of the devices or methods described herein, the releasing of the therapeutic is triggered by degradation of a release component located in the device. In some embodiments of any of the devices or methods described herein, the releasing of the therapeutic is dependent on enzymatic activity at or in the vicinity of the location. In some embodiments of any of the devices or methods described herein, the composition includes a plurality of electrodes including a coating, and releasing the therapeutic is triggered by an electric signal by the electrodes resulting from the interaction of the coating with an intended site of release of the therapeutic. In some embodiments of any of the devices or methods described herein, the release of the therapeutic is triggered by a remote electromagnetic signal. In some embodiments of any of the devices or methods described herein, the release of the therapeutic is triggered by generation in the composition of a gas in an amount sufficient to expel the therapeutic. In some embodiments of any of the devices or methods described herein, the release of the therapeutic is triggered by an electromagnetic signal generated within the device according to a predetermined drug release profile.

Therapeutics for Delivery

Therapeutics suitable for use with the devices and methods described herein include both small molecules and large molecules. In some embodiments, the therapeutic agent is a large molecule. Examples of large molecules include, but are not limited to, biologic drugs, proteins including fusion proteins, peptides including cyclic peptides, cells including stem cells, and nucleic acids such as inhibitory nucleic acids, antisense nucleic acids, siRNA, ribozymes, and the like. In some embodiments, the therapeutic agent is a large molecule with a molecular weight of at least about 60 kilodaltons (kDa), or about 60 kDa to about 200 kDa, about 60 kDa to about 175 kDa, or about 60 kDa to about 150 kDa. In some other embodiments, the therapeutic agent has a molecular weight of at least about 20 kDa, at least about 30 kDa, at least about 40 kDa, or at least about 50 kDa, or from about 20 kDa to about 200 kDa, about 20 kDa to about 175 kDa or about 20 kDa to about 150 kDa.

In some embodiments, the therapeutic agent is a molecule with a molecular weight of greater than about 1.5 kDa and less than about 20 kDa, less than about 30 kDa, less than about 40 kDa, less than about 50 kDa or less than about 60 kDa. In some other embodiments, the therapeutic agent has a molecular weight of from about 5 kDa to about 10 kDa, 20 kDa, 30 kDa, 40 kDa or 50 kDa. In some embodiments, the therapeutic agent is a molecule with a molecular weight of about 5 kDa to about 10 kDa, such as about 6 kDa. In some embodiments, the therapeutic agent is a protein or peptide. In some embodiments, the therapeutic agent is insulin.

In some embodiments, the therapeutic agent is a small molecule. A "small molecule," as used herein, is a compound, typically an organic compound, having a molecular weight of about 50 Da to about 1500 Da, about 60 Da to about 1500 Da, about 500 Da to about 1000 Da, or no more than about 1500 Da, about 1000 Da, about 750 Da, or about 500 Da. In some embodiments, the therapeutic agent is a small molecule with a molecular weight of about 50 Da to about 1500 Da. In some embodiments, the therapeutic agent is a small molecule with a molecular weight of about 150 Da to about 1500 Da.

Exemplary therapeutic agents for use in the devices and methods provided herein include, but are not limited to, abatacept, teriparatide, emicizumab, pegfilgrastim, semaglutide, dulaglutide, sargramostim, ustekinumab, secukinumab, tocilizumab, vedolizumab, natalizumab, interferon beta-1a, denosumab, alirocumab, evolocumab, adalimumab, etanercept, golimumab, and certolizumab pegol; and biosimilars thereof; and glycosylation variants thereof. Additional exemplary drugs for delivery using any of the devices or methods described herein include those listed in Table 2.

TABLE 2

| Drug (Brand Name) | Potential Dose | Drug concentration | Drug Volume and # capsules needed per equivalent dose$^a$ | Storage temperature |
|---|---|---|---|---|
| Humira ® (adalimumab) | 40, 80, 160 mg | ~40 mg/0.4 mL | 0.8-3.2 mL<br>2-8 Capsules | 2-8° C.<br>25° C.<br>for up to 14 days |
| Remicade ® (infliximab) | 400 mg | Diluted to~4 mg/mL | NA | 2-8° C.<br>30° C.<br>for up to 12 months |
| Cimzia ® (certolizumabpegol) | 400 mg | ~200 mg/mL | 4 mL<br>10 Capsules | 2-8° C.<br>2 hrs at room temp |
| Embrel ® (etanerecpt) | 50 mg | ~50 mg/mL | 2 mL<br>5 Capsules | 2-8° C.<br>25° C.<br>for 14 days |
| Lantis ® (insulin), Novalog ® (insulin) | sq | 1 unit~0.0347 mg, density of crystal is close to 1 g/cm$^3$ | | 2-8° C.<br>30° C.<br>for up to 28 days |
| Victoza ® (liraglutide) | 1.2 mg | ~6 mg/mL | 0.4 mL<br>1 Capsules | 2-8° C.<br>30° C.<br>for up to 30 days |
| Bydureon ® (exenatide) | 2 mg | ~2 mg/0.6 mL | 1.2 mL<br>3 Capsules | 2-8° C.<br>30° C.<br>for up to 28 days |
| (GHIH) (somatostatin) | 0.48-2 mg | | | |
| Sandosatin ® (Octreotide) | 100-500 mcg | ~500 mcg/mL | 0.4-2 mL<br>1-5 Capsules | 2-8° C.<br>30° C.<br>for up to 14 days |
| Avonex ® (interferon beta-1a) | 30 mcg | ~30 mcg/0.5 mL | 1 mL<br>2.5 Capsules | 2-8° C.<br>30° C.<br>for up to 30 days |
| Tysabri ® (natalizumab) | 300 mg | ~2.69 mg/mL | NA | 2-8° C. |
| Avastin ® (bevacizumab) | 5 mg | IFU: Do not administer as bolus, IV | NA | 2-8° C. |
| Entyvio ® (Vedolizumab) | 300 mg | IFU: Do not administer as bolus, IV | NA | |

TABLE 2-continued

| Drug (Brand Name) | Potential Dose | Drug concentration | Drug Volume and # capsules needed per equivalent dose[a] | Storage temperature |
|---|---|---|---|---|
| Fragmin ® (Dalteparin) | 2500-18000 IU | 5000 IU | 0.6 mL 1.5 Capsules | Room Temp |
| Rocephin ® (Ceftriaxone)(or other antimicrobials) | 1 g | ~350 mg/mL | | |
| Interferon alfa-2b | 3-30 million IU | ~50 million IU/mL | 0.12-1.2 mL <1-3 Capsules | 2-8° C. up to seven days at room temp |
| Natpara ® (Parathyroid Hormone) (PTH) | 50-100 mcg | ~1 mg/mL | <<1 Capsules | 2-8° C. |
| Genotropin ® Human Growth Hormone (HGH) | 0.2-2 mg | ~5.3 mg/mL | <1 Capsule | 2-8° C. 4 weeks after reconstitution |

[a]Number of capsules assumes a drug reservoir of about 400 microliters
sq: subcutaneous
IFU: Instructions for use
IU: International Unit Therapeutics for Growth Disorders In some embodiments, the therapeutic suitable for use with the devices and methods described herein is a therapeutic for treating a growth disorder. In some embodiments, the growth disorder is a growth hormone deficiency or disorder (GHD). In some embodiments, the GHD is acquired, congenital or idiopathic; or a combination thereof. In some embodiments, the GHD is a result of trauma, infection, radiation therapy or tumor growth. In some embodiments, the GHD is adult-onset GHD.

Exemplary therapeutics for treating growth disorders include, but are not limited to, growth hormones, including, but not limited to, somatropin, lonapegsomatropin, YPEG-somatropin, efpegsomatropin, a human growth hormone (HGH), a recombinant HGH (rHGH), a PEGylated rHGH, somapacitan, somatrogon, genotropin, humatrope, norditropin, nutropin, omnitrope, serostim, TJ-101, ALT-P1, and JR-142; and biosimilars and follow-on biologics thereof. In some embodiments, the growth hormone is an rHGH. Examples of suitable rHGHs include, but are not limited to, recombinant somatropin, e.g., genotropin, humatrope, norditropin, nutropin, omnitrope, serostim, Zomacton®, and Saizen®.

In some embodiments, the therapeutic suitable use with the devices and methods described herein for treating a growth disorder is somatropin or biosimilar or follow-on biologic thereof.

In some embodiments, the therapeutic suitable use with the devices and methods described herein for treating a growth disorder is somapacitan or biosimilar or follow-on biologic thereof.

Therapeutics for Fibrosis

In some embodiments, the therapeutic suitable for use with the devices and methods described herein is a therapeutic for treating fibrosis. In some embodiments, the therapeutic is a biological therapeutic. In some embodiments, the therapeutic is a small molecule. In some embodiments, the therapeutic is a non-oral therapeutic.

In some embodiments, the fibrosis is idiopathic pulmonary fibrosis. In some embodiments, the fibrosis is cystic fibrosis.

Exemplary therapeutics for treating fibrosis for delivery using any of the devices or methods described herein include those listed in Table 3.

TABLE 3

Therapeutics adaptable for delivery via ingestible device for the treatment of fibrosis

| Drug Name/Class | Existing Formulation Technologies, Methods of Administration | Exemplary Patent Literature |
|---|---|---|
| Rituximab/Biological therapeutic; Chimeric monoclonal antibody; Recombinant protein | Infusion; Intravenous; Subcutaneous | CN-101041907; CN-108676875; WO-08804936; WO-09411026 |
| Abatacept (Orencia)/ Biological therapeutic; Antibody fragment | Formulation powder; Freeze drying; Infusion; Intravenous; Solution; Subcutaneous | WO-09300431 |
| Tocilizumab (Actemra)/ Biological therapeutic; Monoclonal antibody humanized; Protein recombinant | Immunoglobulin-G; Infusion; Intravenous; Solution | WO-09219759 |
| Rilonacept (Arcalyst)/ Biological therapeutic | Formulation powder; Freeze drying; Subcutaneous | WO-00018932; WO-2004039951 |

TABLE 3-continued

Therapeutics adaptable for delivery via ingestible device for the treatment of fibrosis

| Drug Name/Class | Existing Formulation Technologies, Methods of Administration | Exemplary Patent Literature |
|---|---|---|
| Pirfenidone/Small molecule therapeutic | Aerosol formulation inhalant; Inhalant formulation | WO-2012106382 |
| BB-3/ Small molecule therapeutic | Infusion; Intravenous | |
| Ensifentrine/Small molecule therapeutic | Aerosol; Inhalant formulation; Nasal formulation; Suspension; Sustained release | WO-00058308 |
| GSK-3008348/Small molecule therapeutic | Inhalant formulation | |
| PLN-74809/Small molecule therapeutic | Systemic | |
| AVID-200/ Small molecule therapeutic | Systemic | WO-2017037634 |
| RES-529 (Restorgenex)/Small molecule therapeutic | Ophthalmic (intravitreal/subconjunctival) | WO-2007101247 |
| Fulvestrant/ Small molecule therapeutic | Intramuscular; Sustained release | EP-00138504 |
| Sodium pyruvate/Small molecule therapeutic | Inhalant | WO-09710818 |
| Glutathione/ascorbic acid/bicarbonate combination/ Small molecule therapeutic | Aerosol formulation inhalant | WO-2014070769 |
| CHF-6333/Small molecule therapeutic | Inhalant; Powder inhalant | |

Therapeutics for Metabolic and/or Endocrine Diseases or Conditions

In some embodiments, the therapeutic suitable for use with the devices and methods described herein is a therapeutic for treating a metabolic or endocrine disease or condition. Examples of metabolic or endocrine diseases or conditions include, but are not limited to, diabetes, insulin resistance, hyperglycemia, hyperlipidemia, obesity, hepatic steatosis, hyperinsulinemia, obstructive sleep apnea, non-alcoholic fatty liver disease (NAFLD), non-alcoholic steatohepatitis (NASH), liver fibrosis, liver cirrhosis, hypertension, pulmonary artery hypertension, primary sclerosing cholangitis, hyperlipoproteinemia type I, familial hypercholesterolemia, hypercholesterolemia, lipodystrophy, acromegaly, myocardial infarction, and thromboembolism; and combinations thereof. In some embodiments, the metabolic or endocrine disease or condition is obesity.

Therapeutics suitable for treating a metabolic or endocrine disease or condition include, but are not limited to, abatacept, aldesleukin, allogeneic human islets of langerhans, alogliptin, alpha-1 antitrypsin, anagliptin, benaglutide, berberine, bermekimab, bimagrumab, cibinetide, cotadutide, diabecell, diamyd, dutogliptin ebenatide, efpeglenatide, evogliptin, FSI-965, gemigliptin, glutazumab, gosogliptin, hinsbet, LAI-287, linagliptin, mecasermin, omarigliptin, otelixizumab, pegapamodutide, peg-loxenatide, pramlintide acetate, prolastin, protrans, rexmyelocel-t, saxagliptin, sitagliptin, somatostatin, teneligliptin, teplizumab, tirzepatide, trelagliptin, vildagliptin, and combinations thereof. In some embodiments, therapeutic suitable for treating a metabolic or endocrine disease or condition is selected from bortezomib, fulvestrant, bendamustine, itolizumab, golimumab, canakinumab, *Trichuris suis* ova, NNC-0385-0434, NGM-282, BMS-986036, and remestemcel-L; and biosimilars thereof. In some embodiments, the therapeutic suitable for treating a metabolic or endocrine disease or condition is a proprotein convertase subtilisin/kexin type 9 (PCSK9) inhibitor. In some embodiments, the PCSK9 inhibitor is alirocumab or evolocumab. Other exemplary PCSK9 inhibitors for treating a metabolic or endocrine disease or disorder include those listed in Table 10.

Therapeutics for Diabetes

In some embodiments, the metabolic or endocrine disease or condition is diabetes. In some embodiments, the diabetes is type I or type II diabetes. In some embodiments, the diabetes is an insulin dependent diabetes. In some embodiments, the diabetes is a non-insulin dependent diabetes. In some embodiments, the diabetes is gestational diabetes.

In some embodiments, the metabolic or endocrine disease or condition is diabetes in combination with another disease or condition, including, but not limited to, diabetes with Alzheimer's disease, diabetes with dementia, diabetes with Alzheimer's disease and dementia, diabetes with obesity, diabetes with NAFLD, diabetes with NASH, diabetes with NAFLD and NASH, and diabetes with a cardiovascular disease. In some embodiments, the diabetes is diabetes with obesity.

Therapeutics suitable for treating a metabolic or endocrine disease or condition include, but are not limited to, an insulin, a glucagon receptor agonist or a glucagon-like peptide-1 (GLP-1) receptor agonist, peptide YY ligand, and an amylin analong.

In some embodiments, the therapeutic suitable for use with the devices and methods described herein is a peptide YY ligand. The gut hormone peptide YY (PYY), also known as peptide tyrosine, is a 36-amino acid peptide that is synthesized and released from specialized enteroendocrine cells called L-cells found predominantly within the distal GI tract (see, e.g., Karra et al., J. Physiol. 587(Pt 1):19-25 (2009)). In some embodiments, the peptide YY ligand is NN-9747, NN-9748, NN-9775 or any peptide YY ligand disclosed in WO 2016/198682, which is encorporated by reference herein in its entirety. In some embodiments, the peptide YY ligand is NN-9747 (PYY 1562, NNC0165-1562, NN-9748), analogue of the appetite-regulating hormone, PYY, which can be used for mono- or combination treatment with the GLP-1 analogue semaglutide. In some embodiments, NN-9747 or NN-9748 is administered subcutaneously qd. In some embodiments, NN-9747 is indicated for obesity. In October 2015, a phase I trial was initiated and completed in February 2017; N=93 (Clinical Trials identifier: NCT02568306; source: Novo Nordisk Annual Report 2018). In some embodiments, NN-9748 is indicated for diabetes. In some embodiments, the peptide YY ligand is NN-9775 (NNC0165-1875), a peptide tyrosine 1875 analog (PYY 1875 analog), for the potential sc treatment of obesity and overweight. NN-9748 is an analogue of the appetite-regulating hormone, PYY, intended for mono- or combination treatment with the GLP-1 analogue semaglutide. In October 2018, a first-human dose, phase I study of NNC0165-1875 as monotherapy and in combination with semaglutide was initiated; N=88 (clinical trials identifier: NCT03707990; source: Novo Nordisk Annual Report 2018). In some embodiments, NN-9747 is the same drug substance as NN-9748.

In some embodiments, the therapeutic suitable for use with the devices and methods described herein is an amylin analog. In some embodiments, the amylin analog is AM-833.

In some embodiments, the metabolic or endocrine disease or condition is obesity or diabetes with obesity.

In some embodiments, the therapeutic is NNC0247-0829. In some embodiments, the metabolic or endocrine disease or condition is obesity or diabetes with obesity.

In some embodiments, the therapeutic suitable for use with the devices and methods described herein is a glucagon receptor agonist or a glucagon-like peptide-1 (GLP-1) receptor agonist. In some embodiments, the glucagon receptor agonist or the GLP-1 receptor agonist is glucagon. In some embodiments, the glucagon receptor agonist or the GLP-1 receptor agonist is NN-9277 (see, e.g., Brandt et al., J. Endocrinol. 283(2):R109-R119 (2018)). In some embodiments, the glucagon receptor agonist or the GLP-1 receptor agonist is semaglutide; or a biosimilar thereof. In some embodiments, the glucagon receptor agonist or the GLP-1 receptor agonist is dulaglutide; or a biosimilar thereof. In some embodiments, the glucagon receptor agonist or the GLP-1 receptor agonist is albiglutide; or a biosimilar thereof. In some embodiments, the glucagon receptor agonist or the GLP-1 receptor agonist is exenatide; or a biosimilar thereof. In some embodiments, the glucagon receptor agonist or the GLP-1 receptor agonist is liraglutide; or a biosimilar thereof. In some embodiments, the glucagon receptor agonist or the GLP-1 receptor agonist is lixisenatide; or a biosimilar thereof. In some embodiments, the glucagon receptor agonist or the GLP-1 receptor agonist is NNC-0090-2746.

In some embodiments, the therapeutic suitable for use with the devices and methods described herein is a therapeutic for treating diabetes.

In some embodiments, the therapeutic for treating diabetes that is suitable for use with the devices and methods described herein is an insulin. In some embodiments, the insulin is selected from human insulin, insulin aspart, ultrafast acting insulin aspart, insulin degludec, insulin detemir, insulin glargine, insulin glulisine, insulin lispro, and insulin tregopil.

In some embodiments, the therapeutic for treating diabetes that is suitable for use with the devices and methods described herein is a dipeptidyl peptidase-4 inhibitor (DPP-4). DPP-4 inhibitors are oral hypoglycemics which are used to treat diabetes mellitus type-2. These drugs include, but are not limited to: sitagliptin, vildagliptin, saxagliptin, linagliptin, gemigliptin, anagliptin, teneligliptin, alogliptin, trelagliptin, omarigliptin, evogliptin, gosogliptin, dutogliptin and berberine.

Exemplary therapeutics for treating diabetes for delivery using any of the devices or methods described herein include those listed in Table 4, and any combination thereof.

TABLE 4

Therapeutics adaptable for delivery via ingestible device for the treatment of diabetes

| Drug Name/ Company | Existing Formulation Technologies, Methods of Administration | Exemplary Patent Literature |
|---|---|---|
| Dulaglutide | Biological therapeutic; Immunoglobulin-G; Protein fusion; Solution; Subcutaneous | WO2004110472 |
| Semaglutide/Novo Nordisk | Biological therapeutic; Peptide; Subcutaneous; Oral sustained release; Tablet | WO2006097537; WO2012080471 |
| Exenatide/Astrazeneca; Intarcia/Servier; Peptron | Biological therapeutic; Intravenous Subcutaneous, Injectable controlled release; Suspension; Sustained release; Subcutaneous drug implant; Drug combination | WO09830231 US05424286; WO2004035754; WO00066629; WO2006083761; WO2008133908; WO2017200943; WO2017200944; WO2018075901 |
| Insulin degludec | Biological therapeutic; Cloning technology; Peptide; Solution; Subcutaneous; Sustained release | WO-2005012347 |
| Liraglutide | Biological therapeutic; Peptide; Protein recombinant; Solution; Subcutaneous | WO-09727866; WO09808871; WO09832825; WO09943341; WO09943705; WO09943708; WO09947160 |
| Insulin lispro/Sanofi; Gan & Lee Pharmaceuticals; Eli Lilly; | Biological therapeutic; Biosimilar product; Follow on biologic; Protein | EP00383472; WO2004078239; |

TABLE 4-continued

Therapeutics adaptable for delivery via ingestible device for the treatment of diabetes

| Drug Name/ Company | Existing Formulation Technologies, Methods of Administration | Exemplary Patent Literature |
|---|---|---|
| Wanbang Biopharma; Adocia/ Tonghua; Diasome Pharmaceuticals | recombinant; DNA technology; Infusion; Intravenous; Peptide; Quick release; Solution; Subcutaneous; Suspension | CN104587455; WO2014076422 |
| Insulin glargine/Sanofi; Biocon/Mylan/pisa/Fujifilm/ GC Pharma; Eli Lilly/ Boehringer; Wockhardt; Gan & Lee Pharmaceuticals/ LG; Life Sciences; Incepta; Getz Pharma; Tonghua Dongbao; Jiangsu Wanbang Biochemical Pharmaceutical | Biological therapeutic; Biosimilar product; Follow on biologic; Protein recombinant; Solution; Subcutaneous; Sustained release | WO2004078239; EP00368187; WO2011018745; WO00210411; WO2004050672; WO2012152175; CN103439512; CN104587455 |
| Insulin aspart/Novo Nordisk; Gan & Lee Pharmaceuticals; Sanofi; Zhunhai United Laboratories; Dongbao Group; Biocon/Mylan; Zhejiang Hisun Pharmaceutical | Biological therapeutic; Biosimilar product; Infusion; Intravenous; Intramuscular; Protein recombinant; Subcutaneous; Quick release; Solution; Suspension; Ultra-fast acting | WO2010149772; EP00214826; WO09426778; CN103060335 |
| Insulin glargine + lixisenatide/ Sanofi/Zealand Pharma | Biological therapeutic; Drug combination; Protein recombinant; Subcutaneous | WO00104156 |
| Insulin degludec + insulin aspart | Biological therapeutic; Drug combination; Peptide; Solution; Subcutaneous | WO2005012347; WO2012080320 |
| Insulin degludec + limglutide/ Novo Nordisk | Biological therapeutic; Drug combination; Peptide; Subcutaneous; Sustained release | WO09727866; WO09808871; WO09832825; WO09943341; WO09943705; WO09943708; WO09947160; WO2005012347; WO2009063072 |
| Insulin glulisine | Biological therapeutic; Infusion; Intravenous; Peptide; Solution; Subcutaneous | EP-00885961 |
| Insulin detemir | Biological therapeutic; Injectable controlled release; Peptide; Protein recombinant; Solution; Subcutaneous | AU-00745983; WO-09507931 |
| Alpha-1 antitrypsin/ Kamada/Shire | Biological therapeutic; Intravenous; Liquid | WO09856821 |
| Insulin human/Eli Lilly | Biological therapeutic; Protein recombinant; Solution; Subcutaneous; Suspension | EP00037256 |
| Pramlintide acetate | Biological therapeutic; Peptide; Solution; Subcutaneous | WO09215317; WO09310146 |
| Albiglutide | Biological therapeutic; Powder; Freeze drying; Liquid; Protein fusion; Protein recombinant; Subcutaneous; Sustained release | US20080167238; WO03059934 |
| Insulin/Generex | Biological therapeutic; Buccal formulation systemic; Formulation aerosol unspecified; Protein recombinant | WO00037053 |
| Lixisenatide | Biological therapeutic; Peptide; Subcutaneous | CN103467365; CN106167528; WO00104156 |
| Prolastin | Biological therapeutic; Powder; Freeze drying; Infusion; Intravenous; Peptide; | EP-00097274 |
| Benaglutide | Biological therapeutic; Protein recombinant; Subcutaneous | WO-03016349 |
| Insulin Technosphere/Sanofi | Biological therapeutic; Inhalant; Microparticle; Powder Protein recombinant | WO-09636314 |

TABLE 4-continued

Therapeutics adaptable for delivery via ingestible device for the treatment of diabetes

| Drug Name/ Company | Existing Formulation Technologies, Methods of Administration | Exemplary Patent Literature |
|---|---|---|
| Human insulin/Novo Nordisk A/S; Sanofi-Aventis; Bioton/Scigen/Actavis; Tonghua Dongbao; Wockhardt; Geropharm; Horizon; Pharma/IBA Tech; SEDICO; United Laboratories International Holdings; Square Pharmaceuticals; Rechon Life Sciences | Biological therapeutic; DNA technology, Follow on biologic; Peptide; Subcutaneous; Suspension; Yeast recombinant; Cloning technology; Drug implant; Intravenous; Intramuscular; Protein recombinant; Solution | EP-00427296; US-04029642; WO-2013119132; CN-103439512; WO-2004024862; WO-00204515; WO-09965941 |
| Isophane insulin/Biocon | Biological therapeutic; Follow on biologic; Protein recombinant; Subcutaneous; Sustained release | WO-2010016069 |
| Insulin/Biocon; MJ Bioton Life Science/MJ Biopharm/Medipolis/Marvel Life Sciences/Pharmstandard; Shenzhen Kexing Biotech; Hefei Tianma Biotechnology; Valin Technologies | Biological therapeutic; Biosimilar product; Follow on biologic; Protein recombinant; Quick release; Subcutaneous | WO-09426778; CN-202530010; CN-202983284 |
| Glucagon/Lilly | Biological therapeutic; DNA technology; Injectable; Parenteral formulation unspecified; Protein recombinant | US-04033941 |
| Mecasermin/Fujisawa | Biological therapeutic; Intravenous; Protein recombinant | WO-09103253 |
| Short acting insulin/Popular Pharmaceuticals | Biological therapeutic; Follow on biologic; Protein recombinant; Solution; Subcutaneous: Suspension | |
| Recombinant human insulin/ Scigen | Biological therapeutic; Protein recombinant; Transdermal; Transdermal high velocity particle formulation | |
| Rosinsulin | Biological therapeutic; Subcutaneous; Suspension | |
| Somatostatin/Lunan Pharmaceutical | Biological therapeutic; Follow on biologic; Intravenous; Peptide | |
| Insulin isophane/Wanbang Biopharma; Shenzhen Kexing Biotech | Biological therapeutic; Follow on biologic; Protein recombinant; Solution; Subcutaneous | CN-101173006 |
| Diabecell | Biological therapeutic; Cell therapy; Intraperitoneal; Microparticle; Xenogeneic transplant | WO-00152871 |
| Bermekimab | Biological therapeutic; Immunoglobulin-G; Infusion; Intravenous; Monoclonal antibody human; Subcutaneous | WO-2009148575 |
| UNI-RE-4 | Biological therapeutic; Powder; Liquid; Parenteral formulation unspecified; Protein recombinant | CN-102370624 |
| PEG-loxenatide | Biological therapeutic; PEGylated formulation; Peptide; Subcutaneous; Sustained release | WO-2012155780 |
| Tirzepatide | Biological therapeutic; PEGylated formulation; Peptide; Subcutaneous | WO-2016111971 |
| Efpeglenatide | Antibody fragment; Biological therapeutic; Protein conjugated; Subcutaneous; Sustained release | WO-2008082274 |
| Teplizumab | Biological therapeutic; Infusion; Intravenous; Monoclonal antibody humanized; Subcutaneous | WO-09428027 |
| Insulin tregopil | Biological therapeutic; Oral; Protein conjugated | WO-2004083234 |
| Insulin/Alkermes/Eli Lilly | Biological therapeutic; Infusion; Peptide; Subcutaneous | |
| Rexmyelocel-T | Biological therapeutic; Cell therapy; Infusion; Intra-arterial; Leukocyte cell therapy | WO-2018037134 |
| RE-4 | Biological therapeutic; Protein recombinant; Subcutaneous; Systemic formulation unspecified | |

TABLE 4-continued

Therapeutics adaptable for delivery via ingestible device for the treatment of diabetes

| Drug Name/ Company | Existing Formulation Technologies, Methods of Administration | Exemplary Patent Literature |
|---|---|---|
| Allogeneic human islets of Langerhans/University of Illinois | Biological therapeutic; Cell therapy; Systemic formulation unspecified | WO-2009006600 |
| Pegapamodutide | Biological therapeutic; Injectable controlled release; PEGylated formulation; Peptide; Subcutaneous; Sustained release | WO-2011087672 |
| LAI-287 | Biological therapeutic; Peptide; Subcutaneous; Sustained release; | |
| CLBS-03 | Biological therapeutic; Parenteral formulation unspecified; T-lymphocyte | WO-2006031926 |
| Insulin/Diabetology | Biological therapeutic; Capsule; Enteric coated; Oral absorption enhancer; Oral; Peptide | WO-2007093806 |
| IONIS-gcgrrx | Biological therapeutic; Infusion; Intravenous; Oligonucleotide antisense; RNA antisense; Subcutaneous | WO-2008017081 |
| Bimagrumab | Biological therapeutic; Infusion; Intravenous; Monoclonal antibody human; Protein recombinant | WO-2010125003 |
| IONIS-ANGPTL3-lrx | Biological therapeutic; Oligonucleotide antisense; Subcutaneous | WO-2015100394 |
| Aldesleukin/ILTOO Pharma | Biological therapeutic; Protein recombinant; Subcutaneous | |
| HM-12525a | Antibody conjugated; Biological therapeutic; Parenteral formulation unspecified; Peptide; Protein conjugated; Subcutaneous; Sustained release | WO-2012173422 |
| ORMD-0901 | Biological therapeutic; Capsule; Oral; Peptide | WO-2009136392 |
| Diamyd/Diamyd Medical | Antigen; Biological therapeutic; Parenteral formulation unspecified; Protein recombinant | |
| Pec-direct | Biological therapeutic; Cell therapy; Drug implant; Pluripotent stem cell therapy | WO-2018089011 |
| GNBAC-1 | Biological therapeutic; Immunoglobulin-G; Infusion; Intravenous; Monoclonal antibody humanized; Protein recombinant | WO-2010003977 |
| Insulin/Oramed | Biological therapeutic; Capsule; Oral; Protein recombinant | WO-2007029238 |
| TOL-3021 | Biological therapeutic; Intramuscular | WO-2007044394 |
| MPC-300-iv | Allogenic stem cell therapy; Biological therapeutic; Infusion; Intravenous; Mesenchymal stem cell therapy | WO-2012000064 |
| Glutazumab | Biological therapeutic; Monoclonal antibody; Protein fusion; Subcutaneous | |
| Cotadutide | Biological therapeutic; Peptide; Solution; Subcutaneous | WO-2015086686 |
| REMD-477 | Biological therapeutic; Monoclonal antibody human; Subcutaneous | WO-2015189698 |
| PEC-encap | Biological therapeutic; Cell therapy; Pluripotent stem cell therapy; Subcutaneous drug implant | WO-2005063971 |
| Cibinetide/Araim | Biological therapeutic; Infusion; Intravenous; Peptide; Subcutaneous | WO-2007019545; WO-2009094172 |
| LY-3209590 | Biological therapeutic; Peptide; Subcutaneous | |
| Otelixizumab | Biological therapeutic; Infusion; Intravenous; Monoclonal antibody humanized; Subcutaneous | WO-09319196 |
| AG-019 | Bacteria recombinant; Biological therapeutic; Capsule; Oral; Peptide | WO-2007063075 |

TABLE 4-continued

Therapeutics adaptable for delivery via ingestible device for the treatment of diabetes

| Drug Name/<br>Company | Existing Formulation<br>Technologies, Methods of<br>Administration | Exemplary Patent<br>Literature |
|---|---|---|
| GABA + antigen based therapy/Diamyd | Antigen; Biological therapeutic; Drug combination; Oral; Tablet | WO-2017058074 |
| Allogeneic human mesenchymal stem cells/Longeveron | Allogenic stem cell therapy; Biological therapeutic; Infusion; Intravenous; Local formulation unspecified; Mesenchymal stem cell therapy | WO-2018089752 |
| Cell therapy/Sernova | Biological therapeutic; Cell therapy; Subcutaneous | WO-09528167 |
| Insulin Diabetology | Biological therapeutic; Capsule; Enteric coated; Oral absorption enhancer; Oral; Peptide | WO-2007093806 |
| PB-119 | Biological therapeutic; PEGylated formulation; Peptide; Subcutaneous | WO-2010121559 |
| Ionis-DGAT2Rx | Biological therapeutic; Oligonucleotide antisense; Subcutaneous | WO-2017011276 |
| Abatacept/NIDDK | Biological therapeutic; Immunoglobulin-G; Intravenous; Protein fusion | WO-2013177505 |
| Ebenatide | Biological therapeutic; Protein conjugated; Subcutaneous; Sustained release | WO-2007053946 |
| Protrans | Allogenic stem cell therapy; Biological therapeutic; Infusion; Intravenous; Mesenchymal stem cell therapy; Umbilical cord stem cell therapy | |
| Hinsbet | Biological therapeutic; Injectable; Parenteral formulation unspecified; Peptide; Protein recombinant; Quick release | WO-2010122385 |
| Glucagon-like peptide-1 analog/Radboud University | Imaging; Infusion; Peptide; Radiolabeling; Systemic formulation unspecified | |
| Insulin (long-acting iv, hepatic directed vesicles (HDV)) Diasome Pharmaceuticals | Biological therapeutic; Nanoparticle formulation injectable; Parenteral formulation unspecified; Protein recombinant | WO-2011022396 |
| Human insulin/Dance/Harmony/Dongbao | Aerosol formulation inhalant; Biological therapeutic; Inhalant; Protein recombinant | WO-2011088070 |
| Anti-IL-21 + liraglutide/Novo Nordisk | Biological therapeutic; Intravenous; Monoclonal antibody human; Subcutaneous | WO-2012098113 |
| NNC-0090-2746 | Biological therapeutic; PEGylated formulation; Peptide; Subcutaneous | WO-2010096052 |
| BIOD-531 | Biological therapeutic; Parenteral formulation unspecified; Protein recombinant; Subcutaneous | |
| Allogenic umbilical cord-derived mesenchymal stem cell therapy/Nanjing University | Allogenic stem cell therapy; Biological therapeutic; Intravenous; Mesenchymal stem cell therapy | |
| Insulin/Diasome Pharmaceuticals | Biological therapeutic; Nanoparticle formulation injectable; Intravenous; Capsule; Oral; Nanoparticle formulation oral; Protein recombinant | |

Therapeutics for NASH/NAFLD

In some embodiments, the disease or condition is NASH and/or NAFLD. In some embodiments, the therapeutic suitable for use with the devices and methods described herein is a therapeutic for treating non-alcoholic steatohepatitis (NASH) and/or non-alcoholic fatty liver disease (NAFLD). NASH (non-alcoholic steatohepatitis) is a fatty liver disease affecting as many as 12% of the U.S. adults. There are many potential drugs to treat this disease illustrated by: selonsertib, cenicriviroc, elafibranor, ocaliva, tropifexor, firocostat, cilofexor, aramchol, ARX618, BI 1467335, DS 102, EDP-305, emricasan, gemcabene, GR-MD-02, GRI-0621, GS-0976, GS-9674, IMM-124E, IONIS-DGAT2Rx, IVA-337, lipaglyn, LJN452, LLMB763, MGL-3196, MN-001, MSDC-0602K, NC101, NGM282, NGM313, NS-0200, ozempic, PF-05221304, PF-06835919, remogliflozin etabonate, SHP626, TVB-2640, VK2809, butanoic acid, CER209, evogliptin, DUR928, MK-4074, OPRX-106, PF06865571, PF06882961, PXS-5382A, RG-125, RYI-018, seladelpar, SGM-1019 and TVB-2640. In some embodiments, the therapeutic suitable for use with the devices and methods described herein is selected from the therapeutic agent is selected from the group consisting of selonsertib, cenicriviroc, elafibinor, ocaliva, tropifexor, firocostat and cilofexor. These represent several biological mechanisms. A combination of multiple drugs may be required. In some embodiments, the drug is selected from selonsertib, cenicriviroc, elafibinor, ocaliva, tropifexor, firocostat and cilofexor. Exemplary therapeutics for treating NASH and/or NAFLD for delivery using any of the devices or methods described herein include those listed in Table 5.

TABLE 5

Therapeutics adaptable for delivery via ingestible device for the treatment of NASH/NAFLD

| Drug Name | Existing Formulation Technologies and Methods of Administration | Exemplary Patent Literature |
| --- | --- | --- |
| NGM-282 | Biological therapeutic; Protein recombinant; Subcutaneous | WO-2013006486 |
| IONIS-ANGPTL3-LRx | Biological therapeutic; Oligonucleotide antisense; Subcutaneous | WO-2015100394 |
| Insulin/Oramed | Biological therapeutic; Capsule; Oral; Protein recombinant | WO-2007029238 |
| BMS-986036 | Biological therapeutic; PEGylated formulation; Protein recombinant; Subcutaneous | WO-2008121563 |
| IMM-124-E | Antibody polyclonal; Biological therapeutic; Powder; Immunoglobulin-G; Oral | WO-2010125565 |
| Semaglutide/Novo Nordisk | Biological therapeutic; Peptide; Subcutaneous; Sustained release | |
| IONIS-DGAT2Rx | Biological therapeutic; Oligonucleotide antisense; Subcutaneous | WO-2017011276 |

Therapeutics for Rheumatoid Arthritis

In some embodiments, the therapeutic suitable for use with the devices and methods described herein is a therapeutic for treating rheumatoid arthritis. Exemplary therapeutics for treating rheumatoid arthritis for delivery using any of the devices or methods described herein include those listed in Table 6.

TABLE 6

Therapeutics adaptable for delivery via ingestible device for the treatment of rheumatoid arthritis

| Drug Name/Company | Existing Formulation Technologies, Methods of Administration | Exemplary Patent Literature |
| --- | --- | --- |
| Certolizumab pegol | Antibody fragment; Biological therapeutic; Powder; Freeze drying; Monoclonal antibody humanized; PEGylated formulation; Protein conjugated; Protein recombinant; Solution; Subcutaneous | WO-00194585 |
| Corticotropin/Mallinckrodt | Biological therapeutic; Gel; Injectable controlled release; Intramuscular; Peptide; Subcutaneous; Sustained release | WO-2011143152 |
| Ciclosporin/Novartis; Chong Kun Dang | Biological therapeutic; Capsule; Emulsion; Infusion; Intravenous; Oral; Oral gel; Peptide; Solution | GB-01491509; US-06306825; WO-09522982 |
| Etanercept/Sandoz/Hexal; Zhejiang Hisun Pharmaceutical; Shanghai Citic Pacific Guojian Pharmaceutical; Samsung Bioepis; Shanghai Celgen Biopharmaceutical; LG Chem/Mochida; Viropro; Aryogen; AXXO; Amega; Pfizer; Hanwha; Lupin; Coherus Biosciences; Qilu Pharmaceutical | Biological therapeutic; Biosimilar product; Cell culture; Powder; Freeze drying; Immunoglobulin-G; Liquid; Protein fusion; Solution; Subcutaneous | EP-00417563; EP-00835939; WO-09013575; WO-09103553; WO-2014060551; WO-00036092; WO-2014102814; WO-2012165917; WO-2010099153; WO-2014064637; WO-2013059405 |
| Abatacept | Biological therapeutic; Powder; Freeze drying; Immunoglobulin-G; Infusion; Intravenous; Protein conjugated; Protein fusion; Solution; Subcutaneous | WO-09300431 |

TABLE 6-continued

Therapeutics adaptable for delivery via ingestible device for the treatment of rheumatoid arthritis

| Drug Name/Company | Existing Formulation Technologies, Methods of Administration | Exemplary Patent Literature |
|---|---|---|
| Adalimumab/Actavis/Amgen/ Daiichi Sankyo/Orion; Samsung Bioepis; Sandoz; Zydus Cadilla/Glenmark Pharmaceuticals; Fujifilm Kyowa Kirin Biologics/Mylan; Hetero; Reliance Life Sciences, AXXO; Boehringer Ingelheim; Zhejiang Hisun Pharmaceutical; Pfizer; Innovent Biologics; Fresenius; Shanghai Henlius Biotech; Bio-Thera Solutions; Celltrion; Momenta/Shire; LG Life Sciences | Biological therapeutic; Biosimilar product; Immunoglobulin-G; DNA technology; Monoclonal antibody human; Protein recombinant; Solution; Subcutaneous | US-07517963; US-20130122018; WO-09102078; WO-09729131; WO-2016019726; WO-2018119142; WO-2016000813; WO-2015007912; WO-2014207763; WO-2013021148; WO-2013186230; WO-2014099636; WO-2019024783; WO-2013181577; WO-2018169348 |
| Tocilizumab/Roche/Chugai; Bio-Thera Solutions | Biological therapeutic; Biosimilar; Monoclonal antibody humanized; Protein recombinant; Subcutaneous; Infusion; Intravenous; Solution | WO-00117542; WO-09219759; WO-2016103093 |
| Itolizumab | Biological therapeutic; Intravenous; Monoclonal antibody humanized; Subcutaneous | WO-09719111; WO-2009113083 |
| Infliximab/Pfizer/Sandoz; Samsung Bioepis/Merck & Co; Celltrion/Nippon Kayaku/Hospira/Orion/EGIS Gyogyszergyar; Bionovis/ Fiocruz/IVB; Aprogen/Nichi-Iko Pharm/Sanofi; Celltrion Healthcare; Amgen; Biomab Pharmaceuticals; Mabtech/Sorrento; Biocad; Genor | Biological therapeutic; Biosimilar product; Cell culture technique; Chimeric monoclonal antibody; Protein recombinant; Powder; Freeze drying; Immunoglobulin-G; Infusion; Intra-articular; Intravenous | US-07517963; US-20050255104; WO-09102078; WO-09216553; WO-03045400; WO-2006122187; WO-2006093397; WO-2009026122; WO-2011103700; WO-2017120614 |
| Sarilumab | Biological therapeutic; Monoclonal antibody human; Solution; Subcutaneous | WO-2007143168 |
| Rituximab/Celltrion/ Mundipharm/Teva/ Nippon Kayaku; Sandoz; Aryogen; Reliance Life Sciences, AXXO; Biocad; Hetero; Dr Reddy's/CFR Pharmaceuticals/Cinnagen; Intas Biopharmaceuticals; Shanghai Henlius; Mabion; Allergan/Amgen | Biological therapeutic; Biosimilar product; Chimeric monoclonal antibody; Immunoglobulin-G; Infusion; Intravenous; Protein recombinant; Subcutaneous | CN-101041907; WO-09411026; WO-08804936; CN-108676875; WO-2006093397; WO-00027428; WO-2009007993; WO-2013126813 |
| Golimumab/Johnson & Johnson | Biological therapeutic; Immunoglobulin-G; Monoclonal antibody human; Solution; Subcutaneous; Infusion; Intravenous | US-07691378; WO-00212502; WO-2018140121 |
| Canakinumab | Biological therapeutic; DNA technology; Powder; Freeze drying; Immunoglobulin-G; Infusion; Intra-articular; Liquid; Monoclonal antibody human; Protein recombinant; Subcutaneous | WO-00216436 |
| Opinercept | Biological therapeutic; Freeze drying; Protein fusion; Solution; Subcutaneous | |
| Trichuris suis ova, ovamed/Dr Falk/Fortress Biotech | Biological therapeutic; Cell therapy; Oral; Oral suspension | WO-09933479 |
| Anakinra/AXXO | Biological therapeutic; Follow on biologic; Intramuscular; Intravenous; Peptide; Protein recombinant; Subcutaneous | WO-08911540 |
| Interleukin-2/Changchun Institute of Biological Products; Changchun changsheng Gene Pharmaceutical; Guangdong Weilun Biological Products; Beijing SL Pharmaceutical; Shandong Quangang Pharmaceutical; Shenzhen Neptunus | Biological therapeutic; Follow on biologic; Injectable; Parenteral formulation unspecified; Protein recombinant; Subcutaneous; Freeze drying; Intratumoral; Intravenous | WO-2011106991 |
| Cartistem | Biological therapeutic; Mesenchymal stem cell therapy; Parenteral formulation unspecified | WO-2010131917 |
| Interferon gamma/Livzon Pharmaceutical Group; Shanghai Chemo Wanbang Biopharma | Biological therapeutic; Follow on biologic; Freeze drying; Intramuscular; Protein recombinant; Subcutaneous | CN-01799626 |
| Ka shu ning | Biological therapeutic; Intramuscular; Oligosaccharide; Solution | |

TABLE 6-continued

Therapeutics adaptable for delivery via ingestible device for the treatment of rheumatoid arthritis

| Drug Name/Company | Existing Formulation Technologies, Methods of Administration | Exemplary Patent Literature |
|---|---|---|
| VAY-736 | Biological therapeutic; Immunoglobulin-G; Infusion; Monoclonal antibody human; Subcutaneous | WO-2010007082 |
| Tadekinig alfa/AB2 Bio | Biological therapeutic; Protein recombinant; Subcutaneous | WO-2015032932 |
| Olokizumab | Biological therapeutic; Intravenous; Monoclonal antibody humanized; Subcutaneous | WO-2007066082 |
| Recombinant human CD22 monoclonal antibody, Lonn Ryonn Pharma/sinomab Bioscience | Biological therapeutic; Infusion; Intravenous; Monoclonal antibody | WO-2013188864 |
| RCT-18 | Biological therapeutic; Monoclonal antibody humanized; Protein fusion; Protein recombinant; Subcutaneous | |
| Ocaratuzumab | Biological therapeutic; Immunoglobulin-G; Infusion; Intravenous; Monoclonal antibody humanized; Protein recombinant | WO-2004103404 |
| Otilimab | Biological therapeutic; Immunoglobulin-G; Infusion; Intravenous; Monoclonal antibody human; Protein recombinant; Subcutaneous | WO-2006122797 |
| E-6011/EA Pharma | Biological therapeutic; Monoclonal antibody humanized; Subcutaneous | EP-03159007 |
| MPC-300-iv | Allogenic stem cell therapy; Biological therapeutic; Infusion; Intravenous; Mesenchymal stem cell therapy | WO-2012000064 |
| ASP-5094 | Biological therapeutic; Intravenous; Monoclonal antibody human; Systemic formulation unspecified | |
| Cibinetide/Araim | Biological therapeutic; Infusion; Intravenous; Peptide; Subcutaneous | WO-2007019545; WO-2009094172 |
| Pf-06687234 | Biological therapeutic; Intravenous; Protein fusion; Subcutaneous | WO-2009056268 |
| $^{99m}$Tc labelled annexin V-128/ Advanced Accelerator Applications | Imaging; Intravenous; Protein recombinant; Radiolabeling | WO-2018069409 |
| Cx-611 | Adipose stem cell therapy; Allogenic stem cell therapy; Biological therapeutic; Intravenous; Mesenchymal stem cell therapy | WO-2006037649 |
| CreaVax-RA | Autoantigen; Biological therapeutic; Cell therapy; Parenteral formulation unspecified; Subcutaneous | WO-2008102937 |
| AMG-592 | Biological therapeutic; Protein fusion; Protein recombinant; Subcutaneous | WO-2014153063 |
| Ozoralizumab | Biological therapeutic; Intravenous; Monoclonal antibody humanized; Subcutaneous | WO-2006122786; WO-2010077422 |
| NI-0101 | Biological therapeutic; Immunoglobulin-G; Infusion; Intravenous; Monoclonal antibody humanized | WO-2009101479 |
| PRTX-100 | Biological therapeutic; Infusion; Intravenous | WO-03086317 |
| Vobarilizumab/Ablynx | Biological therapeutic; Multivalent antibody; Subcutaneous | WO-2008020079 |
| BCD-089 | Biological therapeutic; Monoclonal antibody human; Subcutaneous | WO-2018034597 |
| Theralizumab | Biological therapeutic; Immunoglobulin-G; Infusion; Intravenous; Monoclonal antibody humanized | WO-09854225 |
| AT-132 | Biological therapeutic; Monoclonal antibody humanized; Subcutaneous | WO-2012116595 |
| Oralgam | Biological therapeutic; Immunoglobulin; Oral | WO-03028668 |
| INV-103 | Biological therapeutic; Intravenous; Protein recombinant; Subcutaneous | WO-2004041300 |
| Umbilical cord-derived mesenchymal stem cells/ Alliancells/Zhongyuan Union | Biological therapeutic; Intravenous Mesenchymal stem cell therapy | |

Therapeutics for IBD

In some embodiments, the therapeutic suitable for use with the devices and methods described herein is a therapeutic for treating inflammatory bowel disease (IBD). Exemplary therapeutics for treating TBD for delivery using any of the devices or methods described herein include those listed in Table 7.

TABLE 7

Therapeutics adaptable for delivery via ingestible device for the treatment of IBD

| Drug Name/Company | Existing Formulation Technologies and Methods of Administration | Exemplary Patent Literature |
|---|---|---|
| Certolizumab pegol | Biological therapeutic; Powder; Freeze drying; Monoclonal antibody humanized; PEGylated formulation; Protein conjugated; Protein recombinant; Solution; Subcutaneous | WO-00194585 |
| Ustekinumab | Biological therapeutic; Cell culture; Immunoglobulin-G; Infusion; Intravenous; Monoclonal antibody human; Subcutaneous | WO-00212500 |
| Adalimumab/Actavis/ Amgen/Daiichi Sankyo/ Orion; Samsung Bioepis; Sandoz; Fujifilm Kyowa Kirin Biologics/Mylan; CinnaGen; Reliance Life Sciences; Boehringer Ingelheim; Fresenius; Bio-Thera Solutions | Biological therapeutic; DNA technology; Biosimilar product; Immunoglobulin-G; Monoclonal antibody human; Protein recombinant; Solution; Subcutaneous | US-07517963; US-20130122018; WO-09102078; WO-09729131; WO-2016019726; WO-2018119142; WO-2016000813; WO-2015007912; WO-2013021148; WO-2013186230; WO-2014099636; WO-2019024783 |
| Vedolizumab | Biological therapeutic; Powder; Freeze drying; Immunoglobulin-G; Infusion; Intravenous; Monoclonal antibody humanized; Subcutaneous | WO-09806248 |
| Infliximab/Celltrion/Nippon Kayaku/Hospira/Orion/EGIS Gyogyszergyar; Pfizer/Sandoz; Bionovis/ Fiocruz/IVB Samsung Bioepis/Merck & Co; Aprogen/Nichi-Iko Pharm/ Sanofi; AXXO | Biological therapeutic; Cell culture technique; Biosimilar product; Protein recombinant; Chimeric monoclonal antibody; Powder; Freeze drying; Immunoglobulin-G; Infusion; Intra-articular; Intravenous | US-07517963; US-20050255104; WO-09102078; WO-09216553; WO-2006093397; WO-03045400; WO-2006122187 |
| Natalizumab | Biological therapeutic; Cell culture technique; Immunoglobulin-G; Infusion; Intravenous; Monoclonal antibody humanized; Solution; Subcutaneous | WO-09519790 |
| Guselkumab | Biological therapeutic; Intravenous; Monoclonal antibody human; Subcutaneous | WO-2007005955; WO-2007076524 |
| Golimumab | Biological therapeutic; Immunoglobulin-G; Monoclonal antibody human; Monthly dosing; Solution; Subcutaneous | US-07691378; WO-00212502 |
| Adipose-derived stem cell therapy (Celution System), Cytori | Adipose stem cell therapy; Aerosol formulation dermatological; Autologous stem cell therapy; Biological therapeutic; Dermatological; Infusion; Intravenous; Subcutaneous | US-07887795; WO-03053346 |
| Remestemcel-L | Allogenic stem cell therapy; Biological therapeutic; Haematopoietic stem cell therapy; Intravenous; Mesenchymal stem cell therapy | WO-09623058 |
| Anakinra | Biological therapeutic; Intramuscular; Intravenous; Peptide; Protein recombinant; Subcutaneous | WO-08911540 |
| *Clostridium butyricum*/ Qingdao Eastsea Pharmaceuticals | Biological therapeutic; Capsule; Oral | US-08092793 |
| *Bacillus Licheniformis*, Northeast Pharmaceutical Group Shenyang No.1 Pharmaceutical Co. | Biological therapeutic; Capsule; Oral | |
| Risankizumab | Biological therapeutic; Immunoglobulin-G; Infusion; Intravenous; Monoclonal antibody humanized; Subcutaneous | WO-2012061448 |
| Alicaforsen | Biological therapeutic; Oligonucleotide antisense; Rectal formulation; Rectal formulation local | WO-09405333 |
| Bimekizumab | Biological therapeutic; Immunoglobulin-G; Infusion; Intravenous; Monoclonal antibody humanized; Subcutaneous | WO-2008047134 |

TABLE 7-continued

Therapeutics adaptable for delivery via ingestible device for the treatment of IBD

| Drug Name/Company | Existing Formulation Technologies and Methods of Administration | Exemplary Patent Literature |
|---|---|---|
| Mirikizumab | Biological therapeutic; Humanized antibody; Immunoglobulin-G; Intravenous; Subcutaneous | WO-2014137962 |
| BI-655130 | Biological therapeutic; Immunoglobulin-G; Infusion; Intravenous; Monoclonal antibody humanized | WO-2013074569 |
| Brazikumab | Biological therapeutic; Infusion; Intravenous; Monoclonal antibody human; Subcutaneous | WO-2011056600 |
| SHP-647 | Biological therapeutic; Immunoglobulin-G; Intravenous; Monoclonal antibody human; Subcutaneous | WO-2019014572 |
| Cobitolimod | Biological therapeutic; Oligonucleotide; Rectal; Rectal formulation local | WO-09535032; WO-2010053430 |
| Umbilical cord blood-derived stem cell therapy, Kang Stem Biotech/Daewoong | Biological therapeutic; Parenteral formulation unspecified; Umbilical cord stem cell therapy | WO-2016048107 |
| Etrolizumab | Biological therapeutic; Immunoglobulin-G; Intravenous; Monoclonal antibody humanized; Protein recombinant; Subcutaneous | WO-2006026759 |
| BBT-401 | Biological therapeutic; Capsule; Oral; Peptide | |
| SER-287 | Bacterium novel; Biological therapeutic; Capsule; Cell therapy; Oral | WO-2017008026 |
| KHK-4083 | Biological therapeutic; Intravenous; Monoclonal antibody human; Subcutaneous | WO-2007062245 |
| AbGn-168H | Biological therapeutic; Infusion; Intravenous; Monoclonal antibody humanized | EP-01663290; WO-03013603 |
| RG-7880 | Biological therapeutic; Immunoglobulin; Infusion; Intravenous; Protein fusion; Protein recombinant; Subcutaneous | WO-2005009238 |
| SB-012 | Biological therapeutic; DNA technology; Oligonucleotide antisense; Rectal formulation; Rectal formulation local | |
| Olamkicept | Biological therapeutic; Intravenous; Protein fusion | WO-2007071449 |
| Bertilimumab | Biological therapeutic; Immunoglobulin-G; Infusion; Intravenous; Monoclonal antibody human; Parenteral formulation unspecified; Subcutaneous | WO-00166754 |
| PF-06480605 | Biological therapeutic; Intravenous; Subcutaneous | |
| PF-06687234 | Antibody fragment; Biological therapeutic; Intravenous; Protein fusion; Subcutaneous | WO-2009056268 |
| IBP-9414 | Biological therapeutic; Natural product; Oral | WO-2016113363 |
| Molgramostim + fosfomycin + carbapenem)/Reponex | Antibiotic; Biological therapeutic; Capsule; Follow on biological product; Local formulation unspecified; Oral; Peptide; Protein recombinant; Rectal formulation; Rectal formulation local | |
| STNM-01 | Biological therapeutic; Injectable; Local formulation unspecified; Oligonucleotide; Parenteral formulation unspecified; Transmucosal | WO-2008020489 |
| Adrenomedullin/University of Miyazaki | Biological therapeutic; Intravenous; Parenteral formulation unspecified; Peptide | |
| Tulinercept | Antibody fragment; Biological therapeutic; Immunoglobulin-G; Oral; Protein fusion | WO-2014136113 |
| E-6011, EA Pharma | Biological therapeutic; Intravenous; Monoclonal antibody | EP-03211007 |
| STP-206 | Biological therapeutic; Natural product; Parenteral formulation unspecified | WO-2005032567 |
| FFP-104 | Biological therapeutic; Monoclonal antibody; Parenteral formulation unspecified | WO-09858678 |
| Ciclosporin/Sublimity Therapeutics/Dr Falk Pharma | Biological therapeutic; Capsule; Oral controlled release; Oral; Peptide | WO-2004084870 |
| AEVI-002 | Biological therapeutic; Monoclonal antibody human; Parenteral formulation unspecified; Subcutaneous | WO-2013148350 |

TABLE 7-continued

Therapeutics adaptable for delivery via ingestible device for the treatment of IBD

| Drug Name/Company | Existing Formulation Technologies and Methods of Administration | Exemplary Patent Literature |
|---|---|---|
| Midismase | Biological therapeutic; Controlled release; Infusion; Intravenous; Protein conjugated | EP-00406804 |
| V-565 | Antibody; Biological therapeutic; Oral; Protein recombinant; Tablet | WO-2016156465; WO-2016156468; WO-2016156474; WO-2016156475 |

Therapeutics for Hemophilia

In some embodiments, the therapeutic suitable for use with the devices and methods described herein is a therapeutic for treating hemophilia. In some embodiments, the hemophilia is hemophilia A, hemophilia B, or Von Willebrand disease.

In some embodiments, the therapeutic for treating hemophilia is an alternative coagulation promotor (ACP). In some embodiments, the ACP is an anti-tissue factor pathway inhibitor (anti-TFPI). Exemplary anti-TFPIs include, but are not limited to, concizumab, MG-1113A (GC Pharma, Gyeonggi-do, South Korea), marstacimab (PF-6741086) or BAY-1093884; or biosimilars thereof. In some embodiments, the anti-TFPI is concizumab or a biosimilar thereof.

In some embodiments, the therapeutic for treating hemophilia is a factor VIII mimetic. In some embodiments, the factor VIII mimetic is emicizumab or a biosimilar thereof.

In some embodiments, the therapeutic for treating hemophilia is selected from albutrepenonacog alfa, AMT-061, beroctocog alpha, betafact, BIVV-001, BS027125, byclot, catridecacog, clotnine, dalcinonacog alfa, damoctocog alfa pegol, DTX-201, eftrenonacog alfa, eptacog alfa, Factor VIII, Factor IX, Factor X, fidanacogene elaparvovec, fitusiran, FLT-180a, hemoleven, lonoctocog alfa, LR-769, marzeptacog alfa, monofix, moroctocog alfa, NIBX-2101, nonacog alfa, nonacog beta pegol, octocog alfa, OPK-88005, recolyl, recombinate, rurioctocog alfa pegol, simoctocog alfa, SiuP-654, S-525, SPK-8011, SPK-8016, SCT-800, AAV2/8-HILP-FVIIJ-v3, susoctocog alfa, trenonacog alfa and valoctocogene roxaparvovec; and biosimilars thereof.

In some embodiments, the therapeutic for treating hemophilia is a recombinant factor VIIa. Exemplary recombinant factor VIJa include OPK-88005 (OPKO Health, Miami, Fla.) and LR-769 (see, e.g., Chevreux et al., Haemophilia 23(4):e324-e334 (2017)). Additional exemplary therapeutics for treating hemophilia for delivery using any of the devices or methods described herein include those listed in Table 8.

TABLE 8

Therapeutics adaptable for delivery via ingestible device for the treatment of hemophilia

| Drug Name/Class/Company | Existing Formulation Technologies and Methods of Administration | Exemplary Patent Literature |
|---|---|---|
| Damoctocog alfa pegol | Biological therapeutic; Infusion; Intravenous; PEGylated formulation; Protein recombinant; Sustained release | WO-2010083536 |
| Efmoroctocog alfa | Antibody fragment; Biological therapeutic; Cell culture technique; Powder; Freeze drying; Immunoglobulin-G; Injectable controlled release; Protein fusion; Protein recombinant | WO-2011069164 |
| Octocog alfa/Bayer; Baxalta; Genentech/ Bayer/Aventis | Biological therapeutic; Plasma-free, sucrose-formulated; Intravenous; Peptide; Protein recombinant; Powder; Freeze drying; Glycoprotein; Infusion | EP-00160457; EP-00818204; EP-00152746; EP-00160457; EP-00818204 |
| Rurioctocog alfa pegol | Biological therapeutic; Formulation powder; Freeze drying; Intravenous; PEGylated formulation; Protein recombinant; Sustained release | US-07884075; WO-2004075923; WO-2006071801 |
| Albutrepenonacog alfa | Biological therapeutic; Infusion; Intravenous; Protein fusion; Protein recombinant; Sustained release | WO-00177137; WO-2007144173 |
| Lonoctocog alfa | Biological therapeutic; Infusion; Parenteral formulation unspecified; Protein recombinant | WO-2004067566 |
| Trenonacog alfa | Biological therapeutic; Freeze drying; Infusion; Intravenous; Protein recombinant | WO-2009082648 |
| Nonacog gamma | Biological therapeutic; Cloning technology; Powder; Freeze drying; Infusion; Intravenous; Protein recombinant; Solution | WO-2011135071 |

TABLE 8-continued

Therapeutics adaptable for delivery via ingestible device for the treatment of hemophilia

| Drug Name/Class/Company | Existing Formulation Technologies and Methods of Administration | Exemplary Patent Literature |
|---|---|---|
| Turoctocog alfa/Novo Nordisk | Biological therapeutic; Powder; Freeze drying; Intravenous; PEGylated; Sustained release; Protein recombinant | WO-2007055789; WO-2009108806 |
| Von Willebrand/Factor VIII therapy/Alpha Therapeutic | Biological therapeutic; Intravenous; Peptide | EP-00144709 |
| Emicizumab | Biological therapeutic; Immunoglobulin-G; Monoclonal antibody humanized; Multivalent monoclonal antibody; Protein recombinant; Subcutaneous | WO-2005035753; WO-2012067176 |
| Nonacog alfa/IBC Generium/CJSC Generium/Stragen | Biological therapeutic; Biosimilar product; Powder; Freeze drying; Infusion; Intravenous; Peptide; Protein recombinant | EP-00430930 |
| Nonacog beta pegol | Biological therapeutic; Powder; Freeze drying; Glycoprotein; Infusion; Intravenous; PEGylated formulation; Protein recombinant; Sustained release | WO-03031464; WO-03045980; WO-03046150; WO-2004099231; WO-2006127896; WO-2008060780 |
| Eptacog alfa (activated)/ Aryogen; IBC Generium/CJSC Generium/Stragen; Revo Biologics/LFB | Biological therapeutic; Biosimilar product; Powder; Freeze drying; Intravenous; Protein recombinant; Solution; Transgenic animal | EP-00200421; WO-2008155509; |
| Factor VIII concentrate (albumin-free), CSL | Biological therapeutic; Blood constituents; Infusion; Intravenous | |
| Simoctocog alfa | Biological therapeutic; Infusion; Intravenous; Protein recombinant | WO-00170968 |
| Eftrenonacog alfa | Antibody fragment; Biological therapeutic; Powder; Freeze drying; Immunoglobulin-G; Injectable controlled release; Intravenous; Protein fusion | WO-2004101740; WO-2007112005 |
| Susoctocog alfa | Biological therapeutic; Formulation powder; Freeze drying; Infusion; Intravenous; Protein recombinant | WO-09749725 |
| Factor VIII follow-on biologic, AXXO | Biological therapeutic; Follow on biological product; Intravenous; Protein recombinant | |
| Moroctocog alfa | Biological therapeutic; Injectable; Parenteral formulation unspecified; Protein recombinant | WO-08606101 |
| Factor VIII (plasma-derived)/Octapharma/Shire | Biological therapeutic; Intravenous; Peptide; Blood constituents; Freeze drying; Infusion | WO-09110439; US-03631018 |
| Factor XIII concentrate, CSL | Biological therapeutic; Intravenous; Peptide | WO-2005079839 |
| Monofix | Biological therapeutic; Intravenous; Peptide | EP-00118256 |
| Hemoleven | Biological therapeutic; Blood constituents; Parenteral formulation unspecified; Peptide; Systemic formulation unspecified | |
| Catridecacog | Biological therapeutic; Formulation powder; Freeze drying; Intravenous; Protein recombinant | EP-00268772 |
| Byclot | Biological therapeutic; Drug combination; Freeze drying; Intravenous; Peptide | JP-04046377 |
| Factor VIII/von Willebrand Factor complex, CSL | Biological therapeutic; Infusion; Intravenous; Peptide | WO-2008151817 |
| Recombinant moroctocog alfa (plasma/albumin-free), Wyeth | Biological therapeutic; Powder; Freeze drying; Glycoprotein; Infusion; Intravenous; Protein recombinant | WO-08606101 |
| Beroctocog alpha (albumin-five)/GC Pharma | Biological therapeutic; Infusion; Intravenous; Protein recombinant | EP-01712223 |
| Moroctocog alfa biosimilar, IBC Generium/CJSC Generium/Stragen | Biological therapeutic; Biosimilar product; Intravenous; Protein recombinant | |
| Beroctocog alfa | Biological therapeutic; Infusion; Intravenous; Protein recombinant | KR-00251286 |
| Factor VIII concentracte, Kedrion Biopharma | Blood constituents; Infusion; Intravenous; Small molecule therapeutic | |
| Factor XI concentrate, CSL Behring | Blood constituents; Parenteral formulation unspecified; Small molecule therapeutic; Systemic formulation unspecified | |

TABLE 8-continued

Therapeutics adaptable for delivery via ingestible device for the treatment of hemophilia

| Drug Name/Class/Company | Existing Formulation Technologies and Methods of Administration | Exemplary Patent Literature |
|---|---|---|
| Factor VIII/ Tonrol Biopharmaceutical; Nordisk | Biological therapeutic; Blood constituents; Novo Intravenous; Peptide | WO-08403628 |
| Recombinate | Biological therapeutic; Powder; Freeze drying; Glycoprotein; Intravenous; Protein recombinant | WO-08501961 |
| Factor XP/Behring | Biological therapeutic; Freeze drying; Intravenous; Peptide | |
| Human coagulation factor VIII, Hemarus | Biological therapeutic; Blood constituents; Intravenous; Protein recombinant | WO-2015114664 |
| Clotnine | Biological therapeutic; Blood constituents; Intravenous; Protein recombinant | WO-2015114664 |
| Betafact | Biological therapeutic; Peptide; Systemic formulation unspecified | EP-00317376 |
| Factor VIII follow-on biologic, Shandong Taibang Biological Products | Biological therapeutic; Follow on biological product; Parenteral formulation unspecified; Protein recombinant | CN-102295696 |
| Moroctocog alfa follow-on biologic, Amega | Biological therapeutic; Follow on biological product; Parenteral formulation unspecified; Protein recombinant | |
| Plasma derived factor VIII (pegylated liposomal (neclip), Recoly | Biological therapeutic; Liposome; PEGylated formulation; Protein conjugated | WO-09955306 |
| Human prothrombin complex concentrate (plasma-derived), Nanyue Biopharming; Shanxi Kangbao Biological Products | Biological therapeutic; Blood constituents; Infusion; Intravenous; Peptide | |
| Factor IX, Shandong Taibang Biological Products | Biological therapeutic; Intravenous; Peptide | |
| Factor VIII biosimilar, Shanxi Kangbao Biological Products | Biological therapeutic; Biosimilar product; Intravenous | |
| Factor VIII (plasma-derived), Beijing Tiantan Biological Products | Biological therapeutic; Blood constituents; Parenteral formulation unspecified | |
| FLT-180a | Biological therapeutic; Infusion; Virus recombinant | |
| SPK-8011 | Biological therapeutic; Infusion; Intravenous; Nanoparticle formulation injectable; Virus recombinant | WO-2018017956 |
| Fitusiran | Biological therapeutic; Oligonucleotide; Subcutaneous | WO-2004015107 |
| Valoctocogene roxaparvovec | Biological therapeutic; Infusion; Intravenous; Virus recombinant | WO-2013186563 |
| AMT-061 | Biological therapeutic; Infusion; Intravenous; Virus recombinant | WO-2009014445 |
| Fidanacogene elaparvovec | Biological therapeutic; Infusion; Intravenous; Virus recombinant | WO-02063025; WO-08400560; WO-09841240 |
| Plasma-derived Factor VIII, CSL/Zhong Yuan Rui De Biological Products | Biological therapeutic; Blood constituents; Parenteral formulation unspecified | |
| SCT-800 | Biological therapeutic; Intravenous; Protein recombinant | |
| Moroctocog alfa/Chia Tai Tianqing Pharmaceutical Group | Biological therapeutic; Biosimilar product; Intravenous; Peptide; Protein recombinant | |
| Factor IX/Sichuan Yuanda Shuyang Pharmaceutical | Biological therapeutic; Powder; Infusion; Intravenous; Peptide | |
| Factor VIII/Guangdong Danxia Biopharm | Biological therapeutic; Biosimilar product; Blood constituents; Intravenous | |
| Dalcinonacog alfa/Catalyst Biosciences | Biological therapeutic; Intravenous; Protein recombinant; Subcutaneous | WO-2012061654 |
| Marzeptacog alfa (activated) | Biological therapeutic; Infusion; Intravenous; Protein recombinant; Subcutaneous; Sustained release | WO-2008127702; WO-2009126307 |

TABLE 8-continued

Therapeutics adaptable for delivery via ingestible device for the treatment of hemophilia

| Drug Name/Class/Company | Existing Formulation Technologies and Methods of Administration | Exemplary Patent Literature |
|---|---|---|
| DTX-201 | Biological therapeutic; Infusion; Intravenous; Virus recombinant | |
| Factor IX gene therapy, Sangamo | Biological therapeutic; Intravenous; Virus recombinant | WO-2010021692; WO-2012051343 |
| BIVV-001 | Biological therapeutic; Intravenous; Protein fusion; Protein recombinant; Subcutaneous | WO-2013122617 |
| SHP-654 | Biological therapeutic; Infusion; Intravenous; Nanoparticle formulation injectable; Protein recombinant; Virus recombinant | WO-2018128688; WO-2018128689 |
| Marstacimab | Biological therapeutic; Immunoglobulin-G; Infusion; Intravenous; Monoclonal antibody humanized; Subcutaneous | WO-2017029583 |
| SPK-8016 | Biological therapeutic; Infusion; Intravenous; Virus recombinant | |
| BAY-1093884 | Biological therapeutic; Immunoglobulin-G; Intravenous; Monoclonal antibody human; Subcutaneous | |
| AAV2/8-HLP-FVIII-v3 | Biological therapeutic; Infusion; Intravenous; Virus recombinant | |
| SB-525 | Biological therapeutic; Gene transfer system non-viral; Infusion; Intravenous; Virus recombinant | WO-2015089046 |
| Concizumab | Biological therapeutic; Immunoglobulin-G; Monoclonal antibody humanized; Subcutaneous | WO-2010072691 |
| Factor VIIa-CTP | Biological therapeutic; Intravenous; Protein fusion; Subcutaneous; Sustained release | WO-2011004361; WO-2013121416 |

Therapeutics for Hepatocellular Carcinoma

In some embodiments, the therapeutic suitable for use with the devices and methods described herein is a hepatocellular carcinoma drug. Hepatocellular carcinoma is the most common type of primary liver cancer and the most common cause of death in people with cirrhosis. Drugs to treat hepatocellular carcinoma include but are not limited to nivolumab, lenvatinib, sorafenib, regorafenib and carbozantinib.

Target-Based Therapeutics

GLP-1 Receptor Agonists

In some embodiments, the therapeutic suitable for use with the devices and methods described herein is a glucagon-like peptide 1 (GLP-1) receptor agonist. The GLP-1 pathway has been indicated in the treatment of type 2 diabetes mellitus (T2DM). In some embodiments, the GLP-1 receptor agonist is a peptide. In some embodiments, the GLP-1 receptor agonist is a small molecule. In some embodiments, the GLP-1 receptor agonist is formulated with a carrier, or delivery agent. In some embodiments, the carrier or delivery agent is a salt of a medium chain fatty acid derivative. In some embodiments, the carrier or delivery agent is the sodium salt of N-[8-(2-hydroxybenzoyl)amino] caprylate (SNAC). In some embodiments, the carrier or delivery agent is biotin.

In some embodiments, the GLP-1 receptor agonist is exanatide (synthetic exendin-4), a 39-residue peptide which shares 53% sequence identity with GLP-1, having the sequence:

HGEGTFTSDLSKQMEEEAVRLFIEW-LKNGGPSSGAPPPS-NH$_2$ (SEQ ID NO:1).

In some embodiments, the GLP-1 receptor agonist is a compound with a structure selected from:

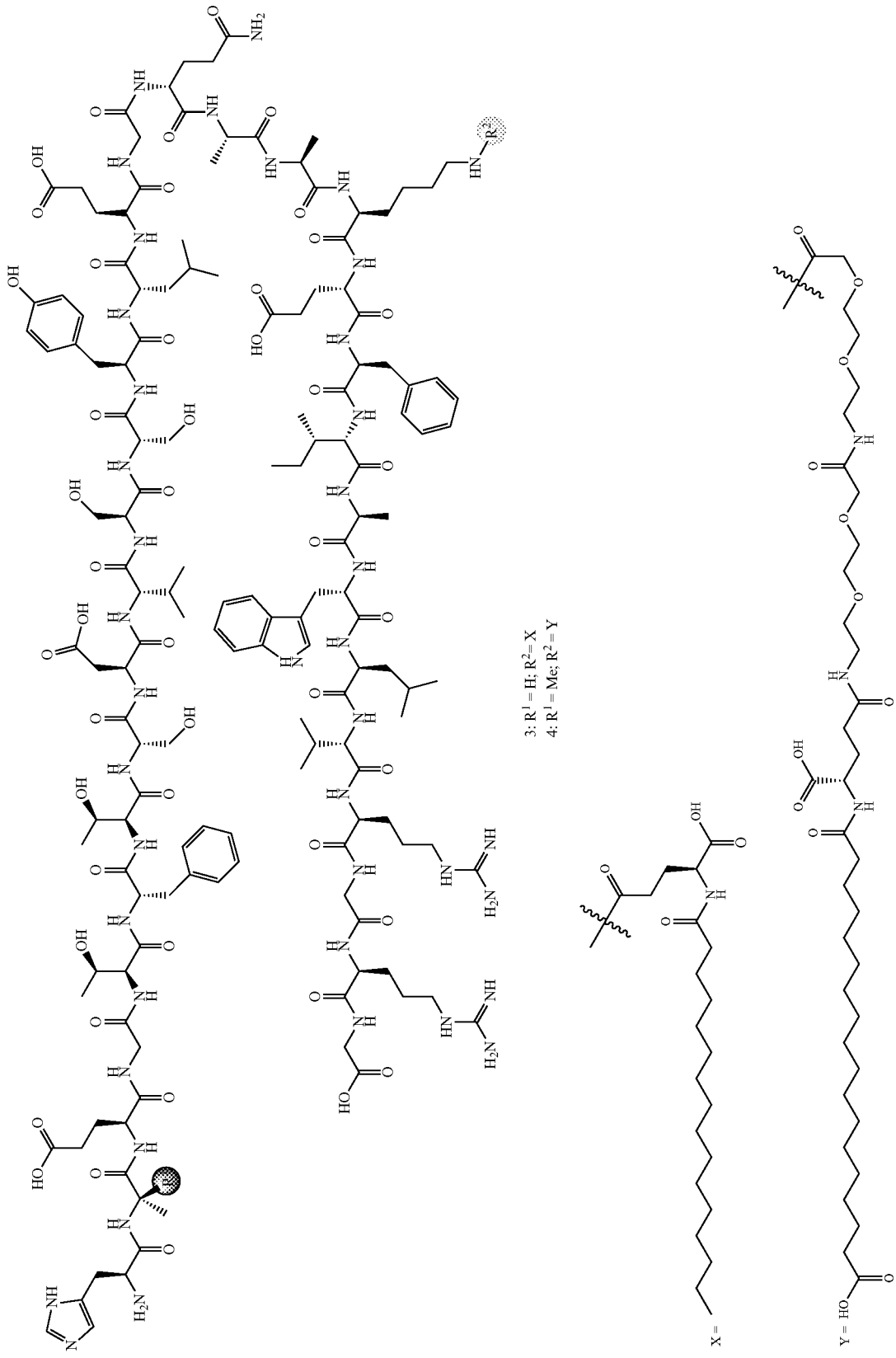

or any pharmaceutically acceptable salt thereof. In some embodiments, the GLP-1 receptor agonist is liraglutide (compound 3) or a pharmaceutically acceptable salt thereof. In some embodiments, the GLP-1 receptor agonist is semaglutide (compound 4) or a pharmaceutically acceptable salt thereof.

In some embodiments, the GLP-1 receptor agonist is a compound having the structure:

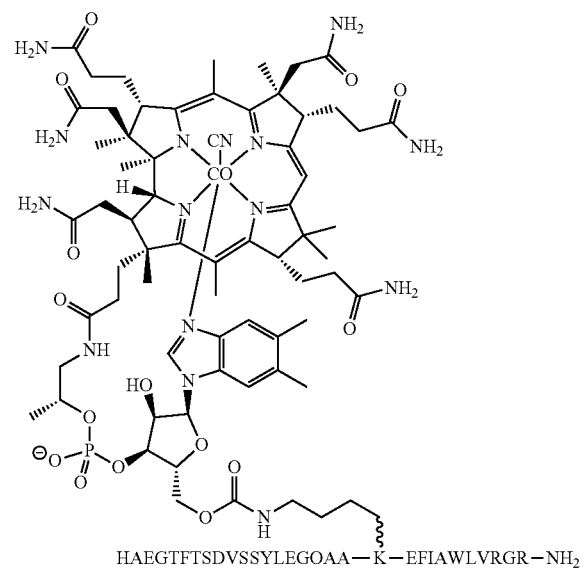

HAEGTFTSDVSSYLEGOAA—K—EFIAWLVRGR—NH$_2$ or a pharmaceutically acceptable salt thereof.

In some embodiments, the GLP-1 receptor agonist is an 11-mer GLP-1 receptor agonist. Exemplary 11-mer GLP-1 receptor agonists are represented by the structures and the table below.

| Cpd | R$^1$ | R$^2$ | R$^3$ | R$^4$ | R$^5$ | R$^6$ | hGLP-1R cAMP EC$_{50}$ (nM) |
|---|---|---|---|---|---|---|---|
| 8 | H | Me | H | Bn | BIP | BIP | 545 |
| 9 | H | Me | H | Bn | BIP(2'-Et,4'-OMe) | BIP(2'-Me) | 7.0 |
| 10 | Me | Me | Me | 2-F—Bn | BIP(2'-Et,4'-OMe) | BIP(2'-Me) | 0.087 |

In some embodiments, the GLP-1 receptor agonist is a compound having the structure:

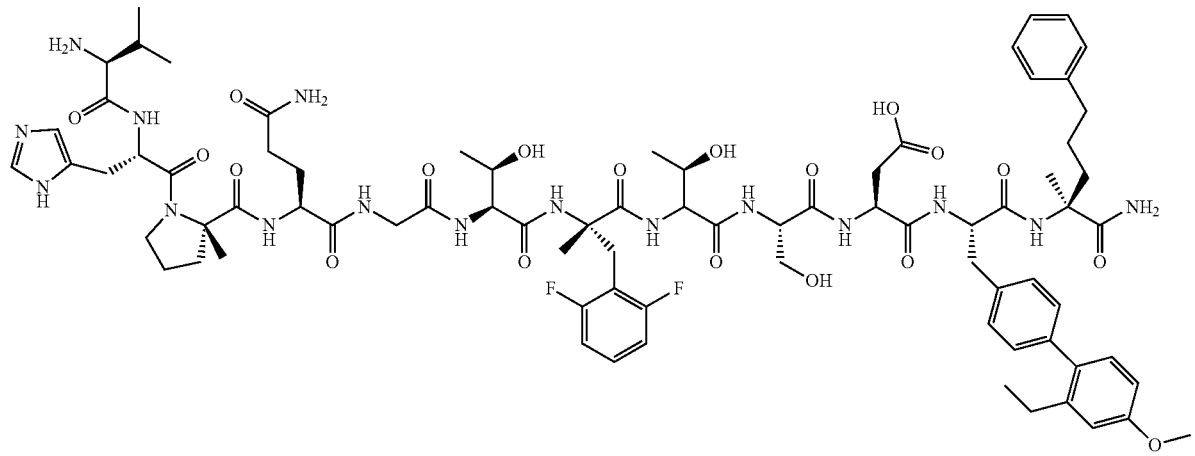 [SMILES: CCc1cc(OC)ccc1-c1ccc(C[C@H](NC(=O)[C@H](CC(=O)O)NC(=O)[C@H](CO)NC(=O)C(NC(=O)[C@](C)(Cc2c(F)cccc2F)NC(=O)[C@@H](NC(=O)CNC(=O)[C@H](CCC(N)=O)NC(=O)[C@]2(C)CCCN2C(=O)[C@H](Cc2cnc[nH]2)NC(=O)[C@@H](N)C(C)C)[C@@H](C)O)[C@@H](C)O)C(=O)N[C@@](C)(CCCc2ccccc2)C(N)=O)cc1]

or a pharmaceutically acceptable salt thereof.

In some embodiments, the GLP-1 receptor agonist is a compound with a structure selected from:

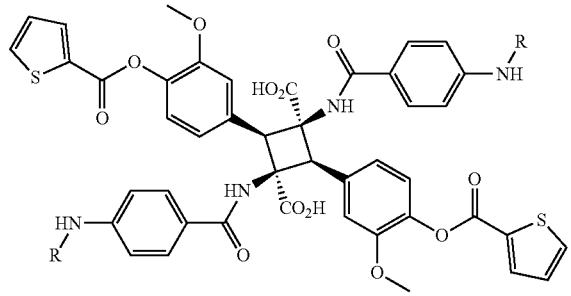

12: R = Boc
14: R = C(O)i-Pr

-continued

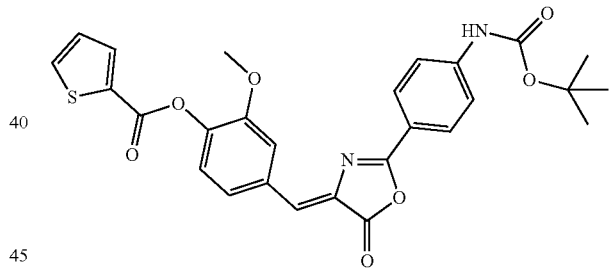

13 or a pharmaceutically acceptable salt thereof. In some embodiments, the GLP-1 receptor agonist is Boc5 (compound 12) or a pharmaceutically acceptable salt thereof.

In some embodiments, the GLP-1 receptor agonist is a compound with a structure selected from:

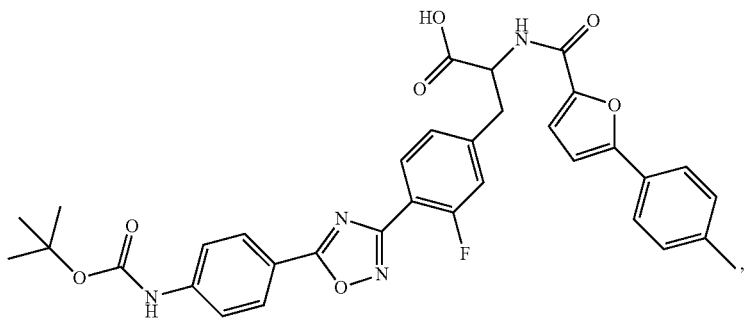

-continued

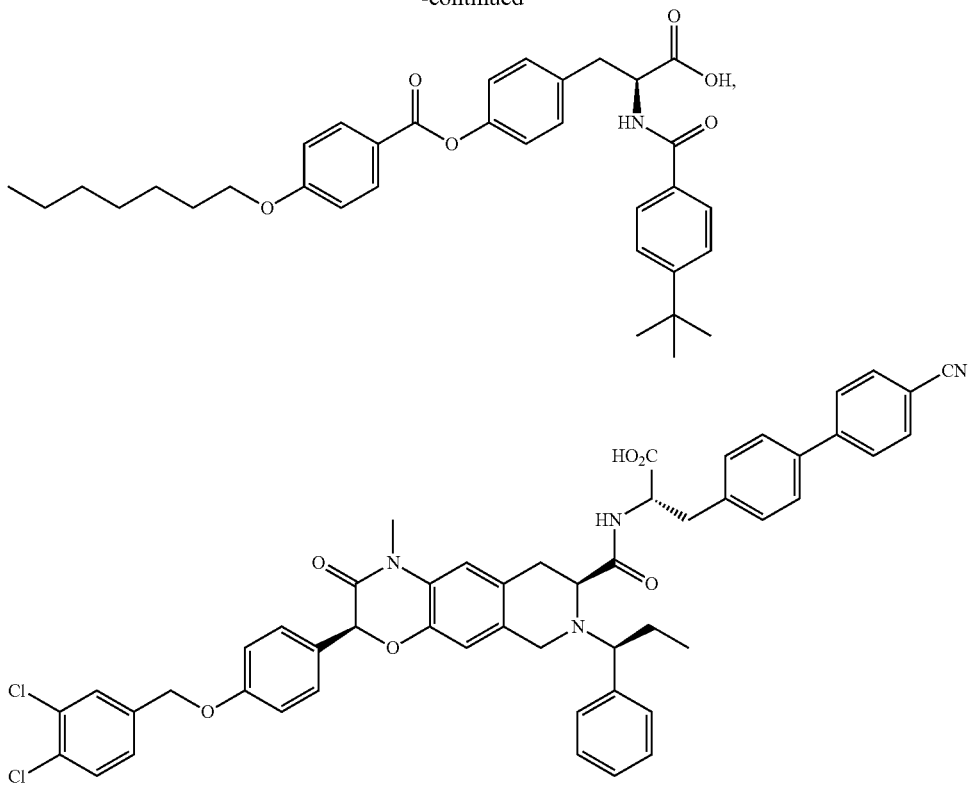

or pharmaceutically acceptable salts thereof. In some embodiments, the GLP-1 receptor agonist is TTP-054 or a pharmaceutically acceptable salt thereof, such as described in Edmonds et al., Annu. Rep. Med. Chem. (2013) 48:119-130, which is herein incorporated by reference in its entirety.

In some embodiments, the GLP-1 receptor agonist is OWL883, such as described in Kawai et al., Diabetes (2018) 67(Supplement 1):1118-P, which is herein incorporated by reference in its entirety.

In some embodiments, the GLP-1 receptor agonist is a compound described in Edmonds and Price, "Chapter Nine: Oral GLP-1 Modulators for the Treatment of Diabetes," Ann. Rep. Med. Chem. (2013) 48:119-130, which is herein incorporated by reference in its entirety.

Other exemplary GLP-1 receptor agonists for delivery using any of the devices or methods described herein include those listed in Table 9.

TABLE 9

GLP-1 receptor agonists adaptable for delivery via ingestible device for the treatment of the listed diseases and conditions

| GLP-1 Agonist (Company) | Tradename | Dosage and Administration | Comments |
|---|---|---|---|
| Albiglutide (GSK) | Tanzeum EU: Eperzan | 30 mg/dose (0.82 μmol); up to 50 mg/dose; Once weekly, subcutaneus injection | GLP-1 (7-36) dimer fused to recombinant human albumin. MWt~73 kDa. |
| Dulaglutide (Eli Lilly) | Trulicity | 0.75 mg/dose (0.024 μmol); up to 1.5 mg/dose; Once weekly, subcutaneus injection | GLP-1(7-37) covalently linked to an Fc fragment of human IgG4. MWt~63 kDa |
| Exenatide (Astra Zeneca) | Byetta | 5 μg/dose (1.2 nmol); up to 10 μg/dose; Twice daily, subcutaneus injection | Synthetic form of exendin-4, a peptide isolated from *H. suspectum* venom. MWt~4 KDa |
|  | Bydureon, Bydureon Bcise | 2 mg/dose (0.48 μmole), Once weekly, subcutaneus injection | Extended release microsphere formulations. |
| Liraglutide (Novo Nordisk) | Victoza | 0.6 mg/dose (0.16 μmol; up to 1.8 mg/dose; Once daily, subcutaneus injection | Fatty acylated GLP-1 analog. MWt~4 KDa. |
|  | Saxenda | 0.6 mg/dose (0.16 μmol; up to 3 mg/dose; Once daily, subcutaneus injection | |

TABLE 9-continued

GLP-1 receptor agonists adaptable for delivery via ingestible device for the treatment of the listed diseases and conditions

| GLP-1 Agonist (Company) | Tradename | Dosage and Administration | Comments |
|---|---|---|---|
| Lixisenatide (Sanofi-Aventis) | Adlyxin EU: Lyxumia | 10 µg/dose (2.06 nmol); up to 20 µg/dose; Once daily, subcutaneus injection | Recombinant DNA-produced GLP-1 analog. MWt~5 KDa. |
| Semaglutide (Novo Nordisk) | Ozempic | 0.25 mg/dose (0.061 µmol; up to 1 mg/dose; Once weekly, subcutaneus injection | GLP-1-like peptide-1 analog. MWt~4 KDa. Longer acting alternative to liraglutide. |

PCSK9 Inhibitors

In some embodiments, the therapeutic suitable for use with the devices and methods described herein is a proprotein convertase subtilisin/kexin type 9 (PCSK9) inhibitor. In some embodiments, the PCSK9 inhibitor treats one or more of endocrine and/or metabolic diseases or conditions, cardiovascular diseases, and infection. In some embodiments, the endocrine and/or metabolic disease or condition is familial hypercholesterolemia, hypercholesterolemia, or hyperlipidemia.

In some embodiments, the PCSK9 inhibitor is alirocumab. In some embodiments, the PCSK9 inhibitor is evolocumab. Other exemplary PCSK9 inhibitors for delivery using any of the devices or methods described herein include those listed in Table 10.

TABLE 10

PCSK9 inhibitors adaptable for delivery via ingestible device for the treatment of the listed diseases and conditions

| Drug Name | Existing Formulation Technologies and Methods of Administration | Therapy Area | Active Indications | Exemplary Patent Literature & Other |
|---|---|---|---|---|
| alirocumab | Biological therapeutic; Cell culture technique; Immunoglobuin-G; Monoclonal antibody human; Solution; Subcutaneous formulation | Endocrine/Metabolic; Cardiovascular; Infection | Atherosclerosis; Familial hypercholesterolemia; Hypercholesterolemia; Lipid metabolism disorder; Sepsis; Septic shock | WO2010077854 Tavori, Hagai, Michelle Melone, and Shirya Rashid. "Alicrocumab: PCSK9 inhibitor for LDL cholesterol reduction." Expert review of cardiovascular therapy 12.10 (2014): 1137-1144. |
| evolocumab | Biological therapeutic; Cell culture technique; Immunoglobuin-G; Monoclonal antibody human; Solution; Subcutaneous formulation | Endocrine/Metabolic | Familial hypercholesterolemia; Hypercholesterolemia; Hyperlipidemia; Lipid metabolism disorder | WO2009026558 Kasichayanula, Sreenerranj. et al. "Clinical pharmacokinetics and pharmacodynamics of evolocumab, a PCSK9 inhibitor." Clinical pharmacokinetics 57.7 (2018): 769-779. |
| bococizumab | Biological therapeutic; Humanized monoclonal antibody | Endocrine/Metabolic | Hypercholesterolemia; Hyperlipidemia | Ridker, Paul M. et al. "Cardiovascular efficacy and safety of bococizumab in high-risk patients." New England Journal of Medicine 376.16 (2017); 1527-1539. |

TABLE 10-continued

PCSK9 inhibitors adaptable for delivery via ingestible device for the treatment of the listed diseases and conditions

| Drug Name | Existing Formulation Technologies and Methods of Administration | Therapy Area | Active Indications | Exemplary Patent Literature & Other |
|---|---|---|---|---|
| frovocimab | Biological therapeutic; humanized immunoglobulin G4 (IgG4) monoclonal antibody | Endocrine/Metabolic | Hypercholesterolemia; Hyperlipidemia | Kastelein, John JP, et al. "Safety and efficacy of LY3015014, a monoclonal antibody to proprotein convertase subtilisin/kexin type 9 (PCSK9): a randomized, placebo-controlled Phase 2 study." European heart journal 37.17 (2016): 1360-1369 |
| 1D05-IgG2 | Biological therpeutic; fully humanized monoclonal antibody | Endocrine/Metabolic | Hypercholesterolemia; Hyperlipidemia | Ni, Yan G., et al. "A PCSK9-binding antibody that structurally mimics the EGF (A) domain of LDL-receptor reduces LDL cholesterol in vivo." Journal of lipid reserach 52.1 (2011): 78-86 |
| evinacumab | Biological therpeutic; a fully human monoclonal antibody to ANGPTL3 | Endocrine/Metabolic | Hypercholesterolemia; Hyperlipidemia | US9018356 Gaudet, Daniel, et al. "Safety and efficacy of evinacumab, a monoclonal antibody to ANGPTL3, in patients with homozygous familial hypercholesterolemia; A single-arm, open-label, proof-of-concept study." Atherosclerosis 263 (2017): e9. |
| Lodelcizumab | Biological therapeutic; monoclonal antibody | Endocrine/Metabolic; Cardiovascular; Infection | Hypercholesterolemia; Lipid metabolism disorder; Sepsis; Septic shock | WO2011072263 |
| SHR-1209 | Antibody; Biological therapeutic; freeze drying; Subcutaneous formulation | Endocrine/Metabolic | Hypercholesterolemia; Hyperlipidemia | WO2017114230 |
| IBI-306 | Biological therapeutic; Intravenous formulation; Monoclonal antibody human; Protein recombinant; Subcutaneous formulation | Endocrine/Metabolic | Hypercholesterolemia; Hyperlipidemia | WO2018113781 |

TABLE 10-continued

PCSK9 inhibitors adaptable for delivery via ingestible device for the treatment of the listed diseases and conditions

| Drug Name | Existing Formulation Technologies and Methods of Administration | Therapy Area | Active Indications | Exemplary Patent Literature & Other |
|---|---|---|---|---|
| LIB-003 | Biological therapeutic; Infusion; Intravenious formulation; Protein fusion; Proten recombinant; Subcutaneous formulation | Endocrine/Metabolic | Familial hypercholesterolemia; Hypercholesterolemia | WO201130354 |
| JS-002 | Biological therapeutic; Infusion; Intravenous formulation; Monoclonal antibody humanized; Protein recombinant; Subcutaneous formulation | Endocrine/Metabolic | Hypercholesterolemia; Lipid metabolism disorder | WO2017088782 |
| AK-102 | Biological therapeutic; Humanized antibody; Subcutaneous formulation | Endocrine/Metabolic | Familial hypercholesterolemia | WO206127912 |
| ATH-06 | Biological therapeutic; Peptide; Subcutaneous formulation | Cardiovascular; Endocrine/Metabolic | Hypercholesterolemia | WO2015128287 |
| ATH-04 | Biological therapeutic; Peptide; Subcutaneous formulation | Cardiovascular; Endocrine/Metabolic | Hypercholesterolemia | WO2015128287 |
| C-8304 | Oral formulation; Small molecule therapeutic; Tablet formulation | Endocrine/Metabolic | Hyperlipidemia | WO2010075469 |

TNFα Inhibitors

In some embodiments, the therapeutic suitable for use with the devices and methods described herein is a TNFα inhibitor. The terms "TNFα inhibitor" or "TNF-alpha inhibitor" refer to an agent which directly or indirectly inhibits, impairs, reduces, down-regulates, or blocks TNFα activity and/or expression. In some embodiments, a TNFα inhibitor is an inhibitory nucleic acid, an antibody or an antigen-binding fragment thereof, a fusion protein, a soluble TNFα receptor (a soluble TNFR1 or a soluble TNFR2), or a small molecule TNFα antagonist. In some embodiments, the inhibitory nucleic acid is a ribozyme, small hairpin RNA, a small interfering RNA, an antisense nucleic acid, or an aptamer.

In other examples, such indirect TNFα inhibitors can be a small molecule inhibitor of a signaling component downstream of a TNFα receptor (e.g., any of the signaling components downstream of a TNFα receptor described herein or known in the art), a small molecule inhibitor of a protein encoded by a TNFα-induced gene (e.g., any protein encoded by a TNFα-induced gene known in the art), and a small molecule inhibitor of a transcription factor selected from the group of NF-κB, c-Jun, and ATF2.

Inhibitory Nucleic Acids of TNFα

Exemplary TNFα inhibitors that are inhibitory nucleic acids targeting TNFα include, e.g., antisense DNA (e.g., Myers et al., J. Pharmacol Exp Ther. 304(1):411-424, 2003; Wasmuth et al., Invest. Opthalmol. Vis. Sci, 2003; Dong et al., J. Orthop. Res. 26(8):1114-1120, 2008; U.S. Patent Application Serial Nos. 2003/0083275, 2003/0022848, and 2004/0770970; ISIS 104838; U.S. Pat. Nos. 6,180,403, 6,080,580, and 6,228,642; Kobzik et al., Inhibition of TNF Synthesis by Antisense Oligonucleotides, in Manual of Antisense Methodology, Kluwer Academic Publishers, Vol. 4, pp. 1107-123, 1999; Taylor et al., Antisense Nucleic Acid Drug Develop. 8(3):199-205, 1998; Mayne et al., Stroke 32:240-248, 2001; Mochizuki et al., J. Controlled Release 151(2):155-161, 2011; Dong et al., J. Orthopaedic Res.

26(8):1114-1120, 2008; Dong et al., *Pharm. Res.* 28(6): 1349-1356, 2011; and Pampfer et al., *Biol. Reproduction* 52(6):1316-1326, 1995), antisense RNA, short interfering RNA (siRNA) (e.g., Taishi et al., *Brain Research* 1156:125-132, 2007; Presumey et al., *Eur. J. Pharm. Biopharm.* 82(3):457-467, 2012; Laroui et al., *J. Controlled Release* 186:41-53, 2014; D'Amore et al., *Int. J. Immunopathology Pharmacol.* 21:1045-1047, 2008; Choi et al., *J. Dermatol. Sci.* 52:87-97, 2008; Qin et al., *Artificial Organs* 35:706-714, 2011; McCarthy et al., *J. Controlled Release* 168: 28-34, 2013; Khoury et al., *Current Opin. Mol. Therapeutics* 9(5):483-489, 2007; Lu et al., *RNA Interference Technology From Basic Science to Drug Development* 303, 2005; Xie et al., *PharmaGenomics* 4(6):28-34, 2004; Aldawsari et al., *Current Pharmaceutical Design* 21(31):4594-4605, 2015; Zheng et al., *Arch. Med. Sci.* 11:1296-1302, 2015; Peng et al., *Chinese J. Surgery* 47(5):377-380, 2009; Aldayel et al., *Molecular Therapy. Nucleic Acids* 5(7):e340, 2016; Bai et al., *Current Drug Targets* 16:1531-1539, 2015; U.S. Patent Application Publications Nos. 2008/0097091, 2009/0306356, and 2005/0227935; and WO 14/168264), short hairpin RNA (shRNA) (e.g., Jakobsen et al., *Mol. Ther.* 17(10): 1743-1753, 2009; Ogawa et al., *PLoS One* 9(3): e92073, 2014; Ding et al., *Bone Joint* 94-6(Suppl. 11):44, 2014; and Hernandez-Alejandro et al., *J. Surgical Res.* 176(2):614-620, 2012), and microRNAs (see, e.g., WO 15/26249). In some embodiments, the inhibitory nucleic acid blocks pre-mRNA splicing of TNFα (e.g., Chiu et al., *Mol. Pharmacol.* 71(6): 1640-1645, 2007).

In some embodiments, the inhibitory nucleic acid, e.g., an aptamer (e.g., Orava et al., *ACS Chem Biol.* 2013; 8(1): 170-178, 2013), can block the binding of a TNFα protein with its receptor (TNFR1 and/or TNFR2).

In some embodiments, the inhibitory nucleic acid can down-regulate the expression of a TNFα-induced downstream mediator (e.g., TRADD, TRAF2, MEKK1/4, MEKK4/7, JNK, AP-1, ASK1, RIP, MEKK 3/6, MAPK, NIK, IKK, NF-κB, p38, JNK, IκB-α, or CCL2). Further teachings of downstream TNFα-induced mediators can be found in, e.g., Schwamborn et al., *BMC Genomics* 4:46, 2003; and Zhou et al., *Oncogene* 22: 2034-2044, 2003, incorporated by reference herein. Additional aspects of inhibitory nucleic acids are described in Aagaard et al., *Adv. Drug Delivery Rev.* 59(2):75-86, 2007, and Burnett et al., *Biotechnol. J.* 6(9):1130-1146, 2011.

TNFα Inhibitor Antibodies

In some embodiments, the TNFα inhibitor is an antibody or an antigen-binding fragment thereof (e.g., a Fab or a scFv). In some embodiments, an antibody or antigen-binding fragment described herein binds specifically to any one of TNFα, TNFR1, or TNFR2. In some embodiments, an antibody or antigen-binding fragment of an antibody described herein can bind specifically to TNFα. In some embodiments, an antibody or antigen-binding fragment of an antibody described herein can bind specifically to an TNFα receptor (TNFR1 or TNFR2).

Non-limiting examples of TNF inhibitors that are antibodies that specifically bind to TNFα are described in Elliott et al., *Lancet* 1994; 344: 1125-1127, 1994; Rankin et al., *Br. J. Rheumatol.* 2:334-342, 1995; Butler et al., *Eur. Cytokine Network* 6(4):225-230, 1994; Lorenz et al., *J. Immunol.* 156(4):1646-1653, 1996; Hinshaw et al., *Circulatory Shock* 30(3):279-292, 1990; Wanner et al., *Shock* 11(6):391-395, 1999; Bongartz et al., *JAMA* 295(19):2275-2285, 2006; Knight et al., *Molecular Immunol.* 30(16):1443-1453, 1993; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Ordas et al., *Clin. Pharmacol. Therapeutics* 91(4):635-646, 2012; Cohen et al., *Canadian J. Gastroenterol. Hepatol.* 15(6):376-384, 2001; Feldmann et al., *Ann. Rev. Immunol.* 19(1):163-196, 2001; Ben-Horin et al., *Autoimmunity Rev.* 13(1):24-30, 2014; and U.S. Pat. Nos. 6,090,382; 6,258,562; and 6,509,015).

In certain embodiments, the TNFα inhibitor can include or is infliximab (Remicade™), CDP571, CDP 870, golimumab (Golimumab™), adalimumab (Humira™) or certolizumab pegol (Cimzia™). In certain embodiments, the TNFα inhibitor can be a TNFα inhibitor biosimilar. Examples of approved and late-phase TNFα inhibitor biosimilars include, but are not limited to, infliximab biosimilars such as Remsima™ and Inflectra® (CT-P13) from Celltrion/Pfizer, GS071 from Aprogen, Flixabi™ (SB2) from Samsung Bioepis, PF-06438179 from Pfizer/Sandoz, NI-071 from Nichi-Iko Pharmaceutical Co., and ABP 710 from Amgen; adalimumab biosimilars such as Exemptia™ (ZRC3197) from Zydus Cadila, India, Solymbic® and Amgevita® (ABP 501) from Amgen, Imraldi (SB5) from Samsung Bioepis, GP-2017 from Sandoz, Switzerland, ONS-3010 from Oncobiologics/Viropro, U.S.A., M923 from Momenta Pharmaceuticals/Baxalta (Baxter spinoff USA), PF-06410293 from Pfizer, BMO-2 or MYL-1401-A from Biocon/Mylan, CHS-1420 from Coherus, FKB327 from Fujifilm/Kyowa Hakko Kirin (Fujifilm Kyowa Kirin Biologics), Cyltezo (BI 695501) from Boehringer Ingelheim, CT-P17 from Celltrion, BAX 923 from Baxalta (now a part of Shire), MSB11022 from Fresenius Kabi (bought from Merck kGaA (Merck Group) in 2017), LBAL from LG Life Sciences/Mochida Pharmaceutical, South Korea/Japan, PBP1502 from Prestige Biopharma, Adfrar from Torrent Pharmaceuticals, India, a biosimilar of adalimumab in development by Adello Biologics, a biosimilar of adalimumab in development by AET Biotech/BioXpress Therapeutics, Germany/Switzerland, a biosimilar of adalimumab from mAbxience, Spain, a biosimilar of adalimumab in development by PlantForm, Canada; and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, and CHS-0214 from Coherus.

In some embodiments, the TNFα inhibitor can be SAR252067 (e.g., a monoclonal antibody that specifically binds to TNFSF14, described in U.S. Patent Application Publication No. 2013/0315913) or MDGN-002 (described in U.S. Patent Application Publication No. 2015/0337046). In some embodiments, the TNFα inhibitor can be PF-06480605, which binds specifically to TNFSF15 (e.g., described in U.S. Patent Application Publication No. 2015/0132311). Additional examples of TNFα inhibitors include DLCX105 (described in Tsianakas et al., *Exp. Dermatol.* 25:428-433, 2016) and PF-06480605, which binds specifically to TNFSF15 (described in U.S. Patent Application Publication No. 2015/0132311). Further examples of TNFα inhibitors that are antibodies or antigen-binding antibody fragments are described in, e.g., WO 17/158097, EP 3219727, WO 16/156465, and WO 17/167997.

In some embodiments, the TNFα inhibitor is DLX-105, e.g., the gel formulation.

In some embodiments, the TNFα inhibitor is adalimumab. Adalimumab is a recombinant human IgG1 monoclonal antibody specific for human tumor necrosis factor and is indicated for the treatment of various inflammatory diseases such as rheumatoid arthritis, Crohn's disease, and ulcerative colitis.

Adalimumab is currently delivered as an SC injection of 40 mg in 0.4-0.8 mL once every 1-2 weeks. It is sold in prefilled pen injectors for self-administration. The bioavailability is approximately 64% by SC injection, the half-life is approximately 2 weeks, and intracellular catabolism is the primary mode of elimination. Adalimumab must be refrigerated but can be temporarily stored at room temperature before use.

Adalimumab is a suitable therapeutic for delivery via ingestible device as described herein. It is currently available as a liquid, administered by self-injection, and, because adverse injection site reactions are not uncommon, patients may readily adopt an alternative dosage form. Lastly, the probability of acute reactions to overdose is low which, theoretically, could allow an increase in dose to compensate for lower bioavailability than SC injection.

TNFα Inhibitor Fusion Proteins

In some embodiments, the TNFα inhibitory agent is a fusion protein (e.g., an extracellular domain of a TNFR fused to a partner peptide, e.g., an Fc region of an immunoglobulin, e.g., human IgG) (see, e.g., Peppel et al., *J. Exp. Med.* 174(6):1483-1489, 1991; Deeg et al., *Leukemia* 16(2): 162, 2002) or a soluble TNFR (e.g., TNFR1 or TNFR2) that binds specifically to TNFα. In some embodiments, the TNFα inhibitor includes or is etanercept (Enbrel™) (see, e.g., WO 91/03553 and WO 09/406,476, incorporated by reference herein). In some embodiments, the TNFα inhibitor includes or is r-TBP-I (e.g., Gradstein et al., *J. Acquir. Immune Defic. Syndr.* 26(2): 111-117, 2001). In some embodiments, the TNFα inhibitor includes or is a soluble TNFα receptor (e.g., Watt et al., *J. Leukoc Biol.* 66(6):1005-1013, 1999; Tsao et al., *Eur Respir J.* 14(3):490-495, 1999; Kozak et al., *Am. J. Physiol. Reg. Integrative Comparative Physiol.* 269(1):R23-R29, 1995; Mohler et al., *J. Immunol.* 151(3):1548-1561, 1993; Nophar et al., *EMBO J.* 9(10): 3269, 1990; Bjornberg et al., *Lymphokine Cytokine Res.* 13(3):203-211, 1994; Piguet et al., *Eur. Respiratory J.* 7(3):515-518, 1994; and Gray et al., *Proc. Natl. Acad. Sci. U.S.A.* 87(19):7380-7384, 1990).

In some embodiments, the TNFα inhibitor is tulinercept.

TNFα Inhibitor Small Molecules

In some embodiments, the TNFα inhibitor is a small molecule. In some embodiments, the TNFα inhibitor is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the small molecule is a tumor necrosis factor-converting enzyme (TACE) inhibitor (e.g., Moss et al., *Nature Clinical Practice Rheumatology* 4: 300-309, 2008). In some embodiments, the TACE inhibitor is TMI-005 and BMS-561392. Additional examples of small molecule inhibitors are described in, e.g., He et al., *Science* 310(5750):1022-1025, 2005.

In some examples, the TNFα inhibitor is a small molecule that inhibits the activity of one of TRADD, TRAF2, MEKK1/4, MEKK4/7, INK, AP-1, ASK1, RIP, MEKK 3/6, MAPK, NIK, IKK, and NF-κB, in a mammalian cell.

In some examples, the TNFα inhibitor is a small molecule that inhibits the activity of one of CD14, MyD88 (see, e.g., Olson et al., *Scientific Reports* 5:14246, 2015), IRAK (Chaudhary et al., *J. Med. Chem.* 58(1):96-110, 2015), lipopolysaccharide binding protein (LBP) (see, e.g., U.S. Pat. No. 5,705,398), TRAF6 (e.g., 3-[(2,5-Dimethylphenyl) amino]-1-phenyl-2-propen-1-one), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, R05126766 (CH5126766), PLX7904, and MLN2480), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, JNK (e.g., AEG 3482, BI 78D3, CEP 1347, c-JUN peptide, IQ 1S, JIP-1 (153-163), SP600125, SU 3327, and TCS JNK6o), c-jun (e.g., AEG 3482, BI 78D3, CEP 1347, c-JUN peptide, IQ 1S, JIP-1 (153-163), SP600125, SU 3327, and TCS JNK6o), MEK3/6 (e.g., Akinleye et al., *J. Hematol. Oncol.* 6:27, 2013), $p^{38}$ (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), and MK2 (PF 3644022 and PHA 767491).

IL-1 Inhibitors

In some embodiments, the therapeutic suitable for use with the devices and methods described herein is an IL-1 inhibitor. The term "IL-1 inhibitor" refers to an agent that decreases the expression of an IL-1 cytokine or an IL-1 receptor and/or decreases the ability of an IL-1 cytokine to bind specifically to an IL-1 receptor. Non-limiting examples of IL-1 cytokines include IL-1α, IL-1β, IL-18, IL-36α, IL-36β, IL-36γ, IL-38, and IL-33. In some examples, an IL-1 cytokine is IL-1α. In some examples, an IL-1 cytokine is IL-10.

In some embodiments, an IL-1 inhibitory agent is an inhibitory nucleic acid, an antibody or fragment thereof, or a fusion protein. In some embodiments, the inhibitory nucleic acid is an antisense nucleic acid, a ribozyme, or a small interfering RNA.

Inhibitory Nucleic Acids of IL-1

Inhibitory nucleic acids that can decrease the expression of IL-1α, IL-1β, IL-18, IL-36α, IL-36β, IL-36γ, IL-38, IL-33, IL-1R1, IL1RAP, IL-18Rα, IL-1RL2, or IL1RL1 mRNA expression in a mammalian cell include antisense nucleic acid molecules, i.e., nucleic acid molecules whose nucleotide sequence is complementary to all or part of an IL-1α, IL-10, IL-18, IL-36α, IL-36β, IL-36γ, IL-38, IL-33, IL-1R1, IL1RAP, IL-18Rα, IL-1RL2, or IL1RL1 mRNA (e.g., complementary to all or a part of any one of SEQ ID NOs: 85-125).

Examples of modified nucleotides which can be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Inhibitory nucleic acids preferentially bind (e.g., hybridize) to a nucleic acid encoding IL-1α, IL-1β, IL-18, IL-36α, IL-36β, IL-36γ, IL-38, IL-33, IL-1R1, IL1RAP, IL-18Rα, IL-1RL2, or IL1RL1 protein to treat allergic diseases (e.g., asthma (Corren et al., *N. Engl. J. Med.* 365: 1088-1098, 2011)), radiation lung injury (Chung et al., *Sci. Rep.* 6: 39714, 2016), ulcerative colitis (Hua et al., *Br. J. Clin. Pharmacol.* 80:101-109, 2015), dermatitis (Guttman-Yassky et al., *Exp. Opin. Biol. Ther.* 13(4):1517, 2013), and chronic obstructive pulmonary disease (COPD) (Walsh et al. (2010) *Curr. Opin. Investig Drugs.* 11(11):1305-1312, 2010).

Exemplary IL-1 inhibitors that are antisense nucleic acids are described in Yilmaz-Elis et al., *Mol. Ther.* Nucleic Acids 2(1): e66, 2013; Lu et al., *J. Immunol.* 190(12): 6570-6578, 2013), small interfering RNA (siRNA) (e.g., Ma et al., *Ann. Hepatol.* 15(2): 260-270, 2016), or combinations thereof. In certain embodiments, a therapeutically effective amount of an inhibitory nucleic acid targeting a nucleic acid encoding IL-1α, IL-1β, IL-18, IL-36α, IL-36β, IL-36γ, IL-38, IL-33, IL-1R1, IL1RAP, IL-18Rα, IL-1RL2, or IL1RL1 protein can be administered to a subject (e.g., a human subject) in need thereof.

IL-1 Inhibitor Antibodies

In some embodiments, the IL-1 inhibitor is an antibody or an antigen-binding fragment thereof (e.g., a Fab or a scFv). In some embodiments, the IL-1 inhibitor is canakinumab (ACZ885, Ilaris® (Dhimolea, *MAbs* 2(1): 3-13, 2010; Yokota et al., *Clin. Exp. Rheumatol.* 2016; Torene et al., *Ann. Rheum. Dis.* 76(1):303-309, 2017; Gram, *Curr. Opin. Chem. Biol.* 32:1-9, 2016; Kontzias et al., *Semin. Arthritis Rheum* 42(2):201-205, 2012). In some embodiments, the IL-1 inhibitor is anakinra (Kineret®; Beynon et al., *J. Clin. Rheumatol.* 23(3):181-183, 2017; Stanam et al., *Oncotarget* 7(46):76087-76100, 2016; Nayki et al., *J. Obstet Gynaecol. Res.* 42(11):1525-1533, 2016; Greenhalgh et al., *Dis. Model Mech.* 5(6):823-833, 2012), or a variant thereof. In some embodiments, the IL-1 inhibitor is gevokizumab (XOMA 052; Knicklebein et al., *Am. J. Ophthalmol.* 172:104-110, 2016; Roubille et al., *Atherosclerosis* 236(2):277-285, 2014; Issafras et al., *J. Pharmacol. Exp. Ther* 348(1):202-215, 2014; Handa et al., *Obesity* 21(2):306-309, 2013; Geiler et al., *Curr. Opin. Mol. Ther.* 12(6):755-769, 2010), LY2189102 (Bihorel et al., *AAPS J.* 16(5):1009-1117, 2014; Sloan-Lancaster et al., *Diabetes Care* 36(8):2239-2246, 2013), MABp1 (Hickish et al., *Lancey Oncol.* 18(2):192-201, 2017; Timper et al., *J. Diabetes Complications* 29(7): 955-960, 2015), CDP-484 (Braddock et al., *Drug Discov.* 3:330-339, 2004), or a variant thereof (Dinarello et al., *Nat. Rev. Drug Discov.* 11(8): 633-652, 2012).

Further teachings of IL-1 inhibitors that are antibodies or antigen-binding fragments thereof are described in U.S. Pat. Nos. 5,075,222; 7,446,175; 7,531,166; 7,744,865; 7,829,093; and 8,273,350; US 2016/0326243; US 2016/0194392, and US 2009/0191187, each of which is incorporated by reference in its entirety.

IL-1 Inhibitor Fusion Proteins or Soluble Receptors

In some embodiments, the IL-1 inhibitor is a fusion protein or a soluble receptor. For example, a fusion can include an extracellular domain of any one of IL-1R1, IL1RAP, IL-18Rα, IL-1RL2, and IL1RL1 fused to a partner amino acid sequence (e.g., a stabilizing domain, e.g., an IgG Fc region, e.g., a human IgG Fc region). In some embodiments, the IL-1 inhibitor is a soluble version of one or both of IL-1RL1 and IL1RAP. In some embodiments, the IL-1 inhibitor is a soluble version of IL-18Rα. In some embodiments, the IL-1 inhibitor is a soluble version of one or both of IL-1RL2 and IL-1RAP.

In some embodiments, the IL-1 inhibitor is a fusion protein comprising or consisting of rilonacept (IL-1 Trap, Arcalyst®) (see, e.g., Kapur & Bonk, P. T 34(3):138-141, 2009; Church et al., *Biologics* 2(4):733-742, 2008; McDermott, *Drugs Today* (Barc) 45(6):423-430, 2009). In some embodiments, the IL-1 inhibitor is a fusion protein that is chimeric (e.g., EBI-005 (Isunakinra®) (Furfine et al., *Invest. Ophthalmol. Vis. Sci.* 53(14):2340-2340, 2012; Goldstein et al., *Eye Contact Lens* 41(3):145-155, 2015; Goldstein et al., *Eye Contact Lens*, 2016)).

In some embodiments, the IL-1 inhibitor is a soluble receptor that comprises or consists of sIL-1RI and/or sIL-1RII (Svenson et al., *Eur. J. Immunol.* 25(10): 2842-2850, 1995).

IL-1 Inhibitor Endogenous Peptides

In some embodiments, the IL-1 inhibitor can be an endogenous ligand or an active fragment thereof, e.g., IL-1Rα or IL-36Rα. IL-1Rα is an endogenous soluble protein that decreases the ability of IL-1α and IL-1β to bind to their receptor (e.g., a complex of IL-1R1 and IL1RAP proteins). IL-36Rα is an endogenous soluble protein that decreases the ability of IL-36α, IL-36β, and IL-36γ to bind to their receptor (e.g., a complex of IL-1RL2 and IL-1RAP proteins). Exemplary sequences for IL-1Rα and IL-36Rα are shown below.

In some embodiments, the IL-1 inhibitor is K(D)PT.

IL-6 Receptor Inhibitors

In some embodiments, the therapeutic suitable for use with the devices and methods described herein is an IL-6 receptor inhibitor. The term "IL-6 receptor inhibitor" refers to an agent which decreases IL-6 receptor expression and/or the ability of IL-6 to bind to an IL-6 receptor. In some embodiments, the IL-6 receptor inhibitor targets the IL-6 receptor β-subunit, glycoprotein 130 (sIL6gp130). In other embodiments, the IL-6 receptor inhibitor targets the IL-6 receptor subunit (IL6R). In other embodiments, the IL-6 receptor inhibitor targets the complex consisting of both the IL-6 receptor subunit (IL6R) and the IL-6 receptor β-subunit, glycoprotein 130 (sIL6gp130). In some embodiments, the IL-6 receptor inhibitor targets IL-6.

In some embodiments, an IL-6 receptor inhibitor is an inhibitory nucleic acid, an antibody or an antigen-binding fragment thereof, a fusion protein, a IL-6 receptor antagonist, or a small molecule. In some embodiments, the inhibitory nucleic acid is a small interfering RNA, an antisense nucleic acid, an aptamer, or a microRNA. Exemplary IL-6 receptor inhibitors are described herein. Additional examples of IL-6 receptor inhibitors are known in the art.

Inhibitory Nucleic Acids of IL-6

An antisense nucleic acid molecule can be complementary to all or part of a non-coding region of the coding strand of a nucleotide sequence encoding an IL6R, sIL6gp130, or IL-6 protein. Non-coding regions (5' and 3' untranslated regions) are the 5' and 3' sequences that flank the coding region in a gene and are not translated into amino acids.

Exemplary antisense nucleic acids that are IL-6 receptor inhibitors are described in Keller et al., *J. Immunol.* 154(8): 4091-4098, 1995; and Jiang et al., *Anticancer Res.* 31(9): 2899-2906, 2011.

Non-limiting examples of short interfering RNA (siRNA) that are IL-6 receptor inhibitors are described in Yi et al., *Int. J. Oncol.* 41(1):310-316, 2012; and Shinriki et al., *Clin. Can. Res.* 15(17):5426-5434, 2009). Non-limiting examples of microRNAs that are IL-6 receptor inhibitors are described in miR34a (Li et al., *Int. J. Clin. Exp. Pathol.* 8(2):1364-1373, 2015) and miR-451 (Liu et al., *Cancer Epidemiol.* 38(1): 85-92, 2014).

Non-limiting examples of aptamers that are IL-6 receptor inhibitors are described in Meyer et al., *RNA Biol.* 11(1): 57-65, 2014; Meyer et al., *RNA Biol.* 9(1):67-80, 2012; and Mittelberger et al., *RNA Biol.* 12(9):1043-1053, 2015. Additional examples of inhibitory nucleic acids that are IL-6 receptor inhibitors are described in, e.g., WO 96/040157.

IL-6 Inhibitor Antibodies

In some embodiments, the IL-6 receptor inhibitor is an antibody or an antigen-binding fragment thereof (e.g., a Fab or a scFv). In some embodiments, an antibody or antigen-binding fragment described herein binds specifically to IL-6. In some embodiments, an antibody or antigen-binding fragment described herein binds specifically to IL-6 receptor (e.g., one or both of IL6R and sIL6gp130).

In certain embodiments, the antibody comprises or consists of an antigen-binding fragment or portion of tocilizumab (artlizumab, Actemra®; Sebba, *Am. J. Health Syst. Pharm.* 65(15):1413-1418, 2008; Tanaka et al., *FEBS Letters* 585(23):3699-3709, 2011; Nishimoto et al., *Arthritis Rheum.* 50:1761-1769, 2004; Yokota et al., *Lancet* 371 (9617):998-1006, 2008; Emery et al., *Ann. Rheum. Dis.* 67(11):1516-1523, 2008; Roll et al., *Arthritis Rheum.* 63(5): 1255-1264, 2011); lazakizumab (BMS945429; ALD518, a humanized monoclonal antibody that binds circulating IL-6 cytokine rather than the IL-6 receptor, blocking both classic signaling and trans-signaling (Weinblatt, Michael E., et al. "The Efficacy and Safety of Subcutaneous Clazakizumab in Patients With Moderate-to-Severe Rheumatoid Arthritis and an Inadequate Response to Methotrexate: Results From a Multinational, Phase IIb, Randomized, Double-Blind, Placebo/Active-Controlled, Dose-Ranging Study." Arthritis & Rheumatology 67.10 (2015): 2591-2600)); sarilumab (REGN88 or SAR153191; Huizinga et al., *Ann. Rheum. Dis.* 73(9):1626-1634, 2014; Sieper et al., *Ann. Rheum. Dis.* 74(6):1051-1057, 2014; Cooper, Immunotherapy 8(3): 249-250, 2016); MR-16 (Hartman et al., *PLosOne* 11(12): e0167195, 2016; Fujita et al., *Biochim. Biophys. Acta.* 10:3170-80, 2014; Okazaki et al., *Immunol. Lett.* 84(3):231-40, 2002; Noguchi-Sasaki et al., *BMC Cancer* 16:270, 2016; Ueda et al., *Sci. Rep.* 3:1196, 2013); rhPM-1 (MRA; Nishimoto et al., *Blood* 95: 56-61, 2000; Nishimoto et al., *Blood* 106: 2627-2632, 2005; Nakahara et al., *Arthritis Rheum.* 48(6): 1521-1529, 2003); NI-1201 (Lacroix et al., *J. Biol. Chem.* 290(45):26943-26953, 2015); EBI-029 (Schmidt et al., *Eleven Biotherapeutics Poster #B0200*, 2014). In some embodiments, the antibody is a nanobody (e.g., ALX-0061 (Van Roy et al., *Arthritis Res. Ther.* 17: 135, 2015; Kim et al., *Arch. Pharm. Res.* 38(5):575-584, 2015)). In some embodiments, the antibody is NRI or a variant thereof (Adachi et al., *Mol. Ther.* 11(1):5262-263, 2005; Hoshino et al., *Can. Res.* 67(3): 871-875, 2007). In some embodiments, the antibody is PF-04236921 (Pfizer) (Wallace et al., *Ann. Rheum. Dis.* 76(3):534-542, 2017).

In some embodiments, the IL-6 receptor inhibitor is olokizumab (CDP-6038).

IL-6 Inhibitor Fusion Proteins

In some embodiments, the IL-6 receptor inhibitor is a fusion protein, a soluble receptor, or a peptide (see e.g., U.S. Pat. No. 5,591,827). In some embodiments, the IL-6 receptor fusion protein comprises or consists of soluble gp130 (Jostock et al., *Eur. J Biochem.* 268(1):160-167, 2001; Richards et al., *Arthritis Rheum.* 54(5):1662-1672, 2006; Rose-John et al., *Exp. Opin. Ther. Targets* 11(5):613-624, 2007).

In some embodiments, the IL-6 receptor fusion protein comprises or consists of FE999301 (Jostock et al., *Eur. J. Biochem.* 268(1):160-167, 2001) or sgp130Fc protein (Jones et al., *J. Clin. Invest.* 121(9):3375-3383, 2011). In some embodiments, the IL-6 receptor inhibitor is a peptide (e.g., S7 (Su et al., *Cancer Res.* 65(11):4827-4835, 2005). In some embodiments, the IL-6 receptor inhibitor is a triterpenoid saponin (e.g., chikusetsuaponin IVa butyl ester (CS-Iva-Be) (Yang et al., *Mol. Cancer. Ther.* 15(6):1190-200, 2016).

IL-6 Inhibitor Small Molecules

In some embodiments, the IL-6 receptor inhibitor is a small molecule (see, e.g., U.S. Pat. No. 9,409,990). In some embodiments, the small molecule is LMT-28 (Hong et al., *J. Immunol.* 195(1): 237-245, 2015); ERBA (Enomoto et al., *Biochem. Biophys. Res. Commun.* 323:1096-1102, 2004; Boos et al., *J. Nat. Prod.* 75(4):661-668, 2012), ERBF (TB-2-081) (Hayashi et al., *J. Pharmacol. Exp. Ther.* 303: 104-109, 2002; Vardanyan et al., *Pain* 151(2):257-265, 2010; Kino et al., *J. Allergy Clin. Immunol.* 120(2):437-444, 2007), or a variant thereof.

In some embodiments, the IL-6 receptor inhibitor is YSIL6.

IL-10 Receptor Agonists

In some embodiments, the therapeutic suitable for use with the devices and methods described herein is an IL-10 receptor agonist. The term "IL-10 receptor agonist" is any molecule that binds to and activates a receptor for IL-10 expressed on a mammalian cell or a nucleic acid that encodes any such molecule. A receptor for IL-10 can include, e.g., a complex of two IL-10 receptor-1 (IL-10R1) proteins and two IL-10 receptor 2 (IL-10R2) proteins. In some examples, an IL-10 receptor agonist is an antibody or an antigen-binding antibody fragment that specifically binds to and activates a receptor for IL-10 (e.g., a human receptor for IL-10). In some examples, an IL-10 receptor agonist is a recombinant IL-10 (e.g., human recombinant IL-10). In some examples, an IL-10 receptor agonist is a pegylated recombinant IL-10 (e.g., pegylated recombinant human IL-10). In some examples, an IL-10 receptor agonist is a fusion protein. In some examples, an IL-10 receptor agonist is an IL-10 peptide mimetic.

Nucleic Acids and Vectors that Encode an IL-10 Receptor Agonist

In some examples, an IL-10 receptor agonist can be a nucleic acid (e.g., a vector) that includes a sequence encoding an IL-10 receptor agonist (e.g., any of the IL-10 proteins described herein). A non-limiting example of a composition including a nucleic acid that encodes an IL-10 receptor agonist is XT-150 (Xalud Therapeutics).

IL-10 Inhibitor Antibodies and Antigen-Binding Fragments

In some embodiments, the IL-10 receptor agonist is an antibody or an antigen-binding antibody fragment that binds to and activates an IL-10 receptor (e.g., a human IL-receptor). In some embodiments, the antibody or antigen-binding antibody fragment that specifically binds to an epitope on IL-10R-1 protein (e.g., human IL-10R-1 protein). In some embodiments, the antibody or antigen-binding antibody fragment that specifically binds to an epitope on IL-10R-2 protein (e.g., a human IL-10R-2 protein). In some embodiments, the antibody or the antigen-binding antibody fragment that specifically binds to an epitope on IL-10R-1 and IL-10R-2 proteins (e.g., human IL-10R-1 and human IL-10R-2 proteins).

In some embodiments, the IL-10 receptor agonist is an antibody, e.g., F8-IL10 (also known as DEKAVIL) or a variant thereof (see, e.g., Schwager et al., *Arthritis Res. Ther.* 11(5):R142, 2009; Franz et al., *Int. J. Cardiol.* 195:311-322, 2015; Galeazzi et al., *Isr. Med. Assoc. J.* 16(10):666, 2014).

IL-10 Inhibitor Fusion Proteins

In some embodiments, the IL-10 receptor agonist is a fusion protein. In some embodiments, the fusion protein comprises the amino acid sequence of an IL-10 protein (or a functional fragment thereof) and a fusion partner (e.g., an Fc region (e.g., human IgG Fc) or human serum albumin). In some embodiments the fusion partner can be an antibody or an antigen-binding antibody fragment (e.g., an scFv) that targets IL-10 receptor agonist to an inflamed tissue. In some embodiments, the antibody or antigen-binding fragment that is a fusion partner can bind specifically, or preferentially, to inflamed gastrointestinal cells by, e.g., CD69. In some embodiments, an IL-10 receptor agonist that is a fusion protein can be, e.g., F8-IL-10, such as Dekavil (Philogen).

In some embodiments, the fusion protein is a L19-IL-10 fusion protein, a HyHEL10-IL-10 fusion protein, or a variant thereof. See, e.g., Trachsel et al., *Arthritis Res. Ther.* 9(1):R9, 2007, and Walmsley et al., *Arthritis Rheum.* 39: 495-503, 1996.

In some embodiments, the IL-10 receptor agonist is RG-7880.

IL-10 Peptide Mimetic

In some embodiments, the IL-10 receptor agonist is an IL-10 peptide mimetic. A non-limiting example of an IL-10 peptide mimetic is IT 9302 or a variant thereof (Osman et al., *Surgery* 124(3):584-92, 1998; Lopez et al., *Immunobiology* 216(10):1117-1126, 2011). Additional examples of IL-10 peptide mimetics are described in DeWitt, *Nature Biotech.* 17:214, 1999, and Reineke et al., *Nature Biotech.* 17:271-275, 1999.

Recombinant IL-10

In some examples, an IL-10 receptor agonist is a recombinant IL-10 protein. In some examples, a recombinant human IL-10 protein can be Tenovil™ (Schering Corporation). In some examples, a recombinant IL-10 protein is a functional fragment of human IL-10 protein (e.g., SEQ ID NO: 140).

In some embodiments, the IL-10 receptor agonist is rhuIL-10 (Tenovil) or a variant thereof. See, e.g., McHutchison et al., *J. Interferon Cytokine Res.* 1:1265-1270, 1999; Rosenblum et al., *Regul. Toxicol. Pharmacol.* 35:56-71, 2002; Schreiber et al., *Gastroenterology* 119(6):1461-1472, 2000; Maini et al., *Arthritis Rheum.* 40(Suppl):224, 1997.

Exemplary methods of making a recombinant human IL-10 are described in Pajkrt et al., *J. Immunol.* 158: 3971-3977, 1997). Additional exemplary methods of making recombinant IL-10 are described herein and are known in the art.

In some embodiments, a recombinant IL-10 is a pegylated recombinant IL-10 (e.g., pegylated recombinant human IL-10) (e.g., a 5 kDa N-terminally PEGylated form of IL-10; AM0010) (Infante et al., *ASCO Meeting Abstracts* 33(15_suppl):3017, 2015; Chan et al., *PLoS One* 11(6): e0156229, 2016; Mumm et al., *Cancer Cell* 20(6):781-796, 2011; Teng et al., *Cancer Cell* 20(6):691-693, 2011; U.S. Pat. Nos. 8,691,205; 8,865,652; 9,259,478; and 9,364,517; and U.S. Patent Application Publication Nos. 2008/0081031; 2009/0214471; 2011/0250163; 2011/0091419; 2014/0227223; 2015/0079031; 2015/0086505; 2016/0193352; 2016/0367689; 2016/0375101; and 2016/0166647).

In some embodiments, a recombinant IL-10 is a stabilized isoform of a recombinant IL-10. In some embodiments, the stabilized isoform of a recombinant IL-10 is a viral IL-10 protein (e.g., a human cytomegalovirus IL10 (e.g., cmv-IL10, LA-cmv-IL-10 (e.g., Lin et al., *Virus Res.* 131(2):213-223, 2008; Jenkins et al., *J. Virol.* 78(3):1440-1447, 2004; Kotenko et al., *Proc. Natl. Acad. Sci. U.S.A.* 97(4):1695-1700, 2000; Jones et al., *Proc. Natl. Acad. Sci. U.S.A.* 99(14):9404-9409, 2002) or a latency-associated viral IL-10 protein (e.g., Poole et al., *J. Virol.* 88(24):13947-13955, 2014).

In some embodiments, the recombinant IL-10 is a mammalian IL-10 homolog (see, e.g., WO 00/073457). In some embodiments, a mammalian IL-10 homolog is BCRF1, an EBV homolog of human IL-10, also known as viral IL-10, or a variant thereof (Liu et al., *J. Immunol.* 158(2):604-613, 1997).

Cells Producing a Recombinant IL-10

In some embodiments, any of the devices or compositions described herein can include a recombinant cell (e.g., a recombinant mammalian cell) that secretes a recombinant IL-10 (e.g., any of the recombinant IL-10 proteins described herein). In some embodiments, any of the devices or compositions described herein can include a cell (e.g., a mammalian cell) that secretes IL-10 (e.g., human IL-10). In some embodiments, the mammalian cell can be a mammalian cell obtained from the subject, and after introduction of a nucleic acid encoding the recombinant IL-10 (e.g., any of the recombinant IL-10 proteins described herein) into the cell obtained from the subject, the cell is incorporated into any of the compositions or devices described herein.

Non-limiting examples of methods that can be used to introduce a vector or a nucleic acid into a cell (e.g., a mammalian cell) include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. These and other methods of introducing a vector or a nucleic acid into a cell are well known in the art.

In some examples, the recombinant mammalian cell can be a Chinese Hamster Ovary (CHO) cell, a B cell, a CD8+ T cell, a dendritic cell, a keratinocyte or an epithelial cell. See, e.g., Mosser et al., *Immunol. Rev.* 226:205-218, 2009; Fillatreau et al., *Nat. Rev. Immunol.* 8:391-397, 2008; Ryan et al., *Crit. Rev. Immunol.* 27:15-32, 2007; Moore et al., *Annu. Rev. Immunol.* 19:683-765, 2001. In some embodiments, the recombinant mammalian cell can be a mesenchymal stem cell (e.g., Gupte et al., *Biomed J.* 40(1):49-54, 2017).

Additional Examples of IL-10 Inhibitors

In some embodiments, the recombinant cell is a recombinant Gram-positive bacterial cell (e.g., a genetically modified *Lactococcus lactis* (LL-Thy12) (see, e.g., Steidler et al., *Science* 289:1352-1355, 2000; Braat et al., *Clin. Gastroenterol. Heptal.* 4:754-759, 2006). In some embodiments, the recombinant cell is a recombinant Gram-negative bacterial cell (e.g., a *Shigella flexneri* cell) that secretes an IL-10 receptor agonist (e.g., a recombinant IL-10 protein) (Chamekh et al., *J. Immunol.* 180(6): 4292-4298, 2008).

In some embodiments, the IL-10 receptor agonist is a cell (e.g., a *Clostridium butyricum* cell) that induces IL-10 production and secretion by a different cell (e.g., a macrophage) (e.g., Hayashi et al., *Cell Host Microbe* 13:711-722, 2013). In some embodiments, the IL-10 receptor agonist is a recombinant bacterial cell (e.g., a *Lactobacillus acidophilus* cell) that is deficient in lipoteichoic acid and induces IL-10 production and secretion by a different cell (e.g., a dendritic cell) (e.g., Mohamadzadeh et al., *Proc. Natl. Acad Sci. U.S.A.* 108(suppl 1):4623-4630, 2011; Konstantinov et al., *Proc. Natl. Acad Sci. U.S.A.* 105(49):19474-9, 2008). In some embodiments, the IL-10 receptor agonist is a bacterial cell or a fragment of a bacterial cell that is maintained in the supernatant that induces IL-10 secretion in a different cell (e.g., an immune cell) (e.g., a *Faecalibacterium prausnitzii* cell or a *Faecalibacterium prausnitzii* supernatant) (see, e.g., Sokol et al., *Proc. Natl. Acad Sci. U.S.A.* 105(43):16731-16736, 2008).

Additional examples of other IL-10 receptor agonists are described in, e.g., U.S. Pat. No. 6,936,586; WO 96/01318; WO 91/00349; WO 13/130913; each incorporated in its entirety herein.

IL-12/IL-23 Inhibitors

In some embodiments, the therapeutic suitable for use with the devices and methods described herein is an IL-12/IL-23 inhibitor. The term "IL-12/IL-23 inhibitor" refers to an agent which decreases IL-12 or IL-23 expression and/or the ability of IL-12 to bind to an IL-12 receptor or the ability of IL-23 to bind to an IL-23 receptor. In some embodiments, the IL-12/IL-23 inhibitory agent targets IL-12B (p40) subunit. In some embodiments, the IL-12/IL-23 inhibitory agent targets IL-12A (p35). In some embodiments, the IL-12/IL-23 inhibitory agent targets IL-23 (p19). In some embodiments, the IL-12/IL-23 inhibitory agent targets the receptor for IL-12 (one or both of IL-12R β1 or IL-12R β2). In some embodiments, the IL-12/IL-23 inhibitory agent targets the receptor for IL-23 (one or both of IL-12R β1 and IL-23R).

In some embodiments, an IL-12/IL-23 inhibitor can be an inhibitory nucleic acid.

In some embodiments, the inhibitory nucleic acid can be an antisense nucleic acid, a ribozyme, and a small interfering RNA (siRNA).

Non-limiting examples of siRNAs targeting IL-12A (p35), IL-12B (p40), IL-23 (p19), IL-12R β1, IL-12R β2, or IL-23R are described in Tan et al., *J. Alzheimers Dis.* 38(3): 633-646, 2014; Niimi et al., *J. Neuroimmunol.* 254(1-2):39-45, 2013. Non-limiting examples of short hairpin RNA (shRNA) targeting IL-12A (p35), IL-12B (p40), IL-23 (p19), IL-12R β1, IL-12R β2, or IL-23R are described in Bak et al., *BMC Dermatol.* 11:5, 2011.

Non-limiting examples of inhibitory nucleic acids are microRNAs (e.g., microRNA-29 (Brain et al., *Immunity* 39(3):521-536, 2013), miR-10a (Xue et al., *J. Immunol.* 187(11):5879-5886, 2011), microRNA-155 (Podsiad et al., *Am. J. Physiol. Lung Cell Mol. Physiol.* 310(5):L465-75, 2016).

IL-12/IL-23 Inhibitor Antibodies

In some embodiments, the IL-12/IL-23 inhibitor is an antibody or an antigen-binding fragment thereof (e.g., a Fab or a scFv). In some embodiments, an antibody or antigen-binding fragment described herein binds specifically to any one of IL-12A (p35), IL-12B (p40), IL-23 (p19), IL-12R β1, IL-12R β2, or IL-23R, or a combination thereof.

In some embodiments, the antibody is ustekinumab (CNTO 1275, Stelara®) or a variant thereof (Krueger et al., *N. Engl. J. Med.* 356(6):580-592, 2007; Kauffman et al., *J. Invest. Dermatol.* 123(6):1037-1044, 2004; Gottlieb et al., *Curr. Med. Res. Opin.* 23(5):1081-1092, 2007; Leonardi et al., *Lancet* 371(9625):1665-1674, 2008; Papp et al., *Lancet* 371(9625):1675-1684, 2008). In some embodiments, the antibody is briakinumab (ABT-874, J-695) or a variant thereof (Gordon et al., *J. Invest. Dermatol.* 132(2):304-314, 2012; Kimball et al., *Arch Dermatol.* 144(2): 200-207, 2008).

In some embodiments, the antibody is guselkumab (CNTO-1959) (Callis-Duffin et al., *J. Am. Acad. Dermatol.* 70(5 Suppl 1), 2014); AB162 (Sofen et al., *J. Allergy Clin. Immunol.* 133: 1032-40, 2014); tildrakizumab (MK-3222, SCH900222) (Papp et al. (2015) *Br. J. Dermatol.* 2015); Langley et al., Oral Presentation at: American Academy of Dermatology, March 21-25, Denver Colo., 2014); AMG 139 (MEDI2070, brazikumab) (Gomollon, *Gastroenterol. Hepatol.* 38(Suppl. 1):13-19, 2015; Kock et al., *Br. J. Pharmacol.* 172(1):159-172, 2015); FM-202 (Tang et al., *Immunology* 135(2):112-124, 2012); FM-303 (Tang et al., *Immunology* 135(2):112-124, 2012); ADC-1012 (Tang et al., *Immunology* 135(2):112-124, 2012); LY-2525623 (Gaffen et al., *Nat. Rev. Immunol.* 14:585-600, 2014; Sands, *Gastroenterol. Hepatol.* 12(12):784-786, 2016), LY-3074828 (Coskun et al., *Trends Pharmacol. Sci.* 38(2):127-142, 2017), BI-655066 (risankizumab) (Singh et al., *MAbs* 7(4):778-791, 2015; Krueger et al., *J. Allergy Clin. Immunol.* 136(1):116-124, 2015) or a variant thereof.

Further teachings of IL-12/IL-23 antibodies and antigen-binding fragments thereof are described in U.S. Pat. Nos. 6,902,734; 7,247,711; 7,252,971; and 7,491,391; US 2012/0288494; and US 2013/0302343, each of which is incorporated by reference in its entirety.

In some embodiments, the IL-12/IL-23 inhibitor is PTG-200, an IL-23R inhibitor currently in preclinical development by Protagonist Therapeutics.

In some embodiments, the IL-12/IL-23 inhibitor is Mirikizumab (LY 3074828), an IL-23R inhibitor currently in clinical development (Phase II) by Eli Lilly.

In some embodiments, the IL-12/IL-23 inhibitor is AK-101.

IL-12/IL-23 Inhibitor Fusion Proteins

In some embodiments, the IL-12/IL-23 inhibitor is a fusion protein, a soluble antagonist, or an antimicrobial peptide. In some embodiments, the fusion protein comprises a soluble fragment of a receptor of IL-12 or a soluble fragment of a receptor of IL-23. In some embodiments, the fusion protein comprises an extracellular domain of a receptor of IL-12 or an extracellular domain of a receptor of IL-23.

In some embodiments, the fusion protein is adnectin or a variant thereof (Tang et al., *Immunology* 135(2):112-124, 2012). In some embodiments, the soluble antagonist is a human IL-23Rα-chain mRNA transcript (Raymond et al., *J. Immunol.* 185(12):7302-7308, 2010). In some embodiments, the IL-12/IL-23 is an antimicrobial peptide (e.g., MP-196 (Wenzel et al., *PNAS* 111(14):E1409-E1418, 2014)).

IL-12/IL-23 Inhibitor Small Molecules

In some embodiments, the IL-12/IL-23 inhibitor is a small molecule. In some embodiments, the small molecule is STA-5326 (apilimod) or a variant thereof (Keino et al., *Arthritis Res. Ther.* 10: R122, 2008; Wada et al., *Blood* 109(3):1156-1164, 2007; Sands et al., *Inflamm. Bowel Dis.* 16(7):1209-1218, 2010).

IL-13 Inhibitors

In some embodiments, the therapeutic suitable for use with the devices and methods described herein is an IL-13 inhibitor. The term "IL-13 inhibitor" refers to an agent which decreases IL-13 expression and/or decreases the binding of IL-13 to an IL-13 receptor. In some embodiments, the IL-13 inhibitor decreases the ability of IL-13 to bind an IL-13 receptor (e.g., a complex including IL-4Rα and IL-13Rα1, or a complex including IL-13Rα1 and IL-13Rα2).

In some embodiments, an IL-13 inhibitor is an inhibitory nucleic acid, an antibody or an antigen-binding fragment thereof, or a fusion protein. In some embodiments, the inhibitory nucleic acid can be an antisense nucleic acid, a ribozyme, a small interfering RNA, a small hairpin RNA, or a microRNA. Examples of aspects of these different inhibitory nucleic acids are described below. Any of the examples of inhibitory nucleic acids that can decrease expression of an IL-13, IL-13Rα1, IL-13Rα2, or IL-4Rα mRNA in a mammalian cell can be synthesized in vitro.

Non-limiting examples of short interfering RNA (siRNA) that are IL-13 inhibitors are described in Lively et al., *J. Allergy Clin. Immunol.* 121(1):88-94, 2008). Non-limiting examples of short hairpin RNA (shRNA) that are IL-13 inhibitors are described in Lee et al., *Hum Gene Ther.* 22(5):577-586, 2011, and Shilovskiy et al., *Eur. Resp. J.* 42:P523, 2013).

In some embodiments, an inhibitory nucleic acid can be a microRNA. Non-limiting examples of microRNAs that are IL-13 inhibitors are let-7 (Kumar et al., *J. Allergy Clin. Immunol.* 128(5):1077-1085, 2011).

IL-13 Inhibitor Antibodies

In some embodiments, the IL-13 inhibitor is an antibody or an antigen-binding fragment thereof (e.g., a Fab or a scFv). In some embodiments, an antibody or antigen-binding fragment described herein binds specifically to any one of IL-13, IL-13Rα1, IL-13Rα2, or IL-4Rα, or a combination thereof. In some embodiments, an antibody or antigen-binding fragment of an antibody described herein can bind specifically to IL-13. In some embodiments, an antibody or antigen-binding fragment of an antibody described herein can bind specifically to an IL-13 receptor (e.g., a complex including IL-4Rα and IL-13Rα1, or a complex including IL-13Rα1 and IL-13Rα2).

In some embodiments, the IL-13 inhibitor is a monoclonal antibody (Bagnasco et al., *Int. Arch. Allergy Immunol.* 170:122-131, 2016). In some embodiments, the IL-13 inhibitor is QAX576 (Novartis) or an antigen-binding fragment thereof (see, e.g., Kariyawasam et al., *B92 New Treatment Approaches for Asthma and Allergy* San Diego, 2009; Rothenberg et al., *J. Allergy Clin. Immunol.* 135:500-507, 2015). In some embodiments, the IL-13 inhibitor is ABT-308 (Abbott) or an antigen-binding fragment thereof (see, e.g., Ying et al., American Thoracic Society 2010 International Conference, May 14-19, 2010, New Orleans; Abstract A6644). In some embodiments, the IL-13 inhibitor is CNTO-5825 (Centrocore) or an antigen-binding fragment thereof (see, e.g., van Hartingsveldt et al., *British J. Clin. Pharmacol.* 75:1289-1298, 2013). In some embodiments, the IL-13 inhibitor is dupilumab (REGN668/SAR231893) or an antigen-binding fragment thereof (see, e.g., Simpson et al., *N. Eng. J. Med.* 375:2335-2348, 2016; Thaci et al., *Lancet* 387:40-52, 2016). In some embodiments, the IL-13 inhibitor is AMG317 (Amgen) or an antigen-binding fragment thereof (Polosa et al., *Drug Discovery Today* 17:591-599, 2012; Holgate, *British J. Clinical Pharmacol.* 76:277-291, 2013). In some embodiments, the IL-13 inhibitor is an antibody that specifically binds to IL-13Rα1 (see, e.g., U.S. Pat. No. 7,807,158; WO 96/29417; WO 97/15663; and WO 03/080675).

In some embodiments, the IL-13 inhibitor is a humanized monoclonal antibody (e.g., lebrikizumab (TNX-650) (Thomson et al., *Biologics* 6:329-335, 2012; and Hanania et al., *Thorax* 70(8):748-756, 2015). In some embodiments, the IL-13 inhibitor is an anti-IL-13 antibody, e.g., GSK679586 or a variant thereof (Hodsman et al., *Br. J. Clin. Pharmacol.* 75(1):118-128, 2013; and De Boever et al., *J. Allergy Clin. Immunol.* 133(4):989-996, 2014). In some embodiments, the IL-13 inhibitor is tralokinumab (CAT-354) or a variant thereof (Brightling et al., *Lancet* 3(9): 692-701, 2015; Walsh et al. (2010) *Curr. Opin. Investig. Drugs* 11(11):1305-1312, 2010; Piper et al., *Euro. Resp. J.* 41:330-338, 2013; May et al., *Br. J. Pharmacol.* 166(1): 177-193, 2012; Singh et al., *BMC Pulm Med.* 10:3, 2010; Blanchard et al., *Clin. Exp. Allergy* 35(8): 1096-1103, 2005). In some embodiments, the Il-13 inhibitor is anrukinzumab (IMA-638) (Hua et al., *Br. J. Clin. Pharmacol.* 80: 101-109, 2015; Reinisch et al., *Gut* 64(6): 894-900, 2015; Gauvreau et al., *Am. J. Respir. Crit. Care Med.* 183(8):1007-1014, 2011; Bree et al., *J. Allergy Clin. Immunol.* 119(5):1251-1257, 2007). Further teachings of IL-13 inhibitors that are antibodies or antigen-binding fragments thereof are described in U.S. Pat. Nos. 8,067,199; 7,910,708; 8,221,752; 8,388,965; 8,399,630; and 8,734,801; US 2014/0341913; US 2015/0259411; US 2016/0075777; US 2016/0130339, US 2011/0243928, and US 2014/0105897 each of which is incorporated by reference in its entirety.

IL-13 Inhibitor Fusion Proteins

In some embodiments, the IL-13 inhibitor is a fusion protein or a soluble antagonist. In some embodiments, the fusion protein comprises a soluble fragment of a receptor of IL-13 (e.g., a soluble fragment of a complex including IL-13Rα1 and IL-4Rα, a soluble fragment of a complex including IL-13Rα1 and IL-13Rα2, a soluble fragment of IL-13Rα1, a soluble fragment of IL-13Rα2, or soluble fragment of IL-4Rα). In some embodiments, the fusion protein comprises an extracellular domain of a receptor of IL-13 (e.g., a fusion protein including an extracellular domain of both IL-13Rα1 and IL-4Rα, a fusion protein including an extracellular domain of both IL-13Rα1 and IL-13Rα2, a fusion protein including an extracellular domain of IL-13Rα1, a fusion protein including an extracellular domain of IL-13Rα2, or a fusion protein including an extracellular domain of IL-4Rα).

In some embodiments, the fusion protein comprises or consists of sIL-13Rα2-Fc (see, e.g., Chiaramonte et al., *J. Clin. Invest.* 104(6):777-785, 1999; Kasaian et al., *Am. J. Respir. Cell. Mol. Biol.* 36(3):368-376, 2007; Miyahara et al., *J. Allergy Clin. Immunol.* 118(5):1110-1116, 2006; Rahaman et al., *Cancer Res.* 62(4):1103-1109, 2002; incorporated by reference herein). In some embodiments, the fusion protein comprises or consists of an IL-13 fusion cytotoxin (e.g., IL-13/diphtheria toxin fusion protein (Li et al., *Protein Eng.* 15(5):419-427, 2002), IL-13-PE38QQR (IL-13-PE) (Blease et al. (2001) *J. Immunol.* 167(11):6583-6592, 2001; and Husain et al., *J. Neuro-Oncol.* 65(1):37-48, 2003)).

CD3 Inhibitors

In some embodiments, the therapeutic suitable for use with the devices and methods described herein is a CD3 inhibitor. The term "CD3 inhibitor" refers to an agent which decreases the ability of one or more of CD3γ, CD3δ, CD3ε, and CD3ζ to associate with one or more of TCR-α, TCR-β, TCR-δ, and TCR-γ. In some embodiments, the CD3 inhibitor can decrease the association between one or more of CD3γ, CD3δ, CD3ε, and CD3ζ and one or more of TCR-α, TCR-β, TCR-δ, and TCR-γ by blocking the ability of one or more of CD3γ, CD3δ, CD3ε, and CD3ζ to interact with one or more of TCR-α, TCR-β, TCR-δ, and TCR-γ.

In some embodiments, the CD3 inhibitor is an antibody or an antigen-binding fragment thereof, a fusion protein, or a small molecule. Exemplary CD3 inhibitors are described herein. Additional examples of CD3 inhibitors are known in the art.

CD3 Inhibitor Antibodies

In some embodiments, the CD3 inhibitor is an antibody or an antigen-binding fragment thereof (e.g., a Fab or a scFv). In some embodiments, the CD3 inhibitor is an antibody or antigen-binding fragment that binds specifically to CD3γ. In some embodiments, the CD3 inhibitor is an antibody or antigen-binding fragment that binds specifically to CD3δ. In some embodiments, the CD3 inhibitor is an antibody or antigen-binding fragment that binds specifically to CD3F. In some embodiments, the CD3 inhibitor is an antibody or antigen-binding fragment that binds specifically to CD3ζ. In some embodiments, the CD3 inhibitor is an antibody or an antigen-binding fragment that can bind to two or more (e.g., two, three, or four) of CD3γ, CD3δ, CD3ε, and CD3ζ.

In certain embodiments, the antibody comprises or consists of an antigen-binding fragment or portion of visiluzumab (Nuvion; HuM-291; M291; SMART anti-CD3 antibody) (Carpenter et al., *Biol. Blood Marrow Transplant* 11(6): 465-471, 2005; Trajkovic *Curr. Opin. Investig. Drugs* 3(3): 411-414, 2002; Malviya et al., *J. Nucl. Med.* 50(10): 1683-1691, 2009); muromonab-CD3 (orthoclone OKT3) (Hori et al., *Surg. Today* 41(4): 585-590, 2011; Norman *Ther. Drug Monit.* 17(6): 615-620, 1995; and Gramatzki et al., *Leukemia* 9(3): 382-390, 19); otelixizumab (TRX4) (Vossenkamper et al., *Gastroenterology* 147(1): 172-183, 2014; and Wiczling et al., *J. Clin. Pharmacol.* 50(5): 494-506, 2010); foralumab (NI-0401) (Ogura et al., *Clin. Immunol.* 183: 240-246; and van der Woude et al., *Inflamm. Bowel Dis.* 16: 1708-1716, 2010); ChAgly CD3; teplizumab (MGA031) (Waldron-Lynch et al., *Sci. Transl. Med.* 4(118): 118ra12, 2012; and Skelley et al., *Ann. Pharmacother.* 46(10): 1405-1412, 2012); or catumaxomab (Removab®) (Linke et al., *Mabs* 2(2): 129-136, 2010; and Bokemeyer et al., *Gastric Cancer* 18(4): 833-842, 2015).

Additional examples of CD3 inhibitors that are antibodies or antibody fragments are described in, e.g., U.S. Patent Application Publication Nos. 2017/0204194, 2017/0137519, 2016/0368988, 2016/0333095, 2016/0194399, 2016/0168247, 2015/0166661, 2015/0118252, 2014/0193399, 2014/0099318, 2014/0088295, 2014/0080147, 2013/0115213, 2013/0078238, 2012/0269826, 2011/0217790, 2010/0209437, 2010/0183554, 2008/0025975, 2007/0190045, 2007/0190052, 2007/0154477, 2007/0134241, 2007/0065437, 2006/0275292, 2006/0269547, 2006/0233787, 2006/0177896, 2006/0165693, 2006/0088526, 2004/0253237, 2004/0202657, 2004/0052783, 2003/0216551, and 2002/0142000, each of which is herein incorporated by reference in its entirety (e.g., the sections describing the CD3 inhibitors). Additional CD3 inhibitors that are antibodies or antigen-binding antibody fragments are described in, e.g., Smith et al., *J. Exp. Med.* 185(8):1413-1422, 1997; Chatenaud et al., *Nature* 7:622-632, 2007.

In some embodiments, the CD3 inhibitor comprises or consists of a bispecific antibody (e.g., JNJ-63709178) (Gaudet et al., *Blood* 128(22): 2824, 2016); JNJ-64007957 (Girgis et al., *Blood* 128: 5668, 2016); MGD009 (Tolcher et al., *J. Clin. Oncol.* 34:15, 2016); ERY974 (Ishiguro et al., *Sci. Transl. Med.* 9(410): pii.eaa14291, 2017); AMV564 (Hoseini and Cheung *Blood Cancer J.* 7:e522, 2017); AFM11 (Reusch et al., *MAbs* 7(3): 584-604, 2015); duvortuxizumab (JNJ 64052781); R06958688; blinatumomab (Blincyto®; AMG103) (Ribera *Expert Rev. Hematol.* 1:1-11, 2017; and Mori et al., *N Engl. J. Med.* 376(23):e49, 2017); XmAb13676; or REGN1979 (Bannerji et al., *Blood* 128: 621, 2016; and Smith et al., *Sci. Rep.* 5:17943, 2015)).

In some embodiments, the CD3 inhibitor comprises or consists of a trispecific antibody (e.g., ertumaxomab (Kiewe and Thiel, *Expert Opin. Investig. Drugs* 17(10): 1553-1558, 2008; and Haense et al., *BMC Cancer* 16:420, 2016); or FBTA05 (Bi20; Lymphomun) (Buhmann et al., *J. Transl. Med.* 11:160, 2013; and Schuster et al., *Br. J. Haematol.* 169(1): 90-102, 2015)).

CD3 Inhibitor Fusion and Truncated Proteins and Peptides

In some embodiments, the CD3 inhibitor is a fusion protein, a truncated protein (e.g., a soluble receptor), or a peptide. In some embodiments, the CD3 inhibitor can be a fusion protein (see, e.g., Lee et al., *Oncol. Rep.* 15(5): 1211-1216, 2006).

CD3 Inhibitor Small Molecules

In some embodiments, the CD3 inhibitor comprises or consists of a bispecific small molecule-antibody conjugate (see, e.g., Kim et al., *PNAS* 110(44): 17796-17801, 2013; Viola et al., *Eur. J. Immunol.* 27(11):3080-3083, 1997).

CD14 Inhibitors

In some embodiments, the therapeutic suitable for use with the devices and methods described herein is a CD14 inhibitor. The term "CD14 inhibitors" refers to an agent which decreases the ability of CD14 to bind to lipopolysaccharide (LPS). CD14 acts as a co-receptor with Toll-like receptor 4 (TLR4) that binds LPS in the presence of lipopolysaccharide-binding protein (LBP).

In some embodiments, the CD14 inhibitor can decrease the binding between CD14 and LPS by blocking the ability of CD14 to interact with LPS.

In some embodiments, the CD14 inhibitor is an antibody or an antigen-binding fragment thereof. In some embodiments, the CD14 inhibitor is a small molecule. Exemplary CD14 inhibitors are described herein. Additional examples of CD14 inhibitors are known in the art.

CD14 Inhibitor Antibodies

In some embodiments, the CD14 inhibitor is an antibody or an antigen-binding fragment thereof (e.g., a Fab or a scFv). In some embodiments, the CD14 inhibitor is an antibody or antigen-binding fragment that binds specifically to CD14.

In certain embodiments, the antibody comprises or consists of an antigen-binding fragment or portion of IC14 (Axtelle and Pribble, *J. Endotoxin Res.* 7(4): 310-314, 2001; Reinhart et al., *Crit. Care Med.* 32(5): 1100-1108, 2004; Spek et al., *J. Clin. Immunol.* 23(2): 132-140, 2003). Additional examples of anti-CD14 antibodies and CD14 inhibitors can be found, e.g., in WO 2015/140591 and WO 2014/122660, incorporated in its entirety herein.

Additional examples of CD14 inhibitors that are antibodies or antibody fragments are described in, e.g., U.S. Patent Application Serial No. 2017/0107294, 2014/0050727, 2012/0227412, 2009/0203052, 2009/0029396, 2008/0286290, 2007/0106067, 2006/0257411, 2006/0073145, 2006/0068445, 2004/0092712, 2004/0091478, and 2002/0150882, each of which is herein incorporated by reference (e.g., the sections that describe CD14 inhibitors).

CD14 Inhibitor Small Molecules

In some embodiments, the CD14 inhibitor is a small molecule. Non-limiting examples of CD14 inhibitors that are small molecules are described in, e.g., methyl 6-deoxy-6-N-dimethyl-N-cyclopentylammonium-2, 3-di-O-tetradecyl-α-D-glucopyranoside iodide (IAXO-101); methyl 6-Deoxy-6-amino-2,3-di-O-tetradecyl-α-D-glucopyranoside (IAXO-102); N-(3,4-bis-tetradecyloxy-benzyl)-N-cyclopentyl-N,N-dimethylammonium iodide (IAXO-103); and IMO-9200.

CD20 Inhibitors

In some embodiments, the therapeutic suitable for use with the devices and methods described herein is a CD20 inhibitor. The term "CD20 inhibitors" refers to an agent that binds specifically to CD20 expressed on the surface of a mammalian cell.

In some embodiments, the CD20 inhibitor is an antibody or an antigen-binding fragment thereof, or a fusion protein or peptide. Exemplary CD20 inhibitors are described herein. Additional examples of CD20 inhibitors are known in the art.

CD20 Inhibitor Antibodies

In some embodiments, the CD20 inhibitor is an antibody or an antigen-binding fragment thereof (e.g., a Fab or a scFv).

In certain embodiments, the antibody comprises or consists of an antigen-binding fragment or portion of rituximab (Rituxan®, MabThera®, MK-8808) (Ji et al., *Indian J. Hematol. Blood Transfus.* 33(4): 525-533, 2017; and Calderon-Gomez and Panes *Gastroenterology* 142(1): 1741-76, 2012); —PF-05280586; ocrelizumab (Ocrevus™) (Sharp *N. Engl. J. Med.* 376(17): 1692, 2017); ofatumumab (Arzerra®; HuMax-CD20) (AlDallal *Ther. Clin. Risk Manag.* 13:905-907, 2017; and Furman et al., *Lancet Haematol.* 4(1): e24-e34, 2017); PF-05280586 (Williams et al., *Br. J. Clin. Pharmacol.* 82(6): 1568-1579, 2016; and Cohen et al., *Br. J. Clin. Pharmacol.* 82(1): 129-138, 2016); obinutuzumab (Gazyva®) (Reddy et al., *Rheumatology* 56(7): 1227-1237, 2017; and Marcus et al., *N. Engl. J. Med.* 377(14): 1331-1344, 2017); ocaratuzumab (AME-133v; LY2469298) (Cheney et al., *Mabs* 6(3): 749-755, 2014; and Tobinai et al., *Cancer Sci.* 102(2): 432-8, 2011); GP2013 (Jurczak et al., *Lancet Haenatol.* 4(8): e350-e361, 2017); BI301; HLXO1; veltuzumab (hA20) (Kalaycio et al., *Leuk. Lymphoma* 57(4): 803-811, 2016; and Ellebrecht et al., *JAMA Dermatol.* 150(12): 1331-1335, 2014); SCT400 (Gui et al., *Chin. J. Cancer Res.* 28(2): 197-208); ibritumomab tiuxetan (Zevalin®) (Philippe et al., *Bone Marrow Transplant* 51(8): 1140-1142, 2016; and Lossos et al., *Leuk. Lymphoma* 56(6): 1750-1755, 2015); ublituximab (TG1101) (Sharman et al., *Blood* 124: 4679, 2014; and Sawas et al., *Br. J. Haematol.* 177(2): 243-253, 2017); LFB-R603 (Esteves et al., *Blood* 118: 1660, 2011; and Baritaki et al., *Int. J. Oncol.* 38(6): 1683-1694, 2011); or tositumomab (Bexxar) (Buchegger et al., *J. Nucl. Med.* 52(6): 896-900, 2011; and William and Bierman *Expert Opin. Biol. Ther.* 10(8): 1271-1278, 2010). Additional examples of CD20 antibodies are known in the art (see, e.g., WO 2008/156713).

In certain embodiments, the antibody comprises or consists of an antigen-binding fragment or portion of a bispecific antibody (e.g., XmAbl3676; REGN1979 (Bannerji et al., *Blood* 128: 621, 2016; and Smith et al., *Sci. Rep.* 5: 17943, 2015); PRO131921 (Casulo et al., *Clin. Immnol.* 154(1): 37-46, 2014; and Robak and Robak *BioDrugs* 25(1): 13-25, 2011); or Acellbia).

In some embodiments, the CD20 inhibitor comprises or consists of a trispecific antibody (e.g., FBTA05 (Bi20; Lymphomun) (Buhmann et al., *J. Transl. Med.* 11:160, 2013; and Schuster et al., *Br. J. Haematol.* 169(1): 90-102, 2015)).

Additional examples of CD20 inhibitors that are antibodies or antigen-binding fragments are described in, e.g., U.S. Patent Application Publication Nos. 2017/0304441, 2017/0128587, 2017/0088625, 2017/0037139, 2017/0002084, 2016/0362472, 2016/0347852, 2016/0333106, 2016/0271249, 2016/0243226, 2016/0115238, 2016/0108126, 2016/0017050, 2016/0017047, 2016/0000912, 2016/0000911, 2015/0344585, 2015/0290317, 2015/0274834, 2015/0265703, 2015/0259428, 2015/0218280, 2015/0125446, 2015/0093376, 2015/0079073, 2015/0071911, 2015/0056186, 2015/0010540, 2014/0363424, 2014/0356352, 2014/0328843, 2014/0322200, 2014/0294807, 2014/0248262, 2014/0234298, 2014/0093454, 2014/0065134, 2014/0044705, 2014/0004104, 2014/0004037, 2013/0280243, 2013/0273041, 2013/0251706, 2013/0195846, 2013/0183290, 2013/0089540, 2013/0004480, 2012/0315268, 2012/0301459, 2012/0276085, 2012/0263713, 2012/0258102, 2012/0258101, 2012/0251534, 2012/0219549, 2012/0183545, 2012/0100133, 2012/0034185, 2011/0287006, 2011/0263825, 2011/0243931, 2011/0217298, 2011/0200598, 2011/0195022, 2011/0195021, 2011/0177067, 2011/0165159, 2011/0165152, 2011/0165151, 2011/0129412, 2011/0086025, 2011/0081681, 2011/0020322, 2010/0330089, 2010/0310581, 2010/0303808, 2010/0183601, 2010/0080769, 2009/0285795, 2009/0203886, 2009/0197330, 2009/0196879, 2009/0191195, 2009/0175854, 2009/0155253, 2009/0136516, 2009/0130089, 2009/0110688, 2009/0098118, 2009/0074760, 2009/0060913, 2009/0035322, 2008/0260641, 2008/0213273, 2008/0089885, 2008/0044421, 2008/0038261, 2007/0280882, 2007/0231324, 2007/0224189, 2007/0059306, 2007/0020259, 2007/0014785, 2007/0014720, 2006/0121032, 2005/0180972, 2005/0112060, 2005/0069545, 2005/0025764, 2004/0213784, 2004/0167319, 2004/0093621, 2003/0219433, 2003/0206903, 2003/0180292, 2003/0026804, 2002/0039557, 2002/0012665, and 2001/0018041, each herein incorporated by reference in their entirety (e.g., sections describing CD20 inhibitors).

CD20 Inhibitor Peptides and Fusion Proteins

In some embodiments, the CD20 inhibitor is an immunotoxin (e.g., MT-3724 (Hamlin *Blood* 128: 4200, 2016).

In some embodiments, the CD20 inhibitor is a fusion protein (e.g., TRU-015 (Rubbert-Roth *Curr. Opin. Mol. Ther.* 12(1): 115-123, 2010). Additional examples of CD20 inhibitors that are fusion proteins are described in, e.g., U.S. Patent Application Publication Nos. 2012/0195895, 2012/0034185, 2009/0155253, 2007/0020259, and 2003/0219433, each of which are herein incorporated by reference in their entirety (e.g., sections describing CD20 inhibitors).

CD25 Inhibitors

In some embodiments, the therapeutic suitable for use with the devices and methods described herein is a CD25 inhibitor. The term "CD25 inhibitors" refers to an agent which decreases the ability of CD25 (also called interleukin-2 receptor alpha chain) to bind to interleukin-2. CD25 forms a complex with interleukin-2 receptor beta chain and interleukin-2 common gamma chain.

In some embodiments, the CD25 inhibitor is an antibody or an antigen-binding fragment thereof, or a fusion protein. Exemplary CD25 inhibitors are described herein. Additional examples of CD25 inhibitors are known in the art.

CD25 Inhibitor Antibodies

In some embodiments, the CD25 inhibitor is an antibody or an antigen-binding fragment thereof (e.g., a Fab or a scFv). In some embodiments, a CD25 inhibitor is an antibody or an antigen-binding fragment thereof that specifically binds to CD25. In some embodiments, a CD25 inhibitor is an antibody that specifically binds to IL-2.

In certain embodiments, the antibody comprises or consists of an antigen-binding fragment or portion of basiliximab (Simulect™) (Wang et al., *Clin. Exp. Immunol.* 155(3):

496-503, 2009; and Kircher et al., *Clin. Exp. Immunol.* 134(3): 426-430, 2003); daclizumab (Zenapax; Zinbryta®) (Berkowitz et al., *Clin. Immunol.* 155(2): 176-187, 2014; and Bielekova et al., *Arch Neurol.* 66(4): 483-489, 2009); or IMTOX-25.

In some embodiments, the CD25 inhibitor is an antibody-drug-conjugate (e.g., ADCT-301 (Flynn et al., *Blood* 124: 4491, 2014)).

Additional examples of CD25 inhibitors that are antibodies are known in the art (see, e.g., WO 2004/045512). Additional examples of CD25 inhibitors that are antibodies or antigen-binding fragments are described in, e.g., U.S. Patent Application Publication Nos. 2017/0240640, 2017/0233481, 2015/0259424, 2015/0010539, 2015/0010538, 2012/0244069, 2009/0081219, 2009/0041775, 2008/0286281, 2008/0171017, 2004/0170626, 2001/0041179, and 2010/0055098, each of which is incorporated herein by reference (e.g., sections that describe CD25 inhibitors).

CD25 Inhibitor Fusion Proteins

In some embodiments, the CD25 inhibitor is a fusion protein. See, e.g., Zhang et al., *PNAS* 100(4): 1891-1895, 2003.

CD28 Inhibitors

In some embodiments, the therapeutic suitable for use with the devices and methods described herein is a CD28 inhibitor. The term "CD28 inhibitors" refers to an agent which decreases the ability of CD28 to bind to one or both of CD80 and CD86. CD28 is a receptor that binds to its ligands, CD80 (also called B7.1) and CD86 (called B7.2).

In some embodiments, the CD28 inhibitor can decrease the binding between CD28 and CD80 by blocking the ability of CD28 to interact with CD80. In some embodiments, the CD28 inhibitor can decrease the binding between CD28 and CD86 by blocking the ability of CD28 to interact with CD86. In some embodiments, the CD28 inhibitor can decrease the binding of CD28 to each of CD80 and CD86.

In some embodiments, the CD28 inhibitor is an antibody or an antigen-binding fragment thereof, a fusion protein, or peptide. Exemplary CD28 inhibitors are described herein. Additional examples of CD28 inhibitors are known in the art.

CD28 Inhibitor Antibodies

In some embodiments, the CD28 inhibitor is an antibody or an antigen-binding fragment thereof (e.g., a Fab or a scFv).

In some embodiments, the CD28 inhibitor is a monovalent Fab' antibody (e.g., CFR104) (Poirier et al., *Am. J. Transplant* 15(1): 88-100, 2015).

Additional examples of CD28 inhibitors that are antibodies or antigen-binding fragments are described in, e.g., U.S. Patent Application Publication Nos. 2017/0240636, 2017/0114136, 2016/0017039, 2015/0376278, 2015/0299321, 2015/0232558, 2015/0150968, 2015/0071916, 2013/0266577, 2013/0230540, 2013/0109846, 2013/0078257, 2013/0078236, 2013/0058933, 2012/0201814, 2011/0097339, 2011/0059071, 2011/0009602, 2010/0266605, 2010/0028354, 2009/0246204, 2009/0117135, 2009/0117108, 2008/0095774, 2008/0038273, 2007/0154468, 2007/0134240, 2007/0122410, 2006/0188493, 2006/0165690, 2006/0039909, 2006/0009382, 2006/0008457, 2004/0116675, 2004/0092718, 2003/0170232, 2003/0086932, 2002/0006403, 2013/0197202, 2007/0065436, 2003/0180290, 2017/0015747, 2012/0100139, and 2007/0148162, each of which is incorporated by reference in its entirety (e.g., sections that described CD28 inhibitors).

CD28 Inhibitor Fusion Proteins and Peptides

In some embodiments, the CD28 inhibitor is a fusion protein (see, e.g., U.S. Pat. No. 5,521,288; and US 2002/0018783). In some embodiments, the CD28 inhibitor is abatacept (Orencia®) (Herrero-Beaumont et al., *Rheumatol. Clin.* 8: 78-83, 2012; and Korhonen and Moilanen *Basic Clin. Pharmacol. Toxicol.* 104(4): 276-284, 2009).

In some embodiments, the CD28 inhibitor is a peptide mimetic (e.g., AB103) (see, e.g., Bulger et al., *JAMA Surg.* 149(6): 528-536, 2014), or a synthetic peptoid (see, e.g., Li et al., *Cell Mol. Immunol.* 7(2): 133-142, 2010).

CD40/CD40L Inhibitors

In some embodiments, the therapeutic suitable for use with the devices and methods described herein is a CD40/CD40L inhibitor. The term "CD40/CD40L inhibitors" refers to an agent which decreases CD40 or CD40L (CD154) expression and/or the ability of CD40 to bind to CD40L (CD154). CD40 is a costimulatory receptor that binds to its ligand, CD40L (CD154).

In some embodiments, the CD40/CD40L inhibitor can decrease the binding between CD40 and CD40L by blocking the ability of CD40 to interact with CD40L. In some embodiments, the CD40/CD40L inhibitor can decrease the binding between CD40 and CD40L by blocking the ability of CD40L to interact with CD40. In some embodiments, the CD40/CD40L inhibitor decreases the expression of CD40 or CD40L. In some embodiments, the CD40/CD40L inhibitor decreases the expression of CD40. In some embodiments, the CD40/CD40L inhibitor decreases the expression of CD40L.

In some embodiments, the CD40/CD40L inhibitor is an inhibitory nucleic acid, an antibody or an antigen-binding fragment thereof, a fusion protein, or a small molecule. In some embodiments, the inhibitory nucleic acid is a small interfering RNA, an antisense nucleic acid, an aptamer, or a microRNA. Exemplary CD40/CD40L inhibitors are described herein. Additional examples of CD40/CD40L inhibitors are known in the art.

Inhibitory Nucleic Acids of CD40/CD40L

Some exemplary antisense nucleic acids that are CD40 or CD40L inhibitors are described, e.g., in U.S. Pat. Nos. 6,197,584 and 7,745,609; Gao et al., *Gut* 54(1):70-77, 2005; Arranz et al., *J. Control Release* 165(3):163-172, 2012; Donner et al., *Mol. Ther. Nucleic Acids* 4:e265, 2015.

Non-limiting examples of short interfering RNA (siRNA) that are CD40/CD40L inhibitors are described in, e.g., Pluvinet et al., *Blood* 104:3642-3646, 2004; Karimi et al., *Cell Immunol.* 259(1):74-81, 2009; and Zheng et al., *Arthritis Res. Ther.* 12(1):R13, 2010. Non-limiting examples of short hairpin RNA (shRNA) targeting CD40/CD40L are described in Zhang et al., *Gene Therapy* 21:709-714, 2014. Non-limiting examples of microRNAs that are CD40/CD40L inhibitors include, for example, miR146a (Chen et al., *FEBS Letters* 585(3):567-573, 2011), miR-424, and miR-503 (Lee et al., *Sci. Rep.* 7:2528, 2017).

Non-limiting examples of aptamers that are CD40/CD40L inhibitors are described in Soldevilla et al., *Biomaterials* 67:274-285, 2015.

CD40/CD40L Inhibitor Antibodies

In certain embodiments, the antibody comprises or consists of an antigen-binding fragment or portion of PG102 (Pangenetics) (Bankert et al., *J. Immunol.* 194(9):4319-4327, 2015); 2C10 (Lowe et al., *Am. J. Transplant* 12(8): 2079-2087, 2012); ASKP1240 (Bleselumab) (Watanabe et al., *Am. J. Transplant* 13(8):1976-1988, 2013); 4D11 (Imai et al., *Transplantation* 84(8):1020-1028, 2007); BI 655064 (Boehringer Ingelheim) (Visvanathan et al., 2016 American College of Rheumatology Annual Meeting, Abstract 1588, Sep. 28, 2016); 5D12 (Kasran et al., *Aliment. Pharmacol. Ther.*, 22(2):111-122, 2005; Boon et al., *Toxicology* 174(1): 53-65, 2002); ruplizumab (hu5c8) (Kirk et al., *Nat. Med.* 5(6):686-693, 1999); CHIR12.12 (HCD122) (Weng et al., *Blood* 104(11):3279, 2004; Tai et al., *Cancer Res.* 65(13): 5898-5906, 2005); CDP7657 (Shock et al., *Arthritis Res. Ther.* 17(1):234, 2015); BMS-986004 domain antibody (dAb) (Kim et al., *Am. J Transplant.* 17(5):1182-1192, 2017); 5c8 (Xie et al., *J. Immunol.* 192(9):4083-4092, 2014); dacetuzumab (SGN-40) (Lewis et al., *Leukemia* 25(6):1007-1016, 2011; and Khubchandani et al., *Curr. Opin. Investig. Drugs* 10(6):579-587, 2009); lucatumumab (HCD122) (Bensinger et al., *Br. J. Haematol.* 159: 58-66, 2012; and Byrd et al., *Leuk. Lymphoma* 53(11): 10.3109/10428194.2012.681655, 2012); PG102 (FFP104) (Bankert et al., *J. Immunol.* 194(9):4319-4327, 2015); Chi Lob 7/4 (Johnson et al., *J. Clin. Oncol.* 28:2507, 2019); and ASKP1240 (Okimura et al., *Am. J. Transplant.* 14(6): 1290-1299, 2014; or Ma et al., *Transplantation* 97(4): 397-404, 2014).

Further teachings of CD40/CD40L antibodies and antigen-binding fragments thereof are described in, for example, U.S. Pat. Nos. 5,874,082; 7,169,389; 7,271,152; 7,288,252; 7,445,780; 7,537,763, 8,277,810; 8,293,237, 8,551,485; 8,591,900; 8,647,625; 8,784,823; 8,852,597; 8,961,976; 9,023,360, 9,028,826; 9,090,696, 9,221,913; US2014/0093497; and US2015/0017155 each of which is incorporated by reference in its entirety.

CD40/CD40L Inhibitor Fusion and Truncated Proteins and Peptides

In some embodiments, the CD40/CD40L inhibitor is a fusion protein, a truncated protein (e.g., a soluble receptor) or a peptide. In some embodiments, the CD40/CD40L inhibitor is a truncated protein as disclosed in, for example, WO 01/096397. In some embodiments, the CD40/CD40L inhibitor is a peptide, such as a cyclic peptide (see, e.g., U.S. Pat. No. 8,802,634; Bianco et al., *Org. Biomol. Chem.* 4:1461-1463, 2006; Deambrosis et al., *J. Mol. Med.* 87(2): 181-197, 2009; Vaitaitis et al., *Diabetologia* 57(11):2366-2373, 2014). In some embodiments, the CD40/CD40L inhibitor is a CD40 ligand binder, for example, a Tumor Necrosis Factor Receptor-associated Factor (TRAF): TRAF2, TRAF3, TRAF6, TRAF5 and TTRAP, or E3 ubiquitin-protein ligase RNF128.

CD40/CD40L Inhibitor Small Molecules

In some embodiments, the CD40/CD40L inhibitor is a small molecule (see, e.g., U.S. Pat. No. 7,173,046, U.S. Patent Application No. 2011/0065675). In some embodiments, the small molecule is Bio8898 (Silvian et al., *ACS Chem. Biol.* 6(6):636-647, 2011); Suramin (Margolles-Clark et al., *Biochem. Pharmacol.* 77(7):1236-1245, 2009); a small-molecule organic dye (Margolles-Clark et al., *J. Mol. Med.* 87(11):1133-1143, 2009; Buchwald et al., *J. Mol. Recognit.* 23(1):65-73, 2010), a naphthalenesulfonic acid derivative (Margolles-Clark et al., *Chem. Biol. Drug Des.* 76(4):305-313, 2010), or a variant thereof.

CD49 Inhibitors

In some embodiments, the therapeutic suitable for use with the devices and methods described herein is a CD49 inhibitor. The term "CD49 inhibitors" refers to an agent which decreases the ability of CD49 to bind to one of its ligands (e.g., MMP1). In some embodiments, the CD49 inhibitor is an antibody or an antigen-binding fragment thereof. Exemplary CD49 inhibitors are described herein. Additional examples of CD49 inhibitors are known in the art.

CD49 Inhibitor Antibodies

In some embodiments, the CD49 inhibitor is an antibody or an antigen-binding fragment thereof (e.g., a Fab or a scFv).

In certain embodiments, the antibody comprises or consists of an antigen-binding fragment or portion of natalizumab (Tysabri®; Antegren®) (see, e.g., Pagnini et al., *Expert Opin. Biol. Ther.* 17(11): 1433-1438, 2017; and Chataway and Miller *Neurotherapeutics* 10(1): 19-28, 2013; or vatelizumab (ELND-004)).

CD89 Inhibitors

In some embodiments, the therapeutic suitable for use with the devices and methods described herein is a CD89 inhibitor. The term "CD89 inhibitors" refers to an agent which decreases the ability of CD89 to bind to IgA. CD89 is a transmembrane glycoprotein that binds to the heavy-chain constant region of IgA. In some embodiments, the CD89 inhibitor can decrease the binding between CD89 and IgA by blocking the ability of CD89 to interact with IgA. In some embodiments, the CD89 inhibitor is an antibody or an antigen-binding fragment thereof. Exemplary CD89 inhibitors are described herein. Additional examples of CD89 inhibitors are known in the art.

CD89 Inhibitor Antibodies

In some embodiments, the CD89 inhibitor is an antibody or an antigen-binding fragment thereof (e.g., a Fab or a scFv).

In certain embodiments, the antibody comprises or consists of an antigen-binding fragment or portion of HF-1020. Additional examples of CD89 antibodies are known in the art (see, e.g., WO 2002/064634).

Integrin Inhibitors

In some embodiments, the therapeutic suitable for use with the devices and methods described herein is an integrin inhibitor. The term "integrin inhibitor" refers to an agent which decreases the expression of one or more integrins and/or decreases the binding of an integrin ligand to one or more integrins that play a role in the recruitment, extravasation, and/or activation of a leukocyte. In some embodiments, the integrin inhibitor specifically binds to at least a portion of a ligand binding site on a target integrin. In some embodiments, the integrin inhibitor specifically binds to a target integrin at the same site as an endogenous ligand. In some embodiments, the integrin inhibitor decreases the level of expression of the target integrin in a mammalian cell. In some embodiments, the integrin inhibitor specifically binds to an integrin ligand.

Non-limiting examples of integrins that can be targeted by any of the integrin inhibitors described herein include: α2β1 integrin, α1β1 integrin, α4β7 integrin, integrin α4β1 (VLA-4), E-selectin, ICAM-1, α5β1 integrin, α4β1 integrin, VLA-4, α2β1 integrin, α5β3 integrin, α5β5 integrin, αIIbβ3 integrin, and MAdCAM-1. A non-limiting example of integrin inhibitor that can decrease the expression and/or activity of α4β7 integrin is FTY720. A non-limiting example of an integrin inhibitor that specifically targets MAdCAM is PF-547659 (Pfizer). Non-limiting examples of an integrin inhibitor that specifically targets α4β7 is AJM300 (Ajinomoto), etrolizumab (Genentech), and vedolizumab (Millenium/Takeda).

In some embodiments, the integrin inhibitor is an αIIbβ3 integrin inhibitor. In some embodiments, the αIIbβ3 integrin inhibitor is abciximab (ReoPro®, c7E3; Kononczuk et al., *Curr. Drug Targets* 16(13):1429-1437, 2015; Jiang et al., *Appl. Microbiol. Biotechnol.* 98(1):105-114, 2014), eptifibatide (Integrilin®; Scarborough et al., *J. Biol. Chem.* 268: 1066-1073, 1993; Tcheng et al., *Circulation* 91:2151-2157, 1995) or tirofiban (Aggrastat®; Hartman et al., *J. Med. Chem.* 35:4640-4642, 1992; Pierro et al., *Eur. J. Ophthalmol.* 26(4):e74-76, 2016; Guan et al., *Eur. J. Pharmacol* 761:144-152, 2015). In some embodiments, the integrin inhibitor is an αL-selective integrin inhibitor. In some embodiments, the integrin inhibitor is a β2 integrin inhibitor.

In some embodiments, the integrin inhibitor is an α4 integrin (e.g., an α4β1 integrin (e.g., Very Late Antigen-4 (VLA-4), CD49d, or CD29)) inhibitor, an α4β7 integrin inhibitor. In some embodiments, the integrin inhibitor targets endothelial VCAM1, fibronectin, mucosal addressin cellular adhesion molecule-1 (MAdCAM-1), vitronectin, tenascin-C, osteopontin (OPN), nephronectin, agiostatin, tissue-type transglutaminase, factor XIII, Von Willebrand factor (VWF), an ADAM protein, an ICAM protein, collagen, e-cadherin, laminin, fibulin-5, or TGFβ. In some embodiments, the α4 integrin inhibitor is natalizumab (Tysabri®; Targan et al., *Gastroenterology* 132(5):1672-1683, 2007; Sandborn et al., *N. Engl. J. Med.* 353(18):1912-1925, 2005; Nakamura et al., *Intern. Med.* 56(2):211-214, 2017; and Singh et al., *J. Pediatr. Gastroenterol. Nutr.* 62(6):863-866, 2016). In some embodiments, the integrin inhibitor is an endogenous integrin inhibitor (e.g., SHARPIN (Rantala et al., *Nat. Cell. Biol.* 13(11):1315-1324, 2011).

In some embodiments, the integrin inhibitor is an αv integrin (e.g., an α5β1 integrin, an α5β3 integrin, an α5β5 integrin inhibitor, and/or an α5β6 integrin) inhibitor.

In some embodiments, the integrin inhibitor is an α5β1 integrin inhibitor.

In some embodiments, an integrin inhibitor is an inhibitory nucleic acid, an antibody or antigen-binding fragment thereof, a fusion protein, an integrin antagonist, a cyclic peptide, a disintegrin, a peptidomimetic, or a small molecule. In some embodiments, the inhibitory nucleic acid is a small hairpin RNA, a small interfering RNA, an antisense, an aptamer, or a microRNA.

Inhibitory Nucleic Acids of Integrins

In some embodiments, the inhibitory nucleic acid can be an antisense nucleic acid, a ribozyme, a small interfering RNA, a small hairpin RNA, or a microRNA. Examples of aspects of these different inhibitory nucleic acids are described below.

Exemplary integrin inhibitors that are antisense nucleic acids include ATL1102 (e.g., Limmroth et al., *Neurology* 83(20):1780-1788, 2014; Li et al., *Dig. Liver Dis.* 39(6):557-565, 2007; Goto et al., *Inflamm. Bowel Dis.* 12(8):758-765, 2006).

Non-limiting examples of integrin inhibitors that are short interfering RNAs (siRNAs) are described in Wang et al., *Cancer Cell Int.* 16:90, 2016). In some embodiments, the integrin inhibitor is a short hairpin RNA (shRNA).

Non-limiting examples of integrin inhibitors that are microRNA include miR-124 (Cai et al., *Sci. Rep.* 7:40733, 2017), miR-134 (Qin et al., *Oncol. Rep.* 37(2):823-830, 2017), miR-92b (Ma et al., *Oncotarget* 8(4):6681-6690, 2007), miR-17 (Gong et al., *Oncol. Rep.* 36(4), 2016), miR-338 (Chen et al., *Oncol. Rep.* 36(3):1467-74, 2016), and miR-30a-5p (Li et al., *Int. J. Oncol.* 48(3):1155-1164, 2016).

In some embodiments, the integrin inhibitor can include modified bases/locked nucleic acids (LNAs). In some embodiments, the integrin inhibitor is an aptamer (e.g., Berg et al., *Mol. Ther. Nucl. Acids* 5:e294, 2016; and Hussain et al., *Nucleic Acid Ther.* 23(3):203-212, 2013). Additional examples of integrin inhibitors that are inhibitory nucleic acids are described in Juliano et al., *Theranostics* 1:211-219, 2011; Millard et al., *Theranostics* 1:154-188, 2011; and Teoh et al., *Curr. Mol. Med.* 15:714-734, 2015. In some embodiments, the integrin inhibitor is an antisense nucleic acid, e.g., alicaforsen (Yacyshyn et al., *Clin. Gastroenterol. Hepatol.* 5(2):215-220, 2007).

Integrin Inhibitor Antibodies

In some embodiments, the antibody is a pan-31 antibody (e.g., OS2966 (Carbonell et al., *Cancer Res.* 73(10):3145-3154, 2013). In some embodiments, the integrin antibody is a monoclonal antibody (e.g., 17E6 (Castel et al., *Eur. J. Cell. Biol.* 79(7):502-512, 2000); Mitjans et al., *Int. J. Cancer* 87(5):716-723, 2000)). In some embodiments, the monoclonal antibody is vedolizumab (e.g., Entyvio®) or a variant thereof (Feagan et al., *N. Engl. J. Med.* 369:699-710, 2013; Sandborn et al., *N. Engl. J. Med.* 369:711-721, 2013; Sands et al., *Gastroenterology* 147:618-627, 2014; and Milch et al., *Neuroimmunol.* 264:123-126, 2013; Wyant et al., *J. Crohns Colitis* 10(12):1437-1444, 2016; and Feagan et al., *Gastroenterology* 142(5):S160-S161, 2012).

In some embodiments, the antibody can be a Fab fragment of a monoclonal chimeric mouse-human antibody (e.g., abciximab (ReoPro, c7E3), Kononczuk et al., *Curr. Drug Targets* 16(13):1429-1437, 2015; Jiang et al., *Appl. Microbiol. Biotechnol.* 98(1):105-114, 2014), or a variant thereof. In some embodiments, the integrin antibody is a humanized monoclonal antibody. In some embodiments, the humanized monoclonal antibody is natalizumab (Tysabri®) (Targan et al., *Gastroenterology* 132(5):1672-1683, 2007; Sandborn et al., *N. Engl. J. Med.* 353(18):1912-1925, 2005; Nakamura et al., *Intern Med.* 56(2):211-214, 2017; Singh et al., *J. Pediatr. Gastroenterol. Nutr.* 62(6):863-866, 2016). In some embodiments, the humanized monoclonal antibody is vitaxin (EDI-523) or a variant thereof (Huveneers et al., *Int. J. Radiat. Biol.* 81(11-12):743-751, 2007; Coleman et al., *Circ. Res.* 84(11):1268-1276, 1999). In some embodiments, the humanized monoclonal antibody is etaracizumab (Abegrin®, MEDI-522, LM609) or a variant thereof (Hersey et al., *Cancer* 116(6):1526-1534, 2010; Delbaldo et al., *Invest New Drugs* 26(1):35-43, 2008). In some embodiments, the humanized monoclonal antibody is CNTO95 (Intetumumab®) or a variant thereof (Jia et al., *Anticancer Drugs* 24(3):237-250, 2013; Heidenreich et al., *Ann. Oncol.* 24(2):329-336, 2013; Wu et al., *J. Neurooncol.* 110(1):27-36, 2012). In some embodiments, the humanized monoclonal antibody is efalizumab (Raptiva®) or a variant thereof (Krueger et al., *J. Invest. Dermatol.* 128(11):2615-2624, 2008; Li et al., *PNAS* 106(11):4349-4354, 2009; Woolacott et al., *Health Technol. Assess* 10:1-233, 2006). In some embodiments, the humanized monoclonal antibody is STX-100 (Stromedix®) or a variant thereof (van Aarsen et al., *Cancer Res.* 68:561-570, 2008; Lo et al., *Am. J. Transplant.* 13(12):3085-3093, 2013). In some embodiments, the humanized monoclonal antibody is 264RAD or a variant thereof (Eberlein et al., *Oncogene* 32(37):4406-4417, 2013).

In some embodiments, the humanized monoclonal antibody is rovelizumab or a variant thereof (Goodman et al., *Trends Pharmacol. Sci* 33:405-412, 2012). In some embodiments, the humanized monoclonal antibody is Cytolin® or a variant thereof (Rychert et al., *Virology J.* 10:120, 2013). In some embodiments, the humanized monoclonal antibody is etrolizumab or a variant thereof (Vermeire et al., *Lancet* 384:309-318, 2014; Rutgeerts et al., *Gut* 62:1122-1130, 2013; Lin et al., *Gastroenterology* 146:307-309, 2014; Ludviksson et al., *J. Immunol.* 162(8):4975-4982, 1999; Stefanich et al., *Br. J. Pharmacol.* 162(8):1855-1870, 2011). In some embodiments, the humanized monoclonal antibody is abrilumab (AMG 181; MEDI-7183) or a variant thereof (Pan et al., *Br. J. Pharmacol.* 169(1):51-68, 2013; Pan et al., *Br. J. Clin. Pharmacol.* 78(6):1315-1333, 2014). In some embodiments, the humanized monoclonal antibody is PF-00547659 (SHP647) or a variant thereof (Vermeire et al., *Gut* 60(8):1068-1075, 2011; Sandborn et al., *Gastroenterology* 1448(4):S-162, 2015). In some embodiments, the humanized monoclonal antibody is SAN-300 (hAQC2) or a variant thereof (Karpusas et al., *J. Mol. Biol.* 327:1031-1041, 2003). In some embodiments, the humanized monoclonal antibody is DI176E6 (EMD 5257) or a variant thereof (Goodman et al., *Trends Pharmacol. Sci* 33:405-412, 2012; and Sheridan et al., *Nat. Biotech.* 32:205-207, 2014).

In some embodiments, the integrin antibody is a chimeric monoclonal antibody. In some embodiments, the chimeric monoclonal antibody is volociximab or a variant thereof (Kuwada et al., *Curr. Opin. Mol. Ther.* 9(1):92-98, 2007; Ricart et al., *Clin. Cancer Res.* 14(23):7924-7929, 2008; Ramakrishnan et al., *J. Exp. Ther. Oncol.* 5(4):273-86, 2006; Bell-McGuinn et al., *Gynecol. Oncol.* 121:273-279, 2011; Almokadem et al., *Exp. Opin. Biol. Ther.* 12:251-7, 2012).

In some embodiments, the antibody specifically binds one or more (e.g., 1, 2, 3, 4, or 5) integrin. In some embodiments, the antibody specifically binds an integrin dimer (e.g., MLN-00002, MLNO2 (Feagan et al., *Clin. Gastroenterol. Hepatol.* 6(12):1370-1377, 2008; Feagan et al., *N. Engl. J. Med.* 352(24):2499-2507, 2005). In certain embodiments, the antibody comprises or consists of an antigen-binding fragment of abciximab (Reopro™) (Straub et al., *Eur. J. Cardiothorac Surg.* 27(4):617-621, 2005; Kim et al., *Korean J. Intern. Med.* 19(4):220-229, 2004). In some embodiments, the integrin inhibitor is an antibody-drug conjugate (e.g., IMGN388 (Bendell et al., *EJC Suppl* 8(7):152, 2010).

Further examples of antibodies and antigen-binding fragments thereof are described in U.S. Pat. Nos. 5,919,792; 6,214,834; 7,074,408; 6,833,373; 7,655,624; 7,465,449; 9,558,899; 7,659,374; 8,562,986; 8,398,975; and 8,853,149; US 2007/0117849; US 2009/0180951; US 2014/0349944; US 2004/0018192; WO 11/137418; and WO 01/068586; each of which is incorporated by reference in its entirety.

Integrin Inhibitor Fusion Proteins

In some embodiments, the integrin inhibitor is a fusion protein (e.g., an Fc fusion protein of an extracellular domain of an integrin or an integrin receptor), a soluble receptor (e.g., the extracellular domain of an integrin or an integrin receptor), or a recombinant integrin binding protein (e.g., an integrin ligand). See, e.g., Lode et al., *PNAS* 96(4):1591-1596, 1999; Stephens et al., *Cell Adhesion Comm.* 7:377-390, 2000; and US 2008/0739003; incorporated by reference herein). Non-limiting examples of fusion proteins that are integrin inhibitors include Ag25426 (Proteintech).

Integrin Inhibitor Small Molecule Antagonists

In some embodiments, the integrin inhibitor is a small molecule. In some embodiments, the small molecule is a non-peptide small molecule. In some embodiments, the non-peptide small molecule is a RGD (ArgGlyAsp)-mimetic antagonist (e.g., tirofiban (Aggrastat®); Pierro et al., *Eur. J. Ophthalmol.* 26(4):e74-76, 2016; Guan et al., *Eur. J. Pharmacol* 761:144-152, 2015. In some embodiments, the small molecule is α4 antagonist (e.g., firategrast (Miller et al., *Lancet Neurol.* 11(2):131-139, 2012) AJM300 (Yoshimura et al., *Gastroenterology* 149(7):1775-1783, 2015; Takazoe et al., *Gastroenterology* 136(5):A-181, 2009; Sugiura et al., *J. Crohns Colitis* 7(11):e533-542, 2013)). In some embodiments, the small molecule is α4β1 antagonist (e.g., IVL745 (Norris et al., *J. Allergy Clin. Immunol.* 116(4):761-767, 2005; Cox et al., *Nat. Rev. Drug Discov.* 9(10):804-820, 2010)), BIO-1211 (Abraham et al., *Am. J. Respir. Crit. Care Med.* 162:603-611, 2000; Ramroodi et al., *Immunol. Invest.* 44(7):694-712, 2015; Lin et al., *J. Med. Chem.* 42(5):920-934, 1999), HMR 1031 (Diamant et al., *Clin. Exp. Allergy* 35(8):1080-1087, 2005); valategrast (R411) (Cox et al., *Nat. Rev. Drug Discov.* 9(10):804-820, 2010), GW559090X (Ravensberg et al., *Allergy* 61(9):1097-1103, 2006), TR14035 (Sircar et al., *Bioorg. Med. Chem.* 10(6):2051-2066, 2002; Cortijo et al., *Br. J. Pharmacol.* 147(6):661-670, 2006)). In some embodiments, the small molecule is αvβ antagonist (e.g., L0000845704, SB273005). In some embodiments, the small molecule is α5β1 antagonist (e.g., JSM6427). In some embodiments, the small molecule is GLPG0974 (Vermeire et al., *J. Crohns Colitis* Suppl. 1:539, 2015). In some embodiments, the small molecule is MK-0429 (Pickarksi et al., *Oncol. Rep.* 33(6):2737-45, 2015; Rosenthal et al., *Asia Pac J. Clin. Oncol.* 6:42-8, 2010). In some embodiments, the small molecule is JSM-6427 or a variant thereof (Zahn et al., *Arch. Ophthalmol.* 127(10):1329-1335, 2009; Stragies et al., *J. Med Chem.* 50:3786-94, 2007).

In some embodiments, the small molecule integrin inhibitor can be PTG-100, which is described in, e.g., Shames et al., "Pharmakokinetics and Pharmacodynamics of the Novel Oral Peptide Therapeutic PTG-100 (α4β7 Integrin Antagonist) in Normal Healthy Volunteers," 24$^{th}$ *United European Gastroenterology Week*, October 15-19, Vienna, Austria, 2016.

In some embodiments, the small molecule targets a β2 integrin. In some embodiments, the small molecule is SAR-118 (SAR1118) or a variant thereof (Zhong et al., *ACS Med. Chem. Lett.* 3(3):203-206, 2012; Suchard et al., *J. Immunol.* 184:3917-3926, 2010; Yandrapu et al., *J. Ocul. Pharmacol. Ther.* 29(2):236-248, 2013; Semba et al., *Am. J. Ophthalmol.* 153:1050-60, 2012). In some embodiments, the small molecule is BMS-587101 or a variant thereof (Suchard et al., *J. Immunol.* 184(7):3917-3926, 2010; Potin et al., *J. Med. Chem.* 49:6946-6949, 2006). See e.g., Shimaoka et al., *Immunity* 19(3):391-402, 2003; U.S. Pat. Nos. 7,138,417; 7,928,113; 7,943,660; and 9,216,174; US 2008/0242710; and US 2008/0300237.

Other exemplary integrin inhibitors include the following: SMART anti-L-selectin Mab from PDL BioPharma Inc., which is L-Selectin antagonist, and described in WO-09706822, and Co M S, et al. "Properties and pharmacokinetics of two humanized antibodies specific for L-selectin"; Immunotechnology; 1999 4 253-266; both of which are hereby incorporated by reference; SEL-K2, an anti-PSGL-1 antibody, from Tetherex Pharmaceuticals Inc, which is described in Barbara Muz, et al. "Inhibition of P-Selectin and PSGL-1 Using Humanized Monoclonal Antibodies Increases the Sensitivity of Multiple Myeloma Cells to Proteasome Inhibitors" American Society of Hematology Annual Meeting and Exposition; 2014 56th (December 08) Abs 4758, which is hereby incorporated by reference; Vatelizumab described in I. A. Antonijevic, et al. "Safety, tolerability and pharmacodynamic characterization of vatelizumab, a monoclonal antibody targeting very-late-antigen (VLA)-2: a randomized, double-blind, placebo-controlled phase 1 study" Abstract release date: Sep. 23, 2015) ECTRIMS Online Library. Oct. 9, 2015; and WO-2010095031; WO-2011104604; WO-2010052556, which are all hereby incorporated by reference; and anti-VCAM mAb, which is described in Soriano, Antonio, et al. "VCAM-1, but not ICAM-1 or MAdCAM-1, immunoblockade ameliorates DSS-induced colitis in mice." Laboratory investigation 80.10 (2000): 1541; and Gerritsen M E, et al.

(1995). Activation-dependent isolation and culture of murine pulmonary microvascular endothelium. Microcirculation 2:151-163.

Integrin Inhibitor Cyclic Peptides

In some embodiments, the integrin inhibitor is a cyclic peptide. In some embodiments, the synthetic cyclic peptide is eptifabitide (Integrilin™), or a variant thereof.

In some embodiments, the cyclic peptide comprises a heterocyclic nucleic (e.g., a benzodiazepinone, a piperazine, a benzoazepinone, a nitroaryl, an isoxazoline, an indazole, or a phenol; Spalluto et al., Curr. Med. Chem. 12:51-70, 2005). In some embodiments, the cyclic peptide is a macrocycle (see, e.g., Halland et al., ACS Med. Chem. Lett. 5(2):193-198, 2014). In some embodiments, the peptide is ALG-1001 or a variant thereof (Mathis et al., Retin. Phys. 9:70, 2012). In some embodiments, the cyclic peptide is an imidazolone-phenylalanine derivative, a heteroaryl, hetrocyclic, and aryl derivative, a bicyclic-aromatic amino acid derivative, a cyclohexane-carboxylic acid derivative, a diaryl substituted urea derivative, a multimeric L-alanine derivative, a L-alanine derivative, or a pyrimidyl-sulfonamide derivative (see, e.g., U.S. Pat. Nos. 6,630,492; 6,794, 506; 7,049,306; 7,371,854; 7,759,387; 8,030,328; 8,129, 366; 7,820,687; 8,350,010; and 9,345,793).

Integrin Inhibitor Peptidomimetics

In some embodiments, the integrin inhibitor is a peptidomimetic. In some embodiments, the peptidomimetic has an integrin-ligand recognition motif (e.g., RGD, KTS, or MLD). See, e.g., Carron et al., Cancer Research 58:1930-1935, 1998; Fanelli et al., Vascular Cell 6:11, 2014; and De Marco et al., Curr. Top. Med. Chem. 16(3):343-359, 2016.

In some embodiments, the peptidomimetic is an RGD (ArgGlyAsp)-based peptide (U.S. Pat. No. 8,809,338, incorporated by reference in its entirety herein). In some embodiments, the RGD-based peptide can be cilengitide or a variant thereof (EMD 12974) (Mas-Moruno et al., Anticancer Agents Med. Chem. 10:753-768, 2010; Reardon et al., Future Oncol. 7(3):339-354, 2011; Beekman et al., Clin. Genitourin Cancer 4(4):299-302, 2006; SC56631 (e.g., Engleman et al., Am Soc. Clin. Invest. 99(9):2284-2292, 1997; Peng et al., Nature Chem Biol. 2:381-389, 2006). In some embodiments, the peptidomimetic can be a Lys-Gly-Asp (KGD)-based peptide. In some embodiments, the peptidomimetic can be vipegitide or a variant thereof (Momic et al., Drug Design Devel. Therapy 9:291-304, 2015). In some embodiments, the peptidomimetic can be a peptide conjugated with an antimicrobial synthetic peptide. (e.g., ACDCRGDCFC conjugated with (KLAKLAK)$_2$ (Ellerby et al., Nat. Med. 5(9):1032-1038, 1999). See, e.g., U.S. Pat. No. 8,636,977.

Disintegrins

In some embodiments, the integrin inhibitor can be a disintegrin. The term "disintegrin" as used herein refers to a low molecular weight peptide integrin inhibitor derived from a snake venom (e.g., pit viper venom). In some embodiments, the disintegrin is a RGD(ArgGlyAsp)-, a KTS- or an MLD-based disintegrin.

Non-limiting examples of disintegrins include accutin, accurhagin-C, albolabrin, alternagin-c, barbourin, basilicin, bitisgabonin-1, bitisgabonin-2, bitistatin, cerastin, cereberin, cumanastatin 1, contortrostatin, cotiarin, crotatroxin, dendroaspin, disba-01, durissin, echistatin, EC3, elegantin, eristicophin, eristostatin, EMS11, E04, E05, flavoridin, flavostatin, insularin, jarastatin, jerdonin, jerdostatin, lachesin, lebein (e.g., lebein-1, lebein-2), leberagin-C, lebestatin, lutosin, molossin, obtustatin, ocellatusin, rhodocetin, rhodostomin, R-mojastin 1, salmosin, saxatilin, schistatin, tablysin-15, tergeminin, triflavin, trigramin, trimestatin, VA6, vicrostatin, viridin, viperstatin, VB7, VLO4, and VLO5, or a variant thereof. See, e.g., Arruda Macedo et al., Curr. Protein. Pept. Sci. 16(6):532-548, 2015; Hsu et al., Sci. Rep. 6:23387, 2016; Kele et al. Curr. Protein Pept. Sci. 6:532-548, 2015; Koh et al., Toxicon 59(4):497-506, 2012; Scarborough et al., J. Biol. Chem. 268:1058-1065, 1993; Kisiel et al., FEBS Lett. 577:478-482, 2004; Souza et al., Arch. Biochem. Biophys. 384:341-350, 2000; Eble et al., J. Biol. Chem. 278:26488-26496, 2003; Marcinkiewicz et al., J. Biol. Chem. 274:12468-12473, 1999; Calvete et al., J. Proteome Res. 6:326-336, 2007; Scibelli et al., FEMS Microbiol. Lett. 247:51-57, 2005; Oliva et al., Toxicon 50:1053-1063, 2007; Minea et al., Toxicon 59:472-486, 2012; Smith et al., FEBS Lett. 512:111-115, 2002; Tselepis et al., J. Biol. Chem. 272:21341-21348, 1997; Da Silva et al., Tromb. Res. 123:731-739, 2009; Thibault et al., Mol. Pharmacol. 58:1137-1145, 2000; Lu et al., Biochem. J. 304:818-825, 1994; Yeh et al., Biochim. Biophys. Acta. 1425:493-504, 1998; Huang et al., Exp. Hematol. 36:1704-1713, 2008; Shih et al., Matrix Biol. 32:152-159, 2013; Wang et al., Br. J. Pharmacol. 160:1338-1351, 2010; Della-Casa et al., Toxicon 57:125-133, 2011; Sheu et al., Biochim. Biophys. Acta. 1336:445-454, 1997; Fujii et al., J. Mol. Biol. 332: 115-122, 2003; Bilgrami et al., J. Mol. Biol. 341:829-837, 2004; Zhou et al., Toxicon 43:69-75, 2004; Scarborough et al., J. Biol. Chem. 268:1066-1073, 1993; Shebuski et al., J. Biol. Chem. 264:21550-21556, 1989; Lu et al., Biochem. J. 304:929-936, 1994; McLane et al., Biochem. J. 301:429-436, 1994; Juarez et al., Toxicon 56:1052-1058, 2010; Olfa et al., Lab. Invest. 85:1507-1516, 2005; Elbe et al., Matrix Biol. 21:547-558, 2002; Bazan-Socha et al., Biochemistry 43:1639-1647, 2004; Danen et al., Exp. Cell. Res. 238:188-196, 1998; Marcinkiewicz et al., Biochemistry 38(40): 13302-13309, 1999; Calvete et al., Biochem. J. 372:725-734, 2003; Swenson et al., Pathophysiol. Haemost. Thromb. 34:169-176, 2005; Kwon et al., PLoS One 8; e81165, 2013; Yang et al., Toxicon 45:661-669, 2005; Limam et al., Matrix Biol. 29:117-126, 2010; Gan et al., J. Biol. Chem. 263: 19827-19832, 1988; Ma et al., Thromb. Haemost. 105(6): 1032-1045, 2011; and U.S. Pat. No. 7,074,408, incorporated in their entirety herein.

CXCL10 (IP-10) Inhibitors

In some embodiments, the therapeutic suitable for use with the devices and methods described herein is a CXCL10 (IP-10) inhibitor. As used herein "CXCL10", "interferon gamma-induced protein 10" and "IP-10" can be used interchangeably. CXCL10 binds to the CXCR3 receptor (e.g., CXCR3-A or CXCR3-B). The term "CXCL10 inhibitor" refers to an agent which decreases the ability of CXCL10 to bind to a CXCR3 receptor (e.g., CXCR3-A and/or CXCR3-B).

CXCL10 (IP-10) Inhibitor Antibodies

In some embodiments, the CXCL10 inhibitor is an antibody or an antigen-binding fragment thereof (e.g., a Fab or a scFv). In some embodiments, an antibody or antigen-binding fragment described herein binds specifically to CXCL10 or a CXCR3 receptor (e.g., CXCR3-A and/or CXCR3-B), or both a CXCL10 and a CXCR3 receptor (e.g., CXCR3-A and/or CXCR3-B). In some embodiments, a CXCL10 inhibitor can bind to both CXCR3-A and CXCR3-B.

In some instances, the CXCL10 inhibitor is a monoclonal antibody (mAb) (see, e.g., WO 05/58815). For example, the CXCL10 inhibitor can be Eldelumab® (MDX-1100 or BMS-936557), BMS-986184 (Bristol-Meyers Squibb), or NI-0801 (NovImmune). See, e.g., Kuhne et al., J. Immunol.

178(1):5241, 2007; Sandborn et al., *J. Crohns Colitis* 11(7): 811-819, 2017; and Danese et al., *Gastroenterology* 147(5): 981-989, 2014. Additional examples of CXCL10 inhibitors that are antibodies are described in U.S. Patent Application Publication Nos. 2017/0158757, 2017/0081413, 2016/ 0009808, 2015/0266951, 2015/0104866, 2014/0127229, 2014/0065164, 2013/0216549, 2010/0330094, 2010/ 0322941, 2010/0077497, 2010/0021463, 2009/0285835, 2009/0169561, 2008/0063646, 2005/0191293, 2005/ 0112119, 2003/0158392, 2003/0031645, and 2002/ 0018776; and WO 98/11218, each of which is incorporated by reference in its entirety (e.g., the description of CXCL10 inhibitors).

CXCL10 (IP-10) Inhibitor Small Molecules and Peptides

In some instances, the CXCL10 inhibitor is a small molecule. For example, the CXCL10 inhibitor can be ganodermycin (see, e.g., Jung et al., *J. Antiobiotics* 64:683-686, 2011). Additional exemplary small molecule CXCL10 inhibitors are described in: U.S. Patent Application Publication No. 2005/0075333; U.S. Patent Application Publication No. 2004/0242498; U.S. Patent Application Publication No. 2003/0069234; U.S. Patent Application Publication No. 2003/0055054; U.S. Patent Application Publication No. 2002/0169159; WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25):15687-15692 (1998); and Howard et al., *J. Med. Chem.* 41(13):2184-2193 (1998).

In some examples, the CXCL10 inhibitor is a peptide antagonist of a CXCR3 receptor (e.g., as described in U.S. Patent Application Publication No. 2007/0116669, 2006/ 0204498, and WO 98/09642). In some examples, the CXCL10 inhibitor is a chemokine mutant or analogue, e.g., those described in U.S. Pat. No. 5,739,103, WO 96/38559, and WO 98/06751. Additional examples of CXCL10 inhibitors that are small molecules or peptides are known in the art.

CCL11 Inhibitors

In some embodiments, the therapeutic suitable for use with the devices and methods described herein is a CCL11 inhibitor. The term "CCL11 inhibitor" refers to an agent which decreases the ability of CCL11 to bind to one or more of CCR2, CCR3, and CCR5. In some embodiments, a CCL11 inhibitor is an antibody or an antigen-binding fragment thereof.

CCL11 Inhibitor Antibodies

In some embodiments, the CCL11 inhibitor is an antibody or an antigen-binding fragment thereof (e.g., a Fab or a scFv). In some embodiments, an antibody or antigen-binding fragment described herein binds specifically to CCL11, CCR2, CCR3, or CCR5, or can specifically bind to two or more of CCL11, CCR2, CCR3, and CCR5. In some embodiments, a CCL11 inhibitor can bind to two or more of CCR2, CCR3, and CCR5.

In some examples the chemokine/chemokine receptor inhibitor is bertilimumab (Immune Pharmaceuticals), an anti-eotaxin-1 monoclonal antibody that targets CCL11, and is currently in a Phase II clinical study for ulcerative colitis. Additional examples of CCL11 inhibitors are described in U.S. Patent Application Publication Nos. 2016/0289329, 2015/0086546, 2014/0342450, 2014/0178367, 2013/ 0344070, 2013/0071381, 2011/0274696, 2011/0038871, 2010/0074886, 2009/0297502, 2009/0191192, 2009/ 0169541, 2009/0142339, 2008/0268536, 2008/0241923, 2008/0241136, 2005/0260139, 2005/0048052, 2004/ 0265303, 2004/0132980, 2004/0126851, 2003/0165494, 2002/0150576, 2002/0150570, 2002/0051782, 2002/ 0051781, 2002/0037285, 2002/0028436, 2002/0015700, 2002/0012664, 2017/0131282, 2016/0368979, 2016/ 0208011, 2011/0268723, 2009/0123375, 2007/0190055, 2017/0049884, 2011/0165182, 2009/0226434, 2009/ 0110686, 2009/0047735, 2009/0028881, 2008/0107647, 2008/0107595, 2008/0015348, 2007/0274986, 2007/ 0231327, 2007/0036796, 2007/0031408, 2006/0229336, 2003/0228306, 2003/0166870, 2003/0003440, 2002/ 0019345, and 2001/0000241, each of which is incorporated by reference in its entirety (e.g., the description of CCL11 inhibitors).

CCR2 Inhibitors

In some embodiments, the therapeutic suitable for use with the devices and methods described herein is a CCR2 inhibitor. As used herein "CCR2," "CC chemokine receptor 2," or "MCP-1" can be used interchangeably. CCL2, CCL8, and CCL16 each individually bind to CCR2. The term "CCR2 inhibitor" refers to an agent which decreases the ability of CCR2 to bind to one or more (e.g., two, or three) of CCL2, CCL8, and CCL16.

In some instances, the CCR2 inhibitor is a small molecule. In some instances, the CCR2 inhibitor is an antibody or an antigen-binding antibody fragment. In some instances, the CCR2 inhibitor is a peptide.

CCR2 Inhibitor Antibodies

In some embodiments, the CCR2 inhibitor is an antibody or an antigen-binding fragment thereof (e.g., a Fab or a scFv). In some embodiments, an antibody or antigen-binding fragment described herein binds specifically to CCR2. In some embodiments, an antibody or antigen-binding fragment described herein binds specifically to CCL2. In some embodiments, an antibody or antigen-binding fragment described herein binds specifically to CCL8. In some embodiments, an antibody or antigen-binding fragment described herein binds specifically to CCL16. In some embodiments, an antibody or antigen-binding fragment described herein binds specifically to CCR2 and one or more of (e.g., one, two, or three) of CCL2, CCL8, and CCL16.

In some embodiments, the CCR2 inhibitor is a monoclonal antibody. For example, the CCR2 inhibitor can be MLN1202 (Millennium Pharmaceuticals), C775, STI-B0201, STI-B0211, STI-B0221, STI-B0232, carlumab (CNTO 888; Centocor, Inc.), or STI-B0234, or an antigen-binding fragment thereof. See also, e.g., Vergunst et al., *Arthritis Rheum.* 58(7):1931-1939, 2008. Additional examples of CCR2 inhibitors that are antibodies or antigen-binding antibody fragments are described in, e.g., U.S. Patent Application Publication Nos. 2015/0086546, 2016/ 0272702, 2016/0289329, 2016/0083482, 2015/0361167; 2014/0342450, 2014/0178367, 2013/0344070, 2013/ 0071381, 2011/0274696, 2011/0059107, 2011/0038871, 2009/0068109, 2009/0297502, 2009/0142339, 2008/ 0268536, 2008/0241923, 2008/0241136, 2007/0128112, 2007/0116708, 2007/0111259, 2006/0246069, 2006/ 0039913, 2005/0232923, 2005/0260139, 2005/0058639, 2004/0265303, 2004/0132980, 2004/0126851, 2004/ 0219644, 2004/0047860, 2003/0165494, 2003/0211105, 2002/0150576, 2002/0051782, 2002/0042370, and 2002/ 0015700; and U.S. Pat. Nos. 6,312,689, 6,084,075, 6,406, 694, 6,406,865, 6,696,550, 6,727,349, 7,442,775, 7,858,318, 5,859,205, 5,693,762, and 6,075,181, each of which is incorporated by reference (e.g., the description of the CCR2 inhibitors). Additional examples of CCR2 inhibitors are described in, e.g., WO 00/05265. Additional examples of CCR2 inhibitors that are antibodies or antigen-binding antibodies fragments are described in, e.g., Loberg et al., *Cancer Res.* 67(19):9417, 2007.

CCR2 Inhibitor Small Molecules and Peptides

In some examples, the CCR2 inhibitor is a small molecule. For example, the CCR2 inhibitor can be elubrixin, PF-04634817, BMS-741672, or CCX872. See, e.g., U.S. Pat. No. 9,434,766; U.S. Patent Application Publication No. 20070021466; Deerberg et al., *Org. Process Rev. Dev.* 20(11):1949-1966, 2016; and Morganti et al., *J. Neurosci.* 35(2):748-760, 2015.

Additional non-limiting examples of CCR2 inhibitors that are small molecules include, e.g., the phenylamino substituted quaternary salt compounds described in U.S. Patent Application Publication No. 2009/0112004; the biaryl derivatives described in U.S. Patent Application Publication No. 2009/0048238; the pyrazol derivatives described in U.S. Patent Application Publication No. 2009/0029963; the heterocyclic compounds described in U.S. Patent Application Publication No. 2009/0023713; the imidazole derivatives described in U.S. Patent Application Publication No. 2009/0012063; the aminopyrrolidines described in U.S. Patent Application Publication No. 2008/0176883; the heterocyclic cyclopentyl tetrahydroisoquinolones and tetrahydropyridopyridines described in U.S. Patent Application Publication No. 2008/0081803; the heteroaryl sulfonamides described in U.S. Patent Application Publication No. 2010/0056509; the triazolyl pyridyl benzenesulfonamides described in U.S. Patent Application Publication No. 2010/0152186; the bicyclic and bridged nitrogen heterocycles described in U.S. Patent Application Publication No. 2006/0074121; the fused heteroaryl pyridyl and phenyl benzenesulfonamides described in WO 09/009740; and the 3-aminopyrrolidene derivatives described in WO 04/050024.

Additional non-limiting examples of CCR2 inhibitors include: N-((1R,3S)-3-isopropyl-3-{[3-(trifluoromethyl)-7,8-dihydro-1,6-naph-thyri-din-6(5H)-yl]carbonyl}cyclopentyl)-N-[(3S,4S)-3-methoxytetrahydro-2H-pyran-4-yl]amine; 3[(3S,4R)-1-((1R,3S)-3-isopropyl-2-oxo-3-{[6-(trifluoromethyl)-2H-1,3-ben-z-oxazin-3(4H)-yl]methyl}cyclopentyl)-3-methylpiperidin-4-yl]benzoic acid; (3S,4S)-N-((1R,3S)-3-isopropyl-3-{[7-(trifluoromethyl)-3,4-dihydroisoquin-olin-2(1B)-yl]carbonyl}cyclopentyl)-3-methyltetrahydro-2H-p-yran-4-aminium; 3-[(3S,4R or 3R,4S)-1-((1R,3S)-3-Isopropyl-3-{[6-(trifluoromethyl)-2H-1,3-benzoxazin-3-(4H)-yl]carbonyl}cyclopentyl)-3-methylpiperidin-4-yl]benzoic acid; INCB3284; Eotaxin-3; PF-04178903 (Pfizer), and pharmaceutically acceptable salts thereof.

Additional non-limiting examples of CCR2 inhibitors include: bindarit (2-((1-benzyl-1H-indazol-3-yl)methoxy)-2-methylpropionic acid); AZD2423 (AstraZeneca); the indole describes described in U.S. Pat. Nos. 7,297,696, 6,962,926, 6,737,435, and 6,569,888; the bicyclic pyrrole derivatives described in U.S. Pat. Nos. 6,441,004 and 6,479,527; the CCR2 inhibitors described in U.S. Patent Application Publications Nos. 2005/0054668, 2005/0026975, 2004/0198719, and 2004/0047860, and Howard et al., *Expert Opin. Ther. Patents* 11(7):1147-1151 (2001).

Additional non-limiting examples of CCR2 inhibitors that are small molecules are described in, e.g., WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25): 15687-15692, 1998; and Howard et al., *J. Med. Chem.* 41(13):2184-2193, 1998.

In some embodiments, the CCR2 inhibitor is a small nucleic acid, e.g., NOX-E36 (a 40-nucleotide L-RNA oligonucleotide that is linked to a 40-kDa PEG; NOXXON Pharma AG).

In some embodiments, the CCR2 inhibitor is a peptide, e.g., a dominant negative peptide described in, e.g., Kiyota et al., *Mol. Ther.* 17(5):803-809, 2009, and U.S. Patent Application Publication No. 20070004906, or an antagonistic peptide, e.g., the antagonistic peptides described in WO 05/037305 and Jiang-Hong Gong, et al., *J. Exp. Med.* 186:131, 1997. Additional examples of CCR2 inhibitors that are peptides are described in, e.g., U.S. Pat. No. 5,739,103; WO 96/38559; WO 98/06751; and WO 98/09642. In some embodiments, a CCR2 inhibitor is a CCR2 mutein (e.g., U.S. Patent Application Publication No. 2004/0185450).

Additional examples of CCR2 inhibitors that are small molecules and peptides are known in the art.

CCR9 Inhibitors

In some embodiments, the therapeutic suitable for use with the devices and methods described herein is a CCR9 inhibitor. As used herein "CCR9" or "CC chemokine receptor 9" can be used interchangeably. CCR9 specifically binds to CCL25. The term "CCR9 inhibitor" refers to an agent which decreases the ability of CCR9 to bind to CCL25.

CCR9 Inhibitor Antibodies

In some embodiments, the CCR9 inhibitor is an antibody or an antigen-binding fragment thereof (e.g., a Fab or a scFv). In some embodiments, an antibody or antigen-binding fragment described herein binds specifically to CCR9. In some embodiments, an antibody or antigen-binding fragment described herein binds specifically to CCL25. In some embodiments, an antibody or antigen-binding fragment described herein binds specifically to both CCR9 and CCL25.

In other instances, the CCR9 inhibitor is a monoclonal antibody. For example, the CCR9 antibody can be 91R, see, e.g., Chamorro et al., *MAbs* 6(4): 1000-1012, 2014. Additional non-limiting examples of CCR9 inhibitors are described in, e.g., U.S. Patent Application Publication Nos. 2012/0100554, 2012/0100154, 2011/0123603, 2009/0028866, and 2005/0181501.

CCR9 Inhibitor Small Molecules

In some instances, the CCR9 inhibitor is a small molecule. For example, the CCR9 inhibitor can be Traficet-EN® (also called Vercirnon, CCX282, and GSK1605786) or Tu1652 CCX507. See, e.g., Eksteen et al., *IDrugs* 13(7): 472-481, 2010; and Walters et al., *Gastroenterology* 144(5): S-815, 2013. Additional examples of CCR9 inhibitors that are small molecules are known in the art.

ELR Chemokine Inhibitors

In some embodiments, the therapeutic suitable for use with the devices and methods described herein is an ELR chemokine inhibitor. ELR chemokines are CXC chemokines that have a glutamic acid-leucine-arginine (ELR) motif See, e.g., Strieter et al., *J. Biol. Chem.* 270:27348-27357, 1995. The term "ELR chemokine inhibitor" refers to an agent which decreases the ability of CXCR1 and/or CXCR2 to bind to one or more (e.g., two, three, four, five, six, seven, or eight) of CXCL1, CXCL2, CXCL3, CXCL4, CXCL5, CXCL6, CXCL7, and CXCL8.

In some instances, the ELR chemokine inhibitor is a small molecule. In some instances, the ELR chemokine inhibitor is an antibody or an antigen-binding antibody fragment.

ELR Chemokine Inhibitor Antibodies

In some embodiments, the ELR chemokine inhibitor is an antibody or an antigen-binding fragment thereof (e.g., a Fab or a scFv). In some embodiments, an antibody or antigen-binding fragment binds specifically to CXCR1 and/or CXCR2. In some embodiments, an antibody or antigen-binding fragment described herein binds specifically to one or more (e.g., two, three, four, five, six, seven, or eight) of: CXCL1, CXCL2, CXCL3, CXCL4, CXCL5, CXCL6, CXCL7, and CXCL8 (TL-8).

An ELR chemokine inhibitor can be, e.g., a monoclonal antibody. A non-limiting example of an ELR inhibitor is TAB-099MZ. Additional examples of ELR chemokine inhibitors that are antibodies or antigen-binding antibody fragments are described in, e.g., U.S. Pat. No. 9,290,570; and U.S. Patent Application Publication Nos. 2004/0170628, 2010/0136031, 2015/0160227, 2015/0224190, 2016/0060347, 2016/0152699, 2016/0108117, 2017/0131282, 2016/0060347, 2014/0271647, 2014/0170156, 2012/0164143, 2010/0254941, 2009/0130110, 2008/0118517, 2004/0208873, 2003/0021790, 2002/0082396, and 2001/0006637, each of which is herein incorporated by reference (e.g., the portions describing ELR chemokine inhibitors).

ELR Chemokine Inhibitor Small Molecules

In some instances, the ELR chemokine inhibitor is, e.g., a small molecule. For example, the ELR chemokine inhibitor can be, e.g., LY-3041658 or repertaxin (Reparixin; DF 1681Y). Additional non-limiting examples of ELR chemokine inhibitors that are small molecules are described in, e.g., U.S. Patent Application Publication Nos. 2007/0248594, 2006/0014794, 2004/0063709, 2004/0034229, 2003/0204085, 2003/0097004, 2004/0186142, 2004/0235908, 2006/0025453, 2017/0224679, 2017/0190681, 2017/0144996, and 2017/0128474, each of which are incorporated by reference (e.g., the portions describing the ELR chemokine inhibitors).

In some embodiments, the ELR chemokine inhibitor is a peptide, e.g., any of the peptides described in U.S. Patent Application Publication Nos. 2009/0270318, 2009/0118469, and 2007/0160574, 2007/0021593, 2003/0077705, and 2007/0181987, each of which is incorporated by reference (e.g., the portions describing the ELR chemokine inhibitors).

Phosphodiesterase 4 (PDE4) Inhibitors

In some embodiments, the therapeutic suitable for use with the devices and methods described herein is a PDE4 inhibitor. The term "PDE4 inhibitor" refers to an agent which decreases PDE4 activity in vitro or in a mammalian cell, e.g., as compared to the level of PDE4 activity in the absence of the agent; and/or decreases the level of a PDE4 protein in a mammalian cell contacted with the agent, e.g., as compared to the same mammalian cell not contacted with the agent. A non-limiting example of PDE4 activity is the degradation of cAMP.

In some embodiments, a PDE4 inhibitor can be a small molecule (e.g., an organic, an inorganic, or bioinorganic molecule) having a molecule weight of less than 900 Daltons (e.g., less than 500 Daltons). In some embodiments, a PDE4 inhibitor can be an inhibitory nucleic acid.

Inhibitory Nucleic Acids of PDE4

In some embodiments, a PDE4 inhibitor can be an inhibitory nucleic acid. In some embodiments, the inhibitory nucleic acid can be an antisense nucleic acid, a ribozyme, and a small interfering RNA (siRNA).

Examples of modified nucleotides which can be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Another example of an inhibitory nucleic acid is a ribozyme that has specificity for a nucleic acid encoding a PDE4 protein (e.g., specificity for a PDE4 mRNA, e.g., specificity for SEQ ID NO: 1, 2, 3, 4, or 5). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. A ribozyme having specificity for a PDE4 mRNA can be designed based upon the nucleotide sequence of any of the PDE4 mRNA sequences disclosed herein. For example, a derivative of a Tetrahymena L-19 IVS RNA can be constructed in which the nucleotide sequence of the active site is complementary to the nucleotide sequence to be cleaved in a PDE4 mRNA (see, e.g., U.S. Pat. Nos. 4,987,071 and 5,116,742). Alternatively, a PDE4 mRNA can be used to select a catalytic RNA having a specific ribonuclease activity from a pool of RNA molecules. See, e.g., Bartel et al., *Science* 261:1411-1418, 1993.

An inhibitor nucleic acid can also be a nucleic acid molecule that forms triple helical structures. For example, expression of a PDE4 polypeptide can be inhibited by targeting nucleotide sequences complementary to the regulatory region of the gene encoding the PDE4 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Helene, *Anticancer Drug Des.* 6(6):569-84, 1991; Helene, *Ann. N.Y Acad. Sci.* 660:27-36, 1992; and Maher, *Bioassays* 14(12):807-15, 1992.

Non-limiting examples of siRNAs targeting PDE4 are described in Takakura et al., *PLosOne* 10(12):e0142981, 2015; Watanabe et al., *Cell Signal* 27(7):1517-1524, 2015; Suzuki et al., *PLos One* 11(7):e0158967, 2016; Kai et al., *Mol. Ther. Nucl. Acids* 6: 163-172, 2017). See, e.g., Cheng et al. *Exp Ther Med.* 12(4): 2257-2264, 2016; Peter et al., *J Immunol* 178)8): 4820-4831; and Lynch et al. *J Biolog Chem*

280: 33178-33189. Additional examples of PDE4 inhibitory nucleic acids are described in U.S. Patent Application Publication Nos. 2010/0216703 and 2014/0171487, which are incorporated by reference in its entirety.

PDE4 Inhibitor Small Molecules

In some embodiments, a PDE4 inhibitor is a small molecule. Non-limiting examples of small molecules that are PDE4 inhibitors include: Apremilast (CC-10004; CC-110004; CDC-104; Otezla®; lead selCID (2); selCID); CC-1088 (CC-1088; CC-5048; CC-801; CDC-801; lead SelCID (1)); Tetomilast (OPC-6535); KF-19514; PF-06266047; SKF-107806; PDB-093; Tolafentrine (BY-4070); TAK-648; CH-928; CH-673; CH-422; ABI-4 (18F-PF-06445974; Fluorine-18-PF-06445974); roflumilast; RoflumilastN-oxide (APTA-2217; B9302-107; BY-217; BYK-20860; Daliresp®; Dalveza; Daxas®; Libertek; Xevex; roflumist); NVP-ABE-171; BYK-321084; WAY-127093B; NCS-613; SDZ-ISQ-844; GS-5759; Ro-20-1724; Hemay-005; KCA-1490; TVX-2706; Nitraquazone; Filaminast (PDA-641; WAY-PDA-641); LASSBio-596; ASP-3258; TAS-203; AN-2889; AN-5322; AN-6414; AN-6415; Lotamilast (E-6005; RVT-501); GPD-1116; Cipamfylline (BRL-61063; HEP-688); MNP-001; MS-23; MSP-001; K-34; KF-66490; AL-38583 (cilomast); ZL-N-91; Almirall; CDP-840; GSK-356728; Cilomilast (Ariflo; SB-207499); OCID-2987; AN-2898; CBS-3595; ASP-9831 (ASP9831); E-4021 (4-Piperidinecarboxylic acid, 1-[4-[(1,3-benzodioxol-5-ylmethyl)amino]-6-chloro-2-quinazolinyl]); Piclamilast (RP-73401; RPR-73401); CD-160130; GSK-256066 (256066); 4AZA-PDE4; YM-393059; Revamilast (GRC-4039); AN-2728 (PF-06930164; crisaborole (Eucrisa™)); MK-0952 (MK-952); Ibudilast (AV-411; MN-166; KC-404); GP-0203; ELB-526; Theophylline (Teonova); CHF-6001 (CHF-5480); Elbimilast (AWD-12-353; ELB-353; ronomilast); AWD-12-281 (842470); OS-0217; Oglemilast (GRC-3886); R-1627; ND-1510; ND-1251; WAY-122331; GRC-3566; Tofimilast (CP-325366); BAY-61-9987; Rolipram (ME-3167; ZK-62711); MEM-1414 (R-1533); Adenosine A3 antagonists (CGH-2466); RPL-554 (RPL-565; VMX-554; VMX-565; VRP-554; trequinsin analog); CT-5357; Etazolate (EHT-0202; SQ-20009; etazolate hydrochloride); Z-15370 (Z-15370A); Org-30029; Org-20241; Arofylline (LAS-31025); Arofylline derivatives; KW-4490; HT-0712 (IPL-455903); HT-0712; IPL-455903; CT-2450; CT-2820; CT-3883; CT-5210; L-454560; L-787258; L-791943; L-826141; L-869298; MK-0359; OX-914 (BLX-028914; BLX-914; IPL-4088; IPL-4182; IPL-4722); SDZ-PDI-747; AP-0679; Sch-351591 (D-4396; Sch-365351); TA-7906 (T-2585; TA-7906); HMR-1571; Lirimilast (BAY-19-8004); Daxalipram (Mesopram; SH-636; ZK-117137); SelCIs (CC-10036; CC-10083; CC-110007; CC-110036; CC-110037; CC-110038; CC-110049; CC-110052; CC-110083; CC-11069; CC-111050; CC-13039; CC-14046; CC-17034; CC-17035; CC-17075; CC-17085; CC-18062; CC-7075); RPR-117658; AWD-12-281 (842470; AWD-12-343; GW842470X); 256066 (GSK-256066; SB-207499); RPR-132294 (RPR-132703); CI-1018; CI-1044; PD-168787; PD-189659; PD-190036; PD-190749; YM-976; XT-611; Losartan derivatives; DWP-205 derivatives (DWP-205297); WAY-126120; YM-58997; CP-293321; V-11294A; CH-3697; CP-353164; Atizoram (CP-80633); D-4418; RPR-114597; IC-197; IC-246; IC-247; IC-485; IC-86518; IC-86518/IC-86521; IC-86521; CP-220629; ZL-n-91; D-22888 (AWD-12-232); GW-3600; GSK356278; TPI 1100; BPN14770; and MK-0873. See, e.g., Schafter et al. (2014) Cellular Signaling 26(9): 2016-2029); Gurney et al. (2011) Handb Exp Pharmacol 204: 167-192; Spadaccini et al. (2017) Intl J Mol Sciences 18: 1276; Bickston et al. (2012) Expert Opinion Invest Drugs 21:12, 1845-1849; Keshavarzian et al. (2007) Expert Opinion Invest Drugs 16:9, 1489-1506.

Additional examples of small molecules that are PDE4 inhibitors are described in, e.g., U.S. Patent Application Publication Nos. 2017/0348311, 20176/0319558, 2016/0213642, 2015/0328187, 2015/0306079, 2015/0272949, 2015/0272936, 2015/0080359, 2015/0051254, 2014/0350035, 2014/0148420, 2014/0121221, 2013/0252928, 2013/0237527, 2013/0225609, 2012/0309726, 2012/0196867, 2012/0088743, 2012/0059031, 2012/0035143, 2012/0028932, 2011/0021478, 2011/0021476, 2010/0234382, 2010/0129363, 2010/0069392, 2010/0056604, 2010/0048616, 2010/0048615, 2009/0099148, 2009/0093503, 2008/0287522, 2008/0255209, 2008/0255186, 2008/0221111, 2007/0232637, 2007/0208181, 2007/0167489, 2006/0269600, 2006/0183764, 2006/0154934, 2006/0094723, 2006/0079540, 2005/0267135, 2005/0234238, 2005/0033521, 2003/0229134, 2003/0220352, 2003/0212112, 2003/0158189, 2003/0069260, 2003/0050329, 2002/0058687, and 2002/0028842. Additional examples of small molecules that are PDE4 inhibitors are known in the art.

Additional Inhibitors

In some embodiments, the therapeutic agent suitable for use with the devices and methods described herein is selected from a non-oral small molecule therapeutic, a heparin, a JAK inhibitor (e.g., PF-06700841, PF-06651600); live biotherapeutics (e.g., Neuregulin 4, NN8555), an immune modulator (e.g., KHK-4083, GSK2618960, Toralizumab), a chemokine (e.g., GSK3050002 (previously known as KANAb071), E-6011, HGS-1025), a CHST15 inhibitor (e.g., SB-012), a TLR agonist (e.g., BL-7040; EN-101; Monarsen), and combinations thereof.

Non-Oral Small Molecule Therapeutics

In some embodiments, the therapeutic suitable for use with the devices and methods described herein is a non-oral small molecule.

In some embodiments, the therapeutic suitable for use with the devices and methods described herein is a non-oral antibiotic. Antibiotics which are not given orally include: amikacin, ampicillin sulbactam, azlocillin, aztreonam, cefazolin, cefeprime, cefoperazone, cefotaxime, cefotetan, cefoxitin, ceftaroline, ceftazidime, ceftizoxime, ceftobiprole, ceftriaxone, cephalothin, colistin, daptomycin, doripenem, ertapenem, gentamicin, imipenem, kanamycin, meropenem, mezlocillin, mupirocin, nafcillin, ofloxicin, oritovacin, piperacillin, piperacillin tazobactam, polymyxin B, quinupristin dalfopristin, spectinomycin, streptomycin, teicoplanin, telavancin, ticarcillin, ticarcillin clavulanic acid, tigecycline and tobramycin.

Other exemplary non-oral small molecules for delivery using any of the devices or methods described herein include, but are not limited to, those listed in Table 11.

TABLE 11

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| Enoxaparin sodium | Intravenous; Subcutaneous | EP-00040144; US-04486420; WO-08102737 | Hematologic; Cardiovascular (Myocardial infarction; Thromboembolism) [Low molecular weight heparin] |
| Hydroxyprogesterone caproate | Intramuscular; Solution; Subcutaneous; Sustained release | WO-00009186 | Genitourinary/sexual function (Premature labor; long-acting, preterm birth prevention) [Progesterone receptor agonist] |
| Plerixafor | Infusion; Intravenous; Solution; Subcutaneous | EP-00434385 | Cancer; Cardiovascular; Dermatologic; Hematologic; Immune; Infection (Bone marrow transplantation; Sickle cell anemia) [CXCR4 chemokine antagonist; Neuroplastin inhibitor] |
| Ferumoxytol | Drug coating; Infusion; Intravenous; Nanoparticle formulation injectable; | WO-00061191 | Cancer; Hematologic; Cardiovascular (Iron deficiency anemia) |
| Bortezomib | Formulation powder; Freeze drying; Infusion; Intravenous; Subcutaneous | WO-02059130; WO-09613266 | Hematologic; Endocrine/Metabolic; Immune; Neurology/Psychiatric; Cancer (Acute lymphoblastic leukemia; Acute myelogenous leukemia; Chronic lymphocytic leukemia; Graft versus host disease; Lymphoplasmacytic lymphoma; Macroglobulinemia; Mantle cell lymphoma; Multiple myeloma; Myelodysplastic syndrome; Non-Hodgkin lymphoma; Non-small-cell lung cancer) [26S proteasome complex inhibitor; Proteasome inhibitor] |
| Pemetrexed disodium | Formulation powder; Freeze drying; Infusion; Intravenous | EP-00432677; HU-00211941 | Cancer (Mesothelioma; Metastatic bladder cancer; Metastatic non-small cell lung cancer) [DHFR inhibitor; GAR transformylase inhibitor; Thymidylate synthase inhibitor; Transferase inhibitor] |
| Fulvestrant | Intramuscular; Sustained release | EP-00138504 | Cancer; Inflammatory; Genitourinary/Sexual Function; Endocrine/Metabolic (Fallopian tube cancer; Metastatic breast cancer; Metastatic ovary cancer; Peritoneal tumor; Precocious puberty) [Estrogen receptor antagonist] |
| Carfilzomib | Formulation powder; Freeze drying; Infusion; Intravenous | WO-2005105827 | Cancer; Hematologic (Acute lymphoblastic leukemia; Cutaneous T-cell lymphoma; Hormone refractory prostate cancer; Mantle cell lymphoma; Multiple myeloma; Neuroendocrine tumor; Non-Hodgkin lymphoma; Peripheral T-cell lymphoma; Renal cell carcinoma; Small-cell lung cancer; Solid tumor) [Proteasome inhibitor; Ubiquitin inhibitor] |
| Azacitidine | Formulation powder; Freeze drying; Intravenous; Subcutaneous | US-04965251 | Cancer; Hematologic (Acute myelogenous leukemia; Chronic myelomonocytic leukemia; Myelodysplastic syndrome) [DNA methyltransferase inhibitor] |
| Bendamustine | Formulation powder; Freeze drying; Infusion; Intravenous; Solution | WO-2005034944 | Endocrine/Metabolic; Cancer (Amyloidosis; B-cell lymphoma; Chronic lymphocytic leukemia; Diffuse large B-cell lymphoma; Follicle center lymphoma; Lymphoma; Mantle cell lymphoma; Multiple myeloma; Non-Hodgkin lymphoma) [PARP modulator] |
| Cabazitaxel | Infusion; Intravenous; Intravesical; Solution | WO-09630356 | Cancer (Hormone refractory prostate cancer; Liposarcoma; Metastatic breast cancer; Metastatic prostate cancer; Transitional cell carcinoma) |
| Oxaliplatin | Infusion; Intravenous Solution | CN-101289468; US-04169846 | Cancer (Colon tumor; Colorectal tumor; Hepatocellular carcinoma; Metastatic colorectal cancer; Metastatic pancreas cancer; Metastatic stomach cancer; Pancreas tumor; Small intestine cancer; Stomach tumor) |
| Eribulin mesylate | Infusion; Intravenous; Solution | WO-09965894 | Cancer (Angiosarcoma; Ewing sarcoma; Liposarcoma; Metastatic bladder cancer; Metastatic breast cancer; Rhabdomyosarcoma; Soft tissue sarcoma) |

TABLE 11-continued

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| Docetaxel | Infusion; Intravenous; Solution | EP-00253738 | Cancer (Breast tumor; Cancer; Endometrioid carcinoma; Esophagus tumor; Head and neck tumor; Hormone refractory prostate cancer; Metastatic breast cancer; Metastatic non-small cell lung cancer; Metastatic stomach cancer; Ovary tumor; Prostate tumor; Squamous cell carcinoma) |
| Sugammadex | Intravenous; Solution | WO-00140316; WO-2008065142 | Neurology/Psychiatric (general anesthesia) |
| Cefoperazone sodium + sulbactam sodium | Intramuscular; Intravenous | US-04234579 | Genitourinary/Sexual Function; Gastrointestinal; Infection (Bacterial infection; Bacterial meningitis; Bacterial respiratory tract infection; Bacterial urinary tract infection; Bone and joint infection; Cholangitis; Cholecystitis; Complicated skin and skin structure infection; Endometriosis; *Neisseria gonorrhoeae* infection; Peritonitis; Sepsis) [Beta lactamase inhibitor] |
| Rotigotine | Drug coating; Patch; Transdermal | WO-02089777; WO-09949852 | Musculoskeletal; Neurology/Psychiatric (Parkinsons disease; Restless legs syndrome) [5-HT receptor agonist; adrenergic receptor agonist; Dopamine D1, D2, D3, D4, D5 receptor agonist] |
| Caspofungin | Formulation powder; Freeze drying; Infusion; Intravenous; Solution | US-05792746; WO-09421677 | Gastrointestinal; Infection (Abdominal abscess; *Aspergillus* infection; *Candida* infection; Fungal infection; Peritonitis) [1,3 beta glucan synthase inhibitor] |
| Iron sucrose injection, | Intravenous | WO-2004019032 | Neurology/Psychiatric; Other/Miscellaneous; Hematologic (Anemia; Iron deficiency anemia) |
| Piperacillin + tazobactam (injectable) | Antibiotic; Formulation powder; Freeze drying; Infusion; Intravenous; Solution | EP-00097446 | Gastrointestinal; Genitourinary/Sexual Function; Hematologic; Dermatologic; Cardiovascular; Infection (Abdominal abscess; Abscess; Acinetobacter infection; Appendicitis; Bacterial infection; Bacterial pneumonia; Bacterial skin infection; Bacterial urinary tract infection; *Bacteroides fragilis* infection; *Bacteroides* infection; Cellulitis; Cholangitis; Cholecystitis; Cystitis; Diabetic foot ulcer; *Escherichia coli* infection; Febrile neutropenia; *Haemophilus influenzae* infection; *Klebsiella pneumoniae* infection; Lower respiratory tract infection; Pelvic inflammatory disease; Peritonitis; *Pseudomonas aeruginosa* infection; Pyelonephritis; Sepsis; *Staphylococcus aureus* infection) [Beta lactamase inhibitor] |
| Dexmedetomidine | Infusion; Intravenous; Solution | EP-00300652 | Neurology/Psychiatric (Anesthesia; Delirium) [Alpha 2 adrenoceptor agonist] |
| Dalteparin sodium | Subcutaneous | WO-08001383 | Hematologic; Dermatologic; Cardiovascular (coronary thrombosis; deep vein thrombosis; lung embolism; thromboembolism) [Factor IIa antagonist; Factor Xa antagonist; Low molecular weight heparin] |
| Bupivacaine | Liposome; Subcutaneous; Suspension; Sustained/extended release; depot foam | EP-00280503 | Neurology/Psychiatric (pain; topical anesthesia, post-operative pain) [Sodium channel inhibitor] |
| Imipenem + cilastatin | Antibiotic; Infusion; Intramuscular; Intravenous | EP-00048025 | Dermatologic; Gastrointestinal; Genitourinary/Sexual Function; Cardiovascular; Infection; Respiratory; Inflammatory; Musculoskeletal; Ocular (Abscess; Acinetobacter infection; Acute bronchitis; Appendicitis; Bacterial infection; Bacterial pneumonia; Bacterial respiratory tract infection; Bacterial skin infection; Bacterial urinary tract infection; *Bacteroides fragilis* infection; *Bacteroides* infection; Bartholinitis; *Bifidobacterium* infection; Bone and joint infection; Cellulitis; Cholangitis; Cholecystitis; *Citrobacter* infection; *Clostridium* infection; Complicated urinary tract infection; Corneal ulcer; Cystitis; Empyema; Endocarditis; Endophthalmitis; *Enterobacter* infection; *Enterococcus faecalis* infection; *Escherichia coli* infection; Female genital tract infection; Gram negative bacterium infection; Gram positive bacterium infection; |

TABLE 11-continued

Non-oral small molecule therapeutics adaptable for delivery via ingestible device for the treatment of the listed diseases and conditions

| Drug Name | Existing Formulation Technologies and Methods of Administration | Exemplary Patent Literature | Therapeutic Area (Exemplary Indications) [Target-based Action] |
|---|---|---|---|
| | | | *Haemophilus* infection; *Haemophilus influenzae* infection; Infectious arthritis; Keratitis; *Klebsiella* infection; *Klebsiella pneumoniae* infection; *Morganella* infection; Osteomyelitis; Panophthalmitis; Pelvic inflammatory disease; Peritonitis; Prostatitis; *Proteus* infection; *Providencia* infection; *Pseudomonas aeruginosa* infection; Pyelonephritis; Sepsis; *Serratia* infection; Skin ulcer; *Staphylococcus aureus* infection; *Staphylococcus* infection; *Streptococcus agalactiae* infection; *Streptococcus* infection; *Streptococcus pneumoniae* infection; *Streptococcus pyogenes* infection) [Dehydropeptidase-1 inhibitor] |
| Tigecycline | Antibiotic; Infusion; Intravenous | EP-00536515 | Dermatologic; Infection (*Acinetobacter* infection; Bacterial infection; Bacterial pneumonia; Bacterial skin infection; *Bacteroides fragilis* infection; *Bacteroides* infection; *Citrobacter* infection; Clostridiaceae infection; *Clostridium* infection; *Enterobacter* infection; *Enterococcus faecalis* infection; *Escherichia coli* infection; *Haemophilus influenzae* infection; *Klebsiella* infection; *Klebsiella pneumoniae* infection; *Legionella pneumophila* infection; MRSA infection; *Staphylococcus aureus* infection; *Streptococcus agalactiae* infection; *Streptococcus* infection; *Streptococcus pneumoniae* infection; *Streptococcus pyogenes* infection) |
| Meropenem | Antibiotic; Infusion; Intravenous | EP-00126587 | Gastrointestinal; Infection; Respiratory (Appendicitis; Bacterial infection; Bacterial meningitis; Bacterial pneumonia; Bacterial respiratory tract infection; Bacterial skin infection; Bacterial urinary tract infection; *Bacteroides fragilis* infection; *Bacteroides* infection; *Bacteroides thetaiotaomicron* infection; Complicated skin and skin structure infection; Complicated urinary tract infection; Cystic fibrosis; *Enterococcus faecalis* infection; *Escherichia coli* infection; *Haemophilus influenzae* infection; *Klebsiella pneumoniae* infection; *Neisseria meningitidis* meningitis; *Peptostreptococcus* infection; Peritonitis; Pneumonia; *Proteus mirabilis* infection; *Pseudomonas aeruginosa* infection; *Staphylococcus aureus* infection; *Streptococcus agalactiae* infection; *Streptococcus* infection; *Streptococcus pneumoniae* infection; *Streptococcus pyogenes* infection; viridans group *Streptococcus* infection) [Penicillin binding protein inhibitor] |
| Ceftaroline fosamil | Antibiotic; Formulation powder; Infusion; Intravenous; Prodrug Solution | WO-09932497 | Bacterial pneumonia; Bacterial skin infection; Complicated skin and skin structure infection; *Escherichia coli* infection; *Haemophilus influenzae* infection; *Klebsiella* infection; *Klebsiella pneumoniae* infection; MRSA infection; Osteomyelitis; *Staphylococcus aureus* infection; *Streptococcus agalactiae* infection; *Streptococcus pneumoniae* infection; *Streptococcus pyogenes* infection [Penicillin binding protein 2X inhibitor] |
| Gemcitabine | Formulation powder; Freeze drying; Infusion; Intravenous | CN-104650169; EP-00122707; KR-00858842 | Cancer (Bladder tumor; Hepatobiliary system tumor; Lymphoma; Metastatic bladder cancer; Metastatic breast cancer; Metastatic non-small cell lung cancer; Metastatic ovary cancer; Metastatic pancreas cancer; Ovary tumor) |

Heparins

In some embodiments, the therapeutic suitable for use with the devices and methods described herein is a heparin. In some embodiments, the heparin is a low molecular weight heparin.

An exemplary heparin is dalteparin. Dalteparin is a low molecular weight heparin. Like other low molecular weight heparins, dalteparin is used for prophylaxis or treatment of deep vein thrombosis, pulmonary embolism, venous thromboembolism, unstable angina, and non-Q-wave myocardial infarction.

Dalteparin is delivered as an SC injection of 2500-18000 units once or twice daily, depending on the reason for treatment. It is available in single-dose vials, multi-dose vials, and pre-filled syringes for self-administration by the patient. The maximum concentration in currently available formulations is 25,000 units/mL, and many formulations contain only water and HCl/NaOH for pH adjustment. The bioavailability is approximately 8700 by SC injection, the half-life is approximately 3-5 hours, and it is primarily eliminated by the kidneys. Dalteparin is stable at room temperature and studies have demonstrated 30 days stability in commercial off-the-shelf syringes.

The primary risk of dalteparin overdose is uncontrolled hemorrhage at the site of injection. There are few cases of dalteparin overdose in the literature but, in most cases, the patients were discharged after observation without any intervention. One case describes self-administration of 360,000 units of dalteparin that was successfully managed with medical observation followed by discharge from the hospital with no notable sequelae. In the case of overdose, the action of dalteparin may be partially reversed by the administration of protamine sulphate.

Dalteparin is a suitable therapeutic for delivery via ingestible device as described herein. It is currently available as a liquid, administered by self-injection, and, because adverse injection site reactions are not uncommon, patients may readily adopt an alternative dosage form. The primary method of elimination is renal so first-pass through the liver should not present an obstacle to using the DDS. Lastly, the probability of acute reactions to overdose is low which, theoretically, could allow an increase in dose to compensate for lower bioavailability than SC injection. Dalteparin dose is normally specified as a single value based on the condition being treated and the weight range of the patient. Each weight range can span 10-15 kg, suggesting that precise dosing is not critical to achieving therapeutic effect.

Immune Modulators

In some embodiments, the therapeutic suitable for use with the devices and methods described herein is an immune modulator. As used herein, an "immune modulator" or "immune modulatory agent" is an agent that stimulates or suppresses the immune system and can help the body fight cancer, infection, or other diseases. The immune modulator can be a therapeutic agent that decreases the activation of an immune cell (e.g., a T cell, e.g., memory T cell), decreases the secretion or expression of a pro-inflammatory cytokine, decreases the recruitment or migration of T-lymphocytes (e.g., memory T lymphocytes), and/or increases the secretion or expression of an anti-inflammatory cytokine.

In some embodiments, an immune modulator is an antibody or antigen-binding fragment, a nucleic acid (e.g., inhibitory nucleic acid), a small molecule, or a live biotherapeutic, such as a probiotic. In some embodiments, the immune modulator is a therapeutic agent used for the treatment of inflammatory bowel disease (IBD), for example, Crohn's Disease or Ulcerative Colitis (UC). Non-limiting immune modulators that are useful for treating or preventing inflammatory bowel disease include substances that suppress cytokine production, down-regulate or suppress self-antigen expression, or mask MHC antigens.

Non-limiting examples of immune modulators include, without limitation: CHST15 inhibitors (e.g., STNM01); IL-6 receptor inhibitors (e.g., tocilizumab); IL-12/IL-23 inhibitors (e.g., ustekinumab and brazikumab); integrin inhibitors (e.g., vedolizumab and natalizumab); JAK inhibitors (e.g., tofacitinib); SMAD7 inhibitors (e.g., Mongersen); IL-13 inhibitors; IL-1 receptor inhibitors; TLR agonists (e.g., Kappaproct); stem cells (e.g., Cx601); 2-amino-6-aryl-5-substituted pyrimidines (see U.S. Pat. No. 4,665,077); non-steroidal anti-inflammatory drugs (NSAIDs); ganciclovir; tacrolimus; glucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); NN-9499; alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251:430-432 (1991); WO 90/11294; Ianeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol., 23:113-5 (2002)); biologic agents that interfere with T cell helper signals, such as anti-CD40 receptor or anti-CD40 ligand (CD 154), including blocking antibodies to CD40-CD40 ligand (e.g., Durie et al., Science, 261:1328-30 (1993); Mohan et al., J. Immunol., 154:1470-80 (1995)) and CTLA4-Ig (Finck et al., Science, 265:1225-7 (1994)); CD40/CD40L inhibitors; CD3 inhibitors; CD14 inhibitors; CD20 inhibitors; CD25 inhibitors; CD28 inhibitors; CD49 inhibitors; CD89 inhibitors; and T-cell receptor antibodies (EP 340,109) such as T10B9. Non-limiting examples of agents also include the following: budesonide; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinylimidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TPlO; T Cell Sciences, Inc.); slow-release mesalazine; antagonists of platelet activating factor (PAF); ciprofloxacin; and lignocaine.

Non-limiting examples of immune modulators that are useful for treating ulcerative colitis include sulfasalazine and related salicylate-containing drugs for mild cases and corticosteroid drugs for severe cases. Non-limiting examples of immune modulators that are useful for treating a liver disease or disorder (e.g., liver fibrosis or NASH) include: elafibranor (GFT 505; Genfit Corp.), obeticholic acid (OCA; Intercept Pharmaceuticals, Inc.), cenicriviroc (CVC; Allergan plc), selonsertib (formerly GS-4997; Gilead Sciences, Inc.), an anti-LOXL2 antibody (simtuzumab (formerly GS 6624; Gilead Sciences, Inc.)), GS-9450 (Gilead Sciences, Inc.), GS-9674 (Gilead Sciences, Inc.), GS-0976 (formerly NDI-010976; Gilead Sciences, Inc.), Emricasan (Conatus Pharmaceuticals, Inc.), Arachidyl-amido cholanoic acid (Aramchol™; Galmed Pharmaceuticals Ltd.), AKN-083 (Allergan plc (Akarna Therapeutics Ltd.)), TGFTX4 (Genfit Corp.), TGFTX5 (Genfit Corp.), TGFTX1 (Genfit Corp.), a RoRγ agonist (e.g., LYC-55716; Lycera Corp.), an ileal bile acid transporter (iBAT) inhibitor (e.g., elobixibat, Albireo Pharma, Inc.; GSK2330672, GlaxoSmithKline plc; and A4250; Albireo Pharma, Inc.), stem cells, a CCR2 inhibitor, bardoxolone methyl (Reata Pharmaceuticals, Inc.), a bone morphogenetic protein-7 (BMP-7) mimetic (e.g., THR-123 (see, e.g., Sugimoto et al. (2012) Nature Medicine 18: 396-404)), an anti-TGF-β antibody (e.g., fresolimumab; see also U.S. Pat. Nos. 7,527,791 and 8,383,780, incorporated herein by reference), pirfenidone (Esbriet®, Genentech USA Inc.), an anti-integrin αvβ6 antibody, an anti-connective tissue growth factor (CTGF) antibody (e.g., pamrevlumab; FibroGen Inc.), pentoxifylline, vascular endothelial growth factor (VEGF), a renin angiotensin aldosterone system (RAAS) inhibitor (e.g., a rennin inhibitor (e.g. pepstatin, CGP2928, aliskiren), or an ACE inhibitor (e.g., captopril, zofenopril, enalapril, ramipril, quinapril, perindopril, lisinopril, benazepril, imidapril, fosinopril, and trandolapril)), thrombospondin, a statin, bardoxolone, a PDE5 inhibitor (e.g., sidenafil, vardenafil, and tadalafil), a NADPH oxidase-1 (NOX1) inhibitor (see, e.g., U.S. Publication No. 2011/0178082, incorporated herein by reference), a NADPH oxidase-4 (NOX4) inhibitor (see, e.g., U.S. Publication No. 2014/0323500, incorporated herein by reference), an ETA antagonist (e.g., sitaxentan, ambrisentan, atrasentan, BQ-123, and zibotentan), nintedanib (Boehringer Ingelheim), INT-767 (Intercept Pharmaceuticals, Inc.), VBY-376 (Virobay Inc.), PF-04634817(Pfizer), EXC 001 (Pfizer), GM-CT-01 (Galectin Therapeutics), GCS-100 (La Jolla Pharmaceuticals), hepatocyte growth factor mimetic (Refanalin®; Angion Biomedica), SAR156597 (Sanofi), tralokinumab (AstraZeneca), pomalidomide (Celgene), STX-100 (Biogen IDEC), CC-930 (Celgene), anti-miR-21 (Regulus Therapeutics), PRM-151 (Promedior), BOT191 (BiOrion), Palomid 529 (Paloma Pharamaceuticals), IMD1041 (IMMD, Japan), serelaxin (Novartis), PEG-relaxin (Ambrx and Bristol-Myers Squibb), ANG-4011 (Angion Biomedica), FTO11 (Fibrotech Therapeutics), pirfenidone (InterMune), F351 (pirfenidone derivative (GNI Pharma), vitamin E (e.g., tocotrienol (alpha, beta, gamma, and delta) and tocopherol (alpha, beta, gamma, and delta)), pentoxifylline, an insulin sensitizer (e.g., rosiglitazone and pioglitazone), cathepsin B inhibitor R-3020, etanercept and biosimilars thereof, peptides that block the activation of Fas (see, e.g., International Publication No. WO 2005/117940, incorporated herein by reference), caspase inhibitor VX-166, caspase inhibitor Z-VAD-fmk, fasudil, belnacasan (VX-765), and pralnacasan (VX-740).

In some embodiments, the immune modulator is an anti-inflammatory agent. Examples of anti-inflammatory agents include, but are not limited to, IL-12/IL-23 inhibitors, TNFα inhibitors, IL-6 receptor inhibitors, immune modulatory agents (e.g., CD40/CD40L inhibitors), IL-1 inhibitors, IL-13 inhibitors, IL-10 receptor agonists, chemokine/chemokine receptor inhibitors, integrin inhibitors, and S1P modulators.

In some embodiments, the immune modulator is an integrin inhibitor. Examples of integrin inhibitors include, but are not limited to, β7 (beta-7) integrin inhibitors, such as α4β7 (alpha4beta7) integrin inhibitors.

In some embodiments, the immune modulator is a PDE4 inhibitor.

In some embodiments of any of the devices or methods described herein, the therapeutic is an immune modulator. In some embodiments of any of the devices or methods described herein, the immune modulator is an IL-12/IL-23 inhibitor, a TNFα inhibitor, a CD40/CD40L inhibitor, an anti-integrin, or an IL-1 inhibitor. In some embodiments, the therapeutic is an immune modulator for use in a method of treating an inflammatory disease or condition that arises in a tissue originating from the endoderm in a subject, where the method includes orally administering to the subject an ingestible device loaded with the immune modulator, wherein the immune modulator is released by the device into the submucosa and/or the mucosa (e.g., into the lamina propria) of the gastrointestinal tract of the subject.

Pharmaceutical Formulations

Agents such as antibodies and other therapeutic proteins and the other therapeutic agents disclosed herein can be delivered using the devices and methods described herein, including an ingestible device as disclosed herein. The therapeutic agents can be incorporated into pharmaceutical formulations, which can be loaded into a device for release and delivery to a subject, or more particularly, for delivery of the formulation and/or antibody or therapeutic protein or agent to the gastrointestinal tract of a subject. In some embodiments, the formulation is delivered to the tissue of the GI tract. In some embodiments, the formulation is delivered onto or into tissue of the GI tract, e.g., the mucus, mucosa or submucosa of the GI tract. In some embodiments, the formulations are fluid. In some embodiments, the fluid is a solution or a suspension. In some embodiments, the formulation is a liquid, but can be semi-solid, or solid formulations that are later converted to a liquid formulation. The formulations can comprise the agent and a physiologically acceptable carrier. Some formulations, which may be commercially or otherwise available for IV or subcutaneous delivery, and which may be available in pre-loaded syringes or pens, may alternatively be incorporated or loaded into a device, such as an ingestible device, as disclosed herein, for release and topical delivery of the formulation and/or antibody or therapeutic protein to the gastrointestinal tract of a subject.

In some embodiments, the therapeutic agent is formulated as a solution (e.g., an aqueous solution formulation) or a suspension or dispersion. In some embodiments, the formulation contains an antibody. Formulations can be prepared, for example, by incorporating an antibody in the required amount in an appropriate solvent with at least one, or a combination of, ingredients described herein. Generally, dispersions can be prepared by incorporating an antibody into a vehicle that contains a basic dispersion medium and/or other ingredients. In some embodiments, proper fluidity of a formulation is maintained using an appropriate coating, by the maintenance of the required particle size in the case of dispersion, and/or by the use of surfactants. Prolonged absorption of compositions can be brought about by including in the composition an agent that delays absorption. In some embodiments, formulations further comprise one or more additional excipients to enhance performance, such as tissue or mucosa permeation enhancement, disruption of tight epithelial junctions, absorption and/or stability. Excipients that can be incorporated to enhance absorption by the GI tract and/or at the disease site within the GI tract include, for example, bile salts, chelators, surfactants, anti-oxidants, fatty acids and derivatives thereof, cationic polymers, anionic polymers, and acylcarnitines.

In some embodiments, the formulation contains a high concentration of the therapeutic agent (e.g., about 50 mg/mL, about 100 mg/mL or about 150 mg/mL or greater).

In some embodiments, the formulation suitable for use with the devices and methods described herein optionally includes a topical anesthetic agent. Thus, in some embodiments, the formulation includes an additional agent, for example, an anesthetic agent in an amount effective to mitigate pain experienced on delivery of the drug. Examples of anesthetic agents include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine propoxycaine, pseudococaine, pyrrocaine, ropivacaine, salicyl alcohol, tetracaine, tolycaine, trimecaine, and zolamine; and pharmaceutically acceptable salts thereof.

Formulations Containing Insulin

In some embodiments, the pharmaceutical preparation or formulation that can be used in the described methods and device contains insulin. As used herein, the term "insulin" includes animal-derived insulin (such as a bovine, pig, or bovine-pig insulin, for example, as obtained from a bovine or pig pancreas), native human insulin, and recombinant human insulin. The formulation can be a liquid, semi-solid, or solid. In some embodiments, the formulation contains the insulin and a physiologically acceptable carrier.

In some embodiments, the insulin preparation is provided at a concentration of about 40 units/mL to about 500 units/mL (U-40 to U-500). In some embodiments, the insulin is provided at a concentration of about 100 units/mL (U-100). In other embodiments, the insulin is provided at a concentration of about 300 units/mL (U-300). In yet other embodiments, the insulin is provided at a concentration of about 500 units/mL (U-500). In yet another embodiment, there is provided an insulin preparation containing about 40 units/mL (U-40).

In some embodiments, the insulin preparation is an excipient-free insulin.

In other embodiments, the insulin preparation contains one or more excipients. In some embodiments, the insulin preparation is an aqueous formulation comprising the insulin, an aqueous medium, and one or more excipients. In some embodiments, the aqueous medium is water, such as water for injection (WFI), a buffer or a pH-adjusted water. In some embodiments, the buffer is a phosphate buffer. In some embodiments, the water (e.g., the WFI) or the final formulation pH is adjusted to a neutral pH, for example, a pH of about 6.5 to about 8, about pH 6.8 to about 7.8, about pH 7 to about pH 7.8, about pH 7, or more particularly, about pH 7.3 or about 7.4. A mineral acid or base can be used to adjust the pH. In some embodiments, the mineral acid or base is selected from hydrochloric acid (e.g., about 1N to about 2N) and sodium hydroxide (e.g., about 1N to about 2N).

In some embodiments, the one or more excipients is a preservative. In some embodiments, the preservative is a phenolic excipient, such as phenol, m-cresol or a combination thereof.

In some embodiments, the one or more excipients is a salt or buffering agent. In some embodiments, the salt or buffering agent is tromethamine (tris(hydroxymethyl)aminomethane), sodium chloride, or a combination thereof. In some embodiments, the salt is zinc chloride.

In some embodiments, the one or more excipients is a surfactant. In some embodiments, the surfactant is a non-ionic surfactant. In some embodiments, the non-ionic surfactant is a polysorbate, such as polysorbate 20, 40, 60 or 80. In some embodiments, the surfactant is a poloxamer, such as 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and/or 407.

In some embodiments, the one or more excipients is at least one stabilizing agent. In some embodiments, the stabilizing agent is a tonicity stabilizer. In some embodiments, the stabilizing agent inhibits insulin aggregation. In some embodiments, an excipient provides one or more functions in the formulation, for example, to provide both sterility and stabilization from aggregation. In some embodiments, the stabilizing agent is albumin, serum (e.g., a patient's serum), or blood (e.g., a patient's blood). In some embodiments, the one or more stabilizing agents is glycerol (glycerin), a phenolic excipient, and/or a source of zinc ions, such as zinc chloride and/or zinc oxide.

In some embodiments, the formulation is a zinc-free or low zinc formulation, for example, as described in U.S. Pat. No. 7,205,276B2, the entire content of which is hereby incorporated by reference in its entirety.

In some embodiments, the at least one stabilizing agent is a phenolic excipient. In some embodiments, the phenolic excipient is incorporated into the formulation in order to stabilize the insulin molecule, for example, in a hexameric form to avoid aggregation, and/or to maintain sterility of the solution. In some embodiments, the phenolic excipient is phenol, meta-cresol, or a combination thereof. In some embodiments, the phenolic excipient is present at a concentration of about 25-35 millimolar, or more particularly, about 29-32 millimolar, or about 2.5 to 3.5 mg/mL, or more particularly, about 2.7 to 3.2 mg/mL. (See Toxicology Reports, V2:194-202 (2015)).

In some embodiments, the formulation does not contain a phenolic excipient.

In some embodiments, the insulin formulation is an aqueous solution comprising the insulin, an aqueous medium, glycerol, and one or more agents selected from a phenolic excipient a source of zinc ions, and/or a surfactant.

In some embodiments, the formulation is an aqueous solution comprising an insulin, an aqueous medium, glycerol, a phenolic excipient and a source of zinc ions. In some embodiments, the phenolic excipient is phenol or m-cresol. In a further embodiment, the phenolic excipient is m-cresol. In some embodiments, the source of zinc ions is zinc chloride. In some embodiments the aqueous medium is water for injection (WFI). In other embodiments, the aqueous medium is a buffer or pH-adjusted water. In some embodiments, the formulation pH is adjusted to a neutral pH 7, or more particularly, to 7.4. In some embodiments, the formulation is an aqueous solution containing insulin, glycerol, metacresol, zinc chloride and water for injection, which may be pH adjusted. In some particular embodiments, the formulation is an aqueous solution containing insulin (e.g., 100 units/mL), glycerol (16 mg/mL), metacresol (3 mg/mL), zinc chloride (approximately 7 mcg/mL) and water for injection, and the pH is adjusted to 7.4 (for example, using hydrochloric acid 2N or sodium hydroxide 2N). In a more particular embodiment, the insulin is recombinant human insulin. In an even more particular embodiment, the formulation is Novolin® R or a generic equivalent thereof, which may be commercially or otherwise available, for example, for IV or subcutaneous delivery.

In some embodiments, the formulation is an aqueous solution containing an insulin (e.g., insulin glulisine), an aqueous medium, a phenolic excipient, a surfactant, and one or more salts and/or buffering agents. In some embodiments, the phenolic excipient is phenol or m-cresol. In a further embodiment, the phenolic excipient is m-cresol. In some embodiments, the surfactant is polysorbate 20 or polysorbate 80. In some embodiments, the surfactant is polysorbate 20. In some embodiments the aqueous medium is water for injection (WFI). In other embodiments, the aqueous medium is a buffer or pH-adjusted water. In some embodiments, the formulation pH is adjusted to a neutral pH 7, or more particularly, to 7.3. In some embodiments, the aqueous medium further comprises sodium chloride and/or trimethylamine. In some particular embodiments, the formulation is an aqueous solution containing insulin glulisine, metacresol, trometamine, sodium chloride, polysorbate 20, and water for injection, which may be pH adjusted. In some particular embodiments, the formulation is an aqueous solution containing insulin glulisine (e.g., 100 units/mL), metacresol (3.15 mg/mL), trometamine (6 mg/mL), 5 mg sodium chloride (5 mg/mL), polysorbate 20 (0.01 mg/mL), and water for injection, wherein the pH is adjusted by addition of aqueous solutions of hydrochloric acid and/or sodium hydroxide. In an even more particular embodiment, the formulation is APIDRA or a generic equivalent thereof, which may be commercially or otherwise available, for example, for IV or subcutaneous delivery.

In some embodiments, the formulation is an aqueous solution containing insulin, an aqueous medium, glycerol, a phenolic excipient, a surfactant, a source of zinc ions, and one or more salts and/or buffering agents. In some embodiments, the surfactant is a polysorbate or a poloxamer. In a further embodiment, the surfactant is poloxamer 171. In some embodiments, the phenolic excipient is phenol or m-cresol. In a further embodiment, the phenolic excipient is phenol. In some embodiments, the source of zinc ions is zinc chloride. In some embodiments, the salt or buffering agent is trometamol or a combination thereof. In some embodiments, the aqueous medium is pH-adjusted water for injections. In some embodiments, the formulation is an aqueous solution containing insulin (e.g., 100 units/mL), phenol, zinc chloride, trometamol, poloxamer 171, glycerol, hydrochloric acid (for pH adjustment), and water for injections. In a more particular embodiment, the formulation is Insuman Infusat or a generic equivalent thereof, which may be commercially or otherwise available, for example, for IV or subcutaneous delivery.

In some embodiments, the formulation is an aqueous solution containing an insulin (e.g., insulin lispro), an aqueous medium, glycerin, a phenolic excipient, a source of zinc ions, and one or more salts and/or buffering agents. In some embodiments, the phenolic excipient is phenol or m-cresol. In a further embodiment, the phenolic excipient is m-cresol, which may contain trace amounts of phenol. In some embodiments, the source of zinc ions is zinc oxide. In some embodiments, the salt or buffering agent is a phosphate buffer, such has dibasic sodium phosphate. In some embodiments, the aqueous medium is an aqueous buffer containing the dibasic sodium phosphate and water for injections. In some embodiments, the formulation is an aqueous solution containing insulin or insulin lispro (e.g., 100 units/mL), glycerin, m-cresol (which may contain trace phenol), zinc oxide, sodium phosphate dibasic and WFI, which may be pH adjusted, for example, to a pH of between about pH 7.0 and 7.8. In a more particular embodiment, the formulation contains insulin lispro (100 units/mL), glycerin (16 mg/mL), dibasic sodium phosphate (1.88 mg/mL), 3.15 mg metacresol (3.15 mg/mL), zinc oxide content adjusted to provide 0.0197 mg/mL zinc ion, trace amounts of phenol, and Water for Injection, such that the final formulation solution has a pH of 7.0 to 7.8, which can be achieved by addition of aqueous solutions of hydrochloric acid 10% and/or sodium hydroxide 10%. In an even more particular embodiment, the formulation is HUMALOG or a generic equivalent thereof, which may be commercially or otherwise available, for example, for IV or subcutaneous delivery.

In some embodiments, the formulation is an aqueous solution containing an insulin, an aqueous medium, glycerol, a phenolic excipient, a source of zinc ions, and one or more salts and/or buffering agents. In some embodiments, the phenolic excipient is phenol, m-cresol, or a combination thereof. In a further embodiment, the phenolic excipient is phenol and m-cresol. In some embodiments, the source of zinc ions is zinc chloride. In some embodiments, the salt and/or buffering agent is sodium chloride and a phosphate buffer, such has disodium phosphate dihydrate. In some embodiments, the aqueous medium is an aqueous buffer containing the sodium chloride, the disodium phosphate dihydrate and water for injections. In some embodiments, the formulation is an aqueous solution containing insulin (e.g., 100 units/mL), glycerol, phenol, m-cresol, zinc chloride, sodium chloride, disodium phosphate dihydrate, water for injections, and hydrochloric acid and/or sodium hydroxide (for pH adjustment). In a more particular embodiment, the formulation is NovoRapid or a generic equivalent thereof, which may be commercially or otherwise available, for example, for IV or subcutaneous delivery.

In some embodiments, the formulation is an aqueous solution containing an insulin, an aqueous medium, glycerin, a phenolic excipient, and a source of zinc ions. In some embodiments, the phenolic excipient is phenol or m-cresol. In a further embodiment, the phenolic excipient is m-cresol. In some embodiments, the source of zinc ions is zinc oxide. In some embodiments, the aqueous medium is pH-adjusted water for injections. In some embodiments, the formulation is an aqueous solution containing insulin (e.g., 500 units/mL), glycerin, m-cresol, zinc oxide, water for injections, and hydrochloric acid and/or sodium hydroxide (for pH adjustment). In a more particular embodiment, the formulation is an aqueous solution containing insulin (500 units/mL), glycerin (16 mg/mL), m-cresol (2.5 mg/mL), zinc oxide (to supplement endogenous zinc to obtain a total zinc content of 0.017 mg/100 units), water for injections, and hydrochloric acid and/or sodium hydroxide (for pH adjustment). In an even more particular embodiment, the formulation is HUMULIN R U-500 or a generic equivalent thereof, which may be commercially or otherwise available, for example, for IV or subcutaneous delivery.

In some embodiments, the insulin is a commercially available insulin or generic formulation thereof (see Donner T. Insulin—Pharmacology, Therapeutic Regimens And Principles Of Intensive Insulin Therapy. [Updated 2015 Oct. 12]. In: De Groot L J, Chrousos G, Dungan K, et al., editors. Endotext [Internet]. South Dartmouth (MA): MDText.com, Inc.; 2000. Available from: https://www.ncbi.nlm.nih.gov/ books/NBK278938/), the entire content of which is hereby incorporated by reference in its entirety). Examples of commercially available insulins include, but are not limited to, rapid-acting insulins such as insulin lispro (Humalog®, Lilly), insulin aspart (NovoLog®, Novo Nordisk), insulin glulisine (Apidra®, Sanofi-Aventis), and technosphere insulin (Afrezza®); short-acting insulins such as regular human insulin (Humulin® R, Lilly; Novolin® R, Novo Nordisk); intermediate-acting insulins such as NPH (isophane) human insulin (Humulin® N, Lilly; Novolin® N, Novo Nordisk); long-acting insulins such as insulin detemir (Levemir®, Novo Nordisk) and insulin glargine (Lantus®, Sanofi-Aventis); and insulin mixtures, for example, NPH/regular mixtures, such as 70% NPH/30% regular (Humulin® 70/30, Lilly; Novolin® 70/30, Novo Nordisk), protamine/lispro mixtures, such as 50% protamine/50% lispro (Humalog® Mix 50/50, Lilly) and 75% protamine/25%; ispro (Humalog® Mix 75/25, Lilly), and protamine/aspart mixtures, such as 70% protamine/30% aspart (Novolog® Mix 70/30, Novo Norkisk); and generic versions thereof. Commercially available insulin preparations, and generics thereof, are available in vials, cartridges, disposable pens, and/or inhalers.

Some insulin preparations disclosed herein, which may be commercially or otherwise available in pre-loaded vials, cartridges, syringes, inhalers or pens, may alternatively be incorporated or loaded into a device as disclosed herein, for release and topical delivery of the insulin formulation to the gastrointestinal tract of a subject.

In some embodiments, an insulin preparation as described herein can be further diluted prior to administration, for example, with 0.9% sodium chloride, 5% dextrose, or 10% dextrose with 40 mmol/L potassium chloride.

Dosages

In some embodiments of the devices and methods described herein, the amount of the therapeutic that is administered is about 0.01 mg to about 500 mg. In some embodiments, the therapeutic is a therapeutic agent as disclosed herein. In some embodiments of any of the methods described herein, the therapeutic is an antibody or an antigen-binding antibody fragment. In some embodiments of any of the methods described herein, the antibody is a humanized antibody.

In some embodiments, a formulation can include a dose of about 0.01-1.0 mg, about 0.1-1.0 mg, about 0.5-5.0 mg, about 1.0-5 mg, about 2.0-10 mg, about 5.0-20 mg, about 5.0-30 mg, about 30-90 mg, about 70-90 mg, about 30-110 mg, about 70-110 mg, about 150-450 mg, or about 300-1200 mg of a therapeutic agent. In some embodiments, the therapeutic agent is an antibody, an antigen-binding portion or a biosimilar thereof, or other therapeutic protein. In some embodiments, an effective dose of the therapeutic agent in a formulation is about 30 mg, about 40 mg, about 50 mg, about 60 mg, about 70 mg, about 80 mg, about 90 mg, about 100 mg, about 125 mg, about 150 mg, about 160 mg, about 175 mg, about 200 mg, about 300 mg, about 400 mg, about 450 mg, about 500 mg, about 600 mg, about 750 mg, about 1000 mg, or about 1200 mg. In some embodiments, the dose is an induction dose. In other embodiments, the dose is a maintenance dose.

In some embodiments, the subject is administered the dose of the therapeutic once a day. In some embodiments, the subject is administered the dose of the therapeutic once every two days. In some embodiments, the subject is administered the dose of the therapeutic once every three days. In some embodiments, the subject is administered the dose of the therapeutic once every four days. In some embodiments, the subject is administered the dose of the therapeutic once every five days. In some embodiments, the subject is administered the dose of the therapeutic once every six days. In some embodiments, the subject is administered the dose of the therapeutic once every seven days. In some embodiments, the subject is administered the dose of the therapeutic once every eight days. In some embodiments, the subject is administered the dose of the therapeutic once every nine days. In some embodiments, the subject is administered the dose of the therapeutic once every ten days. In some embodiments, the subject is administered the dose of the therapeutic once every two weeks. In some embodiments, the subject is administered the dose of the therapeutic once every three weeks. In some embodiments, the subject is administered the dose of the therapeutic once every month.

In some embodiments, the amount of therapeutic agent absorbed by the body, as measured in blood or plasma over time and expressed as AUC (µg·day/mL), when delivered using any of the devices or methods described herein, is between about 10% and about 95% of the amount when the therapeutic agent is administered subcutaneously or intramuscularly (IM), such as about 10% to about 90%, about 10% to about 80%, about 10% to about 70%, about 10% to about 60%, about 10% to about 50%, about 10% to about 40%, about 10% to about 30%, about 10% to about 20%, about 20% to about 95%, about 20% to about 90%, about 20% to about 80%, about 20% to about 70%, about 20% to about 60%, about 20% to about 50%, about 20% to about 40%, about 20% to about 30%, about 30% to about 95%, about 30% to about 90%, about 30% to about 80%, about 30% to about 70%, about 30% to about 60%, about 30% to about 50%, about 30% to about 40%, about 40% to about 95%, about 40% to about 90%, about 40% to about 80%, about 40% to about 70%, about 40% to about 60%, about 40% to about 50%, about 50% to about 95%, about 50% to about 90%, about 50% to about 80%, about 50% to about 70%, about 50% to about 60%, about 60% to about 95%, about 60% to about 90%, about 60% to about 80%, about 60% to about 70%, about 70% to about 95%, about 70% to about 90%, about 70% to about 80%, about 80% to about 95%, about 80% to about 90%, about 90% to about 95%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the amount when the therapeutic agent is administered subcutaneously or intramuscularly (IM).

In some embodiments, the amount of therapeutic agent absorbed by the body, as measured in blood or plasma over time and expressed as AUC (µg·day/mL), when delivered using any of the devices or methods described herein, is between about 10% and about 95% of the amount when the therapeutic agent is administered intravenously, such as about 10% to about 90%, about 10% to about 80%, about 10% to about 70%, about 10% to about 60%, about 10% to about 50%, about 10% to about 40%, about 10% to about 30%, about 10% to about 20%, about 20% to about 95%, about 20% to about 90%, about 20% to about 80%, about 20% to about 70%, about 20% to about 60%, about 20% to about 50%, about 20% to about 40%, about 20% to about 30%, about 30% to about 95%, about 30% to about 90%, about 30% to about 80%, about 30% to about 70%, about 30% to about 60%, about 30% to about 50%, about 30% to about 40%, about 40% to about 95%, about 40% to about 90%, about 40% to about 80%, about 40% to about 70%, about 40% to about 60%, about 40% to about 50%, about 50% to about 95%, about 50% to about 90%, about 50% to about 80%, about 50% to about 70%, about 50% to about 60%, about 60% to about 95%, about 60% to about 90%, about 60% to about 80%, about 60% to about 70%, about 70% to about 95%, about 70% to about 90%, about 70% to about 80%, about 80% to about 95%, about 80% to about 90%, about 90% to about 95%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the amount when the therapeutic agent is administered intravenously.

Bioavailability (AUC) and other measures can be used to assess the pharmacokinetic (PK) characteristics of administration of therapeutics administered according to the devices and methods of the disclosure and compare with other routes of administration. Example PK parameters include plasma half-life ($t_{1/2}$ (min)), maximum plasma concentration ($C_{max}$ (pg/mL)), time to maximum plasma concentration ($T_{max}$ (min)), and clearance rate (CL). For individual drugs, pharmacodynamic (PD) characteristics can be measured and compared with other routes of administration. PD characteristics can be specific to the drug being administered. For example, where insulin is the drug being administered, PD characteristics can include dextrose infusion rate (mg/kg/min) and total amount of glucose (mg/kg) infused (from 20% dextrose infusion) required to maintain the target blood glucose concentration, as well as plasma glucose levels at select time points. Tables 12-14 show the number of capsules needed for a given relative bioavailability % for several exemplary drugs. The asterisk (*) indicates that dosing frequency can be increased to reduce number of capsules per dose, particularly for Humira and Interferon alpha-2b.

TABLE 12

Relative bioavailability for 0.5 mL ingestible device capsules of various drugs

| Drug | Potential Dose | Dosing Frequency (IFU) | Selected Dose | Commercially Available Drug Concentration | Number of Capsules Needed (for a given Relative Bioavailability %) | | | | | | | | | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Humira (adalimumab) | 40, 80, 160 mg | q 2 wk | 80 mg | 0.4 mL ~40 mg | 1.6 | 1.8 | 2.0 | 2.3 | 2.7 | 3.2 | 4.0 | 5.3 | 8.0 | q 2 wk |
| Victoza (liraglutide) | 1.2 mg | qd | 1.2 mg | 1 mL ~6 mg | 0.4 | 0.4 | 0.5 | 0.6 | 0.7 | 0.8 | 1.0 | 1.3 | 2.0 | qd |
| Trulicity (dulaglutide) | 0.75 mg | qwk | 0.75 mg | 1.5 mg ~0.5 mL | 0.5 | 0.6 | 0.6 | 0.7 | 0.8 | 1.0 | 1.3 | 1.7 | 2.5 | qwk |
| Avonex (interferon beta-1a) | 30 μg | qwk | 30 μg | 0.5 mL ~30 μg | 1.0 | 1.1 | 1.3 | 1.4 | 1.7 | 2.0 | 2.5 | 3.3 | 5.0 | qwk |
| Interferon alfa-2b | 3-30 million IU | 3 times a week | 15 million IU | 1 mL ~50 million IU | 0.6 | 0.7 | 0.8 | 0.9 | 1.0 | 1.2 | 1.5 | 2.0 | 3.0 | 3 times a week |
| Natpara (parathyroid hormone; PTH) | 50-100 μg | qd | 75 μg | 1 mL ~1 mg | 0.2 | 0.2 | 0.2 | 0.2 | 0.3 | 0.3 | 0.4 | 0.5 | 0.8 | qd |

TABLE 13

Relative bioavailability for 0.4 mL ingestible device capsules of various drugs

| Drug | Potential Dose | Dosing Frequency (IFU) | Selected Dose | Commercially Available Drug Concentration | Number of Capsules Needed (for a given Relative Bioavailability %) | | | | | | | | | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Humira (adalimumab) | 40, 80, 160 mg | q 2 wk | 80 mg | 0.4 mL ~40 mg | 2.0 | 2.2 | 2.5 | 2.9 | 3.3 | 4.0 | 5.0 | 6.7 | 10.0 | q 2 wk |
| Victoza (liraglutide) | 1.2 mg | qd | 1.2 mg | 1 mL ~6 mg | 0.5 | 0.6 | 0.6 | 0.7 | 0.8 | 1.0 | 1.3 | 1.7 | 2.5 | qd |
| Trulicity (dulaglutide) | 0.75 mg | qwk | 0.75 mg | 1.5 mg ~0.5 mL | 0.6 | 0.7 | 0.8 | 0.9 | 1.0 | 1.3 | 1.6 | 2.1 | 3.1 | qwk |
| Avonex (interferon beta-1a) | 30 μg | qwk | 30 μg | 0.5 mL ~30 μg | 1.3 | 1.4 | 1.6 | 1.8 | 2.1 | 2.5 | 3.1 | 4.2 | 6.3 | qwk |
| Interferon alfa-2b | 3-30 million IU | 3 times a week | 15 million IU | 1 mL ~50 million IU | 0.8 | 0.8 | 0.9 | 1.1 | 1.3 | 1.5 | 1.9 | 2.5 | 3.8 | 3 times a week |
| Natpara (parathyroid hormone; PTH) | 50-100 μg | qd | 75 μg | 1 mL ~1 mg | 0.2 | 0.2 | 0.2 | 0.3 | 0.3 | 0.4 | 0.5 | 0.6 | 0.9 | qd |

TABLE 14

Relative bioavailability for 0.3 mL ingestible device capsules of various drugs

| Drug | Potential Dose | Dosing Frequency (IFU) | Selected Dose | Commercially Available Drug Concentration | Number of Capsules Needed (for a given Relative Bioavailability %) | | | | | | | | | Dosing Freq.* |
|---|---|---|---|---|---|---|---|---|---|---|---|---|---|---|
| | | | | | 100% | 90% | 80% | 70% | 60% | 50% | 40% | 30% | 20% | |
| Humira (adalimumab) | 40, 80, 160 mg | q 2 wk | 80 mg | 0.4 mL ~40 mg | 2.7 | 3.0 | 3.3 | 3.8 | 4.4 | 5.3 | 6.7 | 8.9 | 13.3 | q 2 wk |
| Victoza (liraglutide) | 1.2 mg | qd | 1.2 mg | 1 mL ~6 mg | 0.7 | 0.7 | 0.8 | 1.0 | 1.1 | 1.3 | 1.7 | 2.2 | 3.3 | qd |
| Trulicity (dulaglutide) | 0.75 mg | qwk | 0.75 mg | 1.5 mg ~0.5 mL | 0.8 | 0.9 | 1.0 | 1.2 | 1.4 | 1.7 | 2.1 | 2.8 | 4.2 | qwk |
| Avonex (interferon beta-1a) | 30 µg | qwk | 30 µg | 0.5 mL ~30 µg | 1.7 | 1.9 | 2.1 | 2.4 | 2.8 | 3.3 | 4.2 | 5.6 | 8.3 | qwk |
| Interferon alfa-2b | 3-30 million IU | 3 times a week | 15 million IU | 1 mL ~50 million IU | 1.0 | 1.1 | 1.3 | 1.4 | 1.7 | 2.0 | 2.5 | 3.3 | 5.0 | 3 times a week |
| Natpara (parathyroid hormone; PTH) | 50-100 µg | qd | 75 µg | 1 mL ~1 mg | 0.3 | 0.3 | 0.3 | 0.4 | 0.4 | 0.5 | 0.6 | 0.8 | 1.3 | qd |

TABLE 15

Additional drugs for consideration for delivery via ingestible device

| Drug | Potential Dose | Dosing Frequency |
|---|---|---|
| Remicade ® (infliximab) | 400 mg* | q 0, 2, 6, 8 wk |
| Cimzia ® (certolizumab pegol) | 400 mg | q 4 wk |
| Enbrel ® (etanercept) | 50 mg | q 2 wk |
| Lantus ® (insulin) | sq | qd |
| NovoLog ® (insulin) | sq | qd |
| Bydureon ® (exenatide) | 2 mg | qwk |
| Tanzeum ® (albiglutide) | 30 mg | qwk |
| Growth hormone-inhibiting hormone (GHIH; somatostatin) | 0.48-2 mg* | qd |
| Sandostatin ® (octreotide) | 100-500 µg | qd; bid; tid |
| Avastin ® (bevacizumab) | 5 mg | q 2 wk; 3 wk |
| Entyvio ® (vedolizumab) | 300 mg | |
| Fragmin ® (dalteparin) | 2500-18000 IU | qd |
| Rocephin ® (ceftriaxone) (or other antimicrobials) | 1 g | qd |
| Genotropin ® (human growth hormone; HGH) | 0.2-2 mg | qd |

Tables 16 and 17 show illustrative dosing regimens for different therapeutics agents delivered with ingestible devices described herein. For the purposes of the tables, the ingestible devices have two different payload sizes: 200 µL in 00-sized device and 400 µL in 000-sized device. The dosing regimens were generated using a model that accounts for different therapeutic agent characteristics (e.g., approved dose, approved dosing frequency, and bioavailability via intravenous (IV), subcutaneous (SC) or intramuscular (IM) administration). The model assumes each drug can be formulated for the device to a maximum concentration of 175 mg/mL. Given the payload size, therapeutic agent characteristics, and a 175 mg/mL drug concentration, bioavailability benchmarks ("Required Bioavailability") for different dosing regimens ("PGN Regimen") are shown in the table. For example, as shown in Table 16 for adalimumab, an approved 40 mg subcutaneous injection provides an effective dose of 25.6 mg given adalimumab's subcutaneous bioavailability of 64%. This dose is approved in the U.S. for subcutaneous administration every two weeks. Administration of adalimumab at a concentration of 175 mg/mL using a 000-sized ingestible device with a payload of 400 µL achieves the same effective dose when administered weekly (qwk) given a bioavailability of 18.3%. Likewise, using a 00-sized ingestible device with a payload of 200 µL achieves the same effective dose when administered daily (qd) given a bioavailability of 5.2%. If, for example, the bioavailability for the ingestible device is fixed at 25% for a therapeutic agent, similar calculations can be used to calculate the required drug concentration to achieve a desired effective dose.

Table 17 provides the same information for a different set of therapeutic agents. For non-approved therapeutic agents, dose information was sourced from publicly available clinical trial information. Also, for dose based on patient weight, the assumed weight is 70 kg.

TABLE 16

| | Approved Dosing Info | | | | | 000 Capsule Dosing Profile | | 00 Capsule Dosing Profile | | |
|---|---|---|---|---|---|---|---|---|---|---|
| Drug Name | Dose (mg) | Bio Avail | Eff Dose (mg) | Freq | Admin | PGN Regimen | Req. Bioav. | PGN Regimen | Req. Bioav. | Class |
| adalimumab | 40 | 64% | 25.6 | q 2 wk | SC | qwk | 18.3% | qd | 5.2% | TNF |
| etanercept | 50 | 58% | 29.0 | qwk | SC | qwk | 41.4% | qd | 11.8% | TNF |
| semaglutide | 0.5 | 89% | 0.45 | qwk | SC | qwk | 0.6% | qwk | 1.3% | GLP-1 |
| dulaglutide | 0.75 | 65% | 0.49 | qwk | SC | qwk | 0.7% | qwk | 1.4% | GLP-1 |
| interferon beta-1a | 0.03 | 40% | 0.01 | qwk | IM | qwk | 0.02% | qwk | 0.03% | Interferon beta |
| alirocumab | 75 | 85% | 63.8 | q 2 wk | SC | qwk | 45.5% | qd | 13.0% | PCSK9 |

TABLE 16-continued

|  | Approved Dosing Info | | | | | 000 Capsule Dosing Profile | | 00 Capsule Dosing Profile | | |
| --- | --- | --- | --- | --- | --- | --- | --- | --- | --- | --- |
| | | Eff | | | | | | | | |
| Drug Name | Dose (mg) | Bio Avail | Dose (mg) | Freq | Admin | PGN Regimen | Req. Bioav. | PGN Regimen | Req. Bioav. | Class |
| evolocumab | 140 | 82% | 114.8 | q 2 wk | SC | qwk | 82.0% | qd | 23.4% | PCSK9 |
| emicizumab | 105 | 85% | 89.3 | qwk | SC | qd | 18.2% | qd | 36.4% | ACP |
| ustekinumab | 45 | 78% | 35.1 | q 12 wk | SC | q 8 wk | 33.4% | q 4 wk | 33.4% | IL-12/23 |
| pegfilgrastim | 6 | 70% | 4.2 | x1 | SC | qd | 6.0% | qd | 12.0% | GCSF |
| denosumab | 60 | 61% | 36.6 | q 6 mo | SC | q 8 wk | 16.1% | q 8 wk | 32.2% | Osteclast |
| golimumab | 50 | 51% | 25.5 | q mo | SC | q 4 wk | 36.4% | q 2 wk | 36.4% | TNF |
| certolizumab pegol | 200 | 80% | 160 | q 2 wk | SC | qd | 16.3% | qd | 32.7% | TNF |
| vedolizumab | 300 | 100% | 300 | q 8 wk | IV | qwk | 53.6% | qd | 15.3% | Intergrin |
| secukinumab | 150 | 73% | 109.5 | q 4 wk | SC | qwk | 39.1% | qd | 11.2% | IL-17 |
| abatacept | 125 | 79% | 98.8 | qwk | SC | qd | 20.2% | qd | 40.3% | CD28 inhibitor |
| natalizumab | 300 | 100% | 300 | q 4 wk | IV | qd | 15.3% | qd | 30.6% | Intergrin |
| tocilizumab | 162 | 80% | 129.6 | qwk | SC | qd | 26.4% | qd | 52.9% | IL-6 |
| teriparatide | 0.02 | 95% | 0.02 | qd | SC | qd | 0.03% | qd | 0.05% | Parathyroid |
| sargramostim | 0.25 | 100% | 0.025 | qd | IV | qd | 0.66% | qd | 1.32% | GM-CSF |

TABLE 17

| | | Baseline dose | | | | | | |
| --- | --- | --- | --- | --- | --- | --- | --- | --- |
| Drug | Target-based Actions | Dose (mg) | Bioavail. | Eff. Dose (mg) | Freq. | Admin. | PGN Regimen | Notes |
| | | | Hemophilia A + B | | | | | |
| concizumab | Tissue factor pathway inhibitor inhibitor | 17.5 | 93.0% | 16.3 | qd | SC | qd | Feasible; min. bioavailability of 32.6% (0.35 mg/kg) or 23.3% (0.25 mg/kg) required for 000 capsule |
| | | | Growth disorders | | | | | |
| somatropin | Growth hormone ligand; Skeletal muscle MLCK stimulator | 1.0 | 80.5% | 0.8 | qd | SC | qd | Feasible; min. bioavailability of 2.3% required for 00 capsule |
| somapacitan | Growth hormone ligand; Insulin like GF1 ligand modulator | 11.2 | 100.0% | 11.20 | qwk | SC | qwk | Feasible; min. bioavailability of 32% required for 00 capsule |
| | | | Obesity | | | | | |
| AM-833 | Amylin receptor agonist | 2.4 | 100.0% | 2.4 | qwk | SC | qwk | Feasible; mm. bioavailability of 6.9% required for 00 capsule |
| NN-9277 | Glucagon receptor agonist; GLP-1 agonist | 6 | 100.0% | 6.0 | qwk | SC | qwk | Feasible; min. bioavailability of 17.1% required for 00 capsule |
| NN-9775 | Peptide YY ligand | 2.4 | 100.0% | 2.4 | x1 | SC | qd | Feasible; min. bioavailability of 6.9% required for 00 capsule |
| | | | Diabetes | | | | | |
| glucagon (SC) | | 2 | 100.0% | 2.0 | qd | SC | qd | Feasible; min. bioavailability of 5.7% required for 00 capsule |

In some embodiments of any of the devices or methods described herein, the effective amount of the therapeutic administered is generally less than an amount that is effective when the therapeutic is administered subcutaneously, intramuscularly, or intravenously. In some embodiments of any of the methods described herein, the methods include administering (i) an amount of the therapeutic that is a maintenance dose. In some embodiments of any of the methods described herein, the methods include administering (i) an amount of the therapeutic that is an induction dose. Some embodiments of any of the methods described herein further include (ii) administering an amount of the therapeutic that is a maintenance dose following the administration of the induction dose. In some embodiments of any of the methods described herein, the induction dose is administered by another delivery means, for example, topically, subcutaneously, intramuscularly, or intravenously. In some embodiments of any of the methods described herein, step (ii) is repeated one or more times. In some embodiments of any of the methods described herein, step (ii) is repeated once a day, once every two days, once every three days, once every four days, once every five days, once a week over a period of about 6-8 weeks.

In some embodiments of any of the methods described herein, the induction dose is equal to the maintenance dose. In some embodiments of any of the methods described herein, the induction dose is greater than the maintenance dose. In some embodiments of any of the methods described herein, the induction dose is 5 times greater than the maintenance dose. In some embodiments of any of the methods described herein, the induction dose is 2 times greater than the maintenance dose.

In some embodiments, the release mechanism is an actuation system. In some embodiments, the release mechanism is an enteric actuation system. In some embodiments, the release mechanism is a mechanical actuation system. In some embodiments, the release mechanism is an electrical actuation system. In some embodiments, the actuation system comprises an enteric actuation system coupled to a mechanical actuation system. In some embodiments, the actuation system comprises a pre-pressurized air reservoir that drives a piston.

In some embodiments, the formulation comprises a therapeutically effective amount of the therapeutic agent as disclosed herein. In some embodiments, the formulation comprises a human equivalent dose (HED) of the therapeutic agent as disclosed herein.

Methods of Treatment

In some embodiments, provided herein is a method of treating a disease as disclosed herein, the method comprising: administering to the subject a pharmaceutical formulation that comprises a therapeutic agent as disclosed herein, wherein the pharmaceutical formulation is released at a location in the gastrointestinal tract of the subject. In some embodiments, the pharmaceutical formulation is released from the device with sufficient power, pressure and/or force for trans-epithelial delivery of the therapeutic agent to the gastrointestinal tract. In some embodiments, the pharmaceutical formulation is released from the device with sufficient power, pressure and/or force for epithelial delivery of the therapeutic agent to the gastrointestinal tract. In some embodiments, the pharmaceutical formulation is released from the device with sufficient power, pressure and/or force for topical delivery of the therapeutic agent to the gastrointestinal tract.

Trans-Epithelial Administration

In some embodiments, the method comprises trans-epithelial administration of a therapeutic agent to the GI tract of the subject. In some embodiments, the method provides systemic uptake of the therapeutic agent of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, relative to intravenous or subcutaneous administration of the same amount of the therapeutic agent. In some embodiments, the same amount of therapeutic agent is an approved or commercially-available dose. In some more particular embodiments, the systemic uptake is at least about 10% relative to intravenous or subcutaneous administration of the same amount of the therapeutic agent. In other embodiments, the systemic uptake is at least about 15% relative to intravenous or subcutaneous administration of the same amount of the therapeutic agent. In yet other embodiments, the systemic uptake is at least about 20% relative to intravenous or subcutaneous administration of the same amount of the therapeutic agent. In yet other embodiments, the systemic uptake is at least about 25% relative to intravenous or subcutaneous administration of the same amount of the therapeutic agent. In yet other embodiments, the systemic uptake is at least about 30% relative to intravenous or subcutaneous administration of the same amount of the therapeutic agent. In yet other embodiments, the systemic uptake is at least about 35% relative to intravenous or subcutaneous administration of the same amount of the therapeutic agent. In yet other embodiments, the systemic uptake is at least about 40%, or even higher, relative to intravenous or subcutaneous administration of the same amount of the therapeutic agent.

In some embodiments, the trans-epithelial administration provides an area under a curve ($AUC_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) ($AUC_{IV}$). In some embodiments, the same amount of therapeutic agent is an approved or commercially-available dose. In some more particular embodiments, the area under a curve ($AUC_{TE}$) of the therapeutic agent in systemic circulation versus time is at least about 15% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 20% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 25% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 30% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 35% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 40% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 45% of the AUC obtained when the same amount of the therapeutic agent is administered intravenously ($AUC_{IV}$). In some embodiments, particularly when an AUC is determined from a plurality of subjects, the AUC is a mean AUC obtained from the plurality of subjects. Thus, in some further embodiments, $AUC_{TE}$ or $AUC_{IV}$ may refer to a mean $AUC_{TE}$ or mean $AUC_{IV}$, respectively. In some other embodiments, an individual AUC value obtained for a single subject may be compared to a mean AUC obtained from a plurality of subjects.

In some embodiments, the trans-epithelial administration provides an area under a curve ($AUC_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($AUC_{SC}$). In some embodiments, the same amount of therapeutic agent is an approved or commercially-available dose. In some more particular embodiments, the area under a curve ($AUC_{TE}$) of the therapeutic agent in systemic circulation versus time is at least about 15% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 20% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 25% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 30% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 35% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 40% of the AUC obtained when the same amount of the therapeutic agent is delivered subcutaneously ($AUC_{SC}$). In some other embodiments, the area under a curve ($AUC_{TE}$) of the therapeutic agent in systemic circulation versus time is at least about 45% of the AUC obtained when the same amount of the therapeutic agent is administered subcutaneously ($AUC_{SC}$). In some embodiments, particularly when an AUC is determined from a plurality of subjects, the AUC is a mean AUC obtained from the plurality of subjects. Thus, in some further embodiments, $AUC_{TE}$ or $AUC_{SC}$ may refer to a mean $AUC_{TE}$ or mean $AUC_{SC}$, respectively. In some other embodiments, an individual AUC value obtained for a single subject may be compared to a mean AUC obtained from a plurality of subjects.

In some embodiments, the trans-epithelial administration provides an area under a curve ($AUC_{TE}$) of the therapeutic agent in systemic circulation versus time that is at least about 100%, at least about 150%, at least about 200%, at least about 250%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, at least about 1900%, at least about 2000%, at least about 2200%, at least about 2300%, at least about 2400%, at least about 2500%, at least about 2600%, at least about 2700%, at least about 2800%, at least about 2900%, at least about 3000%, at least about 3100%, at least about 3200%, at least about 3300%, at least about 3400%, at least about 3500%, at least about 3600%, at least about 3700%, at least about 3800%, at least about 3900%, at least about 4000%, at least about 4100%, at least about 4200%, at least about 4300%, at least about 4400%, at least about 4500%, at least about 4600%, at least about 4700%, at least about 4800%, at least about 4900%, at least about 5000%, at least about 5100%, at least about 5200%, at least about 5300%, at least about 5400%, at least about 5500%, at least about 5600%, at least about 5700%, at least about 5800%, at least about 5900%, at least about 6000%, at least about 6100%, at least about 6200%, at least about 6300%, at least about 6400%, at least about 6500%, at least about 6600%, at least about 6700%, at least about 6800%, at least about 6900%, at least about 7000%, at least about 7100%, at least about 7200%, at least about 7300%, at least about 7400%, at least about 7500%, at least about 7600%, at least about 7700%, at least about 7800%, at least about 7900%, at least about 8000%, at least about 8100%, at least about 8200%, at least about 8300%, at least about 8400%, at least about 8500%, at least about 8600%, at least about 8700%, at least about 8800%, at least about 8900%, at least about 9000%, at least about 9100%, at least about 9200%, at least about 9300%, at least about 9400%, at least about 9500%, at least about 9600%, at least about 9700%, at least about 9800%, at least about 9900%, or at least about 10,000% as that obtained when the same amount of the therapeutic agent is administered orally (to the same subject, or to a population of subjects). In some embodiments, the same amount of therapeutic agent is an approved or commercially-available dose. In some embodiments, the AUC is the mean AUC.

In some embodiments, the trans-epithelial administration provides a maximum plasma concentration ($(C_{max})_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) ($(C_{max})_{IV}$). In some embodiments, the same amount of therapeutic agent is an approved or commercially-available dose. In some more particular embodiments, the maximum plasma concentration ($(C_{max})_{TE}$) of the therapeutic agent in systemic circulation versus time is at least about 15% of the AUC obtained when the same amount of the therapeutic agent is delivered intravenously ($(C_{max})_{IV}$). In some other embodiments, the maximum plasma concentration ($(C_{max})_{TE}$) of the therapeutic agent in systemic circulation versus time is at least about 20% of the AUC obtained when the same amount of the therapeutic agent is delivered intravenously ($(C_{max})_{IV}$). In some other embodiments, the maximum plasma concentration ($(C_{max})_{TE}$) of the therapeutic agent in systemic circulation versus time is at least about 25% of the AUC obtained when the same amount of the therapeutic agent is delivered intravenously ($(C_{max})_{IV}$). In some other embodiments, the maximum plasma concentration ($(C_{max})_{TE}$) of the therapeutic agent in systemic circulation versus time is at least about 30% of the AUC obtained when the same amount of the therapeutic agent is delivered intravenously ($(C_{max})_{IV}$). In some other embodiments, the maximum plasma concentration ($(C_{max})_{TE}$) of the therapeutic agent in systemic circulation versus time is at least about 35% of the AUC obtained when the same amount of the therapeutic agent is delivered intravenously ($(C_{max})_{IV}$). In some other embodiments, the maximum plasma concentration ($(C_{max})_{TE}$) of the therapeutic agent in systemic circulation versus time is at least about 40% of the AUC obtained when the same amount of the therapeutic agent is delivered intravenously ($(C_{max})_{IV}$). In some other embodiments, the maximum plasma concentration ($(C_{max})_{TE}$) of the therapeutic agent in systemic circulation versus time is at least about 45% of the AUC obtained when the same amount of the therapeutic agent is delivered intravenously ($(C_{max})_{IV}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_{TE}$ or $(C_{max})_{IV}$ may refer to a mean $(C_{max})_{TE}$ or mean $(C_{max})_{IV}$, respectively. In some other embodiments, an individual $C_{max}$ value obtained for a single subject may be compared to a mean $C_{max}$ obtained from a plurality of subjects.

In some embodiments, the trans-epithelial administration provides a maximum plasma concentration ($(C_{max})_{TE}$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($(C_{max})_{SC}$). In some embodiments, the same amount of therapeutic agent is an approved or commercially-available dose. In some more particular embodiments, the maximum plasma concentration ($(C_{max})_{TE}$) of the therapeutic agent in systemic circulation versus time is at least about 15% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 20% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 25% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 30% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 35% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 40% of the AUC obtained when the same amount of the therapeutic agent is delivered subcutaneously ($(C_{max})_{SC}$). In some other embodiments, the maximum plasma concentration ($(C_{max})_{TE}$) of the therapeutic agent in systemic circulation versus time is at least about 45% of the AUC obtained when the same amount of the therapeutic agent is delivered subcutaneously ($(C_{max})_{SC}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_{TE}$ or $(C_{max})_{SC}$ may refer to a mean $(C_{max})_{TE}$ or mean $(C_{max})_{SC}$, respectively. In some other embodiments, an individual $C_{max}$ value obtained for a single subject may be compared to a mean $C_{max}$ obtained from a plurality of subjects.

Epithelial Administration

In some embodiments, the method comprises epithelial administration of a therapeutic agent to the GI tract of the subject. In some embodiments, the method provides systemic uptake of the therapeutic agent of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, relative to topical delivery or a non-device oral delivery. In some embodiments, the same amount of therapeutic agent is an approved or commercially-available dose. In some more particular embodiments, the systemic uptake is at least about 10% relative to topical delivery or non-device oral delivery of the same amount of the therapeutic agent. In other embodiments, the systemic uptake is at least about 15% relative to topical delivery or non-device oral delivery of the same amount of the therapeutic agent. In yet other embodiments, the systemic uptake is at least about 20% relative to topical delivery or non-device oral delivery of the same amount of the therapeutic agent. In yet other embodiments, the systemic uptake is at least about 25% relative to topical delivery or non-device oral delivery of the same amount of the therapeutic agent. In yet other embodiments, the systemic uptake is at least about 30% relative to topical delivery or non-device oral delivery of the same amount of the therapeutic agent. In yet other embodiments, the systemic uptake is at least about 35% relative to topical delivery or non-device oral delivery of the same amount of the therapeutic agent. In yet other embodiments, the systemic uptake is at least about 40%, or even higher, relative to topical delivery or non-device oral delivery of the same amount of the therapeutic agent.

In some embodiments, the epithelial administration provides systemic uptake of the therapeutic agent of about 0.5% to about 10% or more, for example, about 0.5%, about 1%, about 2%, about 3%, about 4%, about 5%, about 6%, about 7%, about 8%, about 9%, about 10%, or more, relative to intravenous or subcutaneous administration of the same amount of the therapeutic agent. In some embodiments, the same amount of therapeutic agent is an approved or commercially-available dose. In some more particular embodiments, the systemic uptake is at least about 0.5% relative to intravenous or subcutaneous administration of the same amount of the therapeutic agent. In other embodiments, the systemic uptake is at least about 2% relative to intravenous or subcutaneous administration of the same amount of the therapeutic agent. In yet other embodiments, the systemic uptake is at least about 3% relative to intravenous or subcutaneous administration of the same amount of the therapeutic agent. In yet other embodiments, the systemic uptake is at least about 4% relative to intravenous or subcutaneous administration of the same amount of the therapeutic agent. In yet other embodiments, the systemic uptake is at least about 5% relative to intravenous or subcutaneous administration of the same amount of the therapeutic agent. In yet other embodiments, the systemic uptake is at least about 6% relative to intravenous or subcutaneous administration of the same amount of the therapeutic agent. In yet other embodiments, the systemic uptake is at least about 7% relative to intravenous or subcutaneous administration of the same amount of the therapeutic agent. In yet other embodiments, the systemic uptake is at least about 8% relative to intravenous or subcutaneous administration of the same amount of the therapeutic agent. In yet other embodiments, the systemic uptake is at least about 9% relative to intravenous or subcutaneous administration of the same amount of the therapeutic agent. In yet other embodiments, the systemic uptake is at least about 10%, or even higher, relative to intravenous or subcutaneous administration of the same amount of the therapeutic agent.

In some embodiments, the systemic uptake of the therapeutic agent is greater than the systemic uptake provided by topical administration of the same amount of the therapeutic agent, but less than the systemic uptake provided by transepithelial administration of the same amount of the therapeutic agent. In some embodiments, epithelial administration provides systemic uptake of the therapeutic agent of about 10%, about 15%, about 20%, about 25%, about 30%, about 35%, about 40%, about 45%, about 50%, about 55%, about 60%, about 65%, about 70%, about 75%, about 80%, about 85%, about 90%, about 100%, about 125%, about 150%, about 175%, about 200%, about 225%, about 250%, about 275%, about 300%, about 325%, about 350%, about 375%, about 400%, about 425%, about 450%, about 475%, or about 500% greater than the systemic uptake of the same amount of the therapeutic agent provided by topical administration. In some embodiments, the same amount of therapeutic agent is an approved or commercially-available dose.

In some embodiments, the epithelial administration provides an area under a curve ($AUC_E$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) ($AUC_{IV}$). In some embodiments, the same amount of therapeutic agent is an approved or commercially-available dose. In some more particular embodiments, the area under a curve ($AUC_E$) of the therapeutic agent in systemic circulation versus time is at least about 15% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 20% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 25% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 30% of the AUC obtained when the same amount of the therapeutic agent is delivered intravenously ($AUC_{IV}$). In some other embodiments, the area under a curve ($AUC_{TE}$) of the therapeutic agent in systemic circulation versus time is at least about 35% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 40% of the AUC obtained when the same amount of the therapeutic agent is delivered intravenously ($AUC_{IV}$). In some other embodiments, the area under a curve ($AUC_E$) of the therapeutic agent in systemic circulation versus time is at least about 45% of the AUC obtained when the same amount of the therapeutic agent is administered intravenously ($AUC_{IV}$). In some embodiments, particularly when an AUC is determined from a plurality of subjects, the AUC is a mean AUC obtained from the plurality of subjects. Thus, in some further embodiments, $AUC_E$ or $AUC_{IV}$ may refer to a mean $AUC_E$ or mean $AUC_{IV}$, respectively. In some other embodiments, an individual AUC value obtained for a single subject may be compared to a mean AUC obtained from a plurality of subjects.

In some embodiments, the epithelial administration provides an area under a curve ($AUC_E$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($AUC_{SC}$). In some embodiments, the same amount of therapeutic agent is an approved or commercially-available dose. In some more particular embodiments, the area under a curve ($AUC_E$) of the therapeutic agent in systemic circulation versus time is at least about 15% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 20% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 25% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 30% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 35% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 40% of the AUC obtained when the same amount of the therapeutic agent is delivered subcutaneously ($AUC_{SC}$). In some other embodiments, the area under a curve ($AUC_E$) of the therapeutic agent in systemic circulation versus time is at least about 45% of the AUC obtained when the same amount of the therapeutic agent is administered subcutaneously ($AUC_{SC}$). In some embodiments, particularly when an AUC is determined from a plurality of subjects, the AUC is a mean AUC obtained from the plurality of subjects. Thus, in some further embodiments, $AUC_E$ or $AUC_{SC}$ may refer to a mean $AUC_E$ or mean $AUC_{SC}$, respectively. In some other embodiments, an individual AUC value obtained for a single subject may be compared to a mean AUC obtained from a plurality of subjects.

In some embodiments, the epithelial administration provides an area under a curve ($AUC_E$) of the therapeutic agent in systemic circulation versus time that is at least about 100%, at least about 150%, at least about 200%, at least about 250%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, at least about 1900%, at least about 2000%, at least about 2200%, at least about 2300%, at least about 2400%, at least about 2500%, at least about 2600%, at least about 2700%, at least about 2800%, at least about 2900%, at least about 3000%, at least about 3100%, at least about 3200%, at least about 3300%, at least about 3400%, at least about 3500%, at least about 3600%, at least about 3700%, at least about 3800%, at least about 3900%, at least about 4000%, at least about 4100%, at least about 4200%, at least about 4300%, at least about 4400%, at least about 4500%, at least about 4600%, at least about 4700%, at least about 4800%, at least about 4900%, at least about 5000%, at least about 5100%, at least about 5200%, at least about 5300%, at least about 5400%, at least about 5500%, at least about 5600%, at least about 5700%, at least about 5800%, at least about 5900%, at least about 6000%, at least about 6100%, at least about 6200%, at least about 6300%, at least about 6400%, at least about 6500%, at least about 6600%, at least about 6700%, at least about 6800%, at least about 6900%, at least about 7000%, at least about 7100%, at least about 7200%, at least about 7300%, at least about 7400%, at least about 7500%, at least about 7600%, at least about 7700%, at least about 7800%, at least about 7900%, at least about 8000%, at least about 8100%, at least about 8200%, at least about 8300%, at least about 8400%, at least about 8500%, at least about 8600%, at least about 8700%, at least about 8800%, at least about 8900%, at least about 9000%, at least about 9100%, at least about 9200%, at least about 9300%, at least about 9400%, at least about 9500%, at least about 9600%, at least about 9700%, at least about 9800%, at least about 9900%, or at least about 10,000% as that obtained when the same amount of the therapeutic agent is administered orally (to the same subject, or to a population of subjects). In some embodiments, the same amount of therapeutic agent is an approved or commercially-available dose. In some embodiments, the AUC is the mean AUC.

In some embodiments, the epithelial administration provides a maximum plasma concentration ($(C_{max})_E$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered intravenously (to the same subject, or to a population of subjects) ($(C_{max})_{IV}$). In some embodiments, the same amount of therapeutic agent is an approved or commercially-available dose. In some more particular embodiments, the maximum plasma concentration ($(C_{max})_E$) of the therapeutic agent in systemic circulation versus time is at least about 15% of the AUC obtained when the same amount of the therapeutic agent is delivered intravenously ($(C_{max})_{IV}$). In some other embodiments, the maximum plasma concentration ($(C_{max})_E$) of the therapeutic agent in systemic circulation versus time is at least about 20% of the AUC obtained when the same amount of the therapeutic agent is delivered intravenously ($(C_{max})_{IV}$). In some other embodiments, the maximum plasma concentration ($(C_{max})_E$) of the therapeutic agent in systemic circulation versus time is at least about 25% of the AUC obtained when the same amount of the therapeutic agent is delivered intravenously ($(C_{max})_{IV}$). In some other embodiments, the maximum plasma concentration ($(C_{max})_E$) of the therapeutic agent in systemic circulation versus time is at least about 30% of the AUC obtained when the same amount of the therapeutic agent is delivered intravenously ($(C_{max})_{IV}$). In some other embodiments, the maximum plasma concentration ($(C_{max})_E$) of the therapeutic agent in systemic circulation versus time is at least about 35% of the AUC obtained when the same amount of the therapeutic agent is delivered intravenously ($(C_{max})_{IV}$). In some other embodiments, the maximum plasma concentration ($(C_{max})_E$) of the therapeutic agent in systemic circulation versus time is at least about 40% of the AUC obtained when the same amount of the therapeutic agent is delivered intravenously ($(C_{max})_{IV}$). In some other embodiments, the maximum plasma concentration ($(C_{max})_E$) of the therapeutic agent in systemic circulation versus time is at least about 45% of the AUC obtained when the same amount of the therapeutic agent is delivered intravenously ($(C_{max})_{IV}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_E$ or $(C_{max})_{IV}$ may refer to a mean $(C_{max})_E$ or mean $(C_{max})_{IV}$, respectively. In some other embodiments, an individual $C_{max}$ value obtained for a single subject may be compared to a mean $C_{max}$ obtained from a plurality of subjects.

In some embodiments, the epithelial administration provides a maximum plasma concentration ($(C_{max})_E$) of the therapeutic agent in systemic circulation versus time of about 10% to about 99%, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as the AUC obtained when the same amount of the therapeutic agent is delivered subcutaneously (to the same subject, or to a population of subjects) ($(C_{max})_{SC}$). In some embodiments, the same amount of therapeutic agent is an approved or commercially-available dose. In some more particular embodiments, the maximum plasma concentration ($(C_{max})_E$) of the therapeutic agent in systemic circulation versus time is at least about 15% of the AUC obtained when the same amount of the therapeutic agent is delivered subcutaneously ($(C_{max})_{SC}$). In some other embodiments, the maximum plasma concentration ($(C_{max})_E$) of the therapeutic agent in systemic circulation versus time is at least about 20% of the AUC obtained when the same amount of the therapeutic agent is delivered subcutaneously ($(C_{max})_{SC}$). In some other embodiments, the maximum plasma concentration ($(C_{max})_E$) of the therapeutic agent in systemic circulation versus time is at least about 25% of the AUC obtained when the same amount of the therapeutic agent is delivered subcutaneously ($(C_{max})_{SC}$). In some other embodiments, the maximum plasma concentration ($(C_{max})_E$) of the therapeutic agent in systemic circulation versus time is at least about 30% of the AUC obtained when the same amount of the therapeutic agent is delivered subcutaneously ($(C_{max})_{SC}$). In some other embodiments, the maximum plasma concentration ($(C_{max})_E$) of the therapeutic agent in systemic circulation versus time is at least about 35% of the AUC obtained when the same amount of the therapeutic agent is delivered subcutaneously (($(C_{max})_{SC}$). In some other embodiments, the maximum plasma concentration (($(C_{max})_E$) of the therapeutic agent in systemic circulation versus time is at least about 40% of the AUC obtained when the same amount of the therapeutic agent is delivered subcutaneously (($(C_{max})_{SC}$). In some other embodiments, the maximum plasma concentration (($(C_{max})_E$) of the therapeutic agent in systemic circulation versus time is at least about 45% of the AUC obtained when the same amount of the therapeutic agent is delivered subcutaneously (($(C_{max})_{SC}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_E$ or $(C_{max})_{SC}$ may refer to a mean $(C_{max})_E$ or mean $(C_{max})_{SC}$, respectively. In some other embodiments, an individual $C_{max}$ value obtained for a single subject may be compared to a mean $C_{max}$ obtained from a plurality of subjects.

Topical Administration

In some embodiments, the method comprises topical administration of a therapeutic agent to the GI tract of the subject. In some embodiments, the method provides systemic uptake of the therapeutic agent of about 0.1% to about 20%, for example, at most about 1%, at most about 3%, at most about 5%, at most about 10%, at most about 15%, or at most about 20%, relative to intravenous or subcutaneous administration of the same amount of the therapeutic agent. In some embodiments, the same amount of therapeutic agent is an approved or commercially-available dose. In some more particular embodiments, the systemic uptake is at most about 1% relative to intravenous or subcutaneous administration of the same amount of the therapeutic agent. In some more particular embodiments, the systemic uptake is at most about 3% relative to intravenous or subcutaneous administration of the same amount of the therapeutic agent. In other embodiments, the systemic uptake is at most about 5% relative to intravenous or subcutaneous administration of the same amount of the therapeutic agent. In yet other embodiments, the systemic uptake is at most about 10% relative to intravenous or subcutaneous administration of the same amount of the therapeutic agent. In yet other embodiments, the systemic uptake is at most about 15% relative to intravenous or subcutaneous administration of the same amount of the therapeutic agent. In yet other embodiments, the systemic uptake is at most about 20% relative to intravenous or subcutaneous administration of the same amount of the therapeutic agent.

In some embodiments, the topical administration provides an area under a curve ($AUC_{TOP}$) of the therapeutic agent in systemic circulation versus time of about 0.1% to about 20%, for example, at most about 1%, at most about 3%, at most about 5%, at most about 10%, at most about 15%, or at most about 20%, as the AUC obtained when the same amount of the therapeutic agent is delivered intravenously (to the same subject, or to a population of subjects) ($AUC_{IV}$). In some embodiments, the same amount of therapeutic agent is an approved or commercially-available dose. In some more particular embodiments, the area under a curve ($AUC_{TOP}$) of the therapeutic agent in systemic circulation versus time is at most about 1% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 3% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 5% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 10% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 15% of the AUC obtained when the same amount of the therapeutic agent is delivered intravenously ($AUC_{IV}$). In some other embodiments, the area under a curve ($AUC_{TOP}$) of the therapeutic agent in systemic circulation versus time is at most about 20% of the AUC obtained when the same amount of the therapeutic agent is delivered intravenously ($AUC_{IV}$). In some embodiments, particularly when an AUC is determined from a plurality of subjects, the AUC is a mean AUC obtained from the plurality of subjects. Thus, in some further embodiments, $AUC_{TOP}$ or $AUC_{IV}$ may refer to a mean $AUC_{TOP}$ or mean $AUC_{IV}$, respectively. In some other embodiments, an individual AUC value obtained for a single subject may be compared to a mean AUC obtained from a plurality of subjects.

In some embodiments, the topical administration provides an area under a curve ($AUC_{TOP}$) of the therapeutic agent in systemic circulation versus time of about 0.1% to about 20%, for example, at most about 1%, at most about 3%, at most about 5%, at most about 10%, at most about 15%, or at most about 20%, as that obtained when the same amount of the therapeutic agent is delivered subcutaneously (to the same subject, or to a population of subjects) ($AUC_{SC}$). In some embodiments, the same amount of therapeutic agent is an approved or commercially-available dose. In some more particular embodiments, the area under a curve ($AUC_{TOP}$) of the therapeutic agent in systemic circulation versus time is at most about 1% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 3% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 5% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 10% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 15% of the AUC obtained when the same amount of the therapeutic agent is delivered subcutaneously ($AUC_{SC}$). In some other embodiments, the area under a curve ($AUC_{TOP}$) of the therapeutic agent in systemic circulation versus time is at most about 20% of the AUC obtained when the same amount of the therapeutic agent is delivered subcutaneously ($AUC_{SC}$). In some embodiments, particularly when an AUC is determined from a plurality of subjects, the AUC is a mean AUC obtained from the plurality of subjects. Thus, in some further embodiments, $AUC_{TOP}$ or $AUC_{SC}$ may refer to a mean $AUC_{TOP}$ or mean $AUC_{SC}$, respectively. In some other embodiments, an individual AUC value obtained for a single subject may be compared to a mean AUC obtained from a plurality of subjects.

In some embodiments, the topical administration provides a maximum plasma concentration ($(C_{max})_{TOP}$) of the therapeutic agent in systemic circulation versus time of about 0.1% to about 20%, for example, at most about 1%, at most about 3%, at most about 5%, at most about 10%, at most about 15%, or at most about 20%, as that obtained when the same amount of the therapeutic agent is delivered intravenously (to the same subject, or to a population of subjects) ($(C_{max})_{IV}$). In some embodiments, the same amount of therapeutic agent is an approved or commercially-available dose. In some more particular embodiments, the maximum plasma concentration ($(C_{max})_{TOP}$) of the therapeutic agent in systemic circulation versus time is at most about 1% of the AUC obtained when the same amount of the therapeutic agent is delivered intravenously ($(C_{max})_{IV}$). In some other embodiments, the maximum plasma concentration ($(C_{max})_{TOP}$) of the therapeutic agent in systemic circulation versus time is at most about 3% of the AUC obtained when the same amount of the therapeutic agent is delivered intravenously ($(C_{max})_{IV}$). In some other embodiments, the maximum plasma concentration ($(C_{max})_{TOP}$) of the therapeutic agent in systemic circulation versus time is at most about 5% of the AUC obtained when the same amount of the therapeutic agent is delivered intravenously ($(C_{max})_{IV}$). In some other embodiments, the maximum plasma concentration ($(C_{max})_{TOP}$) of the therapeutic agent in systemic circulation versus time is at most about 10% of the AUC obtained when the same amount of the therapeutic agent is delivered intravenously ($(C_{max})_{IV}$). In some other embodiments, the maximum plasma concentration ($(C_{max})_{TOP}$) of the therapeutic agent in systemic circulation versus time is at most about 15% of the AUC obtained when the same amount of the therapeutic agent is delivered intravenously ($(C_{max})_{IV}$). In some other embodiments, the maximum plasma concentration ($(C_{max})_{TOP}$) of the therapeutic agent in systemic circulation versus time is at most about 20% of the AUC obtained when the same amount of the therapeutic agent is delivered intravenously ($(C_{max})_{IV}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_{TOP}$ or $(C_{max})_{IV}$ may refer to a mean $(C_{max})_{TOP}$ or mean $(C_{max})_{IV}$, respectively. In some other embodiments, an individual $C_{max}$ value obtained for a single subject may be compared to a mean $C_{max}$ obtained from a plurality of subjects.

In some embodiments, the topical administration provides a maximum plasma concentration ($(C_{max})_{TOP}$) of the therapeutic agent in systemic circulation versus time of about 0.1% to about 20%, for example, at most about 1%, at most about 3%, at most about 5%, at most about 10%, at most about 15%, or at most about 20%, as that obtained when the same amount of the therapeutic agent is delivered subcutaneously (to the same subject, or to a population of subjects) ($(C_{max})_{SC}$). In some embodiments, the same amount of therapeutic agent is an approved or commercially-available dose. In some more particular embodiments, the maximum plasma concentration ($(C_{max})_{TOP}$) of the therapeutic agent in systemic circulation versus time is at most about 1% of the AUC obtained when the same amount of the therapeutic agent is delivered subcutaneously ($(C_{max})_{SC}$). In some other embodiments, the maximum plasma concentration ($(C_{max})_{TOP}$) of the therapeutic agent in systemic circulation versus time is at most about 3% of the AUC obtained when the same amount of the therapeutic agent is delivered subcutaneously ($(C_{max})_{SC}$). In some other embodiments, the maximum plasma concentration ($(C_{max})_{TOP}$) of the therapeutic agent in systemic circulation versus time is at most about 5% of the AUC obtained when the same amount of the therapeutic agent is delivered subcutaneously ($(C_{max})_{SC}$). In some other embodiments, the maximum plasma concentration ($(C_{max})_{TOP}$) of the therapeutic agent in systemic circulation versus time is at most about 10% of the AUC obtained when the same amount of the therapeutic agent is delivered subcutaneously ($(C_{max})_{SC}$). In some other embodiments, the maximum plasma concentration ($(C_{max})_{TOP}$) of the therapeutic agent in systemic circulation versus time is at most about 15% of the AUC obtained when the same amount of the therapeutic agent is delivered subcutaneously ($(C_{max})_{SC}$). In some other embodiments, the maximum plasma concentration ($(C_{max})_{TOP}$) of the therapeutic agent in systemic circulation versus time is at most about 20% of the AUC obtained when the same amount of the therapeutic agent is delivered subcutaneously ($(C_{max})_{SC}$). In some embodiments, particularly when the $C_{max}$ is determined from a plurality of subjects, the $C_{max}$ is a mean $C_{max}$ obtained from the plurality of subjects. Thus, in some further embodiments, $(C_{max})_{TOP}$ or $(C_{max})_{SC}$ may refer to a mean $(C_{max})_{TOP}$ or mean $(C_{max})_{SC}$, respectively. In some other embodiments, an individual $C_{max}$ value obtained for a single subject may be compared to a mean $C_{max}$ obtained from a plurality of subjects.

Diseases of the Endoderm

Also provided herein is a method of treating a disease or condition that arises in a tissue originating from the endoderm of a subject. In some embodiments, the method comprises: releasing a pharmaceutical formulation containing a therapeutically effective amount of a therapeutic agent from an ingestible device as disclosed herein to the gastrointestinal tract of a subject. In some embodiments, the pharmaceutical formulation is released with sufficient power, pressure and/or force for trans-epithelial delivery of the therapeutic agent to the gastrointestinal tract. In some embodiments, the pharmaceutical formulation is released with sufficient power, pressure and/or force for epithelial delivery of the therapeutic agent to the gastrointestinal tract. In some embodiments, the pharmaceutical formulation is released with sufficient power, pressure and/or force for topical delivery of the therapeutic agent to the gastrointestinal tract.

In some embodiments of the methods described herein, the tissue originating from the endoderm is selected from the group of: the stomach, the colon, the liver, the pancreas, the urinary bladder, the epithelial parts of the trachea, the lungs, the pharynx, the thyroid, the parathyroid, the intestines, and the gallbladder. In some embodiments of any of the methods described herein, the disease or condition that arises in a tissue originating from the endoderm is selected from the group of: gastritis, Celiac disease, hepatitis, alcoholic lever disease, fatty liver disease (hepatic steatosis), non-alcoholic fatty liver disease (NASH), cirrhosis, primary schlerosing cholangitis, pancreatitis, insterstitial cystitits, asthma, chronic obstructic pulmonary disease, pulmonary fibrosis, pharyngitis, thyroiditis, hyperthyroidism, parathyroiditis, nephritis, Hashimoto's disease, Addison's disease, Graves' disease, Sjögren syndrome, type 1 diabetes, pelvic inflammatory disease, auditory canal inflammation, tinnitus, vestibular neuritis, otitis media, auditory canal inflammation, tracheitis, cholestatic liver disease, primary biliary sclerosis, liver parenchyma, an inherited metabolic disorder of the liver, Byler syndrome, cerebrotendinous, xanthomatosis, Zellweger's syndrome, neonatal hepatitis, cystic fibrosis, ALGS (Alagilles syndrome), PFIC (progressive familial intrahepatic cholestasis), autoimmune hepatitis, primary biliary cirrhosis (PBC), liver fibrosis, NAFLD, portal hypertension, general cholestasis, such as in jaundice due to drugs or during pregnancy, intra- and extrahepatic cholestasis, such as hereditary forms of cholestasis, such as PFIC1, gall stones and choledocholithiasis, malignancy causing obstruction of the biliary tree, symptoms (scratching, pruritus) due to cholestasis/jaundice, chronic autoimmune liver disease leading to progressive cholestasis, and pruritus of cholestatic liver disease, duodenal ulcers, enteritis (radiation-, chemotherapy-, or infection-induced enteritis), diverticulitis, pouchitis, cholecystitis, and cholangitis. In some embodiments of any of the methods described herein, the inflammatory disease or condition that arises in a tissue originating from the endoderm is inflammation of the liver.

In some embodiments, the disease or condition that arises in a tissue originating from the endoderm is a disease or condition related to the gut-brain axis. In some embodiments, the disease or condition is selected from the group consisting of multiple sclerosis, Parkinson's disease, mild cognitive impairment, Alzheimer's, disease, encephalitis, and hepatic encephalopathy.

Administration of Additional Therapeutic Agents

Some embodiments of the methods described herein further include administering a one or more additional therapeutic agents. In some embodiments, the additional therapeutic agent is administered orally, intravenously or subcutaneously, where the additional therapeutic agent is the same therapeutic agent; a different therapeutic agent; or an agent having the same or a different biological target from the therapeutic agent. In some embodiments of the methods described herein, the therapeutic agent is administered prior to the additional therapeutic agent. In some embodiments of the methods described herein, the therapeutic agent is administered after the additional therapeutic agent. In some embodiments of the methods described herein, the therapeutic agent and the additional therapeutic agent are administered substantially at the same time. In some embodiments of the methods described herein, the additional therapeutic agent is administered orally. In some embodiments of the methods described herein, the additional therapeutic agent is administered intravenously. In some embodiments of the methods described herein, the additional therapeutic agent is administered subcutaneously. In some embodiments of the methods described herein, the amount of the additional therapeutic agent when administered alone is less than the amount of the additional therapeutic agent when the therapeutic agent and the additional therapeutic agent are both administered systemically. In some embodiments of the methods described herein, the method does not include administering an additional therapeutic agent.

Exemplary Conditions or Diseases

The presently described devices and methods can be used to treat numerous conditions and diseases. In some embodiments, the conditions and diseases are inflammatory and immune conditions and diseases. Exemplary inflammatory and immune conditions and diseases include, but are not limited to allergy, asthma, autoimmune diseases, coeliac disease, glomerulonephritis, chronic peptic ulcer, tuberculosis, rheumatoid arthritis, juvenile rheumatoid arthritis, spondylarthritis, psoriasis, psoriatic arthritis, hidradenitis suppurativa, pyoderma gangrenosum, ankylosing spondylitis, periodontitis, ulcerative colitis and Crohn's disease, sinusitis, active hepatitis, non-alcoholic fatty liver disease (NAFLD), non-alcoholic steatohepatitis (NASH), liver fibrosis, liver cirrhosis, alcoholic fatty liver disease, alcoholic hepatitis, alcoholic liver disease, systemic lupus erythematosus (SLE, Lupus), preperfusion injury, multiple sclerosis (MS), transplant rejection, graft versus host disease, dermatomyositis, interstitial lung disease, lupus nephritis, motor neurone disease, osteoarthritis, myasthenia gravis, polymyositis, cholecystitis, scleroderma, Sjoegrens syndrome, and Wegener granulomatosis. In some embodiments, the inflammatory and immune conditions and disease is selected from the group consisting of rheumatoid arthritis, psoriasis, psoriatic arthritis, ankylosing spondylitis, ulcerative colitis and Crohn's disease, non-alcoholic fatty liver disease (NAFLD), non-alcoholic steatohepatitis (NASH), liver fibrosis, liver cirrhosis.

In some embodiments, the conditions and diseases are metabolic, endocrine and cardiovascular conditions and diseases. Exemplary metabolic, endocrine and cardiovascular conditions and diseases include, but are not limited to diabetes mellitus, insulin dependent diabetes, obesity, obstructive sleep apnea, NAFLD, NASH, liver fibrosis, liver cirrhosis, hypertension, pulmonary artery hypertension, primary sclerosing cholangitis, hyperlipidemia, hyperlipoproteinemia type I, lipodystrophy, acromegaly, myocardial infarction, and thromboembolism. In some embodiments, the metabolic, endocrine and cardiovascular conditions and diseases are selected from the group consisting of diabetes mellitus, obesity, NAFLD, NASH, liver fibrosis, liver cirrhosis, and acromegaly.

In some embodiments, the conditions and diseases are hematologic conditions and diseases. Exemplary hematologic conditions and diseases include, but are not limited to hemophilia, Factor VIII deficiency, Factor IX deficiency, Von Willebrands disease, Sickle cell anemia, Iron deficiency anemia, Neurology/Psychiatric, and Parkinsons disease. In some embodiments, the hematologic condition is hemophilia.

In some embodiments, the conditions and diseases are musculoskeletal conditions and diseases. Exemplary musculoskeletal conditions and diseases include, but are not limited to bone resorption; joint injury; male osteoporosis; osteogenesis imperfecta; osteoporosis; and postmenopausal osteoporosis.

In some embodiments, the conditions and diseases are infections. Exemplary infections include, but are not limited to, bacterial infection, bacterial meningitis, bacterial respiratory tract infection, bacterial urinary tract infection, bone and joint infection, cholangitis, complicated skin and skin structure infection, *Neisseria gonorrhoeae* infection, peritonitis, sepsis, abdominal abscess, *Aspergillus* infection, *Candida* infection, fungal infection, *Acinetobacter* infection, appendicitis, *Escherichia coli* infection, febrile neutropenia, *Haemophilus influenzae* infection; *Klebsiella pneumoniae* infection; lower respiratory tract infection; and pelvic inflammatory disease. In some embodiments, the conditions and diseases are infections selected from the group consisting of bacterial infections and sepsis.

In some embodiments, the conditions and diseases are respiratory conditions and diseases. Exemplary respiratory conditions and diseases include, but are not limited to, idiopathic pulmonary fibrosis.

In some embodiments, the conditions and diseases are cancers. Exemplary cancers include, but are not limited to acute myelogenous leukemia; anal tumor; niliary cancer; bladder cancer; bone tumor; breast tumor; central nervous system tumor; chronic lymphocytic leukemia; chronic myelocytic leukemia; diffuse large B-cell lymphoma; endometrioid carcinoma; esophagus tumor; fallopian tube cancer; follicle center lymphoma; germ cell and embryonic cancer; glioblastoma; gonad tumor; head and neck tumor; hematological neoplasm; hepatitis C virus infection; hepatocellular carcinoma; Hodgkins disease; hormone dependent prostate cancer; Kaposis sarcoma; leukoplakia; liver tumor; melanoma; Merkel cell carcinoma; mesothelioma; metastatic bladder cancer; metastatic breast cancer; metastatic esophageal cancer; metastatic head and neck cancer; metastatic liver cancer; metastatic non-small cell lung cancer; metastatic ovary cancer; metastatic pancreas cancer; metastatic prostate cancer; metastatic renal cancer; metastatic renal cell carcinoma; metastatic stomach cancer; mouth tumor; multiple myeloma; myelodysplastic syndrome; neoplastic meningitis; non-Hodgkin lymphoma; non-small-cell lung cancer; ocular melanoma; osteosarcoma; ovary tumor; pancreas tumor; pancreatic ductal adenocarcinoma; peritoneal tumor; prostate tumor; rectal tumor; renal cell carcinoma; salivary gland cancer; sepsis; small-cell lung cancer; soft tissue sarcoma; solid tumor; squamous cell carcinoma; stage III melanoma; stage IV melanoma; stomach tumor; gestis tumor; uterine cervix tumor; uterus tumor; uveal melanoma. In some embodiments, the cancer is selected from the group consisting of leukemia, lymphoma, hepatocellular carcinoma and metastatic cancer.

Inflammatory Conditions or Diseases

In some embodiments, the condition or disease that can be treated with the methods and devices disclosed herein is an inflammatory condition or disease. The presently described devices and methods are based, in part, on the unexpected discovery that administration of an immune modulator into the tissue of a subject's gastrointestinal tract can result in the observation of pharmacodynamics effects in tissues beyond the site of deposition. For example, an immune modulator administered into the tissue (e.g., mucosa or submucosa) of a subject's gastrointestinal tract can result in one or more of the following: changes in anatomical features, including suppressed or reduced development, aggregation, or accumulation of one or more of intestinal lymphoid tissues, isolated lymphoid follicles (ILFs), or intestinal lymphoid aggregates; suppressed immune response, including fewer T cells measured in lymph nodes or lymph tissues (which results in greater T cells forced into circulation, i.e., blood); decreased differentiation of immune cells (e.g., as measured using histology or through the use of a sampling device, or using a sampling device); a decreased level of inflammatory cytokine levels (e.g., as measured using biopsy or through the use of a sampling device); decreased endoscopic scoring; and improved efficacy of treatment for IBD (e.g., using any of the clinical assessments of a treatment for IBD described herein) or other inflammatory conditions of the GI tract or endoderm (e.g., in the liver).

In some embodiments, the presently described devices provide for a higher concentration of α4β7 expressing cells in the periphery (e.g., blood) when an immune modulator is delivered into the GI tissue (e.g., mucosa or submucosa) of one or more parts of the GI tract distal to the stomach (e.g., the small or large intestine) as compared to when the same dose of the immune modulator is orally (without a device), intravenously, or subcutaneously administered. The presently described devices can, e.g., result in trafficked cells being forced out of the local gastrointestinal tissue (including the mucosa) and lymph system, and back into systemic circulation of a subject.

Accordingly, also provided herein are methods of treating a disease or condition that arises in a tissue originating from the endoderm. The endoderm forms the gastrointestinal tract, respiratory tract, endocrine glands, and organs, the auditory system and urinary system. Thus, the present disclosure includes compositions and devices for treating diseases and conditions found in the following tissues that originate from the endoderm (e.g., the stomach, the colon, the liver, the pancreas, the urinary bladder, the epithelial parts of the trachea, the lungs, the pharynx, the thyroid, the parathyroid, the intestines, and the gallbladder). Also provided herein are methods of treating a disease or a condition that arises in a tissue originating from the endoderm (e.g., any of the exemplary diseases or conditions that arise in a tissue originating from the endoderm described herein) that include depositing one or more immune modulators into the tissue of the small intestine using any of the devices or compositions described herein. In a preferred embodiment, the compositions, devices and methods are for treating inflammatory diseases and conditions found in the liver (e.g., NAFLD, NASH, or cirrhosis).

Non-limiting examples of an inflammatory disease or condition that arises in a tissue originating from the endoderm includes gastritis, celiac disease, hepatitis, alcoholic lever disease, fatty liver disease (hepatic steatosis), non-alcoholic fatty liver disease (NASH), cirrhosis, primary schlerosing cholangitis, pancreatitis, insterstitial cystitits, asthma, chronic obstructive pulmonary disease, pulmonary fibrosis, pharyngitis, thyroiditis, hyperthyroidism, parathyroiditis, nephritis, Hashimoto's disease, Addison's disease, Graves' disease, Sjögren syndrome, type 1 diabetes, pelvic inflammatory disease, auditory canal inflammation, tinnitus, vestibular neuritis, otitis media, auditory canal inflammation, tracheitis, cholestatic liver disease, primary biliary schlerosis, liver parenchyma, an inherited metabolic disorder of the liver, Byler syndrome, cerebrotendinous, xanthomatosis, Zellweger's syndrome, neonatal hepatitis, cystic fibrosis, ALGS (Alagilles syndrome), PFIC (progressive familial intrahepatic cholestasis), autoimmune hepatitis, primary biliary cirrhosis (PBC), liver fibrosis, NAFLD, portal hypertension, general cholestasis, such as in jaundice due to drugs or during pregnancy, intra- and extrahepatic cholestasis, such as hereditary forms of cholestasis, such as PFIC1, gall stones and choledocholithiasis, malignancy causing obstruction of the biliary tree, symptoms (scratching, pruritus) due to cholestasis/jaundice, chronic autoimmune liver disease leading to progressive cholestasis, and pruritus of cholestatic liver disease, duodenal ulcers, enteritis (radiation-, chemotherapy-, or infection-induced enteritis), diverticulitis, pouchitis, cholecystitis, and cholangitis. Additional examples of diseases and conditions that arise in a tissue originating from the endoderm are known in the art.

In some embodiments of any of the devices or methods described herein, the methods result in the introduction of the immune modulator to one or more of the following, or the PD effects of the immune modulator (e.g., any of the PD effects of immune modulators described herein) are detectable in one or more of the following: throughout or in part of the paraaortic lymph nodes, throughout or in part of the MALT, throughout or in part of the GALT, throughout or in part of the inferior and superior mesenteric lymph nodes, and in one or more sections or subsections of the subject's gastrointestinal tract that is different than the section or subsection of the subject's gastrointestinal tract where the immune modulator is released. In some embodiments of any of the devices or methods described herein, the devices or methods result in the presence or accumulation of the immune modulator in tissues or organs of the endoderm (e.g., the liver) at higher doses as compared to administration of the immune modulator orally (without a device), intravenously, or subcutaneously.

In some embodiments of any of the methods described herein, the methods do not result in (or do not result in a significant effect in) pharmacodynamics effect(s) (e.g., any of the clinical effects or measurements of an immune modulator described herein) outside of the paraaortic lymph nodes.

In some embodiments of any of the methods described herein, the methods do not result in (or do not result in a significant effect in) pharmacodynamics effect(s) (e.g., any of the clinical effects or measurements of an immune modulator described herein) outside of the MALT.

In some embodiments of any of the methods described herein, the methods do not result in (or do not result in a significant effect in) pharmacodynamics effect(s) (e.g., any of the clinical effects or measurements of an immune modulator described herein) outside of the GALT.

In any of the methods described herein, the subject can be any mammal (e.g., an animal model of any of the diseases described herein).

In some embodiments of any of the methods described herein, the method results in the suppression of the subject's immune response in one or more of the paraaortic lymph nodes.

In some embodiments of any of the methods described herein, the method results in the suppression of the subject's immune response in mucosa-associated lymphoid tissue (MALT).

In some embodiments of any of the methods described herein, the method results in the suppression of the subject's immune response throughout or in part of the gut-associated lymphoid tissue (GALT). For example, in some embodiments of any of the methods described herein, the method results in a reduction of T cells (e.g., any of the T cells described herein, e.g., memory T cells) in Peyer's patches and/or mesenteric lymph nodes found in the GALT. In some embodiments of any of the methods described herein, the method results in a decreased level of T cells (e.g., any of the types of T cells described herein or known in the art) in a section or subsection of the subject's gastrointestinal tract that is different than the section or subsection of the subject's gastrointestinal tract where the immune modulator is released.

In some embodiments of any of the methods described herein, the method results in the suppression or reduction in the development, the aggregation, or accumulation of one or more of intestinal lymphoid tissues, isolated lymphoid follicles (ILFs), or intestinal lymphoid aggregates in mucosa-associated lymphoid tissue (MALT). In some embodiments of any of the methods described herein, the method results in the suppression of the development of one or more of intestinal lymphoid tissues, isolated lymphoid follicles, or intestinal lymphoid aggregates in gut-associated lymphoid tissue (GALT). In some embodiments of any of the methods described herein, the method results in the suppression of the immune response in one or more sections or subsections of the subject's gastrointestinal tract that is different than the section or subsection of the subject's gastrointestinal tract where the drug is released.

In some embodiments of any of the methods described herein, the methods result in pharmacodynamics effects proximal ("upstream") to the site of disease in the subject. For example, in some embodiments of any of the methods described herein, the immune modulator is deposited in the tissue of the small intestine (e.g., duodenum or jejunum), but pharmacodynamics effects of the immune modulator are observed in the liver. In some embodiments of any of the methods described herein, the immune modulator is deposited in the tissue of the small intestine (e.g., the duodenum or jejunum) and immune suppression is observed throughout the mesenteric lymph system and other systems of the paraaortic lymph nodes, including the hepatic lymph nodes of the celiac group of the preaortic lymph nodes (preaortic lymph nodes are part of the paraaortic lymph nodes). In some embodiments of any of the methods described herein, the immune modulator is deposited in the small intestine (e.g., duodenum, jejunum, or ileum) or colon (e.g., ascending colon, transverse colon, descending colon, rectum, or cecum), but pharmacodynamics effects of the immune modulator are throughout or in part of the MALT, GALT, Peyer's patches, mesenteric lymph nodes, paraaortic lymph nodes, or any of the other tissues originating from the endoderm described herein or known in the art, in the mammal.

In some embodiments of any of the methods described herein, the method results in a decreased level or a decreased level of activation of one or more of the following immune cells that participate in mucosal immune response in a mammal: microfold cells (M cells), antigen-presenting cells (e.g., B-lymphocytes, dendritic cells, and macrophages), and effector cells (e.g., T-lymphocytes).

Microfold cells (M cells) are found in the gut-associated lymphoid tissue (GALT) of the Peyer's patches in the small intestine. M cells allow for the transport of microbes and particles across the epithelial cell layer from the gut lumen to the lamina propria where interactions with immune cells can take place. M cells provide for the initiation of mucosal immunity responses on the apical membrane by delivering antigens to antigen-presenting cells.

Antigen-presenting cells (APCs) include B-lymphocytes, dendritic cells, and macrophages. B-lymphocytes, also called B-cells, can internalize antigen that binds to their B-cell receptor. Dendritic cells have the broadest range of antigen presentation and are necessary for activation of naïve T cells. Dendritic cells present antigen to both helper and cytotoxic T cells. Macrophages can be stimulated by T-cell secretion of interferon gamma. After this activation, macrophages are able to express major histocompatibility complex (MIC) class II and co-stimulatory molecules, and can present phagocytosed peptide fragments to helper T cells. The activation of macrophages can assist pathogen-infected macrophages in clearing the infection.

MHCs bind antigens derived from pathogens and display them on the cell surface for recognition by appropriate T-cells. MHC class I presents antigens from intracellular pathogens, such as viruses and bacteria. MHC class II presents antigens from phagocytosed/pinocytosed pathogens.

Effector cells, as used herein, include T-lymphocytes, including $CD4^+$ (also called helper T cells), $CD8^+$ (also called cytotoxic T cells), $CD45Rb^-$ (more IL-10 and less $TNF\alpha$ in IBD) as compared with $CD4^+CD45Rb^+$, and $CD44^+$ T cells. CD44 participates in lymphocytes activation, recirculation, and homing, and is an indicative marker for effector memory T cells.

Exemplary Methods

Provided herein are methods of treating a disease or condition in a subject in need thereof. In some embodiments, the method includes administering a dispensable substance to the gastrointestinal (GI) tract of the subject, where the administration includes orally administering an ingestible device containing the dispensable substance to the subject, where the dispensable substance contains a pharmaceutical formulation including a therapeutically effective amount of a therapeutic agent, and releasing the dispensable substance from the ingestible device as a jet to a desired location of the GI tract of the subject, thereby directly delivering the dispensable substance to the GI tract of the subject.

In some embodiments, the administration is trans-epithelial. In some embodiments, the administration is epithelial. In some embodiments, the administration is topical.

In some embodiments, the direct delivery of the dispensable substance to the submucosa and/or the mucosa (e.g., into the lamina propria) of the subject provides systemic uptake of the therapeutic agent.

In some embodiments, the desired location of the GI tract is the small intestine. In some embodiments, the desired location of the GI tract is one or more of the duodenum, the jejunum, and the ileum. In some embodiments, a portion of the dispensable substance is delivered to the mucosa of the GI tract of the subject.

The disease or condition treatable by the methods provided herein can be any disease or condition described herein. In some embodiments, the disease or condition is selected from an autoimmune disease or condition, fibrosis, rheumatoid arthritis, non-alcoholic steatohepatitis (NASH), non-alcoholic fatty liver disease (NAFLD), an inflammatory disease or disorder (e.g., inflammatory bowel disease (IBD)), hepatocellular carcinoma, a growth disorder (e.g., a growth hormone deficiency or disorder (GHD)), an endocrine or metabolic disease or condition (e.g., diabetes, insulin resistance, hyperglycemia, hyperlipidemia, obesity, hepatic steatosis, hyperinsulinemia, obstructive sleep apnea, liver fibrosis, liver cirrhosis, hypertension, pulmonary artery hypertension, primary sclerosing cholangitis, hyperlipoproteinemia type I, hypercholesterolemia, lipodystrophy, acromegaly, myocardial infarction, and thromboembolism), hemophilia (e.g., hemophilia A, hemophilia B, Von Willebrand disease), and combinations thereof.

In some embodiments, the disease or condition is diabetes, for example, type I or type II diabetes. In some embodiments, the diabetes is selected from diabetes with Alzheimer's disease, diabetes with dementia, diabetes with Alzheimer's disease and dementia, diabetes with obesity, diabetes with NAFLD, diabetes with NASH, diabetes with NAFLD and NASH, and diabetes with a cardiovascular disease.

The therapeutic agent suitable for use in the methods described herein can be any therapeutic agent disclosed herein. In some embodiments, the therapeutic agent is a glucagon receptor agonist or a glucagon-like peptide-1 (GLP-1) receptor agonist. In some embodiments, the therapeutic agent is a growth hormone. In some embodiments, the therapeutic agent is an insulin. In some embodiments, the therapeutic agent is a TNF-alpha inhibitor. In some embodiments, the therapeutic agent is a peptide YY ligand. In some embodiments, the therapeutic agent is an amylin analog. In some embodiments, the therapeutic agent is an alternative coagulation promotor (ACP).

In some embodiments of the methods provided herein, the pharmaceutical formulation is a fluid. In some embodiments, the pharmaceutical formulation is a solution or suspension. In some embodiments, the pharmaceutical formulation has a viscosity of less than or equal to 10 cP. In some embodiments, the pharmaceutical formulation has a viscosity of at least about 0.8 cP.

Particular Medical Approaches

Some embodiments of the invention relate to particular medical approaches, which use the ingestible device to deliver a particular therapeutic agent, or class of agent, by a particular delivery mode to treat a particular disease, or class of disease. Particular medical approaches are disclosed in Table 18. All therapeutic agents disclosed in Table 18 optionally include the pharmaceutically acceptable salts and solvates thereof in the case of small molecules, peptides, and nucleic acids, and the biosimilars thereof, and/or glycosylation variants thereof, in the case of biologics such as antibodies, unless expressly indicated otherwise.

TABLE 18

Particular medical approaches

| Approach | Therapeutic agent | Disease | Delivery mode |
|---|---|---|---|
| 1 | GLP-1 receptor agonist | A disease or condition responsive to treatment with a GLP-1 receptor agonist | Trans-epithelial |
| 2 | GLP-1 receptor agonist | Metabolic or endocrine disorder | Trans-epithelial |
| 3 | GLP-1 receptor agonist | Diabetes | Trans-epithelial |
| 4 | GLP-1 receptor agonist | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 5 | GLP-1 receptor agonist | A liver disease or disorder | Trans-epithelial |
| 6 | GLP-1 receptor agonist | Compensated liver cirrhosis | Trans-epithelial |
| 7 | GLP-1 receptor agonist | Non-alcoholic steatohepatitis (NASH) or non-alcoholic fatty liver disease (NAFLD) | Trans-epithelial |
| 8 | GLP-1 receptor agonist | A binge eating disorder | Trans-epithelial |
| 9 | GLP-1 receptor agonist | Hyperglycemia | Trans-epithelial |
| 10 | GLP-1 receptor agonist | Postprandial hyperglycemia | Trans-epithelial |

TABLE 18-continued

Particular medical approaches

| Approach | Therapeutic agent | Disease | Delivery mode |
|---|---|---|---|
| 11 | GLP-1 receptor agonist | Nicotine dependence | Trans-epithelial |
| 12 | GLP-1 receptor agonist | A central nervous system (CNS) disorder | Trans-epithelial |
| 13 | GLP-1 receptor agonist | Alzheimer's disease or Parkinson's disease | Trans-epithelial |
| 14 | semaglutide | A disease or condition responsive to treatment with a GLP-1 receptor agonist | Trans-epithelial |
| 15 | semaglutide | Metabolic or endocrine disorder | Trans-epithelial |
| 16 | semaglutide | Diabetes | Trans-epithelial |
| 17 | semaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 18 | semaglutide | A liver disease or disorder | Trans-epithelial |
| 19 | semaglutide | Compensated liver cirrhosis | Trans-epithelial |
| 20 | semaglutide | Non-alcoholic steatohepatitis (NASH) or non-alcoholic fatty liver disease (NAFLD) | Trans-epithelial |
| 21 | semaglutide | A binge eating disorder | Trans-epithelial |
| 22 | semaglutide | Hyperglycemia | Trans-epithelial |
| 23 | semaglutide | Postprandial hyperglycemia | Trans-epithelial |
| 24 | semaglutide | Nicotine dependence | Trans-epithelial |
| 25 | semaglutide | A central nervous system (CNS) disorder | Trans-epithelial |
| 26 | semaglutide | Alzheimer's disease or Parkinson's disease | Trans-epithelial |
| 27 | dulaglutide | A disease or condition responsive to treatment with a GLP-1 receptor agonist | Trans-epithelial |
| 28 | dulaglutide | Metabolic or endocrine disorder | Trans-epithelial |
| 29 | dulaglutide | Diabetes | Trans-epithelial |
| 30 | dulaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 31 | dulaglutide | A liver disease or disorder | Trans-epithelial |
| 32 | dulaglutide | Compensated liver cirrhosis | Trans-epithelial |
| 33 | dulaglutide | Non-alcoholic steatohepatitis (NASH) or non-alcoholic fatty liver disease (NAFLD) | Trans-epithelial |
| 34 | dulaglutide | A binge eating disorder | Trans-epithelial |
| 35 | dulaglutide | Hyperglycemia | Trans-epithelial |
| 36 | dulaglutide | Postprandial hyperglycemia | Trans-epithelial |
| 37 | dulaglutide | Nicotine dependence | Trans-epithelial |
| 38 | dulaglutide | A central nervous system (CNS) disorder | Trans-epithelial |
| 39 | dulaglutide | Alzheimer's disease or Parkinson's disease | Trans-epithelial |
| 40 | albiglutide | A disease or condition responsive to treatment with a GLP-1 receptor agonist | Trans-epithelial |
| 41 | albiglutide | Metabolic or endocrine disorder | Trans-epithelial |
| 42 | albiglutide | Diabetes | Trans-epithelial |
| 43 | albiglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 44 | albiglutide | A liver disease or disorder | Trans-epithelial |
| 45 | albiglutide | Compensated liver cirrhosis | Trans-epithelial |

TABLE 18-continued

Particular medical approaches

| Approach | Therapeutic agent | Disease | Delivery mode |
|---|---|---|---|
| 46 | albiglutide | Non-alcoholic steatohepatitis (NASH) or non-alcoholic fatty liver disease (NAFLD) | Trans-epithelial |
| 47 | albiglutide | A binge eating disorder | Trans-epithelial |
| 48 | albiglutide | Hyperglycemia | Trans-epithelial |
| 49 | albiglutide | Postprandial hyperglycemia | Trans-epithelial |
| 50 | albiglutide | Nicotine dependence | Trans-epithelial |
| 51 | albiglutide | A central nervous system (CNS) disorder | Trans-epithelial |
| 52 | albiglutide | Alzheimer's disease or Parkinson's disease | Trans-epithelial |
| 53 | exenatide | A disease or condition responsive to treatment with a GLP-1 receptor agonist | Trans-epithelial |
| 54 | exenatide | Metabolic or endocrine disorder | Trans-epithelial |
| 55 | exenatide | Diabetes | Trans-epithelial |
| 56 | exenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 57 | exenatide | A liver disease or disorder | Trans-epithelial |
| 58 | exenatide | Compensated liver cirrhosis | Trans-epithelial |
| 59 | exenatide | Non-alcoholic steatohepatitis (NASH) or non-alcoholic fatty liver disease (NAFLD) | Trans-epithelial |
| 60 | exenatide | A binge eating disorder | Trans-epithelial |
| 61 | exenatide | Hyperglycemia | Trans-epithelial |
| 62 | exenatide | Postprandial hyperglycemia | Trans-epithelial |
| 63 | exenatide | Nicotine dependence | Trans-epithelial |
| 64 | exenatide | A central nervous system (CNS) disorder | Trans-epithelial |
| 65 | exenatide | Alzheimer's disease or Parkinson's disease | Trans-epithelial |
| 66 | liraglutide | A disease or condition responsive to treatment with a GLP-1 receptor agonist | Trans-epithelial |
| 67 | liraglutide | Metabolic or endocrine disorder | Trans-epithelial |
| 68 | liraglutide | Diabetes | Trans-epithelial |
| 69 | liraglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 70 | liraglutide | A liver disease or disorder | Trans-epithelial |
| 71 | liraglutide | Compensated liver cirrhosis | Trans-epithelial |
| 72 | liraglutide | Non-alcoholic steatohepatitis (NASH) or non-alcoholic fatty liver disease (NAFLD) | Trans-epithelial |
| 73 | liraglutide | A binge eating disorder | Trans-epithelial |
| 74 | liraglutide | Hyperglycemia | Trans-epithelial |
| 75 | liraglutide | Postprandial hyperglycemia | Trans-epithelial |
| 76 | liraglutide | Nicotine dependence | Trans-epithelial |
| 77 | liraglutide | A central nervous system (CNS) disorder | Trans-epithelial |
| 78 | liraglutide | Alzheimer's disease or Parkinson's disease | Trans-epithelial |
| 79 | lixisenatide | A disease or condition responsive to treatment with a GLP-1 receptor agonist | Trans-epithelial |
| 80 | lixisenatide | Metabolic or endocrine disorder | Trans-epithelial |
| 81 | lixisenatide | Diabetes | Trans-epithelial |
| 82 | lixisenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic | Trans-epithelial |

TABLE 18-continued

Particular medical approaches

| Approach | Therapeutic agent | Disease | Delivery mode |
|---|---|---|---|
| | | steatohepatitis (NASH), diabetes with NAFLD and NASH, or diabetes with a cardiovascular disease | |
| 83 | lixisenatide | A liver disease or disorder | Trans-epithelial |
| 84 | lixisenatide | Compensated liver cirrhosis | Trans-epithelial |
| 85 | lixisenatide | Non-alcoholic steatohepatitis (NASH) or non-alcoholic fatty liver disease (NAFLD) | Trans-epithelial |
| 86 | lixisenatide | A binge eating disorder | Trans-epithelial |
| 87 | lixisenatide | Hyperglycemia | Trans-epithelial |
| 88 | lixisenatide | Postprandial hyperglycemia | Trans-epithelial |
| 89 | lixisenatide | Nicotine dependence | Trans-epithelial |
| 90 | lixisenatide | A central nervous system (CNS) disorder | Trans-epithelial |
| 91 | lixisenatide | Alzheimer's disease or Parkinson's disease | Trans-epithelial |
| 92 | NNC-0090-2746 | A disease or condition responsive to treatment with a GLP-1 receptor agonist | Trans-epithelial |
| 93 | NNC-0090-2746 | Metabolic or endocrine disorder | Trans-epithelial |
| 94 | NNC-0090-2746 | Diabetes | Trans-epithelial |
| 95 | NNC-0090-2746 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 96 | NNC-0090-2746 | A liver disease or disorder | Trans-epithelial |
| 97 | NNC-0090-2746 | Compensated liver cirrhosis | Trans-epithelial |
| 98 | NNC-0090-2746 | Non-alcoholic steatohepatitis (NASH) or non-alcoholic fatty liver disease (NAFLD) | Trans-epithelial |
| 99 | NNC-0090-2746 | A binge eating disorder | Trans-epithelial |
| 100 | NNC-0090-2746 | Hyperglycemia | Trans-epithelial |
| 101 | NNC-0090-2746 | Postprandial hyperglycemia | Trans-epithelial |
| 102 | NNC-0090-2746 | Nicotine dependence | Trans-epithelial |
| 103 | NNC-0090-2746 | A central nervous system (CNS) disorder | Trans-epithelial |
| 104 | NNC-0090-2746 | Alzheimer's disease or Parkinson's disease | Trans-epithelial |
| 105 | glucagon | A disease or condition responsive to treatment with a GLP-1 receptor agonist | Trans-epithelial |
| 106 | glucagon | Metabolic or endocrine disorder | Trans-epithelial |
| 107 | glucagon | Diabetes | Trans-epithelial |
| 108 | glucagon | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 109 | glucagon | A liver disease or disorder | Trans-epithelial |
| 110 | glucagon | Compensated liver cirrhosis | Trans-epithelial |
| 111 | glucagon | Non-alcoholic steatohepatitis (NASH) or non-alcoholic fatty liver disease (NAFLD) | Trans-epithelial |
| 112 | glucagon | A binge eating disorder | Trans-epithelial |
| 113 | glucagon | Hyperglycemia | Trans-epithelial |
| 114 | glucagon | Postprandial hyperglycemia | Trans-epithelial |
| 115 | glucagon | Nicotine dependence | Trans-epithelial |
| 116 | glucagon | A central nervous system (CNS) disorder | Trans-epithelial |
| 117 | glucagon | Alzheimer's disease or Parkinson's disease | Trans-epithelial |
| 118 | NN-9277 | A disease or condition responsive to treatment with a GLP-1 receptor agonist | Trans-epithelial |
| 119 | NN-9277 | Metabolic or endocrine disorder | Trans-epithelial |
| 120 | NN-9277 | Diabetes | Trans-epithelial |

TABLE 18-continued

Particular medical approaches

| Approach | Therapeutic agent | Disease | Delivery mode |
|---|---|---|---|
| 121 | NN-9277 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 122 | NN-9277 | A liver disease or disorder | Trans-epithelial |
| 123 | NN-9277 | Compensated liver cirrhosis | Trans-epithelial |
| 124 | NN-9277 | Non-alcoholic steatohepatitis (NASH) or non-alcoholic fatty liver disease (NAFLD) | Trans-epithelial |
| 125 | NN-9277 | A binge eating disorder | Trans-epithelial |
| 126 | NN-9277 | Hyperglycemia | Trans-epithelial |
| 127 | NN-9277 | Postprandial hyperglycemia | Trans-epithelial |
| 128 | NN-9277 | Nicotine dependence | Trans-epithelial |
| 129 | NN-9277 | A central nervous system (CNS) disorder | Trans-epithelial |
| 130 | NN-9277 | Alzheimer's disease or Parkinson's disease | Trans-epithelial |
| 131 | NN-9423 | A disease or condition responsive to treatment with a GLP-1 receptor agonist | Trans-epithelial |
| 132 | NN-9423 | Metabolic or endocrine disorder | Trans-epithelial |
| 133 | NN-9423 | Diabetes | Trans-epithelial |
| 134 | NN-9423 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Trans-epithelial |
| 135 | NN-9423 | A liver disease or disorder | Trans-epithelial |
| 136 | NN-9423 | Compensated liver cirrhosis | Trans-epithelial |
| 137 | NN-9423 | Non-alcoholic steatohepatitis (NASH) or non-alcoholic fatty liver disease (NAFLD) | Trans-epithelial |
| 138 | NN-9423 | A binge eating disorder | Trans-epithelial |
| 139 | NN-9423 | Hyperglycemia | Trans-epithelial |
| 140 | NN-9423 | Postprandial hyperglycemia | Trans-epithelial |
| 141 | NN-9423 | Nicotine dependence | Trans-epithelial |
| 142 | NN-9423 | A central nervous system (CNS) disorder | Trans-epithelial |
| 143 | NN-9423 | Alzheimer's disease or Parkinson's disease | Trans-epithelial |
| 144 | GLP-1 receptor agonist | A disease or condition responsive to treatment with a GLP-1 receptor agonist | Epithelial |
| 145 | GLP-1 receptor agonist | Metabolic or endocrine disorder | Epithelial |
| 146 | GLP-1 receptor agonist | Diabetes | Epithelial |
| 147 | GLP-1 receptor agonist | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 148 | GLP-1 receptor agonist | A liver disease or disorder | Epithelial |
| 149 | GLP-1 receptor agonist | Compensated liver cirrhosis | Epithelial |
| 150 | GLP-1 receptor agonist | Non-alcoholic steatohepatitis (NASH) or non-alcoholic fatty liver disease (NAFLD) | Epithelial |
| 151 | GLP-1 receptor agonist | A binge eating disorder | Epithelial |
| 152 | GLP-1 receptor agonist | Hyperglycemia | Epithelial |

TABLE 18-continued

Particular medical approaches

| Approach | Therapeutic agent | Disease | Delivery mode |
|---|---|---|---|
| 153 | GLP-1 receptor agonist | Postprandial hyperglycemia | Epithelial |
| 154 | GLP-1 receptor agonist | Nicotine dependence | Epithelial |
| 155 | GLP-1 receptor agonist | A central nervous system (CNS) disorder | Epithelial |
| 156 | GLP-1 receptor agonist | Alzheimer's disease or Parkinson's disease | Epithelial |
| 157 | semaglutide | A disease or condition responsive to treatment with a GLP-1 receptor agonist | Epithelial |
| 158 | semaglutide | Metabolic or endocrine disorder | Epithelial |
| 159 | semaglutide | Diabetes | Epithelial |
| 160 | semaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 161 | semaglutide | A liver disease or disorder | Epithelial |
| 162 | semaglutide | Compensated liver cirrhosis | Epithelial |
| 163 | semaglutide | Non-alcoholic steatohepatitis (NASH) or non-alcoholic fatty liver disease (NAFLD) | Epithelial |
| 164 | semaglutide | A binge eating disorder | Epithelial |
| 165 | semaglutide | Hyperglycemia | Epithelial |
| 166 | semaglutide | Postprandial hyperglycemia | Epithelial |
| 167 | semaglutide | Nicotine dependence | Epithelial |
| 168 | semaglutide | A central nervous system (CNS) disorder | Epithelial |
| 169 | semaglutide | Alzheimer's disease or Parkinson's disease | Epithelial |
| 170 | dulaglutide | A disease or condition responsive to treatment with a GLP-1 receptor agonist | Epithelial |
| 171 | dulaglutide | Metabolic or endocrine disorder | Epithelial |
| 172 | dulaglutide | Diabetes | Epithelial |
| 173 | dulaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 174 | dulaglutide | A liver disease or disorder | Epithelial |
| 175 | dulaglutide | Compensated liver cirrhosis | Epithelial |
| 176 | dulaglutide | Non-alcoholic steatohepatitis (NASH) or non-alcoholic fatty liver disease (NAFLD) | Epithelial |
| 177 | dulaglutide | A binge eating disorder | Epithelial |
| 178 | dulaglutide | Hyperglycemia | Epithelial |
| 179 | dulaglutide | Postprandial hyperglycemia | Epithelial |
| 180 | dulaglutide | Nicotine dependence | Epithelial |
| 181 | dulaglutide | A central nervous system (CNS) disorder | Epithelial |
| 182 | dulaglutide | Alzheimer's disease or Parkinson's disease | Epithelial |
| 183 | albiglutide | A disease or condition responsive to treatment with a GLP-1 receptor agonist | Epithelial |
| 184 | albiglutide | Metabolic or endocrine disorder | Epithelial |
| 185 | albiglutide | Diabetes | Epithelial |
| 186 | albiglutide | Diabetes with Alzheimer' s disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |

TABLE 18-continued

Particular medical approaches

| Approach | Therapeutic agent | Disease | Delivery mode |
|---|---|---|---|
| 187 | albiglutide | A liver disease or disorder | Epithelial |
| 188 | albiglutide | Compensated liver cirrhosis | Epithelial |
| 189 | albiglutide | Non-alcoholic steatohepatitis (NASH) or non-alcoholic fatty liver disease (NAFLD) | Epithelial |
| 190 | albiglutide | A binge eating disorder | Epithelial |
| 191 | albiglutide | Hyperglycemia | Epithelial |
| 192 | albiglutide | Postprandial hyperglycemia | Epithelial |
| 193 | albiglutide | Nicotine dependence | Epithelial |
| 194 | albiglutide | A central nervous system (CNS) disorder | Epithelial |
| 195 | albiglutide | Alzheimer's disease or Parkinson's disease | Epithelial |
| 196 | exenatide | A disease or condition responsive to treatment with a GLP-1 receptor agonist | Epithelial |
| 197 | exenatide | Metabolic or endocrine disorder | Epithelial |
| 198 | exenatide | Diabetes | Epithelial |
| 199 | exenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 200 | exenatide | A liver disease or disorder | Epithelial |
| 201 | exenatide | Compensated liver cirrhosis | Epithelial |
| 202 | exenatide | Non-alcoholic steatohepatitis (NASH) or non-alcoholic fatty liver disease (NAFLD) | Epithelial |
| 203 | exenatide | A binge eating disorder | Epithelial |
| 204 | exenatide | Hyperglycemia | Epithelial |
| 205 | exenatide | Postprandial hyperglycemia | Epithelial |
| 206 | exenatide | Nicotine dependence | Epithelial |
| 207 | exenatide | A central nervous system (CNS) disorder | Epithelial |
| 208 | exenatide | Alzheimer's disease or Parkinson's disease | Epithelial |
| 209 | liraglutide | A disease or condition responsive to treatment with a GLP-1 receptor agonist | Epithelial |
| 210 | liraglutide | Metabolic or endocrine disorder | Epithelial |
| 211 | liraglutide | Diabetes | Epithelial |
| 212 | liraglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 213 | liraglutide | A liver disease or disorder | Epithelial |
| 214 | liraglutide | Compensated liver cirrhosis | Epithelial |
| 215 | liraglutide | Non-alcoholic steatohepatitis (NASH) or non-alcoholic fatty liver disease (NAFLD) | Epithelial |
| 216 | liraglutide | A binge eating disorder | Epithelial |
| 217 | liraglutide | Hyperglycemia | Epithelial |
| 218 | liraglutide | Postprandial hyperglycemia | Epithelial |
| 219 | liraglutide | Nicotine dependence | Epithelial |
| 220 | liraglutide | A central nervous system (CNS) disorder | Epithelial |
| 221 | liraglutide | Alzheimer's disease or Parkinson's disease | Epithelial |
| 222 | lixisenatide | A disease or condition responsive to treatment with a GLP-1 receptor agonist | Epithelial |
| 223 | lixisenatide | Metabolic or endocrine disorder | Epithelial |
| 224 | lixisenatide | Diabetes | Epithelial |
| 225 | lixisenatide | Diabetes with Alzheimer's disease, diabetes with dementia, diabetes with Alzheimer's disease and dementia, diabetes with obesity, diabetes with | Epithelial |

TABLE 18-continued

Particular medical approaches

| Approach | Therapeutic agent | Disease | Delivery mode |
|---|---|---|---|
| | | non-alcoholic fatty liver disease (NAFLD), diabetes with non-alcoholic steatohepatitis (NASH), diabetes with NAFLD and NASH, or diabetes with a cardiovascular disease | |
| 226 | lixisenatide | A liver disease or disorder | Epithelial |
| 227 | lixisenatide | Compensated liver cirrhosis | Epithelial |
| 228 | lixisenatide | Non-alcoholic steatohepatitis (NASH) or non-alcoholic fatty liver disease (NAFLD) | Epithelial |
| 229 | lixisenatide | A binge eating disorder | Epithelial |
| 230 | lixisenatide | Hyperglycemia | Epithelial |
| 231 | lixisenatide | Postprandial hyperglycemia | Epithelial |
| 232 | lixisenatide | Nicotine dependence | Epithelial |
| 233 | lixisenatide | A central nervous system (CNS) disorder | Epithelial |
| 234 | lixisenatide | Alzheimer's disease or Parkinson's disease | Epithelial |
| 235 | NNC-0090-2746 | A disease or condition responsive to treatment with a GLP-1 receptor agonist | Epithelial |
| 236 | NNC-0090-2746 | Metabolic or endocrine disorder | Epithelial |
| 237 | NNC-0090-2746 | Diabetes | Epithelial |
| 238 | NNC-0090-2746 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 239 | NNC-0090-2746 | A liver disease or disorder | Epithelial |
| 240 | NNC-0090-2746 | Compensated liver cirrhosis | Epithelial |
| 241 | NNC-0090-2746 | Non-alcoholic steatohepatitis (NASH) or non-alcoholic fatty liver disease (NAFLD) | Epithelial |
| 242 | NNC-0090-2746 | A binge eating disorder | Epithelial |
| 243 | NNC-0090-2746 | Hyperglycemia | Epithelial |
| 244 | NNC-0090-2746 | Postprandial hyperglycemia | Epithelial |
| 245 | NNC-0090-2746 | Nicotine dependence | Epithelial |
| 246 | NNC-0090-2746 | A central nervous system (CNS) disorder | Epithelial |
| 247 | NNC-0090-2746 | Alzheimer's disease or Parkinson's disease | Epithelial |
| 248 | glucagon | A disease or condition responsive to treatment with a GLP-1 receptor agonist | Epithelial |
| 249 | glucagon | Metabolic or endocrine disorder | Epithelial |
| 250 | glucagon | Diabetes | Epithelial |
| 251 | glucagon | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 252 | glucagon | A liver disease or disorder | Epithelial |
| 253 | glucagon | Compensated liver cirrhosis | Epithelial |
| 254 | glucagon | Non-alcoholic steatohepatitis (NASH) or non-alcoholic fatty liver disease (NAFLD) | Epithelial |
| 255 | glucagon | A binge eating disorder | Epithelial |
| 256 | glucagon | Hyperglycemia | Epithelial |
| 257 | glucagon | Postprandial hyperglycemia | Epithelial |
| 258 | glucagon | Nicotine dependence | Epithelial |
| 259 | glucagon | A central nervous system (CNS) disorder | Epithelial |
| 260 | glucagon | Alzheimer's disease or Parkinson's disease | Epithelial |
| 261 | NN-9277 | A disease or condition responsive to treatment with a GLP-1 receptor agonist | Epithelial |

TABLE 18-continued

Particular medical approaches

| Approach | Therapeutic agent | Disease | Delivery mode |
|---|---|---|---|
| 262 | NN-9277 | Metabolic or endocrine disorder | Epithelial |
| 263 | NN-9277 | Diabetes | Epithelial |
| 264 | NN-9277 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 265 | NN-9277 | A liver disease or disorder | Epithelial |
| 266 | NN-9277 | Compensated liver cirrhosis | Epithelial |
| 267 | NN-9277 | Non-alcoholic steatohepatitis (NASH) or non-alcoholic fatty liver disease (NAFLD) | Epithelial |
| 268 | NN-9277 | A binge eating disorder | Epithelial |
| 269 | NN-9277 | Hyperglycemia | Epithelial |
| 270 | NN-9277 | Postprandial hyperglycemia | Epithelial |
| 271 | NN-9277 | Nicotine dependence | Epithelial |
| 272 | NN-9277 | A central nervous system (CNS) disorder | Epithelial |
| 273 | NN-9277 | Alzheimer's disease or Parkinson's disease | Epithelial |
| 274 | NN-9423 | A disease or condition responsive to treatment with a GLP-1 receptor agonist | Epithelial |
| 275 | NN-9423 | Metabolic or endocrine disorder | Epithelial |
| 276 | NN-9423 | Diabetes | Epithelial |
| 277 | NN-9423 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Epithelial |
| 278 | NN-9423 | A liver disease or disorder | Epithelial |
| 279 | NN-9423 | Compensated liver cirrhosis | Epithelial |
| 280 | NN-9423 | Non-alcoholic steatohepatitis (NASH) or non-alcoholic fatty liver disease (NAFLD) | Epithelial |
| 281 | NN-9423 | A binge eating disorder | Epithelial |
| 282 | NN-9423 | Hyperglycemia | Epithelial |
| 283 | NN-9423 | Postprandial hyperglycemia | Epithelial |
| 284 | NN-9423 | Nicotine dependence | Epithelial |
| 285 | NN-9423 | A central nervous system (CNS) disorder | Epithelial |
| 286 | NN-9423 | Alzheimer's disease or Parkinson's disease | Epithelial |
| 287 | GLP-1 receptor agonist | A disease or condition responsive to treatment with a GLP-1 receptor agonist | Topical |
| 288 | GLP-1 receptor agonist | Metabolic or endocrine disorder | Topical |
| 289 | GLP-1 receptor agonist | Diabetes | Topical |
| 290 | GLP-1 receptor agonist | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 291 | GLP-1 receptor agonist | A liver disease or disorder | Topical |
| 292 | GLP-1 receptor agonist | Compensated liver cirrhosis | Topical |
| 293 | GLP-1 receptor agonist | Non-alcoholic steatohepatitis (NASH) or non-alcoholic fatty liver disease (NAFLD) | Topical |
| 294 | GLP-1 receptor agonist | A binge eating disorder | Topical |

TABLE 18-continued

| Particular medical approaches | | | |
|---|---|---|---|
| Approach | Therapeutic agent | Disease | Delivery mode |
| 295 | GLP-1 receptor agonist | Hyperglycemia | Topical |
| 296 | GLP-1 receptor agonist | Postprandial hyperglycemia | Topical |
| 297 | GLP-1 receptor agonist | Nicotine dependence | Topical |
| 298 | GLP-1 receptor agonist | A central nervous system (CNS) disorder | Topical |
| 299 | GLP-1 receptor agonist | Alzheimer's disease or Parkinson's disease | Topical |
| 300 | semaglutide | A disease or condition responsive to treatment with a GLP-1 receptor agonist | Topical |
| 301 | semaglutide | Metabolic or endocrine disorder | Topical |
| 302 | semaglutide | Diabetes | Topical |
| 303 | semaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 304 | semaglutide | A liver disease or disorder | Topical |
| 305 | semaglutide | Compensated liver cirrhosis | Topical |
| 306 | semaglutide | Non-alcoholic steatohepatitis (NASH) or non-alcoholic fatty liver disease (NAFLD) | Topical |
| 307 | semaglutide | A binge eating disorder | Topical |
| 308 | semaglutide | Hyperglycemia | Topical |
| 309 | semaglutide | Postprandial hyperglycemia | Topical |
| 310 | semaglutide | Nicotine dependence | Topical |
| 311 | semaglutide | A central nervous system (CNS) disorder | Topical |
| 312 | semaglutide | Alzheimer's disease or Parkinson's disease | Topical |
| 313 | dulaglutide | A disease or condition responsive to treatment with a GLP-1 receptor agonist | Topical |
| 314 | dulaglutide | Metabolic or endocrine disorder | Topical |
| 315 | dulaglutide | Diabetes | Topical |
| 316 | dulaglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 317 | dulaglutide | A liver disease or disorder | Topical |
| 318 | dulaglutide | Compensated liver cirrhosis | Topical |
| 319 | dulaglutide | Non-alcoholic steatohepatitis (NASH) or non-alcoholic fatty liver disease (NAFLD) | Topical |
| 320 | dulaglutide | A binge eating disorder | Topical |
| 321 | dulaglutide | Hyperglycemia | Topical |
| 322 | dulaglutide | Postprandial hyperglycemia | Topical |
| 323 | dulaglutide | Nicotine dependence | Topical |
| 324 | dulaglutide | A central nervous system (CNS) disorder | Topical |
| 325 | dulaglutide | Alzheimer's disease or Parkinson's disease | Topical |
| 326 | albiglutide | A disease or condition responsive to treatment with a GLP-1 receptor agonist | Topical |
| 327 | albiglutide | Metabolic or endocrine disorder | Topical |
| 328 | albiglutide | Diabetes | Topical |

TABLE 18-continued

Particular medical approaches

| Approach | Therapeutic agent | Disease | Delivery mode |
|---|---|---|---|
| 329 | albiglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 330 | albiglutide | A liver disease or disorder | Topical |
| 331 | albiglutide | Compensated liver cirrhosis | Topical |
| 332 | albiglutide | Non-alcoholic steatohepatitis (NASH) or non-alcoholic fatty liver disease (NAFLD) | Topical |
| 333 | albiglutide | A binge eating disorder | Topical |
| 334 | albiglutide | Hyperglycemia | Topical |
| 335 | albiglutide | Postprandial hyperglycemia | Topical |
| 336 | albiglutide | Nicotine dependence | Topical |
| 337 | albiglutide | A central nervous system (CNS) disorder | Topical |
| 338 | albiglutide | Alzheimer's disease or Parkinson's disease | Topical |
| 339 | exenatide | A disease or condition responsive to treatment with a GLP-1 receptor agonist | Topical |
| 340 | exenatide | Metabolic or endocrine disorder | Topical |
| 341 | exenatide | Diabetes | Topical |
| 342 | exenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 343 | exenatide | A liver disease or disorder | Topical |
| 344 | exenatide | Compensated liver cirrhosis | Topical |
| 345 | exenatide | Non-alcoholic steatohepatitis (NASH) or non-alcoholic fatty liver disease (NAFLD) | Topical |
| 346 | exenatide | A binge eating disorder | Topical |
| 347 | exenatide | Hyperglycemia | Topical |
| 348 | exenatide | Postprandial hyperglycemia | Topical |
| 349 | exenatide | Nicotine dependence | Topical |
| 350 | exenatide | A central nervous system (CNS) disorder | Topical |
| 351 | exenatide | Alzheimer's disease or Parkinson's disease | Topical |
| 352 | liraglutide | A disease or condition responsive to treatment with a GLP-1 receptor agonist | Topical |
| 353 | liraglutide | Metabolic or endocrine disorder | Topical |
| 354 | liraglutide | Diabetes | Topical |
| 355 | liraglutide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 356 | liraglutide | A liver disease or disorder | Topical |
| 357 | liraglutide | Compensated liver cirrhosis | Topical |
| 358 | liraglutide | Non-alcoholic steatohepatitis (NASH) or non-alcoholic fatty liver disease (NAFLD) | Topical |
| 359 | liraglutide | A binge eating disorder | Topical |
| 360 | liraglutide | Hyperglycemia | Topical |
| 361 | liraglutide | Postprandial hyperglycemia | Topical |
| 362 | liraglutide | Nicotine dependence | Topical |
| 363 | liraglutide | A central nervous system (CNS) disorder | Topical |
| 364 | liraglutide | Alzheimer's disease or Parkinson's disease | Topical |

TABLE 18-continued

Particular medical approaches

| Approach | Therapeutic agent | Disease | Delivery mode |
|---|---|---|---|
| 365 | lixisenatide | A disease or condition responsive to treatment with a GLP-1 receptor agonist | Topical |
| 366 | lixisenatide | Metabolic or endocrine disorder | Topical |
| 367 | lixisenatide | Diabetes | Topical |
| 368 | lixisenatide | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 369 | lixisenatide | A liver disease or disorder | Topical |
| 370 | lixisenatide | Compensated liver cirrhosis | Topical |
| 371 | lixisenatide | Non-alcoholic steatohepatitis (NASH) or non-alcoholic fatty liver disease (NAFLD) | Topical |
| 372 | lixisenatide | A binge eating disorder | Topical |
| 373 | lixisenatide | Hyperglycemia | Topical |
| 374 | lixisenatide | Postprandial hyperglycemia | Topical |
| 375 | lixisenatide | Nicotine dependence | Topical |
| 376 | lixisenatide | A central nervous system (CNS) disorder | Topical |
| 377 | lixisenatide | Alzheimer's disease or Parkinson's disease | Topical |
| 378 | NNC-0090-2746 | A disease or condition responsive to treatment with a GLP-1 receptor agonist | Topical |
| 379 | NNC-0090-2746 | Metabolic or endocrine disorder | Topical |
| 380 | NNC-0090-2746 | Diabetes | Topical |
| 381 | NNC-0090-2746 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | |
| 382 | NNC-0090-2746 | A liver disease or disorder | Topical |
| 383 | NNC-0090-2746 | Compensated liver cirrhosis | Topical |
| 384 | NNC-0090-2746 | Non-alcoholic steatohepatitis (NASH) or non-alcoholic fatty liver disease (NAFLD) | Topical |
| 385 | NNC-0090-2746 | A binge eating disorder | Topical |
| 386 | NNC-0090-2746 | Hyperglycemia | Topical |
| 387 | NNC-0090-2746 | Postprandial hyperglycemia | Topical |
| 388 | NNC-0090-2746 | Nicotine dependence | Topical |
| 389 | NNC-0090-2746 | A central nervous system (CNS) disorder | Topical |
| 390 | NNC-0090-2746 | Alzheimer's disease or Parkinson's disease | Topical |
| 391 | glucagon | A disease or condition responsive to treatment with a GLP-1 receptor agonist | Topical |
| 392 | glucagon | Metabolic or endocrine disorder | Topical |
| 393 | glucagon | Diabetes | Topical |
| 394 | glucagon | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 395 | glucagon | A liver disease or disorder | Topical |
| 396 | glucagon | Compensated liver cirrhosis | Topical |
| 397 | glucagon | Non-alcoholic steatohepatitis (NASH) or non-alcoholic fatty liver disease (NAFLD) | Topical |
| 398 | glucagon | A binge eating disorder | Topical |
| 399 | glucagon | Hyperglycemia | Topical |
| 400 | glucagon | Postprandial hyperglycemia | Topical |

TABLE 18-continued

Particular medical approaches

| Approach | Therapeutic agent | Disease | Delivery mode |
|---|---|---|---|
| 401 | glucagon | Nicotine dependence | Topical |
| 402 | glucagon | A central nervous system (CNS) disorder | Topical |
| 403 | glucagon | Alzheimer's disease or Parkinson's disease | Topical |
| 404 | NN-9277 | A disease or condition responsive to treatment with a GLP-1 receptor agonist | Topical |
| 405 | NN-9277 | Metabolic or endocrine disorder | Topical |
| 406 | NN-9277 | Diabetes | Topical |
| 407 | NN-9277 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 408 | NN-9277 | A liver disease or disorder | Topical |
| 409 | NN-9277 | Compensated liver cirrhosis | Topical |
| 410 | NN-9277 | Non-alcoholic steatohepatitis (NASH) or non-alcoholic fatty liver disease (NAFLD) | Topical |
| 411 | NN-9277 | A binge eating disorder | Topical |
| 412 | NN-9277 | Hyperglycemia | Topical |
| 413 | NN-9277 | Postprandial hyperglycemia | Topical |
| 414 | NN-9277 | Nicotine dependence | Topical |
| 415 | NN-9277 | A central nervous system (CNS) disorder | Topical |
| 416 | NN-9277 | Alzheimer's disease or Parkinson's disease | Topical |
| 417 | NN-9423 | A disease or condition responsive to treatment with a GLP-1 receptor agonist | Topical |
| 418 | NN-9423 | Metabolic or endocrine disorder | Topical |
| 419 | NN-9423 | Diabetes | Topical |
| 420 | NN-9423 | Diabetes with Alzheimer's disease, diabetes with dementia, diabetes with Alzheimer's disease and dementia, diabetes with obesity, diabetes with non-alcoholic fatty liver disease (NAFLD), diabetes with non-alcoholic steatohepatitis (NASH), diabetes with NAFLD and NASH, or diabetes with a cardiovascular disease | Topical |
| 421 | NN-9423 | A liver disease or disorder | Topical |
| 422 | NN-9423 | Compensated liver cirrhosis | Topical |
| 423 | NN-9423 | Non-alcoholic steatohepatitis (NASH) or non-alcoholic fatty liver disease (NAFLD) | Topical |
| 424 | NN-9423 | A binge eating disorder | Topical |
| 425 | NN-9423 | Hyperglycemia | Topical |
| 426 | NN-9423 | Postprandial hyperglycemia | Topical |
| 427 | NN-9423 | Nicotine dependence | Topical |
| 428 | NN-9423 | A central nervous system (CNS) disorder | Topical |
| 429 | NN-9423 | Alzheimer's disease or Parkinson's disease | Topical |
| 430 | Growth hormone | Growth disorder | Trans-epithelial |
| 431 | Growth hormone | Growth hormone deficiency or disorder (GHD) | Trans-epithelial |
| 432 | Growth hormone | Acquired, congenital, or idiopathic GHD; or combination thereof | Trans-epithelial |
| 433 | Growth hormone | GHD as a result of trauma, infection, radiation therapy, or tumor growth | Trans-epithelial |
| 434 | Growth hormone | Adult-onset GHD | Trans-epithelial |
| 435 | Recombinant growth hormone (rHGH) | Growth disorder | Trans-epithelial |
| 436 | Recombinant growth hormone (rHGH) | Growth hormone deficiency or disorder (GHD) | Trans-epithelial |
| 437 | Recombinant growth hormone (rHGH) | Acquired, congenital, or idiopathic GHD; or combination thereof | Trans-epithelial |
| 438 | Recombinant growth hormone (rHGH) | GHD as a result of trauma, infection, radiation therapy, or tumor growth | Trans-epithelial |

TABLE 18-continued

Particular medical approaches

| Approach | Therapeutic agent | Disease | Delivery mode |
|---|---|---|---|
| 439 | Recombinant growth hormone (rHGH) | Adult-onset GHD | Trans-epithelial |
| 440 | Somatropin | Growth disorder | Trans-epithelial |
| 441 | Somatropin | Growth hormone deficiency or disorder (GHD) | Trans-epithelial |
| 442 | Somatropin | Acquired, congenital, or idiopathic GHD; or combination thereof | Trans-epithelial |
| 443 | Somatropin | GHD as a result of trauma, infection, radiation therapy, or tumor growth | Trans-epithelial |
| 444 | Somatropin | Adult-onset GHD | Trans-epithelial |
| 445 | Somapacitan | Growth disorder | Trans-epithelial |
| 446 | Somapacitan | Growth hormone deficiency or disorder (GHD) | Trans-epithelial |
| 447 | Somapacitan | Acquired, congenital, or idiopathic GHD; or combination thereof | Trans-epithelial |
| 448 | Somapacitan | GHD as a result of trauma, infection, radiation therapy, or tumor growth | Trans-epithelial |
| 449 | Somapacitan | Adult-onset GHD | Trans-epithelial |
| 450 | Lonapegsomatropin | Growth disorder | Trans-epithelial |
| 451 | Lonapegsomatropin | Growth hormone deficiency or disorder (GHD) | Trans-epithelial |
| 452 | Lonapegsomatropin | Acquired, congenital, or idiopathic GHD; or combination thereof | Trans-epithelial |
| 453 | Lonapegsomatropin | GHD as a result of trauma, infection, radiation therapy, or tumor growth | Trans-epithelial |
| 454 | Lonapegsomatropin | Adult-onset GHD | Trans-epithelial |
| 455 | YPEG-somatropin | Growth disorder | Trans-epithelial |
| 456 | YPEG-somatropin | Growth hormone deficiency or disorder (GHD) | Trans-epithelial |
| 457 | YPEG-somatropin | Acquired, congenital, or idiopathic GHD; or combination thereof | Trans-epithelial |
| 458 | YPEG-somatropin | GHD as a result of trauma, infection, radiation therapy, or tumor growth | Trans-epithelial |
| 459 | YPEG-somatropin | Adult-onset GHD | Trans-epithelial |
| 460 | Efpegsomatropin | Growth disorder | Trans-epithelial |
| 461 | Efpegsomatropin | Growth hormone deficiency or disorder (GHD) | Trans-epithelial |
| 462 | Efpegsomatropin | Acquired, congenital, or idiopathic GHD; or combination thereof | Trans-epithelial |
| 463 | Efpegsomatropin | GHD as a result of trauma, infection, radiation therapy, or tumor growth | Trans-epithelial |
| 464 | Efpegsomatropin | Adult-onset GHD | Trans-epithelial |
| 465 | Somatrogon | Growth disorder | Trans-epithelial |
| 466 | Somatrogon | Growth hormone deficiency or disorder (GHD) | Trans-epithelial |
| 467 | Somatrogon | Acquired, congenital, or idiopathic GHD; or combination thereof | Trans-epithelial |
| 468 | Somatrogon | GHD as a result of trauma, infection, radiation therapy, or tumor growth | Trans-epithelial |
| 469 | Somatrogon | Adult-onset GHD | Trans-epithelial |
| 470 | TJ-101 | Growth disorder | Trans-epithelial |
| 471 | TJ-101 | Growth hormone deficiency or disorder (GHD) | Trans-epithelial |
| 472 | TJ-101 | Acquired, congenital, or idiopathic GHD; or combination thereof | Trans-epithelial |
| 473 | TJ-101 | GHD as a result of trauma, infection, radiation therapy, or tumor growth | Trans-epithelial |
| 474 | TJ-101 | Adult-onset GHD | Trans-epithelial |
| 475 | ALT-P1 | Growth disorder | Trans-epithelial |
| 476 | ALT-P1 | Growth hormone deficiency or disorder (GHD) | Trans-epithelial |
| 477 | ALT-P1 | Acquired, congenital, or idiopathic GHD; or combination thereof | Trans-epithelial |
| 478 | ALT-P1 | GHD as a result of trauma, infection, radiation therapy, or tumor growth | Trans-epithelial |
| 479 | ALT-P1 | Adult-onset GHD | Trans-epithelial |
| 480 | JR-142 | Growth disorder | Trans-epithelial |
| 481 | JR-142 | Growth hormone deficiency or disorder (GHD) | Trans-epithelial |
| 482 | JR-142 | Acquired, congenital, or idiopathic GHD; or combination thereof | Trans-epithelial |
| 483 | JR-142 | GHD as a result of trauma, infection, radiation therapy, or tumor growth | Trans-epithelial |

TABLE 18-continued

Particular medical approaches

| Approach | Therapeutic agent | Disease | Delivery mode |
|---|---|---|---|
| 484 | JR-142 | Adult-onset GHD | Trans-epithelial |
| 485 | Growth hormone | Growth disorder | Epithelial |
| 486 | Growth hormone | Growth hormone deficiency or disorder (GHD) | Epithelial |
| 487 | Growth hormone | Acquired, congenital, or idiopathic GHD; or combination thereof | Epithelial |
| 488 | Growth hormone | GHD as a result of trauma, infection, radiation therapy, or tumor growth | Epithelial |
| 489 | Growth hormone | Adult-onset GHD | Epithelial |
| 490 | Recombinant growth hormone (rHGH) | Growth disorder | Epithelial |
| 491 | Recombinant growth hormone (rHGH) | Growth hormone deficiency or disorder (GHD) | Epithelial |
| 492 | Recombinant growth hormone (rHGH) | Acquired, congenital, or idiopathic GHD; or combination thereof | Epithelial |
| 493 | Recombinant growth hormone (rHGH) | GHD as a result of trauma, infection, radiation therapy, or tumor growth | Epithelial |
| 494 | Recombinant growth hormone (rHGH) | Adult-onset GHD | Epithelial |
| 495 | Somatropin | Growth disorder | Epithelial |
| 496 | Somatropin | Growth hormone deficiency or disorder (GHD) | Epithelial |
| 497 | Somatropin | Acquired, congenital, or idiopathic GHD; or combination thereof | Epithelial |
| 498 | Somatropin | GHD as a result of trauma, infection, radiation therapy, or tumor growth | Epithelial |
| 499 | Somatropin | Adult-onset GHD | Epithelial |
| 500 | Somapacitan | Growth disorder | Epithelial |
| 501 | Somapacitan | Growth hormone deficiency or disorder (GHD) | Epithelial |
| 502 | Somapacitan | Acquired, congenital, or idiopathic GHD; or combination thereof | Epithelial |
| 503 | Somapacitan | GHD as a result of trauma, infection, radiation therapy, or tumor growth | Epithelial |
| 504 | Somapacitan | Adult-onset GHD | Epithelial |
| 505 | Lonapegsomatropin | Growth disorder | Epithelial |
| 506 | Lonapegsomatropin | Growth hormone deficiency or disorder (GHD) | Epithelial |
| 507 | Lonapegsomatropin | Acquired, congenital, or idiopathic GHD; or combination thereof | Epithelial |
| 508 | Lonapegsomatropin | GHD as a result of trauma, infection, radiation therapy, or tumor growth | Epithelial |
| 509 | Lonapegsomatropin | Adult-onset GHD | Epithelial |
| 510 | YPEG-somatropin | Growth disorder | Epithelial |
| 511 | YPEG-somatropin | Growth hormone deficiency or disorder (GHD) | Epithelial |
| 512 | YPEG-somatropin | Acquired, congenital, or idiopathic GHD; or combination thereof | Epithelial |
| 513 | YPEG-somatropin | GHD as a result of trauma, infection, radiation therapy, or tumor growth | Epithelial |
| 514 | YPEG-somatropin | Adult-onset GHD | Epithelial |
| 515 | Efpegsomatropin | Growth disorder | Epithelial |
| 516 | Efpegsomatropin | Growth hormone deficiency or disorder (GHD) | Epithelial |
| 517 | Efpegsomatropin | Acquired, congenital, or idiopathic GHD; or combination thereof | Epithelial |
| 518 | Efpegsomatropin | GHD as a result of trauma, infection, radiation therapy, or tumor growth | Epithelial |
| 519 | Efpegsomatropin | Adult-onset GHD | Epithelial |
| 520 | Somatrogon | Growth disorder | Epithelial |
| 521 | Somatrogon | Growth hormone deficiency or disorder (GHD) | Epithelial |
| 522 | Somatrogon | Acquired, congenital, or idiopathic GHD; or combination thereof | Epithelial |
| 523 | Somatrogon | GHD as a result of trauma, infection, radiation therapy, or tumor growth | Epithelial |
| 524 | Somatrogon | Adult-onset GHD | Epithelial |
| 525 | TJ-101 | Growth disorder | Epithelial |
| 526 | TJ-101 | Growth hormone deficiency or disorder (GHD) | Epithelial |
| 527 | TJ-101 | Acquired, congenital, or idiopathic GHD; or combination thereof | Epithelial |
| 528 | TJ-101 | GHD as a result of trauma, infection, radiation therapy, or tumor growth | Epithelial |
| 529 | TJ 101 | Adult-onset GHD | Epithelial |
| 530 | ALT-P1 | Growth disorder | Epithelial |

TABLE 18-continued

Particular medical approaches

| Approach | Therapeutic agent | Disease | Delivery mode |
|---|---|---|---|
| 531 | ALT-P1 | Growth hormone deficiency or disorder (GHD) | Epithelial |
| 532 | ALT-P1 | Acquired, congenital, or idiopathic GHD; or combination thereof | Epithelial |
| 533 | ALT-P1 | GHD as a result of trauma, infection, radiation therapy, or tumor growth | Epithelial |
| 534 | ALT-P1 | Adult-onset GHD | Epithelial |
| 535 | JR-142 | Growth disorder | Epithelial |
| 536 | JR-142 | Growth hormone deficiency or disorder (GHD) | Epithelial |
| 537 | JR-142 | Acquired, congenital, or idiopathic GHD; or combination thereof | Epithelial |
| 538 | JR-142 | GHD as a result of trauma, infection, radiation therapy, or tumor growth | Epithelial |
| 539 | JR-142 | Adult-onset GHD | Epithelial |
| 540 | Growth hormone | Growth disorder | Topical |
| 541 | Growth hormone | Growth hormone deficiency or disorder (GHD) | Topical |
| 542 | Growth hormone | Acquired, congenital, or idiopathic GHD; or combination thereof | Topical |
| 543 | Growth hormone | GHD as a result of trauma, infection, radiation therapy, or tumor growth | Topical |
| 544 | Growth hormone | Adult-onset GHD | Topical |
| 545 | Recombinant growth hormone (rHGH) | Growth disorder | Topical |
| 546 | Recombinant growth hormone (rHGH) | Growth hormone deficiency or disorder (GHD) | Topical |
| 547 | Recombinant growth hormone (rHGH) | Acquired, congenital, or idiopathic GHD; or combination thereof | Topical |
| 548 | Recombinant growth hormone (rHGH) | GHD as a result of trauma, infection, radiation therapy, or tumor growth | Topical |
| 549 | Recombinant growth hormone (rHGH) | Adult-onset GHD | Topical |
| 550 | Somatropin | Growth disorder | Topical |
| 551 | Somatropin | Growth hormone deficiency or disorder (GHD) | Topical |
| 552 | Somatropin | Acquired, congenital, or idiopathic GHD; or combination thereof | Topical |
| 553 | Somatropin | GHD as a result of trauma, infection, radiation therapy, or tumor growth | Topical |
| 554 | Somatropin | Adult-onset GHD | Topical |
| 555 | Somapacitan | Growth disorder | Topical |
| 556 | Somapacitan | Growth hormone deficiency or disorder (GHD) | Topical |
| 557 | Somapacitan | Acquired, congenital, or idiopathic GHD; or combination thereof | Topical |
| 558 | Somapacitan | GHD as a result of trauma, infection, radiation therapy, or tumor growth | Topical |
| 559 | Somapacitan | Adult-onset GHD | Topical |
| 560 | Lonapegsomatropin | Growth disorder | Topical |
| 561 | Lonapegsomatropin | Growth hormone deficiency or disorder (GHD) | Topical |
| 562 | Lonapegsomatropin | Acquired, congenital, or idiopathic GHD; or combination thereof | Topical |
| 563 | Lonapegsomatropin | GHD as a result of trauma, infection, radiation therapy, or tumor growth | Topical |
| 564 | Lonapegsomatropin | Adult-onset GHD | Topical |
| 565 | YPEG-somatropin | Growth disorder | Topical |
| 566 | YPEG-somatropin | Growth hormone deficiency or disorder (GHD) | Topical |
| 567 | YPEG-somatropin | Acquired, congenital, or idiopathic GHD; or combination thereof | Topical |
| 568 | YPEG-somatropin | GHD as a result of trauma, infection, radiation therapy, or tumor growth | Topical |
| 569 | YPEG-somatropin | Adult-onset GHD | Topical |
| 570 | Efpegsomatropin | Growth disorder | Topical |
| 571 | Efpegsomatropin | Growth hormone deficiency or disorder (GHD) | Topical |
| 572 | Efpegsomatropin | Acquired, congenital, or idiopathic GHD; or combination thereof | Topical |
| 573 | Efpegsomatropin | GHD as a result of trauma, infection, radiation therapy, or tumor growth | Topical |
| 574 | Efpegsomatropin | Adult-onset GHD | Topical |
| 575 | Somatrogon | Growth disorder | Topical |
| 576 | Somatrogon | Growth hormone deficiency or disorder (GHD) | |

TABLE 18-continued

Particular medical approaches

| Approach | Therapeutic agent | Disease | Delivery mode |
|---|---|---|---|
| 577 | Somatrogon | Acquired, congenital, or idiopathic GHD; or combination thereof | Topical |
| 578 | Somatrogon | GHD as a result of trauma, infection, radiation therapy, or tumor growth | Topical |
| 579 | Somatrogon | Adult-onset GHD | Topical |
| 580 | TJ-101 | Growth disorder | Topical |
| 581 | TJ-101 | Growth hormone deficiency or disorder (GHD) | Topical |
| 582 | TJ-101 | Acquired, congenital, or idiopathic GHD; or combination thereof | Topical |
| 583 | TJ-101 | GHD as a result of trauma, infection, radiation therapy, or tumor growth | Topical |
| 584 | TJ 101 | Adult-onset GHD | Topical |
| 585 | ALT-P1 | Growth disorder | Topical |
| 586 | ALT-P1 | Growth hormone deficiency or disorder (GHD) | Topical |
| 587 | ALT-P1 | Acquired, congenital, or idiopathic GHD; or combination thereof | Topical |
| 588 | ALT-P1 | GHD as a result of trauma, infection, radiation therapy, or tumor growth | Topical |
| 589 | ALT-P1 | Adult-onset GHD | Topical |
| 590 | JR-142 | Growth disorder | Topical |
| 591 | JR-142 | Growth hormone deficiency or disorder (GHD) | Topical |
| 592 | JR-142 | Acquired, congenital, or idiopathic GHD; or combination thereof | Topical |
| 593 | JR-142 | GHD as a result of trauma, infection, radiation therapy, or tumor growth | Topical |
| 594 | JR-142 | Adult-onset GHD | Topical |
| 595 | TNF-alpha inhibitor | A disease or condition responsive to treatment with a TNF-alpha inhibitor | Trans-epithelial |
| 596 | TNF-alpha inhibitor | Inflammatory disease or disorder | Trans-epithelial |
| 597 | TNF-alpha inhibitor | Inflammatory bowel disease | Trans-epithelial |
| 598 | TNF-alpha inhibitor | Ulcerative colitis | Trans-epithelial |
| 599 | TNF-alpha inhibitor | Crohn's disease | Trans-epithelial |
| 600 | TNF-alpha inhibitor | Ileal Crohn's disease | Trans-epithelial |
| 601 | TNF-alpha inhibitor | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 602 | Adalimumab | A disease or condition responsive to treatment with a TNF-alpha inhibitor | Trans-epithelial |
| 603 | Adalimumab | Inflammatory disease or disorder | Trans-epithelial |
| 604 | Adalimumab | Inflammatory bowel disease | Trans-epithelial |
| 605 | Adalimumab | Ulcerative colitis | Trans-epithelial |
| 606 | Adalimumab | Crohn's disease | Trans-epithelial |
| 607 | Adalimumab | Ileal Crohn's disease | Trans-epithelial |
| 608 | Adalimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 609 | Certolizumab pegol | A disease or condition responsive to treatment with a TNF-alpha inhibitor | Trans-epithelial |
| 610 | Certolizumab pegol | Inflammatory disease or disorder | Trans-epithelial |
| 611 | Certolizumab pegol | Inflammatory bowel disease | Trans-epithelial |
| 612 | Certolizumab pegol | Ulcerative colitis | Trans-epithelial |
| 613 | Certolizumab pegol | Crohn's disease | Trans-epithelial |

TABLE 18-continued

Particular medical approaches

| Approach | Therapeutic agent | Disease | Delivery mode |
|---|---|---|---|
| 614 | Certolizumab pegol | Ileal Crohn's disease | Trans-epithelial |
| 615 | Certolizumab pegol | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 616 | Etanercept | A disease or condition responsive to treatment with a TNF-alpha inhibitor | Trans-epithelial |
| 617 | Etanercept | Inflammatory disease or disorder | Trans-epithelial |
| 618 | Etanercept | Inflammatory bowel disease | Trans-epithelial |
| 619 | Etanercept | Ulcerative colitis | Trans-epithelial |
| 620 | Etanercept | Crohn's disease | Trans-epithelial |
| 621 | Etanercept | Ileal Crohn's disease | Trans-epithelial |
| 622 | Etanercept | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 623 | Golimumab | A disease or condition responsive to treatment with a TNF-alpha inhibitor | Trans-epithelial |
| 624 | Golimumab | Inflammatory disease or disorder | Trans-epithelial |
| 625 | Golimumab | Inflammatory bowel disease | Trans-epithelial |
| 626 | Golimumab | Ulcerative colitis | Trans-epithelial |
| 627 | Golimumab | Crohn's disease | Trans-epithelial |
| 628 | Golimumab | Ileal Crohn's disease | Trans-epithelial |
| 629 | Golimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Trans-epithelial |
| 630 | Ustekinumab | Inflammatory disease or disorder | Trans-epithelial |
| 631 | Ustekinumab | Inflammatory bowel disease | Trans-epithelial |
| 632 | Vedolizumab | Inflammatory disease or disorder | Trans-epithelial |
| 633 | Vedolizumab | Inflammatory bowel disease | Trans-epithelial |
| 634 | Natalizumab | Inflammatory disease or disorder | Trans-epithelial |
| 635 | Natalizumab | Inflammatory bowel disease | Trans-epithelial |
| 636 | TNF-alpha inhibitor | A disease or condition responsive to treatment with a TNF-alpha inhibitor | Epithelial |
| 637 | TNF-alpha inhibitor | Inflammatory disease or disorder | Epithelial |
| 638 | TNF-alpha inhibitor | Inflammatory bowel disease | Epithelial |
| 639 | TNF-alpha inhibitor | Ulcerative colitis | Epithelial |
| 640 | TNF-alpha inhibitor | Crohn's disease | Epithelial |
| 641 | TNF-alpha inhibitor | Ileal Crohn's disease | Epithelial |
| 642 | TNF-alpha inhibitor | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |

TABLE 18-continued

Particular medical approaches

| Approach | Therapeutic agent | Disease | Delivery mode |
|---|---|---|---|
| 643 | Adalimumab | A disease or condition responsive to treatment with a TNF-alpha inhibitor | Epithelial |
| 644 | Adalimumab | Inflammatory disease or disorder | Epithelial |
| 645 | Adalimumab | Inflammatory bowel disease | Epithelial |
| 646 | Adalimumab | Ulcerative colitis | Epithelial |
| 647 | Adalimumab | Crohn's disease | Epithelial |
| 648 | Adalimumab | Ileal Crohn's disease | Epithelial |
| 649 | Adalimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |
| 650 | Certolizumab pegol | A disease or condition responsive to treatment with a TNF-alpha inhibitor | Epithelial |
| 651 | Certolizumab pegol | Inflammatory disease or disorder | Epithelial |
| 652 | Certolizumab pegol | Inflammatory bowel disease | Epithelial |
| 653 | Certolizumab pegol | Ulcerative colitis | Epithelial |
| 654 | Certolizumab pegol | Crohn's disease | Epithelial |
| 655 | Certolizumab pegol | Ileal Crohn's disease | Epithelial |
| 656 | Certolizumab pegol | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |
| 657 | Etanercept | A disease or condition responsive to treatment with a TNF-alpha inhibitor | Epithelial |
| 658 | Etanercept | Inflammatory disease or disorder | Epithelial |
| 659 | Etanercept | Inflammatory bowel disease | Epithelial |
| 660 | Etanercept | Ulcerative colitis | Epithelial |
| 661 | Etanercept | Crohn's disease | Epithelial |
| 662 | Etanercept | Ileal Crohn's disease | Epithelial |
| 663 | Etanercept | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |
| 664 | Golimumab | A disease or condition responsive to treatment with a TNF-alpha inhibitor | Epithelial |
| 665 | Golimumab | Inflammatory disease or disorder | Epithelial |
| 666 | Golimumab | Inflammatory bowel disease | Epithelial |
| 667 | Golimumab | Ulcerative colitis | Epithelial |
| 668 | Golimumab | Crohn's disease | Epithelial |
| 669 | Golimumab | Ileal Crohn's disease | Epithelial |
| 670 | Golimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Epithelial |

TABLE 18-continued

Particular medical approaches

| Approach | Therapeutic agent | Disease | Delivery mode |
|---|---|---|---|
| 671 | Ustekinumab | Inflammatory disease or disorder | Epithelial |
| 672 | Ustekinumab | Inflammatory bowel disease | Epithelial |
| 673 | Vedolizumab | Inflammatory disease or disorder | Epithelial |
| 674 | Vedolizumab | Inflammatory bowel disease | Epithelial |
| 675 | Natalizumab | Inflammatory disease or disorder | Epithelial |
| 676 | Natalizumab | Inflammatory bowel disease | Epithelial |
| 677 | TNF-alpha inhibitor | A disease or condition responsive to treatment with a TNF-alpha inhibitor | Topical |
| 678 | TNF-alpha inhibitor | Inflammatory disease or disorder | Topical |
| 679 | TNF-alpha inhibitor | Inflammatory bowel disease | Topical |
| 680 | TNF-alpha inhibitor | Ulcerative colitis | Topical |
| 681 | TNF-alpha inhibitor | Crohn's disease | Topical |
| 682 | TNF-alpha inhibitor | Ileal Crohn's disease | Topical |
| 683 | TNF-alpha inhibitor | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 684 | Adalimumab | A disease or condition responsive to treatment with a TNF-alpha inhibitor | Topical |
| 685 | Adalimumab | Inflammatory disease or disorder | Topical |
| 686 | Adalimumab | Inflammatory bowel disease | Topical |
| 687 | Adalimumab | Ulcerative colitis | Topical |
| 688 | Adalimumab | Crohn's disease | Topical |
| 689 | Adalimumab | Ileal Crohn's disease | Topical |
| 690 | Adalimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 691 | Certolizumab pegol | A disease or condition responsive to treatment with a TNF-alpha inhibitor | Topical |
| 692 | Certolizumab pegol | Inflammatory disease or disorder | Topical |
| 693 | Certolizumab pegol | Inflammatory bowel disease | Topical |
| 694 | Certolizumab pegol | Ulcerative colitis | Topical |
| 695 | Certolizumab pegol | Crohn's disease | Topical |
| 696 | Certolizumab pegol | Ileal Crohn's disease | Topical |
| 697 | Certolizumab pegol | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 698 | Etanercept | A disease or condition responsive to treatment with a TNF-alpha inhibitor | Topical |
| 699 | Etanercept | Inflammatory disease or disorder | Topical |
| 700 | Etanercept | Inflammatory bowel disease | Topical |
| 701 | Etanercept | Ulcerative colitis | Topical |
| 702 | Etanercept | Crohn's disease | Topical |
| 703 | Etanercept | Ileal Crohn's disease | Topical |
| 704 | Etanercept | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid | Topical |

TABLE 18-continued

Particular medical approaches

| Approach | Therapeutic agent | Disease | Delivery mode |
|---|---|---|---|
| | | arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | |
| 705 | Golimumab | A disease or condition responsive to treatment with a TNF-alpha inhibitor | Topical |
| 706 | Golimumab | Inflammatory disease or disorder | Topical |
| 707 | Golimumab | Inflammatory bowel disease | Topical |
| 708 | Golimumab | Ulcerative colitis | Topical |
| 709 | Golimumab | Crohn's disease | Topical |
| 710 | Golimumab | Ileal Crohn's disease | Topical |
| 711 | Golimumab | Ankylosing spondylitis, asthma, Behcet's disease, hidradenitis suppurativa, an inflammatory disease, an inflammatory bowel disease, insulin-dependent (type 1) diabetes, type 2 diabetes, juvenile rheumatoid arthritis, Kawasaki disease, lower back pain, osteoarthritis, pouchitis, psoriasis, psoriatic arthritis, pyoderma gangrenosum, rheumatoid arthritis, spondylarthritis, uveitis, or combinations thereof | Topical |
| 712 | Ustekinumab | Inflammatory disease or disorder | Topical |
| 713 | Ustekinumab | Inflammatory bowel disease | Topical |
| 714 | Vedolizumab | Inflammatory disease or disorder | Topical |
| 715 | Vedolizumab | Inflammatory bowel disease | Topical |
| 716 | Natalizumab | Inflammatory disease or disorder | Topical |
| 717 | Natalizumab | Inflammatory bowel disease | Topical |
| 718 | An alternative coagulation promotor (ACP) | Hemophilia | Trans-epithelial |
| 719 | An alternative coagulation promotor (ACP) | Hemophilia A | Trans-epithelial |
| 720 | An alternative coagulation promotor (ACP) | Hemophilia B | Trans-epithelial |
| 721 | An alternative coagulation promotor (ACP) | Von Willebrand disease | Trans-epithelial |
| 722 | An anti-tissue factor pathway inhibitor (anti-TFPI) | Hemophilia | Trans-epithelial |
| 723 | An anti-tissue factor pathway inhibitor (anti-TFPI) | Hemophilia A | Trans-epithelial |
| 724 | An anti-tissue factor pathway inhibitor (anti-TFPI) | Hemophilia B | Trans-epithelial |
| 725 | An anti-tissue factor pathway inhibitor (anti-TFPI) | Von Willebrand disease | Trans-epithelial |
| 726 | Concizumab | Hemophilia | Trans-epithelial |
| 727 | Concizumab | Hemophilia A | Trans-epithelial |
| 728 | Concizumab | Hemophilia B | Trans-epithelial |
| 729 | Concizumab | Von Willebrand disease | Trans-epithelial |
| 730 | Factor VII mimetic | Hemophilia | Trans-epithelial |
| 731 | Factor VII mimetic | Hemophilia A | Trans-epithelial |
| 732 | Factor VII mimetic | Hemophilia B | Trans-epithelial |
| 733 | Factor VII mimetic | Von Willebrand disease | Trans-epithelial |
| 734 | Emicizumab | Hemophilia | Trans-epithelial |
| 735 | Emicizumab | Hemophilia A | Trans-epithelial |
| 736 | Emicizumab | Hemophilia B | Trans-epithelial |
| 737 | Emicizumab | Von Willebrand disease | Trans-epithelial |
| 738 | An alternative coagulation promotor (ACP) | Hemophilia | Epithelial |
| 739 | An alternative coagulation promotor (ACP) | Hemophilia A | Epithelial |
| 740 | An alternative coagulation promotor (ACP) | Hemophilia B | Epithelial |

TABLE 18-continued

Particular medical approaches

| Approach | Therapeutic agent | Disease | Delivery mode |
|---|---|---|---|
| 741 | An alternative coagulation promotor (ACP) | Von Willebrand disease | Epithelial |
| 742 | An anti-tissue factor pathway inhibitor (anti-TFPI) | Hemophilia | Epithelial |
| 743 | An anti-tissue factor pathway inhibitor (anti-TFPI) | Hemophilia A | Epithelial |
| 744 | An anti-tissue factor pathway inhibitor (anti-TFPI) | Hemophilia B | Epithelial |
| 745 | An anti-tissue factor pathway inhibitor (anti-TFPI) | Von Willebrand disease | Epithelial |
| 746 | Concizumab | Hemophilia | Epithelial |
| 747 | Concizumab | Hemophilia A | Epithelial |
| 748 | Concizumab | Hemophilia B | Epithelial |
| 749 | Concizumab | Von Willebrand disease | Epithelial |
| 750 | Factor VII mimetic | Hemophilia | Epithelial |
| 751 | Factor VII mimetic | Hemophilia A | Epithelial |
| 752 | Factor VII mimetic | Hemophilia B | Epithelial |
| 753 | Factor VII mimetic | Von Willebrand disease | Epithelial |
| 754 | Emicizumab | Hemophilia | Epithelial |
| 755 | Emicizumab | Hemophilia A | Epithelial |
| 756 | Emicizumab | Hemophilia B | Epithelial |
| 757 | Emicizumab | Von Willebrand disease | Epithelial |
| 758 | An alternative coagulation promotor (ACP) | Hemophilia | Topical |
| 759 | An alternative coagulation promotor (ACP) | Hemophilia A | Topical |
| 760 | An alternative coagulation promotor (ACP) | Hemophilia B | Topical |
| 761 | An alternative coagulation promotor (ACP) | Von Willebrand disease | Topical |
| 762 | An anti-tissue factor pathway inhibitor (anti-TFPI) | Hemophilia | Topical |
| 763 | An anti-tissue factor pathway inhibitor (anti-TFPI) | Hemophilia A | Topical |
| 764 | An anti-tissue factor pathway inhibitor (anti-TFPI) | Hemophilia B | Topical |
| 765 | An anti-tissue factor pathway inhibitor (anti-TFPI) | Von Willebrand disease | Topical |
| 766 | Concizumab | Hemophilia | Topical |
| 767 | Concizumab | Hemophilia A | Topical |
| 768 | Concizumab | Hemophilia B | Topical |
| 769 | Concizumab | Von Willebrand disease | Topical |
| 770 | Factor VII mimetic | Hemophilia | Topical |
| 771 | Factor VII mimetic | Hemophilia A | Topical |
| 772 | Factor VII mimetic | Hemophilia B | Topical |
| 773 | Factor VII mimetic | Von Willebrand disease | Topical |
| 774 | Emicizumab | Hemophilia | Topical |
| 775 | Emicizumab | Hemophilia A | Topical |
| 776 | Emicizumab | Hemophilia B | Topical |
| 777 | Emicizumab | Von Willebrand disease | Topical |
| 778 | Abatacept | Autoimmune disease or condition | Trans-epithelial |
| 779 | Abatacept | Rheumatoid arthritis | Trans-epithelial |
| 780 | Abatacept | Fibrosis | Trans-epithelial |
| 781 | Teriparatide | Autoimmune disease or condition | Trans-epithelial |
| 782 | Teriparatide | Rheumatoid arthritis | Trans-epithelial |
| 783 | Teriparatide | Fibrosis | Trans-epithelial |
| 784 | Pegfilgrastim | Autoimmune disease or condition | Trans-epithelial |
| 785 | Pegfilgrastim | Rheumatoid arthritis | Trans-epithelial |
| 786 | Pegfilgrastim | Fibrosis | Trans-epithelial |
| 787 | Sargramostim | Autoimmune disease or condition | Trans-epithelial |
| 788 | Sargramostim | Rheumatoid arthritis | Trans-epithelial |
| 789 | Sargramostim | Fibrosis | Trans-epithelial |
| 790 | Tocilizumab | Autoimmune disease or condition | Trans-epithelial |

TABLE 18-continued

Particular medical approaches

| Approach | Therapeutic agent | Disease | Delivery mode |
|---|---|---|---|
| 791 | Tocilizumab | Rheumatoid arthritis | Trans-epithelial |
| 792 | Tocilizumab | Fibrosis | Trans-epithelial |
| 793 | Interferon beta-1a | Autoimmune disease or condition | Trans-epithelial |
| 794 | Interferon beta-1a | Rheumatoid arthritis | Trans-epithelial |
| 795 | Interferon beta-1a | Fibrosis | Trans-epithelial |
| 796 | Abatacept | Autoimmune disease or condition | Epithelial |
| 797 | Abatacept | Rheumatoid arthritis | Epithelial |
| 798 | Abatacept | Fibrosis | Epithelial |
| 799 | Teriparatide | Autoimmune disease or condition | Epithelial |
| 800 | Teriparatide | Rheumatoid arthritis | Epithelial |
| 801 | Teriparatide | Fibrosis | Epithelial |
| 802 | Pegfilgrastim | Autoimmune disease or condition | Epithelial |
| 803 | Pegfilgrastim | Rheumatoid arthritis | Epithelial |
| 804 | Pegfilgrastim | Fibrosis | Epithelial |
| 805 | Sargramostim | Autoimmune disease or condition | Epithelial |
| 806 | Sargramostim | Rheumatoid arthritis | Epithelial |
| 807 | Sargramostim | Fibrosis | Epithelial |
| 808 | Tocilizumab | Autoimmune disease or condition | Epithelial |
| 809 | Tocilizumab | Rheumatoid arthritis | Epithelial |
| 810 | Tocilizumab | Fibrosis | Epithelial |
| 811 | Interferon beta-1a | Autoimmune disease or condition | Epithelial |
| 812 | Interferon beta-1a | Rheumatoid arthritis | Epithelial |
| 813 | Interferon beta-1a | Fibrosis | Epithelial |
| 814 | Abatacept | Autoimmune disease or condition | Topical |
| 815 | Abatacept | Rheumatoid arthritis | Topical |
| 816 | Abatacept | Fibrosis | Topical |
| 817 | Teriparatide | Autoimmune disease or condition | Topical |
| 818 | Teriparatide | Rheumatoid arthritis | Topical |
| 819 | Teriparatide | Fibrosis | Topical |
| 820 | Pegfilgrastim | Autoimmune disease or condition | Topical |
| 821 | Pegfilgrastim | Rheumatoid arthritis | Topical |
| 822 | Pegfilgrastim | Fibrosis | Topical |
| 823 | Sargramostim | Autoimmune disease or condition | Topical |
| 824 | Sargramostim | Rheumatoid arthritis | Topical |
| 825 | Sargramostim | Fibrosis | Topical |
| 826 | Tocilizumab | Autoimmune disease or condition | Topical |
| 827 | Tocilizumab | Rheumatoid arthritis | Topical |
| 828 | Tocilizumab | Fibrosis | Topical |
| 829 | Interferon beta-1a | Autoimmune disease or condition | Topical |
| 830 | Interferon beta-1a | Rheumatoid arthritis | Topical |
| 831 | Interferon beta-1a | Fibrosis | Topical |
| 832 | Natalizumab | Autoimmune disease or condition | Trans-epithelial |
| 833 | Vedolizumab | Autoimmune disease or condition | Trans-epithelial |
| 834 | Ustekinumab | Autoimmune disease or condition | Trans-epithelial |
| 835 | Denosumab | Autoimmune disease or condition | Trans-epithelial |
| 836 | Secukinumab | Metabolic or endocrine disorder | Trans-epithelial |
| 837 | Natalizumab | Autoimmune disease or condition | Epithelial |
| 838 | Vedolizumab | Autoimmune disease or condition | Epithelial |
| 839 | Ustekinumab | Autoimmune disease or condition | Epithelial |
| 840 | Denosumab | Autoimmune disease or condition | Epithelial |
| 841 | Secukinumab | Metabolic or endocrine disorder | Epithelial |
| 842 | Natalizumab | Autoimmune disease or condition | Topical |
| 843 | Vedolizumab | Autoimmune disease or condition | Topical |
| 844 | Ustekinumab | Autoimmune disease or condition | Topical |
| 845 | Denosumab | Autoimmune disease or condition | Topical |
| 846 | Secukinumab | Metabolic or endocrine disorder | Topical |
| 847 | Insulin | Metabolic or endocrine disease or condition | Trans-epithelial |
| 848 | Insulin | Diabetes | Trans-epithelial |
| 849 | Insulin | Obesity | Trans-epithelial |
| 850 | Insulin | Hypercholesterolemia | Trans-epithelial |
| 851 | Insulin | A lipid metabolism disorder | Trans-epithelial |
| 852 | Insulin | Hyperlipidemia | Trans-epithelial |
| 853 | Insulin | Atherosclerosis | Trans-epithelial |
| 854 | TNF-alpha inhibitor | Metabolic or endocrine disease or condition | Trans-epithelial |
| 855 | TNF-alpha inhibitor | Diabetes | Trans-epithelial |
| 856 | TNF-alpha inhibitor | Obesity | Trans-epithelial |
| 857 | TNF-alpha inhibitor | Hypercholesterolemia | Trans-epithelial |
| 858 | TNF-alpha inhibitor | A lipid metabolism disorder | Trans-epithelial |
| 859 | TNF-alpha inhibitor | Hyperlipidemia | Trans-epithelial |
| 860 | TNF-alpha inhibitor | Atherosclerosis | Trans-epithelial |
| 861 | Adalimumab | Metabolic or endocrine disease or condition | Trans-epithelial |
| 862 | Adalimumab | Diabetes | Trans-epithelial |
| 863 | Adalimumab | Obesity | Trans-epithelial |

TABLE 18-continued

Particular medical approaches

| Approach | Therapeutic agent | Disease | Delivery mode |
|---|---|---|---|
| 864 | Adalimumab | Hypercholesterolemia | Trans-epithelial |
| 865 | Adalimumab | A lipid metabolism disorder | Trans-epithelial |
| 866 | Adalimumab | Hyperlipidemia | Trans-epithelial |
| 867 | Adalimumab | Atherosclerosis | Trans-epithelial |
| 868 | A proprotein convertase PC9 (PCSK9) inhibitor | Metabolic or endocrine disease or condition | Trans-epithelial |
| 869 | A proprotein convertase PC9 (PC SK9) inhibitor | Diabetes | Trans-epithelial |
| 870 | A proprotein convertase PC9 (PC SK9) inhibitor | Obesity | Trans-epithelial |
| 871 | A proprotein convertase PC9 (PC SK9) inhibitor | Hypercholesterolemia | Trans-epithelial |
| 872 | A proprotein convertase PC9 (PC SK9) inhibitor | A lipid metabolism disorder | Trans-epithelial |
| 873 | A proprotein convertase PC9 (PC SK9) inhibitor | Hyperlipidemia | Trans-epithelial |
| 874 | A proprotein convertase PC9 (PC SK9) inhibitor | Atherosclerosis | Trans-epithelial |
| 875 | Alirocumab | Metabolic or endocrine disease or condition | Trans-epithelial |
| 876 | Alirocumab | Diabetes | Trans-epithelial |
| 877 | Alirocumab | Obesity | Trans-epithelial |
| 878 | Alirocumab | Hypercholesterolemia | Trans-epithelial |
| 879 | Alirocumab | A lipid metabolism disorder | Trans-epithelial |
| 880 | Alirocumab | Hyperlipidemia | Trans-epithelial |
| 881 | Alirocumab | Atherosclerosis | Trans-epithelial |
| 882 | Evolocumab | Metabolic or endocrine disease or condition | Trans-epithelial |
| 883 | Evolocumab | Diabetes | Trans-epithelial |
| 884 | Evolocumab | Obesity | Trans-epithelial |
| 885 | Evolocumab | Hypercholesterolemia | Trans-epithelial |
| 886 | Evolocumab | A lipid metabolism disorder | Trans-epithelial |
| 887 | Evolocumab | Hyperlipidemia | Trans-epithelial |
| 888 | Evolocumab | Atherosclerosis | Trans-epithelial |
| 889 | Peptide YY ligand | Metabolic or endocrine disease or condition | Trans-epithelial |
| 890 | Peptide YY ligand | Diabetes | Trans-epithelial |
| 891 | Peptide YY ligand | Obesity | Trans-epithelial |
| 892 | Peptide YY ligand | Hypercholesterolemia | Trans-epithelial |
| 893 | Peptide YY ligand | A lipid metabolism disorder | Trans-epithelial |
| 894 | Peptide YY ligand | Hyperlipidemia | Trans-epithelial |
| 895 | Peptide YY ligand | Atherosclerosis | Trans-epithelial |
| 896 | NN-9747 | Metabolic or endocrine disease or condition | Trans-epithelial |
| 897 | NN-9747 | Diabetes | Trans-epithelial |
| 898 | NN-9747 | Obesity | Trans-epithelial |
| 899 | NN-9747 | Hypercholesterolemia | Trans-epithelial |
| 900 | NN-9747 | A lipid metabolism disorder | Trans-epithelial |
| 901 | NN-9747 | Hyperlipidemia | Trans-epithelial |
| 902 | NN-9747 | Atherosclerosis | Trans-epithelial |
| 903 | NN-9748 | Metabolic or endocrine disease or condition | Trans-epithelial |
| 904 | NN-9748 | Diabetes | Trans-epithelial |
| 905 | NN-9748 | Obesity | Trans-epithelial |
| 906 | NN-9748 | Hypercholesterolemia | Trans-epithelial |
| 907 | NN-9748 | A lipid metabolism disorder | Trans-epithelial |
| 908 | NN-9748 | Hyperlipidemia | Trans-epithelial |
| 909 | NN-9748 | Atherosclerosis | Trans-epithelial |
| 910 | NN-9775 | Metabolic or endocrine disease or condition | Trans-epithelial |
| 911 | NN-9775 | Diabetes | Trans-epithelial |
| 912 | NN-9775 | Obesity | Trans-epithelial |
| 913 | NN-9775 | Hypercholesterolemia | Trans-epithelial |
| 914 | NN-9775 | A lipid metabolism disorder | Trans-epithelial |
| 915 | NN-9775 | Hyperlipidemia | Trans-epithelial |
| 916 | NN-9775 | Atherosclerosis | Trans-epithelial |
| 917 | FSI-965 | Metabolic or endocrine disease or condition | Trans-epithelial |
| 918 | FSI-965 | Diabetes | Trans-epithelial |

TABLE 18-continued

Particular medical approaches

| Approach | Therapeutic agent | Disease | Delivery mode |
|---|---|---|---|
| 919 | FSI-965 | Obesity | Trans-epithelial |
| 920 | FSI-965 | Hypercholesterolemia | Trans-epithelial |
| 921 | FSI-965 | A lipid metabolism disorder | Trans-epithelial |
| 922 | FSI-965 | Hyperlipidemia | Trans-epithelial |
| 923 | FSI-965 | Atherosclerosis | Trans-epithelial |
| 924 | NN-0385-0434 | Metabolic or endocrine disease or condition | Trans-epithelial |
| 925 | NN-0385-0434 | Diabetes | Trans-epithelial |
| 926 | NN-0385-0434 | Obesity | Trans-epithelial |
| 927 | NN-0385-0434 | Hypercholesterolemia | Trans-epithelial |
| 928 | NN-0385-0434 | A lipid metabolism disorder | Trans-epithelial |
| 929 | NN-0385-0434 | Hyperlipidemia | Trans-epithelial |
| 930 | NN-0385-0434 | Atherosclerosis | Trans-epithelial |
| 931 | Amylin analog | Metabolic or endocrine disease or condition | Trans-epithelial |
| 932 | Amylin analog | Diabetes | Trans-epithelial |
| 933 | Amylin analog | Obesity | Trans-epithelial |
| 934 | Amylin analog | Hypercholesterolemia | Trans-epithelial |
| 935 | Amylin analog | A lipid metabolism disorder | Trans-epithelial |
| 936 | Amylin analog | Hyperlipidemia | Trans-epithelial |
| 937 | Amylin analog | Atherosclerosis | Trans-epithelial |
| 938 | AM-833 | Metabolic or endocrine disease or condition | Trans-epithelial |
| 939 | AM-833 | Diabetes | Trans-epithelial |
| 940 | AM-833 | Obesity | Trans-epithelial |
| 941 | AM-833 | Hypercholesterolemia | Trans-epithelial |
| 942 | AM-833 | A lipid metabolism disorder | Trans-epithelial |
| 943 | AM-833 | Hyperlipidemia | Trans-epithelial |
| 944 | AM-833 | Atherosclerosis | Trans-epithelial |
| 945 | Insulin | Metabolic or endocrine disease or condition | Epithelial |
| 946 | Insulin | Diabetes | Epithelial |
| 947 | Insulin | Obesity | Epithelial |
| 948 | Insulin | Hypercholesterolemia | Epithelial |
| 949 | Insulin | A lipid metabolism disorder | Epithelial |
| 950 | Insulin | Hyperlipidemia | Epithelial |
| 951 | Insulin | Atherosclerosis | Epithelial |
| 952 | TNF-alpha inhibitor | Metabolic or endocrine disease or condition | Epithelial |
| 953 | TNF-alpha inhibitor | Diabetes | Epithelial |
| 954 | TNF-alpha inhibitor | Obesity | Epithelial |
| 955 | TNF-alpha inhibitor | Hypercholesterolemia | Epithelial |
| 956 | TNF-alpha inhibitor | A lipid metabolism disorder | Epithelial |
| 957 | TNF-alpha inhibitor | Hyperlipidemia | Epithelial |
| 958 | TNF-alpha inhibitor | Atherosclerosis | Epithelial |
| 959 | Adalimumab | Metabolic or endocrine disease or condition | Epithelial |
| 960 | Adalimumab | Diabetes | Epithelial |
| 961 | Adalimumab | Obesity | Epithelial |
| 962 | Adalimumab | Hypercholesterolemia | Epithelial |
| 963 | Adalimumab | A lipid metabolism disorder | Epithelial |
| 964 | Adalimumab | Hyperlipidemia | Epithelial |
| 965 | Adalimumab | Atherosclerosis | Epithelial |
| 966 | A proprote in convertase PC9 (PCSK9) inhibitor | Metabolic or endocrine disease or condition | Epithelial |
| 967 | A proprotein convertase PC9 (PCSK9) inhibitor | Diabetes | Epithelial |
| 968 | A proprotein convertase PC9 (PCSK9) inhibitor | Obesity | Epithelial |
| 969 | A proprotein convertase PC9 (PCSK9) inhibitor | Hypercholesterolemia | Epithelial |
| 970 | A proprotein convertase PC9 (PCSK9) inhibitor | A lipid metabolism disorder | Epithelial |
| 971 | A proprotein convertase PC9 (PCSK9) inhibitor | Hyperlipidemia | Epithelial |
| 972 | A proprotein convertase PC9 (PCSK9) inhibitor | Atherosclerosis | Epithelial |
| 973 | Alirocumab | Metabolic or endocrine disease or condition | Epithelial |

TABLE 18-continued

Particular medical approaches

| Approach | Therapeutic agent | Disease | Delivery mode |
|---|---|---|---|
| 974 | Alirocumab | Diabetes | Epithelial |
| 975 | Alirocumab | Obesity | Epithelial |
| 976 | Alirocumab | Hypercholesterolemia | Epithelial |
| 977 | Alirocumab | A lipid metabolism disorder | Epithelial |
| 978 | Alirocumab | Hyperlipidemia | Epithelial |
| 979 | Alirocumab | Atherosclerosis | Epithelial |
| 980 | Evolocumab | Metabolic or endocrine disease or condition | Epithelial |
| 981 | Evolocumab | Diabetes | Epithelial |
| 982 | Evolocumab | Obesity | Epithelial |
| 983 | Evolocumab | Hypercholesterolemia | Epithelial |
| 984 | Evolocumab | A lipid metabolism disorder | Epithelial |
| 985 | Evolocumab | Hyperlipidemia | Epithelial |
| 986 | Evolocumab | Atherosclerosis | Epithelial |
| 987 | Peptide YY ligand | Metabolic or endocrine disease or condition | Epithelial |
| 988 | Peptide YY ligand | Diabetes | Epithelial |
| 989 | Peptide YY ligand | Obesity | Epithelial |
| 990 | Peptide YY ligand | Hypercholesterolemia | Epithelial |
| 991 | Peptide YY ligand | A lipid metabolism disorder | Epithelial |
| 992 | Peptide YY ligand | Hyperlipidemia | Epithelial |
| 993 | Peptide YY ligand | Atherosclerosis | Epithelial |
| 994 | NN-9747 | Metabolic or endocrine disease or condition | Epithelial |
| 995 | NN-9747 | Diabetes | Epithelial |
| 996 | NN-9747 | Obesity | Epithelial |
| 997 | NN-9747 | Hypercholesterolemia | Epithelial |
| 998 | NN-9747 | A lipid metabolism disorder | Epithelial |
| 999 | NN-9747 | Hyperlipidemia | Epithelial |
| 1000 | NN-9747 | Atherosclerosis | Epithelial |
| 1001 | NN-9748 | Metabolic or endocrine disease or condition | Epithelial |
| 1002 | NN-9748 | Diabetes | Epithelial |
| 1003 | NN-9748 | Obesity | Epithelial |
| 1004 | NN-9748 | Hypercholesterolemia | Epithelial |
| 1005 | NN-9748 | A lipid metabolism disorder | Epithelial |
| 1006 | NN-9748 | Hyperlipidemia | Epithelial |
| 1007 | NN-9748 | Atherosclerosis | Epithelial |
| 1008 | NN-9775 | Metabolic or endocrine disease or condition | Epithelial |
| 1009 | NN-9775 | Diabetes | Epithelial |
| 1010 | NN-9775 | Obesity | Epithelial |
| 1011 | NN-9775 | Hypercholesterolemia | Epithelial |
| 1012 | NN-9775 | A lipid metabolism disorder | Epithelial |
| 1013 | NN-9775 | Hyperlipidemia | Epithelial |
| 1014 | NN-9775 | Atherosclerosis | Epithelial |
| 1015 | FSI-965 | Metabolic or endocrine disease or condition | Epithelial |
| 1016 | FSI-965 | Diabetes | Epithelial |
| 1017 | FSI-965 | Obesity | Epithelial |
| 1018 | FSI-965 | Hypercholesterolemia | Epithelial |
| 1019 | FSI-965 | A lipid metabolism disorder | Epithelial |
| 1020 | FSI-965 | Hyperlipidemia | Epithelial |
| 1021 | FSI-965 | Atherosclerosis | Epithelial |
| 1022 | NN-0385-0434 | Metabolic or endocrine disease or condition | Epithelial |
| 1023 | NN-0385-0434 | Diabetes | Epithelial |
| 1024 | NN-0385-0434 | Obesity | Epithelial |
| 1025 | NN-0385-0434 | Hypercholesterolemia | Epithelial |
| 1026 | NN-0385-0434 | A lipid metabolism disorder | Epithelial |
| 1027 | NN-0385-0434 | Hyperlipidemia | Epithelial |
| 1028 | NN-0385-0434 | Atherosclerosis | Epithelial |
| 1029 | Amylin analog | Metabolic or endocrine disease or condition | Epithelial |
| 1030 | Amylin analog | Diabetes | Epithelial |
| 1031 | Amylin analog | Obesity | Epithelial |
| 1032 | Amylin analog | Hypercholesterolemia | Epithelial |
| 1033 | Amylin analog | A lipid metabolism disorder | Epithelial |
| 1034 | Amylin analog | Hyperlipidemia | Epithelial |
| 1035 | Amylin analog | Atherosclerosis | Epithelial |
| 1036 | AM-833 | Metabolic or endocrine disease or condition | Epithelial |
| 1037 | AM-833 | Diabetes | Epithelial |
| 1038 | AM-833 | Obesity | Epithelial |
| 1039 | AM-833 | Hypercholesterolemia | Epithelial |
| 1040 | AM-833 | A lipid metabolism disorder | Epithelial |

TABLE 18-continued

Particular medical approaches

| Approach | Therapeutic agent | Disease | Delivery mode |
|---|---|---|---|
| 1041 | AM-833 | Hyperlipidemia | Epithelial |
| 1042 | AM-833 | Atherosclerosis | Epithelial |
| 1043 | Insulin | Metabolic or endocrine disease or condition | Topical |
| 1044 | Insulin | Diabetes | Topical |
| 1045 | Insulin | Obesity | Topical |
| 1046 | Insulin | Hypercholesterolemia | Topical |
| 1047 | Insulin | A lipid metabolism disorder | Topical |
| 1048 | Insulin | Hyperlipidemia | Topical |
| 1049 | Insulin | Atherosclerosis | Topical |
| 1050 | TNF-alpha inhibitor | Metabolic or endocrine disease or condition | Topical |
| 1051 | TNF-alpha inhibitor | Diabetes | Topical |
| 1052 | TNF-alpha inhibitor | Obesity | Topical |
| 1053 | TNF-alpha inhibitor | Hypercholesterolemia | Topical |
| 1054 | TNF-alpha inhibitor | A lipid metabolism disorder | Topical |
| 1055 | TNF-alpha inhibitor | Hyperlipidemia | Topical |
| 1056 | TNF-alpha inhibitor | Atherosclerosis | Topical |
| 1057 | Adalimumab | Metabolic or endocrine disease or condition | Topical |
| 1058 | Adalimumab | Diabetes | Topical |
| 1059 | Adalimumab | Obesity | Topical |
| 1060 | Adalimumab | Hypercholesterolemia | Topical |
| 1061 | Adalimumab | A lipid metabolism disorder | Topical |
| 1062 | Adalimumab | Hyperlipidemia | Topical |
| 1063 | Adalimumab | Atherosclerosis | Topical |
| 1064 | A proprotein convertase PC9 (PCSK9) inhibitor | Metabolic or endocrine disease or condition | Topical |
| 1065 | A proprotein convertase PC9 (PCSK9) inhibitor | Diabetes | Topical |
| 1066 | A proprotein convertase PC9 (PCSK9) inhibitor | Obesity | Topical |
| 1067 | A proprotein convertase PC9 (PCSK9) inhibitor | Hyperchole sterolemia | Topical |
| 1068 | A proprotein convertase PC9 (PCSK9) inhibitor | A lipid metabolism disorder | Topical |
| 1069 | A proprotein convertase PC9 (PCSK9) inhibitor | Hyperlipidemia | Topical |
| 1070 | A proprotein convertase PC9 (PCSK9) inhibitor | Atherosclerosis | Topical |
| 1071 | Alirocumab | Metabolic or endocrine disease or condition | Topical |
| 1072 | Alirocumab | Diabetes | Topical |
| 1073 | Alirocumab | Obesity | Topical |
| 1074 | Alirocumab | Hypercholesterolemia | Topical |
| 1075 | Alirocumab | A lipid metabolism disorder | Topical |
| 1076 | Alirocumab | Hyperlipidemia | Topical |
| 1077 | Alirocumab | Atherosclerosis | Topical |
| 1078 | Evolocumab | Metabolic or endocrine disease or condition | Topical |
| 1079 | Evolocumab | Diabetes | Topical |
| 1080 | Evolocumab | Obesity | Topical |
| 1081 | Evolocumab | Hypercholesterolemia | Topical |
| 1082 | Evolocumab | A lipid metabolism disorder | Topical |
| 1083 | Evolocumab | Hyperlipidemia | Topical |
| 1084 | Evolocumab | Atherosclerosis | Topical |
| 1085 | Peptide YY ligand | Metabolic or endocrine disease or condition | Topical |
| 1086 | Peptide YY ligand | Diabetes | Topical |
| 1087 | Peptide YY ligand | Obesity | Topical |
| 1088 | Peptide YY ligand | Hypercholesterolemia | Topical |
| 1089 | Peptide YY ligand | A lipid metabolism disorder | Topical |
| 1090 | Peptide YY ligand | Hyperlipidemia | Topical |
| 1091 | Peptide YY ligand | Atherosclerosis | Topical |
| 1092 | NN-9747 | Metabolic or endocrine disease or condition | Topical |
| 1093 | NN-9747 | Diabetes | Topical |
| 1094 | NN-9747 | Obesity | Topical |
| 1095 | NN-9747 | Hypercholesterolemia | Topical |

TABLE 18-continued

Particular medical approaches

| Approach | Therapeutic agent | Disease | Delivery mode |
|---|---|---|---|
| 1096 | NN-9747 | A lipid metabolism disorder | Topical |
| 1097 | NN-9747 | Hyperlipidemia | Topical |
| 1098 | NN-9747 | Atherosclerosis | Topical |
| 1099 | NN-9748 | Metabolic or endocrine disease or condition | Topical |
| 1100 | NN-9748 | Diabetes | Topical |
| 1101 | NN-9748 | Obesity | Topical |
| 1102 | NN-9748 | Hypercholesterolemia | Topical |
| 1103 | NN-9748 | A lipid metabolism disorder | Topical |
| 1104 | NN-9748 | Hyperlipidemia | Topical |
| 1105 | NN-9748 | Atherosclerosis | Topical |
| 1106 | NN-9775 | Metabolic or endocrine disease or condition | Topical |
| 1107 | NN-9775 | Diabetes | Topical |
| 1108 | NN-9775 | Obesity | Topical |
| 1109 | NN-9775 | Hypercholesterolemia | Topical |
| 1110 | NN-9775 | A lipid metabolism disorder | Topical |
| 1111 | NN-9775 | Hyperlipidemia | Topical |
| 1112 | NN-9775 | Atherosclerosis | Topical |
| 1113 | FSI-965 | Metabolic or endocrine disease or condition | Topical |
| 1114 | FSI-965 | Diabetes | Topical |
| 1115 | FSI-965 | Obesity | Topical |
| 1116 | FSI-965 | Hypercholesterolemia | Topical |
| 1117 | FSI-965 | A lipid metabolism disorder | Topical |
| 1118 | FSI-965 | Hyperlipidemia | Topical |
| 1119 | FSI-965 | Atherosclerosis | Topical |
| 1120 | NN-0385-0434 | Metabolic or endocrine disease or condition | Topical |
| 1121 | NN-0385-0434 | Diabetes | Topical |
| 1122 | NN-0385-0434 | Obesity | Topical |
| 1123 | NN-0385-0434 | Hypercholesterolemia | Topical |
| 1124 | NN-0385-0434 | A lipid metabolism disorder | Topical |
| 1125 | NN-0385-0434 | Hyperlipidemia | Topical |
| 1126 | NN-0385-0434 | Atherosclerosis | Topical |
| 1127 | Amylin analog | Metabolic or endocrine disease or condition | Topical |
| 1128 | Amylin analog | Diabetes | Topical |
| 1129 | Amylin analog | Obesity | Topical |
| 1130 | Amylin analog | Hypercholesterolemia | Topical |
| 1131 | Amylin analog | A lipid metabolism disorder | Topical |
| 1132 | Amylin analog | Hyperlipidemia | Topical |
| 1133 | Amylin analog | Atherosclerosis | Topical |
| 1134 | AM-833 | Metabolic or endocrine disease or condition | Topical |
| 1135 | AM-833 | Diabetes | Topical |
| 1136 | AM-833 | Obesity | Topical |
| 1137 | AM-833 | Hypercholesterolemia | Topical |
| 1138 | AM-833 | A lipid metabolism disorder | Topical |
| 1139 | AM-833 | Hyperlipidemia | Topical |
| 1140 | AM-833 | Atherosclerosis | Topical |

The ingestible device disclosed herein can be used to implement any of medical approaches 1-1140.

The ingestible device of the invention can be configured to deliver the dispensable substance comprising the therapeutic agent via the delivery mode of any of the medical approaches 1-1140 according to particular parameters, which can be defined by particular 'configurations'. In each configuration, the delivery device comprises a housing configured to contain a dispensable substance comprising a therapeutic agent; and an opening in the housing configured to fluidly connect the dispensable substance to an environment outside the housing via the opening.

In configuration 1, the device is configured to deliver the dispensable substance to tissue of the GI tract of a subject as a jet via trans-epithelial delivery.

In some aspects, the device configured for trans-epithelial delivery delivers the dispensable substance to the GI tract of the subject as a jet with a peak jet power of from about one Watt to about three Watts. The peak jet power may be from about 1.3 Watts to about 2.8 Watts; or from about 1.5 Watts to about 2.5 Watts. The peak jet power may be about 2.3 Watts.

In some aspects, the device configured for trans-epithelial delivery provides an internal pressure of from about 225 psig to about 400 psig. The internal pressure may be from about 250 psig to about 375 psig; or from about 300 psig to about 340 psig. In some aspects, the device configured for trans-epithelial delivery contains the dispensable substance at a peak fluid pressure of about 200 psig to about 375 psig. The dispensable substance may be contained at a peak fluid pressure of from about 220 psig to about 350 psig; at a peak fluid pressure of from about 225 psig to about 375 psig; at a peak fluid pressure of from about 225 psig to about 350 psig; at a peak fluid pressure of from about 225 psig to about 325 psig; or at a peak fluid pressure of from about 280 psig to about 320 psig.

In some aspects, the device configured for trans-epithelial delivery delivers the dispensable substance as a jet at a peak jet velocity of from about 25 meters per second to about 45 meters per second. The peak jet velocity may be from about 30 meters per second to about 42 meters per second; or about 34 meters per second to about 39 meters per second. In some aspects, the device configured for trans-epithelial delivery delivers the dispensable substance as a jet at a mean jet velocity of from about 20 meters per second to about 30 meters per second. The mean jet velocity may be from about 25 meters per second to about 30 meters per second.

In some aspects, the device configured for trans-epithelial delivery delivers the dispensable substance as a jet having jet stable length of at least about 0.5 millimeter. The jet may have a jet stable length of from 0.5 millimeter to 20 millimeters; or from about 2 millimeters to 20 millimeters; or from about 5 millimeters to 20 millimeters. In some aspects, the device configured for trans-epithelial delivery delivers the dispensable substance to tissue of the GI tract of a subject as a jet at a peak jet pressure of from about 100 psig to about 250 psig. The peak jet pressure may be from about 140 psig to about 225 psig; or from about 180 psig to about 205 psig.

In some aspects, the device configured for trans-epithelial delivery delivers the dispensable substance to tissue of the GI tract of a subject as a jet at a peak jet force of from about 0.09 N to about 0.15 N. The peak jet force may be from about 0.1 N to about 0.14 N; or from about 0.11 N to about 0.14 N.

In some aspects, the device configured for trans-epithelial delivery delivers the dispensable substance to tissue of the GI tract of a subject as a jet having a diameter of from about 0.1 mm to about 2 mm. The jet diameter may be from about 0.1 mm to about 1 mm; from about 0.2 mm to about 0.8 mm; from about 0.3 mm to about 0.5 mm; from about 0.3 mm to about 0.4 mm; or about 0.35 mm.

In some aspects, the device configured for trans-epithelial delivery releases a dispensable substance volume of from about 50 microliters to about 800 microliters, about 50 microliters to about 500 microliters, from about 100 microliters to about 450 microliters, from about 200 microliters to about 400 microliters, from 250 microliters to about 400 microliters, or from about 300 microliters to about 400 microliters.

In some aspects, the device configured for trans-epithelial delivery to the GI tract of a subject contains a dispensable substance having a viscosity of from about 0.8 cP to about 10 cP.

It is to be understood that each and any of the foregoing aspects of configuration 1 are freely combinable to deliver the dispensable substance as a jet to tissue of the GI tract of a subject via trans-epithelial delivery.

It is to be understood that reference to a jet refers to at least one jet, for example, one, two, three, four, five, six, seven, eight or more jets, optionally two jets, three jets or four jets, and that each jet parameter (e.g., jet power, jet velocity, jet stable length, jet pressure, jet force) refers to each said jet, unless expressly indicated otherwise.

In configuration 2, the device is configured to deliver the dispensable substance to tissue of the GI tract of a subject optionally as a jet via epithelial delivery.

In some aspects, the device configured for epithelial delivery delivers the dispensable substance to the GI tract of the subject as a jet with a peak jet power of from about 1 mW to about 4 mW. The peak jet power of the jet may be from about 1 mW to about 3.5 mW, or from about 2 mW to about 3 mW.

In some aspects, the device configured for epithelial delivery provides an internal pressure of from about 3.62 psig to about 21.76 psig. The internal pressure may be from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, or about 4.35 psig.

In some aspects, the device configured for epithelial delivery contains the dispensable substance at a peak fluid pressure of from about 3.62 psig to about 21.76 psig. The peak fluid pressure may be from about 3.62 psig to about 18.13 psig, from about 3.62 psig to about 14.50 psig, from about 3.62 psig to about 10.88 psig, from about 3.62 psig to about 7.25 psig, from about 4.35 psig to about 7.25 psig, or about 4.35 psig. In some aspects, the device configured for epithelial delivery delivers the dispensable substance as a jet at a peak jet velocity of 2 m/s to about 20 m/s. The peak jet velocity of the jet may be from about 3 m/s to about 15 m/s, from about 4 m/s to about 10 m/s, or from about 5 m/s to about 8 m/s.

In some aspects, the device configured for epithelial delivery delivers the dispensable substance to tissue of the GI tract of a subject as a jet at a peak jet pressure of from about 2 psig to about 10 psig. The peak jet pressure of the jet may be from about 2.5 psig to about 8 psig, from about 3 psig to about 6 psig, from about 3.5 psig to about 5 psig, or from about 4 psig to about 5 psig.

In some aspects, the device configured for epithelial delivery delivers the dispensable substance to tissue of the GI tract of a subject as a jet at a peak jet force of from about 0.5 mN to about 2 mN. The peak jet force of the jet may be from about 0.6 mN to about 1.8 mN, from about 0.7 mN to about 1.6 mN, from about 0.8 mN to about 1.4 mN, from about 0.9 mN to about 1.2 mN.

In some aspects, the device configured for epithelial delivery releases a dispensable substance volume of from about 50 microliters to about 800 microliters, about 100 microliters to about 600 microliters, or from about 200 microliters to about 400 microliters. In some aspects, the device configured for epithelial delivery has from 25 to 50 nozzles. The device may have from 30 to 50 nozzles, 30 nozzles, 31 nozzles, 32 nozzles, 33 nozzles, 34 nozzles, 35 nozzles, 36 nozzles, 37 nozzles, 38 nozzles or 40 nozzles.

In some aspects, each nozzles of the device configured for epithelial delivery has a nozzle diameter of at from about from about 1 mm to about 3 mm. Each nozzle may have a nozzle diameter of from about 1 mm to about 2.5 mm, or from about 2 to 2.5 mm. In some aspects, the device configured for epithelial delivery to the GI tract of a subject contains a dispensable substance having a viscosity of from about 0.8 cP to about 10 cP.

It is to be understood that each and any of the foregoing aspects of configuration 2 are freely combinable to deliver the dispensable substance optionally as a jet to tissue of the GI tract of a subject via epithelial delivery.

It is to be understood that reference to a jet refers to at least one jet, for example, one, two, three, four, five, six, seven, eight or more jets, optionally two jets, three jets or four jets, and that each jet parameter (e.g., jet power, jet velocity, jet stable length, jet pressure, jet force) refers to each said jet, unless expressly indicated otherwise.

In configuration 3, the device is configured to deliver the dispensable substance to tissue of the GI tract of a subject via topical delivery.

In some aspects, the device for topical delivery is configured to provide an internal pressure of from about 5 psig to about 50 psig. The internal pressure may be from about 5 psig to about 30 psig, from about 5 psig to about 20 psig, from about 8 psig to about 20 psig, or from about 10 psig to about 15 psig.

In some aspects, the device for topical delivery is configured to contain a dispensable substance at a peak fluid pressure of from about 5 psig to about 50 psig. The peak fluid pressure may be from about 5 psig to about 30 psig, from about 5 psig to about 20 psig, from about 8 psig to about 20 psig, or from about 10 psig to about 15 psig. In some aspects, the device configured for topical delivery releases a dispensable substance volume of from about 50 microliters to about 800 microliters, about 100 microliters to about 600 microliters, or from about 200 microliters to about 400 microliters. In some aspects, the device configured for topical delivery has from 25 to 50 nozzles. The device may have from 30 to 50 nozzles, 30 nozzles, 31 nozzles, 32 nozzles, 33 nozzles, 34 nozzles, 35 nozzles, 36 nozzles, 37 nozzles, 38 nozzles or 40 nozzles.

In some aspects, each nozzles of the device configured for topical delivery has a nozzle diameter of at from about from about 1 mm to about 3 mm. Each nozzle may have a nozzle diameter of from about 1 mm to about 2.5 mm, or from about 2 to 2.5 mm. In some aspects, the device configured for topical delivery to the GI tract of a subject contains a dispensable substance having a viscosity of from about 0.8 cP to about 10 cP.

It is to be understood that each and any of the foregoing aspects of configuration 3 are freely combinable to deliver the dispensable substance to tissue of the GI tract of a subject via topical delivery.

Based on the present disclosure, the skilled person will appreciate that the physical characteristics of the device are assembled to provide the properties of the device according to the configurations mentioned above. These physical characteristics are discussed further here: As discussed herein, the delivery device comprises a housing. An opening in the housing is configured to fluidly connect the dispensable substance to an environment outside the housing via the opening.

The delivery device also comprises a drive force generator configured to provide a force to the dispensable substance to deliver the dispensable substance through the opening. The drive force generator can be configured to provide an internal pressure as required by the particular device configuration. (As described herein, the drive force generator may comprise a spring, a gas cell, a compressed gas, and a liquid-gas mixture.) The opening in the housing may comprise a nozzle. There may be multiple openings with multiple nozzles. The nozzle(s) can be configured to provide the particular jet properties as required by the particular device configuration. The nozzle and drive force generator can be configured to provide the particular jet properties as required by the particular device configuration.

EXAMPLES

Example 1—Modelling Device Performance

In this Example, modelling was used to determine the performance parameters of an ingestible device for delivering a dispensable substance.

Model

The driving pressure, for a given point in the dose delivery, is related to the delivered liquid volume, and the resulting increase in gas volume, by equations of state for adiabatic expansion. The velocity (e.g., peak jet velocity, average jet velocity, or minimum jet velocity) through the orifice is in turn given by the driving pressure. This is a steady state approximation in which transient effects of fluid acceleration/deceleration are ignored. In other words, the gas expansion is rapid allowing little time for heat transfer/thermal equilibration to the surroundings. Thus, this is treated as an adiabatic (no energy loss).

For an adiabatic process, Pressure P and Volume V of a gas are related as follows, assuming that fluid (liquid) pressure is equal to gas pressure (frictionless piston).

$$\frac{P_2}{P_1} = \left(\frac{V_1}{V_2}\right)^\gamma,$$

where P is pressure, V is volume, and $\gamma$ is the ratio of specific heats.

Pipe shear pressure is given by the Darcy-Weisbach equation:

$$P_{Pipe} = f\frac{\rho L v_o^2}{2 d_o},$$

where $\rho$ is the density of a liquid, L is the nozzle length, $v_o$ is the velocity through the nozzle orifice, $d_o$ is the diameter of an nozzle orifice, and f is the Darcy friction factor for pipe flow.

The friction factor for rough pipes is given by:

$$\frac{1}{f^{1/2}} = -2.0 \log\left(\frac{\epsilon/d_o}{3.7} + \frac{2.51}{Re f^{1/2}}\right),$$

where $\epsilon$ is the pipe surface roughness, and Re is the Reynolds number for the fluid.

Haaland proposed the following explicit approximation, which differs by less than 2% from Colebrook:

$$f^{-1/2} = \frac{1}{f^{1/2}} = -1.8 \log\left(\left(\frac{\epsilon/d_o}{3.7}\right)^{1.11} + \frac{6.9}{Re}\right)$$

$$f = \frac{1}{\left(-1.8 \log\left(\left(\frac{\epsilon/d_o}{3.7}\right)^{1.11} + \frac{6.9}{Re}\right)\right)^2}$$

Therefore, pipe pressure is:

$$P_{Pipe} = \frac{\rho L v_o^2}{2 d_o \left(-1.8 \log\left(\left(\frac{\epsilon/d_o}{3.7}\right)^{1.11} + \frac{6.9}{Re}\right)\right)^2}$$

This explicit approximation requires iterative solution if Re is unknown.

Pipe exit and entry losses are assumed as being given by:

$$P_{Entry} = 1/2 C_{Entry} \rho_l v^2$$

$$P_{Exit} = 1/2 C_{Exit} \rho_l v^2$$

Thus, overall pressure drop across the orifice is:

$$P_{Orifice} = f\frac{\rho L v_o^2}{2 d_o} + \frac{1}{2}(C_{Entry} + C_{Exit})\rho_l v_o^2,$$

Where $C_{entry}$ is the coefficient of discharge on entry, and $C_{exit}$ is the coefficient of discharge on exit.

The total flowrate is:

$$Q = N\pi d_o^2 v_o,$$

where Q is the volumetric flow rate through a single orifice.

Accounting for piston friction, the liquid delivery pressure through the orifice is related to the gas pressure as follows. The force balance on the piston is given by:

$$\frac{\pi}{4} d_{Piston}^2 (P_{gas} - P_{Liquid}) - F_{Friction} = a_{Piston} m_{Piston}$$

Applying a steady state assumption yields:

$$\frac{\pi}{4} d_{Piston}^2 (P_{gas} - P_{Liquid}) - F_{Friction}$$

Rearranging, results in:

$$P_{Orifice} = P_{gas} - \frac{F_{Friction}}{\frac{\pi}{4} d_{Piston}^2}$$

The jet impact force is given by the rate of change of the jet momentum at the impact surface:

$$F = dp/dt = d(mv)/dt = v(dm/dt) + m(dv/dt),$$

Where p is momentum, v is velocity and m is mass.

Assuming constant jet velocity for a given time step, the dV/dt term goes to zero, yielding:

$$F = V(dm/dt),$$

or

F=velocity*mass flow rate

F=density*area*velocity^2

$F = 1/4 * pi * density * diameter^2 * velocity^2$

The jet power has been shown to correlate with needle-free penetration and dispersion by:

Power=1/4*$pi$*density*diameter^2*velocity^3

Device and Fluid Properties
Nozzle diameter=0.35 mm
Nozzle length=2 mm
Number of nozzles=2 or 4
Nozzle throat geometry=circular, sharp-edged orifice (similar to FIG. 6D)
Piston diameter=9.6 mm
Piston friction=10 N due to one O-ring surrounding the piston
Friction pressure loss=about 20 psig
Dispensable substance (fluid)=100 mg/mL adalimumab formulation
Fluid density=1000 kg/m$^3$
Fluid viscosity=7.5 centiPoise
Ratios of specific heat (air)=1.4
Results—Initial Internal Pressure of 320 psig—2 Nozzles
The following properties were used in the model.
Initial internal pressure=320 psig
Fluid pressure=about 300 psig (peak; initial)
Nozzle pressure=about 300 psig (peak; initial)
Initial dose volume of dispensable substance=450 μL Initial gas volume=370 μL With these parameters, the modelling yielded the results shown in Tables 19A-19D (liquid pressure is the same as fluid pressure).

TABLE 19A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 22.1 | 20.7 | 300.0 | 36.5 |
| 2 | 50 | 420 | 18.5 | 17.1 | 247.9 | 33.1 |
| 3 | 100 | 470 | 15.8 | 14.4 | 208.9 | 30.3 |
| 4 | 150 | 520 | 13.7 | 12.3 | 178.7 | 28.0 |
| 5 | 200 | 570 | 12.0 | 10.7 | 154.7 | 26.0 |
| 6 | 250 | 620 | 10.7 | 9.3 | 135.3 | 24.3 |
| 7 | 300 | 670 | 9.6 | 8.2 | 119.3 | 22.8 |
| 8 | 350 | 720 | 8.7 | 7.3 | 160.0 | 21.5 |
| 9 | 400 | 770 | 7.9 | 6.5 | 94.7 | 20.3 |

TABLE 19B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.70E+03 | 7.23E−02 | 2.07E+06 | 20.68 | 0.00 |
| 2 | 1.54E+03 | 7.37E−02 | 1.71E+06 | 17.09 | 0.00 |
| 3 | 1.42E+03 | 7.51E−02 | 1.44E+06 | 14.40 | 0.00 |
| 4 | 1.31E+03 | 7.65E−02 | 1.23E+06 | 12.32 | 0.00 |
| 5 | 1.22E+03 | 7.78E−02 | 1.07E+06 | 10.67 | 0.00 |
| 6 | 1.14E+03 | 7.92E−02 | 9.33E+05 | 9.33 | 0.00 |
| 7 | 1.06E+03 | 8.05E−02 | 8.23E+05 | 8.23 | 0.00 |
| 8 | 1.00E+03 | 8.18E−02 | 7.31E+05 | 7.31 | 0.00 |
| 9 | 9.46E+02 | 8.31E−02 | 6.53E+05 | 6.53 | 0.00 |

TABLE 19C

| Model No. | Jet Impact Force (N) | Jet Impact Pressure (psi) | Jet Power (W) |
|---|---|---|---|
| 1 | 0.128 | 192.7 | 2.3 |
| 2 | 0.105 | 158.9 | 1.7 |
| 3 | 0.089 | 133.5 | 1.3 |
| 4 | 0.076 | 113.9 | 1.1 |
| 5 | 0.065 | 98.4 | 0.8 |
| 6 | 0.057 | 85.8 | 0.7 |
| 7 | 0.050 | 75.5 | 0.6 |
| 8 | 0.044 | 66.9 | 0.5 |
| 9 | 0.040 | 59.6 | 0.4 |

TABLE 19D

| Model No. | Flowrate per Orifice (m/s) | Total Flowrate (μL/s) | Time for Delivered Vol (ms) | Time from Start of Dose (ms) |
|---|---|---|---|---|
| 1 | 3.51E−06 | 7014.2 | | 0.0 |
| 2 | 3.18E−06 | 6368.4 | 7.47 | 7.5 |
| 3 | 2.92E−06 | 5838.1 | 8.19 | 15.7 |
| 4 | 2.70E−06 | 5392.7 | 8.90 | 24.6 |
| 5 | 2.51E−06 | 5011.8 | 9.61 | 34.2 |
| 6 | 2.34E−06 | 4681.3 | 10.32 | 44.5 |
| 7 | 2.20E−06 | 4390.9 | 11.02 | 55.5 |
| 8 | 2.07E−06 | 4133.0 | 11.73 | 67.3 |
| 9 | 1.95E−06 | 3901.7 | 12.45 | 79.7 |

The minimum (final) fluid pressure is about 95 psig, and the minimum (final) nozzle pressure is about 95 psig. The delivered volume of dispensable substance is 400 μL, and the final gas volume is 770 μL. The average velocity is 27.0 m/s. The total delivery time is 79.7 ins. The average velocity based on dispense time is 26.1 m/s.

Results—Initial Internal Pressure of 300 psig—2 Nozzles
The following properties were used in the model.
Initial internal pressure=300 psig
Fluid pressure=about 280 psig (peak; initial)
Nozzle pressure=about 280 psig (peak; initial)
Initial dose volume of dispensable substance=450 μL
Initial gas volume=370 μL With these parameters, the modelling yielded the results shown in Tables 20A-20D (liquid pressure is the same as fluid pressure).

TABLE 20A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 20.7 | 19.3 | 280.0 | 35.2 |
| 2 | 50 | 420 | 17.3 | 15.9 | 231.2 | 31.9 |
| 3 | 100 | 470 | 14.8 | 13.4 | 194.6 | 29.3 |
| 4 | 150 | 520 | 12.8 | 11.5 | 166.3 | 27.0 |
| 5 | 200 | 570 | 11.3 | 9.9 | 143.8 | 25.1 |
| 6 | 250 | 620 | 10.0 | 8.7 | 125.6 | 23.4 |
| 7 | 300 | 670 | 9.0 | 7.6 | 110.6 | 22.0 |
| 8 | 350 | 720 | 8.1 | 6.8 | 98.1 | 20.6 |
| 9 | 400 | 770 | 7.4 | 6.0 | 87.5 | 19.5 |

TABLE 20B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.64E+03 | 7.28E−02 | 1.93E+06 | 19.30 | 0.00 |
| 2 | 1.49E+03 | 7.43E−02 | 1.59E+06 | 15.94 | 0.00 |
| 3 | 1.37E+03 | 7.57E−02 | 1.34E+06 | 13.42 | 0.00 |
| 4 | 1.26E+03 | 7.71E−02 | 1.15E+06 | 11.46 | 0.00 |
| 5 | 1.17E+03 | 7.85E−02 | 9.91E+05 | 9.91 | 0.00 |
| 6 | 1.09E+03 | 7.99E−02 | 8.66E+05 | 8.66 | 0.00 |
| 7 | 1.02E+03 | 8.13E−02 | 7.63E+05 | 7.63 | 0.00 |
| 8 | 9.64E+02 | 8.26E−02 | 6.76E+05 | 6.76 | 0.00 |
| 9 | 9.09E+02 | 8.40E−02 | 6.03E+05 | 6.03 | 0.00 |

TABLE 20C

| Model No. | Jet Impact Force (N) | Jet Impact Pressure (psi) | Jet Power (W) |
|---|---|---|---|
| 1 | 0.119 | 179.7 | 2.10 |
| 2 | 0.098 | 148.0 | 1.57 |
| 3 | 0.082 | 124.2 | 1.21 |
| 4 | 0.070 | 105.9 | 0.95 |
| 5 | 0.061 | 91.3 | 0.76 |
| 6 | 0.053 | 79.6 | 0.62 |
| 7 | 0.046 | 69.9 | 0.51 |
| 8 | 0.041 | 61.8 | 0.42 |
| 9 | 0.037 | 55.0 | 0.36 |

TABLE 20D

| Model No. | Flowrate per Orifice (m/s) | Total Flowrate (μL/s) | Time for Delivered Vol (ms) | Time from Start of Dose (ms) |
|---|---|---|---|---|
| 1 | 3.39E−06 | 6773.1 | | 0.0 |
| 2 | 3.07E−06 | 6146.4 | 7.74 | 7.7 |
| 3 | 2.82E−06 | 5631.4 | 8.49 | 16.2 |
| 4 | 2.60E−06 | 5198.7 | 9.23 | 25.5 |
| 5 | 2.41E−06 | 4828.6 | 9.97 | 35.4 |
| 6 | 2.25E−06 | 4507.1 | 10.71 | 46.1 |
| 7 | 2.11E−06 | 4224.5 | 11.45 | 57.6 |
| 8 | 1.99E−06 | 3973.3 | 12.20 | 69.8 |
| 9 | 1.87E−06 | 3747.9 | 12.95 | 82.8 |

The minimum (final) fluid pressure is about 87.5 psig, and the minimum (final) nozzle pressure is about 87.5 psig. The delivered volume of dispensable substance is 400 μL, and the final gas volume is 770 μL. The average velocity is 26.0 m/s. The total delivery time is 82.8 ins. The average velocity based on dispense time is 25.1 m/s.

Results—Initial Internal Pressure of 270 psig—2 Nozzles
The following properties were used in the model.
Initial internal pressure=270 psig
Fluid pressure=about 250 psig (peak; initial)
Nozzle pressure=about 250 psig (peak; initial)
Initial dose volume of dispensable substance=450 μL
Initial gas volume=370 μL With these parameters, the modelling yielded the results shown in Tables 21A-21D (liquid pressure is the same as fluid pressure).

TABLE 21A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 18.6 | 17.2 | 250.0 | 33.2 |
| 2 | 50 | 420 | 15.6 | 14.2 | 206.1 | 30.1 |
| 3 | 100 | 470 | 13.3 | 11.9 | 173.1 | 27.6 |
| 4 | 150 | 520 | 11.6 | 10.2 | 147.6 | 25.4 |
| 5 | 200 | 570 | 10.2 | 8.8 | 127.4 | 23.6 |
| 6 | 250 | 620 | 9.0 | 7.7 | 111.0 | 22.0 |
| 7 | 300 | 670 | 8.1 | 6.7 | 97.5 | 20.6 |
| 8 | 350 | 720 | 7.3 | 5.9 | 86.3 | 19.3 |
| 9 | 400 | 770 | 6.7 | 5.3 | 76.7 | 18.2 |

TABLE 21B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.55E+03 | 7.36E−02 | 1.72E+06 | 17.23 | 0.00 |
| 2 | 1.41E+03 | 7.52E−02 | 1.42E+06 | 14.21 | 0.00 |
| 3 | 1.29E+03 | 7.68E−02 | 1.19E+06 | 11.94 | 0.00 |
| 4 | 1.19E+03 | 7.83E−02 | 1.02E+06 | 10.18 | 0.00 |
| 5 | 1.10E+03 | 7.98E−02 | 8.78E+05 | 8.78 | 0.00 |
| 6 | 1.03E+03 | 8.12E−02 | 7.66E+05 | 7.66 | 0.00 |
| 7 | 9.61E+02 | 8.27E−02 | 6.73E+05 | 6.73 | 0.00 |
| 8 | 9.02E+02 | 8.42E−02 | 5.95E+05 | 5.95 | 0.00 |
| 9 | 8.50E+02 | 8.57E−02 | 5.29E+05 | 5.29 | 0.00 |

TABLE 21C

| Model No. | Jet Impact Force (N) | Jet Impact Pressure (psi) | Jet Power (W) |
|---|---|---|---|
| 1 | 0.106 | 160.2 | 1.8 |
| 2 | 0.087 | 131.7 | 1.3 |
| 3 | 0.073 | 110.3 | 1.0 |
| 4 | 0.062 | 93.8 | 0.8 |
| 5 | 0.054 | 80.7 | 0.6 |
| 6 | 0.047 | 70.2 | 0.5 |

TABLE 21C-continued

| Model No. | Jet Impact Force (N) | Jet Impact Pressure (psi) | Jet Power (W) |
|---|---|---|---|
| 7 | 0.041 | 61.5 | 0.4 |
| 8 | 0.036 | 54.2 | 0.3 |
| 9 | 0.032 | 48.1 | 0.3 |

TABLE 21D

| Model No. | Flowrate per Orifice (m/s) | Total Flowrate (µL/s) | Time for Delivered Vol (ms) | Time from Start of Dose (ms) |
|---|---|---|---|---|
| 1 | 3.20E−06 | 6394.9 | | 0.0 |
| 2 | 2.90E−06 | 5797.8 | 8.20 | 8.2 |
| 3 | 2.65E−06 | 5306.7 | 9.01 | 17.2 |
| 4 | 2.45E−06 | 4893.8 | 9.80 | 27.0 |
| 5 | 2.27E−06 | 4540.1 | 10.60 | 37.6 |
| 6 | 2.12E−06 | 4232.7 | 11.40 | 49.0 |
| 7 | 1.98E−06 | 3962.1 | 12.20 | 61.2 |
| 8 | 1.86E−06 | 3721.2 | 13.02 | 74.2 |
| 9 | 1.75E−06 | 3504.9 | 13.84 | 88.1 |

The minimum (final) fluid pressure was about 77 psig, and the minimum (final) nozzle pressure was about 77 psig. The delivered volume of dispensable substance was 400 µL, and the final gas volume was 770 µL. The average velocity was 24.5 m/s. The total delivery time was 88.1 ins. The average velocity based on dispense time was 23.6 m/s.

Results—Initial Internal Pressure of 220 psig—2 Nozzles
The following properties were used in the model.
Initial internal pressure=220 psig
Fluid pressure=about 200 psig (peak; initial)
Nozzle pressure=about 200 psig (peak; initial)
Initial dose volume of dispensable substance=450 µL
Initial gas volume=370 µL With these parameters, the modelling yielded the results shown in Tables 22A-22D (liquid pressure is the same as fluid pressure).

TABLE 22A

| Model No. | Delivered Dose (µL) | Gas Vol. (µL) | Gas Pressure (bar) | Liquid Pressure (bar) | Liquid pressure (psi) | Velocity (m/s) |
|---|---|---|---|---|---|---|
| 1 | 0 | 370 | 15.2 | 13.8 | 200.0 | 29.7 |
| 2 | 50 | 420 | 12.7 | 11.3 | 164.2 | 26.8 |
| 3 | 100 | 470 | 10.9 | 9.5 | 137.3 | 24.5 |
| 4 | 150 | 520 | 9.4 | 8.0 | 116.6 | 22.6 |
| 5 | 200 | 570 | 8.3 | 6.9 | 100.1 | 20.9 |
| 6 | 250 | 620 | 7.4 | 6.0 | 86.8 | 19.4 |
| 7 | 300 | 670 | 6.6 | 5.2 | 75.8 | 18.1 |
| 8 | 350 | 720 | 6.0 | 4.6 | 66.6 | 16.9 |
| 9 | 400 | 770 | 5.4 | 4.1 | 58.8 | 15.9 |

TABLE 22B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.38E+03 | 7.55E−02 | 1.38E+06 | 13.79 | 0.00 |
| 2 | 1.25E+03 | 7.73E−02 | 1.13E+06 | 11.32 | 0.00 |
| 3 | 1.14E+03 | 7.90E−02 | 9.47E+05 | 9.47 | 0.00 |
| 4 | 1.05E+03 | 8.07E−02 | 8.04E+05 | 8.04 | 0.00 |
| 5 | 9.74E+02 | 8.24E−02 | 6.90E+05 | 6.90 | 0.00 |
| 6 | 9.05E+02 | 8.41E−02 | 5.98E+05 | 5.98 | 0.00 |
| 7 | 8.45E+02 | 8.58E−02 | 5.22E+05 | 5.22 | 0.00 |
| 8 | 7.90E+02 | 8.75E−02 | 4.59E+05 | 4.59 | 0.00 |
| 9 | 7.42E+02 | 8.93E−02 | 4.06E+05 | 4.06 | 0.00 |

TABLE 22C

| Model No. | Jet Impact Force (N) | Jet Impact Pressure (psi) | Jet Power (W) |
|---|---|---|---|
| 1 | 0.085 | 127.7 | 1.3 |
| 2 | 0.069 | 104.5 | 0.9 |
| 3 | 0.058 | 87.2 | 0.7 |
| 4 | 0.049 | 73.8 | 0.6 |
| 5 | 0.042 | 63.1 | 0.4 |
| 6 | 0.036 | 54.6 | 0.4 |
| 7 | 0.032 | 47.5 | 0.3 |
| 8 | 0.028 | 41.6 | 0.2 |
| 9 | 0.024 | 36.6 | 0.2 |

TABLE 22D

| Model No. | Flowrate per Orifice (m/s) | Total Flowrate (µL/s) | Time for Delivered Vol (ms) | Time from Start of Dose (ms) |
|---|---|---|---|---|
| 1 | 2.86E−06 | 5710.0 | | 0.0 |
| 2 | 2.85E−06 | 5165.8 | 9.19 | 9.2 |
| 3 | 2.36E−06 | 4717.3 | 10.12 | 19.3 |
| 4 | 2.17E−06 | 4339.2 | 11.04 | 30.4 |
| 5 | 2.01E−06 | 4014.7 | 11.97 | 42.3 |
| 6 | 1.87E−06 | 3731.9 | 12.91 | 55.2 |
| 7 | 1.74E−06 | 3482.2 | 13.86 | 69.1 |
| 8 | 1.63E−06 | 3259.4 | 14.83 | 83.9 |
| 9 | 1.53E−06 | 3058.5 | 15.83 | 99.8 |

The minimum (final) fluid pressure was about 59 psig, and the minimum (final) nozzle pressure was about 59 psig. The delivered volume of dispensable substance was 400 µL, and the final gas volume was 770 µL. The average velocity was 21.6 m/s. The total delivery time was 99.8 ms. The average velocity based on dispense time was 20.8 m/s.

Results—Initial Internal Pressure of 350 psig—4 Nozzles
The following properties were used in the model.
Initial internal pressure=350 psig
Fluid pressure=about 330 psig (peak; initial)
Nozzle pressure=about 330 psig (peak; initial)
Initial dose volume of dispensable substance=450 µL
Initial gas volume=370 µL With these parameters, the modelling yielded the results shown in Tables 23A-23D (liquid pressure is the same as fluid pressure).

TABLE 23A

| Model No. | Delivered Dose (µL) | Gas Vol. (µL) | Gas Pressure (bar) | Liquid Pressure (bar) | Liquid pressure (psi) | Velocity (m/s) |
|---|---|---|---|---|---|---|
| 1 | 0 | 370 | 24.1 | 22.8 | 330.0 | 38.3 |
| 2 | 50 | 420 | 20.2 | 18.8 | 273.1 | 34.8 |
| 3 | 100 | 470 | 17.3 | 15.9 | 230.4 | 31.9 |
| 4 | 150 | 520 | 15.0 | 13.6 | 197.3 | 29.5 |
| 5 | 200 | 570 | 13.2 | 11.8 | 171.1 | 27.4 |
| 6 | 250 | 620 | 11.7 | 10.3 | 149.9 | 25.6 |
| 7 | 300 | 670 | 10.5 | 9.1 | 132.4 | 24.1 |
| 8 | 350 | 720 | 9.5 | 8.1 | 117.8 | 22.7 |
| 9 | 400 | 770 | 8.6 | 7.3 | 105.4 | 21.4 |

TABLE 23B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.79E+03 | 7.16E−02 | 2.28E+06 | 22.75 | 0.00 |
| 2 | 1.62E+03 | 7.30E−02 | 1.88E+06 | 18.83 | 0.00 |
| 3 | 1.49E+03 | 7.43E−02 | 1.59E+06 | 15.88 | 0.00 |
| 4 | 1.38E+03 | 7.56E−02 | 1.36E+06 | 13.60 | 0.00 |
| 5 | 1.28E+03 | 7.69E−02 | 1.18E+06 | 11.80 | 0.00 |
| 6 | 1.20E+03 | 7.81E−02 | 1.03E+06 | 10.33 | 0.00 |
| 7 | 1.12E+03 | 7.94E−02 | 9.13E+05 | 9.13 | 0.00 |
| 8 | 1.06E+03 | 8.06E−02 | 8.12E+05 | 8.12 | 0.00 |
| 9 | 1.00E+03 | 8.18E−02 | 7.27E+05 | 7.27 | 0.00 |

TABLE 23C

| Model No. | Jet Impact Force (N) | Jet Impact Pressure (psi) | Jet Power (W) |
|---|---|---|---|
| 1 | 0.141 | 212.3 | 2.7 |
| 2 | 0.116 | 175.2 | 2.0 |
| 3 | 0.098 | 147.4 | 1.6 |
| 4 | 0.084 | 126.0 | 1.2 |
| 5 | 0.072 | 109.0 | 1.0 |
| 6 | 0.063 | 95.3 | 0.8 |
| 7 | 0.056 | 84.0 | 0.7 |
| 8 | 0.049 | 74.5 | 0.6 |
| 9 | 0.044 | 66.6 | 0.5 |

TABLE 23D

| Model No. | Flowrate per Orifice (m/s) | Total Flowrate (μL/s) | Time for Delivered Vol (ms) | Time from Start of Dose (ms) |
|---|---|---|---|---|
| 1 | 3.68E−06 | 14722.3 | | 0.0 |
| 2 | 3.34E−06 | 13375.8 | 3.56 | 3.6 |
| 3 | 3.07E−06 | 12270.4 | 3.90 | 7.5 |
| 4 | 2.84E−06 | 11342.7 | 4.23 | 11.7 |
| 5 | 2.64E−06 | 10550.1 | 4.57 | 16.3 |
| 6 | 2.47E−06 | 9862.8 | 4.90 | 21.2 |
| 7 | 2.31E−06 | 9259.3 | 5.23 | 26.4 |
| 8 | 2.18E−06 | 8723.7 | 5.56 | 32.0 |
| 9 | 2.06E−06 | 8244.0 | 5.89 | 37.8 |

The minimum (final) fluid pressure is about 105.4 psig, and the minimum (final) nozzle pressure is about 105.4 psig. The delivered volume of dispensable substance is 400 μL, and the final gas volume is 770 μL. The average velocity is 28.4 m/s. The total delivery time is 37.8 ins. The average velocity based on dispense time is 27.5 m/s.

Results—Initial Internal Pressure of 320 psig—4 Nozzles
The following properties were used in the model.
Initial internal pressure=320 psig
Fluid pressure=about 300 psig (peak; initial)
Nozzle pressure=about 300 psig (peak; initial)
Initial dose volume of dispensable substance=450 μL
Initial gas volume=370 μL With these parameters, the modelling yielded the results shown in Tables 24A-24D (liquid pressure is the same as fluid pressure).

TABLE 24A

| Model No. | Delivered Dose (μL) | Gas Vol. (μL) | Gas Pressure (bar) | Liquid Pressure (bar) | Liquid pressure (psi) | Velocity (m/s) |
|---|---|---|---|---|---|---|
| 1 | 0 | 370 | 22.1 | 20.7 | 300.0 | 36.5 |
| 2 | 50 | 420 | 18.5 | 17.1 | 247.9 | 33.1 |
| 3 | 100 | 470 | 15.8 | 14.4 | 208.9 | 30.3 |
| 4 | 150 | 520 | 13.7 | 12.3 | 178.7 | 28.0 |
| 5 | 200 | 570 | 12.0 | 10.7 | 154.7 | 26.0 |
| 6 | 250 | 620 | 10.7 | 9.3 | 135.3 | 24.3 |
| 7 | 300 | 670 | 9.6 | 8.2 | 119.3 | 22.8 |
| 8 | 350 | 720 | 8.7 | 7.3 | 106.0 | 21.5 |
| 9 | 400 | 770 | 7.9 | 6.5 | 94.7 | 20.3 |

TABLE 24B

| Model No. | Re | Friction Factor | Est. Pressure Drop (Pa) | Est. Pressure Drop (bar) | Difference: P Est. v. P Set (bar) |
|---|---|---|---|---|---|
| 1 | 1.70E+03 | 7.23E−02 | 2.07E+06 | 20.68 | 0.00 |
| 2 | 1.54E+03 | 7.37E−02 | 1.71E+06 | 17.09 | 0.00 |
| 3 | 1.42E+03 | 7.51E−02 | 1.44E+06 | 14.40 | 0.00 |
| 4 | 1.31E+03 | 7.65E−02 | 1.23E+06 | 12.32 | 0.00 |
| 5 | 1.22E+03 | 7.78E−02 | 1.07E+06 | 10.67 | 0.00 |
| 6 | 1.14E+03 | 7.92E−02 | 9.33E+05 | 9.33 | 0.00 |
| 7 | 1.06E+03 | 8.05E−02 | 8.23E+05 | 8.23 | 0.00 |
| 8 | 1.00E+03 | 8.18E−02 | 7.31E+05 | 7.31 | 0.00 |
| 9 | 9.46E+02 | 8.31E−02 | 6.53E+05 | 6.53 | 0.00 |

TABLE 24C

| Model No. | Jet Impact Force (N) | Jet Impact Pressure (psi) | Jet Power (W) |
|---|---|---|---|
| 1 | 0.128 | 192.7 | 2.3 |
| 2 | 0.105 | 158.9 | 1.7 |
| 3 | 0.089 | 133.5 | 1.3 |
| 4 | 0.076 | 113.9 | 1.1 |
| 5 | 0.065 | 98.4 | 0.8 |
| 6 | 0.057 | 85.8 | 0.7 |
| 7 | 0.050 | 75.5 | 0.6 |
| 8 | 0.044 | 66.9 | 0.5 |
| 9 | 0.040 | 59.6 | 0.4 |

TABLE 24D

| Model No. | Flowrate per Orifice (m/s) | Total Flowrate (μL/s) | Time for Delivered Vol (ms) | Time from Start of Dose (ms) |
|---|---|---|---|---|
| 1 | 3.51E−06 | 14028.4 | | 0.0 |
| 2 | 3.18E−06 | 12736.9 | 3.74 | 3.7 |
| 3 | 2.92E−06 | 11676.1 | 4.10 | 7.8 |
| 4 | 2.70E−06 | 10785.3 | 4.45 | 12.3 |
| 5 | 2.51E−06 | 10023.7 | 4.81 | 17.1 |
| 6 | 2.34E−06 | 9362.7 | 5.16 | 22.2 |
| 7 | 2.20E−06 | 8781.9 | 5.51 | 27.8 |
| 8 | 2.07E−06 | 8266.0 | 5.87 | 33.6 |
| 9 | 1.95E−06 | 7803.5 | 6.22 | 39.8 |

The minimum (final) fluid pressure is about 94.7 psig, and the minimum (final) nozzle pressure is about 94.7 psig. The delivered volume of dispensable substance is 400 L, and the final gas volume is 770 μL. The average velocity is 27.0 m/s. The total delivery time is 39.8 ms. The average velocity based on dispense time is 26.1 m/s.

Results—Summary

A summary of certain data for the ingestible devices with two nozzles is provided in Table 25 and FIGS. 33-47. "Drive Force Generator: Pre-compressed gas pressure (psig)" is the initial internal pressure, and "liquid pressure" is fluid pressure.

TABLE 25

| Drive Force Generator: Pre-compressed gas pressure (psig) | Peak Liquid Pressure (psig) | Peak Jet Velocity (m/s) | Peak Jet Power (W) |
| --- | --- | --- | --- |
| 320 | 300 | 36.5 | 2.3 |
| 300 | 280 | 35.2 | 2.1 |
| 270 | 250 | 33.2 | 1.8 |
| 220 | 200 | 29.7 | 1.3 |

A summary of certain data for the ingestible devices with four nozzles is provided in Table 26. "Drive Force Generator: Pre-compressed gas pressure (psig)" was the initial internal pressure, and "liquid pressure" is fluid pressure.

TABLE 26

| Drive Force Generator: Pre-compressed gas pressure (psig) | Peak Liquid Pressure (psig) | Peak Jet Velocity (m/s) | Peak Jet Power (W) |
| --- | --- | --- | --- |
| 350 | 330 | 38.3 | 2.7 |
| 320 | 300 | 36.5 | 2.3 |

Example 2—Jet Velocity Measurements

A high-speed video camera (Photron Fastcam SA3, using 2,000 frames per second) was used to measure the jet velocities of a dispensable substance (water) delivered from devices having different nozzle diameters and nozzle lengths. The receiving medium (external environment) was air. The nozzles were made of MicroFine Green Resin (an ABS-like material), using micro-resolution stereolithography (SLA).

The results are shown in Tables 27 and 28. The first 12 nozzles in Table 27 correspond to nozzles depicted in FIGS. 6A-6L, respectively.

TABLE 27

| Nozzle Dia. (mm) | Nozzle Length (mm) | Throat Geometry | Internal Pressure (psi) | Avg dispensing time (s) | Jet Dia at 5 mm | Peak (Initial) Jet Velocity based on dispensing time (m/s) | Peak (Initial) Jet Velocity based on Image processing |
| --- | --- | --- | --- | --- | --- | --- | --- |
| 0.35 | 0.5 | Rounded | 220 | 0.10 | 1.0 | 37.2 | 38.0 |
| 0.35 | 0.5 | Sharp | 220 | 0.12 | 1.5 | 32.1 | 33.5 |
| 0.35 | 1.5 | Rounded | 220 | 0.12 | 1.0 | 32.8 | 34.7 |
| 0.35 | 1.5 | Sharp | 220 | 0.13 | 0.8 | 29.7 | 36.0 |
| 0.35 | 1 | Rounded | 220 | 0.12 | 0.9 | 31.9 | 37.3 |
| 0.35 | 1 | Sharp | 220 | 0.12 | 0.9 | 32.3 | 32.0 |
| 0.5 | 0.5 | Rounded | 220 | 0.06 | 1.2 | 34.2 | 34.5 |
| 0.5 | 0.5 | Sharp | 220 | 0.07 | 1.3 | 28.9 | 28.0 |
| 0.5 | 1.5 | Rounded | 220 | 0.06 | 1.1 | 30.6 | 36.7 |
| 0.5 | 1.5 | Sharp | 220 | 0.07 | 1.3 | 27.9 | 26.5 |
| 0.5 | 1 | Rounded | 225 | 0.07 | 1.0 | 29.2 | 35.3 |
| 0.5 | 1 | Sharp | 220 | 0.08 | 1.1 | 25.3 | 32.0 |
| 0.5 | Detailed Geometry | | 220 | 0.06 | 1.2 | 29.7 | 33.3 |

TABLE 28

| Nozzle Dia (mm) | Nozzle entrance Shape | Avg Dispensing time (s) | Avg Velocity (m/s) |
| --- | --- | --- | --- |
| 0.35 | Rounded | 0.115 | 34.0 |
| 0.35 | Sharp | 0.124 | 31.4 |
| 0.5 | Rounded | 0.061 | 31.3 |
| 0.5 | Sharp | 0.070 | 27.4 |

Example 3—Comparison of PK/PD of Human Insulin Delivered by Subcutaneous or Jet Delivery in the Jejunum Using Euglycemic Clamp Technique in Swine A study was carried out to compare the pharmacokinetics (PK) and pharmacodynamics (PD) of regular human insulin (NOVOLIN® R) in swines after subcutaneous (SC) administration or intra-jejunal (IJ) administration via a single nozzle jet delivery device.

A total of 18 Yorkshire female swine in good health and weighing 60-70 kg each were included in this study. Swine were divided into two groups with 9 animals per group. All 9 animals in group 01 were administered a single subcutaneous injection of insulin aspart (NOVOLIN® R) (~40 U) on one side of the neck at a depth of ~5 mm. A sham surgical laparotomy was performed. All 9 animals in group 02 were administrated regular human insulin (NOVOLIN® R) (~40 U) delivered in the proximal jejunum by a jet delivery device placed by surgical laparotomy. The jet delivery device was configured with the single nozzle in an axial orientation. The device was held in place during the laparotomy insertion, and the nozzle outlet was directed to face the jejunal wall to direct the jet of the NOVOLIN® R to the GI tract. The device was pre-pressurized with compressed gas to have an internal pressure of about 225 psi, except where noted.

All animals were fasted overnight prior to the NOVOLIN® R administration. Swine were divided into two groups with 9 animals per group. Prior to NOVOLIN® R administration, the animals were anesthetized, and two vascular access catheters were placed. In all 18 animals, a laparotomy procedure was performed to expose the abdominal cavity. Animals remained under anesthesia during the entire procedure for the PK/PD study.

All 9 animals in group 01 were administered a single subcutaneous injection of insulin aspart (NOVOLIN® R) (~30 U) on one side of the neck at a depth of 5 mm.

All 9 animals in group 02 were dosed with regular human insulin (NOVOLIN® R) in the proximal jejunum by the single nozzle jet delivery device placed by surgical laparotomy.

For the laparotomy in group 02, a small segment of the jejunal mucosa and serosa was exposed by midline laparotomy and the jet delivery device was inserted through antimesenteric incision. Regular human insulin NOVOLIN® R (~40 U) was delivered by the jet delivery device, and the bowel and abdominal wall was closed.

For PK/PD blood collections, blood (approximately 3 mL, EDTA) samples were collected at −20, −10, 0, 10, 20, 30, 40, 50, 60, 75, 90, 105, 120, 150, 180, 210, 240, 270, 300, 330, 360, 390, and 420 minutes after dosing. Blood samples were kept on wet ice until centrifugation and separation of plasma. The plasma samples were stored −80° C. on the days of collection until delivered to AHDC Endocrinology Laboratory at Cornell University for insulin analyses. Glucose was monitored every five (5) minutes during the study by portable glucose analyzer (StatStrip (SS) hospital glucose monitoring system (Nova Biomedical, Waltham, Mass.)). At each time point, approximate 0.1 mL of blood was drawn and immediately placed on a glucose monitoring test strip, and the whole blood glucose concentration was measured by the SS in triplicate.

A euglycemic clamp procedure (ECP) was employed to compare pharmacokinetics and pharmacodynamics of regular human Insulin (NOVOLIN® R) delivered subcutaneously (SC) in the neck versus intra-jejunally (IJ) by the jet delivery device in the small intestine. ECP was used to quantify the amount of glucose required to maintain normoglycemia after exogenous bolus of insulin. ECP allowed both the glucose infusion rate (20% dextrose infusion) and total quantity to be calculated, which represented the effect of exogenous insulin on the disposition of blood glucose. ECP ensured pharmacologic suppression of the production of endogenous insulin. This study evaluated serum insulin concentration (pg/mL) over time and glucose infusion rate (to maintain a constant ~85 mg/dl BG) over the duration of the ECP (7 hours; 420 min.). The animals were anesthetized for the entire ECP. The endpoints included a comparison of selected pharmacokinetic parameters for insulin, including $t_{1/2}$ (min), $C_{max}$ (pg/mL), $T_{max}$ (min) and $AUC_{0-420min}$ (ng·h/mL), as well as pharmacodynamic parameters such as the rate (mg/kg/min) and amount of glucose (mg/kg) infused.

At the end of the study, all animals were euthanized and animals in group 02 underwent gross necropsy for histopathologic evaluation of the proximal jejunum where the NOVOLIN® R was administrated.

Results

Figure 48:
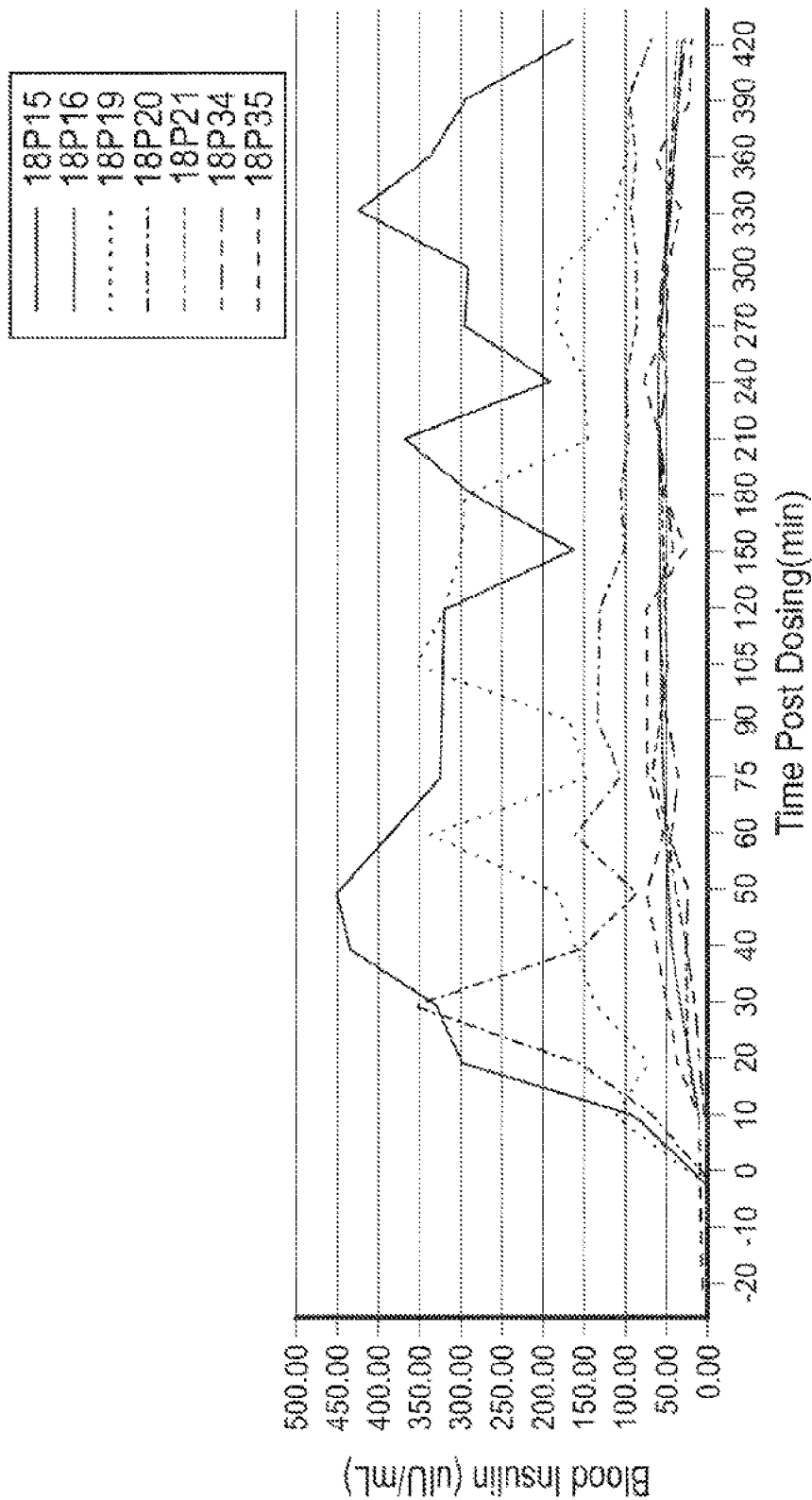
FIG. 48 shows blood insulin levels in swine after subcutaneous (SC) administration.
Figure 49:
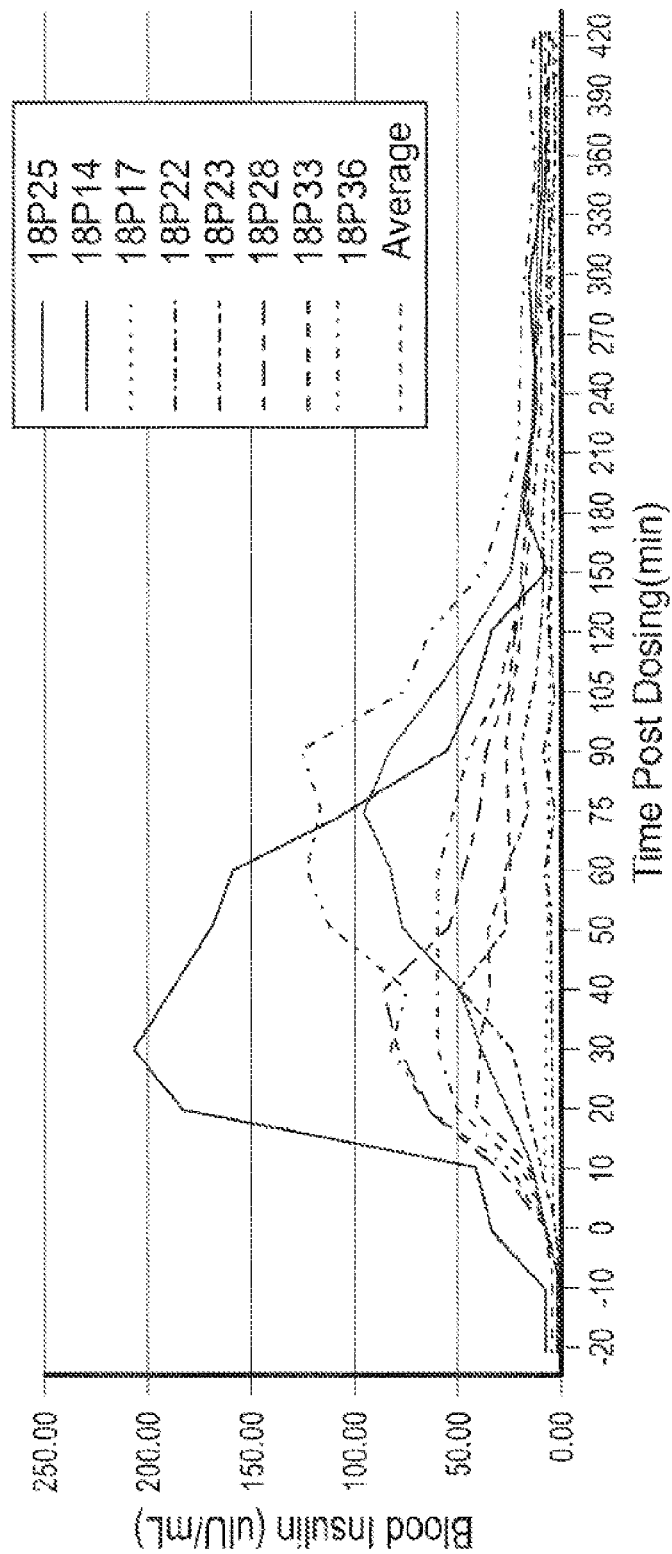
FIG. 49 shows blood insulin levels in swine after jejunum (IJ) administration.

FIG. 48 and FIG. 49 show blood insulin levels for each animal. The area under the concentration-time curve ($AUC_{0-420\ min}$) of the blood insulin, maximum plasma concentration $C_{max}$ (uIU/mL), and time to maximum plasma concentration ($T_{max}$) were calculated for each animal.

Figure 50:
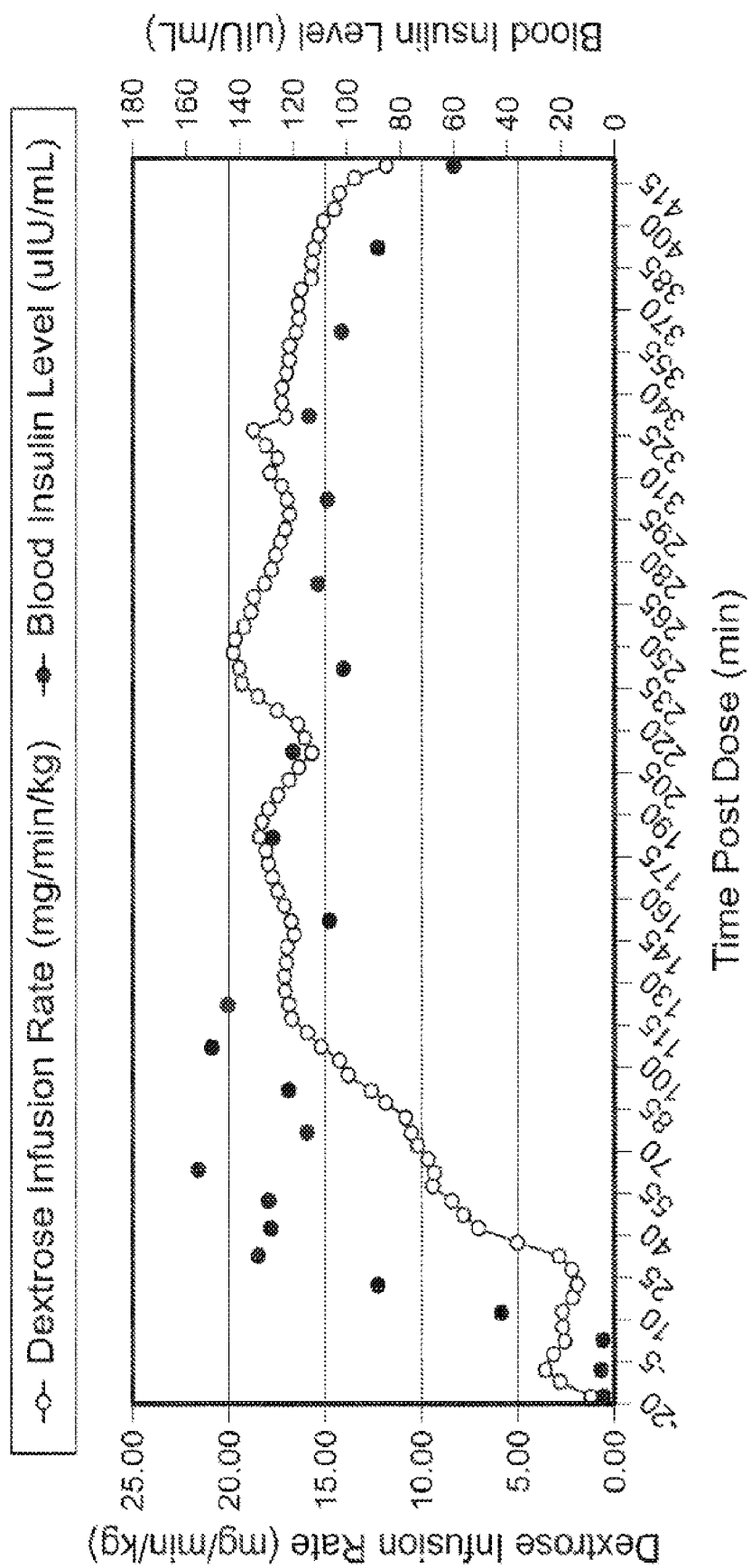
FIG. 50 shows blood insulin levels and dextrose infusion rates in the SC administration group.
Figure 51:
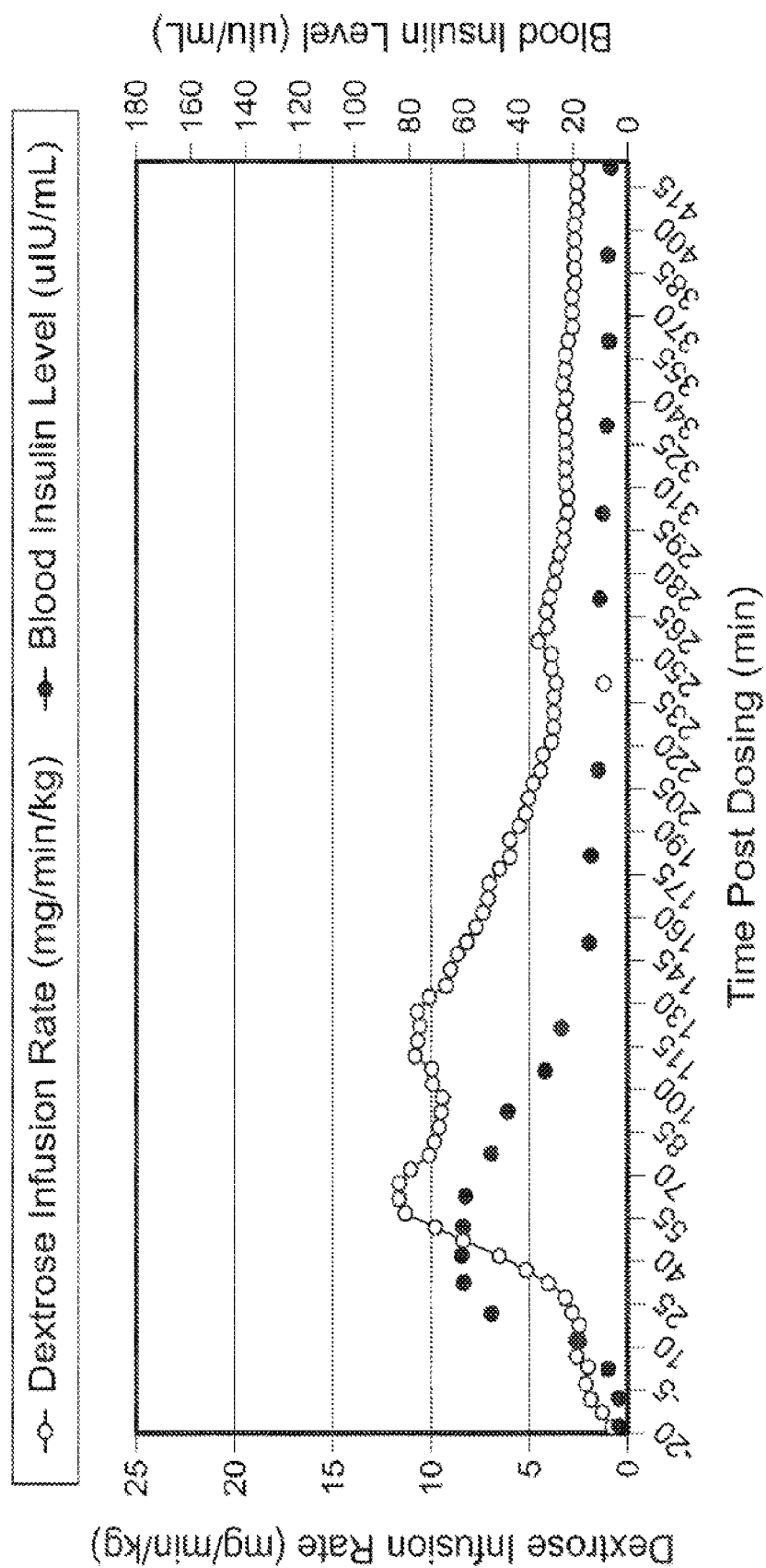
FIG. 51 shows blood insulin levels and dextrose infusion rates in the IJ administration group.

FIG. 50 and FIG. 51 show blood insulin levels (uIU/mL) and dextrose infusion rates (mg/min/kg) in SC and IJ administration groups, respectively.

Blood insulin results for SC and IJ administrations are shown in Tables 29 and 30, respectively.

TABLE 29

| | SC Administration | | | | | | | |
|---|---|---|---|---|---|---|---|---|
| Animal ID | 18P15 | 18P16 | 18P19 | 18P20 | 18P21 | 18P34 | 18P35 | Average* |
| AUC (0-420 min) | 124486 | 20281 | 75580 | 45338 | 19729 | 17811 | 21211 | 46348 |
| $C_{max}$ (uIU/mL) | 451.00 | 60.74 | 354.00 | 356.60 | 65.71 | 59.18 | 73.34 | 202.94 |
| $T_{max}$ (min) | 50 | 180 | 105 | 30 | 75 | 120 | 50 | 87.14 |

TABLE 30

| | IJ Administration | | | | | | | | |
|---|---|---|---|---|---|---|---|---|---|
| Animal ID | 18P25 | 18P14 | 18P17 | 18P22 | 18P23 | 18P28 | 18P33 | 18P36 | Average* |
| AUC (0-420 min) | 7677 | 11588 | 1389 | 2229 | 4024 | 8797 | 17046 | 17075 | 8728 |
| $C_{max}$ (uIU/mL) | 40.93 | 96.77 | 5.03 | 7.96 | 48.77 | 85.38 | 207.96 | 126.39 | 77.40 |
| $T_{max}$ (min) | 20 | 75 | 50 | 90 | 40 | 40 | 40 | 90 | 55.63 |

*: Results from animal 18P29 and 18P24 were excluded from blood insulin PK analysis, blood glucose analysis, and Dextrose infusion calculation; animal 18P29 received only 30 U insulin, while animal 18P24 received 30 U insulin at 150 psig. Animal 18P18 was also excluded from the blood insulin calculation due to unknown abnormal results as compared with all the other animals.

The mean blood glucose level in SC administration group was 83.5 mg/dL, which was very similar to IJ administration group (89.6 mg/dL). The mean dextrose infusion rate was higher in the IJ administration group in the first 70 minutes after Novolin® R administration. From 75 minutes to 420 minutes post-Novolin® R administration, the mean dextrose infusion rate was higher in the SC administration group.

The AUC and the maximum plasma concentration $C_{max}$ in the SC administration group was higher than that of the IJ administration group. The time to maximum plasma concentration ($T_{max}$) was 55.63 minutes in jejunum administration group whereas in the subcutaneous administration group, $T_{max}$ was 87.14 minutes.

The blood insulin level in animal 18P18 (SC administration group) was significantly higher than the rest of the animals in the group. The reason was unknown. The blood insulin levels post-dosing in animal 18P17 and 18P22 were similar to the baseline indicating that IJ administration of the Novolin® R via the jet delivery device in these animals may not have been successful.

Example 4—Evaluation of Target Internal Pressure Range for Submucosal Delivery Using an Ingestible 2-Nozzle Jet Delivery Device by Bench Test Jetting of India Ink into Porcine Jejunal Tissue Ex Vivo A study was conducted to identify the internal pressure range for trans-epithelial delivery of a drug payload into porcine jejunal submucosal tissue ex vivo using India ink as a drug surrogate.

Test Article

India Ink was used in this study.

Ingestible Device Configuration

Each ingestible device used in this study was configured as a capsule containing a substance reservoir (volume: 450 µL); two (2) gas reservoirs; a check valve; a floating piston; two (2) nozzles radially configured 180 degrees apart; a lid at one end of the capsule; and a pneumatic control line ((polyetheretherketone (PEEK) tubing) attached to the lid). The first gas reservoir was positioned behind the substance reservoir and was used to drive the substance (India ink) from the substance reservoir. The floating piston separated the substance reservoir from the first gas reservoir. The second gas reservoir was positioned beneath the lid and used only to open the lid. Although it was previously demonstrated that a single pressurized gas reservoir can be used to both open the lid and eject the substance (e.g., drug; data not shown), the use of two separate gas reservoirs in this study was intended to demonstrate independent assessment of the action of the triggering mechanism (lid opening) and the substance ejection parameters.

Configuration of ingestible device with tissue: Porcine jejunum tissue, previously flash frozen in liquid $N_2$ and then stored at −80° C., was thawed and used as the source tissue for testing. In a biological safety cabinet, one side of the jejunum was sealed with a zap strap and stopper. The ingestible device was then inserted into the lumen of the jejunum. Finally, a zap strap fixed the proximal portion of the jejunum to the pneumatic control line.

Device pressurization: An external pressure chamber was connected to an air compressor. Two pressure gauges were used: one was fitted onto the air compressor and a second NIST-certified pressure gauge was placed in-line with the pressure chamber and the air compressor.

The first and second gas reservoirs of each device were pressurized separately. To pressurize the first gas reservoir, the device was placed in the pressure chamber and then pressurized to its target internal pressure (200 psig to 350 psig). The pressure chamber was then depressurized back to ambient atmospheric pressure. The ingestible device was then removed from the chamber, after which it maintained the target internal pressure by way of the check valve. To pressurize the second gas reservoir, the ingestible device control line was directly attached to the air compressor via an in-line valve. The valve was turned manually to pressurize the second gas reservoir to 350 psig.

Ex Vivo Jetting Study Protocol and Results

Briefly, a total of five (5) capsules were used in this study and a single ingestible device was used per test. Prior to testing, each ingestible device (attached to the control line) was filled with a 450 µL payload of substance (India ink). The first gas reservoir was then pressurized with air to its target internal pressure of 200 psig, 250 psig, 300 psig or 350 psig, as described above; the pressure was read from the in-line NIST gauge, which was in agreement with the pressure reading from the air compressor gauge. At the time of testing, the pressurized device configured with tissue was placed within a blast shield. Then the second gas reservoir (initially at ambient atmospheric pressure) was quickly pressurized to 350 psig, as described above. Pressurizing the second gas reservoir opened the lid, exposing the ingestible device nozzles. The internal pressure in the first gas reservoir ejected the India ink from the substance reservoir through the two (2) radially-configured nozzles towards the porcine jejunum tissue surrounding the ingestible device. Pre- and post-deployment device weights and diameters were recorded throughout the study to confirm proper device loading/dispensing volumes and pressurization, respectively. The jejunal tissue was then removed from the ingestible device and rinsed in 10% neutral buffered formalin (NBF) and deionized water for photography. The deployed device was disinfected and dried prior to obtaining its post-pressurization weight.

Pressure tests were performed at 200 psig, 250 psig, 300 psig and 350 psig, and visual observations were made after washing the tissue. The results are summarized in Table 31. The test result was assigned as PASS if the substance delivered from the device passed through the jejunal tissue without tissue rupture or blow through of ink to the outside of the jejunal tissue, or FAIL if the substance delivered from the device was not observed to pass through the jejunal tissue or if tissue rupture or blow through of ink to the outside of the jejunal tissue occurred.

TABLE 31

| Device ID | Pressure Test (psi) | Result | Observations |
| --- | --- | --- | --- |
| 81 | 200 | FAIL | All ink deployed from device. No conclusive injection sites could be seen after washing the tissue, and no passing through tissue observed. |

TABLE 31-continued

| Device ID | Pressure Test (psi) | Result | Observations |
|---|---|---|---|
| 52 | 250 | PASS | Two injection boluses observed, one of which was very faint. Each was markedly smaller than that observed with the 300 psig or 350 g psi injections. |
| 95 | 300 | PASS | All ink deployed from device. India ink observed inside of the lumen. One ink bolus clearly identified. Second injection site lost during excision process. |
| 92 | 300 | ABORT | Pressure leak detected prior to deployment. Test aborted. |
| 84 | 300 | PASS | All ink deployed from device. Two ink boluses observed. Possible asymmetry noted in bolus sizes. Ink deposited in the lumen. |
| 82 | 350 | PASS | All ink deployed from device. Two ink boluses observed, with one bolus noticeably smaller than other. |

Example 5—Identification of the Target Internal Pressure Range of an Ingestible 2-Nozzle Jet Delivery Device by Evaluating the Bioavailability of Adalimumab in Female Yorkshire Pigs A study was conducted to identify the target internal pressure range of an ingestible 2-nozzle jet delivery device required to achieve systemic uptake of adalimumab. In this study, the plasma pharmacokinetics of adalimumab were evaluated in female Yorkshire pigs after intravenous (IV), subcutaneous (SC), or intraduodenal (ID) administration via an endoscopically placed ingestible device.

Test Article

Adalimumab in an aqueous buffer having an adalimumab concentration of about 106 mg/mL.

Ingestible Device Configuration

Each ingestible device was configured as a capsule comprising a substance reservoir; a gas reservoir; a one-way duckbill valve; a piston; two nozzles radially configured 180 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig, 270 psig, or 220 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the amount of test article delivered was determined. Typically, approximately 0.050 mL was retained in the ingestible device after test article delivery was completed. Thus, approximately 0.400 mL of test article was dispensed from each ingestible device.

A summary of parameters for the delivery of the test article via the ingestible device is provided in Table 32. Initial and final refer to values at the beginning and end of the dispensing period for the test article, respectively

TABLE 32

| | Parameters for test article delivery from ingestible device | | |
|---|---|---|---|
| | Internal pressure (pressure of pre-compressed gas): about 320 psig | Internal pressure (pressure of pre-compressed gas): about 270 psig | Internal pressure (pressure of pre-compressed gas): about 220 psig |
| Pre-compressed gas volume in ingestible device | about 370 microliters (initial) to about 770 microliters (final) | | |
| Nozzle diameter | 0.35 mm | | |
| Nozzle length | 2 mm | | |
| Nozzle throat geometry | circular, sharp-edged orifice | | |
| Piston diameter | 9.6 mm | | |
| Piston friction | 10N (one (1) O-ring on piston) | | |
| Friction pressure loss | about 20 psig | | |
| Nozzle stand-off distance | >1.5 mm | | |
| Device diameter | 11.6 mm | | |
| Device length | about 34 to 36 mm | | |
| Fluid pressure | about 300 psig (peak; initial) to about 95 psig (minimum; final) | about 250 psig (peak; initial) to about 77 psig (minimum; final) | about 200 psig (peak; initial) to about 59 psig (minimum; final) |
| Jet velocity | about 36.5 m/s (peak; initial) to about 20 m/s (minimum; final) | about 33 m/s (peak; initial) to about 18 m/s (minimum; final) | about 30 m/s (peak; initial) to about 16 m/s (minimum; final) |
| Mean jet velocity | about 26 to 27 m/s | about 23 to 25 m/s | about 20 to 22 m/s |
| Fluid dispensing time (total) | about 80 ms | about 88 ms | about 100 ms |
| Jet impact force | about 0.13N (peak; initial) to about 0.04N (minimum; final) | about 0.11N (peak; initial) to about 0.03N (minimum; final) | about 0.09 (peak; initial) to about 0.02 (minimum; final) |
| Jet impact pressure | about 193 psig (peak; initial) to about 60 psig (minimum; final) | about 160 psig (peak; initial) to about 48 psig (minimum; final) | about 128 psig (peak; initial) to about 37 psig (minimum; final) |
| Jet power | about 2.3 W (peak; initial) to about 0.4 W (minimum; final) | about 1.8 W (peak; initial) to about 0.3 W (minimum; final) | about 1.3 W (peak; initial) to about 0.2 W (minimum; final) |
| Jet diameter | about 0.35 mm (initial) | about 0.35 mm (initial) | about 0.35 mm (initial) |

In Vivo Study Design

A total of 21 healthy female Yorkshire pigs (*Sus scrofa domesticus*) having a body weight of 25-30 kg were used in this study. Five (N=5) were used in each of dose Groups 1-3 (intraduodenal (ID) administration via an endoscopically placed ingestible device), and three (N=3) were used in each of dose Group 4 (SC administration) and dose Group 5 (IV administration). The study design is shown below in Table 33.

TABLE 33

| Group # | Dose Route | N | Dose | Dose Conc. | Internal Device Pressure or Volume | Clinical Observations | Blood Collection Time Points | Termination & Necropsy |
|---|---|---|---|---|---|---|---|---|
| 1 | ID (Device) | 5 | 40 mg | 106 mg/mL | 220 PSIG | Twice on the day of each endoscopic event, and 24, 72, 144, and 240 hours post dose | Pre-dose, 1, 3, 6, 8, 24, 72, 144, and 240 hours post dose | Termination and necropsy of the injection site to assess signs of hematoma and gross lesions (Day 10 post-dose) |
| 2 | ID (Device) | 5 | 40 mg | 106 mg/mL | 270 PSIG | | | |
| 3 | ID (Device) | 5 | 40 mg | 106 mg/mL | 320 PSIG | | | |
| 4 | SC | 3 | 40 mg | 107 mg/mL | 0.373 mL | | | N/A, animals are to be survived |
| 5 | IV | 3 | 40 mg | 107 mg/mL | 0.373 mL | | | |

Animals were housed two per cage and fasted for a minimum of 12 hours prior to dosing. Food was returned at 4 hours post-dose. Water was supplied ad libitum. The dosing was as follows: Dose day 1: group 1 (n=3), and group 3 (n=2); Dose day 2: group 2 (n=3), and group 1 (n=2); Dose day 3: group 3 (n=3), and group 2 (n=2); Dose day 4: groups 4 (n=3), and group 5 (n=3). Following the 240-hour post-dose blood collection the animal was euthanized via euthanasia solution IV bolus dose.

Routes of Administration

For intraduodenal (ID) administration, the ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

For intravenous (IV) administration, the test article was administered intravenously via bolus dose into the marginal ear vein followed by a 1 mL flush with saline if necessary.

For subcutaneous (SC) administration, animals were placed in dorsal recumbence and the SC injection site aseptically prepared with alcohol. The test article was administered as an SC injection into a "skin tent" on the belly of the pig.

Sampling and Analysis

Plasma samples were collected at pre-dose, 1, 3, 6, 8, 24, 72, 144, and 240 hours post-dose in all animals. Each blood sample was collected from the pig jugular vein, or other suitable vessel via direct venipuncture, placed into a chilled tube containing K2-EDTA as the anticoagulant, and inverted several times to mix. Blood samples were kept on wet ice until centrifugation. Blood samples were centrifuged at a temperature of 4° C., at 3,000×g, for 5 minutes and chilled throughout processing. Plasma was collected into pre-labeled polypropylene tubes and placed in a freezer set to maintain −60 to −80° C. prior to analysis.

Samples were processed and analyzed by using an adalimumab (anti-TNF-alpha) ELISA kit from Alpha Diagnostics, Inc. (Catalog #200 310-AHG). All plasma samples were diluted by 1:100 dilution. Plasma samples were reanalyzed with a 1:1000 dilution from animals 6287, 6289, 6332, 6334, 6336, 6149, 6335, and 6337. Plasma samples close to the lower limit of quantification (LLOQ) were repeated with a 1:5 dilution from animals 6138 and 6137. The final concentrations of adalimumab in these two animals were lower than previously shown, suggesting that these values were at the limits of detection and were not reliable. Therefore, the data from animal 6138 and 6137 were not included in the final PK analysis. All data and pharmacokinetic parameters were analyzed and graphed by using GraphPad Prism version 7.00 for Windows, GraphPad Software, La Jolla Calif. USA, 0 (GraphPad Prism 7). The area under the concentration curve (AUC) was calculated with the trapezoidal rules.

Results

Figure 52:
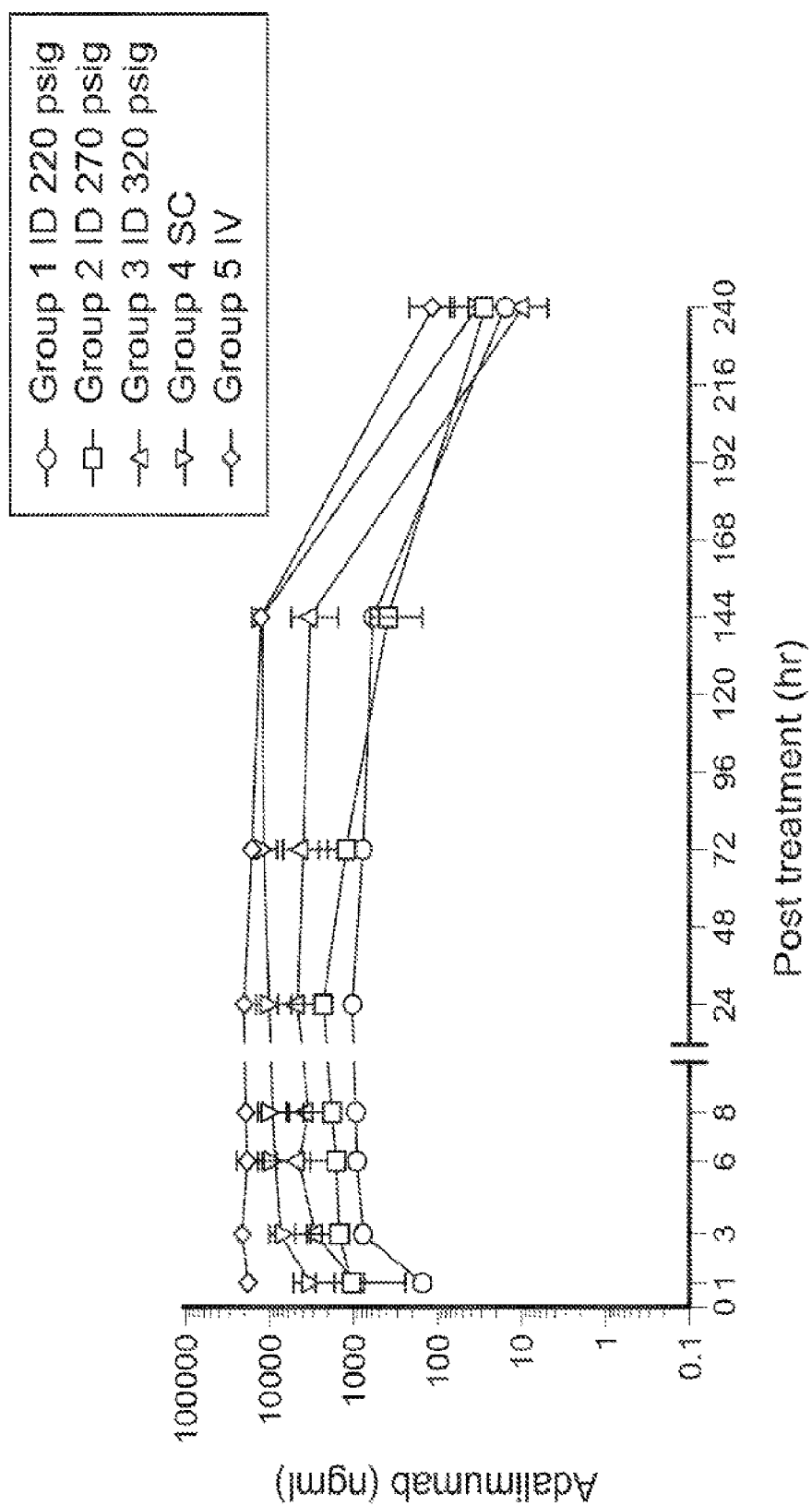
FIG. 52 shows adalimumab concentration in swine plasma over 10 days after: ID administration via the endoscopically placed ingestible device having an internal pressure of 220 psig, 270 psig or 320 psig; SC administration; and IV administration.

The results are summarized in Table 34. FIG. 52 charts the adalimumab plasma concentration over 10 days for each group.

TABLE 34

| | 2 Nozzle Jet Delivery Device | | | Controls | |
|---|---|---|---|---|---|
| | Group 1: 220 PSIG | Group 2: 270 PSIG | Group 3: 320 PSIG | Group 4: SC | Group 5: IV |
| Route | ID | ID | ID | SC | IV |
| N | 2 | 4 | 5 | 3 | 3 |
| $T_{max}$ (days) | 1 | 1 | 1 | 6 | 0.13 |

TABLE 34-continued

|  | 2 Nozzle Jet Delivery Device | | | Controls | |
| --- | --- | --- | --- | --- | --- |
|  | Group 1: 220 PSIG | Group 2: 270 PSIG | Group 3: 320 PSIG | Group 4: SC | Group 5: IV |
| $C_{max}$ (µg/mL) | 0.57 | 2.27 | 5.00 | 12.60 | 20.92 |
| AUC (µg · day/mL) (±SEM) | 3.32 ± 2.59 | 8.50 ± 4.16 | 32.31 ± 8.09 | 91.87 ± 12.58 | 122.67 ± 7.68 |
| AUC (µg · day/mL) Corrected for dose (±SEM) | 3.02 ± 2.31 | 8.19 ± 3.62 | 32.50 ± 8.10 | N/A | N/A |
| Bioavailability over IV$^a$(%) | 2.46 ± 1.88 | 6.68 ± 2.95 | 26.25 ± 6.60 | 74.89 ± 10.26 | 100 |
| Bioavailability over SC$^a$(%) | 3.28 ± 2.51 | 8.92 ± 3.94 | 35.38 ± 8.82 | 100 | Not calculated |

$^a$AUC corrected for dose was used to calculate bioavailability.

Example 6—Evaluation of the Bioavailability of Dulaglutide after Intraduodenal Administration Via an Ingestible 2-Nozzle Jet Delivery Device in Female Yorkshire Pigs A study was performed to determine the plasma pharmacokinetics of dulaglutide in female Yorkshire pigs after intravenous (IV), subcutaneous (SC), or intraduodenal (ID) administration via an endoscopically placed ingestible device.

Test Article

TRULICITY® (dulaglutide solution) having a dulaglutide concentration of 1.5 mg/0.5 mL (i.e., 3 mg/mL) was used in this study. Dulaglutide is a long-acting glucagon-like peptide 1 (GLP-1) receptor agonist having a molecular weight of about 63 kDa. The molecule consists of 2 identical disulfide-linked chains, each containing a modified human GLP-1 analogue sequence covalently linked to a modified human immunoglobulin G4 (IgG4) heavy chain fragment (Fc) by a small peptide linker. The GLP-1 analogue portion of dulaglutide is approximately 90% homologous to native human GLP-1 (7-37).

Ingestible Device Configuration

Each ingestible device was configured as a capsule comprising a substance reservoir; a gas reservoir; a one-way duckbill valve; a piston; two nozzles radially configured 180 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the amount of test article delivered was determined. Typically, approximately 0.050 mL was retained in the ingestible device after test article delivery was completed. Thus, approximately 0.400 mL of test article was dispensed from each ingestible device.

A summary of parameters for the delivery of the test article solution via the ingestible device is provided below. Initial and final refer to values at the beginning and end of the dispensing period for the test article, respectively.

Internal pressure (pressure of pre-compressed gas): about 320 psig

Pre-compressed gas volume in ingestible device: about 370 microliters (initial) to about 770 microliters (final)

Nozzle diameter: 0.35 mm

Nozzle length: 2 mm

Nozzle throat geometry: circular, sharp-edged orifice

Piston diameter: 9.6 mm

Piston friction: 10 N (one (1) O-ring on piston)

Friction pressure loss: about 20 psig

Fluid pressure: about 300 psig (peak; initial) to about 95 psig (minimum; final)

Jet velocity: about 36.5 m/s (peak; initial) to about 20 psig (minimum; final)

Mean jet velocity: about 26 to 27 m/s

Fluid dispensing time (total): about 80 ms

Jet impact force: about 0.13 N (peak; initial) to about 0.04 N (minimum; final)

Jet impact pressure: 193 psig (peak; initial) to about 60 psig (minimum; final)

Jet power: 2.3 W (peak; initial) to about 0.4 W (minimum; final)

Jet diameter: about 0.35 mm (initial)
Nozzle stand-off distance: >1.5 mm
Device diameter: 11.6 mm
Device length: about 34 to 36 mm In Vivo Study Design A total of 11 healthy female Yorkshire pigs (*Sus scrofa domesticus*) were used for the study: n=5 for ID administration, n=3 for IV administration, and n=3 for SC administration. Each pig weighed between about 25-30 kg at the initiation of the study. A 1.2 mg (~0.04 mg/kg) dose of the dulaglutide solution was administered to each pig by either ID administration via the endoscopically placed ingestible device (Group 1), IV administration (Group 2), or SC administration (Group 3). The study design is shown below in Table 35.

TABLE 35

Study Design

| Group # | Dose Route | N | Dose | Dose Conc. (mg/mL) | Clinical Observations | Blood Collection Time Points | Termination & Necropsy |
|---|---|---|---|---|---|---|---|
| 1 | ID | 5 | 1.2 mg | 3 | Twice on the day of each dose administration, and 24, 72, 144, and 240 hours post dose | Pre-dose, 1, 3, 6, 8, 24, 72, 144, and 240 hours post dose | At termination, necropsy of abdominal region to assess signs of hematoma and gross lesions |
| 2 | IV | 3 | (0.4 mL) | | | | |
| 3 | SC | 3 | (~0.04 mg/kg) | | | | |

Dulaglutide solution was administered at t=0 on the day of dosing. The animals were anesthetized with an intramuscular injection of a cocktail containing ketamine (approximately 10-20 mg/kg), xylazine (approximately 1-2 mg/kg) and atropine (approximately 0.02-0.04 mg/kg). The animals were intubated and maintained using isoflurane (approximately 3-5% in oxygen 1 to 4 L/min) as necessary until dosing was complete. The animals were wakened post dose.

Routes of Administration

For intraduodenal (ID) administration, the ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

For intravenous (IV) administration, the test article was administered intravenously via bolus dose into the marginal ear vein followed by a 1 mL flush with saline if necessary.

For subcutaneous (SC) administration, the test article was administered into the dorsal subcutaneous space directly at the base of the pig. Dose sites were gently shaved and circled with marker pen for identifying the injection site.

Sampling

Each blood sample (~2.0 mL) were taken from the jugular vein (or other suitable vessel) of each pig via direct venipuncture. The samples were collected into chilled tubes with K2EDTA as the anticoagulant, and inverted several times to mix. Blood samples were kept on wet ice until centrifugation. The blood samples were centrifuged at a temperature of 4° C., at 3,000×g, for 5 minutes. All samples were maintained chilled throughout processing. Plasma was collected into pre-labeled 2-mL microcentrifuge tubes and placed in a freezer set to maintain a temperature of −60° C. to −80° C. until further analysis by ELISA assay. The samples were taken prior to dosing, then again at 1, 3, 6, 8, 24, 72, 144, and 240 hours post-dose and sent to an off-site laboratory for bioanalytical analysis. Following the 240 hour post dose blood collection, the animals were euthanized via euthanasia solution IV bolus dose.

Analysis

Samples were processed and analyzed by using an enzyme-linked immunosorbent assay (ELISA) modified from a validated ELISA method for detecting dulaglutide in monkey serum (Vahle et al., Toxicol. Pathol. 43:1004-1014, 2015).

Briefly, 96-well microtiter plates were coated with mouse anti-human IgG (Fc) antibody (0.5 µg/mL) (Southern Biotech, Birmingham, Ala.) to capture dulaglutide in swine plasma. Dilutions of dulaglutide standards, quality control samples, and test samples were prepared in 10% swine plasma. Following preparation, the samples were incubated on the coated plates for 1 h at room temperature. The dulaglutide complex on the plate was bound with a mouse IgG2a kappa anti-GLP-1 antibody (ThermoFisher Scientific, Waltham, Mass.) and then detected using a mouse anti-mouse IgG2a-horseradish peroxidase (IgG2a-HPR) (Bethyl, Montgomery, Tex.) with tetramethylbenzidine (TMB) substrate. The standard curve ranged from 4.0-0.031 ng/mL, with 0.31 ng/mL being the lowest limit of quantitation. All plasma samples were diluted by 1:10, 1:50, or 1:100 depending on the concentration of the drug. All data and pharmacokinetic parameters were analyzed and graphed using GraphPad Prism version 7.00 for Windows, (GraphPad Software, La Jolla Calif. USA). The area under the concentration curve (AUC) versus time was calculated with the trapezoidal rules from the first sample collection time points (pre-dose, time 0) to last time point of sample collection (240 h post-dose) (($AUC_{T0-T240h}$)).

Non-compartmental analysis was used to determine PK parameters for each subject. $AUC_{T0-T240h}$, half-life, clearance, $C_{max}$ and $T_{max}$ were determined for each subject. The bioavailability of dulaglutide via ID administration (Group 1) in comparison to the IV (Group 2) and SC (Group 3) administrations was determined.

Results

Figure 53A:
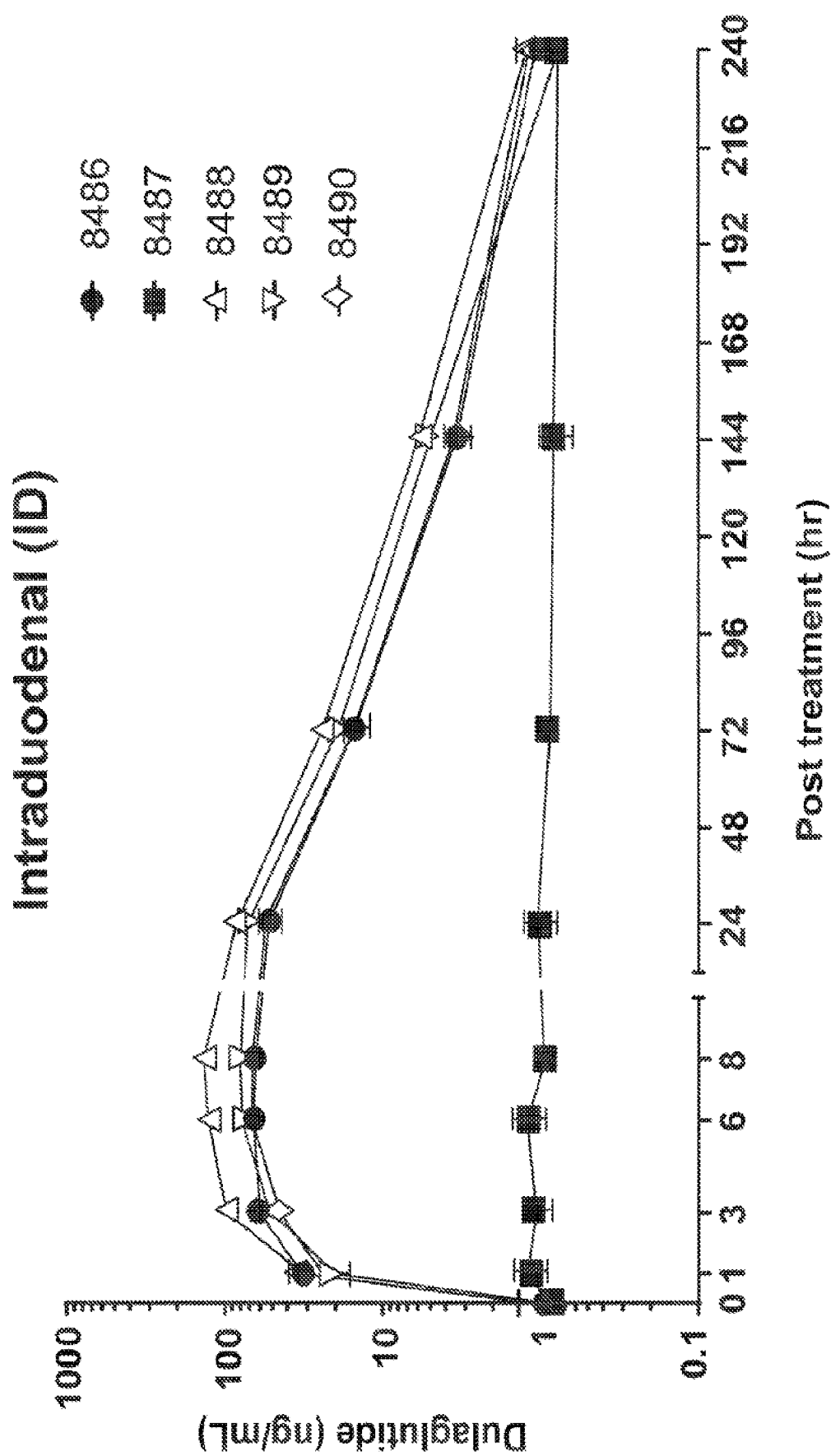
FIGS. 53A-53C show dulaglutide concentration in blood over time after: ID administration via the endoscopically placed ingestible device an internal pressure of 320 psig (FIG. 53A); SC administration (FIG. 53B); and IV administration (FIG. 53C).
Figure 53B:
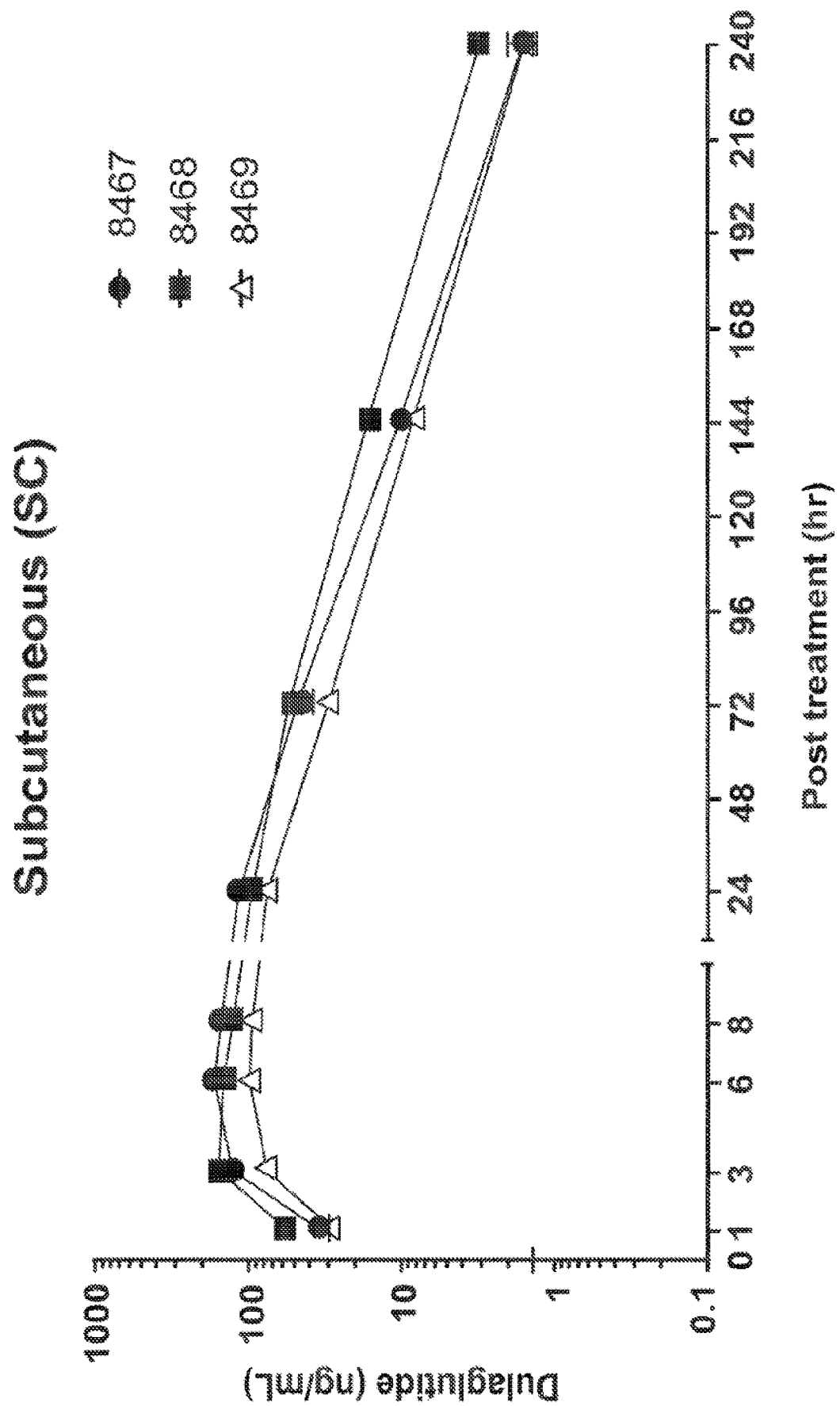
Figure 53C:
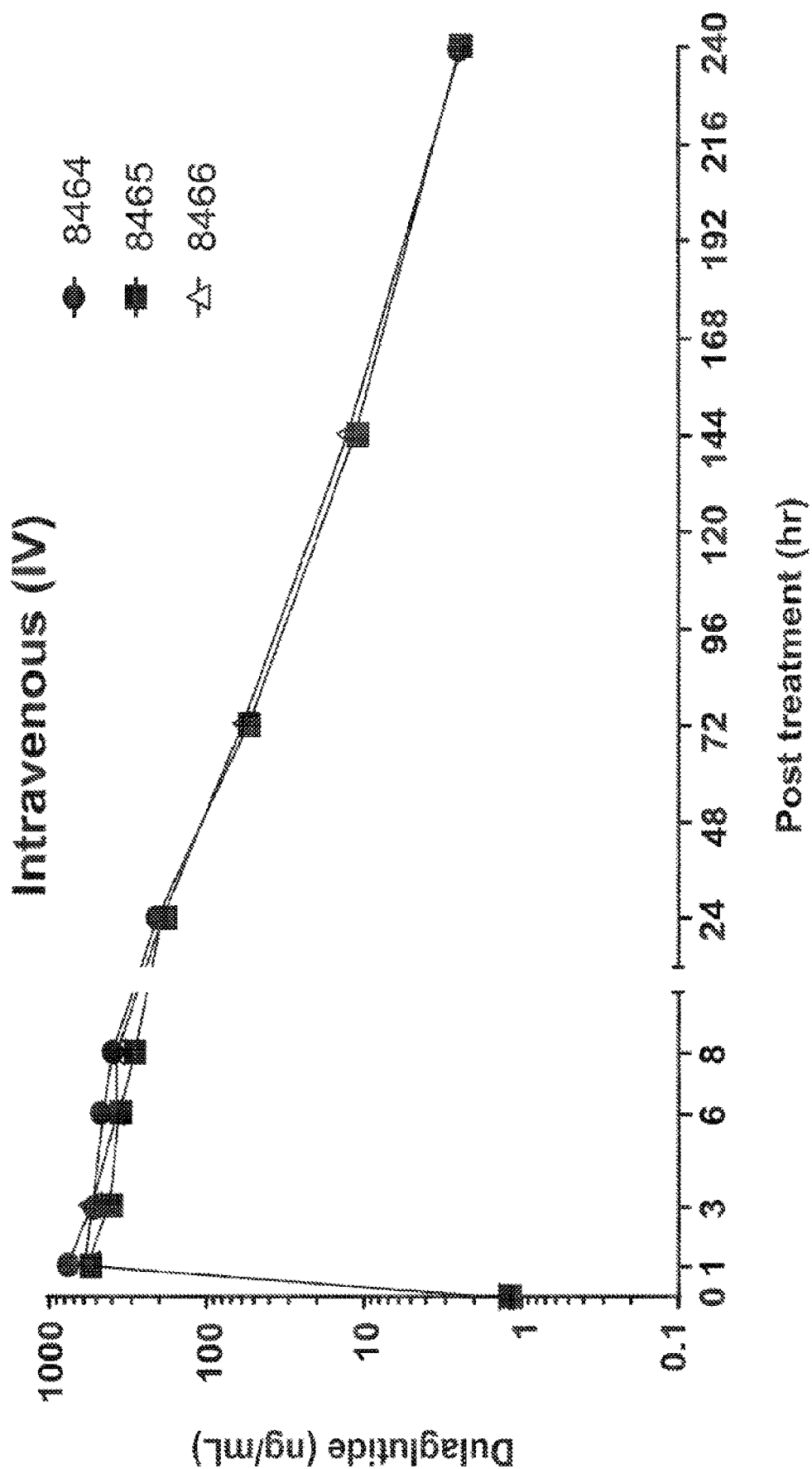

The results of the study are shown in Table 36 and in FIGS. 53A-53C and FIG. 54. FIGS. 53A-53C show the dulaglutide concentration in blood over time after: ID administration via the endoscopically placed ingestible device (FIG. 53A); SC administration (FIG. 53B); and IV administration (FIG. 53C). The plasma level of dulaglutide in one animal in Group 1 (no. 8487; ID) was below the limit of detection of the ELISA assay. Data obtained from this animal were excluded from subsequent bioavailability determinations. Prior to exclusion of these data, the ratio of the area under a curve (AUC) of the therapeutic agent concentration in systemic circulation versus time that was achieved when the drug was administered by the ID route ($AUC_{ID}$ (ng·hr/mL±SEM)) was 3890.00±94.73.

Figure 54:
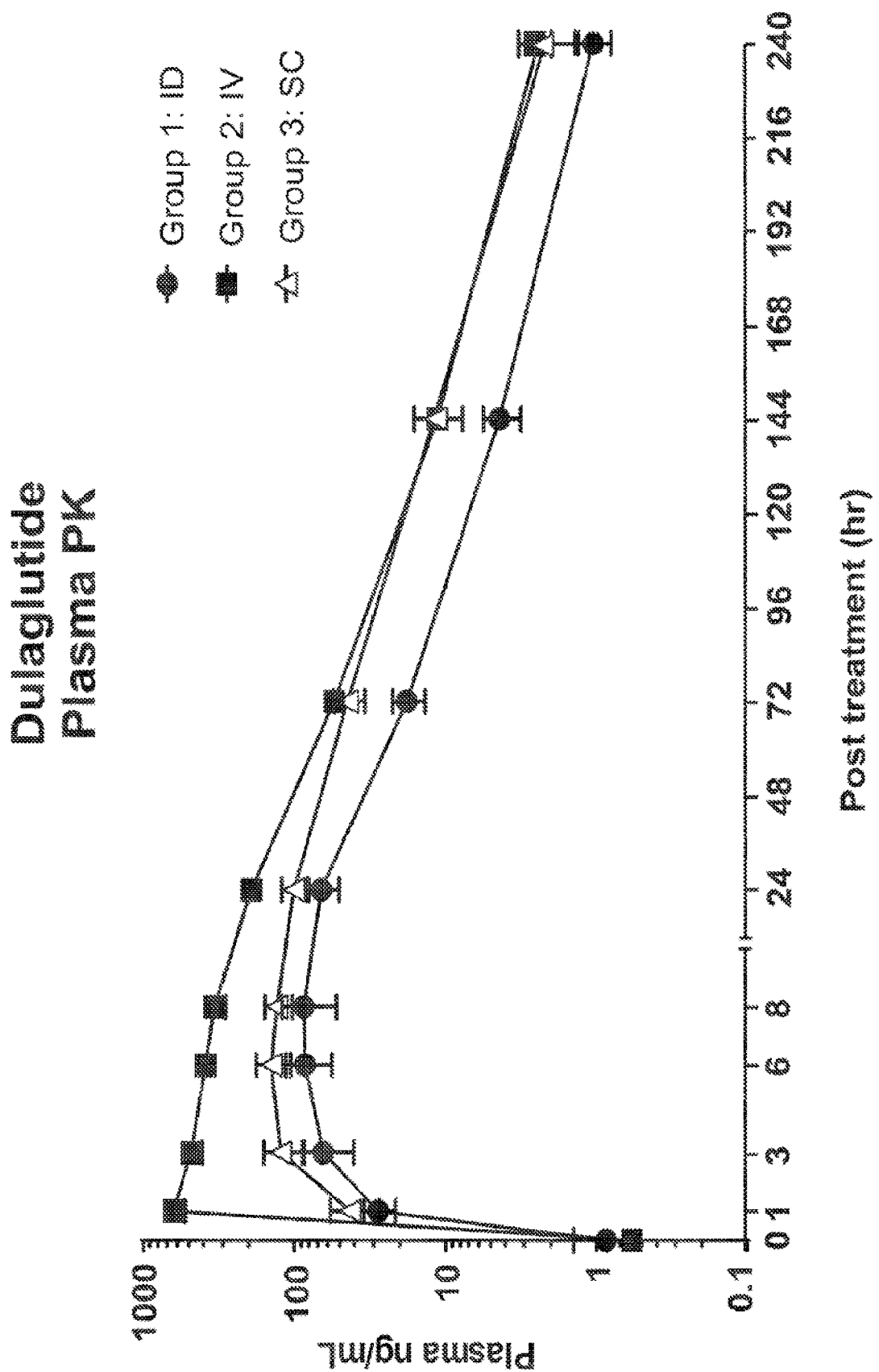
FIG. 54 shows the plasma concentration of dulaglutide over time via ID administration relative to IV or SC administration.

The bioavailability of dulaglutide via ID administration was determined relative to IV or SC administration. The results are shown in FIG. 54. For ID administration, the bioavailability relative to IV administration [$(AUC)_{ID/IV}$*100%] was about 33%, while the bioavailability relative to SC administration [$(AUC)_{ID/SC}$*100%] was about 61%.

TABLE 36

| | Dulaglutide plasma PK in swine | | |
|---|---|---|---|
| Route | ID | IV | SC |
| N | 4 [a] | 3 | 3 |
| $T_{max}$ (hr) | 8 | 1 | 6 |
| $C_{max}$ (ng) | 70.65 ± 19.18 | 632.93 ± 49.68 | 141.3 ± 17.09 |
| $(AUC)_{T0-T240\,h}$ ng · hr/mL ± SEM | 4355.86 ± 1094.57 [a] | 16429.33 ± 600.93 | 8869 ± 887.33 |
| Bioavailability relative to IV | 26.51 ± 6.55% [a] | 100% | 53.98% [a] |
| Bioavailability relative to SC | 49.11 ± 0.08% [a] | Not calculated | 100% |

[a] The plasma level of one animal was lower than the detection limit (see FIG. 53A) and therefore excluded from the $AUC_{ID}$ and $AUC_{ID}$-based calculations. When this animal is included in the analysis, the bioavailability relative to SC administration is 43.9% [$(AUC)_{ID/SC}$ * 100%], and the bioavailability relative to IV administration is 23.7% [$(AUC)_{ID/IV}$ * 100%].

Example 7—Identification of the Target Internal Pressure Range of an Ingestible 4-Nozzle Jet Delivery Device by Evaluating the Bioavailability Adalimumab after Intraduodenal (ID) Administration to Female Yorkshire Pigs A study was conducted to identify the target internal pressure range of an ingestible 4-nozzle jet delivery device required to achieve systemic uptake of adalimumab. In this study, the plasma pharmacokinetics of adalimumab were evaluated in female Yorkshire pigs after intraduodenal (ID) administration via an endoscopically placed ingestible device. The results were compared with those obtained after administration of adalimumab via a 2-nozzle jet delivery device, SC or IV (Example 5).

Test Article

Adalimumab in an aqueous buffer having an adalimumab concentration of about 106 mg/mL.

Ingestible Device Configuration

Each ingestible device was configured as a capsule comprising a substance reservoir; a gas reservoir; a one-way duckbill valve; a piston; four nozzles radially configured 90 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig or 350 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the amount of test article delivered was determined. Typically, approximately 0.050 mL was retained in the ingestible device after test article delivery was completed. Thus, approximately 0.400 mL of test article was dispensed from each jet delivery device.

A summary of parameters for the delivery of the test article via the ingestible device is provided in Table 37. Initial and final refer to values at the beginning and end of the dispensing period for the test article, respectively.

TABLE 37

Parameters for test article delivery from ingestible device

| | Internal pressure (pressure of pre-compressed gas): about 320 psig | Internal pressure (pressure of pre-compressed gas): about 350 psig |
|---|---|---|
| Pre-compressed gas volume in ingestible device | about 370 microliters (initial) to about 770 microliters (final) | |
| Nozzle diameter | 0.35 mm | |
| Nozzle length | 2 mm | |
| Nozzle stand-off distance | ≥1.5 mm | |
| Nozzle throat geometry | circular sharp-edged orifice | |
| Device diameter | 11.6 mm | |
| Device length | about 34 to 36 mm | |
| Piston diameter | 9.6 mm | |
| Piston friction | 10N (one (1) O-ring on piston) | |
| Friction pressure loss | about 20 psig | |
| Fluid pressure | about 300 psig (peak; initial) to about 95 psig (minimum; final) | about 330 psig (peak; initial) to about 105 psig (minimum; final) |
| Jet velocity | about 36.5 m/s (peak; initial) to about 21 m/s (minimum; final) | about 38 m/s (peak; initial) to about 21 m/s (minimum; final) |
| Mean jet velocity | about 26 m/s to 27 m/s | about 26 m/s to 27 m/s |
| Fluid dispensing time (total) | about 40 ms | about 40 ms |
| Jet impact force | about 0.13N (peak; initial) to about 0.04N (minimum; final) | about 0.14N (peak; initial) to about 0.04N (minimum; final) |
| Jet impact pressure | about 193 psig (peak; initial) to about 60 psig (minimum; final) | about 212 psig (peak; initial) to about 67 psig (minimum; final) |
| Jet power | about 2.3 W (peak; initial) to about 0.4 W (minimum; final) | about 2.7 W (peak; initial) to about 0.5 W (minimum; final) |
| Jet diameter | about 0.35 mm (initial) | about 0.35 mm (initial) |

In Vivo Study Design

A total of 9 healthy female Yorkshire pigs (*Sus scrofa domesticus*) having a body weight of 24-30 kg were used in this study. Five (N=5) were used in dose Group 1 and four (N=4) were used in dose Group 2. Each dose group received test article via intraduodenal (ID) administration. The study design is shown below in Table 38.

Animals were housed two per cage and fasted for a minimum of 12 hours prior to dosing. Food was returned at 4 hours post-dose. Water was supplied ad libitum. The dosing was as follows: Dose day 1: group 1 (n=2), and group 2 (n=3); Dose day 2: group 2 (n=3), and group 1 (n=2). Following the 240-hour post-dose blood collection the animals were euthanized via intramuscular bolus dose of euthanasia solution.

Intraduodenal (ID) administration was performed as follows. The ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

Sampling

Each blood sample was collected from the pig jugular vein, or other suitable vessel via direct venipuncture, placed into a chilled tube containing K2-EDTA as the anticoagulant, and inverted several times to mix. Blood samples were kept on wet ice until centrifugation. Blood samples were centrifuged at a temperature of 4° C., at 3,000×g, for 5 minutes and chilled throughout processing. Plasma was collected into pre-labeled polypropylene tubes and placed in a freezer set to maintain −60 to −80° C. prior to analysis.

Plasma samples were collected at pre-dose, 1, 3, 6, 8, 24, 72, 144, and 240 hours post-dose in all animals and sent to an off-site laboratory for bioanalytical analysis. Samples were processed and analyzed by using an adalimumab (anti-TNF-alpha) ELISA kit from Alpha Diagnostics, Inc. (Catalog #200 310-AHG). All plasma samples were diluted by 1:100 dilution. Diluted samples were processed in duplicates and the mean Optical Density (O.D.) was measured using a SpectraMax plate reader and utilizing SoftMax Pro software for analysis. The Lower Limit of Quantification (LLOQ) was calculated by adding IOX the standard deviation value of the blanks O.D. to the average of the blank standard O.D. values. Mean concentrations of adalimumab were back interpolated to a 4-parameter log fit standard curve and subsequently multiplied by the dilution factor to

TABLE 38

| Group # | Dose Route | N | Dose | Dose Conc. | Internal Device Pressure | Clinical Observations | Blood Collection Time Points | Termination & Necropsy |
|---|---|---|---|---|---|---|---|---|
| 1 | ID (Device) | 5 | 40 mg | 106 mg/mL | 320 PSIG | Twice on the day of each endoscopic event, and 24, 72, 144, and 240 hours post dose | Pre-dose, 1, 3, 6, 8, 24, 72, 144, and 240 hours post dose | Termination and necropsy of injection site to assess signs of hematoma and gross lesions (Day 10 post dose) |
| 2 | ID (Device) | 4 | 40 mg | 106 mg/mL | 350 PSIG | | | | obtain a final corrected adalimumab concentration. All data and pharmacokinetic parameters were analyzed and graphed by using GraphPad Prism version 7.00 for Windows, GraphPad Software, La Jolla Calif. USA, www.graphpad.com (GraphPad Prism 7). The area under the concentration curve (AUC) was calculated with the trapezoidal rules.

Results

Figure 55A:
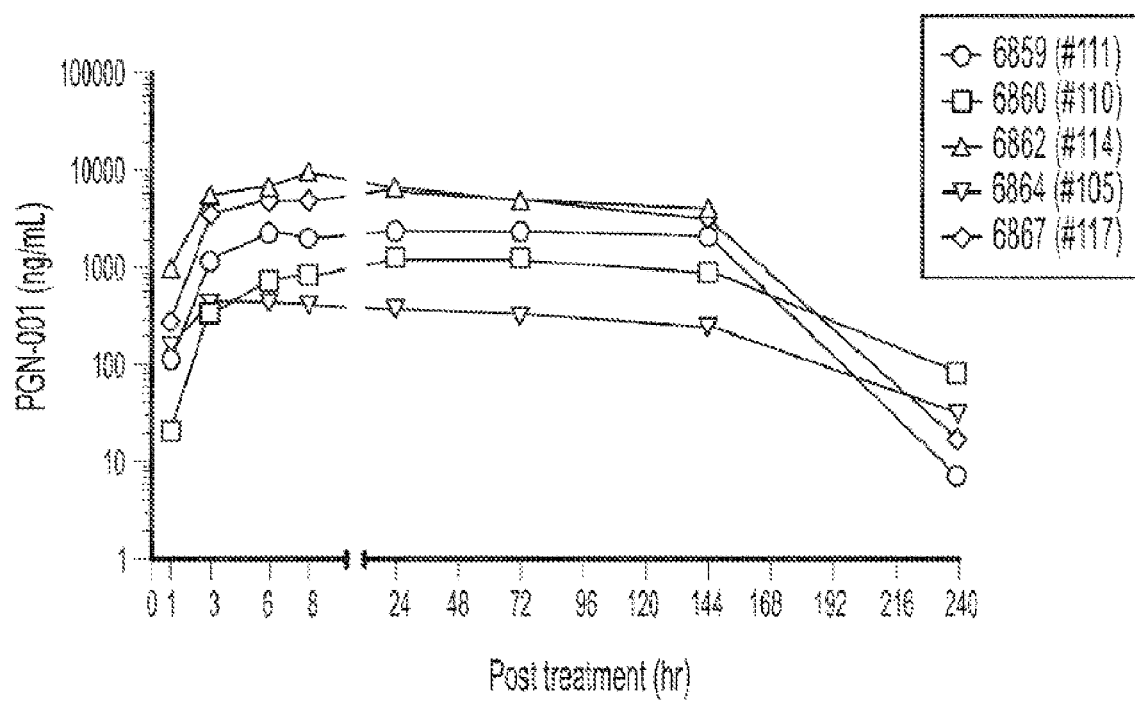
FIGS. 55A-55B show the plasma concentration of adalimumab over time in individual animals.
Figure 55B:
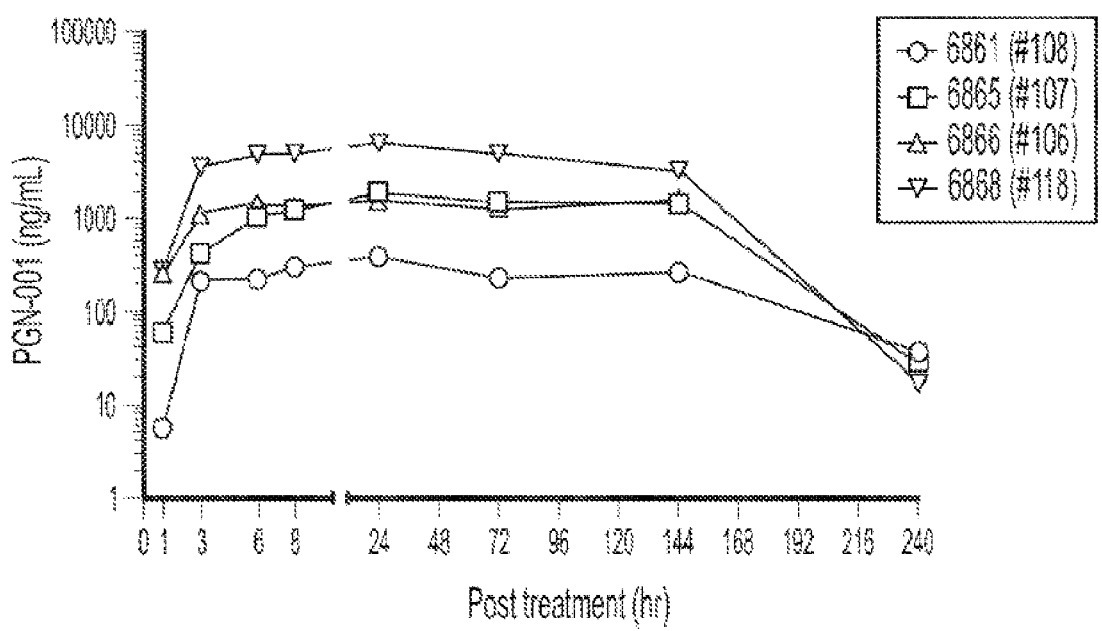

The plasma concentrations of adalimumab over time in individual animals are shown in FIGS. 55A-55B. FIG. 55A represents animals treated with adalimumab after ID administration via the endoscopically placed ingestible device having 4 nozzles and an internal pressure of 320 psig. FIG. 55B represents animals treated with adalimumab after ID administration via the endoscopically placed ingestible device having 4 nozzles and an internal pressure of 350 psig.

The PK results were compared to a subset of data from Example 5. The bioavailability was determined by comparison with Example 5 control arms (SC and IV administration). The results are summarized in Table 39.

TABLE 39

|  | 4 Nozzle | | 2 Nozzle[a] | Controls[a] | |
| --- | --- | --- | --- | --- | --- |
|  | Group 1: 320 PSIG | Group 2: 350 PSIG | Group 3: 320 PSIG | Group 4: SC | Group 5: IV |
| Route | ID | ID | ID | SC | IV |
| N | 4 | 4 | 5 | 3 | 3 |
| $T_{max}$ (day) | 1 | 1 | 1 | 6 | 0.13 |
| $C_{max}$ (ug/mL) | 3.64 | 2.63 | 5.00 | 12.60 | 20.92 |
| $AUC_{0-10}$ (ug · day/mL) (±SEM) | 23.831 ± 5.512 | 14.603 ± 6.305 | 32.31 ± 8.09 | 91.87 ± 12.58 | 122.67 ± 7.68 |
| $AUC_{0-10}$ (ug · day/mL) Corrected for Dose (±SEM) | 23.997 ± 5.6147 | 15.171 ± 6.522 | 32.25 ± 8.10 | N/A | N/A |
| Bioavailability over IV[b] (±SEM) | 19.560 ± 4.577 | 12.367 ± 5.317 | 26.25 ± 6.60 | 74.89 ± 10.26 | 100 |
| Bioavailability over SC[b] (±SEM) | 26.120 ± 3.731 | 16.513 ± 4.334 | 35.38 ± 8.82 | 100 | Not calculated |

[a]Data from Example 5
[b]AUC corrected for dose was used to calculate bioavailability.

Figure 56:
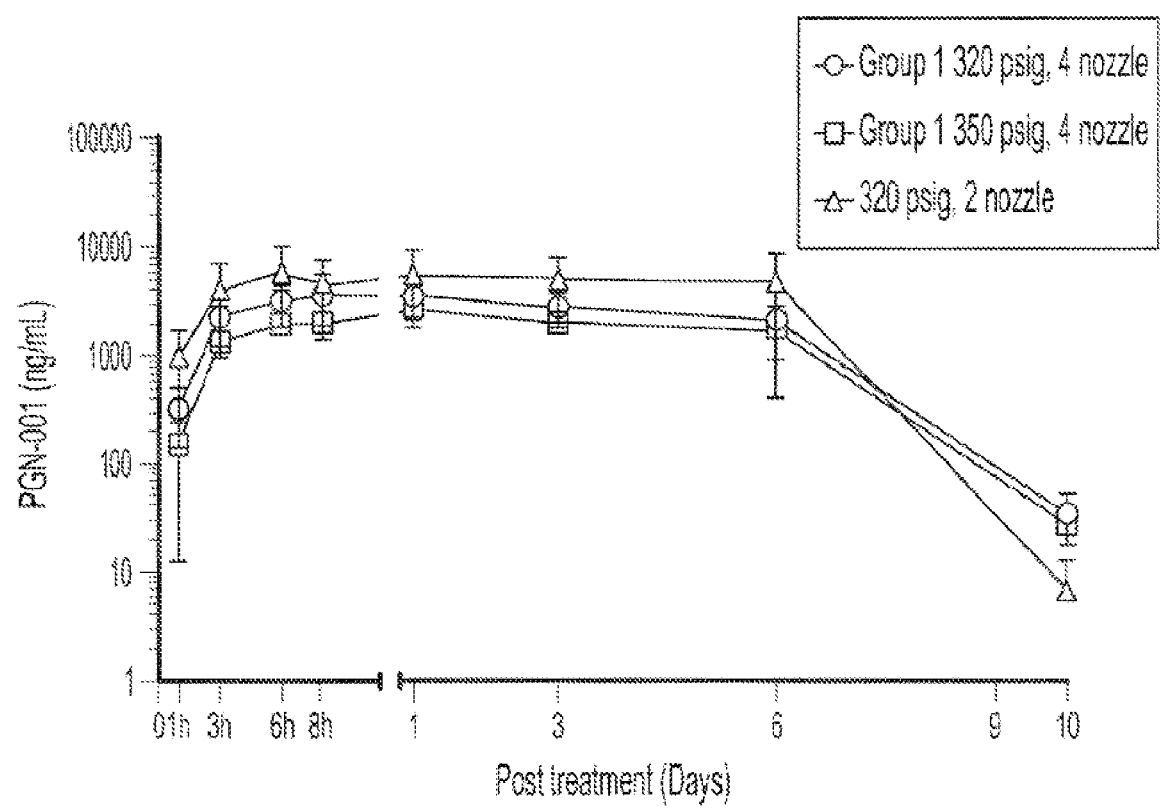
FIG. 56 shows the mean plasma concentration of adalimumab (ng/mL±SEM) over time (0-240 hours) after ID administration via the endoscopically placed ingestible device having: 4 nozzles and an internal pressure of 320 psig (Group 1); 4 nozzles and an internal pressure of 350 psig (Group 2); 2 nozzles and an internal pressure of 320 psig.

FIG. 56 shows the mean plasma concentration of adalimumab (ng/mL+SEM) over time (0-240 hours) after ID administration via the endoscopically placed ingestible device having: 4 nozzles and an internal pressure of 320 psig (Group 1); 4 nozzles and an internal pressure of 350 psig (Group 2); 2 nozzles and an internal pressure of 320 psig (Example 5, Group 3).

Example 8—Evaluation of the Stability and Integrity of Adalimumab After Delivery via an Ingestible Device The effects that various drug dispensing variables, such as nozzle geometry and delivery pressure, have on the structure and function of the target drug adalimumab were evaluated. Delivery pressures up to 300 psi and nozzle dimensions down to 0.35 mm diameter were tested.

The experimental design is as follows. Briefly, a drug (adalimumab) was loaded into a jet device including a piston with a release mechanism. On the back side of the piston, pressure was provided by a hand pump, and the release mechanism was released to release the drug. The end fastener was screwed on to secure the nozzle insert and seal the chamber. The jet device was operated at a target pressure to dispense the drug into a polypropylene tube for collection and analysis. For the minimum pressure test, the jet was operated manually by slowly pushing the piston forward to dispense the drug. For the maximum pressure test, 300 pounds per square inch gauge (psig) were applied to the jet device, and the drug was carefully dispensed into a polypropylene collection tube. After each dose was delivered, the remaining gas pressure was relieved, and the nozzle was cleaned.

Target Binding

Tests were conducted to determine whether certain pressures and nozzle diameters used to deliver adalimumab with an ingestible device would result in physical damage to the drug and affect target drug binding.

Test Method

The drug (adalimumab) was loaded into the ingestible device and fired through a nozzle with varying diameters at various pressure conditions. Table 40 summarizes the samples and delivery conditions used.

TABLE 40

Description of Test Articles

| CODE | SAMPLE | Description |
| --- | --- | --- |
| A | Adalimumab Standard Delivery | Adalimumab delivered from a standard pipette as manufactured. |
| B | Very low Pressure | 0 psi gauge pressure, load device and dispense |
| T1 | Low Pressure | 160 psi gauge pressure, 0.5 mm nozzle diameter |
| T2 | Target Delivery | 230 psi gauge pressure, 0.35 mm nozzle diameter |
| T3 | Aggressive Pressure | 300 psi gauge pressure, 0.35 mm nozzle diameter |
| NC | Negative Control | Adalimumab delivered from a standard syringe as manufactured and pre-processed using Pierce FAb preparation kit |
| C | PBS Control | PBS Control |
| AlphaLISA Kit Parts | AlphaLISA Anti-INFα LOCI Kit | AlphaLISA LOCI Kit |

The drug was extracted utilizing the respective dispensing systems and tested by a competitive inhibition assay as described in Velayudhan et al., "Demonstration of functional similarity of proposed biosimilar ABP 501 to adalimumab," BioDrugs 30:339-351, 2016, and Barbeau et. al., "Application Note: Screening for inhibitors of TNFα/s TNFR1 Binding using AlphaScreen™ Technology," PerkinElmer Technical Note ASC-016, 2002.

Figure 57A:
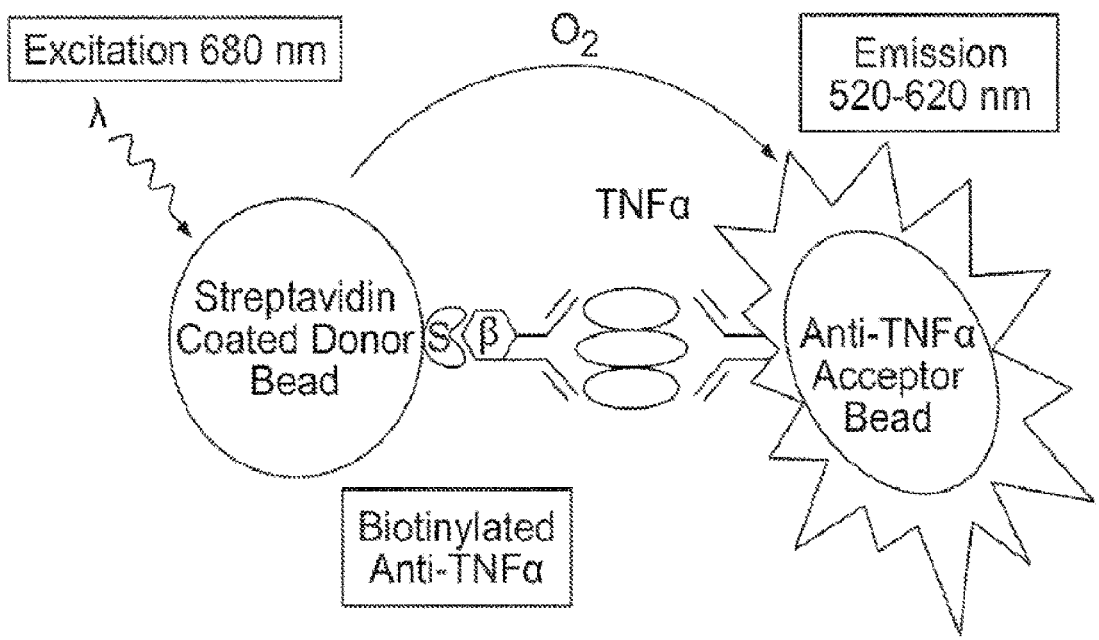
FIGS. 57A-57B illustrate the general principle of a competitive inhibition assay.
Figure 57B:
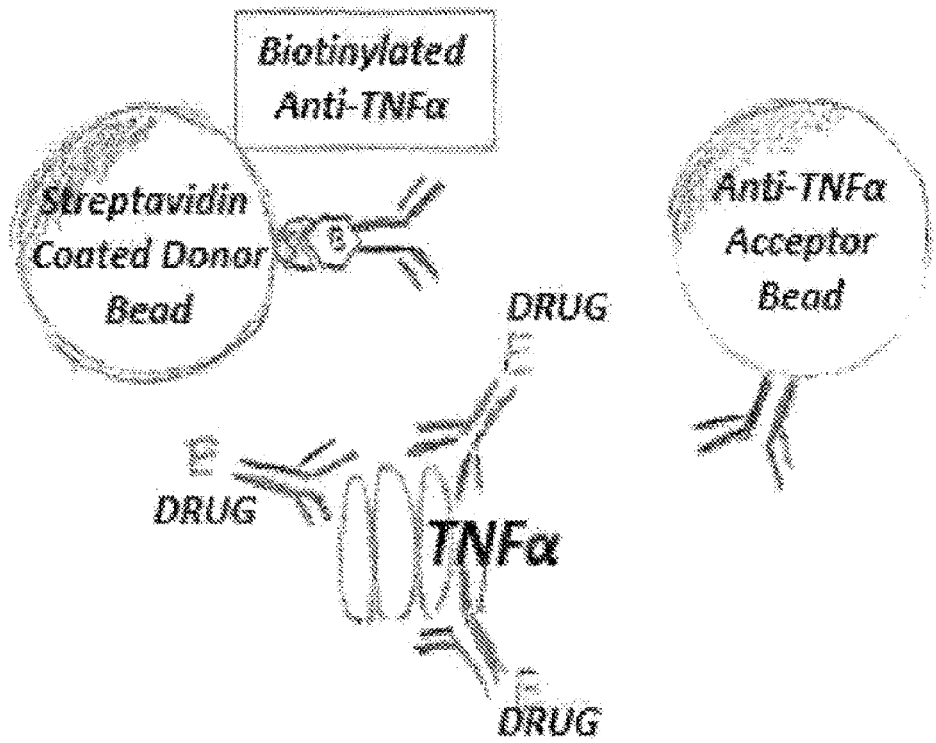

FIGS. 57A-57B illustrate the general principle of the assay. FIG. 57A shows binding of anti-TNFα to the TNFα receptor without drug, where uninhibited binding brings the Donor and Acceptor beads into close proximity for singlet oxygen transfer detection. FIG. 57B shows binding of anti-TNFα to TNFα that is inhibited by drug binding to TNFα, thus preventing binding to anti-TNFα antibodies and proximity oxygen singlet transfer detection.

Drug binding was detected using Luminescent Oxygen Channeling (LOCI™)—a competitive binding assay. Signal was detected by comparing to a non-drug carrier control and an artificially damaged drug using a commercial FAB fragmentation kit.

Drug function was determined through a competition binding assay comparing drug binding function for drug dispensed via standard delivery mechanism and drug delivered via the ingestible device with various pressures.

Results

Figure 58A:
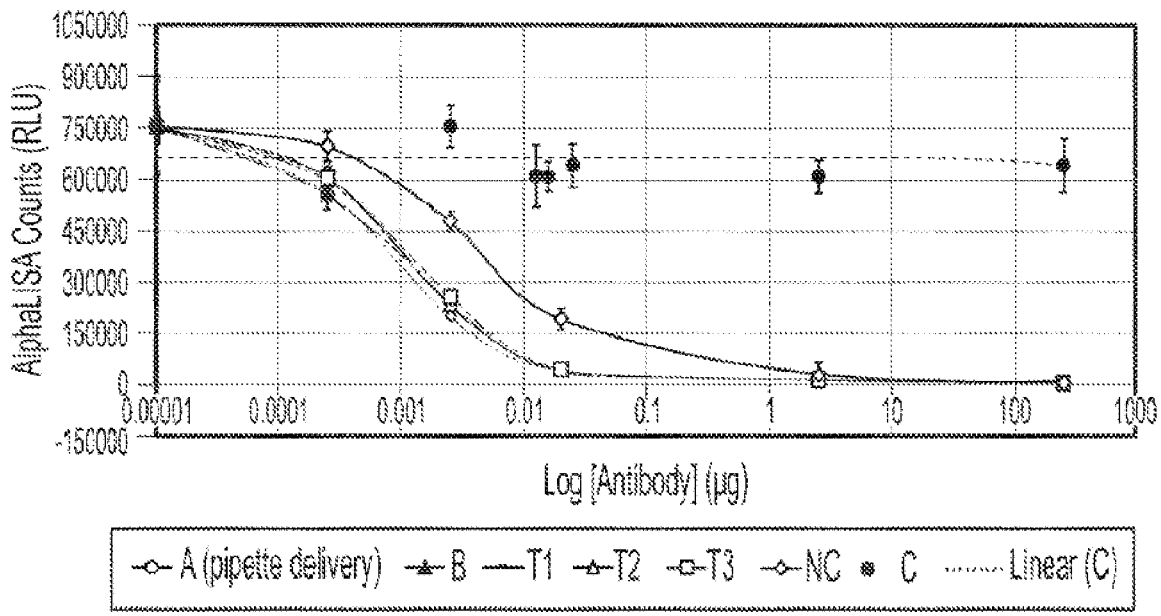
FIGS. 58A-58B are dose response curves of adalimumab binding to TNF-alpha.

The jet delivery pressures and nozzle dimensions utilized did not appear to affect the binding or function of the drug. Under the conditions evaluated in this experiment, the tested pressures did not significantly inhibit the ability of the drug to bind to the target TNFα as measured by the LOCI competitive inhibition assay. Table 41 shows the $IC_{50}$ values of adalimumab binding to TNFα under the various conditions tested. FIG. 58A is a dose response curve generated after adalimumab (10,000 pg/mL) was dispensed into collection tubes under the conditions described in Table 40.

TABLE 41

| IC50 of adalimumab binding to TNFα (10,000 pg/mL) | | | | | | | |
|---|---|---|---|---|---|---|---|
| | A | B | T1 | T2 | T3 | NC | C |
| IC50 (µg) | 0.0007 | 0.0008 | 0.0009 | 0.0009 | 0.001 | 0.0045 | NA |

Figure 58B:
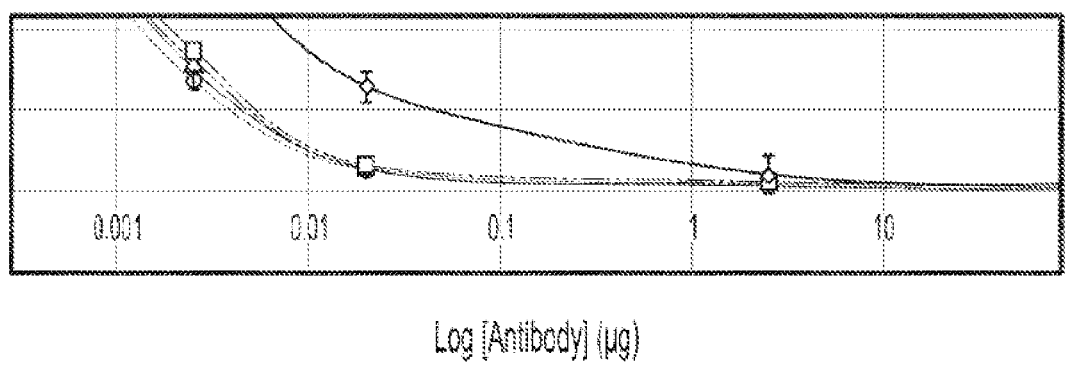

Any observable differences between the tested pressures and nozzle dimensions were within the standard deviation of the assay (FIG. 58B). The negative control (NC) sample curve was shifted to the right, demonstrating that damaged drug binds less to TNFα, allowing for an increase of singlet oxygen transfer due to the proximity of the Donor and Acceptor Beads.

Drug Structure

The purpose of this study was to evaluate the effects that nozzle geometry and delivery pressure have on drug structure when the drug is dispensed from a jet delivery device using different delivery pressures and nozzle sizes. Structural changes in the jet-delivered drug could potentially result in compromised functioning of the drug in vitro.

Test Method

The drug (adalimumab drug substance (DS)) was loaded into the simulated capsule jet delivery device and ejected using different pressures and nozzle geometries. Table 42 summarizes the samples and delivery conditions used.

TABLE 42

| Test articles | | |
|---|---|---|
| CODE | SAMPLE | Description |
| A | Adalimumab Standard Delivery | Adalimumab delivered from a standard pipette as manufactured. |
| B | Very low Pressure | 0 psi gauge pressure, load device and dispense |
| T1 | Low Pressure | 160 psi gauge pressure, 0.5 mm nozzle diameter |
| T2 | Target Delivery | 230 psi gauge pressure, 0.35 mm nozzle diameter |
| T3 | Aggressive Pressure | 300 psi gauge pressure, 0.35 mm nozzle diameter |
| NC | Negative Control | Adalimumab processed using Pierce FAb preparation kit |
| PPC | Pre-papain Positive Control | Adalimumab DS, desalted and diluted; pre-papain column |
| $NC_{gel}$ | Negative Control for Gel Analysis | Old stock adalimumab processed using Pierce Fab preparation kit; known gel profile |
| $PC_{gel}$ | Positive Control for Gel Analysis | Old stock adalimumab delivered from a standard syringe as manufactured; known gel profile |

Figure 59:
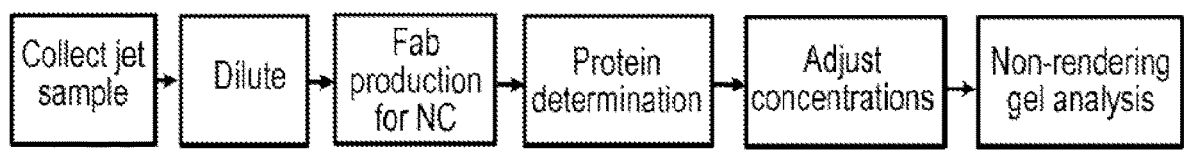
FIG. 59 is a flow chart of the experimental design.
Figure 60:
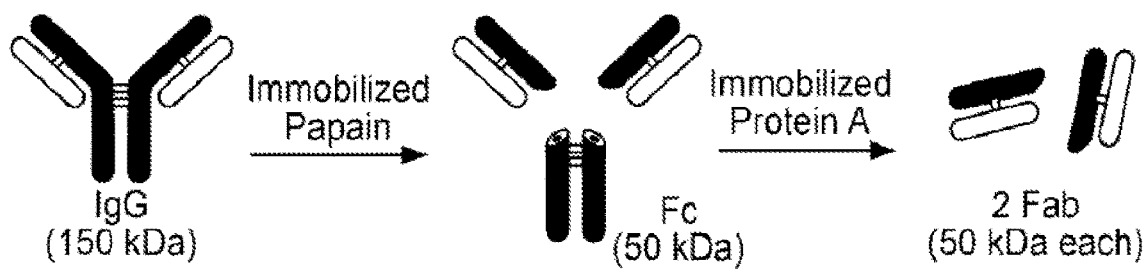
FIG. 60 shows the assay principle of negative control (NC) production.

The experimental design flow is shown in FIG. 59 and the assay principle is shown in FIG. 60. Briefly, OD280 nm readings were taken of pre- and post-dispensed samples, and pre- and post-papain digested adalimumab DS (whole IgG and Fab/Fc fragments, respectively) using a Cytation 5 plate reader and Take 3 micro-volume plate. The resulting protein concentrations were obtained using an extinction coefficient of 1.4 and Gen5 version 3.03.14 program. The samples were then diluted and the protein profiles were analyzed using non-reducing SDS-PAGE. Protein banding patterns of the dispensed samples were compared to that of the unmanipulated drug and the drug artificially damaged (enzymatically degraded) via the papain in a commercial Fab fragmentation kit (Pierce™ Fab Preparation Kit).

For gel analysis, protein was mixed with non-reducing sample buffer. Samples were not heated. 5 µg of samples and controls were loaded per lane of a SDS-PAGE gel (4% Acrylamide-Bis stacking, 12% resolving; see Table 43). The gel was electrophoresed at 195 V and stained in R-250 Coomassie Blue dye.

TABLE 43

| Gel Lane | Code | Quantity |
|---|---|---|
| 1 | MW Standard | 5 µL |
| 2 | A | 5 µg |
| 3 | B | 5 µg |
| 4 | T1 | 5 µg |
| 5 | T2 | 5 µg |
| 6 | T3 | 5 µg |
| 7 | NC | 5 µg |
| 8 | PPC | 5 µg |
| 9 | $PC_{gel}$ | 5 µg |
| 10 | $NC_{gel}$ | 5 µg |

Results

The results are shown in Table 44. None of the jet delivery pressures or nozzle sizes utilized appeared to affect the structure of the drug.

TABLE 44

| Code | Location | 280 Raw | 260 Raw | 320 Raw | 280 | 260 | 260/280 | mg/mL | Mean | CV (%) |
|---|---|---|---|---|---|---|---|---|---|---|
| A | B2 | 0.947 | 0.498 | 0.047 | 0.95 | 0.473 | 0.498 | 13.865 | 13.516 | 3.66 |
|   | B3 | 0.902 | 0.478 | 0.049 | 0.902 | 0.451 | 0.5 | 13.166 |   |   |
| B | C2 | 0.89 | 0.469 | 0.046 | 0.894 | 0.445 | 0.498 | 13.053 | 12.997 | 0.611 |
|   | C3 | 0.885 | 0.469 | 0.051 | 0.886 | 0.441 | 0.498 | 12.941 |   |   |
| T1 | D2 | 0.884 | 0.466 | 0.047 | 0.889 | 0.442 | 0.497 | 12.985 | 12.922 | 0.688 |
|   | D3 | 0.87 | 0.458 | 0.047 | 0.881 | 0.437 | 0.497 | 12.859 |   |   |
| T2 | E2 | 0.872 | 0.461 | 0.049 | 0.874 | 0.435 | 0.497 | 12.765 | 12.782 | 0.193 |
|   | E3 | 0.864 | 0.455 | 0.046 | 0.877 | 0.435 | 0.496 | 12.8 |   |   |
| T3 | F2 | 0.848 | 0.449 | 0.051 | 0.844 | 0.419 | 0.496 | 12.322 | 12.364 | 0.472 |
|   | F3 | 0.841 | 0.443 | 0.045 | 0.85 | 0.421 | 0.496 | 12.405 |   |   |
| NC | C2 | 0.552 | 0.333 | 0.044 | 0.537 | 0.284 | 0.529 | 7.832 | 7.807 | 0.463 |
|   | C3 | 0.552 | 0.335 | 0.05 | 0.533 | 0.281 | 0.527 | 7.781 |   |   |
| PPC | B2 | 0.616 | 0.345 | 0.053 | 0.592 | 0.286 | 0.483 | 8.645 | 8.522 | 2.037 |
|   | B3 | 0.587 | 0.327 | 0.041 | 0.575 | 0.28 | 0.486 | 8.4 |   |   |
| $PC_{gel}$ | B2 | 0.076 | 0.059 | 0.037 | 0.039 | 0.019 | 0.492 | 0.57 | 0.569 | 0.102 |
|   | B3 | 0.076 | 0.059 | 0.037 | 0.039 | 0.019 | 0.493 | 0.569 |   |   |
| $NC_{gel}$ | B2 | 0.08 | 0.089 | 0.044 | 0.033 | 0.02 | 0.604 | 0.485 | 0.486 | 0.09 |
|   | B3 | 0.084 | 0.093 | 0.049 | 0.033 | 0.019 | 0.582 | 0.486 |   |   |

Figure 61:
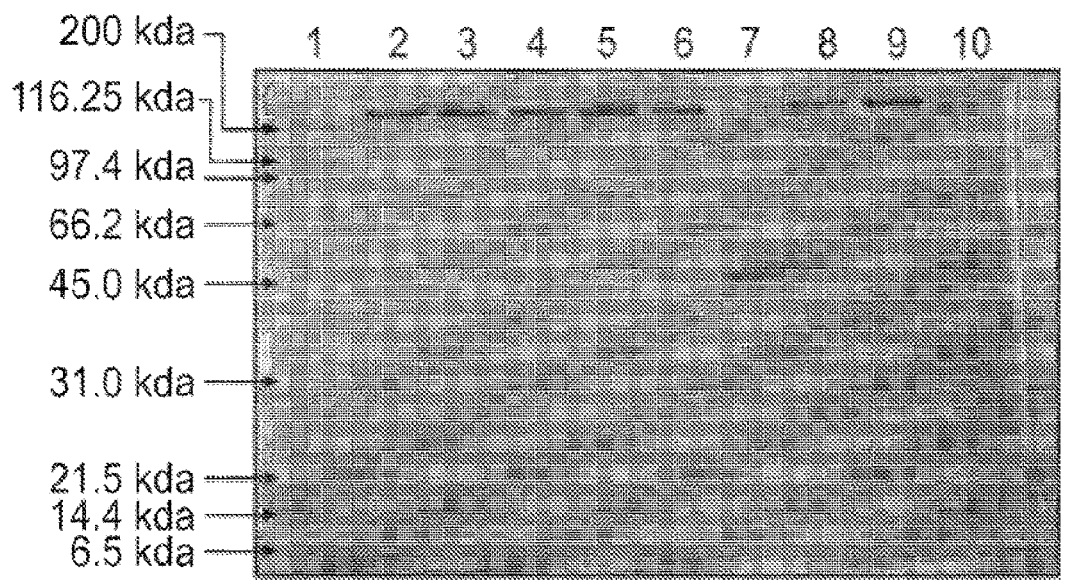
FIG. 61 shows the results of a gel analysis.

FIG. 61 shows the results of the gel analysis. All jet-delivered drug samples showed the same banding pattern as the unmanipulated drug. No subunit fragments were visible in their corresponding gel profiles, in comparison to intentionally degraded controls NC and $Nc_{gel}$. Banding for controls NC and $Nc_{gel}$ differed from each other. NC showed expected bands corresponding to Fab and Fc fragments (running at approx. 45-50 kda). $Nc_{gel}$ showed a lower MW band, likely due to further reduction of adalimumab (digested from a lower starting concentration than NC) to Fab heavy and light chain sub-components (approx. 25 kDa each). Undetermined fragments were also present (see column 8 of FIG. 61) as adalimumab was desalted, prior to its loading on the immobilized papain column.

No structural changes were evident and there was no physical indication that the drug had been inactivated through the dispensing pressures or nozzle sizes employed.

Example 9—Pharmacokinetic and Pharmacodynamic Assessment of Tofacitinib Citrate after Oral or Topical Intracecal Administration in a Dextran Sulfate Sodium (DSS)-Induced Colitis Mouse Model Study Design The overall study design is summarized in Table 45. Briefly, at least 10 days prior to the start of the study (Day −10), a cohort of male C57BL/6 mice underwent surgical implantation of a cecal cannula. Colitis was induced in 110 mice (Groups 2-7) by exposure to 3% DSS-treated drinking water from Day 0 to Day 5. Five animals (Group 1) served as no-disease controls; the other animals received a single dose of vehicle (Group 2) or tofacitinib citrate suspension containing about 0.5% excipients via oral gavage (PO; Groups 3 and 4) or intracecal injection via the surgically implanted indwelling catheter (IC; Groups 5, 6 and 7) once on Day 12 (peak disease status). All animals were weighed daily and assessed visually for the presence of diarrhea and/or blood in stool. A subset of animals per group was sacrificed for terminal PK collections at various time points post-dose. Terminal samples (plasma, cecal contents, colon contents, cecal tissue and colon tissue) were collected at terminal sacrifice. All $K_2EDTA$ plasma and tissue homogenate (proximal colon, cecum and associated lumen contents) were stored at −80° C. until further analysis.

TABLE 45

Description of Treatment Groups

| Group Number | Number of Animals | Cecal Cannula | Colitis Induction | Treatment | Dose (mg/kg) (Day 12)[1] | Route | PK Schedule |
|---|---|---|---|---|---|---|---|
| 1 | 5 | no | (a) | (a) | (a) | (a) | 24 h post-dose (n = 5) 24 h |
| 2 | 10 |   | 3% DSS in drinking water Days 0-5 | Control vehicle | 0 | PO | 1 and 24 h post-dose (n = 5 per timepoint) |
| 3 | 20 |   |   | Tofacitinib citrate suspension | 15 |   | 1, 3, 12, 24 h post-dose |
| 4 | 20 |   |   |   | 45 |   |   |
| 5 | 20 | yes |   |   | 1 | IC | (n = 5 per timepoint) |

TABLE 45-continued

Description of Treatment Groups

| Group Number | Number of Cecal Animals | Cecal Cannula | Colitis Induction | Treatment | Dose (mg/kg) (Day 12)[1] | Route | PK Schedule |
|---|---|---|---|---|---|---|---|
| 6 | 20 | | | | 3 | | |
| 7 | 20 | | | | 10 | | |

DSS = dextran sulfate sodium;
IC = Intracecal injection;
PK = Pharmacokinetics;
PO = oral gavage
(a) Five animals served as no-disease controls.
[1] All dose levels are expressed based on tofacitinib citrate salt form.

Sample Bioanalysis

Plasma samples and tissue homogenate (proximal colon, cecum and associated lumen contents) were assessed for tofacitinib. Briefly, samples were analyzed by LC-MS/MS against matrix-matched standard curves. Three additional samples were above their respective quantitation limits, and extrapolated data was reported.

To evaluate pharmacodynamic (PD) effects of tofacitinib in the DSS-induced colitis mouse model, several cytokines involved in the JAK/STAT signaling pathway, i.e., IL-6, GM-CSF, IL-15, IL-2, IL-12, IL-13, TNFα, and INF-γ, were measured in both plasma and colon tissue by ELISA.

The study design was complex and involved surgical procedure in a disease model. The PK/PD parameters were derived from limited timepoints and should be considered best estimates only.

All PK/PD concentrations are expressed as active drug moiety (anhydrous tofacitinib free base).

Pharmacokinetic Statistical Analysis

PK modeling was performed using mean plasma or tissue concentrations of tofacitinib versus time curves. The following PK parameters were calculated with a one-compartmental model using Excel software: time to maximum concentration: $T_{max}$; half-life: $t_{1/2}$, maximum concentration: $C_{max}$; clearance (Cl), area under the concentration-time curve from the start of dosing to the last protocol-specified time point: $AUC_{(0-24h)}$. The absolute oral bioavailability was estimated to be 74% based on: Xeljanz® (Tofacitinib tablets for oral administration) Prescribing Information Revised November 2012.

Results

Drug Tissue Concentrations

Figures 62A, 62B:
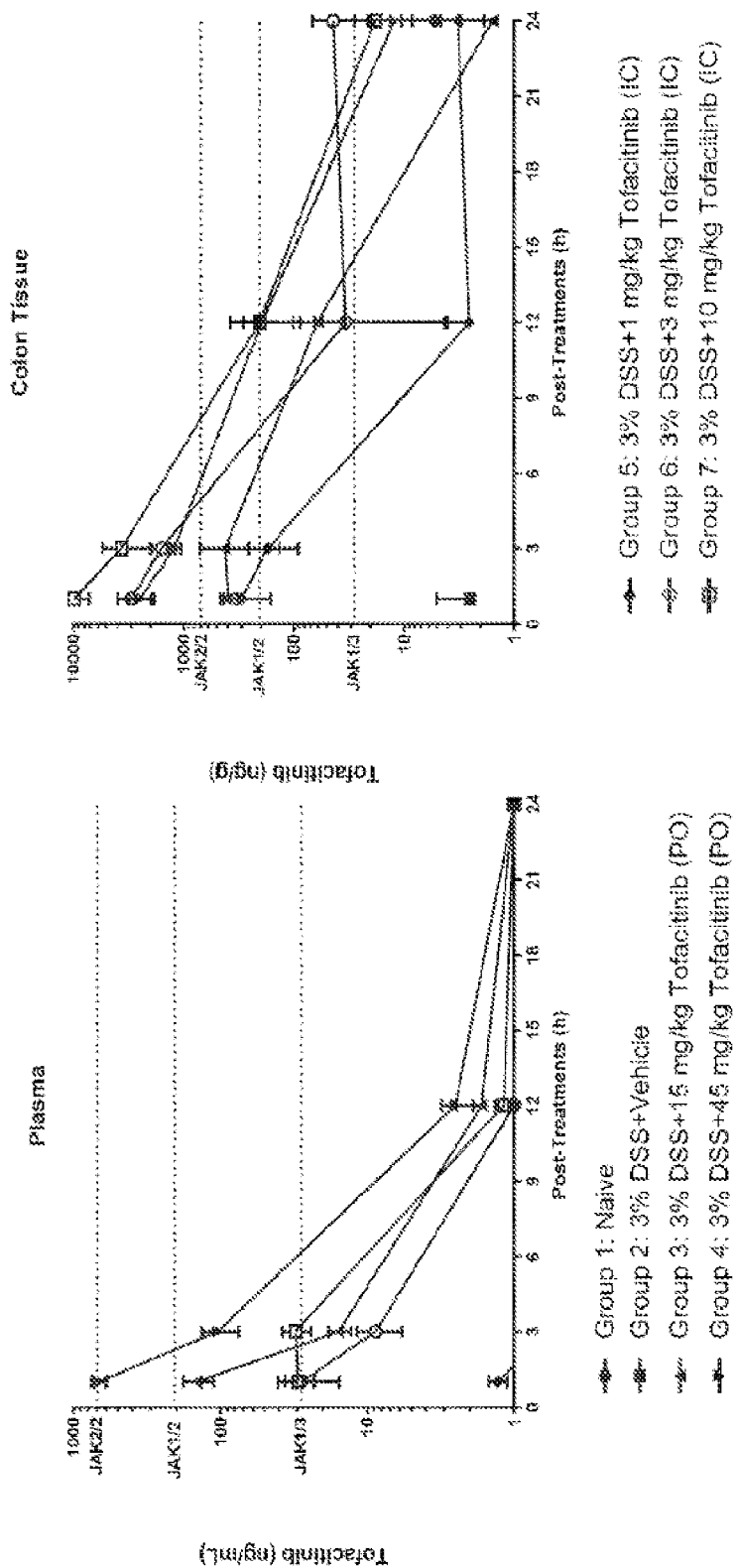
FIGS. 62A-62B show mean plasma (FIG. 62A) and colon tissue (FIG. 62B) concentrations of tofacitinib (free base) over a 24-hour period post-treatment with tofacitinib citrate or vehicle in a DSS-induced colitis mouse model. Dashed lines indicate in vitro $IC_{50}$ values for JAK1/3, JAK1/2 and JAK2/2 in whole blood. Error bars represent standard deviation.

Animals dosed PO with tofacitinib citrate (Groups 3-4) demonstrated the highest mean plasma tofacitinib concentrations at all timepoints, while limited blood exposure was observed in animals treated IC (Groups 5-6) (See FIGS. 62A-62B). Plasma $T_{max}$ occurred between 1.2 and 1.6 h post-dose in all groups, regardless of dosing route. Colon tissue $T_{max}$ occurred between 1.43 and 1.86 h post-dose in all IC groups, and at 2.25 and 2.33 h post-dose in PO groups (Table 46). At similar dose levels, IC delivery of tofacitinib citrate (IC, 10 mg/kg) resulted in an 18-fold higher tofacitinib AUC colon tissue/plasma ratio when compared to PO delivery (PO, 15 mg/kg) (AUC ratio 193.76 vs. 10.6, respectively; Table 46). Plasma and tissue tofacitinib exposure ($AUC_{0-24\ h}$) are also shown in FIGS. 63A-63C.

TABLE 46

Pharmacokinetic and pharmacodynamic parameters for tofacitinib over 24 hours after a single dose administration of tofacitinib citrate suspension on Day 12 in DSS-induced colitis mouse model

| Group Number | Route/Dose | Biological Matrix | Pharmacokinetic Parameters | | | | | | Pharmacodynamics | | |
|---|---|---|---|---|---|---|---|---|---|---|---|
| | | | Cmax (ng/mL) | AUC (ng·h/mL) | Tissue/plasma ratio | Tmax (h) | $T_{1/2}$ (h) | Clearance (mL/h) | $IC_{50}$ coverage (h)[a] | | |
| | | | | | | | | | JAK1/3[b] | JAK1/2[c] | JAK2/2[d] |
| 3 | PO/15 mg/kg | Plasma | 65.5 | 372.09 | 10.6 | 1.61 | 2.53 | 656.28 | 1 | 0 | 0 |
| | | Colon tissue | 552.7 | 3954.9 | | 2.25 | 3.23 | 61.82 | 12 | 3 | 0 |
| 4 | PO/45 mg/kg | Plasma | 467.1 | 1976.24 | 7.09 | 1.36 | 1.64 | 370.7 | 1 | 3 | 1 |
| | | Colon tissue | 1774.9 | 14006.55 | | 2.33 | 3.4 | 52.3 | 12 | 12 | 3 |
| 5 | IC/1 mg/kg | Plasma | 1.3 | 6.13 | 253.05 | 1.56 | 1.73 | 2653.91 | 0 | 0 | 0 |
| | | Colon tissue | 271.7 | 1551.21 | | 1.61 | 2.56 | 10.5 | 3 | 3 | 0 |
| 6 | IC/3 mg/kg | Plasma | 33.2 | 115.45 | 128.76 | 1.21 | 1.19 | 423.05 | 1 | 0 | 0 |
| | | Colon tissue | 2960.2 | 14865.55 | | 1.43 | 2.23 | 3.29 | 24 | 3 | 3 |
| 7 | IC/10 mg/kg | Plasma | 57.8 | 223.27 | 193.76 | 1.27 | 1.47 | 729.17 | 3 | 0 | 0 |
| | | Colon tissue | 7644.9 | 43261.18 | | 1.86 | 2.16 | 3.76 | 24 | 12 | 3 |

PO = oral gavage;
IC = intra-cecal injection;
$IC_{50}$ = half-maximum inhibitory concentration;
Groups 1 and 2: not applicable
[a] Concentrations above the $IC_{50}$ over the 24-hour period;
[b] $IC_{50}$ of JAK1/3 heterodimer = 56 nM[e] (28.25 ng/mL);
[c] $IC_{50}$ of JAK1/2 heterodimer = 406 nM[e] (204.83 ng/mL);
[d] $IC_{50}$ of JAK2/2 homodimer inhibition = 1377 nM[e] (694.7 ng/mL);
[e] Meyer et al. (2010) J. Inflamm. 7-41

Cytokines

Inflammatory cytokine IL-6 has been shown to play a critical role in the response of uncontrolled intestinal inflammation through JAK1/JAK2 and JAK1/TYK2 signaling pathways (Meyer et al. (2010) J. Inflamm. 7-41).

Figure 64A:
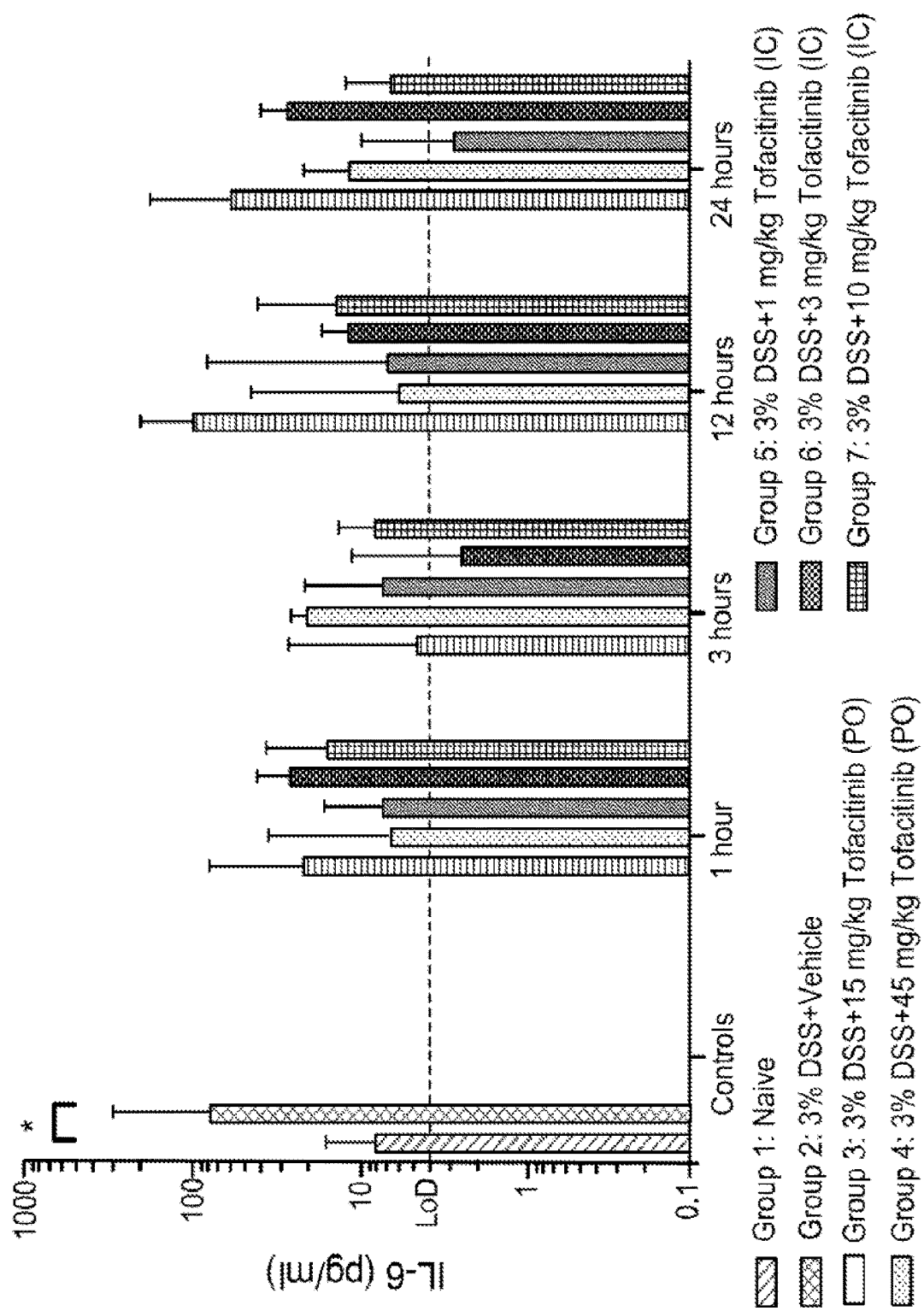
FIGS. 64A-64B show IL-6 concentrations in colon tissue over a 24-hour period post-treatment with vehicle or tofacitinib citrate via per oral (PO) or intracecal (IC) administration in a DSS-induced colitis mouse model on Study Day 12.
Figure 64B:
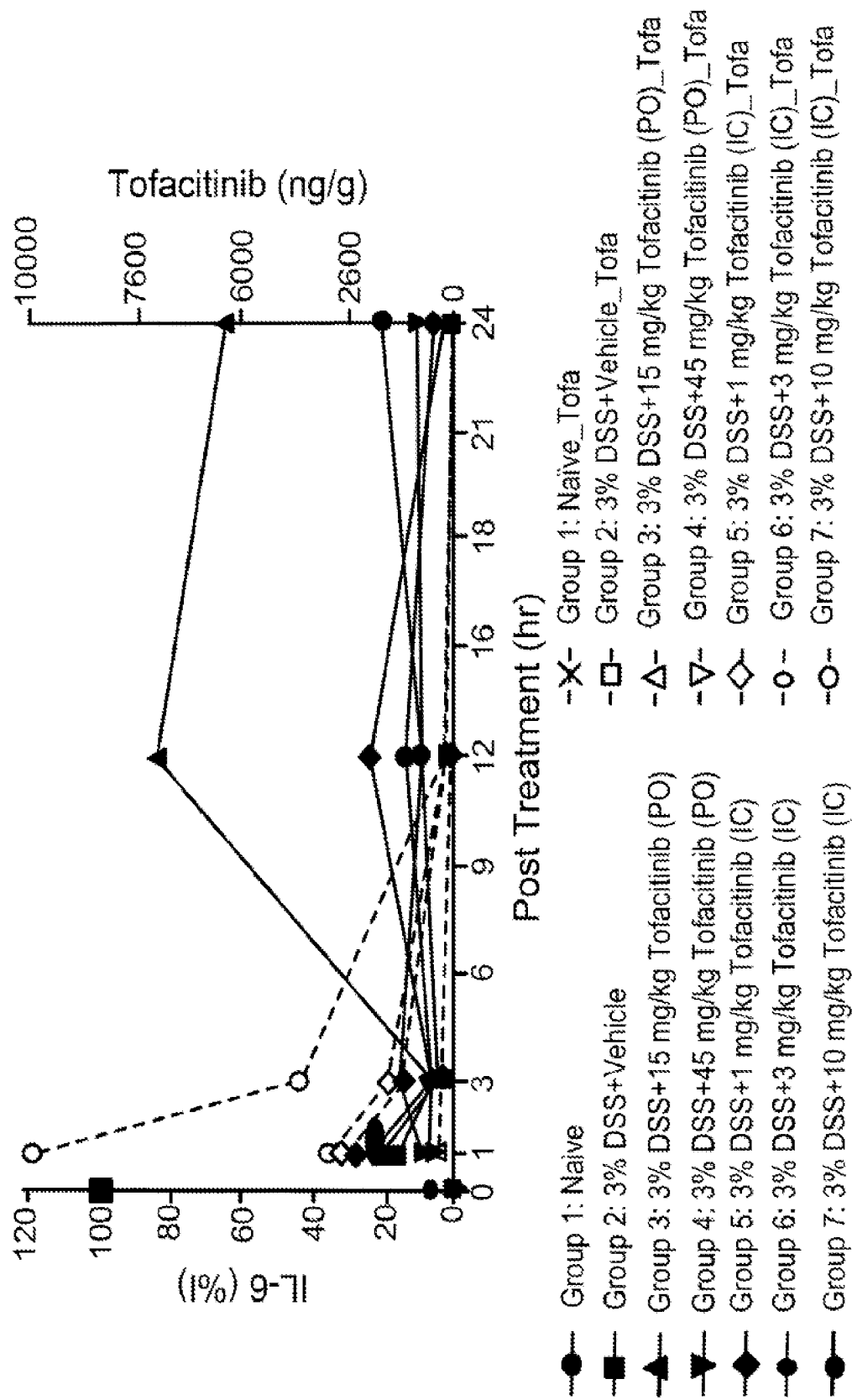

FIGS. 64A-64B show results obtained for IL-6 in colon tissue on Day 12. IL-6 expression was induced by DSS treatment in both plasma (data not shown) and colon tissue (FIG. 64A) of PO and IC treatment groups; significant induction ($p<0.05$) was observed on Day 12 when compared with naïve animals (Group 1).

In plasma, inhibition of IL-6 expression was observed in groups treated with tofacitinib citrate via PO or IC administration at 1 h and 3 h post-treatment; recovery of IL-6 expression (50 to 100%) was observed at 12 h and 24 h post-treatment (data not shown). In colon tissue, inhibition of IL-6 expression was sustained through 24 h post-dose in colon tissue in all IC treated groups and in the high dose PO group (45 mg/kg) (FIG. 64B). Recovery from IL-6 inhibition was observed in the low dose PO group (15 mg/kg) by 12 h post-dose.

The concentration of GM-CSF (a cytokine activated through stimulation of the JAK2/JAK2 pathway) was not significantly different between the DSS-treatment groups and the naïve group, nor was there a significant difference in GM-CSF levels between IC and PO treatment groups in either plasma or colon tissue, despite high exposure of tofacitinib found in colon tissue of IC groups dosed at 3 and 10 mg/kg (data not shown).

Example 10—Topical Intracecal Administration of Therapeutic Antibodies in a Colitis Animal Model that has Previously Received an Adoptive T-Cell Transfer A set of experiments was performed to compare the efficacy of targeted intracecal (IC) anti-mouse-TNFα antibody (a surrogate for adalimumab) and anti-mouse-interleukin (IL) 12p40 antibody (a surrogate of anti-human-IL12p40 antibody) with systemic intraperitoneal (IP) injection in an adoptive T cell transfer induced chronic colitis mouse model.

Materials

Test System

Species/strain: Mice, C57Bl/6 (donors) and RAG2$^{-/-}$ (recipients; C57Bl/6 background)

Physiological state: Normal/immunodeficient

Age/weight range at start of study: 6-8 weeks (20-24 g)

Animal supplier: Taconic

Randomization: Mice were randomized into seven groups of 15 mice each, and two groups of eight mice each.

Justification: T cells isolated from male C57Bl/6 wild type donors were transferred into male RAG2$^{-/-}$ recipient mice to induce colitis.

Replacement: Animals were not replaced during the course of the study.

Animal Housing and Environment

Housing: Mice were housed in groups of 8-15 animals per cage prior to cannulation surgery. After cannulation surgery, cannulated animals were single-housed for seven days post-surgery. After this point, animals were again group-housed as described above. Non-cannulated animals (Group 9) were housed at 8 mice per cage. ALPHA-Dri® bedding was used. Prior to colitis induction (i.e., during the cannulation surgeries), bedding was changed a minimum of once per week. After colitis induction, bedding was changed every two weeks, with ¼ of dirty cage material captured and transferred to the new cage. Additionally, bedding from Group 9 animals was used to supplement the bedding for all other groups at the time of cage change.

Acclimation: Animals were acclimatized for a minimum of 7 days prior to study commencement. During this period, the animals were observed daily in order to reject animals that presented in poor condition.

Environmental conditions: The study was performed in animal rooms provided with filtered air at a temperature of 70+/−5° F. and 50%+/−20% relative humidity. Animal rooms were set to maintain a minimum of 12 to 15 air changes per hour. The room was on an automatic timer for a light/dark cycle of 12 hours on and 12 hours off, with no twilight.

Food/water and contaminants: Animals were maintained with Labdiet 5053 sterile rodent chow. Sterile water was provided ad libitum.

Test Article: IgG Control

Name of the Test Article: InVivoMAb polyclonal rat IgG

Source: BioXCell, catalog #BP0290

Storage conditions: 4° C.

Vehicle: Sterile PBS

Dose: 0.625 mg/mouse; 0.110 mL/mouse IP and IC

Formulation:

Formulation Stability: Prepare fresh daily

For Group 3: On each day of dosing, dilute stock pAb to achieve 2.145 mL of a 5.68 mg/mL solution.

For Group 4: On each day of dosing, dilute stock pAb to achieve 2.145 mL of a 5.68 mg/mL solution Test Article: Anti-IL12 p40

Name of the Test Article: InVivo MAb anti-mouse IL-12 p40

Source: BioXCell, catalog #BE0051

Storage conditions: 4° C.

Vehicle: Sterile PBS

Dose: 0.625 mg/mouse (IP and IC); 0.110 mL/mouse IP and IC

Formulation:

Formulation Stability: Prepare fresh daily

For Group 5: On each dosing day, the stock mAb was diluted to achieve 1.716 mL of a 5.68 mg/mL solution.

For Group 6: On each dosing day, the stock mAb was diluted to achieve 1.716 mL of a 5.68 mg/mL solution.

Test Article: anti-TNFα

Name of the Test Article: InVivoPlus anti-mouse TNFα, clone XT3.11

Source: BioXCell, catalog #BP0058

Storage conditions: 4° C.

Vehicle: Sterile PBS

Dose: 0.625 mg/mouse (IP and IC); 0.110 mL/mouse IP and IC

Formulation:

Formulation Stability: Prepare fresh daily

For Group 7: On each dosing day, the stock mAb was diluted to achieve 1.716 mL of a 5.68 mg/mL solution.

For Group 8: On each dosing day, the stock mAb was diluted to achieve 1.716 mL of a 5.68 mg/mL solution.

Methods

The details of the study design are summarized in Table 47. A detailed description of the methods used in this study is provided below.

TABLE 47

Study Design

| Group | No. Animals | Cecal Cannula | Cell Transfer (Day 0) | Treatment | Dose* | Route | Schedule (Days 0-42**) | Blood Collection (RO) | Endoscopy | Endpoints (Day 42) |
|---|---|---|---|---|---|---|---|---|---|---|
| 1 | 8 | YES | — | — | — | — | — | Day 13 | Days 14, 28, 42 | 3 Hours Post Dose: Colon weight/ length, stool score Terminal collection (all groups): Cecal Contents, Colon Contents, Plasma, small intestinal tissue, colon tissue, mLN, and Peyer's Patches |
| 2 | 15 | | 0.5 × 10⁶ naïve T_H cells | Vehicle (PBS; IP) Vehicle (PBS; IC) | — | IP; IC | IP: 3x/week IC: QD | | | |
| 3 | 15 | | | IgG Control (IP) Vehicle (PBS; IC) | 625 μg | | IP: 3x/week IC: QD | | | |
| 4 | 15 | | | Vehicle (PBS; IP) IgG Control (IC) | 625 μg | | IP: 3x/week IC: QD | | | |
| 5 | 15 | | | Anti-IL12p40 (IP) Vehicle (PBS; IC) | 625 μg | | IP: 3x/week IC: QD | | | |
| 6 | 15 | | | Vehicle (PBS; IP) Anti-IL12p40 (IC) | 625 μg | | IP: 3x/week IC: QD | | | |
| 7 | 15 | | | Anti-TNFα (IP) Vehicle (PBS; IC) | 625 μg | | IP: 3x/week IC: QD | | | |
| 8 | 15 | | | Vehicle (PBS; IP) Anti-TNFα (IC) | 625 μg | | IP: 3x/week IC: QD | | | |
| 9 | 8 | NO | — | — | — | — | — | — | — | — |

*Per mouse;
**Test Article was administered in 0.110 mL/animal IC or IP from Day 0–42;
IC = intracecal injection;
IP = intraperitoneal injection;
QD = once a day;
RO = Retro-Oribital eye bleed A cohort of animals underwent surgical implantation of a cecal cannula at least 10 days to 2 weeks prior to the experiment for the ease of bolus topical delivery to the cecum. A sufficient number of animals underwent implantation to allow for enough cannulated animals to be enrolled in the main study. An additional n=8 animals (Group 9) served as no surgery/no disease controls.

Colitis was induced by intraperitoneal (IP) injection of $0.5 \times 10^6$ CD44/CD62L+ T-cells from C57BL/6 donor mice to male RAG2$^{-/-}$ recipient mice in Groups 2 to 8 on Day 0. The donor cells were processed by first harvesting spleens from 80 C57Bl/6 mice and then isolating the CD44$^-$/CD62L$^+$ T cells using Miltenyi Magnetic-Activated Cell Sorting (MACS) columns.

To minimize variation due to methods of administration, animals were treated both by IP injection every third day (3x/wk) and IC injection once daily for 42 consecutive days (qdx42d) of either the test article or the control (vehicle solution or IgG control). Groups were as outlined in Table 47, also summarized as follows: Group 1=untreated (no disease controls); Group 2=vehicle [phosphate buffer saline (PBS)] (IP)+vehicle (IC); Group 3=IgG (IP)+vehicle (IC); Group 4=vehicle (IP)+IgG (IC); Group 5=anti-IL12p40 (IP)+vehicle (IC); Group 6=vehicle (IC)+anti-IL12p40 (IC); Group 7=anti-TNFα (IP)+vehicle (IC); Group 8=vehicle (IP)+anti-TNFα (IC); Group 9=no surgery, untreated (no-cannulation and no-disease controls (sentinel animals for bedding)). Treatment with test article was initiated on Day 0 and was continued until Day 42 as outlined in Table 47.

All recipient mice were weighed daily and assessed visually for the presence of diarrhea and/or bloody stool. The cages were changed every two weeks starting on Day 7, with care taken to capture ¼ of dirty cage material for transfer to the new cage. On Day 13, blood was collected via RO eye bleed, centrifuged, and plasma was aliquoted (50 μL and remaining) and frozen for downstream analysis. The pelleted cells were re-suspended in buffer to determine the presence of T cells by FACS analysis of CD45$^+$/CD4$^+$ events.

On Day 13, after dosing, peripheral blood from all surviving mice was analyzed by flow cytometry from the presence of CD45$^+$/CD4$^+$ T cells.

The mice underwent high definition video endoscopy on Days 14 (pre-dosing; baseline), 28, and 42 (before euthanasia) to assess the extent of colitis severity. Images were captured from each animal at the most severe region of disease identified during endoscopy. Stool consistency was scored during endoscopy using the parameters described herein on Days 14, 18 and 42.

Disease Activity Index (DAI) was calculated using a combination of body weight (BW) loss score, colitis score, stool consistency score. The DAI (combined value from 0 to 13) was calculated using colitis score, stool consistency score, and BW loss score to provide an overall evaluation of the disease intensity (see Table 48). The score from animals with unscheduled death was carried forward to limit any bias that may be introduced by mortality.

The animals from all groups were euthanized by $CO_2$ inhalation on Day 42 following endoscopy and three hours after dosing. Terminal blood samples were collected for bioanalysis of inflammatory cytokines, and tissues samples were collected and fixed for histopathological evaluation. Plasma obtained from these samples was split into two separate cryotubes, with 50 μL in one tube (Bioanalysis) and the remainder in a second tube (TBD). The cecum and colon contents were removed and the contents collected, weighed, and snap frozen in separate cryovials. The mesenteric lymph nodes were collected and flash-frozen in liquid nitrogen. The small intestine were excised and rinsed, and the most distal 2-cm of ileum was placed in formalin for 24 hours and then transferred to 70% ethanol for subsequent histological evaluation. The Peyer's patches were collected from the small intestine, and were flash-frozen in liquid nitrogen. The colon was rinsed, measured, weighed, and then trimmed to 6-cm in length and divided into 5 pieces as described in the above Examples. The most proximal 1-cm of colon was separately weighed, and flash-frozen for subsequent bioanalysis (PK) of test article levels. Of the remaining 5-cm of colon, the most distal and proximal 1.5-cm sections were each placed in formalin for 24 hours and then transferred to 70% ethanol for subsequent histological evaluation. The middle 2-cm portion was bisected longitudinally, and each piece was weighed, placed into two separate cryotubes, and snap frozen in liquid nitrogen; one of the samples was used for cytokine analysis and the other was used for myeloperoxidase (MPO) analysis. All plasma and frozen colon tissue samples were stored at −80° C. until used for endpoint analysis.

The colon weight (mg) to length (cm) ratio was calculated for individual mice.

A more detailed description of the protocols used in this study are described below.

Cecal Cannulation

Animals were placed under isoflurane anesthesia, and the cecum was exposed via a mid-line incision in the abdomen. A small point incision was made in the distal cecum through which 1-2 cm of the cannula was inserted. The incision was closed with a purse-string suture using 5-0 silk. An incision was made in the left abdominal wall through which the distal end of the cannula was inserted and pushed subcutaneously to the dorsal aspect of the back. The site was washed copiously with warmed saline prior to closing the abdominal wall. A small incision was made in the skin of the back between the shoulder blades, exposing the tip of the cannula. The cannula was secured in place using suture, wound clips, and tissue glue. All of the animals received 1 mL of warm sterile saline (subcutaneous injection) and were monitored closely until fully recovered before returning to the cage. All animals received buprenorphine at 0.6 mg/kg BID for the first 3 days, and Baytril at 10 mg/kg QD for the first 5 days following surgery.

Disease Induction

Colitis was induced on Day 0 in male RAG2$^{-/-}$ mice by IP injection (200 μL) of 0.5×10$^6$ CD44$^-$/CD62L+ T cells (in PBS) isolated and purified from C57Bl/6 recipients.

Donor Cell Harvest

Whole spleens were excised from C57Bl/6 mice and immediately placed in ice-cold PBS. The spleens were dissociated to yield a single cell suspension and the red blood cells were lysed. The spleens were then processed for CD4$^+$ enrichment prior to CD44$^-$ CD62L$^+$ sorting by MACS.

Dosing

See Table 47.

Body Weight and Survival

The animals were observed daily (morbidity, survival, presence of diarrhea and/or bloody stool) in order to assess possible differences among treatment groups and/or possible toxicity resulting from the treatments. Animals were weighed daily and their percent body weight relative to Day 0 was calculated.

Animals Found Dead or Moribund

The animals were monitored on a daily basis and those exhibiting weight loss greater than 30% were euthanized, and did not have samples collected.

Endoscopy

Each mouse underwent video endoscopy on Days 14 (pre-dosing; baseline), 28, and 42 (before euthanasia) using a small animal endoscope (Karl Storz Endoskope, Germany), under isoflurane anesthesia. During each endoscopic procedure, still images as well as video were recorded to evaluate the extent of colitis and the response to treatment. Additionally, an image from each animal at the most severe region of disease identified during endoscopy was captured. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the scoring system described herein.

Sample Collection

Terminal blood (plasma and cell pellet), Peyer's patches (Groups 1-8 only), small intestine and colon mLN (Groups 1-8 only), cecum contents, colon contents, small intestine, and colon were collected at euthanasia, as follows.

Blood: Terminal blood was collected by cardiac puncture and plasma generated from these samples. The resulting plasma was split into two separate cryotubes with 50 μL in one tube (Bioanalysis), and the remainder in a second tube (TBD).

Mesenteric Lymph Nodes: The mesenteric lymph nodes were collected, weighed, snap-frozen in liquid nitrogen, and stored at −80° C.

Small Intestine: The small intestine was excised and rinsed, and the most distal 2-cm of ileum will be placed in formalin for 24 hours and then transferred to 70% ethanol for subsequent histological evaluation.

Peyer's Patches: The Peyer's patches were collected from the small intestine. The collected Peyer's patches were weighed, snap-frozen in liquid nitrogen, and stored at −80° C.

Cecum Colon Contents: The cecum and colon were removed from each animal and contents collected, weighed, and snap-frozen in separate cryovials.

Colon: Each colon was rinsed, measured, weighed, and then trimmed to 6-cm in length and divided into 5 pieces as outlined herein. The most proximal 1-cm of colon was separately weighed, and snap frozen for subsequent bioanalysis (PK) of test article levels. Of the remaining 5-cm of colon, the most distal and proximal 1.5-cm sections were placed in formalin for 24 hours and then transferred to 70% ethanol for subsequent histological evaluation. The middle 2-cm portion was bisected longitudinally, and each piece weighed, placed into two separate cryotubes, and snap-frozen in liquid nitrogen; one of these samples was used for cytokine analysis and the other sample was used for myeloperoxidase analysis.

Cytokine Levels in Colon Tissue

Cytokine levels (IFNγ, IL-2, IL-4, IL-5, IL-1β, IL-6, IL-12 p40, and TNFα) were assessed in colon tissue homogenate (all groups) by multiplex analysis. Myeloperoxidase levels were assessed by ELISA in colon tissue homogenate (all groups).

Histopathology

Ileum, proximal colon, and distal colon samples from seventy-one mice were fixed in 10% neutral buffered formalin. Samples were trimmed into three cross sections per portion and processed routinely into two blocks per animal (ileum in one block, proximal and distal colon in a second block). One slide from each block was sectioned at approximately 5 microns and stained with hematoxylin and eosin (H&E). Glass slides were evaluated with light microscopy by a board-certified veterinary pathologist. Ileum, proximal colon, and distal colon samples were scored individually. Lesions in H&E-stained samples were given a severity score 0-51 (0=not present/normal, 1=minimal, <10% of tissue affected; 2=mild, 10-25% of tissue affected; 3=moderate, 26-50% of tissue affected; 4=marked, 51-79% of tissue affected; 5=severe, >75% of the tissue affected). Inflammation, crypt damage, erosion, and hyperplasia scores were added together to determine a sum colitis score for each sample.

Lymphocyte counts were performed in a subset of samples: proximal and distal colon from Groups 2 (vehicle), 7 (anti-TNF-alpha IP; vehicle IC), and 8 (anti-TNF-alpha IC; vehicle IP). In each piece of tissue, a randomly identified site was divided into approximately four segments extending from the lumen to the muscularis mucosae; 100 µm2 fields were used in the proximal colon, and 50 µm2 fields were used in the distal colon due to the differences in mucosal thickness. Using H&E-stained slides, the number of cells with lymphocyte morphology (small round nucleus with condensed chromatin) were counted within the overlying surface epithelium, in each field from lumen to muscularis mucosae, and within a 100 µm2 field surrounding an adjacent submucosal blood vessel.

Statistical Analysis

As presented in the figures, non-parametric data was analyzed by Kruskal-Wallis test with Dunn's multiple comparisons test used to compare all groups to one another and individual pair-wise comparisons was analyzed by Mann Whitney U-Test. All statistical analyses were performed using GraphPad Prism 7 (La Jolla, Calif.).

Results

Survival

The observed mortality rate was within the expected range given the design including surgical intervention, T-cell transfer in immunologically compromised animals followed by chronic development of colitis over a 6-week study period (Ostanin D V et al. Am J Physiol Gastrointest Liver Physiol. 2009, 296(2):G135-G146).

The survival of animals was compared; no significant difference in survival rate was found in treatments of anti-IL12p40 and anti-TNFα with either route of administration compared to vehicle or IgG controls (p>0.08, log-rank; Kaplan-Meier). The timing of animal deaths did not correspond to changes in efficacy endpoints, such as body weight, that were evaluated longitudinally. As noted above, changes in DAI score which includes, BW loss, stool consistency and colitis severity were carried forward to limit any bias that may be introduced by mortality.

Colon Weight:Length Ratio

The mean colon weight:length ratio was significantly elevated in vehicle control animals (Group 2) compared to naïve (Group 1); no other significant differences in mean colon weight:length ratio were observed.

Disease Activity Index

The Disease Activity Index was determined in each mouse using a total score from the scoring system depicted in Table 48.

TABLE 48

Disease Activity Index scoring system

| Disease Activity Index | Description | Score |
|---|---|---|
| Colitis Severity | Normal | 0 |
| | Loss of vascularity | 1 |
| | Loss of vascularity and friability | 2 |
| | Friability and erosions | 3 |
| | Ulcerations and bleeding | 4 |
| Stool Consistency | Normal | 0 |
| | Loose stool, soft, staying in shape | 1 |
| | Abnormal form with excess moisture | 2 |
| | Watery or diarrhea | 3 |
| | Bloody diarrhea | 4 |
| Body Weight Loss (%) | $X < 0\%$ or gain weight | 0 |
| | $2\% \leq X < 5\%$ | 1 |
| | $5\% \leq X < 10\%$ | 2 |
| | $10\% \leq X < 15\%$ | 3 |
| | $15\% \leq X < 20\%$ | 4 |

TABLE 48-continued

Disease Activity Index scoring system

| Disease Activity Index | Description | Score |
|---|---|---|
| | $20\% \leq X < 25\%$ | 5 |
| | $25\% \leq X < 30\%$ | 6 |
| | $X \geq 35\%$ | 7 |
| Total Score | | 15 |

Figure 65:
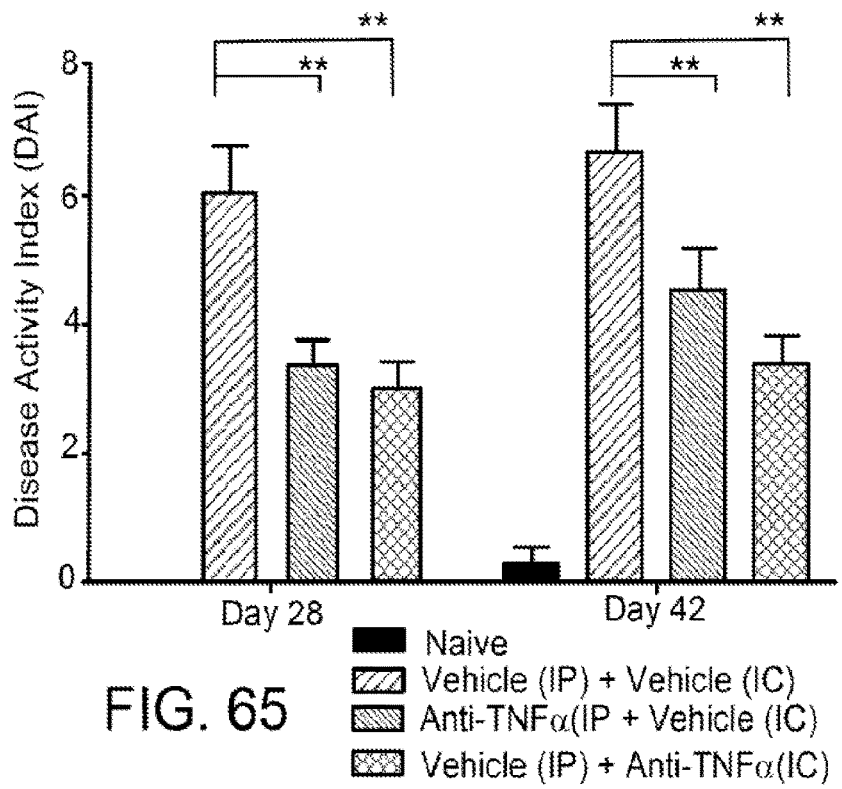
FIG. 65 is a graph showing the Disease Activity Index (DAI) of naïve mice (Group 1), mice administered vehicle only both intraperitoneally (IP) and intra-cecally (IC) (Group 2), mice administered an anti-TNFα antibody IP and vehicle IC (Group 7), and mice administered an anti-TNFα antibody IC and vehicle IP (Group 8) at Day 28 and Day 42 of the study described in Example 10.
Figure 67:
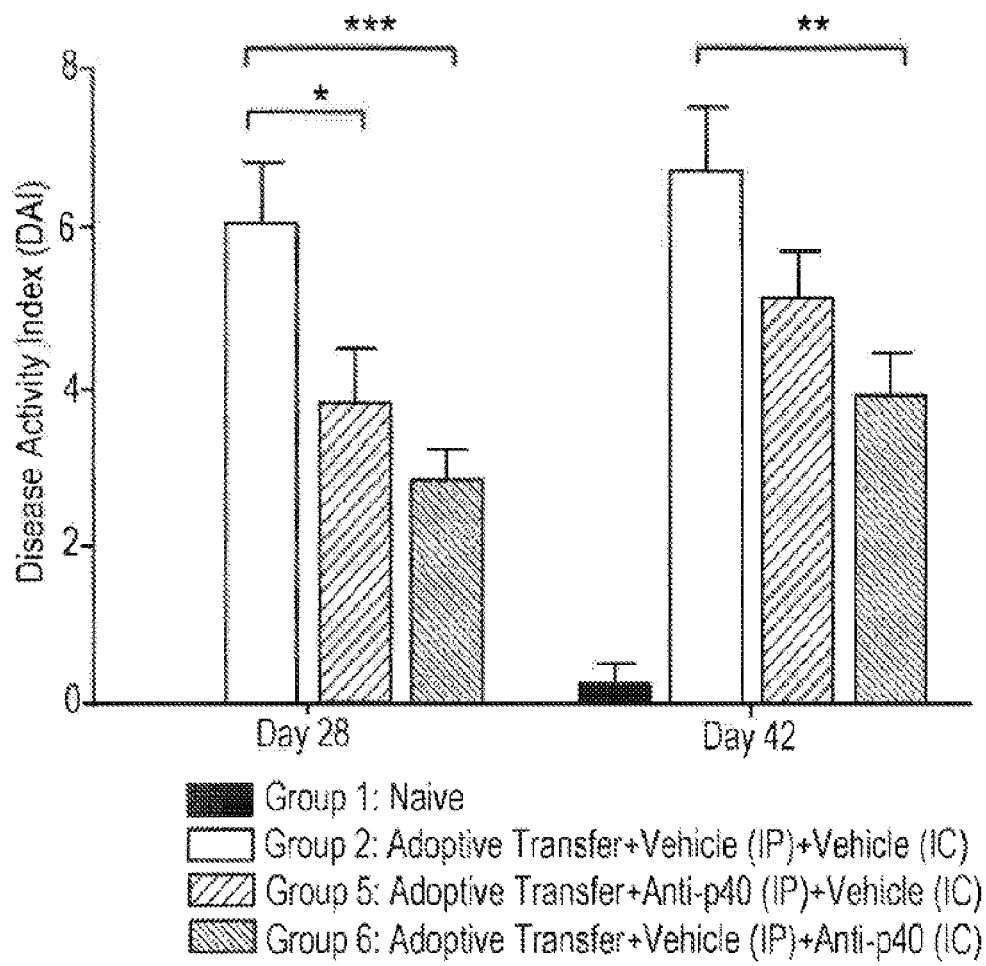
FIG. 67 is a graph showing the Disease Activity Index (DAI) of naïve mice (Group 1), mice administered vehicle only both IP and IC (Group 2), mice administered an anti-IL12 p40 antibody IP and vehicle IC (Group 5), and mice an anti-IL12 p40 antibody IC and vehicle IP (Group 6) at Day 28 and Day 42 of the study described in Example 10.

The data in FIG. 65 show that mice intracecally administered anti-TNFαL antibody (Group 8) had decreased disease activity index (DAI) as compared to mice intraperitoneally administered anti-TNFαL antibody (Group 7) at Day 42 of the study. The data in FIG. 67 show that mice intracecally administered anti-IL12 p40 antibody (Group 6) had decreased disease activity index (DAI) as compared to mice intraperitoneally administered anti-IL12 p40 antibody (Group 5) at Day 28 and Day 42 of the study.

Inflammatory Cytokines in Colonic Tissue

The concentration of inflammatory cytokines was evaluated in the colonic tissue in vehicle or IgG control groups.

Figure 66:
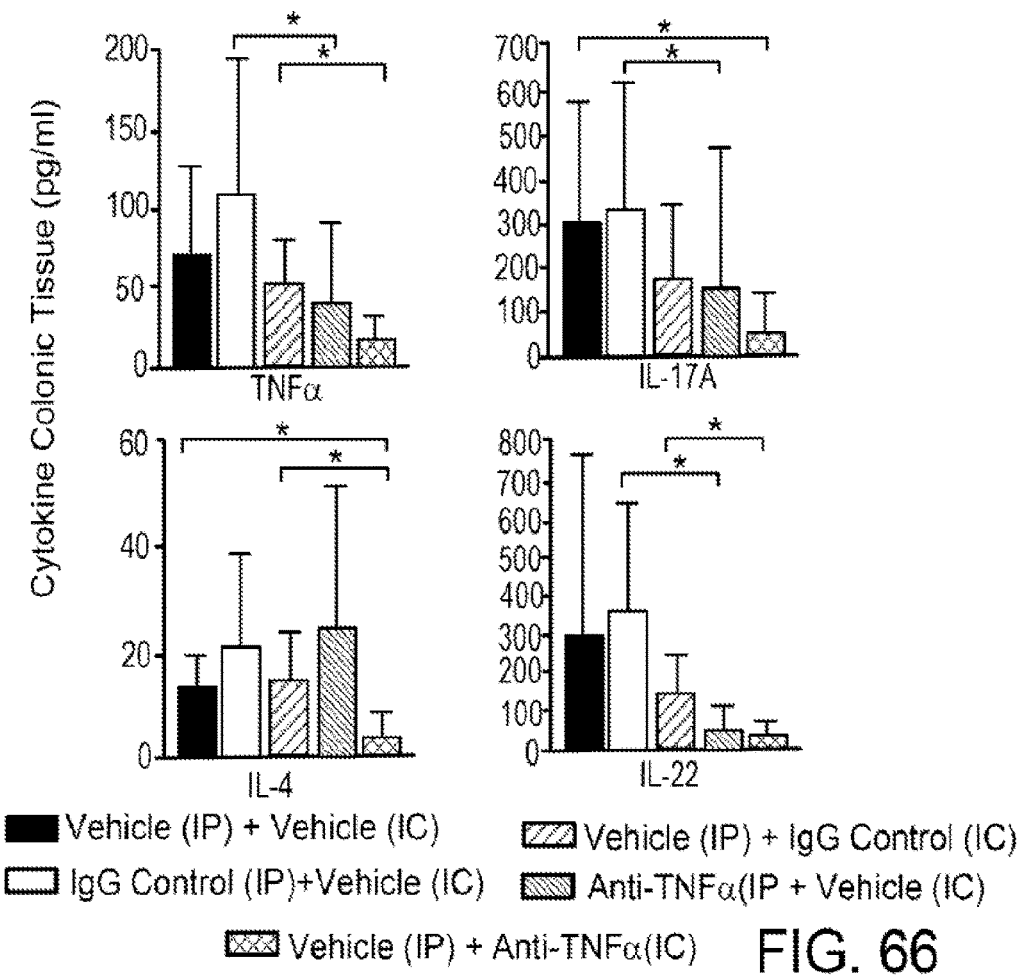
FIG. 66 is a set of graphs showing the colonic tissue concentration of TNFα, IL-17A, IL-4, and IL-22 in mice administered vehicle only both IP and IC (Group 2), mice administered IgG control antibody IP and vehicle IC (Group 3), mice administered IgG control IC and vehicle IP (Group 4), mice administered anti-TNFα antibody IP and vehicle IC (Group 7), and mice administered anti-TNFα antibody IC and vehicle IP (Group 8) at Day 42 of the study described in Example 10.

A significant reduction of inflammatory cytokines, including TL 17A, IL-4, TNFα~, and IL-22, were found in groups treated with anti-TNFαL (IC (Group 8) or IP (Group 7)) when compared with vehicle (IP/IC) control or its respective IgG controls (IC or TP) in colon tissue (FIG. 66). Mice treated with anti-TNFαL antibody IC (Group 8) had decreased levels of TNFα~, IL-17A, and IL-4 in colonic tissue as compared to the levels in colonic tissue of mice treated with anti-TNFαL TP (Group 7) when assessed at Day 42 of the study.

Figure 68:
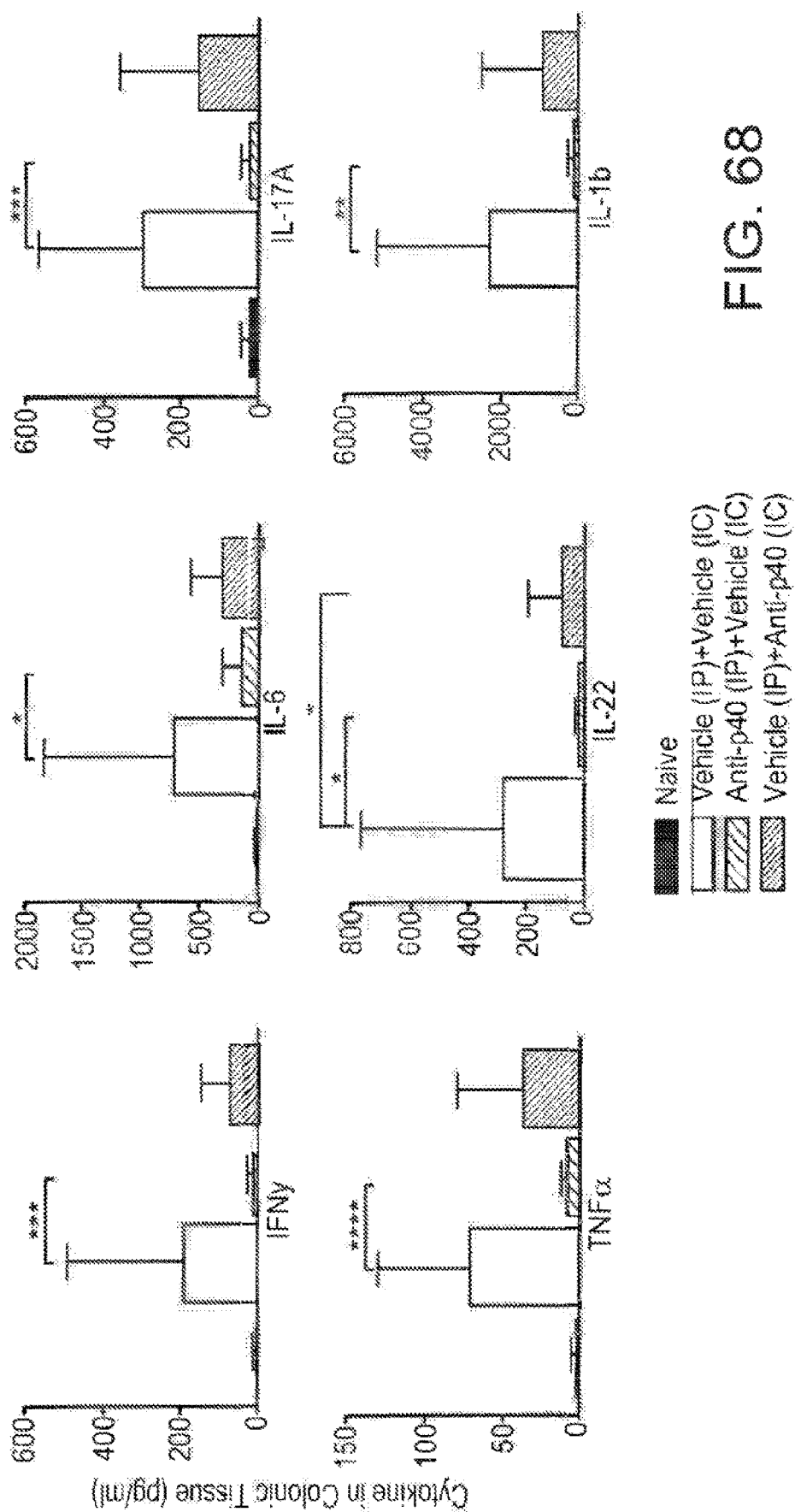
FIG. 68 is a set of graphs showing the colonic tissue concentration of IFN-gamma, IL-6, IL-17A, TNFα, IL-22, and IL-1b in naïve mice (Group 1), mice administered vehicle only both IP and IC (Group 2), mice administered anti-IL12 p40 antibody IP and vehicle IC (Group 5), and mice administered anti-IL12 p40 antibody IC and vehicle IP (Group 8) at Day 42 of the study described in Example 10.

A significant reduction of IL-22, IL-6, IL17A, TNFα~, IL-1b, and IFNγ cytokine was found in groups treated with anti-IL12p40 (IP or IC) when compared with vehicle (IP/IC) control in colon tissue (FIG. 68). Mice intracecally administered anti-IL12 p40 antibody (Group 6) had decreased levels of IFNγ, IL-6, IL-17A, TNFα, IL-22, and IL-1b in colonic tissue as compared to the levels in colonic tissue in vehicle-administered control mice (Group 2).

Body Weight Loss

Treatments with either systemic (IP) or topical (IC) administration of an anti-TNFα antibody or anti-IL12p40 antibody led to a significant decrease in body weight (BW) loss over time from Day 0 to Day 42.

Figure 69A:
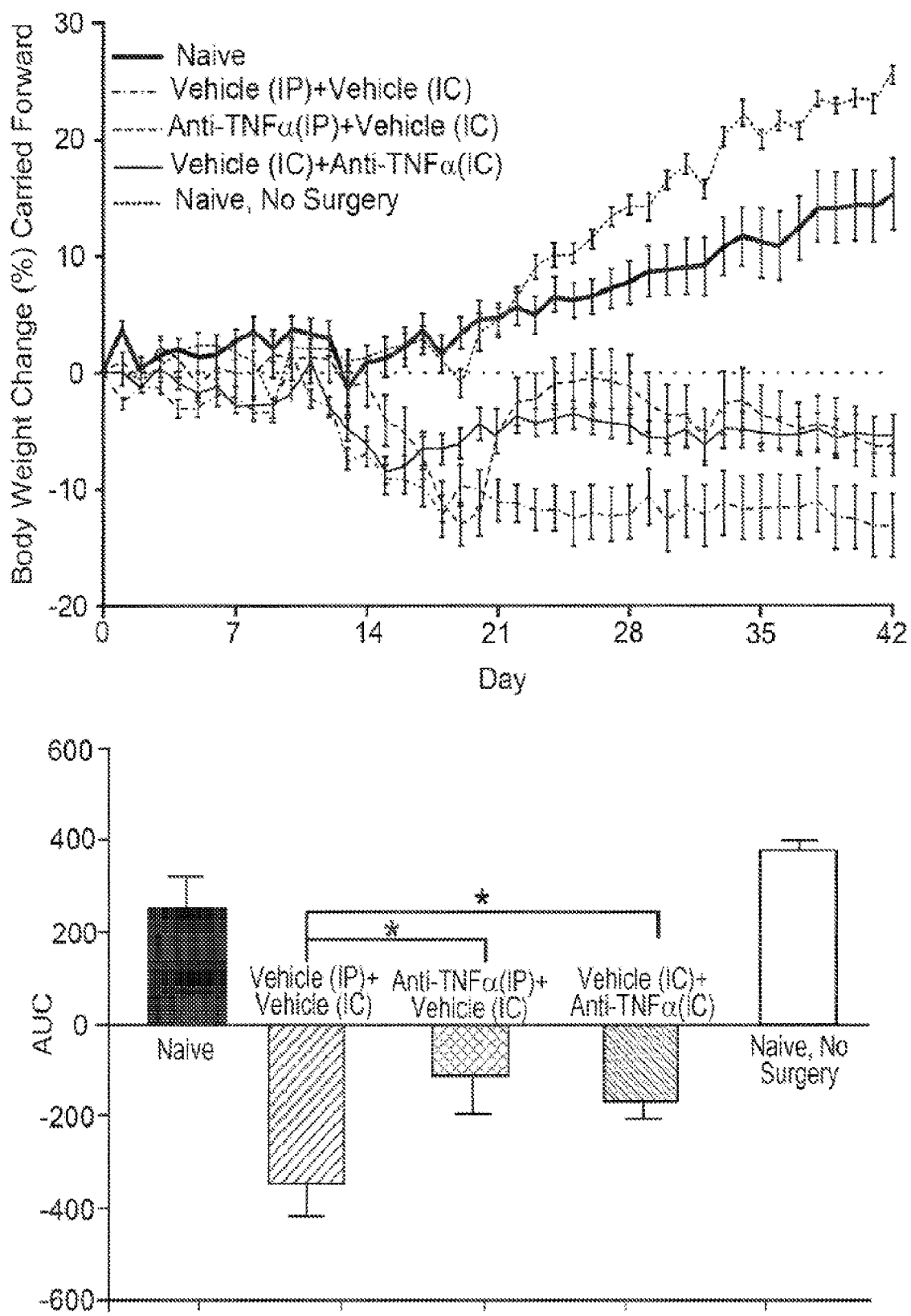
FIGS. 69A-69B show body weight changes (mean % SEM).
Figure 69B:
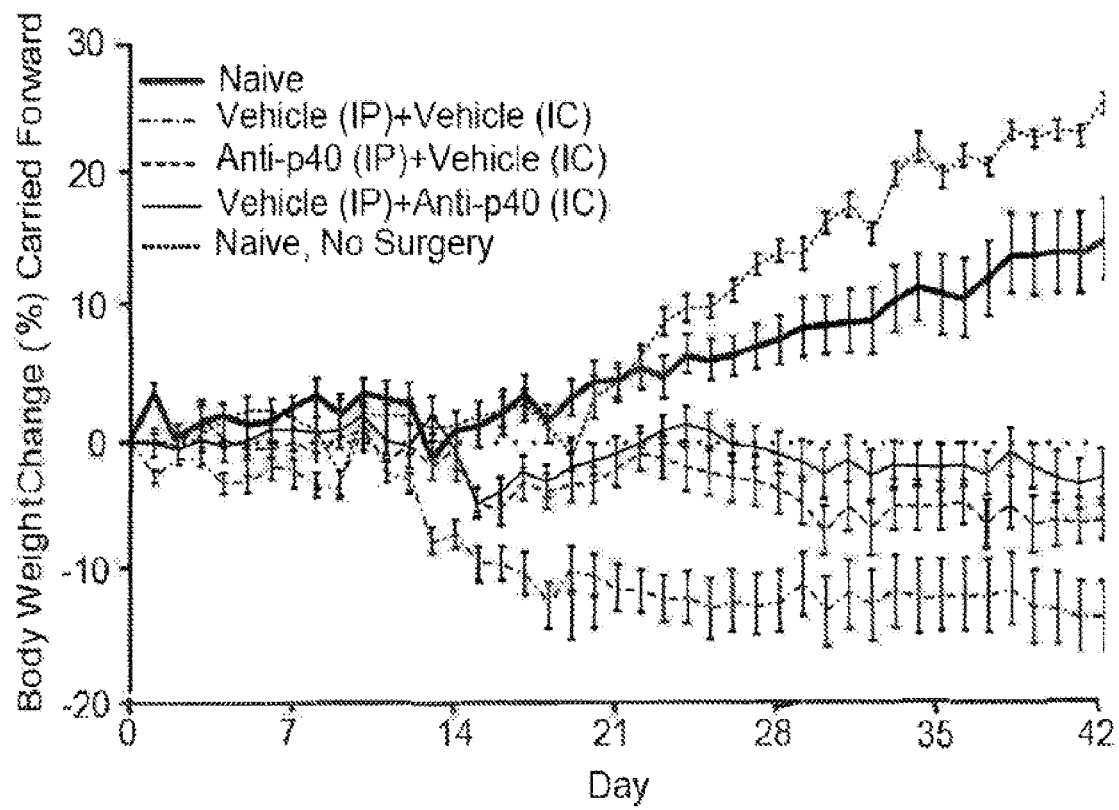
Figure 69B:
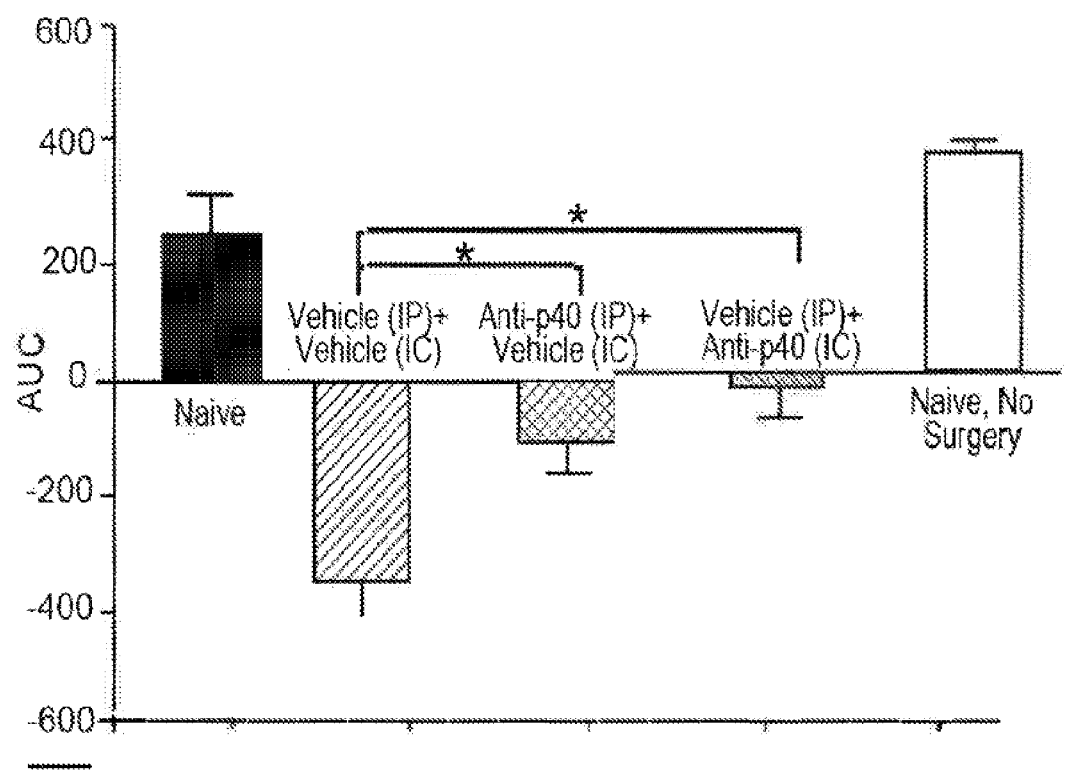

The change in body weight over the course of the experiment from Day 0 through Day 42 is shown in FIGS. 69A and 69B. No apparent signs of disease were observed within the first week after induction of colitis. In control groups treated with PBS vehicle and/or IgG, BW loss did not begin until Days 14 through 16 and continued in the 3rd and 4th week following transfer during the acute phase. The weight loss was maintained until study termination on Day 42. Administration of anti-TNFα antibody or anti-IL12p40 antibody through either IP or IC had a significant reduction in AUC of the BW loss (%) from Day 0 to Day 42 along with the weight increase maintained from Day 21 to Day 42 (FIGS. 69A and 69B). Overall, intracecal administration of anti-IL12p40 antibody had the earliest recovery of weight loss and most significant reduction in overall BW loss from Day 0 Day 42 in comparison to the vehicle control group amount of all treatment groups (FIG. 69B).

Histopathology Colitis Score

Figure 70:
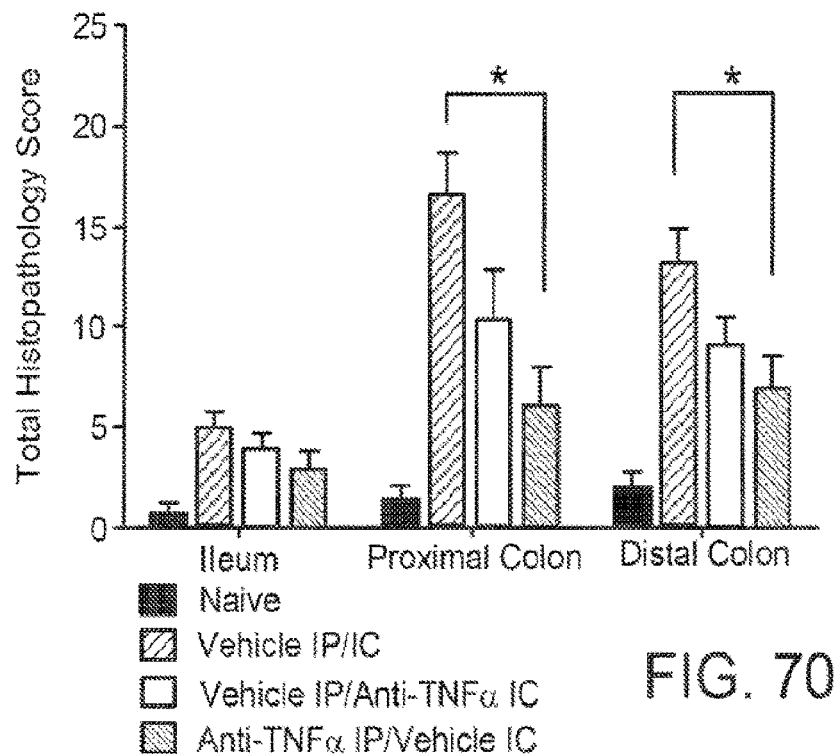
FIG. 70 shows total histopathology score (mean %±SEM) in ileum, proximal colon and distal colon tissues after targeted IC anti-TNF-alpha treatment compared with vehicle and IP treatment groups. Pair-wise comparisons by two-tailed Mann-Whitney U-Test for treatment effects; $p<0.05$*.

Lesions of ileitis and colitis, including inflammation, crypt damage, occasional erosions, and epithelial hyperplasia, were induced with the T-cell transfer in this model. Lesions were the least severe in ileum sections and the most severe in the proximal colon. Both IP and IC administration of anti-IL12p40 and anti-TNFα resulted in a reduction in sum ileitis/colitis scores compared to PBS vehicle control. Targeted IC anti-TNFα treatment showed a significant improvement in the mean histopathologic score when compared with the vehicle controls given by either route (IP or IC) in proximal and distal colon tissues (FIG. 70).

Lymphocyte Counts

Targeted IC anti-TNFα treatment showed the greatest magnitude of lymphocyte reductions in all counted fields, from inner lumen to submucosa of proximal colon when compared to the vehicle control group (Group 8 vs. Group 2, $P<0.05^*$, FIG. 69A). A similar trend in lymphocyte count reductions was found in the distal colon, although to a lesser degree. Results are shown in FIGS. 71A-71D. Mean counts and scores for all fields were generally the highest in vehicle-treated animals (Group 2, data not shown) and lower in those given anti-TNFα by IP (Group 7, data not shown) or IC (Group 8, FIG. 71). Thus, significantly reduced body weight loss (%), decreased Disease Activity Index, improved histological score and reduced tissue inflammatory cytokines were found in animals receiving targeted (IC) anti-TNFα antibody when compared with vehicle controls. Targeted IC delivery was significantly more efficacious when compared to systemic (IP) anti-TNFα antibody in end points of total histologic score and lymphocyte count from inner lumen to submucosa of proximal colon.

Example 11—Evaluation of the Bioavailability of Semaglutide after Intraduodenal Administration Via an Ingestible 2-Nozzle Jet Delivery Device in Female Yorkshire Pigs A study was performed to determine the plasma pharmacokinetics of semaglutide in female Yorkshire pigs after intravenous (IV), subcutaneous (SC), or intraduodenal (ID) administration via an endoscopically placed ingestible device.

Test Article

OZEMPIC® (semaglutide solution) having a semaglutide concentration of 1.34 mg/mL was used in this study.

Ingestible Device Configuration

Each ingestible device was configured as a capsule comprising a substance reservoir; a gas reservoir; a one-way duckbill valve; a piston; two nozzles radially configured 180 degrees apart; two shear pins on opposite sides of the capsule (0.9 mm in diameter, 2.5 mm in length); and a pneumatic control line (polyetheretherketone (PEEK) tubing) attached at one end of the device to allow for remote pneumatic triggering and release of the test article from the ingestible device. The shear pins were brittle 3D-printed polymer materials having finite (shear) strength sufficient to hold back the internal force in the gas reservoir. To use the ingestible device, the substance reservoir is charged with the test article; the gas reservoir is charged with a gas (via the one-way duckbill valve) to provide the drive force for ejecting the test article fluid from the ingestible device as a jet; the pneumatic control line allows for pneumatic triggering and release of the test article from the ingestible device; the shear pins restrain the force provided by the compressed gas and are broken by pneumatic impulse applied via the pneumatic control line; breakage of the shear pins allows the stored/applied pressure to open the nozzles quickly and form the jet.

Shortly before use, each ingestible device was pressurized by placing it in a pressure chamber and attaching the pressure chamber to an air compressor. The target pressure was set to 320 psig, and the pressurized air was stored in the ingestible device gas chamber and retained via the one-way duckbill valve. After pressurizing the ingestible device, a seal plug was applied to the duckbill valve and glued with cyanoacrylate.

Nominally, 0.450 mL of test article was loaded into the substance reservoir of the ingestible device using a manual fill procedure. The ingestible device was weighed before and after loading with test article and the actual amount of test article loaded into the ingestible device was determined. The ingestible device loaded with test article was then shipped to the in vivo study site for use within one week of loading with test article. After test article delivery to the study subject was completed, the ingestible device was weighed again, and the amount of test article delivered was determined. Typically, approximately 0.050 mL was retained in the ingestible device after test article delivery was completed. Thus, approximately 0.400 mL of test article was dispensed from each ingestible device.

A summary of parameters for the delivery of the test article solution via the ingestible device is provided below. Initial and final refer to values at the beginning and end of the dispensing period for the test article, respectively.

Internal pressure (pressure of pre-compressed gas): about 320 psig

Pre-compressed gas volume in ingestible device: about 370 microliters (initial) to about 770 microliters (final)

Nozzle diameter: 0.35 mm

Nozzle length: 2 mm

Nozzle throat geometry: circular, sharp-edged orifice

Piston diameter: 9.6 mm

Piston friction: 10 N (one (1) O-ring on piston)

Friction pressure loss: about 20 psig

Fluid pressure: about 300 psig (peak; initial) to about 95 psig (minimum; final)

Jet velocity: about 36.5 m/s (peak; initial) to about 20 psig (minimum; final)

Mean jet velocity: about 26 to 27 m/s

Fluid dispensing time (total): about 80 ms

Jet impact force: about 0.13 N (peak; initial) to about 0.04 N (minimum; final)

Jet impact pressure: 193 psig (peak; initial) to about 60 psig (minimum; final)

Jet power: 2.3 W (peak; initial) to about 0.4 W (minimum; final)

Jet diameter: about 0.35 mm (initial)

Nozzle stand-off distance: >1.5 mm

Device diameter: 11.6 mm

Device length: about 34 to 36 mm

In Vivo Study Design

A total of 11 healthy female Yorkshire pigs (*Sus scrofa domesticus*) were used for the study: n=5 for ID administration, n=3 for IV administration, and n=3 for SC administration. Each pig weighed between about 25-30 kg at the initiation of the study. A fixed dose of 0.5 mg semaglutide per pig (~0.02 mg/kg) was administered intraduodenally (ID) via the endoscopically placed ingestible device (Group 1); a 0.02 mg/kg dose was administered to each pig in the IV (Group 2) and SC (Group 3) dose groups. The study design is shown below in Table 49.

TABLE 49

Study Design

| Group # | Dose Route | N | Dose | Dose Conc. (mg/mL) | Clinical Observations | Blood Collection Time Points | Termination & Necropsy |
|---|---|---|---|---|---|---|---|
| 1 | ID | 5 | 0.5 mg | 1.34 | Twice on the day of each dose administration, and 24, 72, 144, and 240 hours post dose | Pre-dose, 1, 3, 6, 8, 24, 72, 144, and 240 hours post dose | At termination, necropsy of abdominal region to assess signs of hematoma and gross lesions |
| 2 | IV | 3 | (~0.02 mg/kg) | | | | |
| 3 | SC | 3 | (~0.02 mg/kg) | | | | |

Semaglutide solution was administered at t=0 on the day of dosing. The animals were anesthetized with an intramuscular injection of a cocktail containing ketamine (approximately 10-20 mg/kg), xylazine (approximately 1-2 mg/kg) and atropine (approximately 0.02-0.04 mg/kg). The animals were intubated and maintained using isoflurane (approximately 3-5% in oxygen 1 to 4 L/min) as necessary until dosing was complete. The animals were wakened post dose.

Routes of Administration

For intraduodenal (ID) administration, the ingestible device was attached to an endoscope (Olympus OSF-V60 attached to an Olympus CV60 Tower) via a working channel and maneuvered into the pyloric sphincter with camera visualization to identify the third (inferior/horizontal) part of the duodenum (D3). Following confirmation of placement of the ingestible device in the correct region, the endoscope was retracted out of the pyloric sphincter, leaving the ingestible device in the D3 region of the duodenum. After pausing and observing relaxation of the intestinal walls and obscured vision to the ingestible device, the ingestible device was triggered via the pneumatic control line to deliver the test article to the duodenum. After releasing the dose, the endoscope was advanced again for visual observation of the injection site. The capsule and endoscope were then retracted out of the body.

For intravenous (IV) administration, the test article was administered intravenously via bolus dose into the marginal ear vein followed by a 1 mL flush with saline if necessary.

For subcutaneous (SC) administration, the test article was administered into the dorsal subcutaneous space directly at the base of the pig. Dose sites were gently shaved and circled with marker pen for identifying the injection site.

Sampling

Each blood sample (~2.0 mL) were taken from the jugular vein (or other suitable vessel) of each pig via direct venipuncture. The samples were collected into chilled tubes with K2EDTA as the anticoagulant, and inverted several times to mix. Blood samples were kept on wet ice until centrifugation. The blood samples were centrifuged at a temperature of 4° C., at 3,000×g, for 5 minutes. All samples were maintained chilled throughout processing. Plasma was collected into pre-labeled 2-mL microcentrifuge tubes and placed in a freezer set to maintain a temperature of −60° C. to −80° C. until further analysis. The samples were taken prior to dosing, then again at 1, 3, 6, 8, 24, 72, 144, and 240 hours post-dose and sent to an off-site laboratory for bioanalytical analysis. Following the 240 hour post dose blood collection, the animals were euthanized via euthanasia solution IV bolus dose.

Analysis

Samples were processed and analyzed by using a modified LC-MS/MS method (Kapitza, C. et al., J. Clin. Pharm. (2015) 55(5) pp. 497-504) to quantify in swine plasma in the concentration range 5-500 (for BLQ samples) and 50-1000 ng/mL to quantify in swine plasma. Liraglutide was used as an internal standard (IS). The analysis was carried out using a Waters Xevo-TQ-S LC-MS/MS spectrometer monitoring positive ions in the MRM mode with mass transitions m z 1029.468>136.124 Da (semaglutide) and m z 938.9>1266.99 Da (IS), respectively. The LC system was a Waters Acquity™ UPLC® system and the LC column an InfinityLab Poroshell 120 Bonus-RP, 2.1×150 mm, 2.7 μm. Quantification was performed by peak areas and weighted linear regression ($1/x^2$). The lower limit of quantification (LLOQ) for semaglutide was 5 ng/mL. All data and pharmacokinetic parameters were analyzed and graphed using GraphPad Prism version 7.00 for Windows, (GraphPad Software, La Jolla Calif. USA). The area under the concentration curve (AUC) versus time was calculated with the trapezoidal rules from the first sample collection time points (pre-dose, time 0) to last time point of sample collection (240 h post-dose) (($AUC_{T0-T240h}$)). Non-compartmental analysis was used to determine PK parameters for each subject. $AUC_{T0-T240h}$, $C_{max}$ and $T_{max}$ were determined for each subject. The bioavailability of semaglutide via ID administration (Group 1) in comparison to the IV (Group 2) and SC (Group 3) administrations was determined.

Results

The results of the study are shown in Table 50 and in FIGS. 72A-72C show the semaglutide concentration in blood over time after: ID administration via the endoscopically placed ingestible device (FIG. 72A); IV administration (FIG. 72B); and SC administration (FIG. 72C).

The bioavailability of semaglutide via TD administration was determined relative to IV or SC administration. The results are shown in Table 50.

TABLE 50

Semaglutide plasma PK in swine

| Route | ID | IV | SC |
|---|---|---|---|
| N | 4 [a] | 3 | 3 |
| $T_{max}$ (hr) | 6.67 ± 0.54 | 1.00 ± 0.00 | 18.67 ± 4.53 |
| $C_{max}$ (ng) | 33.57 ± 19.04 | 279.00 ± 9.67 | 98.47 ± 3.49 |
| $(AUC)_{T0-T240\,h}$ ng · hr/mL ± SEM | 1709.4 ± 1108.05 | 11371.67 ± 143.81 | 9695.00 ± 313.95 |
| Corrected $(AUC)_{T0-T240\,h}$ ng · hr/mL ± SEM | 1789.42 ± 1156.76 [a] | N/A | N/A |
| Bioavailability relative to IV ± SEM | 15.74 ± 10.17 [a] | 100% | 85.26 ± 2.96 |
| Bioavailability relative to SC ± SEM | 18.46 ± 11.95 [a] | Not calculated | 100% |

[a] AUC corrected for dose was used to calculate bioavailability.

Example 12—Evaluation of the Bioavailability of Adalimumab after Intraduodenal Administration Via Endoscopic Needle Injection in Female Yorkshire Pigs Two studies were conducted to evaluate the plasma pharmacokinetics of adalimumab in female Yorkshire pigs after intraduodenal (ID) administration via an endoscopic injection needle. The results were compared with those obtained after administration of adalimumab via a 2-nozzle jet delivery device, SC or IV (Example 5).

Test Article

Adalimumab in an aqueous buffer having an adalimumab concentration of about 100 mg/mL.

In Vivo Study Design

A total of 5 healthy female Yorkshire pigs (Sus scrofa domesticus) having a body weight of ~25-40 kg were used in these studies, 3 in a first study and 2 in a second study. Each animal received test article via intraduodenal (ID) administration via an injection needle. The study design is shown below in Table 51.

TABLE 51

| Study | Dose Route | N | Dose | Dose Conc. | Dose volume | Blood Collection Time Points |
|---|---|---|---|---|---|---|
| 1 | ID (endoscopic injection needle) | 3 | 40 mg | 100 mg/mL | 400 microliters | Pre-dose, 1, 3, 6, 8, 24, 72, 144, and 240 hours post dose |
| 2 | ID (endoscopic injection needle) | 2 | 40 mg | 100 mg/mL | 400 microliters | Pre-dose, 1, 3, 6, 8, 24, 72, 144, and 240 hours post dose |

Animals were housed one per cage and fasted for a minimum of 12 hours prior to dosing. Food was returned at 4 hours post-dose. Water was supplied ad libitum.

Intraduodenal (ID) administration was performed as follows. The endoscope (Olympus OSF-V60 attached to an Olympus CV60 Tower) configured with an endoscopic injection needle was maneuvered into the pyloric sphincter with camera visualization to identify the third (inferior/horizontal) part of the duodenum (D3). Following confirmation of placement of the endoscopic injection needle in the correct region, the endoscope was retracted out of the pyloric sphincter, leaving the injection device in the D3 region of the duodenum. Once it was confirmed that the endoscopic injection needle was placed in the correct region, approximately 0.5 mL of saline was injected within the lamina propria of the mucosa to create a small bleb in the mucosa. The formulation was then injected into the bleb and flushed with approximately 0.8 mL of saline. The animals were kept under anesthesia through the 1 hour blood collection time point. All other blood collections were performed on the pigs without the use of anesthesia.

Sampling

Each blood sample was collected from the pig jugular vein, or other suitable vessel via direct venipuncture, placed into a chilled tube containing K2-EDTA as the anticoagulant, and inverted several times to mix. Blood samples were kept on wet ice until centrifugation. Blood samples were centrifuged at a temperature of 4° C., at 3,000×g, for 5 minutes and chilled throughout processing. Plasma was collected into pre-labeled polypropylene tubes and placed in a freezer set to maintain −60 to −80° C. prior to analysis.

Plasma samples were collected at pre-dose, 1, 3, 6, 8, 24, 72, 144, and 240 hours post-dose in all animals and sent to an off-site laboratory for bioanalytical analysis. Samples were processed and analyzed by using an adalimumab (anti-TNF-alpha) ELISA kit from Alpha Diagnostics, Inc. (Catalog #200 310-AHG). All plasma samples were diluted by 1:100 dilution. Diluted samples were processed in duplicates and the mean Optical Density (O.D.) was measured using a SpectraMax plate reader and utilizing SoftMax Pro software for analysis. The Lower Limit of Quantification (LLOQ) was calculated by adding 10× the standard deviation value of the blanks O.D. to the average of the blank standard O.D. values. Mean concentrations of adalimumab were back interpolated to a 4-parameter log fit standard curve and subsequently multiplied by the dilution factor to obtain a final corrected adalimumab concentration. All data and pharmacokinetic parameters were analyzed and graphed by using GraphPad Prism version 7.00 for Windows, GraphPad Software, La Jolla Calif. USA, www.graphpad.com (GraphPad Prism 7). The area under the concentration curve (AUC) was calculated with the trapezoidal rules.

Results

PK analysis showed that one animal from the first study and one animal from the second study had quantifiable levels of adalimumab in plasma. The mean $(AUC)_{T0-T240h}$ for these two animals was determined and the results are shown in FIG. 73 in comparison with subset of data from Example 5, specifically, Example 5 Group 3 (ID administration via ingestible jet delivery device having an internal pressure of 320 psig), Group 4 (SC) and Group 5 (IV).

Example 13—Workflow for Clinical Trial

The following workflow can be used in clinical trials testing the ingestible device 100 described above:
1. Capsule is pre-assembled with a target dispensing location identified.
2. Subject is briefed on device functionality and provides informed consent.
3. Capsule is pre-loaded with a quantified amount of therapeutic drug.
4. Capsule is pressurized (drive mechanism).
5. Capsule is shipped to the clinical site.
6. Subject arrives at clinical site fasted.
7. Site personnel ensures that subject swallows the capsule under medical supervision.
8. Capsule completes delivery of drug at pre-determined dispensing location.
9. Capsule naturally passes through GI tract and is excreted.

Other Embodiments

While certain embodiments have been provided, other embodiments are possible.

As an example, some embodiments have been described in which an ingestible device includes one or more pins. However, the disclosure is not limited in this sense. Rather, in such embodiments, any element having the appropriate shape and size, as well as being made of the appropriate material(s), may be used instead of (or, in some cases, in addition to) one or more of the pins.

As another example, while embodiments have been described in which the dispensable substance is released in a single stage. Other embodiments are possible. In some embodiments, multi-stage (e.g., two stage, three stage, four stage) release of the dispensable substance is used. Multi-staged release can be achieved, for example, via multiple elements (e.g., pins, plugs or the like) formed of different materials (e.g., different enteric materials) that degrade/ dissolve erode under different conditions (e.g., different pH, temperature, enzyme concentration) present in different locations in the GI tract of a subject.

As an additional example, while embodiments have been described in which an ingestible device includes a seal or a coating, the disclosure is not limited in this sense. For example, in some embodiments, an ingestible device housing may be covered in one or more coverings, e.g., to seal the ingestible device and/or to hold two modules of the device together. In certain embodiments, an ingestible device may be sealed to prevent contaminants from entering the ingestible device prior to administration to a subject (e.g., during storage of the device) or after administration to a subject (e.g., during transit through the stomach), or to prevent the contents of the ingestible device (e.g., a dispensable substance) from exiting the ingestible device before desired (e.g., prior to triggering). In certain embodiments, an ingestible device is assembled from two modules: one module contains the dispensable substance ("drug module"), while the other module contains the drive force generator and the drive coupling ("drive module"). One or more coverings can be used to partially or wholly join and/or seal the two modules after they are assembled together to form an ingestible device. In some embodiments, one or more coverings cover the entirety of the housing of the ingestible device, while in other embodiments one or more coverings cover only a portion of the housing the ingestible device (e.g., parts of the housing with an opening, parts of the housing that comprise enteric materials, or parts of the housing assembled from two or more different modules after the modules are joined together to form an ingestible device). Examples of covering materials include foils, films, and other materials that degrade or erode in the GI tract, and/or that are made of a relatively low mechanical strength material (e.g., so that a dispensable substance can pass through the covering and exit in the form of a jet after triggering). In some embodiments, one or more coverings are made of a gelatin material, for example, using a gel-enrobed technology such as Press-Fit® or XPress-Fit® gel cap from Lonza (see, e.g., U.S. Pat. Nos. 5,317,849, 5,460,824, 5,464,631, 5,511,361, 5,795,588, 5,609,010, 6,080,426, and 6,245,350). In some embodiments, the one or more coverings are applied to the device housing using a cold-shrink process. In some embodiments, the one or more coverings degrade or erode in the stomach or in the proximal small intestine (e.g., in the duodenum).

As a further example, while certain embodiments of an ingestible device have been described in relation to certain forms of delivery (trans-epithelial, epithelial, topical), the disclosure is not limited in this sense. As an example, in some embodiments, a device described for use in trans-epithelial delivery or for use in epithelial delivery can be used in topical delivery. Generally, such embodiments involve modifying the relevant parameters (e.g., internal pressure, fluid pressure) accordingly. As another example, in some embodiments, a device described for use in epithelial delivery or for use in epithelial delivery can be used in topical delivery. Generally, such embodiments involve modifying the relevant parameters (e.g., internal pressure, fluid pressure) accordingly.

As an additional example, in some embodiments, the volume of the pharmaceutical formulation deposited in the submucosa and/or the mucosa (e.g., into the lamina propria) is about 1 microliter to about 800 microliters, about 10 microliters to about 800 microliters, about 50 microliters to about 800 microliters, about 100 microliters to about 800 microliters, about 200 microliters to about 800 microliters, about 300 microliters to about 800 microliters, about 400 microliters to about 800 microliters, about 500 microliters to about 800 microliters, about 600 microliters to about 800 microliters, about 700 microliters to about 800 microliters, about 1 microliter to about 700 microliters, about 10 microliters to about 700 microliters, about 50 microliters to about 700 microliters, about 100 microliters to about 700 microliters, about 200 microliters to about 700 microliters, about 300 microliters to about 700 microliters, about 400 microliters to about 700 microliters, about 400 microliters to about 700 microliters, about 500 microliters to about 700 microliters, about 600 microliters to about 700 microliters, about 1 microliter to about 600 microliters, about 10 microliters to about 600 microliters, about 50 microliters to about 600 microliters, about 100 microliters to about 600 microliters, about 200 microliters to about 600 microliters, about 300 microliters to about 600 microliters, about 400 microliters to about 600 microliters, about 400 microliters to about 600 microliters, about 500 microliters to about 600 microliters, about 1 microliter to about 500 microliters, about 10 microliters to about 500 microliters, about 50 microliters to about 500 microliters, about 100 microliters to about 500 microliters, about 200 microliters to about 500 microliters, about 300 microliters to about 500 microliters, about 400 microliters to about 500 microliters, about 1 microliter to about 400 microliters, about 10 microliters to about 400 microliters, about 50 microliters to about 400 microliters, about 100 microliters to about 400 microliters, about 200 microliters to about 400 microliters, or about 300 microliters to about 400 microliters. In some embodiments, the volume of the pharmaceutical formulation deposited in the submucosa and/or the mucosa (e.g., into the lamina propria) is about 1 microliter to about 500 microliters, about 10 microliters to about 400 microliters, about 50 microliters to about 400 microliters, about 100 microliters to about 400 microliters, about 200 microliters to about 400 microliters, 250 microliters to about 400 microliters, or about 300 microliters to about 400 microliters. In some embodiments, the volume represents the total volume delivered by the one or more jets. In some embodiments, the volume represents the total volume delivered (or released from the ingestible device) via one jet, by two jets, by three jets, by four jets, or by five jets. In some embodiments, the volume represents the total volume of the pharmaceutical formulation delivered by two jets. For example, when the volume of the pharmaceutical formulation is about 400 microliters, and when the device has two nozzles, the volume of pharmaceutical formulation delivered by each jet is about 200 microliters.

As a further example, in some embodiments, the formulation is deposited in the submucosa and/or the mucosa (e.g., into the lamina propria) of the small intestine of the subject. In some embodiments, the formulation is deposited in the submucosa and/or the mucosa (e.g., into the lamina propria) of the duodenum of the subject. In some embodiments, the formulation is deposited in the submucosa and/or the mucosa (e.g., into the lamina propria) of the jejunum of the subject. In some embodiments, the formulation is deposited in the submucosa and/or the mucosa (e.g., into the lamina propria) of the ileum of the subject.

As another example, in some embodiments, the volume of the pharmaceutical formulation deposited in the mucosa is about 1 microliter to about 800 microliters, about 10 microliters to about 800 microliters, about 50 microliters to about 800 microliters, about 100 microliters to about 800 microliters, about 200 microliters to about 800 microliters, about 300 microliters to about 800 microliters, about 400 microliters to about 800 microliters, about 500 microliters to about 800 microliters, about 600 microliters to about 800 microliters, about 700 microliters to about 800 microliters, about 1 microliter to about 700 microliters, about 10 microliters to about 700 microliters, about 50 microliters to about 700 microliters, about 100 microliters to about 700 microliters, about 200 microliters to about 700 microliters, about 300 microliters to about 700 microliters, about 400 microliters to about 700 microliters, about 500 microliters to about 700 microliters, about 600 microliters to about 700 microliters, about 1 microliter to about 600 microliters, about 10 microliters to about 600 microliters, about 50 microliters to about 600 microliters, about 100 microliters to about 600 microliters, about 200 microliters to about 600 microliters, about 300 microliters to about 600 microliters, about 400 microliters to about 600 microliters, about 400 microliters to about 600 microliters, about 500 microliters to about 600 microliters, about 1 microliter to about 500 microliters, about 10 microliters to about 500 microliters, about 50 microliters to about 500 microliters, about 100 microliters to about 500 microliters, about 200 microliters to about 500 microliters, about 300 microliters to about 500 microliters, about 400 microliters to about 500 microliters, about 1 microliter to about 400 microliters, about 10 microliters to about 400 microliters, about 50 microliters to about 400 microliters, about 100 microliters to about 400 microliters, about 200 microliters to about 400 microliters, or about 300 microliters to about 400 microliters. In some embodiments, the volume of the pharmaceutical formulation deposited in the mucosa is about 1 microliter to about 500 microliters, about 10 microliters to about 400 microliters, about 50 microliters to about 400 microliters, about 100 microliters to about 400 microliters, about 200 microliters to about 400 microliters, 250 microliters to about 400 microliters, or about 300 microliters to about 400 microliters. In some embodiments, the volume represents the total volume delivered by the one or more jets. In some embodiments, the volume represents the total volume delivered (or released from the ingestible device) via one jet, by two jets, by three jets, by four jets, or by five jets. In some embodiments, the volume represents the total volume of the pharmaceutical formulation delivered by two jets. For example, when the volume of the pharmaceutical formulation is about 400 microliters, and when the device has two nozzles, the volume of pharmaceutical formulation delivered by each jet is about 200 microliters.

As yet another example, in some embodiments, the volume of the pharmaceutical formulation deposited in the mucus is about 1 microliter to about 800 microliters, about 10 microliters to about 800 microliters, about 50 microliters to about 800 microliters, about 100 microliters to about 800 microliters, about 200 microliters to about 800 microliters, about 300 microliters to about 800 microliters, about 400 microliters to about 800 microliters, about 500 microliters to about 800 microliters, about 600 microliters to about 800 microliters, about 700 microliters to about 800 microliters, about 1 microliter to about 700 microliters, about 10 microliters to about 700 microliters, about 50 microliters to about 700 microliters, about 100 microliters to about 700 microliters, about 200 microliters to about 700 microliters, about 300 microliters to about 700 microliters, about 400 microliters to about 700 microliters, about 500 microliters to about 700 microliters, about 600 microliters to about 700 microliters, about 1 microliter to about 600 microliters, about 10 microliters to about 600 microliters, about 50 microliters to about 600 microliters, about 100 microliters to about 600 microliters, about 200 microliters to about 600 microliters, about 300 microliters to about 600 microliters, about 400 microliters to about 600 microliters, about 400 microliters to about 600 microliters, about 500 microliters to about 600 microliters, about 1 microliter to about 500 microliters, about 10 microliters to about 500 microliters, about 50 microliters to about 500 microliters, about 100 microliters to about 500 microliters, about 200 microliters to about 500 microliters, about 300 microliters to about 500 microliters, about 400 microliters to about 500 microliters, about 1 microliter to about 400 microliters, about 10 microliters to about 400 microliters, about 50 microliters to about 400 microliters, about 100 microliters to about 400 microliters, about 200 microliters to about 400 microliters, or about 300 microliters to about 400 microliters. In some embodiments, the volume of the pharmaceutical formulation deposited in the mucus is about 1 microliter to about 500 microliters, about 10 microliters to about 400 microliters, about 50 microliters to about 400 microliters, about 100 microliters to about 400 microliters, about 200 microliters to about 400 microliters, 250 microliters to about 400 microliters, or about 300 microliters to about 400 microliters. In some embodiments, the volume represents the total volume delivered by the one or more jets. In some embodiments, the volume represents the total volume delivered (or released from the ingestible device) via one jet, by two jets, by three jets, by four jets, or by five jets. In some embodiments, the volume represents the total volume of the pharmaceutical formulation delivered by two jets. For example, when the volume of the pharmaceutical formulation is about 400 microliters, and when the device has two nozzles, the volume of pharmaceutical formulation delivered by each jet is about 200 microliters.

As a further example, in some embodiments, the volume of the pharmaceutical formulation released from the device is about 1 microliter to about 800 microliters, about 10 microliters to about 800 microliters, about 50 microliters to about 800 microliters, about 100 microliters to about 800 microliters, about 200 microliters to about 800 microliters, about 300 microliters to about 800 microliters, about 400 microliters to about 800 microliters, about 500 microliters to about 800 microliters, about 600 microliters to about 800 microliters, about 700 microliters to about 800 microliters, about 1 microliter to about 700 microliters, about 10 microliters to about 700 microliters, about 50 microliters to about 700 microliters, about 100 microliters to about 700 microliters, about 200 microliters to about 700 microliters, about 300 microliters to about 700 microliters, about 400 microliters to about 700 microliters, about 500 microliters to about 700 microliters, about 600 microliters to about 700 microliters, about 1 microliter to about 600 microliters, about 10 microliters to about 600 microliters, about 50 microliters to about 600 microliters, about 100 microliters to about 600 microliters, about 200 microliters to about 600 microliters, about 300 microliters to about 600 microliters, about 400 microliters to about 600 microliters, about 500 microliters to about 600 microliters, about 1 microliter to about 500 microliters, about 10 microliters to about 500 microliters, about 50 microliters to about 500 microliters, about 100 microliters to about 500 microliters, about 200 microliters to about 500 microliters, about 300 microliters to about 500 microliters, about 400 microliters to about 500 microliters, about 100 microliters to about 450 microliters, about 225 microliters to about 450 microliters, about 1 microliter to about 400 microliters, about 10 microliters to about 400 microliters, about 50 microliters to about 400 microliters, about 100 microliters to about 400 microliters, about 200 microliters to about 400 microliters, about 250 microliters to about 400 microliters, or about 300 microliters to about 400 microliters. In some embodiments, the total volume of the pharmaceutical formulation released from the device is about 1 microliter to about 500 microliters, about 10 microliters to about 400 microliters, about 50 microliters to about 400 microliters, about 100 microliters to about 400 microliters, about 200 microliters to about 400 microliters, 250 microliters to about 400 microliters, or about 300 microliters to about 400 microliters. In some embodiments, the volume represents the total volume delivered by the one or more jets. In some embodiments, the volume represents the total volume delivered (or released from the ingestible device) via one jet, by two jets, by three jets, by four jets, or by five jets. In some embodiments, the volume represents the total volume of the pharmaceutical formulation delivered by two jets. For example, when the volume of the pharmaceutical formulation is about 400 microliters, and when the device has two nozzles, the volume of pharmaceutical formulation delivered by each jet can be about 200 microliters.

As another example, in some embodiments, the volume of the pharmaceutical formulation topically delivered to the gastrointestinal tract of the subject is about 1 microliter to about 800 microliters, about 10 microliters to about 800 microliters, about 50 microliters to about 800 microliters, about 100 microliters to about 800 microliters, about 200 microliters to about 800 microliters, about 300 microliters to about 800 microliters, about 400 microliters to about 800 microliters, about 500 microliters to about 800 microliters, about 600 microliters to about 800 microliters, about 700 microliters to about 800 microliters, about 1 microliter to about 700 microliters, about 10 microliters to about 700 microliters, about 50 microliters to about 700 microliters, about 100 microliters to about 700 microliters, about 200 microliters to about 700 microliters, about 300 microliters to about 700 microliters, about 400 microliters to about 700 microliters, about 400 microliters to about 700 microliters, about 500 microliters to about 700 microliters, about 600 microliters to about 700 microliters, about 1 microliter to about 600 microliters, about 10 microliters to about 600 microliters, about 50 microliters to about 600 microliters, about 100 microliters to about 600 microliters, about 200 microliters to about 600 microliters, about 300 microliters to about 600 microliters, about 400 microliters to about 600 microliters, about 400 microliters to about 600 microliters, about 500 microliters to about 600 microliters, about 1 microliter to about 500 microliters, about 10 microliters to about 500 microliters, about 50 microliters to about 500 microliters, about 100 microliters to about 500 microliters, about 200 microliters to about 500 microliters, about 300 microliters to about 500 microliters, about 400 microliters to about 500 microliters, about 1 microliter to about 400 microliters, about 10 microliters to about 400 microliters, about 50 microliters to about 400 microliters, about 100 microliters to about 400 microliters, about 200 microliters to about 400 microliters, about 400 microliters, or about 300 microliters to about 400 microliters. In some embodiments, the volume of the pharmaceutical formulation topically delivered to the gastrointestinal tract of the subject is about 1 microliter to about 500 microliters, about 10 microliters to about 400 microliters, about 50 microliters to about 400 microliters, about 100 microliters to about 400 microliters, about 200 microliters to about 400 microliters, 250 microliters to about 400 microliters, or about 300 microliters to about 400 microliters. In some embodiments, the volume represents the total volume delivered by the one or more jets. In some embodiments, the volume represents the total volume delivered (or released from the ingestible device) via one jet, by two jets, by three jets, by four jets, or by five jets. In some embodiments, the volume represents the total volume of the pharmaceutical formulation delivered by two jets. For example, when the volume of the pharmaceutical formulation is about 400 microliters, and when the device has two nozzles, the volume of pharmaceutical formulation delivered by each jet can be about 200 microliters.

As yet another example, in some embodiments, a first portion of the pharmaceutical formulation released from the device is deposited in the submucosa and a second portion is deposited in the mucosa (such as the lamina propria), and/or is released into the lumen, and may subsequently adhere to the mucus of the gastrointestinal tract. In some embodiments, the first portion of the pharmaceutical formulation deposited into the submucosa contains at least about 99% of the total pharmaceutical formulation released from the device, wherein the % is a w/w %, a w/v %, or a v/v % of the pharmaceutical formulation. In other embodiments, the first portion of the pharmaceutical formulation deposited into the submucosa contains at least about 95%, about 90%, about 85%, about 80%, about 75%, about 70%, about 75%, about 70%, about 65%, about 60%, about 55% or about 50% of the pharmaceutical formulation, wherein the % is a w/w %, a w/v %, or a v/v % of the pharmaceutical formulation. In yet other embodiments, the first portion of the pharmaceutical formulation deposited into the submucosa contains at least about 45%, at least about 40%, at least about 35%, at least about 30%, at least about 25%, at least about 20%, at least about 15%, at least about 10%, or at least about 5% of the pharmaceutical formulation, wherein the % is a w/w %, a w/v %, or a v/v % of the pharmaceutical formulation.

As an additional example, in some embodiments, the formulation is topically delivered to the small intestine of the subject. In some embodiments, the formulation is topically delivered to the duodenum of the subject. In some embodiments, the formulation is topically delivered to the jejunum of the subject. In some embodiments, the formulation is topically delivered to the ileum of the subject. In some embodiments, the topical delivery of the formulation to the small intestine of the subject is for use in treating ileal Crohn's disease.

As another example, in some embodiments, the formulation is topically delivered to the large intestine of the subject. In some embodiments, the formulation is topically delivered to the cecum of the subject. In some embodiments, the formulation is topically delivered to the colon of the subject. In some embodiments, the formulation is topically delivered to the rectum of the subject. In some embodiments, the topical delivery of the formulation to the large intestine of the subject is for use in treating an inflammatory bowel disease (IBD), where the IBD is Crohn's disease or ulcerative colitis.

As a further example, in some embodiments of any of the devices or methods described herein, the releasing of the therapeutic is triggered by one or more of: a pH in the jejunum of about 6.1 to about 7.2, a pH in the mid small bowel of about 7.0 to about 7.8, a pH in the ileum of about 7.0 to about 8.0, a pH in the right colon of about 5.7 to about 7.0, a pH in the mid colon of about 5.7 to about 7.4, or a pH in the left colon of about 6.3 to about 7.7, such as about 7.0.

As another example, in some embodiments of any of the devices or methods described herein, the releasing of the therapeutic is triggered by degradation of a release component located in the device. In some embodiments of any of the devices or methods described herein, the releasing of the therapeutic is dependent on enzymatic activity at or in the vicinity of the location. In some embodiments of any of the devices or methods described herein, the composition includes a plurality of electrodes including a coating, and releasing the therapeutic is triggered by an electric signal by the electrodes resulting from the interaction of the coating with an intended site of release of the therapeutic. In some embodiments of any of the devices or methods described herein, the release of the therapeutic is triggered by a remote electromagnetic signal. In some embodiments of any of the devices or methods described herein, the release of the therapeutic is triggered by generation in the composition of a gas in an amount sufficient to expel the therapeutic. In some embodiments of any of the devices or methods described herein, the release of the therapeutic is triggered by an electromagnetic signal generated within the device according to a pre-determined drug release profile.

As another example, in some embodiments, the peak fluid pressure or the internal pressure on the pharmaceutical formulation inside the device, prior to release from the device, is at least about 100 psig, optionally ranging from about 100 psig to about 500 psig, and the mean jet velocity of each of the one or more jets upon release of the pharmaceutical formulation from the device ranges from about 10 m/s to about 50 m/s. In a further embodiment, the total volume of the pharmaceutical formulation released from the device ranges from about 50 microliters to about 500 microliters, from about 100 microliters to about 450 microliters, from about 200 microliters to about 400 microliters, from 250 microliters to about 400 microliters, or from about 300 microliters to about 400 microliters. In yet a further embodiment, the device comprises 1 to 5 nozzles, 2 to 4 nozzles, or 2 nozzles, wherein each nozzle has an inner diameter at the point of exit from the device ranging from about 0.1 mm to about 0.75 mm, or from about 0.30 mm to about 0.50 mm. In some embodiments, the mean jet impact pressure applied by each of the one or more jets at the target surface ranges from about 7.25 psig to 145 psig.

As yet another example, in some embodiments, the peak fluid pressure or the internal pressure on the pharmaceutical formulation inside the device, prior to release from the device, is at least about 100 psig, optionally ranging from about 100 psig to about 450 psig, the mean jet velocity of each of the one or more jets upon release of the pharmaceutical formulation from the device ranges from about 10 m/s to about 50 m/s, the total volume of the pharmaceutical formulation released from the device ranges from about 200 microliters to about 500 microliters, from about 225 microliters to about 450 microliters, or from about 250 to about 400 microliters. In yet a further embodiment, the device comprises 2, 3 or 4 nozzles, in some preferred embodiments, 2 nozzles, wherein each nozzle has an inner diameter at the point of exit from the device ranging from about 0.2 mm to about 0.6 mm, or from about 0.30 mm to about 0.50 mm, for example, 0.35 mm. In some embodiments, the mean jet impact pressure applied by each of the one or more jets at the target surface ranges from about 7.25 psig to 145 psig.

In a further example, in some embodiments, the peak fluid pressure or the internal pressure on the pharmaceutical formulation inside the device, prior to release from the device is at least about 150 psig, optionally ranging from about 150 psig to about 400 psig, and the peak mean jet velocity of each of the one or more jets upon release of the pharmaceutical formulation from the device ranges from about 15 m/s to about 40 m/s, or from about 18 m/s to about 35 m/s. In a further embodiment, the total volume of the pharmaceutical formulation released from the device ranges from about 50 microliters to about 500 microliters, from about 100 microliters to about 450 microliters, from about 200 microliters to about 400 microliters, from 250 microliters to about 400 microliters, or from about 300 microliters to about 400 microliters. In yet a further embodiment, the device comprises 1 to 5 nozzles, 2 to 4 nozzles, or 2 nozzles, wherein each nozzle has an inner diameter at the point of exit from the device ranging from about 0.1 mm to about 0.75 mm, or from about 0.30 mm to about 0.50 mm, for example, about 0.35 mm. In some embodiments, the mean jet impact pressure applied by each of the one or more jets at the target surface ranges from about 21.76 psig to about 72.52 psig, or from about 29 psig to about 65.37 psig.

In still a further example, in some embodiments, the peak fluid pressure or the internal pressure on the pharmaceutical formulation inside the device, prior to release from the device is at least about 150 psig, optionally ranging from about 150 psig to about 350 psig, and the mean velocity of each of the one or more jets upon release of the pharmaceutical formulation from the device ranges from about 18 m/s to about 35 m/s, or from about 20 m/s to about 30 m/s. In a further embodiment, the total volume of the pharmaceutical formulation released from the device ranges from about 200 microliters to about 500 microliters, from about 225 microliters to about 450 microliters, or from about 250 to about 400 microliters. In yet a further embodiment, the device comprises 2, 3 or 4 nozzles, in some preferred embodiments, 2 nozzles, wherein each nozzle has an inner diameter at the point of exit from the device ranging from about 0.2 mm to about 0.6 mm, or from about 0.30 mm to about 0.50 mm, for example, 0.35 mm. In some embodiments, the mean jet impact pressure applied by each of the one or more jets at the target surface ranges from about 21.76 psig to about 72.52 psig, or from about 29 psig to about 65.37 psig.

In another example, in some embodiments, the peak fluid pressure or the internal pressure on the pharmaceutical formulation inside the device, prior to release from the device is at least about 200 psig, optionally ranging from about 200 psig to about 400 psig, and the mean jet velocity of each of the one or more jets upon release of the pharmaceutical formulation from the device ranges from about 23 m/s to about 36 m/s, or from about 25 m/s to about 35 m/s. In a further embodiment, the total volume of the pharmaceutical formulation released from the device ranges from about 50 microliters to about 500 microliters, from about 100 microliters to about 450 microliters, from about 200 microliters to about 400 microliters, from 250 microliters to about 400 microliters, or from about 300 microliters to about 400 microliters. In yet a further embodiment, the device comprises 1 to 5 nozzles, 2 to 4 nozzles, or 2 nozzles, wherein each nozzle has an inner diameter at the point of exit from the device ranging from about 0.1 mm to about 0.75 mm, or from about 0.30 mm to about 0.50 mm, for example, about 0.35 mm. In some embodiments, the mean jet impact pressure applied by each of the one or more jets at the target surface ranges from about 29 psig to about 72.52 psig, from about 36.26 psig to about 72.52 psig, from about 43.51 psig to about 72.52 psig, or from about 26.26 psig to about 65.27 psig.

In still another example, in some embodiments, the peak fluid pressure or the internal pressure on the pharmaceutical formulation inside the device, prior to release from the device is at least about 220 psig, or at least about 225 psig, optionally ranging from about 225 psig to about 400 psig, and the mean jet velocity of each of the one or more jets upon release of the pharmaceutical formulation from the device ranges from about 24 m/s to about 36 m/s, or from about 25 m/s to about 35 m/s. In a further embodiment, the total volume of the pharmaceutical formulation released from the device ranges from about 200 microliters to about 500 microliters, from about 225 microliters to about 450 microliters, or from about 250 to about 400 microliters. In yet a further embodiment, the device comprises 2, 3 or 4 nozzles, in some preferred embodiments, 2 nozzles, wherein each nozzle has an inner diameter at the point of exit from the device ranging from about 0.2 mm to about 0.6 mm, or from about 0.30 mm to about 0.50 mm, for example, 0.35 mm. In some embodiments, the mean jet impact pressure applied by each of the one or more jets at the target surface ranges from about 29 psig to about 72.52 psig, from about 36.26 psig to about 72.52 psig, from about 43.51 psig to about 72.52 psig, or from about 26.26 psig to about 65.27 psig.

In a further example, in some embodiments, the peak fluid pressure or the internal pressure on the pharmaceutical formulation inside the device, prior to release from the device is at least about 225 psig, or at least about 250 psig, optionally ranging from about 250 psig to about 400 psig, and the mean jet velocity of each of the one or more jets upon release of the pharmaceutical formulation from the device ranges from about 25 m/s to about 36 m/s, or from about 25 m/s to about 35 m/s. In a further embodiment, the total volume of the pharmaceutical formulation released from the device ranges from about 50 microliters to about 500 microliters, from about 100 microliters to about 450 microliters, from about 200 microliters to about 400 microliters, from 250 microliters to about 400 microliters, or from about 300 microliters to about 400 microliters. In yet a further embodiment, the device comprises 1 to 5 nozzles, 2 to 4 nozzles, or 2 nozzles, wherein each nozzle has an inner diameter at the point of exit from the device ranging from about 0.1 mm to about 0.75 mm, or from about 0.30 mm to about 0.50 mm, for example, about 0.35 mm. In some embodiments, the mean jet impact pressure applied by each of the one or more jets at the target surface ranges from about 29 psig to about 72.52 psig, from about 36.26 psig to about 72.52 psig, from about 43.51 psig to about 72.52 psig, or from about 26.26 psig to about 65.27 psig.

In another example, in some embodiments, the peak fluid pressure or the internal pressure on the pharmaceutical formulation inside the device, prior to release from the device, is at least about 250 psig, or at least about 275 psig, optionally ranging from about 275 psig to about 375 psig, and the mean jet velocity of each of the one or more jets upon release of the pharmaceutical formulation from the device ranges from about 25 m/s to about 35 m/s, or from about 25 m/s to about 30 m/s. In a further embodiment, the total volume of the pharmaceutical formulation released from the device ranges from about 200 microliters to about 500 microliters, from about 225 microliters to about 450 microliters, or from about 250 to about 400 microliters. In yet a further embodiment, the device comprises 2, 3 or 4 nozzles, in some preferred embodiments, 2 nozzles, wherein each nozzle has an inner diameter at the point of exit from the device ranging from about 0.2 mm to about 0.6 mm, or from about 0.30 mm to about 0.50 mm, for example, 0.35 mm. In some embodiments, the mean impact pressure applied by each of the one or more jets at the target surface ranges from about 43.51 psig to about 72.52 psig, or from about 50.76 psig to about 65.27 psig.

In an additional example, in some embodiments, the peak fluid pressure or the internal pressure on the pharmaceutical formulation inside the device, prior to release from the device is at least about 275 psig, or at least about 300 psig, optionally ranging from about 300 psig to about 375 psig, and the mean velocity of each of the one or more jets upon release of the pharmaceutical formulation from the device ranges from about 25 m/s to about 35 m/s, or from about 25 m/s to about 30 m/s. In a further embodiment, the total volume of the pharmaceutical formulation released from the device ranges from about 50 microliters to about 500 microliters, from about 100 microliters to about 450 microliters, from about 200 microliters to about 400 microliters, from 250 microliters to about 400 microliters, or from about 300 microliters to about 400 microliters. In yet a further embodiment, the device comprises 1 to 5 nozzles, 2 to 4 nozzles, or 2 nozzles, wherein each nozzle has an inner diameter at the point of exit from the device ranging from about 0.1 mm to about 0.75 mm, or from about 0.30 mm to about 0.50 mm, for example, about 0.35 mm. In some embodiments, the mean impact pressure applied by each of the one or more jets at the target surface ranges from about 43.51 psig to about 72.52 psig, or from about 50.76 psig to about 65.27 psig.

In yet a further example, in some embodiments, the peak fluid pressure or the internal pressure on the pharmaceutical formulation inside the device, prior to release from the device, is at least about 300 psig, or at least about 320 psig, optionally ranging from about 320 psig to about 375 psig, and the mean jet velocity of each of the one or more jets upon release of the pharmaceutical formulation from the device ranges from about 26 m/s to about 35 m/s, from about 27 m/s to about 30 m/s, or from about 28 m/s to about 30 m/s. In a further embodiment, the total volume of the pharmaceutical formulation released from the device ranges from about 200 microliters to about 500 microliters, from about 225 microliters to about 450 microliters, or from about 250 to about 400 microliters. In yet a further embodiment, the device comprises 2, 3 or 4 nozzles, in some preferred embodiments, 2 nozzles, wherein each nozzle has an inner diameter at the point of exit from the device ranging from about 0.2 mm to about 0.6 mm, or from about 0.30 mm to about 0.50 mm, for example, 0.35 mm. In some embodiments, the mean impact pressure applied by each of the one or more jets at the target surface ranges from about 58.0 psig to about 72.52 psig, from about 59.47 psig to about 68.17 psig, from about 60.92 psig to about 66.72 psig, from about 63.37 psig to about 65.27 psig.

In another example, in some embodiments, there is provided a method of depositing a pharmaceutical formulation containing a small molecule drug to the submucosa and/or the mucosa of the small intestine of the subject. In some embodiments, the small molecule has a molecular weight ranging from about 50 Da to about 1500 Da, and the peak fluid pressure or the internal pressure of the pharmaceutical formulation, prior to release from the device, is at least about 100 psig. In some embodiments, the internal pressure is at least about 150 psig. In some embodiments, the internal pressure is at least about 200 psig. In some embodiments, the internal pressure is at least about 220 psig. In some embodiments, the internal pressure ranges from about 150 psig to about 450 psig, from about 150 psig to about 400 psig, from about 150 psig to about 375 psig, from about 150 psig to about 350 psig, from about 150 to about 325 psig, or from about 150 to about 300 psig. In other embodiments, the internal pressure for delivering the small molecule drug ranges from about 175 psig to about 450 psig, from about 175 psig to about 400 psig, from about 175 psig to about 375 psig, from about 175 psig to about 350 psig, from about 175 to about 325 psig, or from about 175 psig to about 300 psig. In other embodiments, the internal pressure for delivering the small molecule drug ranges from about 200 psig to about 450 psig, from about 200 psig to about 400 psig, from about 200 psig to about 375 psig, from about 200 psig to about 350 psig, from about 200 to about 325 psig, or from about 200 psig to about 300 psig. In other embodiments, the internal pressure for delivering the small molecule drug ranges from about 220 psig to about 450 psig, from about 220 psig to about 400 psig, from about 220 psig to about 375 psig, from about 220 psig to about 350 psig, from about 220 psig to about 325 psig, or from about 220 psig to about 300 psig. In other embodiments, the internal pressure for delivering the small molecule drug ranges from about 225 psig to about 450 psig, from about 225 psig to about 400 psig, from about 225 psig to about 375 psig, from about 225 psig to about 350 psig, from about 225 psig to about 325 psig, or from about 225 psig to about 300 psig.

In yet another example, in some embodiments, there is provided a method of depositing a pharmaceutical formulation containing a medium sized drug or peptide to the submucosa and/or the mucosa (e.g., into the lamina propria) of the small intestine of the subject. In some embodiments, the drug has a molecular weight is greater than about 1500 Da and less than about 20 kDa, less than about 30 kDa, less than about 40 kDa, less than about 50 kDa or less than about 60 kDa, and the peak fluid pressure or the internal pressure on the pharmaceutical formulation, prior to release from the device, is at least about 150 psig. In some embodiments, the internal pressure is at least about 200 psig. In some embodiments, the internal pressure is at least about 220 psig. In some embodiments, the internal pressure is at least about 225 psig. In some embodiments, the internal pressure ranges from about 200 psig to about 450 psig, about 200 psig to about 400 psig, from about 200 psig to about 375 psig, from about 200 psig to about 350 psig, from about 200 to about 325 psig, or from about 200 to about 300 psig. In other embodiments, the internal pressure ranges from about 220 psig to about 450 psig, about 220 psig to about 400 psig, from about 220 psig to about 375 psig, from about 220 psig to about 350 psig, from about 220 psig to about 325 psig, or from about 220 psig to about 300 psig. In other embodiments, the internal pressure ranges from about 225 psig to about 450 psig, 225 psig to about 400 psig, from about 225 psig to about 375 psig, from about 225 psig to about 350 psig, from about 225 psig to about 325 psig, or from about 225 psig to about 300 psig. In other embodiments, the internal pressure ranges from about 250 psig to about 450 psig, 250 psig to about 400 psig, from about 250 psig to about 375 psig, from about 250 psig to about 350 psig, from about 250 psig to about 325 psig, or from about 250 psig to about 300 psig. In other embodiments, the internal pressure ranges from about 275 psig to about 450 psig, 275 psig to about 400 psig, from about 275 psig to about 375 psig, from about 275 psig to about 350 psig, from about 275 psig to about 325 psig, or from about 275 psig to about 300 psig. In other embodiments, the internal pressure ranges from about 300 psig to about 450 psig, from about 300 psig to about 400 psig, from about 300 psig to about 375 psig, from about 300 psig to about 350 psig, or from about 300 psig to about 325 psig.

In an additional example, in some embodiments, there is provided a method of depositing a pharmaceutical formulation containing a large drug, such a therapeutic protein or antibody, to the submucosa and/or the mucosa (e.g., into the lamina propria) of the small intestine of the subject. In some embodiments, the drug has a molecular weight is at least about 20 kDa, at least about 30 kDa, at least about 40 kDa, at least about 50 kDa or at least about 60 kDa. In some embodiments, the drug has a molecular weight ranging from about 20 kDa to about 200 kDa, from about 20 kDa to about 175 kDa, or from about 20 kDa to about 150 kDa. In some other embodiments, the drug has a molecular weight ranging from about 60 kDa to about 200 kDa, from about 60 kDa to about 175 kDa, or from about 60 kDa to about 150 kDa. In some embodiments, the peak fluid pressure or the internal pressure on the pharmaceutical formulation, prior to release from the device, is at least about 225 psig. In some embodiments, the internal pressure is at least about 230 psig. In some embodiments, the internal pressure is at least about 235 psig, at least about 240 psig, at least about 245 psig, or at least about 250 psig. In some embodiments, the internal pressure is at least about 275 psig, at least about 300 psig, or at least about 320 psig. In some embodiments, the internal pressure ranges from about 225 psig to about 500 psig, from about 225 psig to about 475 psig, from about 225 psig to about 450 psig, from about 225 to about 425 psig, from about 225 to about 400 psig, from about 225 to about 375 psig, from about 225 to about 350 psig, or from about 225 to about 325 psig. In some embodiments, the internal pressure ranges from about 250 psig to about 500 psig, from about 250 psig to about 475 psig from about 250 psig to about 450 psig, from about 250 to about 425 psig, from about 250 to about 400 psig, from about 250 to about 375 psig, from about 250 to about 350 psig, or from about 250 to about 325 psig. In some embodiments, the internal pressure ranges from about 275 psig to about 500 psig, from about 275 psig to about 475 psig, from about 275 psig to about 450 psig, from about 275 to about 425 psig, from about 275 to about 400 psig, from about 275 to about 375 psig, from about 275 to about 350 psig, or from about 275 to about 325 psig. In some embodiments, the internal pressure ranges from about 300 psig to about 500 psig, from about 300 psig to about 475 psig, from about 300 psig to about 450 psig, from about 300 to about 425 psig, from about 300 to about 400 psig, from about 300 to about 375 psig, from about 300 to about 350 psig, or from about 300 to about 325 psig. In some embodiments, the internal pressure ranges from about 320 psig to about 500 psig, from about 320 psig to about 475 psig, from about 320 psig to about 450 psig, from about 320 to about 425 psig, from about 320 to about 400 psig, from about 320 to about 375 psig, or from about 320 to about 350 psig.

In some embodiments, the internal pressure on the pharmaceutical formulation inside the device, prior to release from the device (i.e., the peak fluid pressure), is at least about 100 psig, optionally of about 100 psig to about 450 psig. In a further embodiment, the mean velocity of each of the one or more jets upon release of the pharmaceutical formulation from the device is about 10 m/s to about 50 m/s. In yet a further embodiment, the total volume of the pharmaceutical formulation released from the device is about 200 microliters to about 500 microliters, about 225 microliters to about 450 microliters, or about 250 to about 400 microliters. In yet a further embodiment, the device comprises 2, 3 or 4 nozzles, in some preferred embodiments, 2 nozzles, wherein each nozzle has an inner diameter at the point of exit from the device of about 0.2 mm to about 0.6 mm, or about 0.30 mm to about 0.50 mm, for example, 0.35 mm. In some embodiments, the impact pressure applied by each of the one or more jets at the target surface is about 0.05 MPa (7.25 psig) to about 1 MPa (145 psig).

In some embodiments, the internal pressure on the pharmaceutical formulation inside the device, prior to release from the device (i.e., the peak fluid pressure), is at least about 150 psig, optionally of about 150 psig to about 400 psig. In a further embodiment, the mean velocity of each of the one or more jets upon release of the pharmaceutical formulation from the device is about 15 m/s to about 40 m/s, or about 18 m/s to about 35 m/s. In a further embodiment, the total volume of the pharmaceutical formulation released from the device is about 50 microliters to about 500 microliters, about 100 microliters to about 450 microliters, about 200 microliters to about 400 microliters, 250 microliters to about 400 microliters, or about 300 microliters to about 400 microliters. In yet a further embodiment, the device comprises 1 to 5 nozzles, 2 to 4 nozzles, or 2 nozzles, wherein each nozzle has an inner diameter at the point of exit from the device of about 0.1 mm to about 0.75 mm, or about 0.30 mm to about 0.50 mm, for example, about 0.35 mm. In some embodiments, the impact pressure applied by each of the one or more jets at the target surface is about 0.15 MPa (21.8 psig) to about 0.5 MPa (72.5 psig), or about 0.2 MPa (29 psig) to about 0.45 MPa (65.3 psig).

In some embodiments, the internal pressure on the pharmaceutical formulation inside the device, prior to release from the device (i.e., the peak fluid pressure), is at least about 150 psig, optionally of about 150 psig to about 350 psig. In a further embodiment, the mean velocity of each of the one or more jets upon release of the pharmaceutical formulation from the device is about 18 m/s to about 35 m/s, or about 20 m/s to about 30 m/s. In yet a further embodiment, the total volume of the pharmaceutical formulation released from the device is about 200 microliters to about 500 microliters, about 225 microliters to about 450 microliters, or about 250 to about 400 microliters. In yet a further embodiment, the device comprises 2, 3 or 4 nozzles, in some preferred embodiments, 2 nozzles, wherein each nozzle has an inner diameter at the point of exit from the device of about 0.2 mm to about 0.6 mm, or about 0.30 mm to about 0.50 mm, for example, 0.35 mm. In some embodiments, the impact pressure applied by each of the one or more jets at the target surface is about 00.15 MPa (21.8 psig) to about 0.5 MPa (72.5 psig), or about 0.2 MPa (29 psig) to about 0.45 MPa (65.3 psig).

In some embodiments, the internal pressure on the pharmaceutical formulation inside the device, prior to release from the device (i.e., the peak fluid pressure), is at least about 200 psig, optionally of about 200 psig to about 400 psig. In a further embodiment, the mean velocity of each of the one or more jets upon release of the pharmaceutical formulation from the device is about 23 m/s to about 36 m/s, or about 25 m/s to about 35 m/s. In yet a further embodiment, the total volume of the pharmaceutical formulation released from the device is about 50 microliters to about 500 microliters, about 100 microliters to about 450 microliters, about 200 microliters to about 400 microliters, 250 microliters to about 400 microliters, or about 300 microliters to about 400 microliters. In yet a further embodiment, the device comprises 1 to 5 nozzles, 2 to 4 nozzles, or 2 nozzles, wherein each nozzle has an inner diameter at the point of exit from the device of about 0.1 mm to about 0.75 mm, or about 0.30 mm to about 0.50 mm, for example, about 0.35 mm. In some embodiments, the impact pressure applied by each of the one or more jets at the target surface is about 0.2 MPa (29 psig) to about 0.5 MPa (72.5 psig), about 0.25 (36.3 psig) to about 0.5 MPa (72.5 psig), about 0.3 MPa (43.5 psig) to about 0.5 MPa (72.5 psig), or about 0.25 (36.3 psig) to about 0.45 MPa (65.3 psig).

In some embodiments, the internal pressure on the pharmaceutical formulation inside the device, prior to release from the device (i.e., the peak fluid pressure), is at least about 220 psig, or at least about 225 psig, optionally of about 225 psig to about 400 psig. In a further embodiment, the mean velocity of each of the one or more jets upon release of the pharmaceutical formulation from the device is about 24 m/s to about 36 m/s, or about 25 m/s to about 35 m/s. In a further embodiment, the total volume of the pharmaceutical formulation released from the device is about 200 microliters to about 500 microliters, about 225 microliters to about 450 microliters, or about 250 to about 400 microliters. In yet a further embodiment, the device comprises 2, 3 or 4 nozzles, in some preferred embodiments, 2 nozzles, wherein each nozzle has an inner diameter at the point of exit from the device of about 0.2 mm to about 0.6 mm, or about 0.30 mm to about 0.50 mm, for example, 0.35 mm. In some embodiments, the impact pressure applied by each of the one or more jets at the target surface is about 0.25 (36.3 psig) to about 0.5 MPa (72.5 psig), about 0.3 MPa (43.5 psig) to about 0.5 MPa (72.5 psig), or about 0.25 (36.3 psig) to about 0.45 MPa (65.3 psig).

In some embodiments, the internal pressure on the pharmaceutical formulation inside the device, prior to release from the device (i.e., the peak fluid pressure), is at least about 225 psig, or at least about 250 psig, optionally of about 250 psig to about 400 psig. In a further embodiment, the mean velocity of each of the one or more jets upon release of the pharmaceutical formulation from the device is about 25 m/s to about 36 m/s, or about 25 m/s to about 35 m/s. In yet a further embodiment, the total volume of the pharmaceutical formulation released from the device is about 50 microliters to about 500 microliters, about 100 microliters to about 450 microliters, about 200 microliters to about 400 microliters, 250 microliters to about 400 microliters, or about 300 microliters to about 400 microliters. In yet a further embodiment, the device comprises 1 to 5 nozzles, 2 to 4 nozzles, or 2 nozzles, wherein each nozzle has an inner diameter at the point of exit from the device of about 0.1 mm to about 0.75 mm, or about 0.30 mm to about 0.50 mm, for example, about 0.35 mm. In some embodiments, the impact pressure applied by each of the one or more jets at the target surface is about 0.25 (36.3 psig) to about 0.5 MPa (72.5 psig), about 0.3 MPa (43.5 psig) to about 0.5 MPa (72.5 psig), or about 0.25 (36.3 psig) to about 0.45 MPa (65.3 psig).

In some embodiments, the internal pressure on the pharmaceutical formulation inside the device, prior to release from the device (i.e., the peak fluid pressure), is at least about 250 psig, or at least about 275 psig, optionally of about 275 psig to about 375 psig. In a further embodiment, the mean velocity of each of the one or more jets upon release of the pharmaceutical formulation from the device is about 25 m/s to about 35 m/s, or about 25 m/s to about 30 m/s. In yet a further embodiment, the total volume of the pharmaceutical formulation released from the device is about 200 microliters to about 500 microliters, about 225 microliters to about 450 microliters, or about 250 to about 400 microliters. In yet a further embodiment, the device comprises 2, 3 or 4 nozzles, in some preferred embodiments, 2 nozzles, wherein each nozzle has an inner diameter at the point of exit from the device of about 0.2 mm to about 0.6 mm, or about 0.30 mm to about 0.50 mm, for example, 0.35 mm. In some embodiments, the impact pressure applied by each of the one or more jets at the target surface is about 0.3 MPa (43.5 psig) to about 0.5 MPa (72.5 psig), or about 0.25 (36.3 psig) to about 0.45 MPa (65.3 psig).

In some embodiments, the internal pressure on the pharmaceutical formulation inside the device, prior to release from the device (i.e., the peak fluid pressure), is at least about 275 psig, or at least about 300 psig, optionally of about 300 psig to about 375 psig. In a further embodiment, the mean velocity of each of the one or more jets upon release of the pharmaceutical formulation from the device is about 25 m/s to about 35 m/s, or about 25 m/s to about 30 m/s. In yet a further embodiment, the total volume of the pharmaceutical formulation released from the device is about 50 microliters to about 500 microliters, about 100 microliters to about 450 microliters, about 200 microliters to about 400 microliters, 250 microliters to about 400 microliters, or about 300 microliters to about 400 microliters. In yet a further embodiment, the device comprises 1 to 5 nozzles, 2 to 4 nozzles, or 2 nozzles, wherein each nozzle has an inner diameter at the point of exit from the device of about 0.1 mm to about 0.75 mm, or about 0.30 mm to about 0.50 mm, for example, about 0.35 mm. In some embodiments, the impact pressure applied by each of the one or more jets at the target surface is about 0.35 MPa (50.8 psig) to about 0.5 MPa (72.5 psig), or about 0.4 (58 psig) to about 0.45 MPa (65.3 psig).

In some embodiments, the internal pressure on the pharmaceutical formulation inside the device, prior to release from the device (i.e., the peak fluid pressure), is at least about 300 psig, or at least about 320 psig, optionally of about 320 psig to about 375 psig. In a further embodiment, the mean velocity of each of the one or more jets upon release of the pharmaceutical formulation from the device is about 26 m/s to about 35 m/s, about 27 m/s to about 30 m/s, or about 28 m/s to about 30 m/s. In yet a further embodiment, the total volume of the pharmaceutical formulation released from the device is about 200 microliters to about 500 microliters, about 225 microliters to about 450 microliters, or about 250 to about 400 microliters. In yet a further embodiment, the device comprises 2, 3 or 4 nozzles, in some preferred embodiments, 2 nozzles, wherein each nozzle has an inner diameter at the point of exit from the device of about 0.2 mm to about 0.6 mm, or about 0.30 mm to about 0.50 mm, for example, 0.35 mm. In some embodiments, the impact pressure applied by each of the one or more jets at the target surface is about 0.4 MPa (58.1 psig) to about 0.5 MPa (72.5 psig), about 0.41 (59.5 psig) to about 0.47 MPa (68.2 psig), about 0.42 (60.9 psig) to about 0.46 MPa (66.7 psig), or about 0.43 (62.4 psig) to about 0.45 MPa (65.3 psig).

In some embodiments, there is provided a method of depositing a pharmaceutical formulation containing a small molecule drug to the submucosa and/or mucosa of the small intestine of the subject. In some embodiments, the small molecule has a molecular weight of about 50 Da to about 1500 Da, and the internal pressure on the pharmaceutical formulation, prior to release from the device (i.e., the peak fluid pressure), is at least about 100 psig. In some embodiments, the internal pressure is at least about 150 psig. In some embodiments, the internal pressure is at least about 200 psig. In some embodiments, the internal pressure is at least about 220 psig. In some embodiments, the internal pressure is about 150 psig to about 450 psig, about 150 psig to about 400 psig, about 150 psig to about 375 psig, about 150 psig to about 350 psig, about 150 psig to about 325 psig, or about 150 psig to about 300 psig. In other embodiments, the internal pressure for delivering the small molecule drug is about 175 psig to about 450 psig, about 175 psig to about 400 psig, about 175 psig to about 375 psig, about 175 psig to about 350 psig, about 175 psig to about 325 psig, or about 175 psig to about 300 psig. In other embodiments, the internal pressure for delivering the small molecule drug is about 200 psig to about 450 psig, about 200 psig to about 400 psig, about 200 psig to about 375 psig, about 200 psig to about 350 psig, about 200 to about 325 psig, or about 200 psig to about 300 psig. In other embodiments, the internal pressure for delivering the small molecule drug is about 220 psig to about 450 psig, about 220 psig to about 400 psig, about 220 psig to about 375 psig, about 220 psig to about 350 psig, about 220 psig to about 325 psig, or about 220 psig to about 300 psig. In other embodiments, the internal pressure for delivering the small molecule drug is about 225 psig to about 450 psig, about 225 psig to about 400 psig, about 225 psig to about 375 psig, about 225 psig to about 350 psig, about 225 psig to about 325 psig, or about 225 psig to about 300 psig.

In some embodiments, there is provided a method of depositing a pharmaceutical formulation containing a medium sized drug or peptide to the submucosa and/or the mucosa (e.g., into the lamina propria) of the small intestine of the subject. In some embodiments, the drug has a molecular weight is greater than about 1500 Da and less than about 20 kDa, less than about 30 kDa, less than about 40 kDa, less than about 50 kDa or less than about 60 kDa. In some embodiments, the internal pressure on the pharmaceutical formulation, prior to release from the device (i.e., the peak fluid pressure), is at least about 150 psig. In some embodiments, the internal pressure is at least about 200 psig. In some embodiments, the internal pressure is at least about 220 psig. In some embodiments, the internal pressure is at least about 225 psig. In some embodiments, the internal pressure is about 200 psig to about 450 psig, about 200 psig to about 400 psig, about 200 psig to about 375 psig, about 200 psig to about 350 psig, about 200 psig to about 325 psig, or about 200 psig to about 300 psig. In other embodiments, the internal pressure is about 220 psig to about 450 psig, about 220 psig to about 400 psig, about 220 psig to about 375 psig, about 220 psig to about 350 psig, about 220 psig to about 325 psig, or about 220 psig to about 300 psig. In other embodiments, the internal pressure is about 225 psig to about 450 psig, about 225 psig to about 400 psig, about 225 psig to about 375 PSIG, about 225 psig to about 350 psig, about 225 psig to about 325 psig, or about 225 psig to about 300 psig. In other embodiments, the internal pressure is about 250 psig to about 450 psig, about 250 psig to about 400 psig, about 250 psig to about 375 psig, about 250 psig to about 350 psig, about 250 psig to about 325 psig, or about 250 psig to about 300 psig. In other embodiments, the internal pressure is about 275 psig to about 450 psig, about 275 psig to about 400 psig, about 275 psig to about 375 psig, about 275 psig to about 350 psig, about 275 psig to about 325 psig, or about 275 psig to about 300 psig. In other embodiments, the internal pressure is about 300 psig to about 450 psig, about 300 psig to about 400 psig, about 300 psig to about 375 psig, about 300 psig to about 350 psig, or about 300 psig to about 325 psig.

In some embodiments, there is provided a method of depositing a pharmaceutical formulation containing a large drug, such a therapeutic protein or antibody, to the submucosa and/or the mucosa (e.g., into the lamina propria) of the small intestine of the subject. In some embodiments, the drug has a molecular weight is at least about 20 kDa, at least about 30 kDa, at least about 40 kDa, at least about 50 kDa or at least about 60 kDa.

In some embodiments, the drug has a molecular weight ranging from about 20 kDa to about 200 kDa, from about 20 kDa to about 175 kDa, or from about 20 kDa to about 150 kDa. In some other embodiments, the drug has a molecular weight ranging from about 60 kDa to about 200 kDa, from about 60 kDa to about 175 kDa, or from about 60 kDa to about 150 kDa. In some embodiments, the internal pressure on the pharmaceutical formulation, prior to release from the device (i.e., the peak fluid pressure), is at least about 225 psig. In some embodiments, the internal pressure is at least about 230 psig. In some embodiments, the internal pressure is at least about 235 psig, at least about 240 psig, at least about 245 psig, or at least about 250 psig. In some embodiments, the internal pressure is at least about 275 psig, at least about 300 psig, or at least about 320 psig. In some embodiments, the internal pressure is about 225 psig to about 500 psig, about 225 psig to about 475 psig, about 225 psig to about 450 psig, about 225 psig to about 425 psig, about 225 psig to about 400 psig, about 225 psig to about 375 psig, about 225 psig to about 350 psig, or about 225 psig to about 325 psig. In some embodiments, the internal pressure is about 250 psig to about 500 psig, about 250 psig to about 475 psig, about 250 psig to about 450 psig, about 250 psig to about 425 psig, about 250 psig to about 400 psig, about 250 psig to about 375 psig, about 250 psig to about 350 psig, or about 250 psig to about 325 psig. In some embodiments, the internal pressure is about 275 psig to about 500 psig, about 275 psig to about 475 psig, about 275 psig to about 450 psig, about 275 psig to about 425 psig, about 275 psig to about 400 psig, about 275 psig to about 375 psig, about 275 psig to about 350 psig, or about 275 psig to about 325 psig. In some embodiments, the internal pressure is about 300 psig to about 500 psig, about 300 psig to about 475 psig, about 300 psig to about 450 psig, about 300 psig to about 425 psig, about 300 psig to about 400 psig, about 300 psig to about 375 psig, about 300 psig to about 350 psig, or about 300 psig to about 325 psig. In some embodiments, the internal pressure is about 320 psig to about 500 psig, about 320 psig to about 475 psig, about 320 psig to about 450 psig, about 320 psig to about 425 psig, about 320 psig to about 400 psig, about 320 psig to about 375 psig, or about 320 psig to about 350 psig.

(I) A first set of nonlimiting embodiments includes:

1. An ingestible device, comprising:
a storage reservoir configured to store a dispensable substance; and
a pressurized chamber configured so that, when a restraining force is removed one or more openings in the ingestible device become revealed, and the dispensable substance exits the ingestible device via the openings in the ingestible device.

2. The ingestible device of embodiment 1, further comprising a piston configured so that, when the restraining force is removed, the piston moves to force the dispensable substance out of the ingestible device via the openings.

3. The ingestible device of embodiment 1 or 2, wherein the storage reservoir stores the dispensable substance.

4. The ingestible device of any of the preceding embodiments, wherein the restraining force is provided by restraining elements, wherein the restraining elements have a first state in which they are configured to prevent the dispensable substance from exiting the ingestible device via the openings, and a second state in which they are configured to allow the dispensable substance to exit the ingestible device via the openings.

5. The ingestible device of embodiment 4, wherein the restraining elements comprise an enteric material.

6. The ingestible device of embodiment 5, wherein the restraining elements comprise one or more of polyvinyl acetate phthalate, methacrylic acid, methacrylic copolymers, cellulose acetate phthalate, acrylate copolymer, or cellulose acetate phthalate.

7. The ingestible device of any one of embodiments 4 to 6, wherein the restraining elements comprise at least one pin.

8. The ingestible device of any one of embodiments 4 to 7, wherein the restraining elements comprise at least one dowel, clasp, clamp, flange, or rivet.

9. The ingestible device of any one of embodiments 4 to 8, wherein the restraining elements are configured to transition from the first state to the second state when the restraining elements are exposed to a triggering condition.

10. The ingestible device of embodiment 9, wherein the triggering condition relates to a condition of the GI tract.

11. The ingestible device of embodiment 10, wherein the condition of the GI tract comprises at least one condition selected from the group consisting of temperature, pH, presence of an enzyme, and time.

12. The ingestible device of embodiment 11, wherein the condition of the GI tract is a pH of greater than 5.

13. The ingestible device of any one of the preceding embodiments, wherein the restraining elements comprise a first type of restraining element and a second type of restraining element different from the first type of restraining element.

14. The ingestible device of embodiment 13, wherein the first type of restraining elements are configured to transition to their second state before the second type of restraining element transitions to its second state.

15. The ingestible device of any one of the preceding embodiments, further comprising an enteric coating on the housing of the ingestible device.

16. The ingestible device of any one of the preceding embodiments, wherein the pressurized chamber has an inlet configured to permit fluid to enter the pressurized chamber.

17. The ingestible device of embodiment 16, further comprising a valve within the inlet configured to regulate flow into the pressurized chamber.

18. The ingestible device of embodiment 17, wherein the valve is a check valve.

19. The ingestible device of embodiment 17, wherein the valve is an umbrella valve or a duckbill valve.

20. The ingestible device of any one of the preceding embodiments, wherein the ingestible device comprises a housing.

21. The ingestible device of embodiment 20, wherein the housing is configured to maintain its mechanical integrity during use of the ingestible device.

22. The ingestible device of embodiment 1, wherein the dispensable substance comprises a therapeutic agent comprising small molecules and large molecules including biologic drugs, proteins including fusion proteins, peptides including cyclic peptides, cells including stem cells, and nucleic acids such as inhibitory nucleic acids, antisense nucleic acids, siRNA, ribozymes.

23. The ingestible device of embodiment 1, wherein the restraining elements are comprise a first type of restraining element and a second type of restraining element.

24. The ingestible device of embodiment 1, wherein the dispensable substance exits the device with sufficient velocity to pass through the mucosa of mammalian gastrointestinal tissue.

25. The ingestible device of the preceding embodiments, wherein the opening is a nozzle with a rounded cross section.

26. The ingestible device of embodiment 25, wherein the first actuation component is configured to actuate before the second actuation component.

(II) A second set of nonlimiting embodiments include the following:

1. An ingestible device, comprising:
a housing;
an enteric coating on the housing; and
a storage reservoir within the housing,
wherein the storage reservoir is configured to store a dispensable substance.

2. The ingestible device of embodiment 1, further comprising a trigger mechanism configured to cause the dispensable substance within the storage reservoir to be released under triggering conditions.

3. The ingestible device of embodiment 1, further comprising a piston configured so that, when the restraining force is removed from the pressurized chamber, the piston moves to force the dispensable substance out of the ingestible device via the openings.

4. The ingestible device of any one of embodiments 1 to 3, wherein the restraining force is provided by restraining elements, wherein the restraining elements have a first state in which they are configured to prevent the dispensable substance from exiting the ingestible device via the openings, and a second state in which they are configured to allow the dispensable substance to exit the ingestible device via the openings.

5. The ingestible device of embodiment 4, wherein the restraining elements comprise an enteric material.

6. The ingestible device of embodiment 5, wherein the restraining elements comprise one or more of polyvinyl acetate phthalate, methacrylic acid, methacrylic copolymers, cellulose acetate phthalate, acrylate copolymer, or cellulose acetate phthalate.

7. The ingestible device of any one of embodiments 1 to 6, wherein the restraining elements comprise at least one pin.

8. The ingestible device of any one of embodiments 1 to 6, wherein the restraining elements comprise at least one dowel, clasp, clamp, flange, or rivet.

9. The ingestible device of any one of embodiments 1 to 6, wherein the restraining elements are configured to transition from the first state to the second state when the restraining elements are exposed to a triggering condition.

10. The ingestible device of embodiment 9, wherein the triggering condition relates to a condition of the GI tract.

11. The ingestible device of embodiment 10, wherein the condition of the GI tract comprises at least one condition selected from the group consisting of temperature, pH, presence of an enzyme, and time.

12. The ingestible device of embodiment 11, wherein the condition of the GI tract is a pH of greater than 5.

13. The ingestible device of any one of embodiments 1 to 12, wherein the restraining elements are comprise a first type of restraining element and a second type of restraining element different from the first type of restraining element.

14. The ingestible device of embodiment 13, wherein the first type of restraining elements are configured to transition to their second state before the second type of restraining element transitions to its second state.

15. The ingestible device of any one of embodiments 1 to 14, wherein the pressurized chamber has an inlet configured to permit fluid to enter the pressurized chamber.

16. The ingestible device of embodiment 15, further comprising a valve within the inlet configured to regulate flow into the pressurized chamber.

17. The ingestible device of embodiment 16, wherein the valve is a check valve.

18. The ingestible device of embodiment 16, wherein the valve is an umbrella valve or a duckbill valve.

19. The ingestible device of any one of embodiments 1 to 18, wherein the dispensable substance comprises a therapeutic agent comprising small molecules and large molecules including biologic drugs, proteins including fusion proteins, peptides including cyclic peptides, cells including stem cells, and nucleic acids such as inhibitory nucleic acids, antisense nucleic acids, siRNA, ribozymes.

20. The ingestible device of any one of embodiments 1 to 19, wherein the opening is a nozzle with a rounded cross section.

21. The ingestible device of embodiment 20, wherein the first actuation component is configured to actuate before the second actuation component.

(III) A third set of nonlimiting embodiments include the following:

1. An ingestible device, comprising:
    a housing having a first portion and a second portion;
    a first actuation component on the housing;
    a second actuation component within the housing; and
    a storage reservoir located within the housing,
    wherein the storage reservoir is configured to store a dispensable substance, and the housing has an opening in fluid communication with the storage reservoir.
2. The ingestible device of embodiment 1, wherein the first actuation component is an enteric coating.
3. The ingestible device of embodiment 1, wherein the second actuation component is a restraining mechanism configured to keep the first portion and the second portion of the housing in an open position.
4. The ingestible device of embodiment 3, wherein the second actuation component comprises an enteric material.
5. The ingestible device of any one of embodiments 1 to 4, wherein the first and second actuation components are configured to cause the dispensable substance within the storage reservoir to be released under triggering conditions.
6. The ingestible device of any one of embodiments 1 to 5, wherein the first actuation component has a first triggering condition different from a second triggering condition of the second actuation component.
7. The ingestible device of embodiment 6, wherein the first and second triggering conditions relate to first and second conditions of the GI tract.
8. The ingestible device of embodiment 7, wherein the condition of the GI tract comprises at least one condition selected from the group consisting of temperature, pH, presence of an enzyme, and time.
9. The ingestible device of embodiment 8, wherein the first condition of the GI tract is a pH of greater than 1 and the second condition of the GI tract is a pH of greater than 5.
10. The ingestible device of any one of embodiments 1 to 9, wherein the second actuation component comprises one or more of polyvinyl acetate phthalate, methacrylic acid, methacrylic copolymers, cellulose acetate phthalate, acrylate copolymer, or cellulose acetate phthalate.
11. The ingestible device of any one of embodiments 1 to 10, wherein the second actuation component comprises at least one pin.
12. The ingestible device of any one of embodiments 1 to 10, wherein the second actuation component comprises at least one dowel, clasp, clamp, flange, or rivet.
13. The ingestible device of any one of embodiments 1 to 12, wherein the opening is a nozzle with a rounded cross section.
14. The ingestible device of embodiment 13, wherein the first actuation component is configured to actuate before the second actuation component.

(IV) A fourth set of nonlimiting embodiments include the following:

1. An ingestible device, comprising:
    a storage reservoir configured to store a dispensable substance; and
    a pressurized chamber configured so that, when a restraining force is removed one or more openings in the ingestible device become revealed, and the dispensable substance exits the drug delivery device via the openings in the ingestible device.
2. The ingestible device of embodiment 1, further comprising a piston configured so that, when the restraining force is removed, the piston moves to force the dispensable substance out of the ingestible device via the openings.
3. The ingestible device of embodiment 1 or claim 2, wherein the storage reservoir stores the dispensable substance.
4. The ingestible device of the preceding embodiments, wherein the restraining force is provided by restraining elements, wherein the restraining elements have a first state in which they are configured to prevent the dispensable substance from exiting the ingestible device via the openings, and a second state in which they are configured to allow the dispensable substance to exit the ingestible device via the openings.
5. The ingestible device of embodiment 4, wherein the restraining elements comprise an enteric material.
6. The ingestible device of embodiment 5, wherein the restraining elements comprise one or more of polyvinyl acetate phthalate, methacrylic acid, methacrylic copolymers, cellulose acetate phthalate, acrylate copolymer, or cellulose acetate phthalate.
7. The ingestible device of embodiments 4-6, wherein the restraining elements comprise at least one pin.
8. The ingestible device of embodiments 4-7, wherein the restraining elements comprise at least one dowel, clasp, clamp, flange, or rivet.
9. The ingestible device of any one of embodiments 4-8, wherein the restraining elements are configured to transition from the first state to the second state when the restraining elements are exposed to a triggering condition.
10. The ingestible device of embodiment 9, wherein the triggering condition relates to a condition of the GI tract.
11. The ingestible device of embodiment 10, wherein the condition of the GI tract comprises at least one condition selected from the group consisting of temperature, pH, presence of an enzyme, and time.
12. The ingestible device of embodiment 11, wherein the condition of the GI tract is a pH of greater than 5.
13. The ingestible device of any of the preceding embodiments, wherein the restraining elements comprise a first type of restraining element and a second type of restraining element different from the first type of restraining element.
14. The ingestible device of embodiment 13, wherein the first type of restraining elements are configured to transition to their second state before the second type of restraining element transitions to its second state.
15. The ingestible device of the preceding embodiments, further comprising an enteric coating on the housing of the ingestible device.
16. The ingestible device of the preceding embodiments, wherein the pressurized chamber has an inlet configured to permit fluid to enter the pressurized chamber.
17. The ingestible device of embodiment 16, further comprising a valve within the inlet configured to regulate flow into the pressurized chamber.
18. The ingestible device of embodiment 17, wherein the valve is a check valve.
19. The ingestible device of embodiment 17, wherein the valve is an umbrella valve or a duckbill valve.
20. The ingestible device of the preceding embodiments, wherein the ingestible device comprises a housing.
21. The ingestible device of embodiment 20, wherein the housing is configured to maintain its mechanical integrity during use of the ingestible device.
22. The ingestible device of embodiment 1, wherein the dispensable substance comprises a therapeutic agent comprising small molecules and large molecules including biologic drugs, proteins including fusion proteins, peptides including cyclic peptides, cells including stem cells, and nucleic acids such as inhibitory nucleic acids, antisense nucleic acids, siRNA, ribozymes.

23. The ingestible device of embodiment 1, wherein the restraining elements are comprise a first type of restraining element and a second type of restraining element.

24. An ingestible device, comprising:
a housing;
an enteric coating on the housing; and
a storage reservoir within the housing,
wherein the storage reservoir is configured to store a dispensable substance.

25. The ingestible device of embodiment 24, further comprising a trigger mechanism configured to cause the dispensable substance within the storage reservoir to be released under triggering conditions.

26. The ingestible device of embodiment 24, further comprising a piston configured so that, when the restraining force is removed from the pressurized chamber, the piston moves to force the dispensable substance out of the ingestible device via the openings.

27. The ingestible device of embodiments 24-26, wherein the restraining force is provided by restraining elements, wherein the restraining elements have a first state in which they are configured to prevent the dispensable substance from exiting the ingestible device via the openings, and a second state in which they are configured to allow the dispensable substance to exit the ingestible device via the openings.

28. The ingestible device of embodiment 27, wherein the restraining elements comprise an enteric material.

29. The ingestible device of embodiment 28, wherein the restraining elements comprise one or more of polyvinyl acetate phthalate, methacrylic acid, methacrylic copolymers, cellulose acetate phthalate, acrylate copolymer, or cellulose acetate phthalate.

30. The ingestible device of embodiments 24-29, wherein the restraining elements comprise at least one pin.

31. The ingestible device of embodiments 24-29, wherein the restraining elements comprise at least one dowel, clasp, clamp, flange, or rivet.

32. The ingestible device of embodiments 24-29, wherein the restraining elements are configured to transition from the first state to the second state when the restraining elements are exposed to a triggering condition.

33. The ingestible device of embodiment 32, wherein the triggering condition relates to a condition of the GI tract.

34. The ingestible device of embodiment 33, wherein the condition of the GI tract comprises at least one condition selected from the group consisting of temperature, pH, presence of an enzyme, and time.

35. The ingestible device of embodiment 34, wherein the condition of the GI tract is a pH of greater than 5.

36. The ingestible device of embodiments 24-35, wherein the restraining elements are comprise a first type of restraining element and a second type of restraining element different from the first type of restraining element.

37. The ingestible device of embodiment 36, wherein the first type of restraining elements are configured to transition to their second state before the second type of restraining element transitions to its second state.

38. The ingestible device of embodiments 24-37, wherein the pressurized chamber has an inlet configured to permit fluid to enter the pressurized chamber.

39. The ingestible device of embodiment 38, further comprising a valve within the inlet configured to regulate flow into the pressurized chamber.

40. The ingestible device of embodiment 39, wherein the valve is a check valve.

41. The ingestible device of embodiment 39, wherein the valve is an umbrella valve or a duckbill valve.

42. The ingestible device of embodiments 24-41, wherein the dispensable substance comprises a therapeutic agent comprising small molecules and large molecules including biologic drugs, proteins including fusion proteins, peptides including cyclic peptides, cells including stem cells, and nucleic acids such as inhibitory nucleic acids, antisense nucleic acids, siRNA, ribozymes.

43. An ingestible device, comprising:
a housing having a first portion and a second portion;
a first actuation component on the housing;
a second actuation component within the housing; and
a storage reservoir located within the housing,
wherein the storage reservoir is configured to store a dispensable substance, and the housing has an opening in fluid communication with the storage reservoir.

44. The ingestible device of embodiment 43, wherein the first actuation component is an enteric coating.

45. The ingestible device of embodiment 43, wherein the second actuation component is a restraining mechanism configured to keep the first portion and the second portion of the housing in an open position.

46. The ingestible device of embodiment 45, wherein the second actuation component comprises an enteric material.

47. The ingestible device of embodiments 43-46, wherein the first and second actuation components are configured to cause the dispensable substance within the storage reservoir to be released under triggering conditions.

48. The ingestible device of embodiments 43-47, wherein the first actuation component has a first triggering condition different from a second triggering condition of the second actuation component.

49. The ingestible device of embodiment 48, wherein the first and second triggering conditions relate to first and second conditions of the GI tract.

50. The ingestible device of embodiment 49, wherein the condition of the GI tract comprises at least one condition selected from the group consisting of temperature, pH, presence of an enzyme, and time.

51. The ingestible device of embodiment 50, wherein the first condition of the GI tract is a pH of greater than 1 and the second condition of the GI tract is a pH of greater than 5.

52. The ingestible device of embodiment 43-51, wherein the second actuation component comprises one or more of polyvinyl acetate phthalate, methacrylic acid, methacrylic copolymers, cellulose acetate phthalate, acrylate copolymer, or cellulose acetate phthalate.

53. The ingestible device of embodiments 43-52, wherein the second actuation component comprises at least one pin.

54. The ingestible device of embodiments 43-52, wherein the second actuation component comprises at least one dowel, clasp, clamp, flange, or rivet.

55. The ingestible device of the preceding embodiments, wherein the opening is a nozzle with a rounded cross section.

56. The ingestible device of embodiment 55, wherein the first actuation component is configured to actuate before the second actuation component.

57. The ingestible device of embodiment 1, wherein the dispensable substance exits the device with sufficient velocity to penetrate the mucosa of mammalian gastrointestinal tissue.

A number of embodiments have been described. Nevertheless, various modifications may be made without departing from the spirit and scope of the disclosure. Accordingly, other embodiments are within the scope of the following claims.

the glucagon receptor agonist or the GLP-1 receptor agonist in systemic circulation over time ($AUC_{TE}$) that is at least about 10% of the AUC in systemic circulation over time provided by intravenous administration of an equal amount of the glucagon receptor agonist or the GLP-1 receptor

What is claimed is:

1. A method of treating a disease or condition in a subject in need thereof, the method comprising: trans-epithelially administering a dispensable substance to the gastrointestinal (GI) tract of the subject, wherein the trans-epithelial administration comprises: orally administering an ingestible device comprising the dispensable substance to the subject, wherein the ingestible device is configured for trans-epithelial delivery of the dispensable substance to the GI tract of the subject, and the dispensable substance comprises a pharmaceutical formulation comprising a therapeutically effective amount of a glucagon receptor agonist or a glucagon-like peptide-1 (GLP-1) receptor agonist; and releasing the dispensable substance from the ingestible device as at least one jet to a desired location of the GI tract of the subject; wherein the desired location of the GI tract is the small intestine, wherein the trans-epithelial administration directly delivers the dispensable substance to the submucosa of the GI tract of the subject, and wherein the disease or condition is responsive to treatment with the glucagon receptor agonist or GLP-1 receptor agonist.

2. The method of claim 1, wherein the trans-epithelial administration provides systemic uptake of the glucagon receptor agonist or the GLP-1 receptor agonist that is at least about 20% relative to intravenous or subcutaneous administration of an equal amount of the glucagon receptor agonist or the GLP-1 receptor agonist.

3. The method of claim 1, wherein the glucagon receptor agonist or the GLP-1 receptor agonist has a molecular weight of at least about 1.5 kDa.

4. The method of claim 1, wherein the desired location of the GI tract is the jejunum.

5. The method of claim 1, wherein the trans-epithelial administration provides systemic uptake of the glucagon receptor agonist or the GLP-1 receptor agonist that is at least about 10% relative to intravenous or subcutaneous administration of an equal amount of the glucagon receptor agonist or the GLP-1 receptor agonist.

6. The method of claim 1, wherein the trans-epithelial administration provides an area under the curve (AUC) of agonist ($AUC_{IV}$) or by subcutaneous administration of an equal amount of the glucagon receptor agonist or the GLP-1 receptor agonist ($AUC_{SC}$).

7. The method of claim 1, wherein the trans-epithelial administration provides a maximum plasma concentration ($C_{max}$) of the glucagon receptor agonist or the GLP-1 receptor agonist in systemic circulation (($C_{max})_{TE}$) that is at least about 10% of the $C_{max}$ in systemic circulation provided by intravenous administration of an equal amount of the glucagon receptor agonist or the GLP-1 receptor agonist (($C_{max})_{IV}$) or by subcutaneous administration of an equal amount of the glucagon receptor agonist or GLP-1 receptor agonist (($C_{max})_{SC}$).

8. The method of claim 1, wherein the pharmaceutical formulation is a liquid solution or suspension.

9. The method of claim 1, wherein a volume of the dispensable substance released from the ingestible device is from about 50 microliters to about 800 microliters.

10. The method of claim 1, wherein releasing the dispensable substance from the ingestible device as at least one jet to a desired location of the GI tract of the subject is at a peak jet power of about 1 Watt to about 3 Watts.

11. The method of claim 1, wherein the disease or condition is a metabolic, endocrine, or cardiovascular disease or condition.

12. The method of claim 11, wherein the metabolic or endocrine disease or condition is selected from the group consisting of diabetes, a liver disease or disorder, obesity, hyperglycemia, hyperlipidemia, hyperinsulinemia, hypercholesterolemia, lipodystrophy, obstructive sleep apnea, nicotine dependence, and a central nervous system (CNS) disorder.

13. The method of claim 12, wherein the liver disease or disorder is selected from the group consisting of compensated liver cirrhosis, liver fibrosis, non-alcoholic steatohepatitis (NASH), and non-alcoholic fatty liver disease (NAFLD).

14. The method of claim 11, wherein the cardiovascular disease or condition is selected from the group consisting of myocardial infarction, stroke, coronary artery diseases (CAD), heart failure, transient ischemic attacks, peripheral arterial disease, aortic disease, aortic aneurysms, congestive heart failure, hypertension, hypertensive heart disease, pulmonary artery hypertension, arrhythmia, and thromboembolism.

15. The method of claim 1, wherein the glucagon receptor agonist or the GLP-1 receptor agonist has a molecular weight of from about 1.5 kDa to about 5 kDa.

16. The method of claim 1, wherein the glucagon receptor agonist or the GLP-1 receptor agonist is selected from the group consisting of semaglutide, dulaglutide, cotadutide, exenatide, liraglutide, tirzepatide, NNC-0090-2746, glucagon, NN-9277, and NN-9423; and biosimilars thereof.

17. The method of claim 16, wherein the glucagon receptor agonist or the GLP-1 receptor agonist is cotadutide or a biosimilar thereof.

18. The method of claim 16, wherein the glucagon receptor agonist or the GLP-1 receptor agonist is liraglutide or a biosimilar thereof.

19. The method of claim 16, wherein the glucagon receptor agonist or the GLP-1 receptor agonist is tirzepatide or a biosimilar thereof.

20. A method of treating a disease or condition in a patient, comprising:
   trans-epithelially administering a pharmaceutical formulation to the gastrointestinal tract of patient via the patient swallowing an ingestible device containing the pharmaceutical formulation;
   the ingestible device configured for trans-epithelial delivery of the pharmaceutical formulation to the gastrointestinal tract;
   the pharmaceutical formulation comprising a therapeutically effective amount of a glucagon receptor agonist or a glucagon-like peptide-1 receptor agonist; and
   releasing the pharmaceutical formulation from the ingestible device in the small intestine as one or more jets to directly deliver the pharmaceutical formulation to the submucosa of the gastrointestinal tract.

21. The method of claim 20 wherein the trans-epithelial administration provides systemic uptake of the glucagon receptor agonist or the GLP-1 receptor agonist that is at least about 25% of the systemic uptake of intravenous or subcutaneous administration of an equal amount of glucagon receptor agonist or GLP-1 receptor agonist.

22. The method of claim 20 wherein the trans-epithelial administration provides an area under the curve (AUC) of the glucagon receptor agonist or the GLP-1 receptor agonist in systemic circulation over time ($AUC_{TE}$) that is at least about 25% of the AUC in systemic circulation over time provided by intravenous administration of an equal amount of glucagon receptor agonist or GLP-1 receptor agonist ($AUC_{IV}$) or by subcutaneous administration of an equal amount of glucagon receptor agonist or GLP-1 receptor agonist ($AUC_{SC}$).

23. The method of claim 20 wherein the trans-epithelial administration provides a maximum plasma concentration ($C_{max}$) of the glucagon receptor agonist or the GLP-1 receptor agonist in systemic circulation (($C_{max})_{TE}$) that is at least about 25% of the $C_{max}$ in systemic circulation provided by intravenous administration of an equal amount of glucagon receptor agonist or GLP-1 receptor agonist (($C_{max})_{IV}$) or by subcutaneous administration of an equal amount of glucagon receptor agonist or GLP-1 receptor agonist (($C_{max})_{SC}$).

24. The method of claim 20 wherein a volume of the pharmaceutical formulation released from the ingestible device is about 250 microliters to about 400 microliters.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exanatide (synthetic exendin-4)

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```